(12) United States Patent
Berthel et al.

(10) Patent No.: US 7,935,699 B2
(45) Date of Patent: May 3, 2011

(54) PYRAZOLE GLUCOKINASE ACTIVATORS

(75) Inventors: Steven Joseph Berthel, Mendham Township, Morris County, NJ (US); Robert Francis Kester, West Orange, NJ (US); Douglas Eric Murphy, San Diego, CA (US); Thomas Jay Prins, San Diego, CA (US); Frank Ruebsam, San Diego, CA (US); Ramakanth Sarabu, Towaco, NJ (US); Chinh Viet Tran, San Diego, CA (US); Dionisios Vourloumis, Athens (GR)

(73) Assignee: Hoffmann-La Roche Inc., Nutley, NJ (US)

( * ) Notice: Subject to any disclaimer, the term of this patent is extended or adjusted under 35 U.S.C. 154(b) by 626 days.

(21) Appl. No.: 11/879,935

(22) Filed: Jul. 19, 2007

(65) Prior Publication Data

US 2008/0021032 A1    Jan. 24, 2008

Related U.S. Application Data

(60) Provisional application No. 60/832,907, filed on Jul. 24, 2006, provisional application No. 60/930,819, filed on May 18, 2007.

(51) Int. Cl.
*A61K 31/5377* (2006.01)
*A61K 31/415* (2006.01)
*A61P 3/00* (2006.01)
*C07D 231/00* (2006.01)

(52) U.S. Cl. ............ 514/236.5; 514/407; 544/140; 548/372.5

(58) Field of Classification Search ............ None
See application file for complete search history.

(56) References Cited

U.S. PATENT DOCUMENTS

| 2004/0181067 A1* | 9/2004 | Fyfe et al. ............ 544/331 |
| 2006/0167053 A1 | 7/2006 | Iino et al. |
| 2006/0258701 A1 | 11/2006 | Mitsuya et al. |

FOREIGN PATENT DOCUMENTS

| EP | 1 600 442 A1 | 11/2005 |
| WO | WO 00/58293 | 10/2000 |
| WO | WO 01/83465 A2 | 11/2001 |
| WO | WO 01/85706 A1 | 11/2001 |
| WO | WO 01/85707 A1 | 11/2001 |
| WO | WO 02/46173 | 6/2002 |
| WO | WO 03/015774 A1 | 2/2003 |
| WO | WO 03/095438 A1 | 11/2003 |
| WO | WO 2004/050645 A1 | 6/2004 |
| WO | WO 2004/052869 A1 | 6/2004 |
| WO | WO 2004/072031 A2 | 8/2004 |
| WO | WO 2004/072066 A1 | 8/2004 |
| WO | WO 2004/076420 A1 | 9/2004 |
| WO | WO 2004/081001 A1 | 9/2004 |
| WO | WO 2005/080359 A1 | 9/2005 |
| WO | WO 2005/080360 A1 | 9/2005 |
| WO | WO 2005/090332 A1 | 9/2005 |
| WO | WO 2005/095417 A1 | 10/2005 |
| WO | WO 2005/095418 A1 | 10/2005 |
| WO | WO 2005/103021 A1 | 11/2005 |
| WO | WO 2005/121110 A1 | 12/2005 |
| WO | WO 2006/016178 A | 2/2006 |
| WO | WO 2006/016194 A1 | 2/2006 |
| WO | WO 2006/040529 A1 | 4/2006 |
| WO | WO 2006/058923 A1 | 6/2006 |
| WO | WO 2006/125972 A1 | 11/2006 |
| WO | WO 2007/007040 A1 | 1/2007 |
| WO | WO 2007/007041 A1 | 1/2007 |
| WO | WO 2007/007042 A1 | 1/2007 |
| WO | WO 2007/007886 A1 | 1/2007 |
| WO | WO 2007/017649 A1 | 2/2007 |
| WO | WO 2007/026761 A1 | 3/2007 |
| WO | WO 2007/041365 A2 | 4/2007 |
| WO | WO 2007/041366 A1 | 4/2007 |
| WO | WO 2007/051845 A1 | 5/2007 |
| WO | WO 2007/051846 A1 | 5/2007 |
| WO | WO 2007/051847 A1 | 5/2007 |
| WO | WO 2007/104034 A2 | 9/2007 |
| WO | WO 2007/122482 A1 | 11/2007 |

\* cited by examiner

*Primary Examiner* — Kamal A Saeed
(74) *Attorney, Agent, or Firm* — George W. Johnston; Dennis P. Tramaloni; Samuel H. Megerditchian

(57) ABSTRACT

Disclosed herein are pyrazole glucokinase activators of the formula (I)

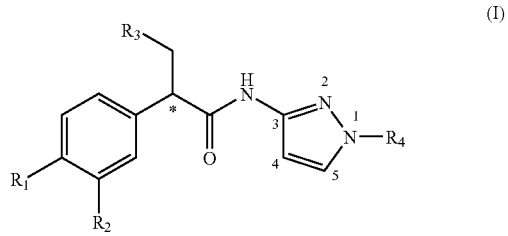

useful for the treatment of metabolic diseases and disorders, preferably diabetes mellitus.

21 Claims, No Drawings

PYRAZOLE GLUCOKINASE ACTIVATORS

PRIORITY TO RELATED APPLICATION(S)

This application claims the benefit of U.S. Provisional Application No. 60/832,907, filed Jul. 24, 2006 and U.S. Provisional Application No. 60/930,819 filed May 18, 2007. The entire contents of the above-identified applications are hereby incorporated by reference.

FIELD OF THE INVENTION

The invention is directed to compounds of the formula (I)

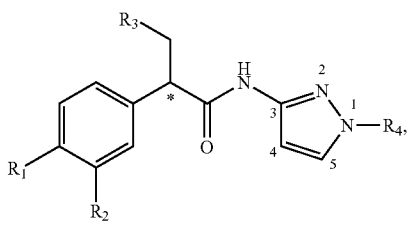

and to pharmaceutical compositions comprising said compounds. The compounds and compositions disclosed herein are glucokinase activators useful for the treatment of metabolic diseases and disorders, preferably diabetes mellitus, more preferably type II diabetes mellitus.

All documents cited or relied upon below are expressly incorporated herein by reference.

BACKGROUND OF THE INVENTION

Glucokinase (GK) is one of four hexokinases that are found in mammals (Colowick, S. P., in *The Enzymes*, Vol. 9 (P. Boyer, ed.) Academic Press, New York, N.Y., pages 1-48, 1973). The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis (Chipkin, S. R., Kelly, K. L., and Ruderman, N. B. in *Joslin's Diabetes* (C. R. Khan and G. C. Wier, eds.), Lea and Febiger, Philadelphia, Pa., pages 97-115, 1994). The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10-15 mM) levels following a carbohydrate-containing meal (Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463-496, 1993). These findings contributed over a decade ago to the hypothesis that GK functions as a glucose sensor in β-cells and hepatocytes (Meglasson, M. D. and Matschinsky, F. M. *Amer. J. Physiol.* 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69-78, 1995; Ferrie, T., Riu, E., Bosch, F. et al., *FASEB J.*, 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226-230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

In one embodiment of the present invention, provided is a compound of the formula (I)

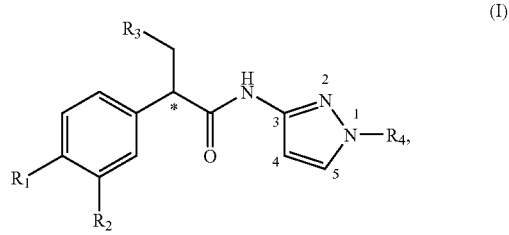

wherein:

$R_1$ and $R_2$ are, independently, hydrogen, halogen, amino, hydroxyamino, cyano, nitro, lower alkyl, —$OR_5$, —$C(O)OR_6$, perfluoro-lower alkyl, lower alkyl thio, perfluoro-lower alkyl thio, lower alkyl sulfinyl, lower alkyl sulfonyl, cycloloweralkyl sulfonyl, lower alkoxy lower alkyl sulfonyl, lower hydroxy lower alkyl sulfonyl, perfluoro-lower alkyl sulfonyl or sulfonamido;

or $R_1$ and $R_2$, together with the phenyl ring to which they are attached, combine to form a 2,3-dihydro-benzo[b]thiophene, 2,3-dihydro-benzo[b]thiophene 1-oxide, 2,3-dihydro-benzo[b]thiophene 1,1-dioxide, benzo[b]thiophene, benzo[b]thiophene 1-oxide, benzo[b]thiophene 1,1-dioxide, thiochroman, thiochroman 1-oxide or thiochroman 1,1-dioxide group;

$R_3$ is a cycloalkyl, a bicycloalkyl or a mono- or bicyclic heterocycle with 1-3 hetero atoms selected from N, O and S, said cycloalkyl or heterocycle being unsubstituted or mono-, bi- or trisubstituted with halogen, lower alkyl, lower alkyoxy, carbonyl or lower alkyl sulfonyl;

$R_4$ is hydrogen,

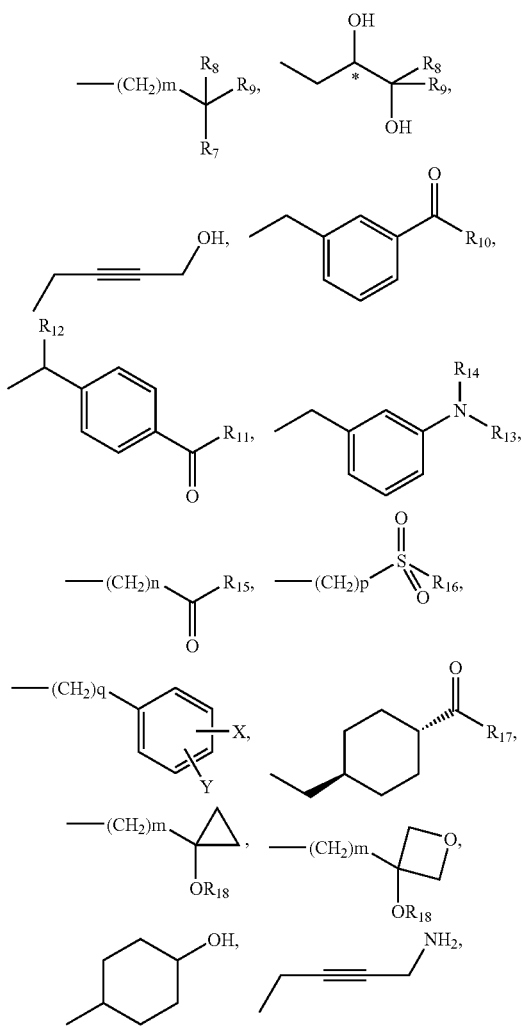

or alkyl having 1 to 10 carbon atoms;
$R_5$ is hydrogen, alkyl having from 1 to 6 carbons, phenyl, benzyl, substituted phenyl or substituted benzyl;
$R_6$ is hydrogen, alkyl having from 1 to 6 carbons, benzyl or substituted benzyl;
$R_7$ is hydrogen, hydroxy, alkoxy, perfluoroalkoxy, amino, alkyl amino, or dialkylamino, methylene hydroxy, C(O)OY', where Y' is H or lower alkyl;
$R_8$ is hydrogen or lower alkyl;
$R_9$ is hydrogen, cycloalkyl or lower alkyl;
$R_{10}$ is hydroxy, lower alkoxy, amino, methylamino, dimethylamino or —NH$_2$CH$_2$-cycloalkyl;
$R_{11}$ is hydroxy, amide, amide-loweralkyl, cyclopropyl methyl amide, methoxy, NHCH$_2$CH$_2$CH$_2$L, wherein L is methoxy, hydroxy or dimethylamino;
$R_{12}$ is hydrogen or lower alkyl;
$R_{13}$ is hydrogen or lower alkyl;
$R_{14}$ is hydrogen, lower alkyl, SO$_2$X', wherein X' is lower alkyl, or C(O)Y", where Y" is lower alkyl or O-alkyl;
$R_{15}$ is hydroxy, methoxy, t-butoxy, lower alkyl, 2-hydroxy-2-methyl-propyl, amino, methylamino, propylamino, dimethylamino, diethylamino, morpholino, anilino, benzylamino, allylcarbamoyl-lower alkyl, allylamino, pyrazin-2-ylamino, and NH—(CH$_2$)$_v$Z, wherein Z is methoxy or morpholino;
$R_{16}$ is lower alkyl;
$R_{17}$ is methoxy;
$R_{18}$ is H, lower alkyl, C(O)R where R is lower alkyl;
X, Y are, independently, hydrogen, halogen, cyano, lower alkyl, methoxy, SO$_2$X" where X" is alkyl, or cycloalkyl
m is 0, 1, 2, 3 or 4, wherein if m=0 $R_7$ can not be hydroxy, alkoxy, perfluoroalkoxy, amino, alkyl amino, or dialkylamino;
n is 0, 1, 2;
p is 0, 1;
q is 0, 1, 2; and
v is 2, 3;
or a pharmaceutically acceptable salt thereof.

In another embodiment of the present invention, provided is a pharmaceutical composition, comprising a therapeutically effective amount of a compound according to formula I and a pharmaceutically acceptable carrier.

In a further embodiment of the present invention, provided is a method for treating a metabolic disease and/or disorder, comprising the step of administering a therapeutically effective amount of a compound according to formula I to a patient in need thereof.

DETAILED DESCRIPTION OF THE INVENTION

The present invention is directed to compounds of the formula I:

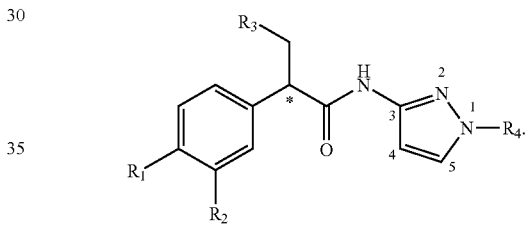

These compounds are glucokinase activators and are useful for the treatment of metabolic diseases and disorders. One such metabolic disease is diabetes mellitus, preferably type II diabetes mellitus.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

In the compound of formula I, the "*" illustrates an asymmetric carbon atom in this compound. The compound of formula I may be present either as a racemate or in the "R" configuration at the asymmetric carbon shown. The "R" enantiomers are preferred.

As used herein, the term "alkyl" means, for example, a branched or unbranched, cyclic (i.e., cycloalkyl) or acyclic, saturated (partially saturated if cyclic) or unsaturated hydrocarbyl radical which may be substituted or unsubstituted. Where cyclic, the alkyl group is preferably $C_3$ to $C_{12}$, more preferably $C_3$ to $C_{10}$, more preferably $C_3$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means, for example, a branched or unbranched, cyclic (i.e., "cyclolower alkyl") or acyclic, saturated (partially saturated if cyclic) or unsaturated hydrocarbyl radical wherein said cyclic lower alkyl group is $C_3$, $C_4$, $C_5$, $C_6$ or $C_7$, and wherein said acyclic lower alkyl group is $C_1$, $C_2$, $C_3$ or $C_4$, and is preferably selected from methyl, ethyl, propyl(n-propyl or isopropyl) or butyl(n-butyl, sec-butyl, isobutyl or tertiary-butyl). It will be appreciated therefore that the term "lower alkyl" as used herein includes lower alkyl (branched or unbranched), lower alkenyl (branched or unbranched), lower alkynyl (branched or unbranched), cycloloweralkyl, cycloloweralkenyl and cycloloweralkynyl.

The lower alkyl groups may be substituted or unsubstituted, preferably unsubstituted. Where substituted, there will generally be, for example, 1 to 3 substituents present, preferably 1 substituent.

As used herein, the term "halogen" is used interchangeably with the word "halo", and, unless otherwise stated, designates all four halogens, i.e. fluorine, chlorine, bromine, and iodine. As used herein, "perfluoro-lower alkyl" means any lower alkyl group wherein all of the hydrogens of the lower alkyl group are substituted or replaced by fluoro. Among the preferred perfluoro-lower alkyl groups are trifluoromethyl, pentafluoroethyl, heptafluoropropyl, etc.

As used herein, the term "lower alkoxy" signifies a lower alkyl group as defined above linked via an oxygen to the remainder of the molecule and includes both straight chain and branched chain alkoxy groups having from 1 to 7 carbon atoms, such as methoxy, ethoxy, propoxy, isopropoxy, preferably methoxy and ethoxy. "Lower alkoxy lower alkyl" signifies a lower alkoxy linked via an oxygen to a lower alkyl group, which is linked to the remainder of the molecule.

As used herein the term "aryl" signifies aryl mononuclear aromatic hydrocarbon groups such as phenyl, tolyl, etc. which can be unsubstituted or substituted in one or more positions with halogen, nitro, lower alkyl, or lower alkoxy substituents and polynuclear aryl groups, such as naphthyl, anthryl, and phenanthryl, which can be unsubstituted or substituted with one or more of the aforementioned groups. Preferred aryl groups are the substituted and unsubstituted mononuclear aryl groups, particularly phenyl. The term "arylalkyl" denotes an alkyl group, preferably lower alkyl, in which one of the hydrogen atoms can be replaced by an aryl group. Examples of arylalkyl groups are benzyl, 2-phenylethyl, 3-phenylpropyl, 4-chlorobenzyl, 4-methoxybenzyl and the like.

As used herein, the term "lower alkanoic acid" denotes lower alkanoic acids containing from 2 to 7 carbon atoms such as propionic acid, acetic acid and the like. The term "lower alkanoyl" denotes monovalent alkanoyl groups having from 2 to 7 carbon atoms such as propionyl, acetyl and the like. The term "aroic acids" denotes aryl alkanoic acids where aryl is as defined above and alkanoic contains from 1 to 6 carbon atoms. The term "aroyl" denotes aroic acids wherein aryl is as defined hereinbefore, with the hydroxide group of the COOH moiety removed. Among the preferred aroyl groups is benzoyl.

As used herein, —C(O)OR represents

and so forth.

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. Examples of ester groups which are cleaved (in this case hydrolyzed) in vivo to the corresponding carboxylic acids are those in which the hydrogen is replaced with -lower alkyl which is optionally substituted, e.g., with heterocycle, cycloalkyl, etc. Examples of substituted lower alkyl esters are those in which lower alkyl is substituted with pyrrolidine, piperidine, morpholine, N-methylpiperazine, etc. The group which is cleaved in vivo may be, for example, ethyl, morpholino ethyl, and diethylamino ethyl. In connection with the present invention, —$CONH_2$ is also considered an ester, as the —$NH_2$ may be cleaved in vivo and replaced with a hydroxy group, to form the corresponding carboxylic acid.

Further information concerning examples of and the use of esters for the delivery of pharmaceutical compounds is available in Design of Prodrugs. Bundgaard H. ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

During the course of the reactions provided below in the Reaction Scheme and discussion, the various functional groups such as the free carboxylic acid or hydroxy groups may be protected via conventional hydrolyzable ester or ether protecting groups. As used herein, the term "hydrolyzable ester or ether protecting groups" designates any ester or ether conventionally used for protecting carboxylic acids or alcohols which can be hydrolyzed to yield the respective carboxyl or hydroxyl group. Exemplary ester groups useful for those purposes are those in which the acyl moieties are derived from a lower alkanoic, aryl lower alkanoic, or lower alkane dicarboxylic acid. Among the activated acids which can be utilized to form such groups are acid anhydrides, acid halides, preferably acid chlorides or acid bromides derived from aryl or lower alkanoic acids. Examples of anhydrides are anhydrides derived from monocarboxylic acid such as acetic anhydride, benzoic acid anhydride, and lower alkane dicarboxylic acid anhydrides, e.g. succinic anhydride as well as chloro formates e.g. trichloro, ethylchloro formate being preferred. A suitable ether protecting group for alcohols are, for example, the tetrahydropyranyl ethers such as 4-methoxy-5,6-dihydroxy-2H-pyranyl ethers. Others are aroylmethylethers such as benzyl, benzhydryl or trityl ethers or α-lower alkoxy lower alkyl ethers, for example, methoxymethyl or allylic ethers or alkyl silylethers such as trimethylsilylether.

Similarly, the term "amino protecting group" designates any conventional amino protecting group which can be cleaved to yield the free amino group. The preferred protecting groups are the conventional amino protecting groups utilized in peptide synthesis. Especially preferred are those amino protecting groups which are cleavable under mildly acidic conditions from about pH 2 to 3. Particularly preferred amino protecting groups are t-butyl carbamate (BOC), benzyl carbamate (CBZ), and 9-fluorenylmethyl carbamate (FMOC).

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of from about 0.01 mg/kg to about 50 mg/kg should be appropriate, although the upper limit may be exceeded when indicated. The dosage is preferably from about 0.3 mg/kg to about 10 mg/kg per day. A preferred dosage may be from about 0.70 mg/kg to about 3.5 mg/kg per day. The daily dosage can be administered as a single dose or in divided doses, or for parenteral administration it may be given as continuous infusion.

The compounds of the present invention can be prepared by any conventional means. Suitable processes for synthesizing these compounds are provided in the Examples. Generally, compounds of formula I can be prepared according to the Schemes described below. The sources of the starting materials for these reactions are also described.

Preferably, the compounds of formula I can be prepared starting from the compounds of formula IV and formula VI by the following Reaction Scheme:

Reaction Scheme 1

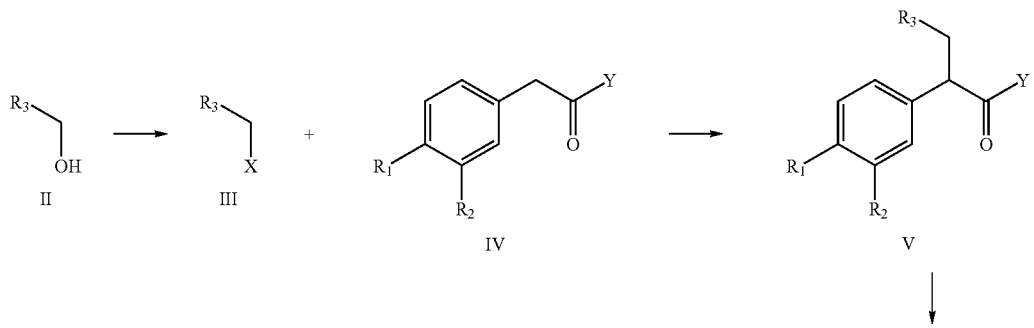

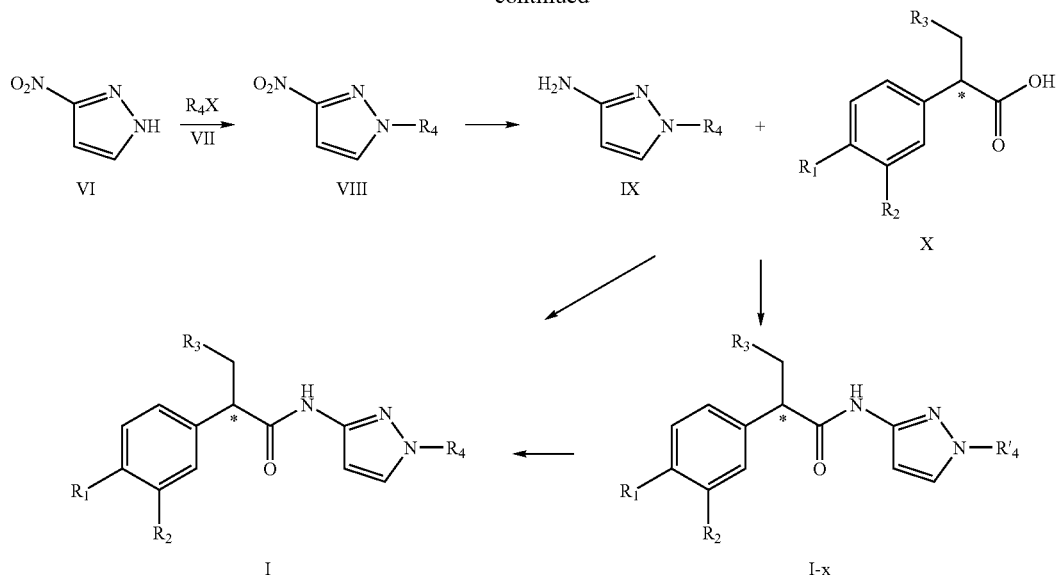

wherein $R_1$, $R_2$, $R_3$ and $R_4$ are as above and Y is lower alkoxy or a chiral auxiliary such as 1R,2R-(-)-pseudoephedrine.

The carboxylic acids or their lower alkyl esters of formula IV wherein one of $R_1$ and $R_2$ is nitro, cyano, thio, thiomethyl, methylsulfonyl, amino, chloro, bromo, or iodo and the other is hydrogen are commercially available. In cases where only the carboxylic acids are available, they can be converted to the corresponding esters of lower alkyl alcohols using any conventional esterification methods. All the reactions hereto forward are to be carried out on lower alkyl esters of the carboxylic acids of formula IV, or may be carried out on the carboxylic acids themselves. The amino substituted compounds of formula IV can be converted to other substituents either before or after conversion to the compounds of formula I. In this respect, the amino groups can be diazotized to yield the corresponding diazonium compound, which in situ can be reacted with the desired lower alkyl thiol, cyclolower alkyl thiol, or perfluoro-lower alkyl thiol (see for example, Baleja, J. D. *Synth. Comm.* 1984, 14, 215; Giam, C. S.; Kikukawa, K., *J. Chem. Soc, Chem. Comm.* 1980, 756; Kau, D.; Krushniski, J. H.; Robertson, D. W, *J. Labelled Compd Rad.* 1985, 22, 1045; Oade, S.; Shinhama, K.; Kim, Y. H., *Bull Chem Soc. Japan.* 1980, 53, 2023; Baker, B. R.; et al, *J. Org. Chem.* 1952, 17, 164) to yield corresponding compounds of formula IV where one of the substituents is lower alkyl thio, cyclolower alkyl thio, or perfluoro-lower alkyl thio and the other is hydrogen. If desired, the lower alkyl thio, cyclolower alkyl thio or perfluoro-lower alkyl thio compounds can then be converted to the corresponding lower alkyl sulfonyl, cyclolower alkyl thio or perfluoro-lower alkyl sulfonyl substituted compounds of formula IV by oxidation. Any conventional method of oxidizing alkyl thio substituents to sulfones can be utilized to effect this conversion. If it is desired to produce compounds of lower alkyl or perfluoro-lower alkyl groups of compounds of formula IV, the corresponding halo substituted compounds of formula IV can be used as starting materials. Any conventional method of converting an aromatic halo group to the corresponding alkyl group (see for example, Katayama, T.; Umeno, M., *Chem. Lett.* 1991, 2073; Reddy, G. S.; Tam., *Organometallics*, 1984, 3, 630; Novak, J.; Salemink, C. A., *Synthesis*, 1983, 7, 597; Eapen, K. C.; Dua, S. S.; Tamboroski, C., *J. Org. Chem.* 1984, 49, 478; Chen, Q, -Y.; Duan, J.-X. *J. Chem. Soc. Chem. Comm.* 1993, 1389; Clark, J. H.; McClinton, M. A.; Jone, C. W.; Landon, P.; Bisohp, D.; Blade, R. J., *Tetrahedron Lett.* 1989, 2133; Powell, R. L.; Heaton, C. A, U.S. Pat. No. 5,113,013) can be utilized to effect this conversion. On the other hand, the thio substituent can be oxidized to a —$SO_3H$ group which then can be converted to —$SO_2Cl$ which is reacted with ammonia to form the sulfonamide substituent —$S(O)_2$—$NH_2$.

For compounds of formula IV where Y=Oalkyl and one of $R_1$ and $R_2$ is hydrogen and the other is hydroxy lower alkyl sulfonyl or lower alkoxy lower alkyl sulfonyl, the corresponding thio compound may be used as a starting material. The compound of formula IV where one of $R_1$ and $R_2$ is hydrogen and the other is thio may be alkoxylated by conventional methods (for example with alkoxy alkyl halide) to the corresponding lower alkoxy lower alkyl sulfanyl of formula IV, which is then hydrolyzed by conventional methods (for example with lithium hydroxide, water, and tetrahydrofuran or sodium hydroxide and methanol) to the corresponding carboxylic acid. The latter is alkylated by conventional methods to add the desired methyl-cycloalkyl $R_3$ substituent. The resulting compound is oxidized by conventional methods at the sulfanyl to provide lower alkoxy lower alkyl sulfonyl compound of formula IV. Conversion of the compound of formula IV to a compound of formula I is described below.

For compounds of formula IV wherein one or both of $R_1$ and $R_2$ is hydroxyamino, the corresponding nitro compounds can be used as starting material and can be converted to the corresponding compounds where $R_1$ and/or $R_2$ are hydroxyamino. Any conventional method of converting a nitro group to the corresponding aromatic hydroxyamino compound can be used to affect this conversion.

The carboxylic acids or esters of formula IV wherein both of $R_1$ and $R_2$ are chloro, or fluoro are commercially available. In cases, where only the carboxylic acids are available, they can converted to the corresponding esters of lower alkyl alcohols using any conventional esterification method. To produce the compound of formula IV where both $R_1$ and $R_2$ are nitro, 3,4-dinitrotoluene can be used as starting material. This compound can be converted to the corresponding 3,4-dinitrophenyl acetic acid. Any conventional method of converting an aryl methyl group to the corresponding aryl acetic acid can be utilized to effect this conversion (see for example, Clark, R. D.; Muchowski, J. M.; Fisher, L. E.; Flippin, L. A.; Repke, D. B.; Souchet, M, *Synthesis*, 1991, 871). The compounds of formula IV where both $R_1$ and $R_2$ substituents are amino can be obtained from the corresponding dinitro compound of formula IV, described above. Any conventional method of reducing a nitro group to an amine can be utilized to effect this conversion. The compound of formula IV where both $R_1$ and $R_2$ are amine groups can be used to prepare the corresponding compound of formula IV where both $R_1$ and $R_2$ are iodine or bromine via a diazotization reaction. Any conventional method of converting an amino group to an iodo or bromo group (see for example, Lucas, H. J.; Kennedy, E. R. *Org. Synth. Coll. Vol, II* 1943, 351) can be utilized to effect this conversion. If it is desired to produce compounds of formula IV where both $R_1$ and $R_2$ are lower alkyl thio or perfluoro-lower alkyl thio groups, the compound of formula IV where $R_1$ and $R_2$ are amino can be used as starting material. Any conventional method of converting an aryl amino group to an aryl thioalkyl group can be utilized to effect this conversion. If it is desired to produce compound of formula IV where $R_1$ and $R_2$ are lower alkyl sulfonyl or lower perfluoro alkyl sulfonyl, the corresponding compounds of formula IV where $R_1$ and $R_2$ are lower alkyl thio or perfluoro-lower alkyl thio can be used as starting material. Any conventional method of oxidizing alkyl thio substituents to sulfones can be utilized to effect this conversion. If it is desired to produce compounds of formula IV where both $R_1$ and $R_2$ are substituted with lower alkyl or perfluoro-lower alkyl groups, the corresponding halo substituted compounds of formula IV can be used as starting materials. Any conventional method of converting an aromatic halo group to the corresponding alkyl or perfluoro-lower alkyl group can be utilized to effect this conversion.

The carboxylic acids corresponding to the compounds of formula IV where one of $R_1$ and $R_2$ is nitro and the other is halo are known from the literature (see for 4-chloro-3-nitrophenyl acetic acid, Tadayuki, S.; Hiroki, M.; Shinji, U.; Mitsuhiro, S. J, JP 71-99504, *Chemical Abstracts* 80:59716; see for 4-nitro-3-chlorophenyl acetic acid, Zhu, J.; Beugelmans, R.; Bourdet, S.; Chastanet, J.; Rousssi, G. *J. Org. Chem.* 1995, 60, 6389; Beugelmans, R.; Bourdet, S.; Zhu, J. *Tetrahedron Lett.* 1995, 36, 1279). These carboxylic acids can be converted to the corresponding lower alkyl esters using any conventional esterification methods. Thus, if it is desired to produce the compound of formula IV where one of $R_1$ and $R_2$ is nitro and the other is lower alkyl thio, cyclolower alkyl thio or perfluoro-lower alkyl thio, the corresponding compound where one of $R_1$ and $R_2$ is nitro and the other is chloro can be used as starting material. In this reaction, any conventional method of nucleophilic displacement of aromatic chlorine group with a lower alkyl thiol or cyclolower alkyl thiol can be used (see for example, Singh, P.; Batra, M. S.; Singh, H, *J. Chem. Res.-S* 1985 (6), S204; Ono, M.; Nakamura, Y.; Sata, S.; Itoh, I, *Chem. Lett,* 1988, 1393; Wohrle, D.; Eskes, M.; Shigehara, K.; Yamada, A, *Synthesis,* 1993, 194; Sutter, M.; Kunz, W, U.S. Pat. No. 5,169,951). Once the compounds of formula IV where one of $R_1$ and $R_2$ is nitro and the other is lower alkyl thio, cyclolower alkyl thio or perfluoro-lower alkyl thio are available, they can be converted to the corresponding compounds of formula IV where one of $R_1$ and $R_2$ is nitro and the other is lower alkyl sulfonyl, cyclolower alkyl sulfonyl or perfluoro-lower alkyl sulfonyl using conventional oxidation procedures. If it is desired to produce compounds of formula IV where one of $R_1$ and $R_2$ is amino and the other is lower alkyl thio, cyclolower alkyl thio or perfluoro-lower alkyl thio, the corresponding compound where one of $R_1$ and $R_2$ is nitro and the other is lower alkyl thio, cyclolower alkyl thio or perfluoro-lower alkyl thio can be used as starting materials. Any conventional method of reducing an aromatic nitro group to an amine can be utilized to effect this conversion. If it is desired to produce compounds of formula IV where one of $R_1$ and $R_2$ is lower alkyl thio or cyclolower alkyl thio and the other is perfluoro-lower alkyl thio, the corresponding compound where one of $R_1$ and $R_2$ is amino and the other is lower alkyl thio, cyclolower alkyl thio or perfluoro-lower alkyl thio can be used as starting materials. Any conventional method of diazotizing aromatic amino group and reacting it in situ with the desired lower alkyl thiol or cyclolower alkyl thiol can be utilized to effect this conversion. If it is desired to produce compounds of formula IV where one of $R_1$ and $R_2$ is lower alkyl sulfonyl or cyclolower alkyl sulfonyl and the other is perfluoro-lower alkyl sulfonyl, the corresponding compounds where one of $R_1$ and $R_2$ is lower alkyl thio or cyclolower alkyl thio and the other is perfluoro-lower alkyl thio can be used as starting materials. Any conventional method of oxidizing an aromatic thio ether group to the corresponding sulfone group can be utilized to effect this conversion If it is desired to produce compounds of formula IV where one of $R_1$ and $R_2$ is halo and the other is lower alkyl thio, cyclolower alkyl thio, or perfluoro-lower alkyl thio, the corresponding compounds where one of $R_1$ and $R_2$ is amino and the other is lower alkyl thio, cyclolower alkyl thio or perfluoro-lower alkyl thio can be used as starting materials. Any conventional method of diazotizing an aromatic amino group and conversion of it in situ to an aromatic halide can be utilized to effect this conversion. If it is desired to produce compounds of formula IV where $R_1$ is cyclolower alkyl thio and $R_2$ is halo or alkyl the corresponding compounds where $R_1$ is a thiol and $R_2$ is a halo or alkyl can be alkylated with cycloalkyl halides using conventional methods, such as sodium hydride in N,N-dimethylformamide and the cycloalkyl halide under reflux conditions (see for example: Bernard, A. M.; Cerioni, G.; Piras, P. P.; Seu, G.; *Synthesis* 1990, 871-874; Cutler, R. A.; Schalit, S.; U.S. Pat. No. 3,272, 814; Imboden, C.; Villar, F.; Renaud, P.; *Organic Letters* 1999, 1, 873-875.; Heuser, S.; Barrett, D. G.; Berg, M.; Bonnier, B.; Kahl, A.; De La Puente, M. L.; Oram, N.; Riedl, R.; Roettig, U.; Gil, G. S.; Seger, E.; Steggles, D. J.; Wanner, J.; Weichert, A. G. *Tetrahedron Letters* 2006, 47, 2675-2678; Masson, E.; Leroux, F. *Helvetica Chimica Acta* 2005, 88, 1375-1386; Makosza, M.; Judka, M. *Synlett* 2004, 717-719; Ono, N.; Miyake, H.; Saito, T.; Kaji, A. *Synthesis* 1980, 952-3; Novokreshchennykh, V. D.; Mochalov, S. S.; Kornyshev, V. N.; Shabarov, Y. S. *Zhurnal Organicheskoi Khimii* 1979, 15, 292-301; Weinstock, J.; Bernardi, J. L.; Pearson, R. G. *J. Am. Chem. Soc* 1958, 80, 4961-4964; Voronkov, M. G.; Nikol'skii, N. S. *Izvestiya Akademii Nauk SSSR, Seriya Khimicheskaya* 1983, 1664-7.

A preferred method of producing the compound of formula IV where Y=OAlkyl, $R_1$ is lower alkyl thio or cyclolower alkyl thio and $R_2$ is halo or alkyl is by the Wolff-Kishner reduction of the corresponding aryl-oxo-acetic acid esters. The aryl-oxo-acetic acid esters can be prepared by Friedel-Crafts acylation of the corresponding 2-halo or 2-methyl substituted alkylsulfanyl-benzenes or cyclolower alkylsulfanyl-benzenes, which in turn can be prepared from the corresponding 2-halo or 2-alkyl substituted alkylated benzenethiols (see examples 1 and 57 in Chen, S.; Corbett, W. L.; Guertin, K. R.; Haynes, N.-E.; Kester, R. F.; Mennona, F. A.; Mischke, S. G.; Qian, Y.; Sarabu, R.; Scott, N. R.; Thakkar, K. C. WO 2004052869). If it is desired to produce compounds of formula IV where one of $R_1$ and $R_2$ is halo and the other is lower alkyl sulfonyl, cyclolower alkyl sulfonyl or perfluoro-lower alkyl sulfonyl, the corresponding compounds where one of $R_1$ and $R_2$ is halo and the other is lower alkyl thio, cyclolower alkyl thio or perfluoro-lower alkyl thio can be used as starting materials. Any conventional method of oxidizing an aromatic thio ether to the corresponding sulfone can be utilized to effect this conversion. If it is desired to produce compounds of various combinations of lower alkyl and per-fluoro-lower alkyl groups of compounds of formula IV, the corresponding halo substituted compounds of formula IV can be used as starting materials. Any conventional method of converting an aromatic halo group to the corresponding alkyl group can be utilized to effect this conversion. If one wishes to prepare the compound of formula IV where one of $R_1$ and $R_2$ is nitro and the other is amino, the compound of formula IV where one of $R_1$ and $R_2$ is nitro and other is chloro can be used as a starting material. The chloro substituent on the phenyl ring can be converted to an iodo substituent (see for example, Bunnett, J. F.; Conner, R. M.; *Org. Synth. Coll Vol V,* 1973, 478; Clark, J. H.; Jones, C. W. *J. Chem. Soc. Chem. Commun.* 1987, 1409), which in turn can be reacted with an azide transferring agent to form the corresponding azide (see for example, Suzuki, H.; Miyoshi, K.; Shinoda, M. *Bull. Chem. Soc. Japan,* 1980, 53, 1765). This azide can then be reduced in a conventional manner to form the amine substituent by reducing it with commonly used reducing agent for converting azides to amines (see for example, Soai, K.; Yokoyama, S.; Ookawa, A. *Synthesis,* 1987, 48).

If it is desired to produce the compound of formula IV where both $R_1$ and $R_2$ are cyano, this compound can be prepared as described hereinbefore from compounds where $R_1$ and $R_2$ are amino via diazotization to produce the diazonium salt followed by reaction with cyano group transferring agent. If it is desired to produce the compound of formula IV where one of $R_1$ and $R_2$ is cyano and the other is not cyano, the compound of formula IV where one of $R_1$ and $R_2$ is nitro and the other is chloro is used as a starting material. Using this starting material, the nitro is converted to the cyano and the halo is converted to any other desired $R_1$ and $R_2$ substituent as described hereinbefore.

If it is desired to produce the compound of formula IV where both $R_1$ and $R_2$ are lower alkoxy lower alkyl sulfonyl, the compound of formula IV where both $R_1$ and $R_2$ are amino can be used as starting material. Any conventional method of converting an aryl amino group to an aryl thio group may be utilized to effect this conversion. The thio groups can then be converted to lower alkoxy lower alkyl sulfonyl groups as described above.

If it is desired to produce the compound of formula IV wherein one of $R_1$ or $R_2$ is a —C(O)—$OR_5$, this compound can be formed from the corresponding compound where $R_1$ or $R_2$ is an amino group by converting the amino group to a diazonium salt and reacting the diazonium salt with a hydrohalic acid to form the corresponding halide and then converting this halide into a Grignard reagent and reacting the Grignard reagent with $CO_2$ to produce the corresponding acid which can be esterified. On the other hand, if one wants to produce the compound of formula IV where both $R_1$ and $R_2$ are carboxylic acid groups. This compound can be produced as described above from the corresponding compound of formula IV where both $R_1$ and $R_2$ are amino groups. In the same manner, the amino groups in the compound of formula IV can be converted to the corresponding compound where $R_1$ or $R_2$ or both of $R_1$ and $R_2$ is —C(O)$OR_5$ by simply reacting the amino group with sodium nitrate in sulfuric acid to convert the amino group to a hydroxy group and thereafter etherifying, if desired, the hydroxy group.

If it is desired to produce the compound of formula IV where $R_1$ and $R_2$ are connected to form a ring, and the ring is comprised of two carbon atoms and a sulfur atom, and the bond between the carbon atoms is a single bond and the sulfur atom is unsubstituted so that a 2,3-dihydro-benzo[b]thiophene is formed, this compound can be prepared as described in (Meyer, M. D.; Hancock, A. A.; Tietje, K.; Sippy, K. B.; Prasad, R.; Stout, D. M.; Arendsen, D. L.; Donner, B. G.; Carroll, W. A. *J. Med. Chem.* 1997, 40, 1049-1062; Meyer, M. D.; DeBernardis, J. F.; Prasad, R.; Sippy, K. B.; Tietje, K. R. WO 9312754; Dunn, J. P.; Ackerman, N. A.; Tomolonis, A. J. *J. Med. Chem.* 1986, 29, 2326-9; Boissier, J. R.; Ratouis, R. DE 2106045).

If it is desired to produce the compound of formula IV as a single enantiomer where $R_1$ and $R_2$ are connected to form a ring, and the ring is comprised of two carbon atoms and a sulfur atom, and the bond between the carbon atoms is a single bond and the sulfur atom is substituted with one oxygen so that a 2,3-dihydro-benzo[b]thiophene 1-oxide is formed, this compound can be prepared from the 2,3-dihydro-benzo[b]thiophene analog using any conventional chemistry of oxidizing a 2,3-dihydro-benzo[b]thiophene to a 2,3-dihydro-benzo[b]thiophene 1-oxide (Boyd, D. R.; Sharma, N. D.; Haughey, S. A.; Kennedy, M. A.; Malone, J. F.; Shepherd, S. D.; Allen, C. C. R.; Dalton, H. *Tetrahedron* 2004, 60, 549-559).

If it is desired to produce the compound of formula IV where $R_1$ and $R_2$ are connected to form a ring, and the ring is comprised of two carbon atoms and a sulfur atom, and the bond between the carbon atoms is a single bond and the sulfur atom is substituted with two oxygens so that a 2,3-dihydro-benzo[b]thiophene 1,1-dioxide is formed, these compounds can be prepared from the 2,3-dihydro-benzo[b]thiophene analog using any conventional chemistry of oxidizing a 2,3-dihydro-benzo[b]thiophene to a 2,3-dihydro-benzo[b]thiophene 1,1-dioxide (Clark, P. D.; Rahman, L. K. A.; Scrowston, R. M. *Journal of the Chemical Society, Perkin Transactions* 1: *Organic and Bio-Organic Chemistry* (1972-1999) 1982, 815-21; Clark, P. D.; Clarke, K.; Ewing, D. F.; Scrowston, R. M.; Kerrigan, F. *J. Chem. Res., Synop.* 1981, 307).

If it is desired to produce the compound of formula IV where $R_1$ and $R_2$ are connected to form a ring, and the ring is comprised of two carbon atoms and a sulfur atom, and the bond between the carbon atoms is a double bond and the sulfur atom is unsubstituted so that a benzo[b]thiophene is formed, this compound can be prepared as described in (Molino, B. F.; Liu, S.; Berkowitz, B. A.; Guzzo, P. R.; Beck, J. P.; Cohen, M. WO 2006020049; Baroni, M.; Bourrie, B.; Cardamone, R.; Casellas, P. WO 2001049684; Ono, S.; Saitoh, A.; Iwakami, N.; Nakagawa, M.; Yamaguchi, S. WO 2000076957; Meyer, M. D.; Hancock, A. A.; Tietje, K.; Sippy, K. B.; Prasad, R.; Stout, D. M.; Arendsen, D. L.; Donner, B. G.; Carroll, W. A. *J. Med. Chem.* 1997, 40, 1049-1062; Naylor, A.; Bradshaw, J.; Bays, D. E.; Hayes, A. G.; Judd, D. B. EP 330469; Matsuki, Y.; Fujieda, K. *Nippon Kagaku Zasshi* 1967, 88, 445-7; Kefford, N. P.; Kelso, J. M. *Australian Journal of Biological Sciences* 1957, 10, 80-4).

If it is desired to produce the compound of formula IV as a racemate where $R_1$ and $R_2$ are connected to form a ring, and the ring is comprised of two carbon atoms and a sulfur atom, and the bond between the carbon atoms is a double bond and the sulfur atom is substituted with one oxygen so that a benzo[b]thiophene 1-oxide is formed, this compound can be prepared from the benzo[b]thiophene analog using any conventional chemistry of oxidizing a benzo[b]thiophene to a benzo[b]thiophene 1-oxide (Pouzet, P.; Erdelmeier, I.; Ginderow, D.; Mornon, J.-P.; Dansette, P.; Mansuy, D. *J. Chem. Soc., Chem. Commun.* 1995, 473-4).

If it is desired to produce the compound of formula IV where $R_1$ and $R_2$ are connected to form a ring, and the ring is comprised of two carbon atoms and a sulfur atom, and the bond between the carbon atoms is a double bond and the sulfur atom is substituted with two oxygens so that a benzo [b]thiophene 1,1-dioxide is formed, these compounds can be prepared from the benzo[b]thiophene analog using any conventional chemistry of oxidizing a benzo[b]thiophene to a 2,3-dihydro-benzo[b]thiophene 1,1-dioxide (Madec, D.; Mingoia, F.; Macovei, C.; Maitro, G.; Giambastiani, G.; Poli, G. *European Journal of Organic Chemistry* 2005, 552-557; Nomura, M.; Murata, S.; Kidena, K. JP 2004168663; Abrantes, M.; Valente, A. A.; Pillinger, M.; Goncalves, I. S.; Rocha, J.; Romao, C. C. *Chemistry—A European Journal* 2003, 9, 2685-2695).

If it is desired to produce the compound of formula IV where $R_1$ and $R_2$ are connected to form a ring, and the ring is comprised of three carbon atoms and a sulfur atom, and the bond between the carbon atoms is a single bond and the sulfur atom is unsubstituted so that a thiochroman is formed, this compound can be prepared as described in (Boissier, J. R.; Ratouis, R. DE 2106045).

If it is desired to produce the compound of formula IV as a racemate where $R_1$ and $R_2$ are connected to form a ring, and the ring is comprised of three carbon atoms and a sulfur atom, and the bond between the carbon atoms is a single bond and the sulfur atom is substituted with one oxygen so that a thiochroman 1-oxide is formed, this compound can be prepared from the thiochroman analog using any conventional chemistry of oxidizing a thiochroman to a thiochroman 1-oxide (Devlin, F. J.; Stephens, P. J.; Scafato, P.; Superchi, S.; Rosini, C. *J. Phys. Chem. A* 2002, 106, 10510-10524; Brunel, J.-M.; Diter, P.; Duetsch, M.; Kagan, H. B. *J. Org. Chem.* 1995, 60, 8086-8; Donnoli, M. I.; Superchi, S.; Rosini, C. *J. Org. Chem.* 1998, 63, 9392-9395).

If it is desired to produce the compound of formula IV where $R_1$ and $R_2$ are connected to form a ring, and the ring is comprised of three carbon atoms and a sulfur atom, and the bond between the carbon atoms is a single bond and the sulfur atom is substituted with two oxygens so that a thiochroman 1,1-dioxide is formed, these compounds can be prepared from the thiochroman analog using any conventional chemistry of oxidizing a thiochroman to a thiochroman 1,1-dioxide (Sakamoto, M.; Tomita, S.; Takashima, Y.; Koga, H. WO 2001040176; Patonay, T.; Adam, W.; Levai, A.; Koever, P.; Nemeth, M.; Peters, E.-M.; Peters, K. *J. Org. Chem.* 2001, 66, 2275-2280).

If it is desired to produce the compound of formula IV where Y=OAlkyl, $R_1$ is lower alkyl sulfonyl or cyclolower alkyl sulfonyl and $R_2$ is cyano the compound of formula IV where Y=OAlkyl, $R_1$ is lower alkyl sulfonyl or cyclolower alkyl sulfonyl and $R_2$ is bromo can be used as a starting material. The bromo substituent on the phenyl ring can be converted to a cyano substituent by reacting with a cyanide salt to form the corresponding aryl nitrile (see example 75 in Bizzarro, F. T.; Corbett, W. L.; Grippo, J. F.; Haynes, N.-E.; Holland, G. W.; Kester, R. F.; Mahaney, P. E.; Sarabu, R. U.S. Pat. No. 6,610,846).

If it is desired to produce the compound of formula IV where Y=OH, $R_1$ is lower alkyl sulfonyl or cyclolower alkyl sulfonyl and $R_2$ is lower alkoxy the compound of formula IV where Y=OH, $R_1$ is lower alkyl sulfonyl or cyclolower alkyl sulfonyl and $R_2$ is chloro can be used as a starting material.

The chloro substituent on the phenyl ring can be converted to an alkoxy by reacting with an alkoxide salt to form the corresponding aryl ether (see for example *J. Org. Chem. USSR Eng. Trans.* 1968, 4, 632-636)

The substituents which form $R_1$ and $R_2$ can be added to the ring after condensation of the compound of formula IV with the compound of formula IX to form the compound of formula I. Hence, all of the reactions described to produce various substituents of $R_1$ and $R_2$ in the compound of formula I can be carried out on the compound of formula I after its formation by the reaction of compound of formula X and IX to form the compound of formula I.

In the first step of this Reaction Scheme, the alkyl halide of formula III is reacted with the compound of formula IV, to produce the compound of formula V. In this reaction, if in the compounds of formula IV, $R_1$ or $R_2$ is an amino group, such amino group(s) have to be protected before carrying out the alkylation reaction with the alkyl halide of formula III. The amino group can be protected with any conventional acid removable group (see for example, for t-butyloxycarbonyl group see, Bodanszky, M. *Principles of Peptide Chemistry*, Springer-Verlag, New York, 1984, p 99). The protecting group has to be removed from the amino groups after preparing the corresponding amine protected compounds of formula I to obtain the corresponding amines. The compound of formula IV is an organic acid derivative or the organic acid having an alpha carbon atom and the compound of formula III is an alkyl halide so that alkylation occurs at the alpha carbon atom of this carboxylic acid. This reaction is carried out by any conventional means of alkylation of the alpha carbon atom of a carboxylic acid or a lower alkyl ester of a carboxylic acid. Generally, in these alkylation reactions any alkyl halide is reacted with the anion generated from any acetic acid ester or the dianion of the acid. The anion can be generated by using a strong organic base such as lithium diisopropylamide, n-butyl lithium as well as other organic lithium bases. In carrying out this reaction, low boiling ether solvents are utilized such as tetrahydrofuran at low temperatures from −80° C. to about −10° C. being preferred. However any temperature from −80° C. to room temperature can be used.

The compound of formula V has an asymmetric carbon atom through which the group —$CH_2R_3$ and the acid amide substituents are connected. In accordance with this invention, the preferred stereoconfiguration of this group is R.

If it is desired to produce the compound of formula V, where $R_3$ is lower alkyl having from 2 to 4 carbon atoms or $R_3$ is an unbranched alkyl chain of 4-6 carbons atoms wherein the chain, in combination with the carbon atom it is bound to, forms a four-, five-, or six-membered ring, the corresponding alkyl halides of formula III are commercially available.

If it is desired to produce the compound of formula V as a racemate, where $R_3$ is an unbranched heteroalkyl chain of 5 carbon atoms plus one oxygen atom wherein the chain, in combination with the carbon atom it is bound to, forms a six-membered ring so that the carbon atom at the ring attachment is symmetrical substituted so as not to produce a chiral center, the corresponding alkyl halide of formula III is commercially available.

If it is desired to produce the compound of formula V as a racemate where $R_3$ is an unbranched heteroalkyl chain of 3 carbon atoms plus one oxygen atom wherein the chain, in combination with the carbon atom it is bound to, forms a four-membered ring so that the carbon atom at the ring attachment is symmetrical substituted so as not to produce a chiral center, the corresponding alkyl halide of formula III can be prepared from the corresponding alcohol of formula II (Nitta, R.; Yuasa, M. JP 2004203827; Cha, S. W.; Choi, D. H.; Jin, J.-I. *Advanced Functional Materials* 2001, 11, 355-360; Kashima, M.; Machida, T. JP 11106380; Akagi, T.; Yamashita, F.; Takaya, Y.; Isozaki, W. JP 10140019; Fiege, H.; Jautelat, M.; Arlt, D. DE 3618135; Watanabe, K.; Arimatsu, Y.; Akiyama, F. JP 49020164; Arimatsu, G.; Watanabe, K. JP 49001506; Skovronek, H. S. U.S. Pat. No. 3,301,923; Luskin, L. S. U.S. Pat. No. 3,105,838; Cheymol, J.; Chabrier, P.; Seyden-Penne, J.; Don, P.-C. *Compt. Rend.* 1962, 254, 2363-5.; Kashelikar, D. V.; Fanta, P. E. *J. Am. Chem. Soc.* 1960, 82, 4930-1.; Schnell, H.; Nentwig, J.; Hintzmann, K.; Raichle, K.; Biedermann, W. U.S. Pat. No. 2,917,468; Issidorides, C. H.; Gulen, R. C.; Aprahamian, N. S. *J. Org. Chem.* 1956, 21, 997-8.; Corrodi, H.; Hardegger, E. *Helv. Chim. Acta* 1957, 40, 193-9).

If it is desired to produce the compound of formula V, as a mixture of diastereomers, where $R_3$ is an unbranched heteroalkyl chain of 4-5 carbon atoms plus one oxygen atom wherein the chain, in combination with the carbon atom it is bound to, forms a five-, or six-membered ring so that the carbon atom at the ring attachment is unsymmetrically substituted so as to produce a chiral center, the corresponding alkyl halides of formula III are commercially available.

If it is desired to produce the compound of formula V, as a mixture of diastereomers, where $R_3$ is an unbranched heteroalkyl chain of 4 carbon atoms plus one oxygen atom wherein the chain, in combination with the carbon atom it is bound to, forms a five-membered ring so that the carbon atom at the ring attachment is unsymmetrically substituted so as to produce a chiral center of the S configuration, the corresponding alkyl halides of formula III can be prepared from the corresponding alcohol of formula II (Wei, W.-L.; Zhu, H.-Y.; Zhao, C.-L.; Huang, M.-Y.; Jiang, Y.-Y. *React. Funct. Polym.* 2004, 59, 33-39; Cervinka, O.; Bajanzulyn, O.; Fabryova, A.; Sackus, A. *Collect. Czech. Chem. Commun.* 1986, 51, 404-407; Brown, H. C.; Gupta, A. K.; Rangaishenvi, M. V.; Prasad, J. V. N. V. *Heterocycles* 1989, 28, 283-294.) using any conventional method of converting an alcohol to a halide.

If it is desired to produce the compound of formula V, as a mixture of diastereomers, where $R_3$ is an unbranched heteroalkyl chain of 4 carbon atoms plus one oxygen atom wherein the chain, in combination with the carbon atom it is bound to, forms a five-membered ring so that the carbon atom at the ring attachment is unsymmetrically substituted so as to produce a chiral center of the R configuration, the corresponding alkyl halides of formula III can be prepared from the corresponding alcohol of formula II (Hartman, F. C.; Barker, R. *J. Org. Chem.* 1964, 29, 873-877; Brown, H. C.; Gupta, A. K.; Rangaishenvi, M. V.; Prasad, J. V. N. V. *Heterocycles* 1989, 28, 283-294.) using any conventional method of converting an alcohol to a halide.

If it is desired to produce the compound of formula V, as a mixture of diastereomers, where $R_3$ is an unbranched heteroalkyl chain of 5 carbon atoms plus one oxygen atom wherein the chain, in combination with the carbon atom it is bound to, forms a six-membered ring so that the carbon atom at the ring attachment is unsymmetrically substituted so as to produce a chiral center of the S configuration, the corresponding alkyl halides of formula III can be prepared from the corresponding alcohols of formula II (Quartey, E. G. K.; Hustad, J. A.; Faber, K.; Anthonsen, T. *Enzyme Microb. Technol.* 1996, 19, 361-366; Beasley, S. C.; Haughan, A. F.; Montana, J.; Watson, R. J. In PCT Int. Appl.; Chiroscience Limited, UK. WO 9611200 A1 19960418) a using any conventional method of converting an alcohol to a halide.

If it is desired to produce the compound of formula V, as a mixture of diastereomers, where $R_3$ is an unbranched heteroalkyl chain of 5 carbon atoms plus one oxygen atom wherein the chain, in combination with the carbon atom it is bound to, forms a six-membered ring so that the carbon atom at the ring attachment is unsymmetrically substituted so as to produce a chiral center of the R configuration, the corresponding alkyl halides of formula III can be prepared from the corresponding alcohols of formula II (Quartey, E. G. K.; Hustad, J. A.; Faber, K.; Anthonsen, T. *Enzyme Microb. Technol.* 1996, 19, 361-366; Beasley, S. C.; Haughan, A. F.; Montana, J.; Watson, R. J. In PCT Int. Appl.; (Chiroscience Limited, UK). WO 9611200 A1 19960418; Cervinka, O.; Bajanzulyn, O.; Fabryova, A.; Sackus, A. *Collect. Czech. Chem. Commun.* 1986, 51, 404-407; E. J.; Bo, Y.; Busch-Petersen, J. *J. Am. Chem. Soc.* 1998, 120, 13000-13001.) using any conventional method of converting an alcohol to a halide.

If it is desired to produce the compound of formula V, as a mixture of diastereomers, where $R_3$ is an unbranched heteroalkyl chain of 3 carbon atoms plus one oxygen atom wherein the chain, in combination with the carbon atom it is bound to, forms a four-membered ring so that the carbon atom at the ring attachment is unsymmetrically substituted so as to produce an asymmetric center, the corresponding racemic alkyl halides of formula III can be prepared from the corresponding alcohol of formula II (Evans, R. D.; Magee, J. W.; Schauble, J. H. *Synthesis* 1988, 862-868.) using any conventional method of converting an alcohol to a halide.

If it is desired to produce the compound of formula V, as a mixture of diastereomers, where $R_3$ is an unbranched heteroalkyl chain of 3 carbon atoms plus one oxygen atom wherein the chain, in combination with the carbon atom it is bound to, forms a four-membered ring so that the carbon atom at the ring attachment is unsymmetrically substituted so as to produce a chiral center of the S configuration, the corresponding alkyl halides of formula III can be prepared from the corresponding alcohol of formula II which in turn can be prepared from the known THP protected derivative (Bachki, A.; Falvello, L. R.; Foubelo, F.; Yus, M. *Tetrahedron: Asymmetry* 1997, 8, 2633-2643.) using any conventional method of converting a THP protected alcohol to an alcohol and any conventional method of converting an alcohol to a halide respectively.

If it is desired to produce the compound of formula V, as a mixture of diastereomers, where $R_3$ is an unbranched heteroalkyl chain of 3 carbon atoms plus one oxygen atom wherein the chain, in combination with the carbon atom it is bound to, forms a four-membered ring so that the carbon atom at the ring attachment is unsymmetrically substituted so as to produce a chiral center of the R configuration, the corresponding alkyl halides of formula III can be prepared from the corresponding alcohol of formula II which in turn can be prepared from the known THP protected derivative (Bachki, A.; Falvello, L. R.; Foubelo, F.; Yus, M. *Tetrahedron: Asymmetry* 1997, 8, 2633-2643.) using any conventional method of converting a THP protected alcohol to an alcohol and any conventional method of converting an alcohol to a halide respectively.

If it is desired to produce the compounds of formula V as a racemate, where $R_3$ is an unbranched heteroalkyl chain of 3 carbon atoms plus one sulfur atom wherein the chain, in combination with the carbon atom it is bound to, forms a four-membered ring so that the carbon atom at the ring attachment is symmetrical substituted so as not to produce a chiral center and the S heteroatom member of the chain is unsubstituted it can be prepared from the corresponding alkyl halides of formula III which can in turn be prepared from the corresponding acids by any conventional method of converting an acid or ester to an alcohol and an alcohol to an alkyl halide (Aitken, S.; Brooks, G.; Dabbs, S.; Frydrych, C. H.; Howard, S.; Hunt, E. WO 2002012199).

If it is desired to produce the compounds of formula V as a mixture of diastereomers, where $R_3$ is an unbranched heteroalkyl chain of 3 carbon atoms plus one sulfur atom wherein the chain, in combination with the carbon atom it is bound to, forms a four-membered ring so that the carbon atom at the ring attachment is symmetrical substituted so as not to produce a chiral center and the S heteroatom member of the chain is substituted with one oxo group it can be prepared from the corresponding alkyl halides of formula III which can in turn be prepared from the corresponding acids by any conventional method of converting an acid or ester to an alcohol and an alcohol to an alkyl halide (Cistaro, C.; Fronza, G.; Mondelli, R.; Bradamante, S.; Pagani, G. A. *Journal of Magnetic Resonance* (1969-1992) 1974, 15, 367-81; Abrahamsson, S.; Rehnberg, G. *Acta Chemica Scandinavica* (1947-1973) 1972, 26, 494-500; Lindberg, B. J.; Hamrin, K.; Johansson, G.; Gelius, U.; Fahlman, A.; Nordling, C.; Siegbahn, K. *Phys. Scr.* 1970, 1, 286-98; Allenmark, S. *Acta Chem. Scand.* 1964, 18, 2197-8).

If it is desired to produce the compounds of formula V as a racemate, where $R_3$ is an unbranched heteroalkyl chain of 3 carbon atoms plus one sulfur atom wherein the chain, in combination with the carbon atom it is bound to, forms a four-membered ring so that the carbon atom at the ring attachment is symmetrical substituted so as not to produce a chiral center and the S heteroatom member of the chain is substituted with two oxo groups it can be prepared from the corresponding alkyl halides of formula III which can in turn be prepared from the corresponding acids by any conventional method of converting an acid or ester to an alcohol and an alcohol to an alkyl halide (Allenmark, S. *Arkiv foer Kemi* 1966, 26, 73-7).

If it is desired to produce the compounds of formula V as a mixture of diastereomers where $R_3$ is an unbranched heteroalkyl chain of 3 carbon atoms plus one sulfur atom wherein the chain, in combination with the carbon atom it is bound to, forms a four-membered ring so that the carbon atom at the ring attachment is unsymmetrically substituted so as to produce an asymmetric center and the S heteroatom member of the chain is unsubstituted it can be prepared from the corresponding racemic alkyl halides of formula III which can in turn be prepared from the corresponding acids by any conventional method of converting an acid or ester to an alcohol and an alcohol to an alkyl halide (Yang, J. M.; Wang, H. C.; Lee, Y. Y.; Goo, Y. M. *Bull. Korean Chem. Soc.* 1992, 13, 6-8). If it is desired to produce the compound in which the S heteroatom member is substituted with one oxo group, any method suitable for oxidizing a sulfur atom to a sulfoxide can be employed. If it is desired to produce the compound in which the S heteroatom member is substituted with two oxo groups, any method suitable for oxidizing a sulfur atom to a sulfone can be employed.

If it is desired to produce the compounds of formula V as a racemate, where $R_3$ is an unbranched heteroalkyl chain of 4 carbon atoms plus one sulfur atom wherein the chain, in combination with the carbon atom it is bound to, forms a five-membered ring where two carbon atoms are double bonded and not adjacent to the S heteroatom and one of the double bonded carbon atoms is the ring attachment, and the S heteroatom member of the chain is unsubstituted, the corresponding alkyl halides of formula III can be prepared from the corresponding alcohol of formula II (Lam, P. Y.; Jadhav, P. K.; Eyermann, C. J.; Hodge, C. N.; De Lucca, G. V.; Rodgers, J. D. U.S. Pat. No. 5,610,294) using any conventional method of converting an alcohol to a halide.

If it is desired to produce the compounds of formula V as a racemate, where $R_3$ is an unbranched heteroalkyl chain of 4 carbon atoms plus one sulfur atom wherein the chain, in combination with the carbon atom it is bound to, forms a five-membered ring where two carbon atoms are double bonded and not adjacent to the S heteroatom and one of the doublebonded carbon atoms is the ring attachment, and the S heteroatom member of the chain is with one oxo group, they can be prepared from the corresponding alkyl halides of formula III (Hegedus, L. S.; Varaprath, S. *Organometallics* 1982, 1, 259-63).

If it is desired to produce the compounds of formula V as a racemate, where $R_3$ is an unbranched heteroalkyl chain of 4 carbon atoms plus one sulfur atom wherein the chain, in combination with the carbon atom it is bound to, forms a five-membered ring where two carbon atoms are double bonded and not adjacent to the S heteroatom and one of the doublebonded carbon atoms is the ring attachment, and the S heteroatom member of the chain is with two oxo groups, they can be prepared from the corresponding alkyl halides of formula III (Bertolini, T. M.; Nguyen, Q. H.; Harvey, D. F. *J. Org. Chem.* 2002, 67, 8675-8678; Chou, T.; Hung, S. C. *Heterocycles* 1986, 24, 2303-9; Rousseau, G.; Drouin, J. *Tetrahedron* 1983, 39, 2307-10; Borg-Visse, F.; Dawans, F.; Marechal, E. *Synthesis* 1979, 817-18; Greuter, H.; Schmid, H. *Helv. Chim. Acta* 1972, 55, 2382-400).

If it is desired to produce the compounds of formula V as a mixture of diastereomers, where $R_3$ is an unbranched heteroalkyl chain of 4 carbon atoms plus one sulfur atom wherein the chain, in combination with the carbon atom it is bound to, forms a five-membered ring so that the carbon atom at the ring attachment is unsymmetrically substituted so as to produce a chiral center, and the S heteroatom member of the chain is unsubstituted or is substituted with two oxo groups, they can be prepared from the corresponding alkyl halides of formula III (Della, E. W.; Graney, S. D. *J. Org. Chem.* 2004, 69, 3824-3835; Leroy, C.; Martin, M.; Bassery, L. *Bull. Soc. Chim. Fr.* 1974, 590-594; X. F.; Turos, E. *Tetrahedron Lett.* 1993, 34, 1575-1578; Culshaw, P. N.; Walton, J. C. *J. Chem. Soc., Perkin Trans.* 2 1991, 1201-1208; Culshaw, P. N.; Walton, J. C. *Tetrahedron Lett.* 1990, 31, 6433-6436; Morita, H.; Oae, S. *Heterocycles* 1976, 5, 29-34; Bernett, R. G.; Doi, J. T.; Musker, W. K. *J. Org. Chem.* 1985, 50, 2048-2050). If it is desired to produce the compound in which the S heteroatom member is substituted with one oxo group, any method suitable for oxidizing a sulfur atom to a sulfoxide can be employed (Colonna, S.; Gaggero, N.; Pasta, P.; Ottolina, G. *J. Chem. Soc., Chem. Commun.* 1996, 2303-2307; Schank, K. *Phosphorus, Sulfur Silicon Relat. Elem.* 1991, 58, 207-221; Kagan, H. B.; Dunach, E.; Nemecek, C.; Pitchen, P.; Samuel, O.; Zhao, S. H. *Pure Appl. Chem.* 1985, 57, 1911-1916). Alternatively, the compound of formula V where the S heteroatom of the ring is substituted with one oxygen atom can be prepared from the corresponding alcohol of formula II (, E. W.; Graney, S. D. *J. Org. Chem.* 2004, 69, 3824-3835; Culshaw, P. N.; Walton, J. C. *J. Chem. Soc., Perkin Trans.* 2 1991, 1201-1208; Culshaw, P. N.; Walton, J. C. *Tetrahedron Lett.* 1990, 31, 6433-6436; Ren, X. F.; Turos, E. *Tetrahedron Lett.* 1993, 34, 1575-1578; Ren, X.-F.; Turos, E.; Lake, C. H.; Churchill, M. R. *J. Org. Chem.* 1995, 60, 6468-6483) using any conventional method of converting an alcohol to a halide.

If it is desired to produce the compounds of formula V as a racemate, where $R_3$ is an unbranched heteroalkyl chain of 5 carbon atoms plus one oxygen atom wherein the chain, in combination with the carbon atom it is bound to, forms a six-membered ring where two carbon atoms are double bonded and not adjacent to the O heteroatom and one of the double bonded carbon atoms is the ring attachment, they can be prepared from the corresponding alkyl halides of formula III (Rueb, L.; Eicken, K.; Plath, P.; Westphalen, K. O.; Wuerzer, B. In *Ger. Offen.*; (BASF A.-G., Germany). DE 3901550 A1 19900726, 1990). The alkyl halides can be prepared from the corresponding alcohols of formula II (Hatano, M.; Mikami, K. *J. Am. Chem. Soc.* 2003, 125, 4704-4705; Belleau, B. *Can. J. Chem.* 1957, 35, 663-672.) using any conventional method of converting an alcohol to a halide.

If it is desired to produce the compound of formula V, as a mixture of diastereomers, where $R_3$ is an unbranched heteroalkyl chain of 5 carbon atoms plus one oxygen atom wherein the chain, in combination with the carbon atom it is bound to, forms a six-membered ring where two carbon atoms are double bonded and not adjacent to the O heteroatom and neither carbon atom is the ring attachment, so that the carbon atom at the ring attachment is unsymmetrically substituted so as to produce a chiral center, the corresponding alkyl halides of formula III can be prepared from the corresponding alcohols of formula II (Snider, B. B.; Phillips, G. B.; Corgdova, R. *J. Org. Chem.* 1983, 48, 3003-3010; Caille, J.-c. In U.S.; (PPG Industries Ohio, Inc., USA)., U.S. Pat. No. 6,300,106 B1 20011009, 2001; Majumdar, K. C.; Ranganayakulu, K.; Brown, R. K. *Indian J. Chem., Sect B* 1984, 23B, 303-306; Herault, V. *Bull. Soc. Chim. Fr.* 1963, 2095-2100; Kimura, G.; Yamamoto, K.; Ito, S. In *Japan. Tokkyo Koho*; (Toyo Koatsu Industries, Inc.). JP 42003304 19670213, 1967) using any conventional method of converting an alcohol to a halide.

If it is desired to produce the compound of formula V, as a mixture of diastereomers, where $R_3$ is an unbranched heteroalkyl chain of 5 carbon atoms plus one oxygen atom wherein the chain, in combination with the carbon atom it is bound to, forms a six-membered ring where two carbon atoms are double bonded and not adjacent to the O heteroatom and neither carbon atom is the ring attachment so that the carbon atom at the ring attachment is unsymmetrically substituted so as to produce a chiral center of the S configuration, the corresponding alkyl halides of formula III can be prepared from the corresponding alcohol of formula II (Kosior, M.; Asztemborska, M.; Jurczak, J. *Synthesis* 2004, 87-91; Caille, J.-C.; Govindan, C. K.; Junga, H.; Lalonde, J.; Yao, Y. *Org. Process Res. Dev.* 2002, 6, 471-476; Johannsen, M.; Joergensen, K. A. *J. Org. Chem.* 1995, 60, 5757-5762; Banfi, L.; Guanti, G.; Paravidino, M.; Riva, R. *Org. Biomol. Chem.* 2005, 3, 1729-1737; In *Japan Kokai Tokkyo Koho*; (Mitsubishi Chemical Industries Co., Ltd., Japan). JP 42003304, 1982) using any conventional method of converting an alcohol to a halide.

If it is desired to produce the compound of formula V, as a mixture of diastereomers, where $R_3$ is an unbranched heteroalkyl chain of 5 carbon atoms plus one oxygen atom wherein the chain, in combination with the carbon atom it is bound to, forms a six-membered ring where two carbon atoms are double bonded and not adjacent to the O heteroatom and neither carbon atom is the ring attachment so as to produce a chiral center of the R configuration at the ring attachment, the corresponding alkyl halides of formula III can be prepared from the corresponding alcohol of formula II (Trost, B. M.; Brown, B. S.; McEachern, E. J.; Kuhn, O. *Chem. Eur. J.* 2003, 9, 4442-4451; Trost, B. M.; McEachern, E. J.; Toste, F. D. In *PCT Int. Appl.*; (The Board of Trustees of the Leland Stanford Junior University, USA; Chirotech Technology Limited). WO 2000014033 A1 20000316, 2000; Kosior, M.; Asztemborska, M.; Jurczak, J. *Synthesis* 2004, 87-91; Kosior, M.; Malinowska, M.; Jozwik, J.; Caille, J.-C.; Jurczak, J. *Tetrahedron: Asymmetry* 2003, 14, 239-244) which in turn can be prepared from the known THP protected derivative (Banfi, L.; Guanti, G.; Paravidino, M.; Riva, R. *Org. Biomol. Chem.* 2005, 3, 1729-1737). using any conventional method of converting a THP protected alcohol to an alcohol and any conventional method of converting an alcohol to a halide respectively.

If it is desired to produce the compound of formula V, as a mixture of diastereomers, where $R_3$ is an unbranched alkyl chain of 4 carbon atoms wherein the chain, in combination with the carbon atom it is bound to, forms a five-membered ring, and one carbon member of the chain is substituted with an oxo group, so that the carbon atom at the ring attachment is unsymmetrically substituted so as to produce a chiral center, it can be prepared from the corresponding alkyl halides of formula III (Cossy, J.; Furet, N. *Tetrahedron Lett.* 1995, 36, 3691-3694; Takahashi, T.; Kato, A.; Matsuoka, S. *Yakugaku Zasshi* 1959, 79, 1087-1091; Mayer, R.; Schubert, H. J. *Chem. Ber.* 1958, 91, 768-772; Mayer, R.; Alder, E. *Chem. Ber.* 1955, 88, 1866-1868; Gault, H.; Skoda, J. *Bull. soc. chim.* 1946, 308,316).

If it is desired to produce the compound of formula V, as a mixture of diastereomers, where $R_3$ is an unbranched alkyl chain of 4 carbon atoms wherein the chain, in combination with the carbon atom it is bound to, forms a five-membered ring, and one carbon member of the chain is substituted with an oxo group so that the carbon atom at the ring attachment is unsymmetrically substituted so as to produce a chiral center of the S configuration, it can be prepared from the corresponding alkyl halides of formula III (Boeckman, R. K., Jr.; Napier, J. J.; Thomas, E. W.; Sato, R. I. *J. Org. Chem.* 1983, 48, 4152-4154). The alkyl halides can be prepared from the corresponding alcohols of formula II (Wang, S.; Chen, G.; Kayser, M. M.; Iwaki, H.; Lau, P. C. K.; Hasegawa, Y. *Can. J. Chem.* 2002, 80, 613-621) using any conventional method of converting an alcohol to a halide.

If it is desired to produce the compound of formula V, as a mixture of diastereomers, where $R_3$ is an unbranched alkyl chain of 4 carbon atoms wherein the chain, in combination with the carbon atom it is bound to, forms a five-membered ring, and one carbon member of the chain is substituted with an oxo group so that the carbon atom at the ring attachment is unsymmetrically substituted so as to produce a chiral center of the R configuration, the corresponding alkyl halides of formula III can be prepared from the corresponding alcohol of formula II (Posner, G. H.; Weitzberg, M.; Jew, S. S. *Synth. Commun.* 1987, 17, 611-620; Tanimori, S.; Tsubota, M.; He, M.; Nakayama, M. *Synth. Commun.* 1997, 27, 2371-2378) which in turn can be prepared from the known protected alcohol derivatives (Adger, B.; Bes, M. T.; Grogan, G.; McCague, R.; Pedragosa-Moreau, S.; Roberts, S. M.; Villa, R.; Wan, P. W. H.; Willetts, A. J. *J. Chem. Soc., Chem. Commun.* 1995, 1563-1564; Gutierrez, M.-C.; Furstoss, R.; Alphand, V. *Adv. Synth. Catal.* 2005, 347, 1051-1059; Suemune, H.; Harabe, T.; Xie, Z. F.; Sakai, K. *Chem. Pharm. Bull.* 1988, 36, 4337-4344) using any conventional method of converting a protected alcohol to an alcohol and any conventional method of converting an alcohol to a halide, respectively.

If it is desired to produce the compound of formula V, as a mixture of diastereomers, where $R_3$ is an unbranched alkyl chain of 4 carbon atoms wherein the chain, in combination with the carbon atom it is bound to, forms a five-membered ring, and one carbon member of the chain which is not the ring attachment carbon is substituted with two flourine atoms, so that the carbon atom at the ring attachment is unsymmetrically substituted so as to produce a chiral center, it can be prepared from the corresponding ketone derivatives of formula V utilizing the DAST reagent (see for example Dolbier, W. R.; Rong, X. X.; Bartberger, M. D.; Koroniak, H.; Smart, B. E.; Yang, Z.-Y. *J. Chem. Soc. Perkin Trans. 2* 1998, 2, 219-232).

If it is desired to produce the compound of formula V, as a racemate, where $R_3$ is an unbranched alkyl chain of 3 carbon atoms wherein the chain, in combination with the carbon atom it is bound to, forms a four membered ring system, and the carbon atom in the 3 position is substituted with two methyl groups, said compound can be prepared from the corresponding alkyl halides of formula III (Hill, E. A.; Link, D. C.; Donndelinger, P.; J. Org. Chem. 1981, 46, 1177-82; Beckwith, A. L. J.; Moad, G.; J. Chem. Soc., Perk. Trans. 2 1980, 7, 1083-92).

If it is desired to produce the compound of formula V, as a mixture of diastereomers, where $R_3$ is an unbranched alkyl chain of 4 carbon atoms wherein the chain, in combination with the carbon atom it is bound to, forms a five-membered ring, and two adjacent carbon atom members of the chain which are not the ring attachment carbon are substituted each with a flourine atom, so that the carbon atom at the ring attachment is unsymmetrically substituted so as to produce an asymmetric center, it can be prepared from the corresponding epoxide derivatives of formula V, where $R_3$ is an unbranched alkyl chain of 4 carbon atoms and an oxygen atom wherein the chain, in combination with the carbon atom it is bound to, forms a 6-oxa-bicyclo[3.1.0]hexane ring system, utilizing a reagent such as DAST (see for example Hudlicky, M. *J. Fluorine Chem* 1987, 36, 373-84). The epoxide derivatives can be prepared from the corresponding alkene derivatives of formula V, where $R_3$ is an unbranched alkyl chain of 4 carbon atoms wherein the chain, in combination with the carbon atom it is bound to, forms a five-membered ring, and two adjacent carbon atom members of the chain which are not the ring attachment carbon are double bonded, utilizing any conventional method of converting an alkene to an epoxide.

If it is desired to produce the compound of formula V, as a mixture of diastereomers, where $R_3$ is an unbranched alkyl chain of 5 carbon atoms wherein the chain, in combination with the carbon atom it is bound to, forms a bicyclo[3.1.0] hexane ring system, and the carbon atom at the ring attachment is in the 5 membered ring and is unsymmetrically substituted so as to produce an asymmetric center, it can be prepared from the corresponding alkene derivatives of formula V, where $R_3$ is an unbranched alkyl chain of 4 carbon atoms wherein the chain, in combination with the carbon atom it is bound to, forms a five-membered ring, and two adjacent carbon atom members of the chain which are not the ring attachment carbon are double bonded, utilizing any conventional method of converting an alkene to a cyclopropane (see for example Moss, R. A.; Fu, X.; *Org. Lett.* 2004, 6, 981-984.)

If it is desired to produce the compound of formula V, as a mixture of diastereomers, where $R_3$ is an unbranched alkyl chain of 4 carbon atoms wherein the chain, in combination with the carbon atom it is bound to, forms a five-membered ring, and one carbon member of the chain is substituted with a hydroxyl group, so that the carbon atom at the ring attachment is unsymmetrically substituted so as to produce a chiral center, it can be prepared from the corresponding alcohol protected alkyl halide of formula III (Julia, M.; Colomer, E. C. R. Acad. Sci., Ser. C 1970, 270, 1305-1307; Corbett, W. L.; Grimsby, J. S.; Haynes, N.-E.; Kester, R. F.; Mahaney, P. E.; Racha, J. K.; Sarabu, R.; Wang, K. In PCT Int. Appl.; (F. Hoffmann-La Roche AG, Switz.). WO 2003095438 A1 20031120, 2003) followed by deprotection of the alcohol using any conventional method of converting a protected alcohol to an alcohol.

If it is desired to produce the compound of formula V, as a mixture of diastereomers, where $R_3$ is an unbranched alkyl chain of 4 carbon atoms wherein the chain, in combination with the carbon atom it is bound to, forms a five-membered ring, and one carbon member of the chain is substituted with a hydroxyl group so that the carbon atom at the ring attachment is unsymmetrically substituted so as to produce a chiral center of the S configuration and the hydroxyl substituted carbon atom is unsymmetrically substituted so as to produce a chiral center of the R configuration, it can be prepared from the corresponding alkyl halide of formula III (Beres, J.; Sagi, G.; Baitz-Gacs, E.; Tomoskozi, I.; Otvos, L. *Tetrahedron* 1988, 44, 6207-6216).

If it is desired to produce the compound of formula V, as a mixture of diastereomers, where $R_3$ is an unbranched alkyl chain of 4 carbon atoms wherein the chain, in combination with the carbon atom it is bound to, forms a five-membered ring, and one carbon member of the chain is substituted with a hydroxyl group so that the carbon atom at the ring attachment is unsymmetrically substituted so as to produce a chiral center of the S configuration and the hydroxyl substituted carbon atom is unsymmetrically substituted so as to produce a chiral center of the S configuration, it can be prepared from the corresponding alkyl halide of formula III (Beres, J.; Sagi, G.; Baitz-Gacs, E.; Tomoskozi, I.; Otvos, L. *Tetrahedron* 1988, 44, 6207-6216).

If it is desired to produce the compound of formula V, as a mixture of diastereomers, where $R_3$ is an unbranched alkyl chain of 4 carbon atoms wherein the chain, in combination with the carbon atom it is bound to, forms a five-membered ring, and one carbon member of the chain is substituted with a hydroxyl group so that the carbon atom at the ring attachment is unsymmetrically substituted so as to produce a chiral center of the R configuration and the hydroxyl substituted carbon atom is unsymmetrically substituted so as to produce a chiral center of the R configuration, the corresponding alkyl halide of formula III can be prepared from the corresponding alcohol of formula II which in turn can be prepared from the known protected alcohol derivative (Klement, I.; Luetgens, H.; Knochel, P. *Tetrahedron Lett.* 1995, 36, 3161-3164) using any conventional method of converting a protected alcohol to an alcohol and any conventional method of converting an alcohol to a halide, respectively.

If it is desired to produce the compound of formula V, as a mixture of diastereomers, where $R_3$ is an unbranched alkyl chain of 4 carbon atoms wherein the chain, in combination with the carbon atom it is bound to, forms a five-membered ring, and one carbon member of the chain is substituted with a hydroxyl group so that the carbon atom at the ring attachment is unsymmetrically substituted so as to produce a chiral center of the R configuration and the hydroxyl substituted carbon atom is unsymmetrically substituted so as to produce a chiral center of the S configuration, the corresponding alkyl halide of formula III can be prepared from the corresponding alcohol of formula II which in turn can be prepared from the known alcohol derivative (Melchiorre, C.; Gualtieri, F.; Giannella, M.; Pigini, M.; Cingolani, M. L.; Gamba, G.; Pigini, P.; Rossini, L. *Farmaco-Ed Sci* 1975, 30, 287-299) using any conventional method of converting a protected alcohol to an alcohol and any conventional method of converting an alcohol to a halide, respectively.

If it is desired to produce the compound of formula V, as a racemate, where $R_3$ is an unbranched alkyl chain of 4 carbons atoms wherein the chain, in combination with the carbon atom it is bound to, forms a five-membered ring, and where the ring attachment carbon atom and an adjacent carbon atom are double bonded and the carbon member of the chain adjacent to the carbon which is double bonded but not the ring attachment carbon is substituted with a methoxy group, it can be prepared from the corresponding alkyl halides of formula III which can be prepared from the corresponding alcohol of formula II (Maag, H.; Rydzewski, R. M. *J. Org. Chem.* 1992, 57, 5823-31.) using any conventional method of converting an alcohol to a halide.

If it is desired to produce the compound of formula V as a racemate where $R_3$ is an unbranched alkyl chain of 3 carbon atoms wherein the chain, in combination with the carbon atom it is bound to, forms a four-membered ring, and one carbon member of the chain is substituted with an oxo group, so that the carbon atom at the ring attachment is symmetrical substituted so as not to produce a chiral center, it can be prepared from the corresponding alkyl halides of formula III (Kabalka, G. W.; Yao, M.-L. *J. Org. Chem.* 2004, 69, 8280-8286; Kabalka, G. W.; Yao, M.-L. *Tetrahedron Lett.* 2003, 44, 1879-1881; Rammeloo, T.; Stevens, C. V.; De Kimpe, N. *J. Org. Chem.* 2002, 67, 6509-6513; Stevens, C.; De Kimpe, N. *J. Org. Chem.* 1996, 61, 2174-2178).

If it is desired to produce the compound of formula V, as a mixture of diastereomers, where $R_3$ is an unbranched alkyl chain of 3 carbon atoms wherein the chain, in combination with the carbon atom it is bound to, forms a four-membered ring, and one carbon member of the chain is substituted with an oxo group, so that the carbon atom at the ring attachment is unsymmetrically substituted so as to produce a chiral center, it can be prepared from the corresponding alkyl halides of formula III (Wasserman, H. H.; Hearn, M. J.; Cochoy, R. E. *J. Org. Chem.* 1980, 45, 2874-2880; Wasserman, H. H. *Angew. Chem. Int. Ed.* 1972, 11, 332; Wasserman, H. H.; Cochoy, R. E.; Baird, M. S. *J. Am. Chem. Soc.* 1969, 91, 2375-2376; Hudkins, R. L.; Reddy, D.; Singh, J.; Stripathy, R.; Underiner, T. L. In PCT Int. Appl.; (Cephalon, Inc., USA). WO 2000047583 A1 20000817; Bon, R. S.; Van Vliet, B.; Sprenkels, N. E.; Schmitz, R. F.; De Kanter, F. J. J.; Stevens, C. V.; Swart, M.; Bickelhaupt, F. M.; Groen, M. B.; Orru, R. V. A. *J. Org. Chem.* 2005, 70, 3542-3553).

If it is desired to produce the compound of formula V, as a mixture of diastereomers, where $R_3$ is an unbranched alkyl chain of 3 carbon atoms wherein the chain, in combination with the carbon atom it is bound to, forms a four-membered ring, and one carbon member of the chain is substituted with an oxo group, so that the carbon atom at the ring attachment is unsymmetrically substituted so as to produce a chiral center of the S configuration, the corresponding alkyl halide of formula III can be prepared from the corresponding alcohol of formula II which in turn can be prepared from the known protected alcohol derivative (Narasaka, K.; Kusama, H.; Hayashi, Y. *Bull. Chem. Soc. Japan.* 1991, 64, 1471-1478.) using any conventional method of converting a protected alcohol to an alcohol and any conventional method of converting an alcohol to a halide, respectively.

If it is desired to produce the compound of formula V, as a mixture of diastereomers, where $R_3$ is an unbranched alkyl chain of 3 carbon atoms wherein the chain, in combination with the carbon atom it is bound to, forms a four-membered ring, and one carbon member of the chain is substituted with an oxo group, so that the carbon atom at the ring attachment is unsymmetrically substituted so as to produce a chiral center of the R configuration, the corresponding alkyl halide of formula III can be prepared from the corresponding alcohol of formula II which in turn can be prepared from the known alcohol protected derivative (Sato, M.; Ohuchi, H. e; Abe, Y.; Kaneko, C. *Tetrahedron: Asymmetry* 1992, 3, 3313-328) using any conventional methods of converting a alcohol protected to an alcohol and any conventional method of converting an alcohol to a halide, respectively.

If it is desired to produce the compound of formula V, as a mixture of diastereomers, where $R_3$ is an unbranched heteroalkyl chain of 4 carbon atoms plus one nitrogen atom, which is unsubstituted, and the carbon adjacent to the nitrogen atom is substituted with an oxo group wherein the chain, in combination with the carbon atom it is bound to, forms a five-membered lactam ring and the carbon atom at the ring attachment is in the 5 position of the lactam and is unsymmetrically substituted so as to produce a chiral center of S configuration, the corresponding alkyl halides of formula III can be prepared from the corresponding alcohol of formula II (Kigoshi, H.; Hayashi, N.; Uemura, D. *Tetrahedron Lett.* 2001, 42, 7469-7471; Bunch, L.; Norrby, P.-O.; Frydenvang, K.; Krogsgaard-Larsen, P.; Madsen, U. *Organic Letters* 2001, 3, 433-435; Altmann, K. H. *Tetrahedron Lett.* 1993, 34, 7721-4.) using any conventional method of converting an alcohol to a halide. If it is desired to produce said compounds in which the nitrogen atom is substituted with an alkyl group, any conventional method of alkylating a lactam (Hanessian, S.; Yun, H.; Hou, Y.; Tintelnot-Blomley, M. *J. Org. Chem.* 2005, 70, 6746-6756; Yeo, H.; Li, Y.; Fu, L.; Zhu, J.-L.; Gullen, E. A.; Dutschman, G. E.; Lee, Y.; Chung, R.; Huang, E.-S.; Austin, D. J.; Cheng, Y.-C. *J. Med. Chem.* 2005, 48, 534-546; Oku, T.; Arita, Y.; Tsuneki, H.; Ikariya, T. *J. Am. Chem. Soc.* 2004, 126, 7368-7377; Oku, T.; Ikariya, T. *Angewandte Chemie, International Edition* 2002, 41, 3476-3479; Shi, T.; Rabenstein, D. L. *Bioorg. Med. Chem. Lett.* 2002, 12, 2237-2240; Gemma, S.; Campiani, G.; Butini, S.; Morelli, E.; Minetti, P.; Tinti, O.; Nacci, V. *Tetrahedron* 2002, 58, 3689-3692; Xu, Q.; Borremans, F.; Devreese, B. *Tetrahedron Lett.* 2001, 42, 7261-7263; Stamatiou, G.; Kolocouris, A.; Kolocouris, N.; Fytas, G.; Foscolos, G. B.; Neyts, J.; De Clercq, E. *Bioorg. Med. Chem. Lett.* 2001, 11, 2137-2142; Santos, P. F.; Almeida, P. S.; Lobo, A. M.; Prabhakar, S. *Heterocycles* 2001, 55, 1029-1043; Oda, K.; Meyers, A. I. *Tetrahedron Lett.* 2000, 41, 8193-8197; Mahboobi, S.; Popp, A.; Burgemeister, T.; Schollmeyer, D. *Tetrahedron: Asymmetry* 1998, 9, 2369-2376; Fache, F.; Jacquot, L.; Lemaire, M. *Tetrahedron Lett.* 1994, 35, 3313-14; Takano, S.; Sato, T.; Inomata, K.; Ogasawara, K. *Heterocycles* 1990, 31, 411-14; Tahara, T.; Hayano, K.; Murakami, S.; Fukuda, T.; Setoguchi, M.; Ikeda, K.; Marubayashi, N. *Chemical & Pharmaceutical Bulletin* 1990, 38, 1609-15; Pathak, T.; Thomas, N. F.; Akhtar, M.; Gani, D. *Tetrahedron* 1990, 46, 1733-44.) can be employed.

If it is desired to produce the compound of formula V, as a mixture of diastereomers, where $R_3$ is an unbranched heteroalkyl chain of 4 carbon atoms plus one nitrogen atom, which is unsubstituted, and the carbon adjacent to the nitrogen atom is substituted with an oxo group wherein the chain, in combination with the carbon atom it is bound to, forms a five-membered lactam ring and the carbon atom at the ring attachment is in the 4 position of the lactam and is unsymmetrically substituted so as to produce an asymmetric center, it can be prepared from the corresponding racemic alkyl halides of formula III (Dooley, D. J.; Taylor, C. P.; Thorpe, A. J.; Wustrow, D. J. US 2004186177; Dooley, D. J.; Taylor, C. P., Jr.; Thorpe, A. J.; Wustrow, D. J. WO 2004054566; Dooley, D. J.; Wustrow, D. J. WO 2003063845; Belliotti, T. R.; Bryans, J. S.; Ekhato, I. V.; Osuma, A. T.; Schelkun, R. M.; Schwarz, R. D.; Thorpe, A. J.; Wise, L. D.; Wustrow, D. J.; Yuen, P.-W. WO 2000076958; Peng, Z.-Y. *Zhongguo Yiyao Gongye Zazhi* 1999, 30, 387; Ikeda, M.; Teranishi, H.; Nozaki, K.; Ishibashi, H. *J. Chem. Soc., Perkin Trans.* 1 1998, 1691-1698; Lehr, E.; Bechtel, W. D.; Schuster, A. DE 3706399; Weber, K. H.; Walther, G.; Schneider, C.; Hinzen, D.; Kuhn, F. J.; Lehr, E. U.S. Pat. No. 4,767,759; Lehr, E.; Bechtel, W. D.; Boeke-Kuhn, K.; Schneider, C.; Walther, G.; Weber, K. H. DE 3634220; Mori, M.; Kanda, N.; Oda, I.; Ban, Y. *Tetrahedron* 1985, 41, 5465-74; Weber, K. H.; Walther, G.; Schneider, C.; Hinzen, D.; Kuhn, F. J.; Lehr, E. DE 3336024; Mori, M.; Oda, I.; Ban, Y. *Tetrahedron Lett.* 1982, 23, 5315-18.) If it is desired to produce said compounds in which the nitrogen atom is substituted with an alkyl group, any conventional method of alkylating a lactam (Hanessian, S.; Yun, H.; Hou, Y.; Tintelnot-Blomley, M. *J. Org. Chem.* 2005, 70, 6746-6756; Yeo, H.; Li, Y.; Fu, L.; Zhu, J.-L.; Gullen, E. A.; Dutschman, G. E.; Lee, Y.; Chung, R.; Huang, E.-S.; Austin, D. J.; Cheng, Y.-C. *J. Med. Chem.* 2005, 48, 534-546; Oku, T.; Arita, Y.; Tsuneki, H.; Ikariya, T. *J. Am. Chem. Soc.* 2004, 126, 7368-7377; Oku, T.; Ikariya, T. *Angewandte Chemie, International Edition* 2002, 41, 3476-3479; Shi, T.; Rabenstein, D. L. *Bioorg. Med. Chem. Lett.* 2002, 12, 2237-2240; Gemma, S.; Campiani, G.; Butini, S.; Morelli, E.; Minetti, P.; Tinti, O.; Nacci, V. *Tetrahedron* 2002, 58, 3689-3692; Xu, Q.; Borremans, F.; Devreese, B. *Tetrahedron Lett.* 2001, 42, 7261-7263; Stamatiou, G.; Kolocouris, A.; Kolocouris, N.; Fytas, G.; Foscolos, G. B.; Neyts, J.; De Clercq, E. *Bioorg. Med. Chem. Lett.* 2001, 11, 2137-2142; Santos, P. F.; Almeida, P. S.; Lobo, A. M.; Prabhakar, S. *Heterocycles* 2001, 55, 1029-1043; Oda, K.; Meyers, A. I. *Tetrahedron Lett.* 2000, 41, 8193-8197; Mahboobi, S.; Popp, A.; Burgemeister, T.; Schollmeyer, D. *Tetrahedron: Asymmetry* 1998, 9, 2369-2376; Fache, F.; Jacquot, L.; Lemaire, M. *Tetrahedron Lett.* 1994, 35, 3313-14; Takano, S.; Sato, T.; Inomata, K.; Ogasawara, K. *Heterocycles* 1990, 31, 411-14; Tahara, T.; Hayano, K.; Murakami, S.; Fukuda, T.; Setoguchi, M.; Ikeda, K.; Marubayashi, N. *Chemical & Pharmaceutical Bulletin* 1990, 38, 1609-15; Pathak, T.; Thomas, N. F.; Akhtar, M.; Gani, D. *Tetrahedron* 1990, 46, 1733-44) can be employed.

If it is desired to produce the compound of formula V, as a mixture of diastereomers, where $R_3$ is an unbranched heteroalkyl chain of 4 carbon atoms plus one nitrogen atom, which is unsubstituted, and the carbon adjacent to the nitrogen atom is substituted with an oxo group wherein the chain, in combination with the carbon atom it is bound to, forms a five-membered lactam ring and the carbon atom at the ring attachment is in the 3 position of the lactam and is unsymmetrically substituted so as to produce an asymmetric center, it can be prepared from the corresponding racemic alkyl halides of formula III (Jiang, B.; Wang, Y. Cn 544452; Jiang, B.; Wang, Y. Cn 1544451; Jiang, B.; Wang, Y. Cn 1544450; Siriwardana, A. I.; Kamada, M.; Nakamura, I.; Yamamoto, Y. *J. Org. Chem.* 2005, 70, 5932-5937.) If it is desired to produce said compounds in which the nitrogen atom is substituted with an alkyl group, any conventional method of alkylating a lactam (Hanessian, S.; Yun, H.; Hou, Y.; Tintelnot-Blomley, M. *J. Org. Chem.* 2005, 70, 6746-6756; Yeo, H.; Li, Y.; Fu, L.; Zhu, J.-L.; Gullen, E. A.; Dutschman, G. E.; Lee, Y.; Chung, R.; Huang, E.-S.; Austin, D. J.; Cheng, Y.-C. *J. Med. Chem.* 2005, 48, 534-546; Oku, T.; Arita, Y.; Tsuneki, H.; Ikariya, T. *J. Am. Chem. Soc.* 2004, 126, 7368-7377; Oku, T.; Ikariya, T. *Angewandte Chemie, International Edition* 2002, 41, 3476-3479; Shi, T.; Rabenstein, D. L. *Bioorg. Med. Chem. Lett.* 2002, 12, 2237-2240; Gemma, S.; Campiani, G.; Butini, S.; Morelli, E.; Minetti, P.; Tinti, O.; Nacci, V. *Tetrahedron* 2002, 58, 3689-3692; Xu, Q.; Borremans, F.; Devreese, B. *Tetrahedron Lett.* 2001, 42, 7261-7263; Stamatiou, G.; Kolocouris, A.; Kolocouris, N.; Fytas, G.; Foscolos, G. B.; Neyts, J.; De Clercq, E. *Bioorg. Med. Chem. Lett.* 2001, 11, 2137-2142; Santos, P. F.; Almeida, P. S.; Lobo, A. M.; Prabhakar, S. *Heterocycles* 2001, 55, 1029-1043; Oda, K.; Meyers, A. I. *Tetrahedron Lett.* 2000, 41, 8193-8197; Mahboobi, S.; Popp, A.; Burgemeister, T.; Schollmeyer, D. *Tetrahedron: Asymmetry* 1998, 9, 2369-2376; Fache, F.; Jacquot, L.; Lemaire, M. *Tetrahedron Lett.* 1994, 35, 3313-14; Takano, S.; Sato, T.; Inomata, K.; Ogasawara, K. *Heterocycles* 1990, 31, 411-14; Tahara, T.; Hayano, K.; Murakami, S.; Fukuda, T.; Setoguchi, M.; Ikeda, K.; Marubayashi, N. *Chemical & Pharmaceutical Bulletin* 1990, 38, 1609-15; Pathak, T.; Thomas, N. F.; Akhtar, M.; Gani, D. *Tetrahedron* 1990, 46, 1733-44.) can be employed.

If it is desired to produce the compound of formula V, as a mixture of diastereomers, where $R_3$ is an unbranched heteroalkyl chain of 5 carbon atoms plus one nitrogen atom, which is unsubstituted, and the carbon adjacent to the nitrogen atom is substituted with an oxo group wherein the chain, in combination with the carbon atom it is bound to, forms a six-membered lactam ring and the carbon atom at the ring attachment is in the 3 position of the lactam and is unsymmetrically substituted so as to produce an asymmetric center, the corresponding racemic alkyl halides of formula III can be prepared from the corresponding racemic alcohol of formula II (Bridger, G.; Skerlj, R.; Kaller, A.; Harwig, C.; Bogucki, D.; Wilson, T. R.; Crawford, J.; McEachern, E. J.; Atsma, B.; Nan, S.; Zhou, Y.; Schols, D.; Smith, C. D.; Di, F. R. M. WO 2002022600; Yang, J.; Cohn, S. T.; Romo, D. *Organics Letters* 2000, 2, 763-766; Klutchko, S.; Hoefle, M. L.; Smith, R. D.; Essenburg, A. D.; Parker, R. B.; Nemeth, V. L.; Ryan, M.; Dugan, D. H.; Kaplan, H. R. *J. Med. Chem.* 1981, 24, 104-9; Matsumoto, I.; Yoshizawa, J. JP 48086876; Horii, Z.; Morikawa, K.; Ninomiya, I. *Chemical & Pharmaceutical Bulletin* 1969, 17, 2230-9.) using any conventional method of converting an alcohol to a halide. If it is desired to produce said compounds in which the nitrogen atom is substituted with an alkyl group, any conventional method of alkylating a lactam (Hanessian, S.; Yun, H.; Hou, Y.; Tintelnot-Blomley, M. *J. Org. Chem.* 2005, 70, 6746-6756; Yeo, H.; Li, Y.; Fu, L.; Zhu, J.-L.; Gullen, E. A.; Dutschman, G. E.; Lee, Y.; Chung, R.; Huang, E.-S.; Austin, D. J.; Cheng, Y.-C. *J. Med. Chem.* 2005, 48, 534-546; Oku, T.; Arita, Y.; Tsuneki, H.; Ikariya, T. *J. Am. Chem. Soc.* 2004, 126, 7368-7377; Oku, T.; Ikariya, T. *Angewandte Chemie, International Edition* 2002, 41, 3476-3479; Shi, T.; Rabenstein, D. L. *Bioorg. Med. Chem. Lett.* 2002, 12, 2237-2240; Gemma, S.; Campiani, G.; Butini, S.; Morelli, E.; Minetti, P.; Tinti, O.; Nacci, V. *Tetrahedron* 2002, 58, 3689-3692; Xu, Q.; Borremans, F.; Devreese, B. *Tetrahedron Lett.* 2001, 42, 7261-7263; Stamatiou, G.; Kolocouris, A.; Kolocouris, N.; Fytas, G.; Foscolos, G. B.; Neyts, J.; De Clercq, E. *Bioorg. Med. Chem. Lett.* 2001, 11, 2137-2142; Santos, P. F.; Almeida, P. S.; Lobo, A. M.; Prabhakar, S. *Heterocycles* 2001, 55, 1029-1043; Oda, K.; Meyers, A. I. *Tetrahedron Lett.* 2000, 41, 8193-8197; Mahboobi, S.; Popp, A.; Burgemeister, T.; Schollmeyer, D. *Tetrahedron: Asymmetry* 1998, 9, 2369-2376; Fache, F.; Jacquot, L.; Lemaire, M. *Tetrahedron Lett.* 1994, 35, 3313-14; Takano, S.; Sato, T.; Inomata, K.; Ogasawara, K. *Heterocycles* 1990, 31, 411-14; Tahara, T.; Hayano, K.; Murakami, S.; Fukuda, T.; Setoguchi, M.; Ikeda, K.; Marubayashi, N. *Chemical & Pharmaceutical Bulletin* 1990, 38, 1609-15; Pathak, T.; Thomas, N. F.; Akhtar, M.; Gani, D. *Tetrahedron* 1990, 46, 1733-44.) can be employed.

If it is desired to produce the compound of formula V, as a mixture of diastereomers, where $R_3$ is an unbranched heteroalkyl chain of 3 carbon atoms plus one oxygen atom and one nitrogen atom, which is unsubstituted, with one carbon atom between the nitrogen and oxygen atoms which is substituted with an oxo group wherein the chain, in combination with the carbon atom it is bound to, forms an oxazolidin-2-one ring and the carbon atom at the ring attachment is in the 4 position of the oxazolidin-2-one and is unsymmetrically substituted so as to produce a chiral center of S configuration, it can be prepared from the corresponding alkyl halides of formula III (Mahler, G.; Serra, G.; Manta, E. *Synth. Commun.* 2005, 35, 1481-1492.) If it is desired to produce said compounds in which the nitrogen atom is substituted with an alkyl group, any conventional method of alkylating an oxazolidin-2-one (Wang, X.; Widenhoefer, R. A. *Organometallics* 2004, 23, 1649-1651; Hollingsworth, R. I.; Wang, G.; Padmakumar, R.; Mao, J.; Zhang, H.; Dai, Z.; Puthuparampil, K; WO 2003106413; Tian, H.; She, X.; Yu, H.; Shu, L.; Shi, Y. *J. Org. Chem.* 2002, 67, 2435-2446; Rajadhyaksha, V. J. WO 9000407; Georgiev, V. S.; Acker, C. G.; Kinsolving, C. R. *Heterocycles* 1987, 26, 469-73; Georgiev, V. S.; Kinsolving, C. R. U.S. Pat. No. 4,600,782; Caroon, J. M.; Clark, R. D.; Kluge, A. F.; Nelson, J. T.; Strosberg, A. M.; Unger, S. H.; Michel, A. D.; Whiting, R. L. *J. Med. Chem.* 1981, 24, 1320-8; Coppola, G. M.; Hardtmann, G. E.; Koletar, G.; Kroin, S. *J. Heterocycl. Chem.* 1981, 18, 31-5; Jaiswal, R. K.; Parmar, S. S. *J Heterocycl. Chem.* 1978, 15, 519-21; Fujimoto, Y.; Suzuki, Y.; Tanaka, Y.; Tominaga, T.; Takeda, H.; Sekine, H.; Morito, N.; Miyaoka, Y. *Heterocycles* 1977, 6, 1604-9; Naumov, Y. A.; Zhelvakova, E. G.; Gudasheva, T. A.; Dremova, V. P.; Stepanova, A. A. *Khim. Geterotsikl. Soedin.* 1976, 768-71; Close, W. J. *J. Am. Chem. Soc.* 1951, 73, 95-8; Bergmann, E. D.; Sulzbacher, M. *J. Org. Chem.* 1951, 16, 84-9) can be employed.

If it is desired to produce single enantiomers of the compound of formula I of either the R or the S configuration at the carbon which is alkylated with compounds of formula III, these compounds can be seated by any conventional chemical or chromatographic means at any stage in the reaction sequence after which the chiral center has been introduced (i.e. after and including compounds of formula V). If it is desired to produce single diastereomers of the compound of formula I when such compounds have multiple chiral centers, these compounds can also be seated by any conventional chemical or chromatographic means at any stage in the reaction sequence after which a chiral center or centers have been introduced (i.e. after and including compounds of formula II). Among the preferred chemical means is to react the compound of formula X with an optically active base. Any conventional optically active base can be utilized to carry out this resolution. Among the preferred optically active bases are the optically active amine bases such as alpha-methylbenzylamine, quinine, dehydroabietylamine and alpha-methylnaphthylamine. Any of the conventional techniques utilized in resolving organic acids with optically active organic amine bases can be utilized in carrying out this reaction. Among the preferred methods of separation utilizes SFC chromatography on chiral supports such as Chiralcel OD, 250 mm×10.0 mm i.d., 5 µm or OJ, 250 mm×25 mm i.d., 5 µm preparative chiral HPLC columns.

In the resolution step, the compound of formula X is reacted with the optically active base in an inert organic solvent medium to produce salts of the optically active amine with both the R and S isomers of the compound of formula X. In the formation of these salts, temperatures and pressure are not critical and the salt formation can take place at room temperature and atmospheric pressure. The R and S salts can be seated by any conventional method such as fractional crystallization. After crystallization, each of the salts can be converted to the respective compounds of formula X in the R and S configuration by hydrolysis with an acid. Among the preferred acids are dilute aqueous acids, i.e., from about 0.001N to 2N aqueous acids, such as aqueous sulfuric or aqueous hydrochloric acid. The configuration of formula X which is produced by this method of resolution is carried out throughout the entire reaction scheme to produce the desired R or S isomer of formula I. The separation of R and S isomers can also be achieved using an enzymatic ester hydrolysis of any lower alkyl esters corresponding to the compound of the formula X (see for example, Ahmar, M.; Girard, C.; Bloch, R, *Tetrahedron Lett,* 1989, 7053), which results in the formation of corresponding chiral acid and chiral ester. The ester and the acid can be seated by any conventional method of seating an acid from an ester. The preferred method of resolution of racemates of the compounds of the formula X is via the formation of corresponding diastereomeric esters or amides. These diastereomeric esters or amides can be preparedly coupling the carboxylic acids of the formula X with a chiral alcohol or a chiral amine. This reaction can be carried out using any conventional method of coupling a carboxylic acid with an alcohol or an amine. The corresponding diastereomers of compounds of the formula X can then be seated using any conventional separation methods. The resulting pure diastereomeric esters or amides can then be hydrolyzed to yield the corresponding pure R or S isomers. The hydrolysis reaction can be carried out using conventional known methods to hydrolyze an ester or an amide without racemization. The preferred method of separation of racemates of the compounds of the formula X utilizes SFC chromatography on chiral supports such as Chiralcel OD, 250 mm×10.0 mm i.d., 5 µm or OJ, 250 mm×25 mm i.d., 5 µm preparative chiral HPLC columns.

If it is desired to produce the R isomer or the S isomer of the compounds of formula I, these compounds can be isolated as the desired isomers by conventional chemical means. The preferred chemical mean is the use of pseudoephedrine as a chiral auxiliary for the asymmetric alkylation of the phenylacetic acids of formula IV (*J. Am. Chem. Soc.* 1997, 119, 6496-6511). To form the desired R acids of the formula X, the compounds of formula IV as described above are first converted to the pseudoephedrine amides using 1R,2R-(−)-pseudoephedrine as the desired enantiomer of pseudoephedrine. Any conventional method for converting a carboxylic acid to a carboxamide can be utilized to effect this conversion. The pseudoephedrine amides of formula IV, where Y=pseudoephedrine, can undergo highly diastereoselective alkylations with alkyl halides to afford the α-substituted amide products of formula V, where Y=pseudoephedrine. These diastereomerically enriched amides can be converted to the enantiomerically enriched R carboxylic acids of formula X, where $R_1$, $R_2$ and $R_3$ are described as above, by conventional acidic hydrolysis methods for converting a carboxamide to a carboxylic acid. These R carboxylic acids of formula X, where, $R_1$, $R_2$ and $R_3$ are described as above, can be converted to the R isomers of formula I where $R_1$, $R_2$ and $R_3$ are described as above. In carrying out this reaction, any conventional method of condensing a primary amine with a carboxylic acid, without racemization, can be utilized to effect this conversion (see example 1 in Chen, S.; Corbett, W. L.; Guertin, K. R.; Haynes, N.-E.; Kester, R. F.; Mennona, F. A.; Mischke, S. G.; Qian, Y.; Sarabu, R.; Scott, N. R.; Thakkar, K. C. WO 2004052869).

The nitropyrazoles of formula VI can be preparedly methods described in Journal of Organic Chemistry (1971), 36(21), 3081-4, Journal of Organic Chemistry (1973), 38(10), 1777-82, and Organic Mass Spectrometry, 17, 7, 299 (1982).

The nitropyrazoles of formula VIII can be preparedly any conventional method for the alkylation, acylation, or sulfonylation of a pyrazole nitrogen with compounds of formula VII.

The nitropyrazoles of formula VIII, where R$_4$=phenyl or substituted phenyl can be preparedly methods described in Iida, T.; Satoh, H.; Maeda, K.; Yamamoto, Y.; Asakawa, K.-i.; Sawada, N.; Wada, T.; Kadowaki, C.; Itoh, T.; Mase, T.; Weissman, S. A.; Tschaen, D.; Krska, S.; Volante, R. P. *J. Org. Chem.* 2005, 70, 9222-9229; Mase, T.; Iida, T.; Kadowaki, C.; Kawasaki, M.; Asakawa, K.; Haga, Y. WO 2004037794; Jagerovic, N.; Cano, C.; Elguero, J.; Goya, P.; Callado, L. F.; Javier Meana, J.; Giron, R.; Abalo, R.; Ruiz, D.; Goicoechea, C.; Martin, M. I. *Bioorganic & Medicinal Chemistry* 2002, 10, 817-827; Tironi, C.; Fruttero, R.; Garrone, A. *Farmaco* 1990, 45, 473-8; Doria, G.; Passarotti, C.; Sala, R.; Magrini, R.; Sberze, P.; Tibolla, M.; Ceserani, R.; Castello, R; *Farmaco, Edizione Scientifica* 1986, 41, 417-29; Gorelik, M. V.; Titova, S. P.; Rybinov, V. I. *Zh. Org. Khim.* 1980, 16, 1322-8; Duffin, G. F.; Kendall, J. D. *Journal of the Chemical Society* 1954, 408-15.

The aminopyrazoles of formula IX can be preparedly any conventional method for reducing a nitro group to an amine.

3-Nitropyrazole can be converted to the compounds of formula VIII via alkylation, acylation, sulfonylation, tosylation, or epoxide opening with electrophiles VII such as alkyl halides, acid chlorides, sulfonyl chlorides, dialkyl carbonates, tosylates or epoxides. Any conventional method of alkylating a nitrogen atom with an electrophile can be utilized to effect this conversion. This conversion can also be accomplished utilizing an alcohol of formula VII, where X=OH under Mitsunobu conditions.

If it is desired to produce the compound of formula IX, where R$_4$ is SO$_2$R, and R is an alkyl chain, the compound of formula VI can be sulfonylated by any conventional method of sulfonylating a nitrogen atom with a sulfonyl chloride (Zhao, W.-G.; Li, Z.-M.; Yuan, P.-W.; Wang, W.-Y. *Chinese Journal of Chemistry* 2001,19, 184-188.) to give compounds of formula VIII. These compounds can then be converted to the corresponding alkylsulfonamides of formula IX by any conventional method of reducing a nitro substituent to an amino substituent.

If it is desired to produce the compound of formula IX, where R$_4$ is an alkyl chain bearing an alkyl sulfonyl group (—SO2R) the compound of formula VI can be alkylated with alkylthio electrophiles of formula VII to produce alkylsulfide compounds of formula VIII using any conventional method of alkylating a nitrogen atom with an electrophile. These compounds can then be converted to the corresponding alkylsulfones of formula VIII using any conventional method of oxidizing an alkylsulfide substituent to an alkylsulfone substituent. These compounds can then be converted to the compounds of formula IX using any conventional method of reducing a nitro substituent to an amino substituent.

If it is desired to produce the compound of formula IX-a, where R$_4$ is a but-2-yn-1-ol moiety, these compounds can be prepared starting from the compound of formula VI as described in reaction scheme 2:

Scheme 2

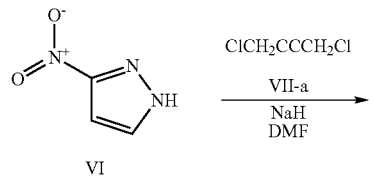

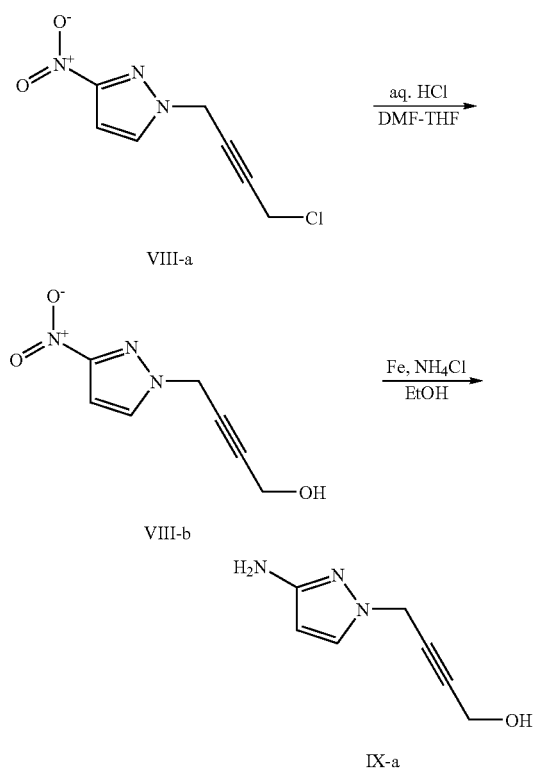

The compound of formula VI can be alkylated with compound VII-a, 1,4-dichloro-but-2-yne, to give compounds of formula VIII-a with a propargyl chloride substituent. Any conventional method for the alkylation of a nitrogen atom with an electrophile can be utilized to effect this conversion. The compound of formula VIII-a can be hydrolyzed to the alcohol compound of formula VIII-b by any conventional method for the hydrolysis of a propargyl halide to a propargyl alcohol. This compound can then be converted to the compound of formula IX-a using any conventional selective method of reducing a nitro substituent to an amino substituent (see for example Zhou, Y.-G.; Yang, P.-Y.; Han, X.-W. *Journal of Organic Chemistry* 2005, 70, 1679-1683.)

If it is desired to produce the compound of formula IX-b, where R$_4$ a Boc protected propargyl amine, these compounds can be prepared starting from the compound of formula VI as described in reaction scheme 3:

Scheme 3

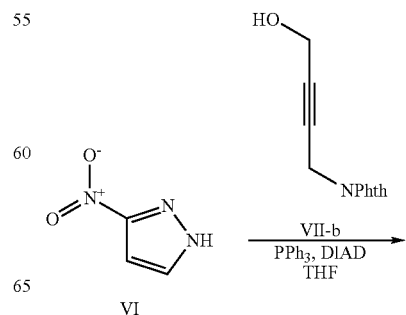

-continued

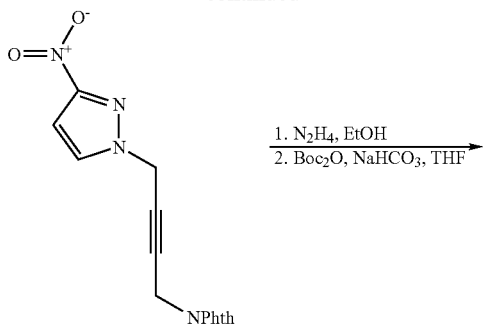

VII-c

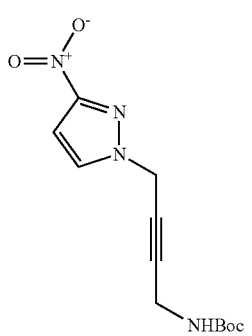

VII-d

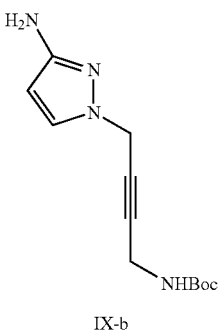

IX-b

The compound of formula VI can be alkylated with compound VII-b, (Thomson, D. W.; Commeureuc, A. G. J.; Berlin, S.; Murphy, J. A. *Synth. Commun.* 2003, 33, 3631-3641), to give compound of formula VIII-c with a phthalyl protected propargyl amino substituent under Mitsunobu conditions. The compound of formula VIII-c can be deprotected and then reprotected with a Boc group to give a compound of formula VIII-d by any conventional method for the deprotection of a phthalyl protected amine and the Boc protection of an amine. This compound can then be converted to the compound of formula IX-b using any conventional selective method of reducing a nitro substituent to an amino substituent (see for example Zhou, Y.-G.; Yang, P.-Y.; Han, X.-W. *Journal of Organic Chemistry* 2005, 70, 1679-1683.)

If it is desired to produce the compound of formula IX-c, where $R_4$ is an alkyl chain bearing a single terminal alcohol group protected as a TBDMS ether or a single terminal amino group protected with a BOC group, these compounds can be prepared starting from the compound of formula VI as described in reaction scheme 4:

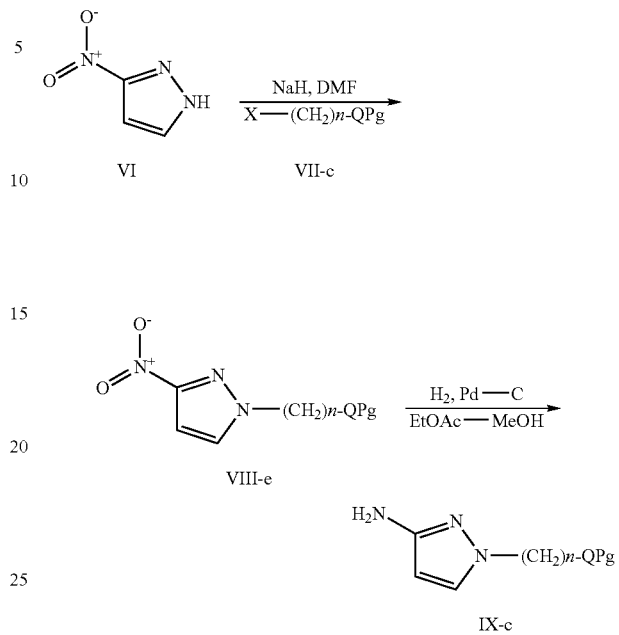

The compound of formula VI can be alkylated with TBDMS protected alkylhalo alcohols of the formula VII-c, (where QPg=OTBDMS, Gu, X.; Sun, M.; Gugiu, B.; Hazen, S.; Crabb, J. W.; Salomon, R. G. *J. Org. Chem.* 2003, 68, 3749-3761; Kerr, D. E.; Kissinger, L. F.; Shoyab, M. *J. Med. Chem.* 1990, 33, 1958-62; Rudisill, D. E.; Stille, J. K. *J. Org. Chem.* 1989, 54, 5856-66; Wilson, S. R.; Zucker, P. A. *J. Org. Chem.* 1988, 53, 4682-93), or alternatively with Boc protected alkyl amines of the formula VII-c (where QPg=NHBoc) which are commercially available, to give compounds of formula VIII-e by any conventional method of alkylating a nitrogen atom with an electrophile. The compounds of formula VIII-e can be converted to the compound of formula IX-c using any conventional method of reducing a nitro substituent to an amino substituent.

If it is desired to produce the compound of formula IX-d, where $R_4$ is a 3 carbon alkyl chain bearing a single terminal alcohol group and two terminal methyl groups this compound can be prepared starting from the compound of formula VI as described in reaction scheme 5:

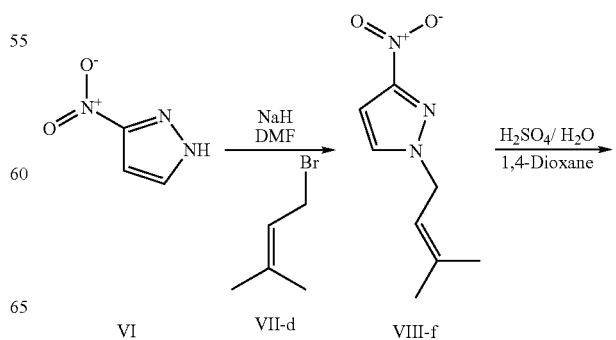

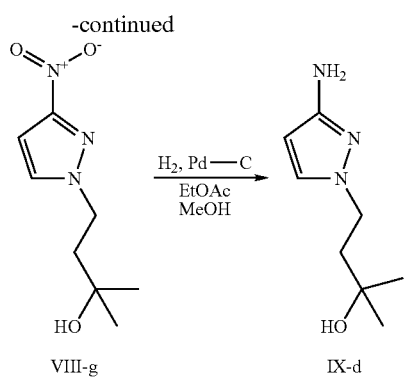

The compound of formula VI can be alkylated with a halide of the formula VII-d, (1-bromo-3-methyl-2-butene), to give compounds of formula VIII-f by any conventional method of alkylating a nitrogen atom with an electrophile. The compound of formula VIII-f can be converted to the compound of formula VIII-g by any conventional method of hydrating a double bond (Katayama, H.; Tachikawa, Y.; Takatsu, N.; Kato, A. *Chemical & Pharmaceutical Bulletin* 1983, 31, 2220-33; Occelli, E.; Fontanella, L.; Diena, A. *Farmaco, Edizione Scientifica* 1978, 33, 401-20; Tamaki, K.; Naitoh, N.; Nishimura, F.; Fujii, K. JP 52003067; Tamaki, K.; Naito, N.; Fujii, K. *Yuki Gosei Kagaku Kyokaishi* 1976, 34, 562-5). The compound of formula VIII-g can be converted to the compound of formula IX-d using any conventional method of reducing a nitro substituent to an amino substituent.

If it is desired to produce the compound of formula IX-e, where $R_4$ is a hydroxycyclopropyl methyl moiety, this compound can be prepared starting from the compound of formula VI as described in reaction scheme 6:

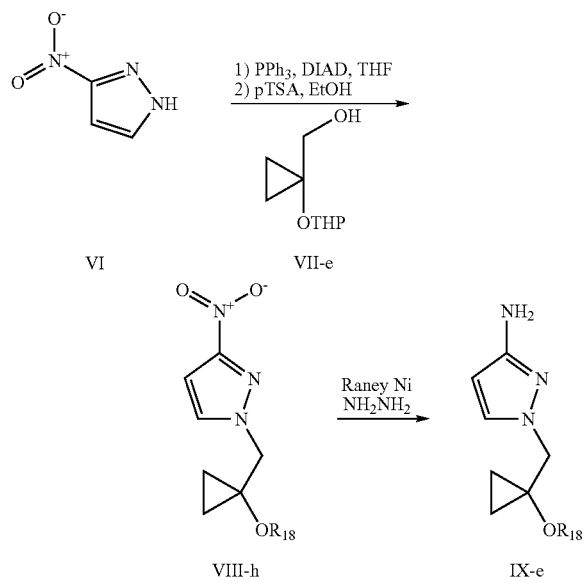

The compound of formula VI can be alkylated with 1-tetrahydropyranyloxycyclopropylcarbinol VII-e, (Ollivier, J.; Salaun, J. *Tetrahedron Lett.* 1984, 25, 1269-72; Salaun, J.; Almirantis, Y. *Tetrahedron* 1983, 39, 2421-8) under Mitsunobu conditions to give compounds of formula. The compound of formula VIII-h where $R_{18}$=THP can be converted to the compound of formula VIII-h where $R_{18}$=H by any conventional method of removing a THP protecting group from an alcohol. The compound of formula VIII-h where $R_{18}$=H can be converted to the compound of formula IX-e where R18=H, using any conventional selective method of reducing a nitro substituent to an amino substituent (see for example Barkoczy, J.; Ling, I.; Simig, G.; Szenasi, G.; Gigler, G.; Kertesz, S.; Szuecs, G.; Szabo, G.; Vegh, M.; H., Laszlo G. WO 2005012265.) If it is desired to produce the compound of formula IX-e, where $R_4$ is an alkoxycyclopropyl methyl moiety, the compound of formula VIII-h where $R_{18}$=H can be converted to the compound of formula VIII-h where $R_{18}$=alkyl using any conventional method of preparing an ether from an alcohol. The compound of formula VIII-h where $R_{18}$=alkyl can be converted to the compound of formula IX-e where $R_{18}$=alkyl, using any conventional selective method of reducing a nitro substituent to an amino substituent (see for example Barkoczy, J.; Ling, I.; Simig, G.; Szenasi, G.; Gigler, G.; Kertesz, S.; Szuecs, G.; Szabo, G.; Vegh, M.; H., Laszlo G. WO 2005012265.)

If it is desired to produce the compound of formula IX-f, where $R_4$ is a 2,3-dihydroxy-propyl moiety ($R_8$=$R_9$=H) or a 2,3-dihydroxy-3-methyl-butyl moiety ($R_8$=$R_9$=Me), as single enantiomers of either R or S configuration at the chiral alcohol carbon, these compounds can be prepared starting from the compound of formula VI as described in reaction scheme 7:

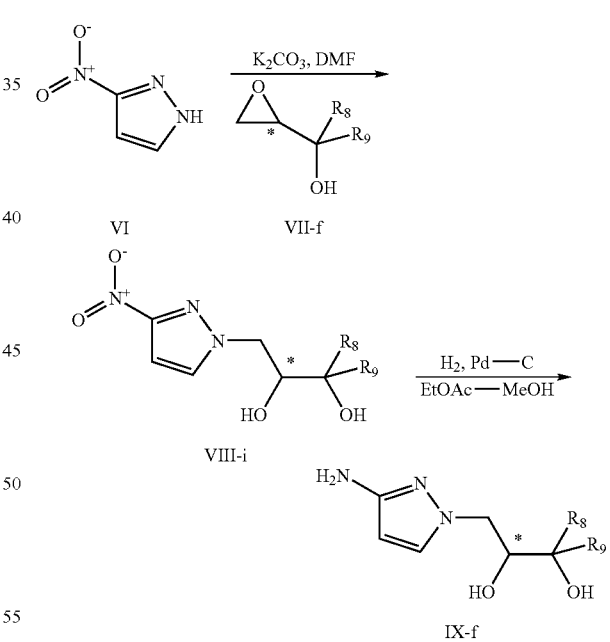

The compound of formula VI can be alkylated with either stereoisomer of glycidols VII-f ($R_8$=$R_9$=H: commerically available, $R_8$=$R_9$=Me R isomer: Takayama, H.; Ohmori, M.; Yamada, S. *Tetrahedron Lett.* 1980, 21, 5027-5028, $R_8$=$R_9$=Me S isomer: Dumont, R.; Pfander, H. *Helv. Chim. Acta* 1983, 66, 814-823) to give the corresponding chiral diols VIII-i ($R_8$=$R_9$=H, Me). The compounds of formula VIII-i ($R_8$=$R_9$=H, Me) can be converted to the compounds of formula IX-f using any conventional method of reducing a nitro substituent to an amino substituent.

If it is desired to produce the compound of formula IX-g, where $R_4$ is an alkyl chain containing a secondary alcohol at the beta carbon ($R_7$=OH, $R_8$=H, $R_9$=alkyl), as a single enantiomer of either R or S configuration at the secondary alcohol carbon, these compounds can be prepared starting from the compounds of formula VI as described in reaction scheme 8:

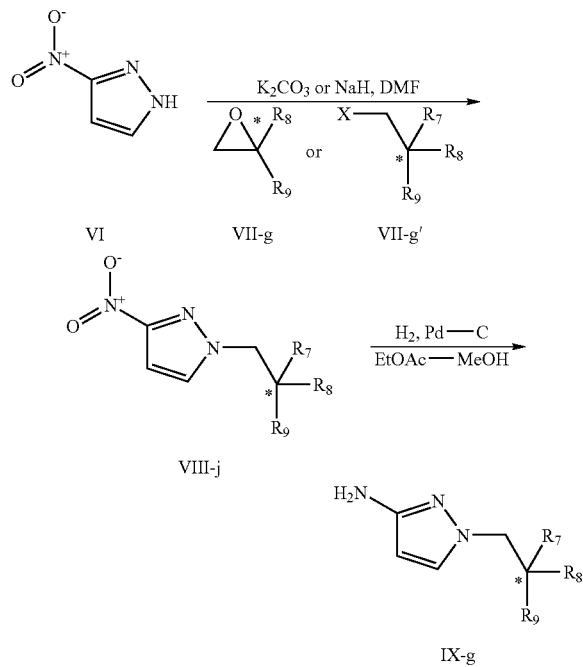

The compound of formula VI can be alkylated with either stereoisomer of epoxides of formula VII-g ($R_8$ or $R_9$=Me are commercially available, for example of chiral epoxide opening see Kotsuki, H.; Hayakawa, H.; Wakao, M.; Shimanouchi, T.; Ochi, M. *Tetrahedron: Asymmetry* 1995, 6, 2665-8; Ariza, X.; Garces, J.; Vilarrasa, J. *Tetrahedron Lett.* 1992, 33, 4069-72; Wigerinck, P.; Van Aerschot, A.; Janssen, G.; Claes, P.; Balzarini, J.; De Clercq, E.; Herdewijn, P. *J. Med. Chem.* 1990, 33, 868-73) to give the corresponding chiral alcohols of formula VIII-j where $R_8$ or $R_9$=alkyl and $R_7$=OH. The compounds of formula VIII-j where $R_8$ or $R_9$=alkyl and $R_7$=OH can be converted to the compounds of formula IX-g where $R_8$ or $R_9$=alkyl and $R_7$=OH using any conventional method of reducing a nitro substituent to an amino substituent. The compounds of formula VIII-j where $R_8$ or $R_9$=alkyl and $R_7$=OH can be converted to the compounds of formula VIII-j where $R_8$ or $R_9$=alkyl and $R_7$=Oalkyl by any conventional method of forming an ether from an alcohol. The compounds of formula VIII-j $R_8$ or $R_9$=alkyl and $R_7$=Oalkyl can be converted to the compounds of formula IX-g $R_8$ or $R_9$=alkyl and $R_7$=Oalkyl using any conventional method of reducing a nitro substituent to an amino substituent.

If it is desired to produce the compounds of formula IX-g, where $R_4$ is an alkyl chain containing a tertiary alcohol at the beta carbon, where $R_8$, $R_9$=alkyl, $R_7$=OH, these compounds can be prepared starting from the compound of formula VI as described in reaction scheme 8. The compound of formula VI can be alkylated with epoxides of formula VII-g, where $R_8$, $R_9$=alkyl, (Regel, E.; Buechel, K. H.; Reinecke, P.; Brandes, W. DE 3313073) to give the corresponding alcohols VIII-j, where $R_8$, $R_9$=alkyl, $R_7$=OH the compounds of formula VIII-j, where $R_8$, $R_9$=alkyl, $R_7$=OH can be converted to the compounds of formula IX-g, where $R_8$, $R_9$=alkyl, $R_7$=OH, using any conventional method of reducing a nitro substituent to an amino substituent.

If it is desired to produce the compounds of formula IX-g, where $R_4$ is a 3-hydroxy-oxetan-3-ylmethyl group ($R_8$, $R_9$=oxetane, $R_7$=OH), these compounds can be prepared starting from the compound of formula VI as described in reaction scheme 8. The compound of formula VI can be alkylated with epoxides of formula VII-g ($R_8$=$R_9$=OBn: Pedersen, D. S.; Boesen, T.; Eldrup, A. B.; Kiaer, B.; Madsen, C.; Henriksen, U.; Dahl, O *J. Chem. Soc. Perkin Trans.* 1 2001, 14, 1656-1661) to give the corresponding alcohols VIII-j, where $R_8$=$R_9$=OBn and $R_7$=OH. The compounds of formula VIII-j, where $R_8$=$R_9$=OBn and $R_7$=OH can be converted to the compounds of formula VIII-j, where $R_8$=$R_9$=OBn and $R_7$=OPG' (where PG' is an alcohol protecting group that will not be removed by hydrogenation) using any conventional method of orthogonally protecting an alcohol. The compounds of formula VIII-j, where $R_8$=$R_9$=OBn and $R_7$=OPG' can be converted to the compounds of formula VIII-j, where $R_8$=$R_9$=OH and $R_7$=OPG' using any conventional method of removing a benzyl group from an alcohol. The compounds of formula VIII-j, where $R_8$=$R_9$=OH and $R_7$=OPG' can be converted to the compounds of formula VIII-j, where $R_8$=$R_9$=oxetane and $R_7$=OPG' by tosylating both free hydroxyl groups and then treating with base (Kanoh, S.; Nishimura, T.; Naka, M.; Motoi, M. *Tetrahedron* 2002, 58, 7065-7074, Kurek-Tyrlik, A.; Wicha, J.; Zarecki, A.; Snatzke, G. *J. Org. Chem.* 1990, 55, 3484-92, Kawakami, Y.; Asai, T.; Umeyama, K.; Yamashita, Y. *J. Org. Chem.* 1982, 47, 3581-5.) The compounds of formula VIII-j, where $R_8$=$R_9$=oxetane and $R_7$=OPG' can be converted to the compounds of formula IX-g where $R_8$=$R_9$=oxetane and $R_7$=orthogonal protecting group, using any conventional method of reducing a nitro substituent to an amino substituent. The compounds of formula IX-g, where $R_8$=$R_9$=oxetane and $R_7$=OPG' can be converted to the compounds of formula IX-g where $R_8$=$R_9$=oxetane and $R_7$=OH using any conventional method of removing an alcohol protecting group. If it is desired to produce the compounds of formula IX-g, where $R_4$ is a 3-alkoxy-oxetan-3-ylmethyl group ($R_8$, $R_9$=oxetane, $R_7$=Oalkyl), the compounds of formula VIII-j, where $R_8$=$R_9$=OBn and $R_7$=OH can be converted to the compounds of formula VIII-j, where $R_8$=$R_9$=OBn and $R_7$=Oalkyl using any conventional method of alkylating an alcohol. The compounds of formula VIII-j, where $R_8$=$R_9$=OBn and $R_7$=Oalkyl can be converted to the compounds of formula VIII-j, where $R_8$=$R_9$=OH and $R_7$=Oalkyl using any conventional method of removing a benzyl group from an alcohol. The compounds of formula VIII-j, where $R_8$=$R_9$=OH and $R_7$=Oalkyl can be converted to the compounds of formula VIII-j, where $R_8$=$R_9$=oxetane and $R_7$=Oalkyl by tosylating both free hydroxyl groups and then treating with base (Kanoh, S.; Nishimura, T.; Naka, M.; Motoi, M. *Tetrahedron* 2002, 58, 7065-7074, Kurek-Tyrlik, A.; Wicha, J.; Zarecki, A.; Snatzke, G. *J. Org. Chem.* 1990, 55, 3484-92, Kawakami, Y.; Asai, T.; Umeyama, K.; Yamashita, Y. *J. Org. Chem.* 1982, 47, 3581-5.) The compounds of formula VIII-j, where $R_8$=$R_9$=oxetane and $R_7$=Oalkyl can be converted to the compounds of formula IX-g, where $R_8$=$R_9$=oxetane and $R_7$=Oalkyl using any conventional method of reducing a nitro substituent to an amino substituent. Alternatively, the compounds of formula VIII-j, where $R_8$=$R_9$=oxetane and $R_7$=OPG' can be converted to the compounds of formula VIII-j, where $R_8$=$R_9$=oxetane and $R_7$=OH by any conventional means of removing an alcohol protecting group. The compounds of formula VIII-j, where $R_8$=$R_9$=oxetane and $R_7$=OH can be converted to the compounds of formula VIII-j, where $R_8$=$R_9$=oxetane and $R_7$=Oalkyl by any conventional means of alkylating an alcohol. The compounds of formula VIII-j, where $R_8$=$R_9$=oxetane and $R_7$=Oalkyl can be converted to the compounds of formula IX-g, where $R_8$=$R_9$=oxetane and $R_7$=Oalkyl using any conventional method of reducing a nitro substituent to an amino substituent.

If it is desired to produce the compound of formula IX-g, where $R_4$ is an alkyl chain containing a primary alcohol at the gamma carbon, where $R_7$=CH$_2$OH, $R_8$, $R_9$=alkyl, these compounds can be prepared starting from the compounds of formula VI. The compound of formula VI can be alkylated with alkyl halides of formula VII-g', where $R_8$, $R_9$=alkyl, $R_7$=CH$_2$OH, and X=Br, to give the compound of formula VIII-j where $R_8$ or $R_9$=alkyl and $R_7$=CH$_2$OH. The compounds of formula VIII-j where $R_8$ or $R_9$=alkyl and $R_7$=CH$_2$OH can be converted to the compounds of formula IX-g where $R_8$ or $R_9$=alkyl and $R_7$=CH$_2$OH using any conventional method of reducing a nitro substituent to an amino substituent. The compounds of formula VIII-j where $R_8$, $R_9$=alkyl and $R_7$=OH can be converted to the compounds of formula VIII-j where $R_8$, $R_9$=alkyl and $R_7$=CH$_2$Oalkyl by any conventional method of forming an ether from an alcohol. The compounds of formula VIII-j $R_8$, $R_9$=alkyl and $R_7$=CH$_2$Oalkyl can be converted to the compounds of formula IX-g $R_8$, $R_9$=alkyl and $R_7$=CH$_2$Oalkyl using any conventional method of reducing a nitro substituent to an amino substituent. If it is desired to produce the compound of formula IX-g, where $R_4$ is an alkyl chain containing a carboxylic acid ester at the beta carbon, where $R_7$=COOalkyl, $R_8$, $R_9$=alkyl, these compounds can be prepared starting from the compounds of formula VI. The compound of formula VI can be alkylated with alkyl halides of formula VII-g', where $R_8$, $R_9$=alkyl, $R_7$=COOalkyl, and X=Br, to give the compound of formula VIII-j where $R_8$ or $R_9$=alkyl and $R_7$=COOalkyl. The compounds of formula VIII-j where $R_8$ or $R_9$=alkyl and $R_7$=COOalkyl can be converted to the compounds of formula IX-g where $R_8$ or $R_9$=alkyl and $R_7$=COOalkyl using any conventional method of reducing a nitro substituent to an amino substituent. If it is desired to produce the compound of formula IX-g, where $R_4$ is an alkyl chain containing a carboxylic acid at the beta carbon, where $R_7$=COOH, $R_8$, $R_9$=alkyl, these compounds can be prepared starting from the compounds of formula VIII-j where $R_8$, $R_9$=alkyl and $R_7$=COOalkyl. The compounds of formula VIII-j where $R_8$, $R_9$=alkyl and $R_7$=COOalkyl can be converted to the compounds of formula VIII-j where $R_8$, $R_9$=alkyl and $R_7$=COOH by any conventional method of saponifying an ester. The compounds of formula VIII-j $R_8$, $R_9$=alkyl and $R_7$=COOH can be converted to the compounds of formula IX-g $R_8$, $R_9$=alkyl and $R_7$=COOH using any conventional method of reducing a nitro substituent to an amino substituent.

If it is desired to produce the compound of formula IX-h, where $R_4$ is an alkyl chain bearing a terminal carboxylic acid ester moiety, these compounds can be prepared starting from the compound of formula VI as described in reaction scheme 9:

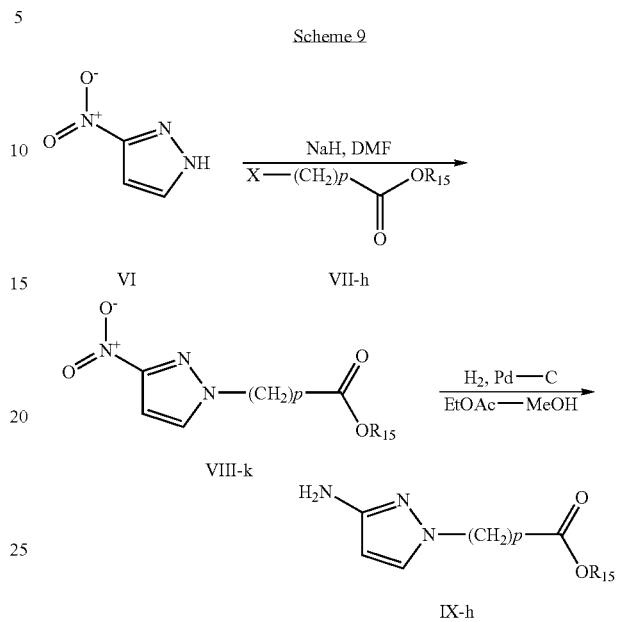

The compound of formula VI can be alkylated with ω-halo carboxylic acid esters VII-h, where $R_{15}$ is lower alkyl, to give the compound of formula VIII-k. The compound of formula VIII-k can be converted to the compound of formula IX-h using any conventional method of reducing a nitro substituent to an amino substituent.

If it is desired to produce the compound of formula IX-i as a racemate, where $R_4$ is a benzyl group bearing a meta or a carboxylic acid ester $R_{11}$=OMe and $R_{12}$ is an alkyl group, these compounds can be prepared starting from the compound of formula VI as described in reaction scheme 10:

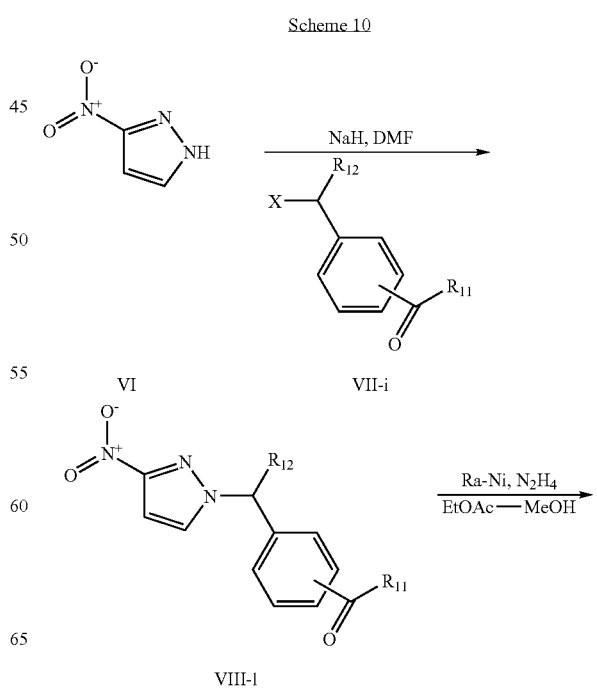

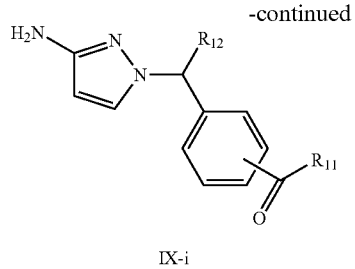

IX-i

The compound of formula VI can be alkylated with halomethyl-benzoic acid esters VII-i (Onishi, Y.; Ogawa, D.; Yasuda, M.; Baba, A. *J. Am. Chem. Soc.* 2002, 124, 13690-13691; Salerno, C. P.; Magde, D.; Patron, A. P. *J. Org. Chem.* 2000, 65, 3971-3981; Strehlke, P.; Bohlmann, R.; Henderson, D.; Nishino, J.; Schneider, M. DE 4014006) where $R_{12}$ is lower alkyl and $R_{11}$ is OMe, to give the compound of formula VIII-l, where $R_{12}$ is lower alkyl and $R_{11}$ is OMe. The compound of formula VIII-l where $R_{12}$ is lower alkyl and $R_{11}$ is OMe, can be converted to the compound of formula IX-i where $R_{12}$ s lower alkyl and $R_{11}$ is OMe using any conventional method of reducing a nitro substituent to an amino substituent.

If it is desired to produce the compound of formula IX-j, where $R_4$ is a benzyl group bearing a BOC protected meta amino group, this compound can be prepared starting from the compound of formula VI as described in reaction scheme 11:

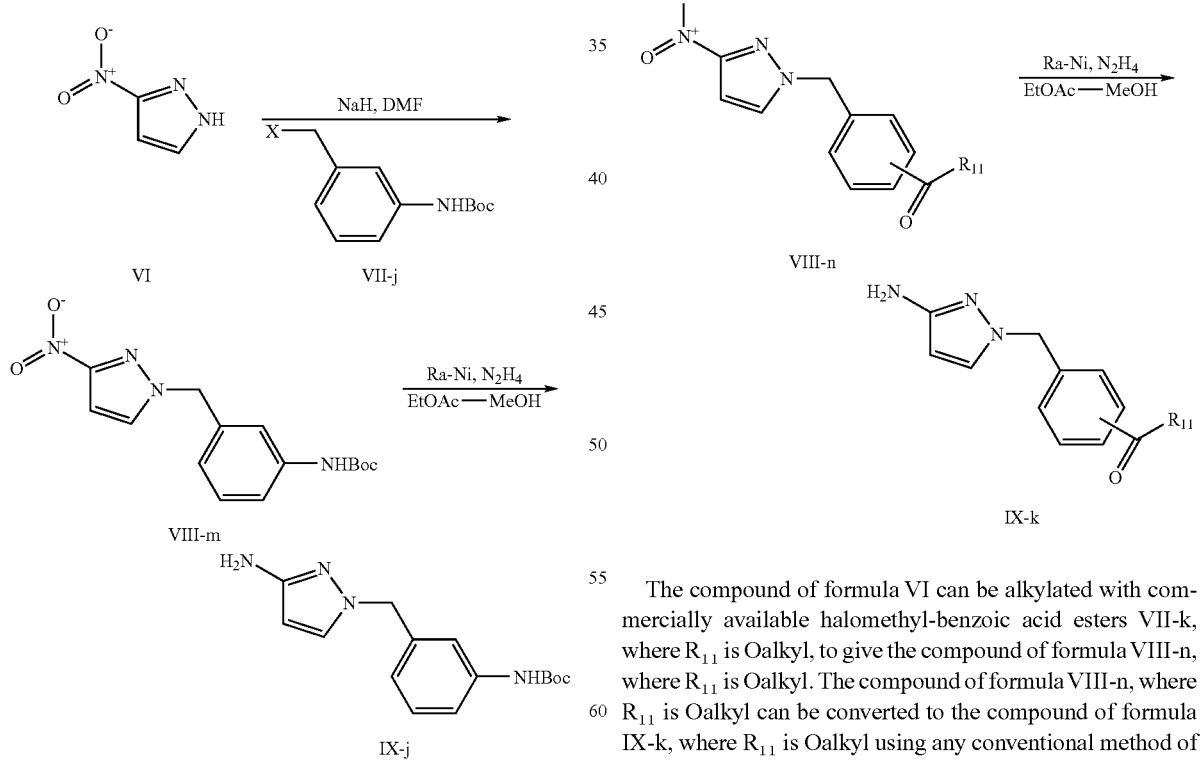

The compound of formula VI can be alkylated with (3-Bromomethyl-phenyl)-carbamic acid tert-butyl ester VII-j, (Brown, F. J.; Bernstein, P. R.; Cronk, L. A.; Dosset, D. L.; Hebbel, K. C.; Maduskuie, T. P., Jr.; Shapiro, H. S.; Vacek, E. P.; Yee, Y. K.; et al. *J. Med. Chem.* 1989, 32, 807-26), to give the compound of formula VIII-m. The compound of formula VIII-m can be converted to the compound of formula IX-j using any conventional method of reducing a nitro substituent to an amino substituent.

If it is desired to produce the compound of formula IX-k, where $R_4$ is a meta or a carboxylic acid ester, this compound can be prepared starting from the compound of formula VI as described in reaction scheme 12:

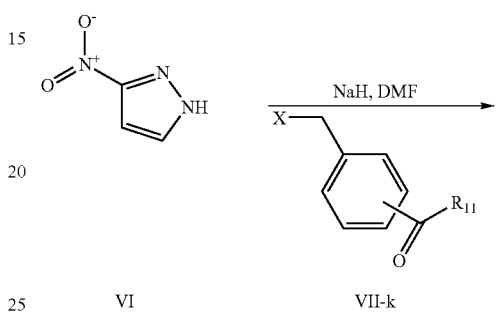

The compound of formula VI can be alkylated with commercially available halomethyl-benzoic acid esters VII-k, where $R_{11}$ is Oalkyl, to give the compound of formula VIII-n, where $R_{11}$ is Oalkyl. The compound of formula VIII-n, where $R_{11}$ is Oalkyl can be converted to the compound of formula IX-k, where $R_{11}$ is Oalkyl using any conventional method of reducing a nitro substituent to an amino substituent.

If it is desired to produce the compound of formula IX-l, where $R_4$ is trans-cyclohexanecarboxylic acid alkyl ester, this compound can be prepared starting from the compound of formula VI as described in reaction scheme 13:

Scheme 13

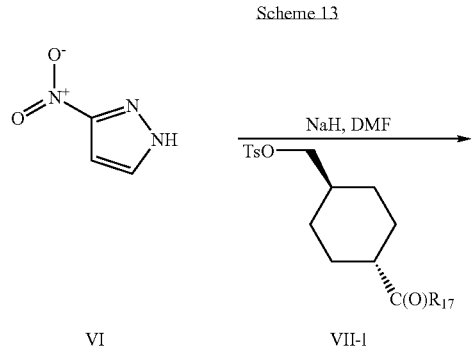

VI          VII-1

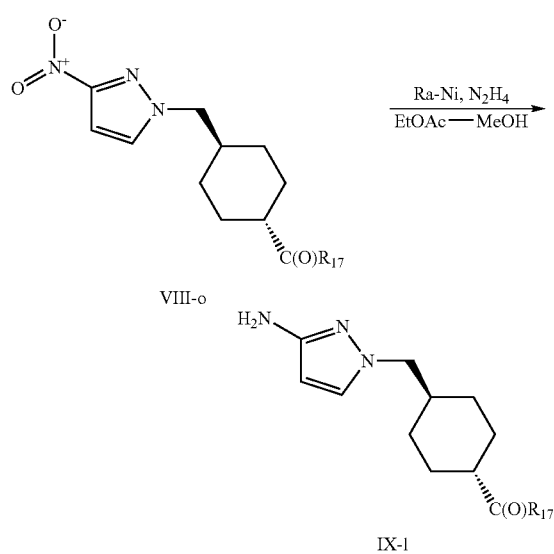

VIII-o

IX-1

The compound of formula VI can be alkylated with 4-(toluene-4-sulfonyloxymethyl)-cyclohexanecarboxylic acid alkyl esters VII-1, (Heckmann, B.; Jouquey, S.; Vevert, J.-P.; Zhang, J. WO 9717339; Didierlaurent, S.; Fortin, M.; Zhang, J. WO 9715570), where $R_{17}$ is lower alkoxy, to give the compound of formula VIII-o. The compound of formula VIII-o can be converted to the compound of formula IX-1 using any conventional method of reducing a nitro substituent to an amino substituent.

In the final steps of this Reaction Scheme 1, the compounds of formula X are condensed with the compounds of formula IX via conventional peptide coupling to produce the compounds of formula I. In carrying out this reaction, any conventional method of condensing a primary amine with a carboxylic acid can be utilized to effect this conversion. In some cases the compounds of formula I-x are formed as a protected intermediate of formula I, and a subsequent deprotection step is necessary to obtain the compound of formula I. Any conventional method of removing protecting groups such as BOC (Johnstone, C.; McKerrecher, D.; Pike, K. G.; Waring, M. J. WO 2005121110; Johnstone, C.; McKerrecher, D.; Pike, K. G. WO 2005080359) from amines, silyl protecting groups such as TBDMS from alcohols (Greene, T. W. *Protective Groups in Organic Synthesis*; John Wiley & Sons, Inc.: New York, 1991; p. 77) or saponifying carboxylic acid esters can be utilized for this transformation.

If it is desired to produce the compound of formula I, where $R_4$ is a carboxylic acid alkylamide, these compounds can be prepared from the compounds of formula I-x where $R_4$ is a hydrogen and an alkyl isocyanate. Any conventional method of reacting an alkyl isocyanate with an amine can be utilized to effect this conversion (Graubaum, H. *J. Prakt. Chem.* 1993; 33, 585-588).

If it is desired to produce the compound of formula I, where $R_4$ is an alkyl chain containing a diol moiety (i.e. 2,3-dihydroxy-3-methyl-butyl moiety), these compounds can be prepared from the compounds of formula I-x where $R_4$ is a group containing an alkene (i.e. 3-methyl-but-2-enyl) by using any conventional method to dihydroxylate an alkene which would result in racemic diols. If it is desired to produce chiral diols conventional Sharpless asymmetric dihydroxylation conditions with either $(DHQD)_2PHAL$ or $(DHQ)_2PHAL$ can be used to produce the chiral diols.

If it is desired to produce the compounds of formula I, where $R_4$ is an alkyl chain containing an oxygen heteroatom, these compounds can be prepared from the compounds of formula I-x where $R_4$ is an alkyl chain bearing a single terminal alcohol group and an electrophile. Any conventional method of forming an ether by treating an alcohol with an alkylating agent can be utilized to effect this conversion.

If it is desired to produce the compounds of formula I, where $R_4$ is an alkyl chain containing an ester linkage, these compounds can be prepared from the compounds of formula I-x where $R_4$ is an alkyl chain bearing a single terminal alcohol group and an electrophile. Any conventional method of forming an ester by treating an alcohol with an acid, acid chloride, acid anhydride agent or other activated acid equivalent can be utilized to effect this conversion.

If it is desired to produce the compounds of formula I, where $R_4$ is an alkyl chain bearing a terminal carboxylic acid amide, these compounds can be prepared from the compounds of formula I-x where $R_4$ is an alkyl chain bearing a terminal carboxylic acid. Any conventional method of condensing an amine with a carboxylic acid can be utilized to effect this conversion.

If it is desired to produce the compounds of formula I, where $R_4$ is a benzyl group bearing a meta or a carboxylic acid amide and $R_{12}$ is an alkyl group, as a mixture of R and S isomers at the benzylic carbon, these compounds can be prepared from the compounds of formula I-x where $R_4$ is a benzyl group bearing a meta or a carboxylic acid. Any conventional method of condensing an amine with a carboxylic acid can be utilized to effect this conversion.

If it is desired to produce the compounds of formula I, where $R_4$ is a benzyl group bearing a meta amide group, these compounds can be prepared from the compounds of formula I-x where $R_4$ is a benzyl group bearing a meta amino group. Any conventional method of condensing an amine with a carboxylic acid can be utilized to effect this conversion.

If it is desired to produce the compounds of formula I, where $R_4$ is a benzyl group bearing a meta sulfonamide group, these compounds can be prepared from the compounds of formula I-x where $R_4$ is a benzyl group bearing a meta amino group. Any conventional method of condensing an amine with a sulfonyl chloride can be utilized to effect this conversion.

If it is desired to produce the compounds of formula I, where $R_4$ is a benzyl group bearing a meta or a carboxylic acid amide, these compounds can be prepared from the compounds of formula I-x where $R_4$ is a benzyl group bearing a meta or a carboxylic acid. Any conventional method of condensing an amine with a carboxylic acid can be utilized to effect this conversion.

The present invention will be better understood from the following examples, which are for purposes of illustration and are not intended to limit the invention defined in the claims which follow thereafter.

Unless otherwise stated all reactions were run with anhydrous solvents under an inert atmosphere using dry glassware.

EXAMPLES

Example 1

3-[2(R)-(3-Chloro-4-methanesulfonyl-phenyl)-3-cyclopentyl-propionylamino]-1-methyl-pyrazole

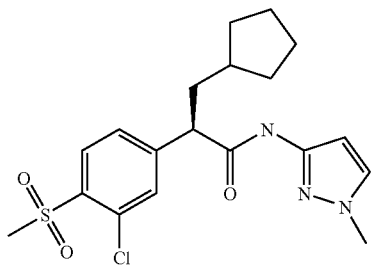

Triphenylphosphine (1.190 g, 4.54 mmol) was dissolved in methylene chloride (40 mL) and cooled to 0° C. To this solution was added N-bromosuccinimide (914 mg, 5.14 mmol) and was stirred at 0° C. until it was completely dissolved and became light purple in color. The 2(R)-(3-chloro-4-methanesulfonyl-phenyl)-3-cyclopentyl-propionic acid (prepared as in PCT WO 2004/052869 A1, Example 1, 1.00 g, 3.02 mmol) was then added and it was stirred at 0° C. for 20 min and then warmed to 25° C. and stirred for 30 min. After such time, 1-methyl-1H-pyrazol-3-ylamine (441 mg, 4.54 mmol) and pyridine (740 µL, 4.53 mmol) were added and it was stirred at 25° C. for 16 h. The reaction was then diluted with water (30 mL) and then extracted with methylene chloride (3×15 mL). The organic layers were then combined and dried over magnesium sulfate, filtered and concentrated in vacuo. Flash column chromatography (Merck silica gel 60, 40-63 µm; 50% ethyl acetate/hexanes) followed by reverse phase preparative HPLC purification (Column: Thomson C18 ODSA, 5 micron, 50×21.2 mm ID; 30% acetonitrile/water to 100% acetonitrile/water; 30 mL/min flow rate for 15 min run) afforded 3-[2(R)-(3-chloro-4-methanesulfonyl-phenyl)-3-cyclopentyl-propionylamino]-1-methyl-pyrazole (590 mg, 48%) as a white solid: ESI-LRMS m/e calcd for $C_{19}H_{24}ClN_3O_3S$ [M+] 409.1. found 410.1 [M+H+]; $^1$H NMR (400 MHz, $CDCl_3$) δ ppm 0.96-1.18 (m, 2H, $CH_2$), 1.35-1.86 (m, 8H, 4×$CH_2$), 2.10-2.21 (m, 1H, CH), 3.24 (s, 3H, $SO_2CH_3$), 3.57 (t, J=7.6 Hz, 1H, CH), 3.73 (s, 3H, $NCH_3$), 6.59 (d, J=2.3 Hz, 1H, Ar), 7.21 (d, J=2.3 Hz, 1H, Ar), 7.38 (dd, $J_o$=8.2, $J_m$=1.7 Hz, 1H, Ar), 7.50 (d, $J_m$=1.7 Hz, 1H, Ar), 7.96 (d, $J_o$=8.2 Hz, 1H, Ar), 8.82 (s, 1H, NH).

Example 2

2(R)-(3-Chloro-4-methanesulfonyl-phenyl)-3-cyclopentyl-N-(1H-pyrazol-3-yl)-propionamide

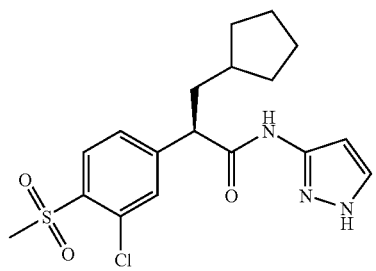

The 2(R)-(3-chloro-4-methanesulfonyl-phenyl)-3-cyclopentyl-propionic acid (prepared as in PCT WO 2004/052869 A1, Example 1, 100 mg, 0.30 mmol) was dissolved in chloroform (1 mL). To this solution was added a 2.0 M solution of oxalylchloride in methylene chloride (151 µL, 0.30 mmol) and N,N-dimethylformamide (23 µL, 0.30 mmol). The solution was allowed to stir for 1 h at 25° C., after which 1H-pyrazol-3-ylamine (25 mg, 0.30 mmol) was added along with 2,6-lutidine (70 µL, 0.60 mmol). The reaction was allowed to proceed for 40 h. The solvent was removed in vacuo and the crude material was purified by reverse phase preparative HPLC (Column: Thomson C18 ODSA, 5 micron, 50×21.2 mm ID; 30% acetonitrile/water to 100% acetonitrile/water; 30 mL/min flow rate for 15 min run) afforded 2(R)-(3-chloro-4-methanesulfonyl-phenyl)-3-cyclopentyl-N-(1H-pyrazol-3-yl)-propionamide (52 mg, 43%) as a white solid: ESI-LRMS m/e calcd for $C_{18}H_{22}ClN_3O_3S$ [M+] 395.1, found 396.1 [M+H+]; $^1$H NMR (400 MHz, $CDCl_3$) δ ppm 1.00-1.19 (m, 2H, $CH_2$), 1.34-1.91 (m, 8H, 4×$CH_2$), 2.08-2.29 (m, 1H, CH), 3.24 (s, 3H, $SO_2CH_3$), 3.65 (t, J=7.6 Hz, 1H, CH), 6.54 (d, 1H, J=1.7, Ar), 7.39 (m, 2H, Ar), 7.54 (d, $J_m$=1.3 Hz, 1H, Ar), 7.94 (d, $J_o$=8.2 Hz, 1H, Ar), 9.26 (s, 1H, NH).

Alternate Procedure:

1H-Pyrazol-3-ylamine (2.00 g, 24.10 mmol) was dissolved in 1,4-dioxane (60 mL), triethylamine (6.77 mL, 48.20 mmol) was added followed by the dropwise addition of di-tert-butyl dicarbonate (5.78 g, 26.50 mmol). The solution was stirred at 25° C. for 4 h. The solution was concentrated in vacuo, diluted with ethyl acetate (100 mL), washed with water (2×50 mL), saturated aqueous brine solution (2×50 mL), dried over magnesium sulfate, filtered and concentrated in vacuo. Flash column chromatography (Merck silica gel 60, 40-63 µm, 20% ethyl acetate/hexanes to 50% ethyl acetate/hexanes) afforded both regioisomers 5-amino-pyrazole-1-carboxylic acid tert-butyl ester (less polar product, 2.53 g, 57%) as a white solid; $H^1$-NMR (400 MHz, $CDCl_3$) δ 1.66 (9H, s), 5.10-5.45 (2H, bs), 5.39 (1H, d, J=2.0 Hz), 7.37 (1H, d, J=2.0 Hz); and 3-amino-pyrazole-1-carboxylic acid tert-butyl ester (760 mg, 17%) as a faintly yellow oil; $H^1$-NMR (400 MHz, $CDCl_3$) δ 1.62 (9H, s), 4.00-4.60 (2H, bs), 5.81 (1H, d, J=2.8 Hz), 7.82 (1H, d, J=2.8 Hz).

Triphenylphosphine (1.61 g, 6.15 mmol) was dissolved in methylene chloride (60 mL) and cooled to 0° C. To this solution was added N-bromosuccinimide (1.24 g, 6.97 mmol) and was stirred at 0° C. until it was completely dissolved and became light purple in color. The 2(R)-(3-chloro-4-methanesulfonyl-phenyl)-3-cyclopentyl-propionic acid (prepared as in PCT WO 2004/052869 A1, Example 1, 1.36 g, 4.1 mmol) was then added and it was stirred at 0° C. for 15 min and then warmed to 25° C. and stirred for another 30 min. The mixture was cooled to 0° C. and 3-amino-pyrazole-1-carboxylic acid tert-butyl ester (0.75 g, 4.1 mmol) was added followed by N-methyl-morpholine (540 μL, 4.92 mmol). The mixture was continued to stir at 0-4° C. for 4 h. The reaction was diluted with ethyl acetate (150 mL), washed with water (50 mL), aqueous 0.1 M hydrochloric acid (2×50 mL) and saturated aqueous brine solution (2×50 mL). The organic layer was dried over magnesium sulfate, filtered and concentrated in vacuo. Flash column chromatography (Merck silica gel 60, 40-63 μm; 5% ethyl acetate/hexanes to 25% ethyl acetate/hexanes) afforded 3-[2(R)-(3-chloro-4-methanesulfonyl-phenyl)-3-cyclopentyl-propionylamino]-pyrazole-1-carboxylic acid tert-butyl ester (2.02 g, 99%) as a light yellow oil: ESI-LRMS m/e calcd for $C_{23}H_{30}ClN_3O_5S$ [M+] 495.2, found 496.4 [M+H+], 395.5 [M–CO$_2$tBu+H+].

3-[2(R)-(3-Chloro-4-methanesulfonyl-phenyl)-3-cyclopentyl-propionylamino]-pyrazole-1-carboxylic acid tert-butyl ester (1.72 g, 3.47 mmol) was dissolved in methylene chloride (12 mL) and trifluoroacetic acid (4 mL) was added. The solution was stirred at 25° C. for 4 h. The mixture was concentrated in vacuo and the resulting oil was dissolved in ethyl acetate (25 mL), washed with saturated aqueous sodium bicarbonate solution (2×15 mL), saturated aqueous brine solution (2×15 mL), dried over magnesium sulfate, filtered and concentrated in vacuo to produce a yellow oil. Purification by ISCO flash column chromatography (Teledyne Isco RediSep Flash Column 120 g; 5% ethyl acetate/hexanes to 75% ethyl acetate/hexanes) afforded 2(R)-(3-chloro-4-methanesulfonyl-phenyl)-3-cyclopentyl-N-(1H-pyrazol-3-yl)-propionamide as a white foam (802 mg, 58%) ESI-LRMS m/e calcd for $C_{18}H_{22}ClN_3O_3S$ [M+] 395.1, found 396.0 [M+H+]; $^1$H NMR (400 MHz, CDCl$_3$) δ ppm 1.00-1.19 (m, 2H, CH$_2$), 1.34-1.91 (m, 8H, 4×CH$_2$), 2.08-2.29 (m, 1H, CH), 3.24 (s, 3H, SO$_2$CH$_3$), 3.65 (t, J=7.6 Hz, 1 H, CH), 6.54 (d, 1H, J=1.7, Ar), 7.39 (m, 2H, Ar), 7.54 (d, J$_m$=1.3 Hz, 1H, Ar), 7.94 (d, J$_o$=8.2 Hz, 1H, Ar), 9.26 (s, 1H, NH).

Example 3

{3-[2(R)-(3-Chloro-4-methanesulfonyl-phenyl)-3-cyclopentyl-propionylamino]-pyrazol-1-yl}-acetic acid

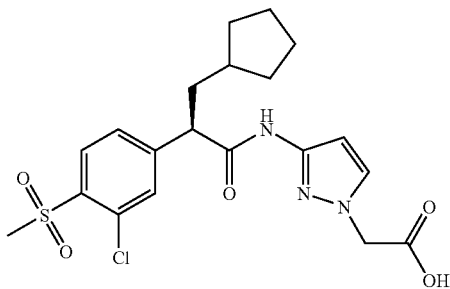

A solution of 1-nitro-1H-pyrazole (4.00 g, 35.4 mmol) in 40 mL of benzonitrile was refluxed for 2 h. After being cooled to 25° C., the mixture was poured into 160 mL of hexanes. A white solid precipitated which was filtered and dried in vacuo, to afford 3-nitro-1H-pyrazole (3.16 g, 79%). H$^1$-NMR (400 MHz, DMSO-d$_6$) δ: 7.01 (1H, d, J=2.4 Hz), 8.01 (d, 1H, J=3.4 Hz).

To a solution of 3-Nitro-1H-pyrazole (1.00 g, 8.84 mmol) in anhydrous N,N-dimethylformamide (20 mL), a 60% dispersion of sodium hydride in mineral oil (390 mg, 9.73 mmol) was added while stirring under nitrogen. After the effervescence ceased and the mixture was stirred for additional 1 h, tert-butyl-bromoacetate (1.44 mL, 9.73 mmol) was added. The mixture was continued to stir under nitrogen for an additional 2 h. The solvent was removed in vacuo and purification by ISCO flash column chromatography (Teledyne Isco RediSep Flash Column 40 g; 0% ethyl acetate/hexanes to 50% ethyl acetate/hexanes, 30 min) afforded (3-nitro-pyrazol-1-yl)-acetic acid tert-butyl ester (1.55 g, 77%) as a white powder. H$^1$-NMR (400 MHz, CDCl$_3$) δ: 1.42 (9H, s), 4.86 (2H, s), 6.87 (1H, d, J=2.4 Hz), 7.54 (1H, d, J=2.3 Hz).

To a solution containing (3-nitro-pyrazol-1-yl)-acetic acid tert-butyl ester (104 mg, 0.46 mmol) in methanol (3 mL), palladium, 10 wt. % on activated carbon, wet (~50 mg) was added to the solution. The vial was charged with hydrogen gas (via balloon) and the mixture was stirred for 16 h at 25° C. The mixture was passed through a plug of celite and concentrated in vacuo to give the desired (3-amino-pyrazol-1-yl)-acetic acid tert-butyl ester (80 mg, 89%) as a light blue oil: ESI-LRMS m/e calcd for $C_9H_{15}N_3O_2$ [M+] 197.1, found 395.2 [2M+H+].

Triphenylphosphine (1.66 g, 6.33 mmol) was dissolved in methylene chloride (40 mL) and cooled to 0° C. To this solution was added N-bromosuccinimide (1.27 g, 7.17 mmol) and was stirred at 0° C. until it was completely dissolved and became light purple in color. The 2(R)-(3-chloro-4-methanesulfonyl-phenyl)-3-cyclopentyl-propionic acid (prepared as in PCT WO 2004/052869 A1, Example 1, 1.40 g, 4.22 mmol) was then added and it was stirred at 0° C. for 20 min and then warmed to 25° C. and stirred for 30 min. After such time, (3-amino-pyrazol-1-yl)-acetic acid tert-butyl ester (833 mg, 4.22 mmol) and pyridine (1.03 mL, 6.33 mmol) were added and it was stirred at 25° C. for 16 h. The reaction was then diluted with water (30 mL) and then extracted with methylene chloride (3×15 mL). The organic layers were then combined and dried over magnesium sulfate, filtered and concentrated in vacuo. Flash column chromatography (Merck silica gel 60, 40-63 μm; 50% ethyl acetate/hexanes) followed by reverse phase preparative HPLC purification (Column: Thomson C18 ODSA, 5 micron, 50×21.2 mm ID; 30% acetonitrile/water to 100% acetonitrile/water; 30 mL/min flow rate for 15 min run) afforded {3-[2(R)-(3-chloro-4-methanesulfonyl-phenyl)-3-cyclopentyl-propionylamino]-pyrazol-1-yl}-acetic acid tert-butyl ester (1.20 g, 56%) as a white solid: ESI-LRMS m/e calcd for $C_{24}H_{32}ClN_3O_5S$ [M+] 509.2, found 510.1 [M+H+].

{3-[2(R)-(3-Chloro-4-methanesulfonyl-phenyl)-3-cyclopentyl-propionylamino]-pyrazol-1-yl}-acetic acid tert-butyl ester (95 mg, 0.19 mmol) was dissolved in 20% trifluoroacetic acid/methylene chloride (2 mL) and allowed to stir at 25° C. for 4 h, after which time the solvent was removed by blowing nitrogen into the reaction vessel. The crude material was purified by ISCO flash column chromatography (Teledyne Isco RediSep Flash Column 4 g; 0% ethyl acetate/hexanes to 75% ethyl acetate/hexanes), afforded {3-[2(R)-(3- chloro-4-methanesulfonyl-phenyl)-3-cyclopentyl-propionylamino]-pyrazol-1-yl}-acetic acid (67 mg, 79%) as a white powder: ESI-LRMS m/e calcd for $C_{20}H_{24}ClN_3O_5S$ [M+] 453.1, found 454.1 [M+H+]; $^1$H NMR (400 MHz, $CDCl_3$) δ ppm 1.03-1.24 (m, 2H, $CH_2$), 1.37-1.97 (m, 8H, 4×$CH_2$), 2.12-2.26 (m, 1H, CH), 3.26 (s, 3H, $SO_2CH_3$), 3.62 (t, J=7.5 Hz, 1H, CH), 4.72 (AB, $J_{gem}$=17.4 Hz, 2H, $NCH_2$), 6.82 (d, J=1.2, 1H, Ar), 7.39 (d, J=1.2, 1H, Ar), 7.43 (d, $J_o$=8.2 Hz, 1H, Ar), 7.58 (s, 1H, Ar), 8.01 (d, $J_o$=8.2 Hz, 1H, Ar), 9.82 (s, 1H, NH).

Example 4

2(R)-(3-Chloro-4-methanesulfonyl-phenyl)-3-cyclopentyl-N-(1-methylcarbamoylmethyl-1H-pyrazol-3-yl)-propionamide

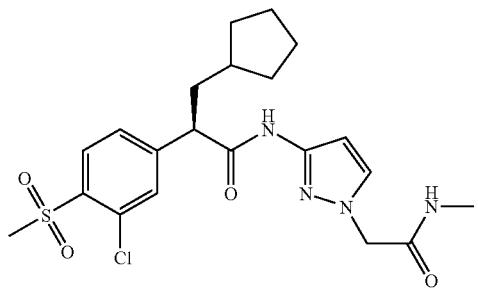

To a solution containing {3-[2(R)-(3-chloro-4-methanesulfonyl-phenyl)-3-cyclopentyl-propionylamino]-pyrazol-1-yl}-acetic acid (prepared in example 3, 100 mg, 0.22 mmol) in methylene chloride (2 mL), was then added a 2.0 M solution of oxalylchloride in methylene chloride (121 μL, 0.24 mmol) at 0° C. and allowed to stir at 25° C. for 1 h, after which time 2,6-lutidine (28 μL, 0.24 mmol) was added to the solution. After 1 h, a 2.0 M solution of methylamine in tetrahydrofuran (121 μL, 0.24 mmol) was added and the reaction was allowed to proceed for 16 h. The reaction solution was washed with saturated aqueous ammonium chloride solution, the organic phase was concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-(1-methylcarbamoylmethyl-1H-pyrazol-3-yl)-propionamide (28 mg, 28%) as a white solid: ESI-LRMS m/e calculated for $C_{21}H_{27}ClN_4O_4S$ [M+] 466.1, found 467.2 [M+H+]; $^1$H NMR (400 MHz, $CDCl_3$) δ ppm 1.03-1.24 (m, 2H, $CH_2$), 1.43-1.97 (m, 8H, 4×$CH_2$), 2.18-2.29 (m, 1H, CH), 2.78 (d, J=4.9 Hz, 3H, $NCH_3$), 3.27 (s, 3H, $SO_2CH_3$), 3.60 (t, J=7.5 Hz, 1H, CH), 4.67 (s, 2H, $NCH_2$), 5.83-5.91 (m, 1H, NH), 6.77 (d, J=2.4 Hz, 1H, Ar), 7.33 (d, J=2.4 Hz, 1H, Ar), 7.49 (dd, $J_o$=8.2, $J_m$=1.7 Hz, 1H, Ar), 7.62 (d, $J_m$=1.7 Hz, 1H, Ar), 8.06 (s, 1H, NH), 8.11 (d, $J_o$=8.2 Hz, 1H, Ar).

Example 5

2(R)-(3-Chloro-4-methanesulfonyl-phenyl)-3-cyclopentyl-N-(1-dimethylcarbamoylmethyl-1H-pyrazol-3-yl)-propionamide

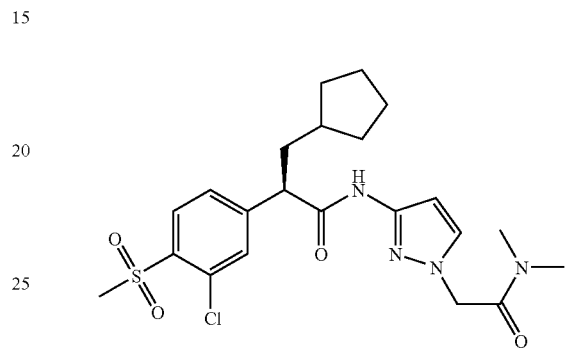

To a solution containing {3-[2(R)-(3-chloro-4-methanesulfonyl-phenyl)-3-cyclopentyl-propionylamino]-pyrazol-1-yl}-acetic acid (prepared in example 3, 100 mg, 0.22 mmol) in methylene chloride (2 mL), was then added a 2.0 M solution of oxalylchloride in methylene chloride (121 μL, 0.24 mmol) at 0° C. and allowed to stir at 25° C. for 1 h, after which time 2,6-lutidine (28 μL, 0.24 mmol) was added to the solution. After 1 h, dimethylamine hydrochloride (20 mg, 0.24 mmol) was added and the reaction was allowed to proceed for 16 h. The reaction solution was washed with saturated aqueous ammonium chloride solution, the organic phase was concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-(1-dimethylcarbamoylmethyl-1H-pyrazol-3-yl)-propionamide (64 mg, 60%) as a white solid: ESI-LRMS m/e calcd for $C_{22}H_{29}ClN_4O_4S$ [M+] 480.2, found 481.3 [M+H+]; $^1$H NMR (400 MHz, $CDCl_3$) δ ppm 1.02-1.22 (m, 2H, $CH_2$), 1.41-1.93 (m, 8H, 4×$CH_2$), 2.18-2.27 (m, 1H, CH), 2.97 (s, 3H, $NCH_3$), 3.03 (s, 3H, $NCH_3$), 3.26 (s, 3H, $SO_2CH_3$), 3.54 (t, J=7.5 Hz, 1H, CH), 4.81 (s, 2H, $NCH_2$), 6.71 (d, J=2.3 Hz, 1H, Ar), 7.34 (d, J=2.3 Hz, 1H, Ar), 7.43

(dd, $J_o$=8.2, $J_m$=1.8 Hz, 1H, Ar), 7.57 (d, $J_m$=1.8 Hz, 1H, Ar), 7.96 (s, 1H, NH), 8.06 (d, $J_o$=8.2 Hz, 1H, Ar).

Example 6

2(R)-(3-Chloro-4-methanesulfonyl-phenyl)-3-cyclopentyl-N-(1-diethylcarbamoylmethyl-1H-pyrazol-3-yl)-propionamide

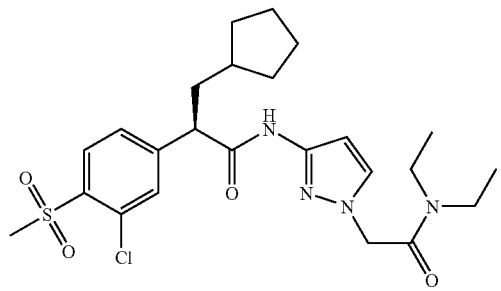

To a solution containing {3-[2(R)-(3-chloro-4-methanesulfonyl-phenyl)-3-cyclopentyl-propionylamino]-pyrazol-1-yl}-acetic acid (prepared in example 3, 100 mg, 0.22 mmol) in methylene chloride (2 mL), was then added a 2.0 M solution of oxalylchloride in methylene chloride (121 µL, 0.24 mmol) at 0° C. and allowed to stir at 25° C. for 1 h, after which time 2,6-lutidine (28 µL, 0.24 mmol) was added to the solution. After 1 h, diethylamine (25 µL, 0.24 mmol) was added and the reaction was allowed to proceed for 16 h. The reaction solution was washed with saturated aqueous ammonium chloride solution, the organic phase was concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-(1-diethylcarbamoylmethyl-1H-pyrazol-3-yl)-propionamide (66 mg, 59%) as a white solid: ESI-LRMS m/e calcd for $C_{24}H_{33}ClN_4O_4S$ [M$^+$] 508.19, found 509.3 [M+H$^+$]; $^1$H NMR (400 MHz, CDCl$_3$) δ ppm 1.08-1.18 (m, 5H, CH$_3$ and CH$_2$), 1.21 (t, J=7.2 Hz, 3H, CH$_3$), 1.43-1.94 (m, 8H, 4×CH$_2$), 2.18-2.27 (m, 1H, CH), 3.26 (s, 3H, SO$_2$CH$_3$), 3.33 (q, J=7.2 Hz, 2H, CH$_2$), 3.39 (q, J=7.2 Hz, 2H, CH$_2$), 3.54 (t, J=7.6 Hz, 1H, CH), 4.80 (s, 2H, NCH$_2$), 6.71 (d, J=2.4 Hz, 1H, Ar), 7.36 (d, J=2.4 Hz, 1H, Ar), 7.43 (dd, $J_o$=8.2, $J_m$=1.7 Hz, 1H, Ar), 7.57 (d, $J_m$=1.7 Hz, 1H, Ar), 7.93 (s, 1H, NH), 8.06 (d, $J_o$=8.2 Hz, 1H, Ar).

Example 7

2(R)-(3-Chloro-4-methanesulfonyl-phenyl)-3-cyclopentyl-N-[1-(2-morpholin-4-yl-2-oxo-ethyl)-1H-pyrazol-3-yl]-propionamide

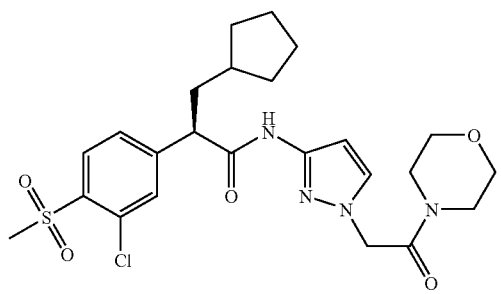

To a solution containing {3-[2(R)-(3-chloro-4-methanesulfonyl-phenyl)-3-cyclopentyl-propionylamino]-pyrazol-1-yl}-acetic acid (prepared in example 3, 100 mg, 0.22 mmol) in methylene chloride (2 mL), was then added a 2.0 M solution of oxalylchloride in methylene chloride (121 µL, 0.24 mmol) at 0° C. and allowed to stir at 25° C. for 1 h, after which time 2,6-lutidine (28 µL, 0.24 mmol) was added to the solution. After 1 h, morpholine (21 µL, 0.24 mmol) was added and the reaction was allowed to proceed for 16 h. The reaction solution was washed with saturated aqueous ammonium chloride solution, the organic phase was concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-[1-(2-morpholin-4-yl-2-oxo-ethyl)-1H-pyrazol-3-yl]-propionamide (71 mg, 62%) as a white solid: ESI-LRMS m/e calcd for $C_{24}H_{31}ClN_4O_5S$ [M$^+$] 522.17, found 523.4 [M+H$^+$]; $^1$H NMR (400 MHz, CDCl$_3$) δ ppm 1.05-1.18 (m, 2H, CH$_2$), 1.41-1.95 (m, 8H, 4×CH$_2$), 2.15-2.24 (m, 1H, CH), 3.26 (s, 3H, SO$_2$CH$_3$), 3.46 (m, 2H, NCH$_2$), 3.55 (t, J=7.5 Hz, 1H, CH),), 3.58-3.70 (m, 6H, 2×OCH$_2$ and NCH$_2$), 4.81 (s, 2H, NCH$_2$), 6.71 (m, 1H, Ar), 7.34 (m, 1H, Ar), 7.42 (m, 1H, Ar), 7.56 (m, 1H, Ar), 8.04 (d, J$_o$=8.1 Hz, 1H, Ar), 8.10 (s, 1H, NH).

Example 8

3-{3-[2(R)-(3-Chloro-4-methanesulfonyl-phenyl)-3-cyclopentyl-propionylamino]-pyrazol-1-yl}-propionic acid tert-butyl ester

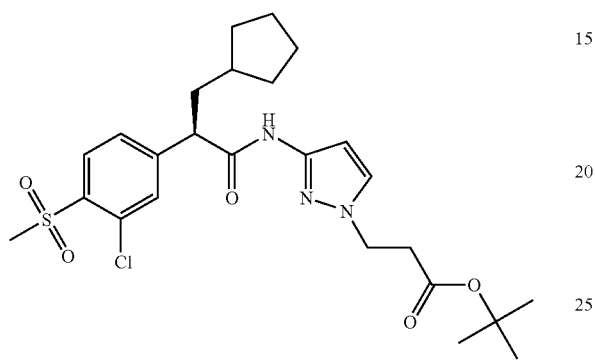

To a solution of 3-nitro-1H-pyrazole (prepared in example 3, 2.00 g, 17.70 mmol) in anhydrous N,N-dimethylformamide (30 mL), a 60% dispersion of sodium hydride in mineral oil (778 mg, 19.50 mmol) was added while stirring under nitrogen. After the effervescence ceased and the mixture was stirred for additional 30 min, 3-bromo-propionic acid tert-butyl ester (3.25 mL, 19.50 mmol) was added. The mixture was continued to stir under nitrogen for an additional 2 h. The solvent was removed in vacuo and purification by ISCO flash column chromatography (Teledyne Isco RediSep Flash Column 40 g; 2% methanol/methylene chloride to 5% methanol/methylene chloride) to afford (3-nitro-pyrazol-1-yl)-propionic acid tert-butyl ester (2.30 g, 57%) as a yellow oil.

To a solution containing (3-nitro-pyrazol-1-yl)-propionic acid tert-butyl ester (2.30 g, 9.53 mmol) in methanol (100 mL), palladium, 10 wt. % on activated carbon, wet (~300 mg) was added to the solution. The vial was charged with hydrogen gas (via balloon) and the mixture was stirred for 16 h at 25° C. The mixture was passed through a plug of celite and concentrated in vacuo to afford (3-amino-pyrazol-1-yl)-propionic acid tert-butyl ester (1.87 g, 93%) as a yellow oil which was used in the following step with no further purification.

To a solution containing 2(R)-(3-chloro-4-methanesulfonyl-phenyl)-3-cyclopentyl-propionic acid (prepared as in PCT WO 2004/052869 A1, Example 1, 2.66 g, 8.04 mmol) in methylene chloride (20 mL), a 2.0 M solution of oxalylchloride in methylene chloride (4.42 mL, 8.84 mmol) was added and allowed to stir for 1 h at 0° C. then for 1 h at 25° C. 2,6-lutidine (1.12 g, 10.0 mmol) was then added dropwise at 0° C., turning the solution light brown and resulting in effervescence. To this solution was added (3-amino-pyrazol-1-yl)-propionic acid tert-butyl ester (1.87 g, 8.84 mmol) dissolved in methylene chloride (5 mL). The reaction was allowed to proceed at 0° C. for 1 h and then overnight at 25° C. The reaction was washed with 1.0 M aqueous hydrochloric acid solution (20 mL) and the organic layer was dried with anhydrous sodium sulfate. The solvent was then removed in vacuo and was purified by ISCO flash column chromatography (Teledyne Isco RediSep Flash Column 120 g; 10% ethyl acetate/methylene chloride) to afford 3-{3-[2(R)-(3-chloro-4-methanesulfonyl-phenyl)-3-cyclopentyl-propionylamino]-pyrazol-1-yl}-propionic acid tert-butyl ester (3.06 g, 73%) as a white solid: ESI-LRMS m/e calcd for C$_{25}$H$_{34}$ClN$_3$O$_5$S [M$^+$] 523.2, found 524.4 [M+H$^+$]; $^1$H NMR (400 MHz, CDCl$_3$) δ ppm 1.03-1.20 (m, 2H, CH$_2$), 1.40 (s, 9H, 3×CH$_3$), 1.39-1.92 (m, 8H, 4×CH$_2$), 2.10-2.31 (m, 1H, CH), 2.70 (t, J=6.6 Hz, 2H, COCH$_2$), 3.25 (s, 3H, SO$_2$CH$_3$), 3.57 (t, J=7.6 Hz, 1H, CH), 4.21 (t, J=6.6 Hz, 2H, NCH2), 6.60 (d, J=2.3 Hz, 1H, Ar), 7.28 (d, J=2.3 Hz, 1H, Ar), 7.45 (dd, J$_o$=8.2, J$_m$=1.7 Hz. 1H, Ar), 7.58 (d, J$_m$=1.7 Hz, 1H, Ar), 8.06 (d, J$_o$=8.2 Hz, 1H, Ar), 8.17 (s, 1H, NH).

Example 9

3-{3-[2(R)-(3-Chloro-4-methanesulfonyl-phenyl)-3-cyclopentyl-propionylamino]-pyrazol-1-yl}-propionic acid

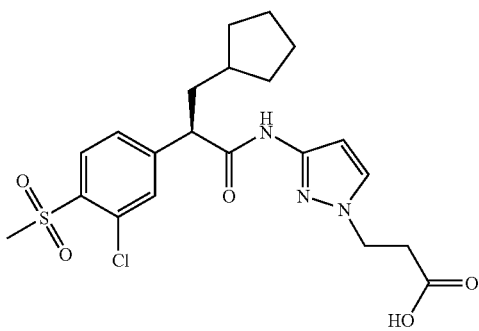

3-{3-[2(R)-(3-chloro-4-methanesulfonyl-phenyl)-3-cyclopentyl-propionylamino]-pyrazol-1-yl}-propionic acid tert-butyl ester (prepared in example 8, 3.00 g, 5.72 mmol) was dissolved in 20% trifluoroacetic acid/methylene chloride (100 mL) and stirred under reflux at 60° C. for 2 h, after which time the solvent was removed in vacuo. The crude material was the purified by ISCO flash column chromatography (Teledyne Isco RediSep Flash Column 120 g; 0% ethyl acetate/hexanes to 75% ethyl acetate/hexanes) to afford 3-{3-[2(R)-(3-chloro-4-methanesulfonyl-phenyl)-3-cyclopentyl-propionylamino]-pyrazol-1-yl}-propionic acid (2.60 g, 97%) as a white solid: ESI-LRMS m/e calcd for C$_{21}$H$_{26}$ClN$_3$O$_5$S [M$^+$] 509.18, found 510.0 [M+H$^+$], 1019.7 [2M+H$^+$]; $^1$H NMR (400 MHz, CDCl$_3$) δ ppm 1.06-1.23 (m, 2H, CH$_2$), 1.42-1.91 (m, 8H, 4×CH$_2$), 2.12-2.29 (m, 1H, CH), 2.83 (t, J=6.4 Hz, 2H, COCH$_2$), 3.25 (s, 3H, SO$_2$CH$_3$), 3.57 (t, J=7.5 Hz, 1H, CH), 4.36 (t, J=6.4 Hz, 2H, NCH2), 6.77 (d, J=2.5 Hz, 1H, Ar), 7.41 (d, J=2.5 Hz, 1 H, Ar), 7.48 (dd, J$_o$=8.1, $J_m$=1.5 Hz. 1H, Ar), 7.62 (d, $J_m$=1.5 Hz, 1H, Ar), 8.06 (d, $J_o$=8.1 Hz, 1H, Ar), 9.85 (br.s., 1H, $CO_2H$), 10.38 (s, 1H, NH).

Example 10

2(R)-(3-Chloro-4-methanesulfonyl-phenyl)-3-cyclopentyl-N-[1-(2-methylcarbamoyl-ethyl)-1H-pyrazol-3-yl]-propionamide

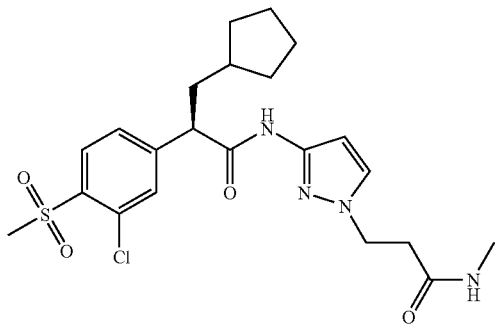

To a solution containing 3-{3-[2(R)-(3-chloro-4-methanesulfonyl-phenyl)-3-cyclopentyl-propionylamino]-pyrazol-1-yl}-propionic acid (prepared in example 9, 50 mg, 0.11 mmol) in methylene chloride (2 mL), was then added a 2.0 M solution of oxalylchloride in methylene chloride (59 μL, 0.12 mmol) at 0° C. and allowed to stir at 25° C. for 1 h, after which time 2,6-lutidine (17 μL, 0.14 mmol) was added to the solution at 0° C. After 1 h, a 2.0 M solution of methylamine in tetrahydrofuran (59 μL, 0.11 mmol) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-[1-(2-methylcarbamoyl-ethyl)-1H-pyrazol-3-yl]-propionamide (11 mg, 21%) as a white solid: ESI-LRMS m/e calcd for $C_{22}H_{29}ClN_4O_4S$ [$M^+$] 480.2, found 481.4 [$M+H^+$]; $^1H$ NMR (400 MHz, $CDCl_3$) δ ppm 1.09-1.20 (m, 2H, $CH_2$), 1.46-1.96 (m, 8H, 4×$CH_2$), 2.17-2.29 (m, 1H, CH), 2.62 (t, J=6.3 Hz, 2H, $COCH_2$), 2.75 (d, J=4.9 Hz, 3H, $CONCH_3$), 3.27 (s, 3H, $SO_2CH_3$), 3.55 (t, J=7.6 Hz, 1H, CH), 4.31 (t, J=6.3 Hz, 2H, $NCH_2$), 5.48 (brm, 1H, NH), 6.58 (d, J=2.3 Hz, 1H, Ar), 7.30 (d, J=2.3 Hz, 1 H, Ar), 7.46 (dd, $J_o$=8.2, $J_m$=1.6 Hz. 1H, Ar), 7.60 (d, $J_m$=1.6 Hz, 1H, Ar), 7.88 (s, 1 H, NH), 8.09 (d, $J_o$=8.2 Hz, 1H, Ar).

Example 11

2(R)-(3-Chloro-4-methanesulfonyl-phenyl)-3-cyclopentyl-N-[1-(2-propylcarbamoyl-ethyl)-1H-pyrazol-3-yl]-propionamide

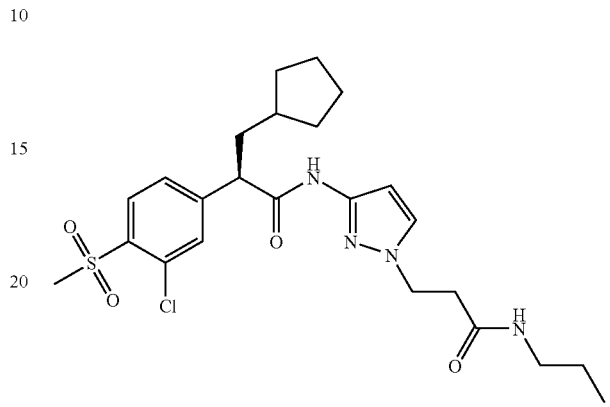

To a solution containing 3-{3-[2(R)-(3-chloro-4-methanesulfonyl-phenyl)-3-cyclopentyl-propionylamino]-pyrazol-1-yl}-propionic acid (prepared in example 9, 50 mg, 0.11 mmol) in methylene chloride (2 mL), was then added a 2.0 M solution of oxalylchloride in methylene chloride (59 μL, 0.12 mmol) at 0° C. and allowed to stir at 25° C. for 1 h, after which time 2,6-lutidine (12 μL, 0.14 mmol) was added to the solution at 0° C. After 1 h, propylamine (10 μL, 0.11 mmol) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-[1-(2-propylcarbamoyl-ethyl)-1H-pyrazol-3-yl]-propionamide (18 mg, 33%) as a white solid: ESI-LRMS m/e calcd for $C_{24}H_{33}ClN_4O_4S$ [$M^+$] 508.2, found 509.5 [$M+H^+$]; $^1H$ NMR (400 MHz, $CDCl_3$) δ ppm 0.84 (t, J=7.4 Hz, 3H, $CH_3$), 1.07-1.22 (m, 2H, $CH_2$), 1.36-1.96 (m, 10H, 5×$CH_2$), 2.18-2.30 (m, 1H, CH), 2.62 (t, J=6.4 Hz, 2H, $COCH_2$), 3.11-3.19 (m, 2H, $CONCH_2$), 3.27 (s, 3H, $SO_2CH_3$), 3.56 (t, J=7.6 Hz, 1H, CH), 4.30 (t, J=6.4 Hz, 2H, $NCH_2$), 5.49 (br.t., 1H, NH), 6.58 (d, J=2.3 Hz, 1H, Ar), 7.29 (d, J=2.3 Hz, 1H, Ar), 7.46 (dd, $J_o$=8.2, $J_m$=1.7 Hz. 1H, Ar), 7.59 (d, $J_m$=1.7 Hz, 1H, Ar), 7.93 (s, 1H, NH), 8.08 (d, $J_o$=8.2 Hz, 1H, Ar).

Example 12

2(R)-(3-Chloro-4-methanesulfonyl-phenyl)-3-cyclopentyl-N-[1-(2-dimethylcarbamoyl-ethyl)-1H-pyrazol-3-yl]-propionamide

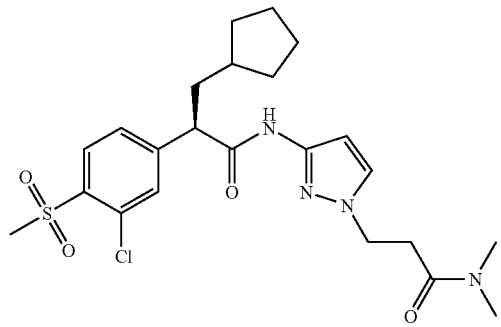

To a solution containing 3-{3-[2(R)-(3-chloro-4-methanesulfonyl-phenyl)-3-cyclopentyl-propionylamino]-pyrazol-1-yl}-propionic acid (prepared in example 9, 50 mg, 0.11 mmol) in methylene chloride (2 mL), was then added a 2.0 M solution of oxalylchloride in methylene chloride (59 μL, 0.12 mmol) at 0° C. and allowed to stir at 25° C. for 1 h, after which time 2,6-lutidine (17 μL, 0.14 mmol) was added to the solution at 0° C. After 1 h, dimethylamine hydrochloride (96 mg, 0.11 mmol) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-[1-(2-dimethylcarbamoyl-ethyl)-1H-pyrazol-3-yl]-propionamide (10 mg, 20%) as a white solid: ESI-LRMS m/e calcd for $C_{23}H_{31}ClN_4O_4S$ [M$^+$] 494.2, found 495.5 [M+H$^+$]; $^1$H NMR (400 MHz, CDCl$_3$) δ ppm 1.08-1.22 (m, 2H, CH$_2$), 1.43-1.95 (m, 8H, 4×CH$_2$), 2.16-2.31 (m, 1H, CH), 2.79 (t, J=6.6 Hz, 2H, COCH$_2$), 2.92 (s, 3H, NCH$_3$), 2.93 (s, 3H, NCH$_3$), 3.26 (s, 3H, SO$_2$CH$_3$), 3.54 (t, J=7.6 Hz, 1H, CH), 4.34 (t, J=6.6 Hz, 2H, NCH$_2$), 6.59 (d, J=2.3 Hz, 1H, Ar), 7.36 (d, J=2.3 Hz, 1H, Ar), 7.46 (dd, $J_o$=8.2, $J_m$=1.8 Hz. 1H, Ar), 7.59 (d, $J_m$=1.8 Hz, 1H, Ar), 7.82 (s, 1H, NH), 8.09 (d, $J_o$=8.2 Hz, 1H, Ar).

Example 13

2(R)-(3-Chloro-4-methanesulfonyl-phenyl)-3-cyclopentyl-N-[1-(3-morpholin-4-yl-3-oxo-propyl)-1H-pyrazol-3-yl]-propionamide To a solution containing 3-{3-[2(R)-(3-chloro-4-methanesulfonyl-phenyl)-3-cyclopentyl-propionylamino]-pyrazol-1-yl}-propionic acid (prepared in example 9, 50 mg, 0.11 mmol) in methylene chloride (2 mL), was then added a 2.0 M solution of oxalylchloride in methylene chloride (59 μL, 0.12 mmol) at 0° C. and allowed to stir at 25° C. for 1 h, after which time 2,6-lutidine (17 μL, 0.14 mmol) was added to the solution at 0° C. After 1 h, morpholine (10 μL, 0.11 mmol) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-[1-(3-morpholin-4-yl-3-oxo-propyl)-1H-pyrazol-3-yl]-propionamide (17 mg, 30%) as a white solid: ESI-LRMS m/e calcd for $C_{25}H_{33}ClN_4O_5S$ [M$^+$] 536.2, found 537.5 [M+H$^+$]; $^1$H NMR (400 MHz, CDCl$_3$) δ ppm 1.07-1.22 (m, 2H, CH$_2$), 1.44-1.93 (m, 8H, 4×CH$_2$), 2.12-2.30 (m, 1H, CH), 2.79 (t, J=6.6 Hz, 2H, COCH$_2$), 3.26 (s, 3H, SO$_2$CH$_3$), 3.31-3.41 (m, 2H, CH$_2$), 3.53 (t, J=7.6 Hz, 1H, CH), 3.55-3.66 (m, 6H, 3×CH$_2$), 4.35 (t, J=6.6 Hz, 2H, NCH$_2$), 6.60 (d, J=2.3 Hz, 1H, Ar), 7.35 (d, J=2.3 Hz, 1H, Ar), 7.45 (dd, $J_o$=8.2, $J_m$=1.7 Hz. 1H, Ar), 7.59 (d, $J_m$=1.7 Hz, 1H, Ar), 7.75 (s, 1H, NH), 8.09 (d, $J_o$=8.2 Hz, 1H, Ar).

Example 14

2(R)-(3-Chloro-4-methanesulfonyl-phenyl)-3-cyclopentyl-N-[1-(2-phenylcarbamoyl-ethyl)-1H-pyrazol-3-yl]-propionamide

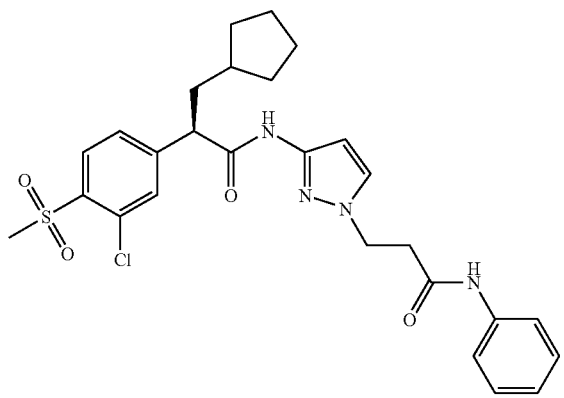

To a solution containing 3-{3-[2(R)-(3-chloro-4-methanesulfonyl-phenyl)-3-cyclopentyl-propionylamino]-pyrazol-1-yl}-propionic acid (prepared in example 9, 100 mg, 0.21 mmol) in methylene chloride (2 mL), was then added a 2.0 M solution of oxalylchloride in methylene chloride (118 μL, 0.24 mmol) at 0° C. and allowed to stir at 25° C. for 1 h, after which time 2,6-lutidine (28 μL, 0.24 mmol) was added to the solution at 0° C. After 1 h, aniline (21 μL, 0.21 mmol) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-[1-(2-phenylcarbamoyl-ethyl)-1H-pyrazol-3-yl]-propionamide was obtained (71 mg, 61%) as a white solid: ESI-LRMS m/e calcd for $C_{27}H_{31}ClN_4O_4S$ [M$^+$] 542.2, found 543.3 [M+H$^+$]; $^1$H NMR (400 MHz, CDCl$_3$) δ ppm 1.01-1.20 (m, 2H, CH$_2$), 1.40-1.88 (m, 8H, 4×CH$_2$), 2.11-2.26 (m, 1H, CH), 2.66-2.76 (m, 2H, COCH$_2$), 3.25 (s, 3H, SO$_2$CH$_3$), 3.64 (t, J=7.5 Hz, 1H, CH), 4.22-4.30 (m, 2H, NCH$_2$), 6.53 (d, J=2.2 Hz, 1H, Ar), 7.05 (t, J=7.4 Hz, 1H, Ar), 7.18-7.25 (m, 3H, Ar), 7.37 (d, $J_o$=7.8 Hz, 2H, Ar), 7.43 (dd, $J_o$=8.3, $J_m$=1.6 Hz. 1H, Ar), 7.58 (d, $J_m$=1.6 Hz, 1H, Ar), 7.88 (s, 1H, NH), 8.01 (d, $J_o$=8.3 Hz, 1H, Ar), 8.62 (s, 1H, NH).

Example 15

N-[1-(2-Benzylcarbamoyl-ethyl)-1H-pyrazol-3-yl]-2(R)-(3-chloro-4-methanesulfonyl-phenyl)-3-cyclopentyl-propionamide

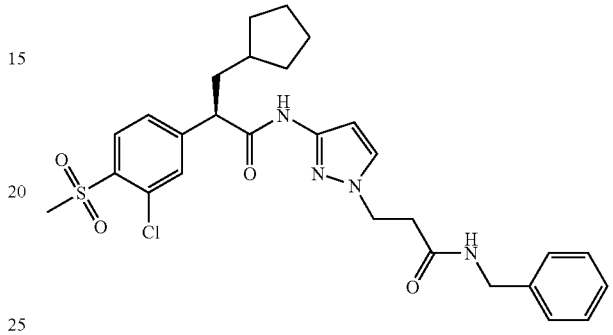

To a solution containing 3-{3-[2(R)-(3-chloro-4-methanesulfonyl-phenyl)-3-cyclopentyl-propionylamino]-pyrazol-1-yl}-propionic acid (prepared in example 9, 50 mg, 0.11 mmol) in methylene chloride (2 mL), was then added a 2.0 M solution of oxalylchloride in methylene chloride (59 μL, 0.12 mmol) at 0° C. and allowed to stir at 25° C. for 1 h, after which time 2,6-lutidine (17 μL, 0.15 mmol) was added to the solution at 0° C. After 1 h, benzylamine (12 μL, 0.11 mmol) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford N-[1-(2-benzylcarbamoyl-ethyl)-1H-pyrazol-3-yl]-2(R)-(3-chloro-4-methanesulfonyl-phenyl)-3-cyclopentyl-propionamide (19 mg, 32%) as a white solid: ESI-LRMS m/e calcd for $C_{28}H_{33}ClN_4O_4S$ [M$^+$] 556.2, found 557.4 [M+H$^+$]; $^1$H NMR (400 MHz, CDCl$_3$), δ ppm 1.04-1.22 (m, 2H, CH$_2$), 1.42-1.93 (m, 8H, 4×CH$_2$), 2.13-2.29 (m, 1H, CH), 2.67 (t, J=6.2 Hz, 2H, COCH$_2$), 3.25 (s, 3H, SO$_2$CH$_3$), 3.52 (t, J=7.6 Hz, 1H, CH), 4.31 (t, J=6.2 Hz, 2H, NCH$_2$), 4.36 (d, J=5.5 Hz, 2H, NCH$_2$Ar), 5.91 (t, J=5.5 Hz, 1H, NH), 6.60 (d, J=2.3 Hz, 1H, Ar), 7.06-7.13 (m, 2H, Ar), 7.21-7.26 (m, 3H, Ar), 7.28

(d, J=2.3 Hz, 1H, Ar), 7.44 (dd, $J_o$=8.2, $J_m$=1.7 Hz. 1H, Ar), 7.58 (d, $J_m$=1.7 Hz, 1 h, Ar), 8.67 (s, 1H, NH), 8.06 (d, $J_o$=8.2 Hz, 1H, Ar).

Example 16

2(R)-(3-Chloro-4-methanesulfonyl-phenyl)-3-cyclopentyl-N-{1-[2-(2-morpholin-4-yl-ethylcarbamoyl)-ethyl]-1H-pyrazol-3-yl}-propionamide

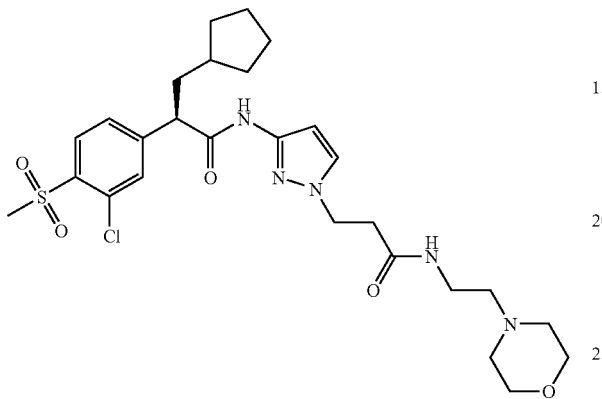

To a solution containing 3-{3-[2(R)-(3-chloro-4-methanesulfonyl-phenyl)-3-cyclopentyl-propionylamino]-pyrazol-1-yl}-propionic acid (prepared in example 9, 50 mg, 0.11 mmol) in methylene chloride (2 mL) was then added a 2.0 M solution of oxalylchloride in methylene chloride (59 μL, 0.12 mmol) at 0° C. and allowed to stir at 25° C. for 1 h, after which time 2,6-lutidine (17 μL, 0.14 mmol) was added to the solution at 0° C. After 1 h, 4-(2-aminoethyl) morpholine (15 μL, 0.11 mmol) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-{1-[2-(2-morpholin-4-yl-ethylcarbamoyl)-ethyl]-1H-pyrazol-3-yl}-propionamide (17 mg, 27%) as a white solid: ESI-LRMS m/e calcd for $C_{27}H_{38}ClN_5O_5S$ [M+] 579.2, found 580.3 [M+H+]; $^1$H NMR (400 MHz, CDCl$_3$) δ ppm 0.99-1.11 (m, 2H, CH$_2$), 1.37-1.85 (m, 8H, 4×CH$_2$), 2.05-2.18 (m, 1H, CH), 2.25-2.37 (m, 6H, 3×NCH$_2$), 2.57 (t, J=6.4 Hz, 2H, COCH$_2$), 3.18 (s, 3H, SO$_2$CH$_3$), 3.21 (q, J=5.4 Hz, 2H, CONCH$_2$), 3.47 (t, J=7.5 Hz, 1H, CH), 3.50-3.58 (m, 4H, 2×OCH$_2$), 4.23 (t, J=6.4 Hz, 2H, NCH$_2$), 5.94 (brm, 1, NH), 6.50 (d, J=2.3 Hz, 1H, Ar), 7.22 (d, J=2.3 Hz, 1H, Ar), 7.38 (dd, $J_o$=8.2, $J_m$=1.7 Hz. 1H, Ar), 7.51 (d, $J_m$=1.7 Hz, 1H, Ar), 7.84 (s, 1H, NH), 8.00 (d, $J_o$=8.2 Hz, 1H, Ar).

Example 17

2(R)-(3-Chloro-4-methanesulfonyl-phenyl)-3-cyclopentyl-N-{1-[2-(3-methoxy-propylcarbamoyl)-ethyl]-1H-pyrazol-3-yl}-propionamide

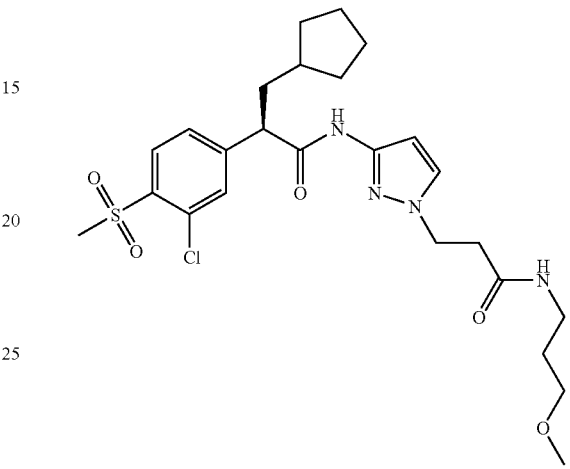

To a solution containing 3-{3-[2(R)-(3-chloro-4-methanesulfonyl-phenyl)-3-cyclopentyl-propionylamino]-pyrazol-1-yl}-propionic acid (prepared in example 9, 50 mg, 0.11 mmol) in methylene chloride (2 mL), was then added a 2.0 M solution of oxalylchloride in methylene chloride (59 μL, 0.12 mmol) at 0° C. and allowed to stir at 25° C. for 1 h, after which time 2,6-lutidine (17 μL, 0.14 mmol) was added to the solution at 0° C. After 1 h, 3-methyoxypropylamine (12 μL, 0.11 mmol) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-{1-[2-(3-methoxy-propylcarbamoyl)-ethyl]-1H-pyrazol-3-yl}-propionamide (16 mg, 27%) as a white solid: ESI-LRMS m/e calcd for $C_{25}H_{35}ClN_4O_5S$ [M+] 538.2, found 539.5 [M+H+]; $^1$H NMR (400 MHz, CDCl$_3$) δ ppm 1.08-1.21 (m, 2H, CH$_2$), 1.43-1.97 (m, 10H, 5×CH$_2$), 2.17-2.28 (m, 1H, CH), 2.61 (t, J=6.3 Hz, 2H, COCH$_2$), 3.26 (s, 3H, SO$_2$CH$_3$), 3.27-3.34 (m, 2H, CONCH$_2$), 3.31 (s, 3H, OCH$_3$), 3.41-3.46 (m, 2H, OCH$_2$), 3.55 (t, J=7.5 Hz, 1H, CH), 4.30 (t, J=6.3 Hz, 2H, NCH$_2$), 6.19 (brm, 1H, NH), 6.60 (d, J=2.3 Hz, 1 H, Ar), 7.29 (d, J=2.3 Hz, 1H, Ar), 7.46 (dd, $J_o$=8.2, $J_m$=1.7 Hz. 1H, Ar), 7.60 (d, $J_m$=1.7 Hz, 1H, Ar), 8.08 (d, $J_o$=8.2 Hz, 1H, Ar), 8.13 (s, 1H, NH).

Example 18

N-[1-(2-Allylcarbamoyl-ethyl)-1H-pyrazol-3-yl]-2(R)-(3-chloro-4-methanesulfonyl-phenyl)-3-cyclopentyl-propionamide

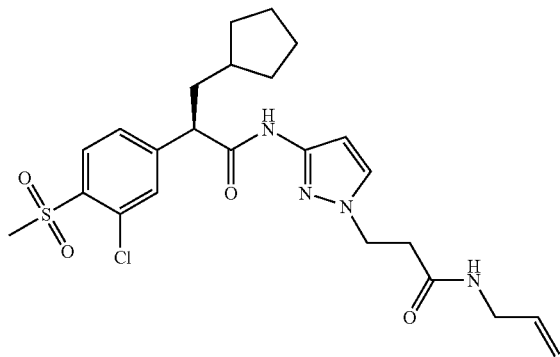

To a solution containing 3-{3-[2(R)-(3-chloro-4-methanesulfonyl-phenyl)-3-cyclopentyl-propionylamino]-pyrazol-1-yl}-propionic acid (prepared in example 9, 50 mg, 0.11 mmol) in methylene chloride (2 mL), was then added a 2.0 M solution of oxalylchloride in methylene chloride (59 μL, 0.12 mmol) at 0° C. and allowed to stir at 25° C. for 1 h, after which time 2,6-lutidine (17 μL, 0.14 mmol) was added to the solution at 0° C. After 1 h, allylamine (9 μL, 0.11 mmol) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford N-[1-(2-allylcarbamoyl-ethyl)-1H-pyrazol-3-yl]-2(R)-(3-chloro-4-methanesulfonyl-phenyl)-3-cyclopentyl-propionamide (9 mg, 16%) as a white solid: ESI-LRMS m/e calcd for $C_{23}H_{29}ClN_4O_4S$ [M$^+$] 506.19, found 507.34 [M+H$^+$]; $^1$H NMR (400 MHz, CDCl$_3$) δ ppm 1.06-1.20 (m, 2H, CH$_2$), 1.42-1.94 (m, 8H, 4×CH$_2$), 2.12-2.30 (m, 1H, CH), 2.65 (t, J=6.3 Hz, 2H, COCH$_2$), 3.26 (s, 3H, SO$_2$CH$_3$), 3.54 (t, J=7.5 Hz, 1H, CH), 3.79-3.84 (m, 2H, CONCH$_2$), 4.31 (t, J=6.3 Hz, 2H, NCH$_2$), 5.02-5.07 (m, 1H, vinylic), 5.06-5.09 (m, 1H, vinylic), 6.55 (brm, 1H, NH), 5.67-5.78 (m, 1H, vinylic), 6.60 (d, J=2.3 Hz, 1H, Ar), 7.30 (d, J=2.3 Hz, 1H, Ar), 7.46 (dd, $J_o$=8.2, $J_m$=1.7 Hz. 1H, Ar), 7.59 (d, $J_m$=1.7 Hz, 1H, Ar), 8.02 (s, 1H, NH), 8.09 (d, $J_o$=8.2 Hz, 1H, Ar).

Example 19

3-{3-[2-(3-Chloro-4-methanesulfonyl-phenyl)-3-cyclopentyl-propionylamino]-pyrazol-1-yl}-propionic acid methyl ester

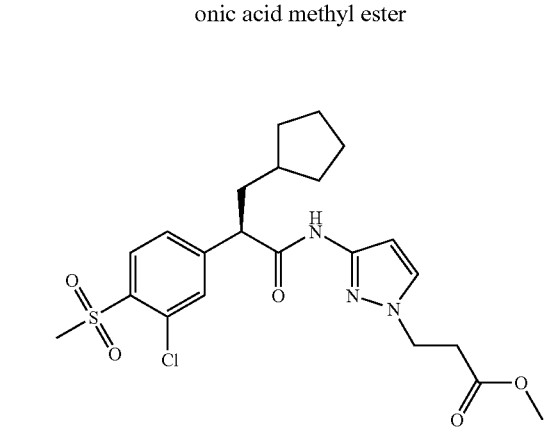

To a solution containing 3-{3-[2(R)-(3-chloro-4-methanesulfonyl-phenyl)-3-cyclopentyl-propionylamino]-pyrazol-1-yl}-propionic acid (prepared in example 9, 50 mg, 0.11 mmol) in methylene chloride (2 mL), was then added a 2.0 M solution of oxalylchloride in methylene chloride (59 μL, 0.12 mmol) at 0° C. and allowed to stir at 25° C. for 1 h, after which time 2,6-lutidine (17 μL, 0.14 mmol) was added to the solution at 0° C. After 1 h, methanol (20 μL, 0.49 mmol) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 3-{3-[2-(3-chloro-4-methanesulfonyl-phenyl)-3-cyclopentyl-propionylamino]-pyrazol-1-yl}-propionic acid methyl ester (28 mg, 55%) as a white solid: ESI-LRMS m/e calcd for $C_{22}H_{28}ClN_3O_5S$ [M$^+$] 481.1, found 482.5 [M+H$^+$]; $^1$H NMR (400 MHz, CDCl$_3$), δ ppm 1.08-1.21 (m, 2H, CH$_2$), 1.40-1.95 (m, 8H, 4×CH$_2$), 2.13-2.28 (m, 1H, CH), 2.82 (t, J=6.5 Hz, 2H, COCH$_2$), 3.26 (s, 3H, SO$_2$CH$_3$), 3.54 (t, J=7.6 Hz, 1H, CH), 3.67 (s, 3H, CO$_2$CH$_3$), 4.27 (t, J=6.5 Hz, 2H, NCH$_2$), 6.62 (d, J=2.3 Hz, 1H, Ar), 7.30 (d, J=2.3 Hz, 1H, Ar), 7.45 (dd, $J_o$=8.2, $J_m$=1.7 Hz. 1H, Ar), 7.59 (d, $J_m$=1.7 Hz, 1H, Ar), 7.89 (s, 1H, NH), 8.08 (d, $J_o$=8.2 Hz, 1H, Ar).

Example 20

N-(1-Carbamoylmethyl-1H-pyrazol-3-yl)-2(R)-(3-chloro-4-methanesulfonyl-phenyl)-3-cyclopentyl-propionamide

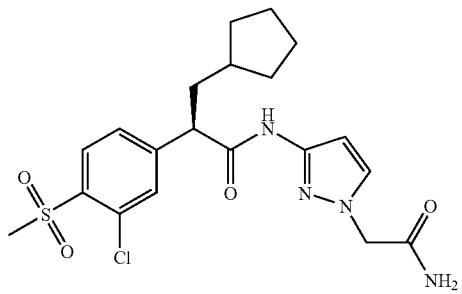

To a solution of 3-nitro-1H-pyrazole (prepared in example 3, 150 mg, 1.33 mmol) in anhydrous N,N-dimethylformamide (2 mL), a 60% dispersion of sodium hydride in mineral oil (58 mg, 1.46 mmol) was added while stirring under nitrogen. After the effervescence ceased and the mixture was stirred for additional 30 min, bromoacetamide (201 mg, 1.46 mmol) was added. The mixture was continued to stir under nitrogen for an additional 2 h. The solvent was removed in vacuo and purification by ISCO flash column chromatography (Teledyne Isco RediSep Flash Column 40 g; 0% ethyl acetate/hexanes to 50% ethyl acetate/hexanes) afforded 2-(3-nitro-pyrazol-1-yl)-acetamide (107 mg, 48%) as a white solid.

To a solution containing 2-(3-nitro-pyrazol-1-yl)-acetamide (51 mg, 0.30 mmol) in methanol (3 mL), palladium, 10 wt. % on activated carbon, wet (~50 mg) was added to the solution. The vial was charged with hydrogen gas (via balloon) and the mixture was stirred for 16 h at 25° C. The mixture was passed through a plug of celite and concentrated in vacuo to give the desired 2-(3-amino-pyrazol-1-yl)-acetamide as a yellow oil which was used in the following step with no further purification.

To a solution containing 2(R)-(3-chloro-4-methanesulfonyl-phenyl)-3-cyclopentyl-propionic acid (prepared as in PCT WO 2004/052869 A1, Example 1, 100 mg, 0.30 mmol) in methylene chloride (20 mL), was then added a 2.0 M solution of oxalylchloride in methylene chloride (166 µL, 0.33 mmol) at 0° C. and allowed to stir at 25° C. for 1 h, after which time 2,6-lutidine (46 µL, 0.39 mmol) was added to the solution at 0° C. After 1 h, the crude 2-(3-amino-pyrazol-1-yl)-acetamide (0.30 mmol based on theory) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford N-(1-Carbamoylmethyl-1H-pyrazol-3-yl)-2(R)-(3-chloro-4-methanesulfonyl-phenyl)-3-cyclopentyl-propionamide (38 mg, 28%) as a white solid: ESI-LRMS m/e calcd for $C_{20}H_{25}ClN_4O_4S$ [M+] 452.13, found 453.2 [M+H+]; $^1$H NMR (400 MHz, CD$_3$OD) δ ppm 1.11-1.27 (m, 2H, CH$_2$), 1.46-1.92 (m, 8H, 4×CH$_2$), 2.07-2.27 (m, 1H, CH), 3.28 (s, 3H, SO$_2$CH$_3$), 3.85 (dd, J=8.6, 6.4 Hz, 1H, CH), 4.73 (s, 2H, NCH$_2$), 6.55 (d, J=2.4 Hz, 1H, Ar), 7.53 (d, J=2.4 Hz, 1H, Ar), 7.59 (dd, $J_o$=8.2, $J_m$=1.5 Hz. 1H, Ar), 7.71 (d, $J_m$=1.5 Hz, 1H, Ar), 8.05 (d, $J_o$=8.2 Hz, 1H, Ar).

Example 21

2(R)-(3-Chloro-4-methanesulfonyl-phenyl)-3-cyclopentyl-N-[1-(4-methanesulfonyl-benzyl)-1H-pyrazol-3-yl]-propionamide

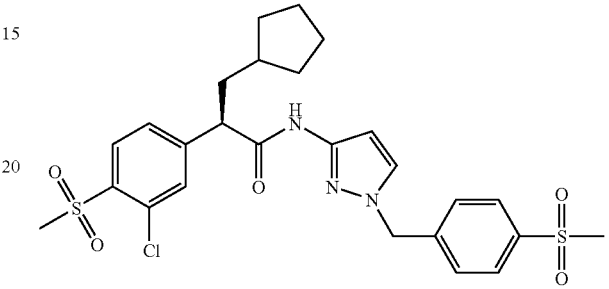

To a solution of 3-nitro-1H-pyrazole (prepared in example 3, 150 mg, 1.33 mmol) in anhydrous N,N-dimethylformamide (2 mL), a 60% dispersion of sodium hydride in mineral oil (58 mg, 1.46 mmol) was added while stirring under nitrogen. After the effervescence ceased and the mixture was stirred for additional 30 min, 1-bromomethyl-4-methanesulfonyl-benzene (364 mg, 1.46 mmol) was added. The mixture was continued to stir under nitrogen for an additional 2 h. The solvent was removed in vacuo and purification by ISCO flash column chromatography (Teledyne Isco RediSep Flash Column 40 g; 0% ethyl acetate/hexanes to 50% ethyl acetate/hexanes) afforded 1-(4-methanesulfonyl-benzyl)-3-nitro-1H-pyrazole (207 mg, 55%) as a white solid.

To a solution containing 1-(4-methanesulfonyl-benzyl)-3-nitro-1H-pyrazole (85 mg, 0.30 mmol) in methanol (3 mL), palladium, 10 wt. % on activated carbon, wet (~50 mg) was added to the solution. The vial was charged with hydrogen gas (via balloon) and the mixture was stirred for 16 h at 25° C. The mixture was passed through a plug of celite and concentrated in vacuo to afford the desired 1-(4-methanesulfonyl-benzyl)-1H-pyrazol-3-ylamine as a yellow oil which was used in the following step with no further purification.

To a solution containing 2(R)-(3-chloro-4-methanesulfonyl-phenyl)-3-cyclopentyl-propionic acid (prepared as in PCT WO 2004/052869 A1, Example 1, 100 mg, 0.30 mmol) in methylene chloride (20 mL), was then added a 2.0 M solution of oxalylchloride in methylene chloride (166 µL, 0.33 mmol) at 0+ C. and allowed to stir at 25° C. for 1 h, after which time 2,6-lutidine (46 µL, 0.39 mmol) was added to the solution at 0° C. After 1 h, 1-(4-methanesulfonyl-benzyl)-1H-pyrazol-3-ylamine (0.30 mmol based on theory) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-[1-(4-methanesulfonyl-benzyl)-1H-pyrazol-3-yl]-propionamide (150 mg, 88%) as a white solid: ESI-LRMS m/e calcd for $C_{26}H_{30}ClN_3O_5S_2$ [M+] 563.13, found 564.5

[M+H⁺]; ¹H NMR (400 MHz, CDCl₃) δ ppm 1.03-1.21 (m, 2H, CH₂), 1.34-1.88 (m, 8H, 4×CH₂), 2.09-2.29 (m, 1H, CH), 2.98 (s, 3 H, SO₂CH₃), 3.22 (s, 3H, SO₂CH₃), 3.56 (t, J=7.5 Hz, 1H, CH), 5.24 (AB, J$_{gem}$=15.9 Hz, 2H, NCH₂), 6.76 (d, J=2.3 Hz, 1H, Ar), 7.14 (d, J$_o$=8.3 Hz, 2H, Ar), 7.38 (dd, J$_o$=8.2, J$_m$=1.7 Hz. 1H, Ar), 7.44 (d, J=2.3 Hz, 1H, Ar), 7.53 (d, J$_m$=1.7 Hz, 1H, Ar), 7.75 (d, J$_o$=8.3 Hz, 2H, Ar), 7.91 (d, J$_o$=8.2 Hz, 1H, Ar), 8.34 (s, 1H, NH).

Example 22

2(R)-(3-Chloro-4-methanesulfonyl-phenyl)-3-cyclopentyl-N-(1-methanesulfonylmethyl-1H-pyrazol-3-yl)-propionamide

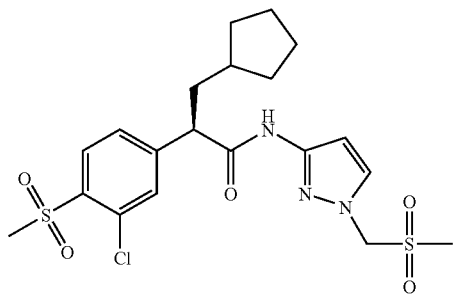

To a solution of 3-nitro-1H-pyrazole (prepared in example 3, 50 mg, 4.42 mmol) in anhydrous N,N-dimethylformamide (5 mL), a 60% dispersion of sodium hydride in mineral oil (230 mg, 5.75 mmol) was added while stirring under nitrogen. After the effervescence ceased and the mixture was stirred for additional 30 min, chloro-methylsulfanyl-methane (555 mg, 5.75 mmol) was added. The mixture was continued to stir under nitrogen for an additional 2 h. The solvent was removed in vacuo and purification by ISCO flash column chromatography (Teledyne Isco RediSep Flash Column 40 g; 0% ethyl acetate/hexanes to 50% ethyl acetate/hexanes) afforded 1-methylsulfanylmethyl-3-nitro-1H-pyrazole (514 mg, 67%) as a white solid.

Oxone (2.05 g, 3.36 mmol) was added to a mixture of 1-methylsulfanylmethyl-3-nitro-1H-pyrazole (194 mg, 1.12 mmol) in methanol (10 mL) and deionized water (100 µL) was allowed to proceed for 16 h with vigorous stirring. The solvent was removed in vacuo and the crude material was purified by ISCO flash column chromatography (Teledyne Isco RediSep Flash Column 10 g; 0% ethyl acetate/hexanes to 50% ethyl acetate/hexanes) afforded 1-methanesulfonylmethyl-3-nitro-1H-pyrazole as a white solid (184 mg, 80%).

To a solution containing 1-methanesulfonylmethyl-3-nitro-1H-pyrazole (62 mg, 0.30 mmol) in methanol (3 mL), palladium, 10 wt. % on activated carbon, wet (~50 mg) was added to the solution. The vial was charged with hydrogen gas (via balloon) and the mixture was stirred for 16 h at 25° C. The mixture was passed through a plug of celite and concentrated in vacuo to give the desired 1-methanesulfonylmethyl-1H-pyrazol-3-ylamine as a yellow oil which was used in the following step with no further purification.

To a solution containing 2(R)-(3-chloro-4-methanesulfonyl-phenyl)-3-cyclopentyl-propionic acid (prepared as in PCT WO 2004/052869 A1, Example 1, 100 mg, 0.30 mmol) in methylene chloride (20 mL), was then added a 2.0 M solution of oxalylchloride in methylene chloride (166 µL, 0.33 mmol) at 0° C. and allowed to stir at 25° C. for 1 h, after which time 2,6-lutidine (46 µL, 0.39 mmol) was added to the solution at 0° C. After 1 h, 1-methanesulfonylmethyl-1H-pyrazol-3-ylamine (0.30 mmol based on theory) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-Chloro-4-methanesulfonyl-phenyl)-3-cyclopentyl-N-(1-methanesulfonylmethyl-1H-pyrazol-3-yl)-propionamide (133 mg, 90%) as a white solid: ESI-LRMS m/e calcd for C₂₀H₂₆ClN₃O₅S₂ [M⁺] 487.1, found 488.4 [M+H⁺]; ¹H NMR (400 MHz, CDCl₃) δ ppm 1.03-1.22 (m, 2H, CH₂), 1.43-1.94 (m, 8H, 4×CH₂), 2.09-2.29 (m, 1H, CH), 2.86 (s, 3H, SO₂CH₃), 3.27 (s, 3H, SO₂CH₃), 3.58 (t, J=7.5 Hz, 1H, CH), 5.25 (s, 2H, NCH₂), 6.87 (d, J=2.5 Hz, 1H, Ar), 7.48 (dd, J$_o$=8.1, J$_m$=1.6 Hz. 1H, Ar), 7.54 (d, J=2.5 Hz, 1H, Ar), 7.61 (d, J$_m$=1.6 Hz, 1H, Ar), 8.01 (d, J$_o$=8.1 Hz, 1H, Ar), 8.10 (brs, 1H, NH).

Example 23

2(R)-(3-Chloro-4-methanesulfonyl-phenyl)-3-cyclopentyl-N-[1-(3-hydroxy-propyl)-1H-pyrazol-3-yl]-propionamide

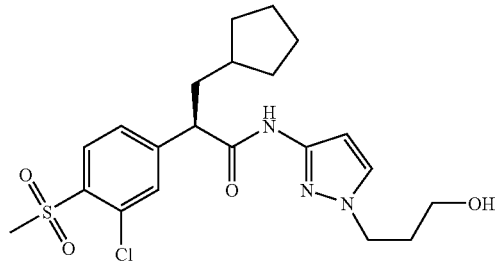

To a solution of 3-nitro-1H-pyrazole (prepared in example 3, 200 mg, 1.77 mmol) in anhydrous N,N-dimethylformamide (2 mL), a 60% dispersion of sodium hydride in mineral oil (92 mg, 2.30 mmol) was added while stirring under nitrogen. After the effervescence ceased and the mixture was stirred for an additional 30 min, bromopropanol (208 µL, 2.30 mmol) was added. The mixture was continued to stir under nitrogen for an additional 2 h. The solvent was removed in vacuo and purification by ISCO flash column chromatography (Teledyne Isco RediSep Flash Column 40 g; 2% methanol/methylene chloride to 5% methanol/methylene chloride) afforded 3-(3-nitro-pyrazol-1-yl)-propan-1-ol (144 mg, 48%) as an oil: H¹-NMR (400 MHz, CDCl₃) δ 2.09 (2H, m), 2.84 (1H, s), 3.60 (2H, t, J=5.8 Hz), 4.32 (2H, t, J=6.8 Hz), 6.82 (1H, D, J=2.4 Hz), 7.51 (1H, d, J=2.4 Hz).

To a solution containing 3-(3-nitro-pyrazol-1-yl)-propan-1-ol (72 mg, 0.42 mmol) in tetrahydrofuran (2 mL), anhydrous hydrazine (100 µL) was added to the clear solution. Raney nickel (~100 mg washed 3 times with 5 mL of anhydrous tetrahydrofuran) was then added in tetrahydrofuran (300 µL). Gas evolved from the mixture and the reaction was allowed to proceed for 5 min, after which time the raney nickel was removed by filtration through a celite plug. The solvent was removed in vacuo to afford 3-(3-amino-pyrazol-1-yl)-propan-1-ol as a yellow oil, which was then immediately used in the next step with no further purification.

To a solution containing 2(R)-(3-chloro-4-methanesulfonyl-phenyl)-3-cyclopentyl-propionic acid (prepared as in PCT WO 2004/052869 A1, Example 1, 100 mg, 0.30 mmol) in methylene chloride (20 mL), was then added a 2.0 M solution of oxalylchloride in methylene chloride (181 µL, 0.36 mmol) at 0° C. and allowed to stir at 25° C. for 1 h, after which time 2,6-lutidine (70 µL, 0.61 mmol) was added to the solution at 0° C. After 1 h, 3-(3-amino-pyrazol-1-yl)-propan-1-ol (0.42 mmol based on theory) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-[1-(3-hydroxy-propyl)-1H-pyrazol-3-yl]-propionamide (47 mg, 34%) as a white solid: ESI-LRMS m/e calcd for $C_{21}H_{28}ClN_3O_4S$ [M+] 453.15, found 454.4 [M+H+]; $^1$H NMR (400 MHz, $CDCl_3$) δ ppm 1.02-1.21 (m, 2H, $CH_2$), 1.40-1.92 (m, 8H, 4×$CH_2$), 1.92-2.02 (m, 2H, $CH_2$), 2.11-2.28 (m, 1H, CH), 2.88 (brs, 1H, OH), 3.26 (s, 3H, $SO_2CH_3$), 3.50-3.67 (m, 3H, $OCH_2$ and CH), 4.11 (t, J=6.4 Hz, 2H, NCH2), 6.63 (d, $J_o$=2.3, 1H, Ar), 7.26 (d, $J_o$=2.3, 1H, Ar), 7.45 (dd, $J_o$=8.2, $J_m$=1.6 Hz. 1H, Ar), 7.58 (d, $J_m$=1.6 Hz, 1H, Ar), 8.05 (d, $J_o$=8.2 Hz, 1H, Ar), 8.38 (s, 1H, NH).

Example 24

N-(1-Benzyl-1H-pyrazol-3-yl)-2(R)-(3-chloro-4-methanesulfonyl-phenyl)-3-cyclopentyl-propionamide

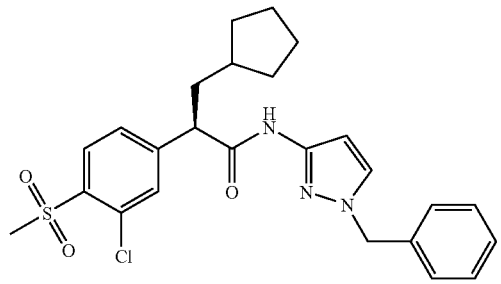

To a solution of 3-nitro-1H-pyrazole (prepared in example 3, 200 mg, 1.77 mmol) in anhydrous N,N-dimethylformamide (2 mL), a 60% dispersion of sodium hydride in mineral oil (92 mg, 2.30 mmol) was added while stirring under nitrogen. After the effervescence ceased and the mixture was stirred for additional 10 min, benzylbromide (273 µL, 2.33 mmol) was added. The mixture was continued to stir under nitrogen for an additional 2 h. The solvent was removed in vacuo and purification by ISCO flash column chromatography (Teledyne Isco RediSep Flash Column 40 g; 2% methanol/methylene chloride to 5% methanol/methylene chloride) afforded 1-benzyl-3-nitro-1H-pyrazole (303 mg, 84%) as a white solid: $H^1$-NMR (400 MHz, $CDCl_3$) δ: 5.33 (2H, s), 6.84 (1H, d, J=2.7 Hz), 7.26 (2H, m), 7.32 (3H, m), 7.40 (1H, d, J=1.5 Hz).

To a solution containing 1-benzyl-3-nitro-1H-pyrazole (86 mg, 0.42 mmol) in tetrahydrofuran (2 mL), anhydrous hydrazine (100 µL) was added to the clear solution. Raney nickel (~100 mg washed 3 times with 5 mL of anhydrous tetrahydrofuran) was then added in tetrahydrofuran (300 µL). Gas evolved from the mixture and the reaction was allowed to proceed for 5 min, after which time the raney nickel was removed by filtration through a celite plug. The solvent was removed in vacuo to afford 1-benzyl-1H-pyrazol-3-ylamine as a yellow oil, which was used in the following step with no further purification.

To a solution containing 2(R)-(3-chloro-4-methanesulfonyl-phenyl)-3-cyclopentyl-propionic acid (prepared as in PCT WO 2004/052869 A1, Example 1, 100 mg, 0.30 mmol) in methylene chloride (20 mL), was then added a 2.0 M solution of oxalylchloride in methylene chloride (181 µL, 0.36 mmol) at 0° C. and allowed to stir at 25° C. for 1 h, after which time 2,6-lutidine (70 µL, 0.61 mmol) was added to the solution at 0° C. After 1 h, crude 1-benzyl-1H-pyrazol-3-ylamine (0.42 mmol based on theory) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford N-(1-benzyl-1H-pyrazol-3-yl)-2(R)-(3-chloro-4-methanesulfonyl-phenyl)-3-cyclopentyl-propionamide (101 mg, 69%) as a white solid: ESI-LRMS m/e calcd for $C_{25}H_{28}ClN_3O_3S$ [M+] 485.2, found 486.4 [M+H+]; $^1$H NMR (400 MHz, $CDCl_3$) δ ppm 1.05-1.18 (m, 2H, $CH_2$), 1.40-1.91 (m, 8H, 4×$CH_2$), 2.10-2.31 (m, 1H, CH), 3.23 (s, 3H, $SO_2CH_3$), 3.56 (t, J=7.6 Hz, 1H, CH), 5.12 (s, 2H, $NCH_2$), 6.69 (d, J=2.3 Hz, 1H, Ar), 7.12 (dd, $J_o$=7.2, $J_m$=1.7 Hz. 2H, Ar), 7.26-7.33 (m, 4H, Ar), 7.43 (dd, $J_o$=8.2, $J_m$=1.6 Hz. 1H, Ar), 7.57 (d, $J_m$=1.6 Hz, 1H, Ar), 8.04 (d, $J_o$=8.2 Hz. 1H, Ar), 8.27 (brs, 1H, NH).

Example 25

N-[1-(4-Chloro-benzyl)-1H-pyrazol-3-yl]-2(R)-(3-chloro-4-methanesulfonyl-phenyl)-3-cyclopentyl-propionamide

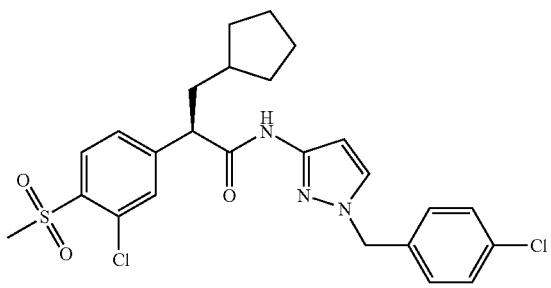

To a solution of 3-nitro-1H-pyrazole (prepared in example 3, 200 mg, 1.77 mmol) in anhydrous N,N-dimethylformamide (2 mL), a 60% dispersion of sodium hydride in mineral oil (92 mg, 2.30 mmol) was added while stirring under nitrogen. After the effervescence ceased and the mixture was stirred for additional 30 min, 4-chlorobenzylbromide (473 mg, 2.30 mmol) was added. The mixture was continued to stir under nitrogen for an additional 2 h. The solvent was removed in vacuo and purification by ISCO flash column chromatography (Teledyne Isco RediSep Flash Column 40 g; 2% methanol/methylene chloride to 5% methanol/methylene chloride) afforded 1-(4-chloro-benzyl)-3-nitro-1H-pyrazole (344 mg, 82%) as a white solid: $H^1$-NMR (400 MHz, $CDCl_3$) δ: 5.33

(2H, s), 6.90 (1H, d, J=2.3 Hz), 7.22 (2H, d, J=8.4 Hz), 7.34 (2H, d J=8.6 Hz), 7.40 (1H, d, J=2.6 Hz).

To a solution containing 1-(4-chloro-benzyl)-3-nitro-1H-pyrazole (101 mg, 0.42 mmol) in tetrahydrofuran (2 mL), anhydrous hydrazine (100 µL) was added to the clear solution. Raney nickel (~100 mg washed 3 times with 5 mL of anhydrous tetrahydrofuran) was then added in tetrahydrofuran (300 µL). Gas evolved from the mixture and the reaction was allowed to proceed for 5 min, after which time the raney nickel was removed by filtration through a celite plug. The solvent was removed in vacuo to afford 1-(4-chloro-benzyl)-1H-pyrazol-3-ylamine as a yellow oil which was used in the following step with no further purification.

To a solution containing 2(R)-(3-chloro-4-methanesulfonyl-phenyl)-3-cyclopentyl-propionic acid (prepared as in PCT WO 2004/052869 A1, Example 1, 100 mg, 0.30 mmol) in methylene chloride (20 mL), was then added a 2.0 M solution of oxalylchloride in methylene chloride (181 µL, 0.36 mmol) at 0° C. and allowed to stir at 25° C. for 1 h, after which time 2,6-lutidine (70 µL, 0.61 mmol) was added to the solution at 0° C. After 1 h, crude 1-(4-chloro-benzyl)-1H-pyrazol-3-ylamine (0.42 mmol based on theory) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford N-[1-(4-chloro-benzyl)-1H-pyrazol-3-yl]-2(R)-(3-chloro-4-methanesulfonyl-phenyl)-3-cyclopentyl-propionamide (117 mg, 74%) as a white solid: ESI-LRMS m/e calcd for $C_{25}H_{27}Cl_2N_3O_3S$ [M$^+$] 519.1, found 520.4 [M+H$^+$]; $^1$H NMR (400 MHz, CDCl$_3$) δ ppm 1.05-1.20 (m, 2H, CH$_2$), 1.40-1.93 (m, 8H, 4×CH$_2$), 2.09-2.31 (m, 1H, CH), 3.24 (s, 3H, SO$_2$CH$_3$), 3.51-3.60 (m, 1H, CH), 5.09 (s, 2H, NCH$_2$), 6.69 (d, J=2.3 Hz, 1H, Ar), 7.06 (d, J$_o$=8.3 Hz, 2H, Ar), 7.26-7.33 (m, 3H, Ar), 7.43 (dd, J$_o$=8.2, J$_m$=1.7 Hz. 1H, Ar), 7.57 (d, J$_m$=1.7 Hz, 1H, Ar), 7.88-8.36 (m, 2H, Ar and NH).

Example 26

2(R)-(3-Chloro-4-methanesulfonyl-phenyl)-N-[1-(4-cyano-benzyl)-1H-pyrazol-3-yl]-3-cyclopentyl-propionamide

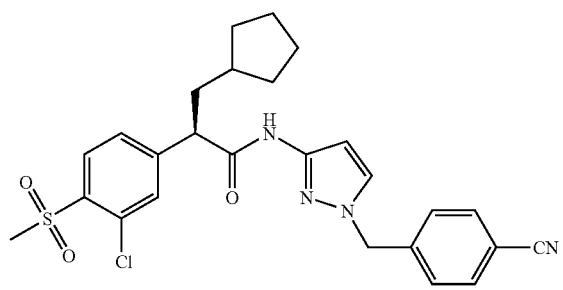

To a solution of 3-nitro-1H-pyrazole (prepared in example 3, 200 mg, 1.77 mmol) in anhydrous N,N-dimethylformamide (2 mL), a 60% dispersion of sodium hydride in mineral oil (92 mg, 2.30 mmol) was added while stirring under nitrogen. After the effervescence ceased and the mixture was stirred for additional 30 min, 4-bromomethyl-benzonitrile (345 mg, 2.30 mmol) was added. The mixture was continued to stir under nitrogen for an additional 2 h. The solvent was removed in vacuo and purification by ISCO flash column chromatography (Teledyne Isco RediSep Flash Column 40 g; 2% methanol/methylene chloride to 5% methanol/methylene chloride) afforded 4-(3-nitro-pyrazol-1-ylmethyl)-benzonitrile (365 mg, 90%) as a white solid. The crude material was used in the following step without any further purification.

To a solution containing 4-(3-nitro-pyrazol-1-ylmethyl)-benzonitrile (97 mg, 0.42 mmol) in tetrahydrofuran (2 mL), anhydrous hydrazine (100 µL) was added to the clear solution. Raney nickel (~100 mg washed 3 times with 5 mL of anhydrous tetrahydrofuran) was then added in tetrahydrofuran (300 µL). Gas evolved from the mixture and the reaction was allowed to proceed for 5 min, after which time the raney nickel was removed by filtration through a celite plug. The solvent was removed in vacuo to afford 4-(3-amino-pyrazol-1-ylmethyl)-benzonitrile as a yellow oil, which was used in the following step with no further purification.

To a solution containing 2(R)-(3-chloro-4-methanesulfonyl-phenyl)-3-cyclopentyl-propionic acid (prepared as in PCT WO 2004/052869 A1, Example 1, 100 mg, 0.30 mmol) in methylene chloride (20 mL), was then added a 2.0 M solution of oxalylchloride in methylene chloride (181 µL, 0.36 mmol) at 0° C. and allowed to stir at 25° C. for 1 h, after which time 2,6-lutidine (70 µL, 0.61 mmol) was added to the solution at 0° C. After 1 h, crude 4-(3-amino-pyrazol-1-ylmethyl)-benzonitrile (0.42 mmol based on theory) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-N-[1-(4-cyano-benzyl)-1H-pyrazol-3-yl]-3-cyclopentyl-propionamide (35 mg, 23%) as a white solid: ESI-LRMS m/e calcd for $C_{26}H_{27}ClN_4O_3S$ [M$^+$] 510.2, found 511.5 [M+H$^+$]; $^1$H NMR (400 MHz, CDCl$_3$) δ ppm 1.06-1.21 (m, 2H, CH$_2$), 1.44-1.92 (m, 8H, 4×CH$_2$), 2.09-2.35 (m, 1H, CH), 3.25 (s, 3H, SO$_2$CH$_3$), 3.56 (t, J=7.5 Hz, 1H, CH), 5.20 (s, 2H, NCH$_2$), 6.74 (d, J=2.3 Hz, 1H, Ar), 7.19 (d, J$_o$=8.4 Hz, 2H, Ar), 7.35 (d, J=2.3 Hz, 1H, Ar), 7.44 (dd, J$_o$=8.2, J$_m$=1.7 Hz. 1H, Ar), 7.54-7.63 (m, 3H, Ar), 7.99 (s, 1H, NH), 8.06 (d, J$_o$=8.2 Hz, 1H, Ar).

Example 27

2(R)-(3-Chloro-4-methanesulfonyl-phenyl)-3-cyclopentyl-N-[1-(4-methyl-benzyl)-1H-pyrazol-3-yl]-propionamide

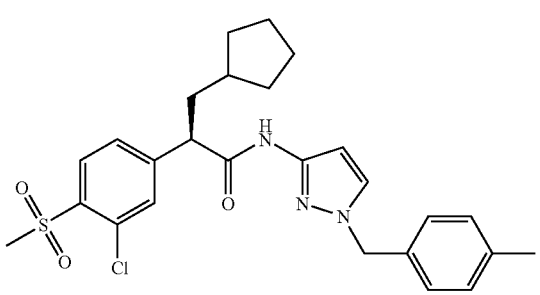

To a solution of 3-nitro-1H-pyrazole (prepared in example 3, 200 mg, 1.77 mmol) in anhydrous N,N-dimethylformamide (2 mL), a 60% dispersion of sodium hydride in mineral oil 92 mg, 2.30 mmol) was added while stirring under nitrogen. After the effervescence ceased and the mixture was stirred for additional 20 min, 4-methylbenzylbromide (426 mg, 2.30 mmol) was added. The mixture was continued to stir under nitrogen for an additional 2 h. The solvent was removed in vacuo and purification by ISCO flash column chromatography (Teledyne Isco RediSep Flash Column 40 g; 2% methanol/methylene chloride to 5% methanol/methylene chloride) afforded 1-(4-methyl-benzyl)-3-nitro-1H-pyrazole (316 mg, 82%) as a white solid: $H^1$-NMR (400 MHz, $CDCl_3$) δ: 2.36 (3H, s), 5.32 (2H, s), 6.87 (1H, d, J=2.3 Hz), 7.19 (4H, s), 7.34 (1H, d, J=2.3 Hz).

To a solution containing 1-(4-methyl-benzyl)-3-nitro-1H-pyrazole (92 mg, 0.42 mmol) in tetrahydrofuran (2 mL), anhydrous hydrazine (100 μL) was added to the clear solution. Raney nickel (~100 mg washed 3 times with 5 mL of anhydrous tetrahydrofuran) was then added in tetrahydrofuran (300 μL). Gas evolved from the mixture and the reaction was allowed to proceed for 5 min, after which time the raney nickel was removed by filtration through a celite plug. The solvent was removed in vacuo to afford 1-(4-methyl-benzyl)-1H-pyrazol-3-ylamine as a yellow oil which was used in the following step with no further purification.

To a solution containing 2(R)-(3-chloro-4-methanesulfonyl-phenyl)-3-cyclopentyl-propionic acid (prepared as in PCT WO 2004/052869 A1, Example 1, 100 mg, 0.30 mmol) in methylene chloride (20 mL), was then added a 2.0 M solution of oxalylchloride in methylene chloride (181 μL, 0.36 mmol) at 0° C. and allowed to stir at 25° C. for 1 h, after which time 2,6-lutidine (70 μL, 0.61 mmol) was added to the solution at 0° C. After 1 h, crude 1-(4-methyl-benzyl)-1H-pyrazol-3-ylamine (0.42 mmol based on theory) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-[1-(4-methyl-benzyl)-1H-pyrazol-3-yl]-propionamide (86 mg, 57%) as a white solid: ESI-LRMS m/e calcd for $C_{26}H_{30}ClN_3O_3S$ [M$^+$] 499.2, found 500.3 [M+H$^+$]; $^1$H NMR (400 MHz, $CDCl_3$) δ ppm 1.05-1.19 (m, 2H, $CH_2$), 1.41-1.95 (m, 8H, 4×$CH_2$), 2.10-2.27 (m, 1H, CH), 2.32 (s, 3H, ArCH$_3$), 3.24 (s, 3H, $SO_2CH_3$), 3.55 (t, J=7.6 Hz, 1H, CH), 5.07 (s, 2H, NCH$_2$), 6.67 (d, J=2.3 Hz, 1H, Ar), 7.04 (d, $J_o$=8.1 Hz, 2H, Ar), 7.11 (d, $J_o$=8.1 Hz, 2H, Ar), 7.26 (d, J=2.3 Hz, 1H, Ar), 7.43 (dd, $J_o$=8.2, $J_m$=1.7 Hz, 1H, Ar), 7.57 (d, $J_m$=1.7 Hz, 1H, Ar), 8.04 (d, $J_o$=8.2 Hz, 1H, Ar), 8.31 (s, 1H, NH).

Example 28

2(R)-(3-Chloro-4-methanesulfonyl-phenyl)-3-cyclopentyl-N-[1-(4-methoxy-benzyl)-1H-pyrazol-3-yl]-propionamide

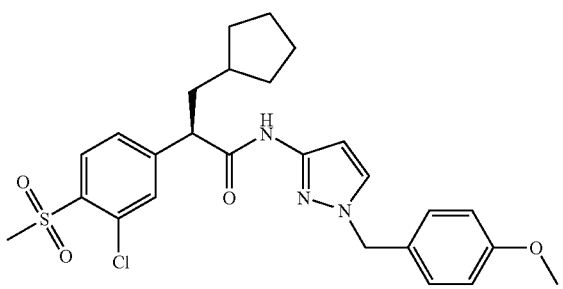

To a solution of 3-nitro-1H-pyrazole (prepared in example 3, 200 mg, 1.77 mmol) in anhydrous N,N-dimethylformamide (2 mL), a 60% dispersion of sodium hydride in mineral oil (92 mg, 2.30 mmol) was added while stirring under nitrogen. After the effervescence ceased and the mixture was stirred for additional 20 min, 4-methyoxybenzylchloride (312 μL, 2.30 mmol) was added. The mixture was continued to stir under nitrogen for an additional 2 h. The solvent was removed in vacuo and purification by ISCO flash column chromatography (Teledyne Isco RediSep Flash Column 40 g; 2% methanol/methylene chloride to 5% methanol/methylene chloride) afforded 1-(4-methoxy-benzyl)-3-nitro-1H-pyrazole (337 mg, 82%) as a white solid: $H^1$-NMR (400 MHz, $CDCl_3$) δ: 3.77 (3H, s), 5.27 (2H, s), 6.83 (1H, d, J=2.3 Hz), 6.86 (2H, d, J=8.6 Hz), 7.22 (2H, d, J=8.5 Hz), 7.35 (1H, d, J=2.3 Hz).

To a solution containing 1-(4-methoxy-benzyl)-3-nitro-1H-pyrazole (99 mg, 0.42 mmol) in tetrahydrofuran (2 mL), anhydrous hydrazine (100 μL) was added to the clear solution. Raney nickel (~100 mg washed 3 times with 5 mL of anhydrous tetrahydrofuran) was then added in tetrahydrofuran (300 μL). Gas evolved from the mixture and the reaction was allowed to proceed for 5 min, after which time the raney nickel was removed by filtration through a celite plug. The solvent was removed in vacuo to afford 1-(4-methoxy-benzyl)-1H-pyrazol-3-ylamine which as a yellow oil was used in the following step with no further purification.

To a solution containing 2(R)-(3-chloro-4-methanesulfonyl-phenyl)-3-cyclopentyl-propionic acid (prepared as in PCT WO 2004/052869 A1, Example 1, 100 mg, 0.30 mmol) in methylene chloride (20 mL), was then added a 2.0 M solution of oxalylchloride in methylene chloride (181 μL, 0.36 mmol) at 0° C. and allowed to stir at 25° C. for 1 h, after which time 2,6-lutidine (70 μL, 0.61 mmol) was added to the solution at 0° C. After 1 h, the crude 1-(4-methoxy-benzyl)-1H-pyrazol-3-ylamine (0.42 mmol based on theory) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-[1-(4-methoxy-benzyl)-1H-pyrazol-3-yl]-propionamide (92 mg, 59%) as a white solid: ESI-LRMS m/e calcd for $C_{26}H_{30}ClN_3O_4S$ [M+] 515.2, found 516.4 [M+H+]; $^1$H NMR (400 MHz, CDCl$_3$) δ ppm 1.03-1.21 (m, 2H, CH$_2$), 1.41-1.91 (m, 8H, 4×CH$_2$), 2.10-2.26 (m, 1H, CH), 3.24 (s, 3H, SO$_2$CH$_3$), 3.54 (t, J=7.6 Hz, 1H, CH), 3.78 (s, 3H, OCH$_3$), 5.05 (s, 2H, NCH$_2$), 6.66 (d, J=2.3 Hz, 1H, Ar), 6.83 (d, J$_o$=8.5 Hz, 2H, Ar), 7.09 (d, J$_o$=8.5 Hz, 2H, Ar), 7.25 (d, J=2.3 Hz, 1H, Ar), 7.43 (dd, J$_o$=8.2, J$_m$=1.7 Hz, 1H, Ar), 7.57 (d, J$_m$=1.7 Hz, 1H, Ar), 8.05 (d, J$_o$=8.2 Hz, 1H, Ar), 8.30 (s, 1H, NH).

Example 29

2(R)-(3-Chloro-4-methanesulfonyl-phenyl)-3-cyclopentyl-N-[1-(3,4-dichloro-benzyl)-1H-pyrazol-3-yl]-propionamide

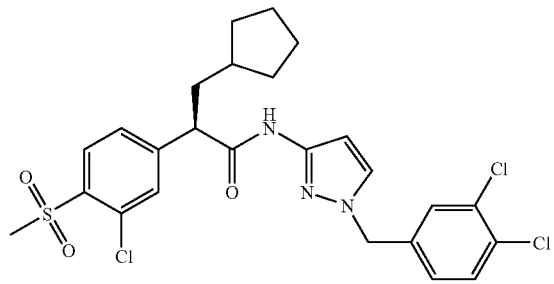

To a solution of 3-nitro-1H-pyrazole (prepared in example 3, 200 mg, 1.77 mmol) in anhydrous N,N-dimethylformamide (2 mL), a 60% dispersion of sodium hydride in mineral oil (92 mg, 2.30 mmol) was added while stirring under nitrogen. After the effervescence ceased and the mixture was stirred for additional 20 min, 3,4-dichlorobenzylbromide (550 mg, 2.30 mmol) was added. The mixture was continued to stir under nitrogen for an additional 2 h. The solvent was removed in vacuo and purification by ISCO flash column chromatography (Teledyne Isco RediSep Flash Column 40 g; 2% methanol/methylene chloride to 5% methanol/methylene chloride) afforded 1-(3,4-dichloro-benzyl)-3-nitro-1H-pyrazole (369 mg, 77%) as a white solid: H$^1$-NMR (400 MHz, CDCl$_3$) δ: 5.32 (2H, s), 6.92 (1H, d, J=2.3 Hz), 7.12 (1H, m), 7.36 (1H, d, J=2.2 Hz), 7.44 (2H, m).

To a solution containing 1-(3,4-dichloro-benzyl)-3-nitro-1H-pyrazole (115 mg, 0.42 mmol) in tetrahydrofuran (2 mL), anhydrous hydrazine (100 μL) was added to the clear solution. Raney nickel (~100 mg washed 3 times with 5 mL of anhydrous tetrahydrofuran) was then added in tetrahydrofuran (300 μL). Gas evolved from the mixture and the reaction was allowed to proceed for 5 min, after which time the raney nickel was removed by filtration through a celite plug. The solvent was removed in vacuo to afford 1-(3,4-dichloro-benzyl)-1H-pyrazol-3-ylamine as a yellow oil which was used in the following step with no further purification.

To a solution containing 2(R)-(3-chloro-4-methanesulfonyl-phenyl)-3-cyclopentyl-propionic acid (prepared as in PCT WO 2004/052869 A1, Example 1, 100 mg, 0.30 mmol) in methylene chloride (20 mL), was then added a 2.0 M solution of oxalylchloride in methylene chloride (181 μL, 0.36 mmol) at 0° C. and allowed to stir at 25° C. for 1 h, after which time 2,6-lutidine (70 μL, 0.61 mmol) was added to the solution at 0° C. After 1 h, the crude 1-(3,4-dichloro-benzyl)-1H-pyrazol-3-ylamine (0.42 mmol based on theory) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-[1-(3,4-dichloro-benzyl)-1H-pyrazol-3-yl]-propionamide (133 mg, 79%) as a white solid: ESI-LRMS m/e calcd for $C_{25}H_{26}Cl_3N_3O_3S$ [M+] 553.1, found 554.2 [M+H+]; $^1$H NMR (400 MHz, CDCl$_3$) δ ppm 1.03-1.22 (m, 2H, CH$_2$), 1.42-1.90 (m, 8H, 4×CH$_2$), 2.09-2.28 (m, 1H, CH), 3.24 (s, 3H, SO$_2$CH$_3$), 3.57 (t, J=7.6 Hz, 1H, CH), 5.07 (s, 2H, NCH$_2$), 6.71 (d, J=2.3 Hz, 1H, Ar), 6.95 (dd, J$_o$=8.2, J$_m$=2.0 Hz, 1H, Ar), 7.21 (d, J$_m$=2.0 Hz, 1H, Ar), 7.31 (d, J=2.3 Hz, 1H, Ar), 7.36 (d, J$_o$=8.2 Hz, 1H, Ar), 7.44 (dd, J$_o$=8.2, J$_m$=1.7 Hz, 1H, Ar), 7.58 (d, J$_m$=1.7 Hz, 1H, Ar), 8.05 (d, J$_o$=8.2 Hz, 1H, Ar), 8.14 (s, 1H, NH).

Example 30

2(R)-(3-Chloro-4-methanesulfonyl-phenyl)-3-cyclopentyl-N-(1-phenethyl-1H-pyrazol-3-yl)-propionamide

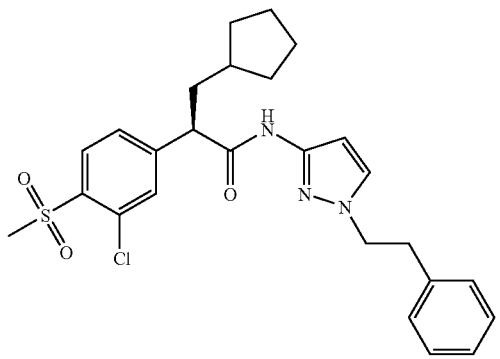

To a solution of 3-nitro-1H-pyrazole (prepared in example 3, 200 mg, 1.77 mmol) in anhydrous N,N-dimethylformamide (2 mL), a 60% dispersion of sodium hydride in mineral oil (92 mg, 2.30 mmol) was added while stirring under nitrogen. After the effervescence ceased and the mixture was stirred for additional 20 min, (2-bromo-ethyl)-benzene (426 mg, 2.30 mmol) was added. The mixture was continued to stir under nitrogen for an additional 2 h. The solvent was removed in vacuo and purification by ISCO flash column chromatography (Teledyne Isco RediSep Flash Column 40 g; 2% methanol/methylene chloride to 5% methanol/methylene chloride) afforded 3-nitro-1-phenethyl-1H-pyrazole (301 mg, 78%) as a white solid: H$^1$-NMR (400 MHz, CDCl$_3$) δ: 3.21 (3H, t, J=7.0 Hz), 4.41 (3H, t, J=6.9 Hz), 6.76 (1H, d, J=2.3 Hz), 7.07 (2H, m), 7.15 (1H, d, J=2.3 Hz), 7.27 (3H, m).

To a solution containing 3-nitro-1-phenethyl-1H-pyrazole (92 mg, 0.42 mmol) in tetrahydrofuran (2 mL), anhydrous hydrazine (100 μL) was added to the clear solution. Raney nickel (~100 mg washed 3 times with 5 mL of anhydrous tetrahydrofuran) was then added in tetrahydrofuran (300 μL). Gas evolved from the mixture and the reaction was allowed to proceed for 5 min, after which time the raney nickel was removed by filtration through a celite plug. The solvent was removed in vacuo to afford 1-phenethyl-1H-pyrazol-3-ylamine as a yellow oil which was used in the following step with no further purification.

To a solution containing 2(R)-(3-chloro-4-methanesulfonyl-phenyl)-3-cyclopentyl-propionic acid (prepared as in PCT WO 2004/052869 A1, Example 1, 100 mg, 0.30 mmol) in methylene chloride (20 mL), was then added a 2.0 M solution of oxalylchloride in methylene chloride (181 µL, 0.36 mmol) at 0° C. and allowed to stir at 25° C. for 1 h, after which time 2,6-lutidine (70 µL, 0.61 mmol) was added to the solution at 0° C. After 1 h, the crude 1-phenethyl-1H-pyrazol-3-ylamine (0.42 mmol based on theory) was added and the reaction was allowed to proceed for 16 h. The reaction solution was washed with 1.0 M aqueous hydrochloric acid solution, dried over sodium sulfate, concentrated in vacuo and purified by ISCO flash column chromatography (Teledyne Isco RediSep Flash Column 10 g; 0% methanol/methylene chloride to 10% methanol/methylene chloride) to afford 2(R)-(3-chloro-4-methanesulfonyl-phenyl)-3-cyclopentyl-N-(1-phenethyl-1H-pyrazol-3-yl)-propionamide (135 mg, 89%) as a white solid: ESI-LRMS m/e calcd for $C_{26}H_{30}ClN_3O_3S$ [M$^+$] 499.2, found 500.4 [M+H$^+$]; 1H NMR (400 MHz, CDCl$_3$) δ ppm 1.06-1.23 (m, 2H, CH$_2$), 1.39-1.93 (m, 8H, 4×CH$_2$), 2.09-2.33 (m, 1H, CH), 3.05 (t, J=7.2 Hz, 2H, ArCH$_2$), 3.26 (s, 3H, SO$_2$CH$_3$), 3.60 (t, J=7.6 Hz, 1H, CH), 4.16 (t, J=7.2 Hz, 2H, NCH$_2$), 6.58 (d, J=2.2 Hz, 1H, Ar), 7.00-7.05 (m, 3H, Ar), 7.16-7.29 (m, 3H, Ar), 7.47 (dd, $J_o$=8.1, $J_m$=1.6 Hz, 1H, Ar), 7.61 (d, $J_m$=1.6 Hz, 1H, Ar), 8.06 (d, $J_o$=8.1 Hz, 1H, Ar), 8.63 (s, 1H, NH).

Example 31

2(R)-(3-Chloro-4-methanesulfonyl-phenyl)-3-cyclopentyl-N-(1-propionyl-1H-pyrazol-3-yl)-propionamide

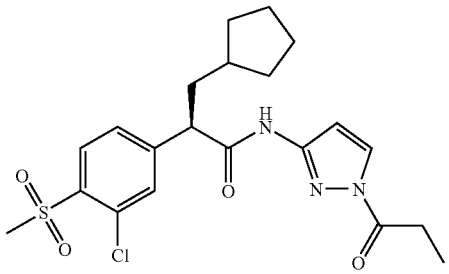

2(R)-(3-Chloro-4-methanesulfonyl-phenyl)-3-cyclopentyl-N-(1H-pyrazol-3-yl)-propionamide (prepared in example 2, 100 mg, 0.25 mmol) was dissolved in methylene chloride (2 mL). N-Methyl-morpholine (31 µL, 0.28 mmol) was added followed by propionyl chloride (26 µL, 0.28 mmol). The reaction stirred at 25° C. for 2.5 h. The solution was diluted with ethyl acetate (25 mL), washed with water (2×15 mL), saturated aqueous saturated aqueous brine solution (2×15 mL), dried over magnesium sulfate, filtered and concentrated in vacuo. Purification by ISCO flash column chromatography (Teledyne Isco RediSep Flash Column 10 g; 5% ethyl acetate/hexanes to 75% ethyl acetate/hexanes) afforded 2(R)-(3-chloro-4-methanesulfonyl-phenyl)-3-cyclopentyl-N-(1-propionyl-1H-pyrazol-3-yl)-propionamide (49 mg, 43%) as a white powder: ESI-LRMS m/e calcd for $C_{21}H_{26}ClN_3O_4S$ [M$^+$] 451.1, found 452.2 [M+H$^+$], 396.0 [M−COCH$_2$CH$_3$+ H$^+$]; $^1$H NMR (400 MHz, CDCl$_3$) δ ppm 1.08-1.24 (m, 2H, CH$_2$), 1.27 (t, J=7.3 Hz, 1H, CH$_3$), 1.44-1.97 (m, 8H, 4×CH$_2$), 2.14-2.32 (m, 1H, CH), 2.99 (q, J=7.3 Hz, 2H, CH$_2$), 3.27 (s, 3H, SO$_2$CH$_3$), 3.57 (t, J=7.5 Hz, 1H, CH), 6.98 (d, J=2.1, 1H, Ar), 7.46 (dd, $J_o$=8.1, $J_m$=1.5 Hz, 1H, Ar), 7.59 (d, $J_m$=1.5 Hz, 1 H, Ar), 7.81 (s, 1H, NH), 8.10-8.15 (m, 2H, Ar).

Example 32

2(R)-(3-Chloro-4-methanesulfonyl-phenyl)-3-cyclopentyl-N-(1-propyl-1H-pyrazol-3-yl)-propionamide

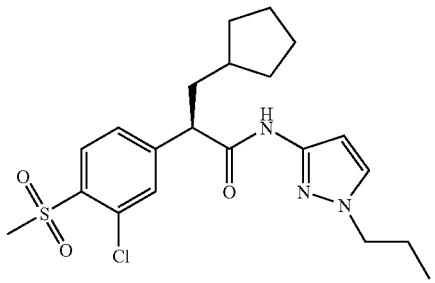

3-Nitro-1H-pyrazole (prepared in example 3, 100 mg, 0.89 mmol) was dissolved in anhydrous N,N-dimethylformamide (4 mL) and a 60% dispersion of sodium hydride in mineral oil (37 mg, 0.93 mmol) was added while stirring under nitrogen. After the effervescence ceased and the mixture was stirred for an additional 10 min, the 1-bromo-propane (91 µL, 1.00 mmol) was added. The mixture was continued to stir under nitrogen for 16 h. The solution was diluted with ethyl acetate (50 mL), washed with water (2×20 mL), saturated aqueous brine solution (2×20 mL), dried over magnesium sulfate, filtered and concentrated in vacuo. Purification by ISCO flash column chromatography (Teledyne Isco RediSep Flash Column 10 g; 25% ethyl acetate/hexanes to 75% ethyl acetate/hexanes) afforded 3-nitro-1-propyl-1H-pyrazole (92 mg, 67%) as a yellow oil: H$^1$-NMR (400 MHz, CDCl$_3$) δ0.89 (3H, t, J=7.6 Hz), 1.90 (2H, sextet, J=7.2 Hz), 6.82 (1H, d, J=2.8 Hz), 7.44 (1H, d, J=2.4 Hz).

3-Nitro-1-propyl-1H-pyrazole (92 mg, 0.59 mmol) was dissolved in ethyl acetate (3 mL) and methanol (3 mL) was added. Palladium, 10 wt. % on carbon, wet (~50 mg) was added to the mixture. The vial was charged with hydrogen gas (via balloon) and the mixture was stirred for 16 h at 25° C. The mixture was passed through a plug of celite and concentrated in vacuo followed by purification by flash column chromatography (Merck silica gel 60, 40-63 µm; 25% ethyl acetate/hexanes to 70% ethyl acetate/hexanes) afforded 1-propyl-1H-pyrazol-3-ylamine (54 mg, 73%) as a golden oil: ESI-LRMS m/e calcd for $C_6H_{11}N_3$ [M$^+$] 125.10, found 126.3 [M+H$^+$], 251.3 [2M+H$^+$].

Triphenylphosphine (173 mg, 0.66 mmol) was dissolved in methylene chloride (8 mL) and cooled to 0° C. To this solution was added N-bromosuccinimide (133 mg, 0.75 mmol) and was stirred at 0° C. until it was completely dissolved and became light purple in color. The 2(R)-(3-chloro-4-methanesulfonyl-phenyl)-3-cyclopentyl-propionic acid (prepared as in PCT WO 2004/052869 A1, Example 1, 146 mg, 0.44 mmol) was then added and it was stirred at 0° C. for 15 min and then warmed to 25° C. and stirred for 30 min. The mixture was chilled to 0° C. and 1-propyl-1H-pyrazol-3-ylamine (54 mg, 0.43 mmol) was added followed by 2,6-lutidine (154 µL, 1.32 mmol). The mixture was continued to stir at 0° C. for 30 min and then at 25° C. for 3 h. The reaction was diluted with ethyl acetate (50 mL), washed with water (3×20 mL) and saturated aqueous brine solution (2×20 mL). The organic layer was dried over magnesium sulfate, filtered and concentrated in vacuo. Purification by ISCO flash column chromatography (Teledyne Isco RediSep Flash Column 10 g; 10% ethyl acetate/hexanes to 70% ethyl acetate/hexanes) afforded 2(R)-(3-chloro-4-methanesulfonyl-phenyl)-3-cyclopentyl-N-(1-propyl-1H-pyrazol-3-yl)-propionamide (104 mg, 55%) as a white foam: ESI-LRMS m/e calcd for $C_{21}H_{28}ClN_3O_3S$ [M$^+$] 437.2, found 438.3 [M+H$^+$]; $^1$H NMR (400 MHz, CDCl$_3$) δ ppm 0.85 (t, J=7.4 Hz, 1H, CH$_3$), 1.04-1.16 (m, 2H, CH$_2$), 1.38-1.93 (m, 10H, 5×CH$_2$), 2.10-2.41 (m, 1H, CH), 3.24 (s, 3H, SO$_2$CH$_3$), 3.59 (t, J=7.5 Hz, 1H, CH), 3.89 (t, J=7.0 Hz, 2H, NCH2), 6.61 (d, J=2.2, 1H, Ar), 7.23 (d, J=2.2, 1H, Ar), 7.44 (dd, J$_o$=8.2, J$_m$=1.3 Hz, 1H, Ar), 7.57 (d, J$_m$=1.3 Hz, 1H, Ar), 8.02 (d, J$_o$=8.2 Hz, 1H, Ar), 8.61 (s, 1H, NH).

Example 33

2(R)-(3-Chloro-4-methanesulfonyl-phenyl)-3-cyclopentyl-N-(1-ethanesulfonyl-1H-pyrazol-3-yl)-propionamide

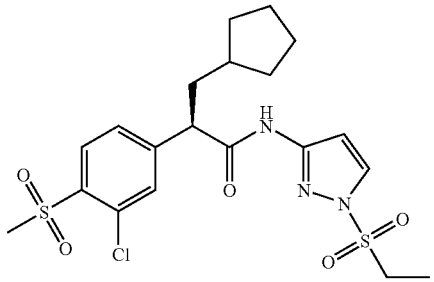

3-Nitro-1H-pyrazole (prepared in example 3, 100 mg, 0.89 mmol) was dissolved in anhydrous N,N-dimethylformamide (4 mL) and a 60% dispersion of sodium hydride in mineral oil (39 mg, 0.94 mmol) was added while stirring under nitrogen. After the effervescence ceased and the mixture was stirred for an additional 10 min, the ethanesulfonyl chloride (94 µL, 1.00 mmol) was added. The mixture was continued to stir under nitrogen for 16 h. The solution was diluted with ethyl acetate (50 mL), washed with water (2×20 mL), saturated aqueous brine solution (2×20 mL), dried over magnesium sulfate, filtered and concentrated in vacuo. Purification by ISCO flash column chromatography (Teledyne Isco RediSep Flash Column 10 g; 25% ethyl acetate/hexanes to 75% ethyl acetate/hexanes) afforded 1-ethanesulfonyl-3-nitro-1H-pyrazole (139 mg, 77%) as a clear, waxy solid: H$^1$-NMR (400 MHz, CDCl$_3$) δ 1.38 (2H, t, J=7.2 Hz), 3.68 (2H, qt, J=7.2 Hz), 7.05 (1H, d, J=2.8 Hz), 8.14 (1H, d, J=2.8 Hz).

Ethanesulfonyl-3-nitro-1H-pyrazole (139 mg, 0.68 mmol) was dissolved in ethyl acetate (3 mL) and methanol (3 mL) was added. Palladium, 10 wt. % on carbon, wet (~50 mg) was added to the mixture. The vial was charged with hydrogen gas (via balloon) and the mixture was stirred for 16 h at 25° C. The mixture was passed through a plug of celite and concentrated in vacuo followed by purification by flash column chromatography (Merck silica gel 60, 40-63 µm; 25% ethyl acetate/hexanes to 90% ethyl acetate/hexanes) afforded 1-ethanesulfonyl-1H-pyrazol-3-ylamine (88 mg, 74%) as a faintly yellow wax: ESI-LRMS m/e calcd for $C_5H_9N_3O_2S$ [M$^+$] 175.04, found 176.3 [M+H$^+$], 351.2 [2M+H$^+$].

Triphenylphosphine (216 mg, 0.83 mmol) was dissolved in methylene chloride (8 mL) and cooled to 0° C. To this solution was added N-bromosuccinimide (166 mg, 0.94 mmol) and was stirred at 0° C. until it was completely dissolved and became light purple in color. The 2(R)-(3-chloro-4-methanesulfonyl-phenyl)-3-cyclopentyl-propionic acid (prepared as in PCT WO 2004/052869 A1, Example 1, 182 mg, 0.55 mmol) was then added and it was stirred at 0° C. for 15 min and then warmed to 25° C. and stirred for 30 min. The mixture was chilled to 0° C. and 1-ethanesulfonyl-1H-pyrazol-3-ylamine (88 mg, 0.50 mmol) was added followed by 2,6-lutidine (192 µL, 1.65 mmol). The mixture was continued to stir at 0° C. for 30 min and then at 25° C. for 3 h. The reaction was diluted with ethyl acetate (50 mL), washed with water (3×20 mL) and saturated aqueous brine solution (2×20 mL). The organic layer was dried over magnesium sulfate, filtered and concentrated in vacuo. Purification by ISCO flash column chromatography (Teledyne Isco RediSep Flash Column 40 g; 10% ethyl acetate/hexanes to 70% ethyl acetate/hexanes) afforded 2(R)-(3-chloro-4-methanesulfonyl-phenyl)-3-cyclopentyl-N-(1-ethanesulfonyl-1H-pyrazol-3-yl)-propionamide (112 mg, 46%) as a white foam: ESI-LRMS m/e calcd for $C_{20}H_{26}ClN_3O_5S_2$ [M$^+$] 487.1. found 488.2 [M+H$^+$], 396.1 [M−SO$_2$CH$_2$CH$_3$+H$^+$]; $^1$H NMR (400 MHz, CDCl$_3$) δ ppm 1.04-1.18 (m, 2H, CH$_2$), 1.22 (t, J=7.3 Hz, 1H, CH$_3$), 1.40-1.89 (m, 8H, 4×CH$_2$), 2.12-2.23 (m, 1H, CH), 3.29 (s, 3H, SO$_2$CH$_3$), 3.38 (q, J=7.3 Hz, 2H, SO$_2$CH$_2$), 3.67 (t, J=7.5 Hz, 1H, CH), 6.99 (d, J=2.7 Hz, 1H, Ar), 7.45 (d, J$_o$=8.1, 1H, Ar), 7.56 (d, J$_m$=1.3 Hz, 1H, Ar), 7.89 (d, J=2.7 Hz, 1H, Ar), 8.06 (d, J$_o$=8.1 Hz, 1H, Ar), 8.74 (s, 1H, NH).

Example 34

2-(R)-(3-Chloro-4-methanesulfonyl-phenyl)-3-cyclopentyl-N-[1-((S)-2,3-dihydroxy-propyl)-1H-pyrazol-3-yl]-propionamide

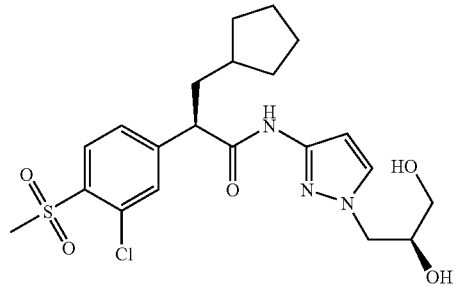

Nitro-1H-pyrazole (prepared in example 3, 205 mg, 1.81 mmol) was dissolved in anhydrous N,N-dimethylformamide (3.5 mL), the (R)-glycidol (148 mg, 2.00 mmol) was added followed by solid potassium carbonate (770 mg, 5.58 mmol). The mixture was heated to 120° C., while stirring in a sealed vial for 1 h. The mixture was diluted with water (15 mL) and the product extracted into ethyl acetate (6×25 mL). The combined organic layers were washed with saturated aqueous brine solution (15 mL), dried over magnesium sulfate and concentrated in vacuo to give a yellow oil. Purification by ISCO flash column chromatography (Teledyne Isco RediSep Flash Column 40 g; 15% ethyl acetate/hexanes to 100% ethyl acetate/hexanes) afforded 3-(3-nitro-pyrazol-1-yl)-propane-(S)-1,2-diol (118 mg, 34%) as a thick yellow oil: H$^1$-NMR (400 MHz, CD$_3$OD) δ 3.55 (2H, d, J=5.2 Hz), 4.02-4.05 (1H, m), 4.20 (1H, dd, J=13.6 Hz, 7.6 Hz), 4.39 (1H, dd, J=14.0 Hz, 3.6 Hz), 6.92 (1H, d, J=2.0 Hz), 7.79 (1H, d, J=2.0 Hz).

3-(3-Nitro-pyrazol-1-yl)-propane-(S)-1,2-diol (118 mg, 0.63 mmol) was dissolved in ethyl acetate (6 mL) and methanol (4 mL) was added. Palladium, 10 wt. % on activated carbon, wet (~50 mg) was added to the mixture. The vial was charged with hydrogen gas (via balloon) and the mixture was stirred for 16 h at 25° C. The mixture was passed through a plug of celite and concentrated in vacuo to give a yellow oil as the desired product, 3-(3-amino-pyrazol-1-yl)-propane-(S)-1,2-diol (81 mg, 82%) ESI-LRMS m/e calcd for $C_6H_{11}N_3O_2$ [M$^+$] 157.09, found 158.1 [M+H$^+$], 315.2 [2M+H$^+$].

Triphenylphosphine (202 mg, 0.77 mmol) was dissolved in methylene chloride (3 mL) and cooled to 0° C. To this solution was added N-bromosuccinimide (156 mg, 0.88 mmol) and was stirred at 0° C. until it was completely dissolved and became light purple in color. The 2(R)-(3-chloro-4-methanesulfonyl-phenyl)-3-cyclopentyl-propionic acid (prepared as in PCT WO 2004/052869 A1, Example 1, 171 mg, 0.52 mmol) was then added and it was stirred at 0° C. for 15 min and then warmed to 25° C. and stirred for 30 min. The reaction was chilled to 0° C. and the combined solution of 3-(3-amino-pyrazol-1-yl)-propane-(S)-1,2-diol (81 mg, 0.52 mmol) and 2,6-lutidine (180 μL, 1.55 mmol) in methylene chloride (4 mL) was added. The mixture was continued to stir at 0° C. for 30 min and then at 25° C. for 3 h. The reaction was diluted with ethyl acetate (50 mL), washed with water (3×20 mL) and saturated aqueous brine solution (2×20 mL). The organic layer was dried over magnesium sulfate, filtered and concentrated in vacuo. Purification by ISCO flash column chromatography (Teledyne Isco RediSep Flash Column 40 g; 15% ethyl acetate/hexanes to 100% ethyl acetate/hexanes) afforded 2-(R)-(3-chloro-4-methanesulfonyl-phenyl)-3-cyclopentyl-N-[1-((S)-2,3-dihydroxy-propyl)-1H-pyrazol-3-yl]-propionamide (56 mg, 23%) as a pale pink powder: ESI-LRMS m/e calcd for $C_{21}H_{28}ClN_3O_5S$ [M$^+$] 469.1, found 470.1 [M+H$^+$]; $^1$H NMR (400 MHz, CDCl$_3$) δ ppm 1.05-1.20 (m, 2H, CH$_2$), 1.32-1.91 (m, 8H, 4×CH$_2$), 2.10-2.33 (m, 1H, CH), 3.24 (s, 3H, SO$_2$CH$_3$), 3.34 (dd, J=11.5, 5.3 Hz, 1H, CH of OCH$_2$), 3.43 (dd, J=11.5, 3.2 Hz, 1H, CH of OCH$_2$), 3.48-3.99 (br.s., 2H, 2×OH), 3.68 (t, J=7.5 Hz, 1H, CH), 3.81-3.97 (m, 3H, OCH and NCH$_2$), 6.57 (d, J=2.2, 1H, Ar), 7.22 (d, J=2.2, 1H, Ar), 7.46 (dd, J$_o$=8.2, J$_m$=1.4 Hz. 1H, Ar), 7.59 (d, J$_m$=1.4 Hz, 1H, Ar), 8.00 (d, J$_o$=8.2, 1 H, Ar), 9.12 (s, 1H, NH).

Example 35

2-(R)-(3-Chloro-4-methanesulfonyl-phenyl)-3-cyclopentyl-N-[1-((R)-2,3-dihydroxy-propyl)-1H-pyrazol-3-yl]-propionamide

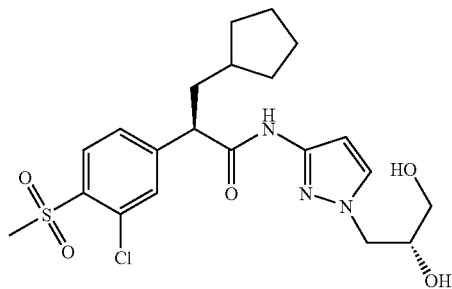

The 3-Nitro-1H-pyrazole (prepared in example 3, 200 mg, 1.77 mmol) was dissolved in anhydrous N,N-dimethylformamide (2 mL), (S)-glycidol (148 mg, 2.00 mmol) was added followed by the addition of solid potassium carbonate (367 mg, 2.60 mmol). The mixture was heated to 120° C., while stirring in a sealed vial for 1 h. The mixture was diluted with water (15 mL) and the product extracted into ethyl acetate (6×25 mL). The combined organic layers were washed with saturated aqueous brine solution (15 mL), dried over magnesium sulfate and concentrated in vacuo to a yellow oil. Purification by ISCO flash column chromatography (Teledyne Isco RediSep Flash Column 40 g; 15% ethyl acetate/hexanes to 100% ethyl acetate/hexanes) afforded 3-(3-nitro-pyrazol-1-yl)-propane-(R)-1,2-diol (95 mg, 29%) as a thick yellow oil: H$^1$-NMR (400 MHz, CD$_3$OD) δ 3.55 (2H, d, J=5.2 Hz), 4.02-4.05 (1H, m), 4.20 (1H, dd, J=13.6 Hz, 7.6 Hz), 4.39 (1H, dd, J=14.0 Hz, 3.6 Hz), 6.92 (1H, d, J=2.0 Hz), 7.79 (1H, d, J=2.0 Hz).

3-(3-Nitro-pyrazol-1-yl)-propane-(R)-1,2-diol (92 mg, 0.49 mmol) was dissolved in ethyl acetate (6 mL) and methanol (4 mL) was added. Palladium, 10 wt. % on carbon powder, wet (~50 mg) was added to the mixture. The vial was charged with hydrogen gas (via balloon) and the mixture was stirred for 16 h at 25° C. The mixture was passed through a plug of celite and concentrated in vacuo to give a yellow oil as the desired product, 3-(3-amino-pyrazol-1-yl)-propane-(R)-1,2-diol (69 mg, 89%) ESI-LRMS m/e calcd for $C_6H_{11}N_3O_2$ [M$^+$] 157.09, found 158.3 [M+H$^+$], 315.2 [2M+H$^+$].

Triphenylphosphine (172 mg, 0.66 mmol) was dissolved in methylene chloride (3 mL) and cooled to 0° C. To this solution was added N-bromosuccinimide (133 mg, 0.75 mmol) and was stirred at 0° C. until it was completely dissolved and became light purple in color. The 2(R)-(3-chloro-4-methanesulfonyl-phenyl)-3-cyclopentyl-propionic acid (prepared as in PCT WO 2004/052869 A1, Example 1, 146 mg, 0.44 mmol) was then added and it was stirred at 0° C. for 15 min and then warmed to 25° C. and stirred for 30 min. The reaction was chilled to 0° C. and the combined solution of 3-(3-amino-pyrazol-1-yl)-propane-(R)-1,2-diol (69 mg, 0.44 mmol) and 2,6-lutidine (154 μL, 1.32 mmol) in methylene chloride (4 mL) was added. The mixture was continued to stir at 0° C. for 30 min and then at 25° C. for 3 h. The reaction was diluted with ethyl acetate (50 mL), washed with water (3×20 mL) and saturated aqueous brine solution (2×20 mL). The organic layer was dried over magnesium sulfate, filtered and concentrated in vacuo. Purification by ISCO flash column chromatography (Teledyne Isco RediSep Flash Column 40 g; 15% ethyl acetate/hexanes to 100% ethyl acetate/hexanes) afforded 2-(R)-(3-chloro-4-methanesulfonyl-phenyl)-3-cyclopentyl-N-[1-((R)-2,3-dihydroxy-propyl)-1H-pyrazol-3-yl]-propionamide (73 mg, 35%) as a pale pink powder: ESI-LRMS m/e calcd for $C_{21}H_{28}ClN_3O_5S$ [M$^+$] 469.1, found 470.1 [M+H$^+$], 452.1 [M−H$_2$O+H$^+$]; $^1$H NMR (400 MHz, CDCl$_3$) δ ppm 1.07-1.20 (m, 2H, CH$_2$), 1.41-1.94 (m, 8H, 4×CH$_2$), 2.14-2.26 (m, 1H, CH), 3.02 (br.s., 2H, 2×OH), 3.27 (s, 3H, SO$_2$CH$_3$), 3.44-3.53 (m, 1H, CH of OCH$_2$), 3.56 (dd, J=11.4, 4.2 Hz, 1H, CH of OCH$_2$), 3.63 (t, J=7.6 Hz, 1H, CH), 3.91-4.11 (m, 3H, OCH and NCH$_2$), 6.65 (d, J=2.3, 1H, Ar), 7.29 (d, J=2.3, 1H, Ar), 7.48 (dd, J$_o$=8.2, J$_m$=1.7 Hz. 1H, Ar), 7.62 (d, J$_m$=1.7 Hz, 1H, Ar), 8.07 (d, J$_o$=8.2, 1H, Ar), 8.44 (s, 1H, NH).

Example 36

3-[2-(R)-(3-Chloro-4-methanesulfonyl-phenyl)-3-cyclopentyl-propionylamino]-pyrazole-1-carboxylic acid methylamide

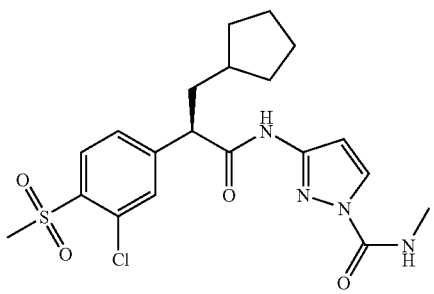

The 2-(R)-(3-chloro-4-methanesulfonyl-phenyl)-3-cyclopentyl-N-(1H-pyrazol-3-yl)-propionamide (prepared in example 2, 115 mg, 0.29 mmol) was dissolved in anhydrous N,N-dimethylformamide (2 mL) and warmed to 60° C. in a sealed vial. Methyl-isocyanate (165 mg, 2.90 mmol) was transferred via syringe to the pyrazole solution. The mixture was heated at 60° C. for 2 h while stirring in the sealed vial. The mixture was diluted with ethyl acetate (25 mL), washed with water (2×15 mL), saturated aqueous brine solution (15 mL), dried over magnesium sulfate and concentrated in vacuo. Purification by ISCO flash column chromatography (Teledyne Isco RediSep Flash Column 10 g; 15% ethyl acetate/hexanes to 100% ethyl acetate/hexanes) afforded 3-[2-(R)-(3-chloro-4-methanesulfonyl-phenyl)-3-cyclopentyl-propionylamino]-pyrazole-1-carboxylic acid methylamide (18 mg, 14%) as a white powder: ESI-LRMS m/e calcd for C$_{20}$H$_{25}$ClN$_4$O$_4$S [M$^+$] 452.1, found 453.2 [M+H$^+$], 395.9 [M−CONCH$_3$+H$^+$]; $^1$H NMR (400 MHz, CDCl$_3$) δ ppm 1.04-1.23 (m, 2H, CH$_2$), 1.43-1.97 (m, 8H, 4×CH$_2$), 2.11-2.34 (m, 1H, CH), 2.95 (d, J=4.6 Hz, 3H, NCH$_3$), 3.27 (s, 3H, SO$_2$CH$_3$), 3.65 (t, J=7.5 Hz, 1H, CH), 6.81 (q, J=4.6 Hz, 1H, NH), 6.84 (d, J=2.7 Hz, 1H, Ar), 7.46 (dd, J$_o$=8.2, J$_m$=1.7 Hz, 1H, Ar), 7.60 (d, J$_m$=1.7 Hz, 1H, Ar), 8.04 (d, J$_o$=8.2 Hz, 1 H, Ar), 8.07 (d, J=2.7 Hz, 1H, Ar), 8.32 (s, 1H, NH).

Example 37

2-(R)-(3-Chloro-4-methanesulfonyl-phenyl)-3-cyclopentyl-N-[1-(3-hydroxy-3-methyl-butyryl)-1H-pyrazol-3-yl]-propionamide

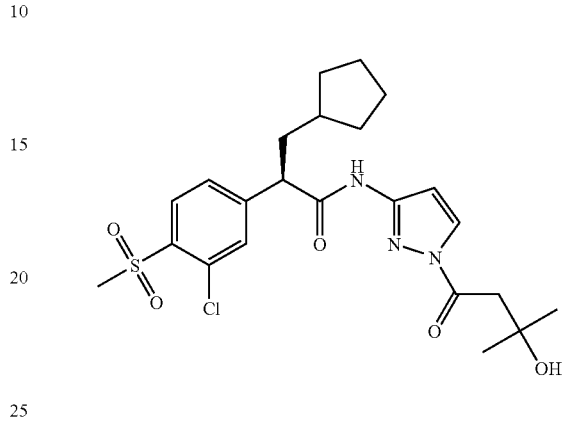

A solution containing N,N-dimethylformamide (0.22 mL, 2.85 mmol) and tetrahydrofuran (10 mL) was chilled to 0° C. under nitrogen. While stirring, oxalyl chloride (156 μL, 1.80 mmol) was added, gas evolution was observed followed by a white precipitate. The mixture was stirred at 0° C. for 5 min and at 25° C. for 15 min. The mixture was chilled to −5° C. and the 3-hydroxy-3-methyl-butyric acid (224 mg, 1.90 mmol) was added as a solution in tetrahydrofuran (3 mL) and the mixture was allowed to stir for 10 min. 3-Nitro-1H-pyrazole (prepared in example 3, 200 mg, 1.77 mmol) was dissolved in anhydrous N,N-dimethylformamide (4 mL) and a 60% dispersion of sodium hydride in mineral oil (78 mg, 1.95 mmol) was added while stirring under nitrogen. After the effervescence ceased and the mixture was stirred for an additional 10 min, the mixture was added to the 3-hydroxy-3-methyl-butyric acid solution at −5° C. and continued to stir at 0° C. for 2 h. The mixture was diluted with ethyl acetate (100 mL), washed with water (2×25 mL), saturated aqueous brine solution (25 mL), dried over magnesium sulfate and concentrated in vacuo. Purification by ISCO flash column chromatography (Teledyne Isco RediSep Flash Column 40 g; 15% ethyl acetate/hexanes to 100% ethyl acetate/hexanes) afforded 3-hydroxy-3-methyl-1-(3-nitro-pyrazol-1-yl)-butan-1-one (101 mg, 27%) as a clear oil: H$^1$-NMR (400 MHz, CDCl$_3$) δ 1.42 (6H, s), 3.41 (2H, s), 7.05 (1H, d, J=2.8 Hz), 8.34 (1H, d, J=2.8 Hz).

Hydroxy-3-methyl-1-(3-nitro-pyrazol-1-yl)-butan-1-one (101 mg, 0.47 mmol) was dissolved in ethyl acetate (8 mL). Palladium, 10 wt. % on carbon powder, wet (~50 mg) was added to the mixture. The vial was charged with hydrogen gas (via balloon) and the mixture was stirred for 16 h at 25° C. The mixture was passed through a plug of celite and concentrated in vacuo to give an orange/yellow oil as the desired product, 1-(3-amino-pyrazol-1-yl)-3-hydroxy-3-methyl-butan-1-one (87 mg, 99%) ESI-LRMS m/e calcd for C$_8$H$_{13}$N$_3$O$_2$ [M$^+$] 183.10, found 184.3 [M+H$^+$],367.2 [2M+H$^+$].

Triphenylphosphine (186 mg, 0.71 mmol) was dissolved in methylene chloride (3 mL) and cooled to 0° C. To this solution was added N-bromosuccinimide (143 mg, 0.81 mmol) and was stirred at 0° C. until it was completely dissolved and became light purple in color. The 2(R)-(3-chloro-4-methanesulfonyl-phenyl)-3-cyclopentyl-propionic acid (prepared as in PCT WO 2004/052869 A1, Example 1, 157 mg, 0.47 mmol) was then added and it was stirred at 0° C. for 15 min and then warmed to 25° C. and stirred for 30 min. The reaction was chilled to 0° C. and the combined solution of 1-(3-amino-pyrazol-1-yl)-3-hydroxy-3-methyl-butan-1-one (87 mg, 0.47 mmol) and 2,6-lutidine (0.165 mL, 1.42 mmol) in methylene chloride (4 mL) was added. The mixture was continued to stir at 0° C. for 30 min and then at 25° C. for 3 h. The reaction was diluted with ethyl acetate (50 mL), washed with water (3×20 mL) and saturated aqueous brine solution (2×20 mL). The organic layer was dried over magnesium sulfate, filtered and concentrated in vacuo. Purification by ISCO flash column chromatography (Teledyne Isco RediSep Flash Column 40 g; 40% ethyl acetate/hexanes) eluted the desired product and an impurity simultaneously. Further purification by flash column chromatography (Merck silica gel 60, 40-63 μm; 20% ethyl acetate/methylene chloride) afforded 2-(R)-(3-chloro-4-methanesulfonyl-phenyl)-3-cyclopentyl-N-[1-(3-hydroxy-3-methyl-butyryl)-1H-pyrazol-3-yl]-propionamide (28 mg, 12%) as a white powder: ESI-LRMS m/e calcd for $C_{23}H_{30}ClN_3O_5S$ [M$^+$] 495.2, found 496.2 [M+H$^+$], 478.0 [M−H$_2$O+H$^+$], 396.0 [M−COCH$_2$C(CH$_3$)$_2$OH]; $^1$H NMR (400 MHz, CDCl$_3$) δ ppm 1.07-1.23 (m, 2H, CH$_2$), 1.37 (s, 6H, 2×CH$_3$), 1.44-1.98 (m, 8H, 4×CH$_2$), 2.09-2.32 (m, 1H, CH), 3.23 (AB, J$_{gem}$=17.4 Hz, 2H, CH$_2$), 3.27 (s, 3H, SO$_2$CH$_3$), 3.64 (t, J=7.5 Hz, 1H, CH), 7.02 (d, J=2.9 Hz, 1 H, Ar), 7.47 (dd, J$_o$=8.2, J$_m$=1.7 Hz, 1H, Ar), 7.60 (d, J$_m$=1.7 Hz, 1H, Ar), 8.08 (d, J$_o$=8.2 Hz, 1H, Ar), 8.14 (d, J=2.9 Hz, 1H, Ar), 8.46 (s, 1H, NH).

Example 38

2-(R)-(3-Chloro-4-methanesulfonyl-phenyl)-3-cyclopentyl-N-(1-ethyl-1H-pyrazol-3-yl)-propionamide

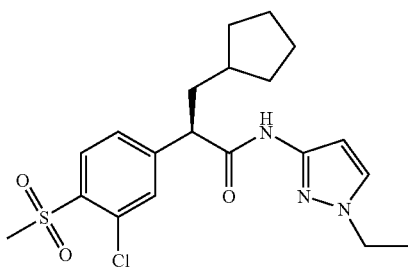

Nitro-1H-pyrazole (prepared in example 3, 100 mg, 0.89 mmol) was dissolved in anhydrous N,N-dimethylformamide (4 mL) and a 60% dispersion of sodium hydride in mineral oil (42 mg, 1.06 mmol) was added while stirring under nitrogen. After the effervescence ceased and the mixture was stirred for an additional 10 min before bromoethane (79 μL, 1.06 mmol) was added. The mixture was continued to stir under nitrogen for 4 h. The mixture was stored at −25° C. for 16 h. The solution was diluted with ethyl acetate (30 mL), washed with water (2×10 mL), saturated aqueous brine solution (10 mL), dried over magnesium sulfate, filtered and concentrated in vacuo. Purification by ISCO flash column chromatography (Teledyne Isco RediSep Flash Column 10 g; 25% ethyl acetate/hexanes to 75% ethyl acetate/hexanes) to afford 3-nitro-1-ethyl-1H-pyrazole (85 mg, 57%) as a clear oil.

3-Nitro-1-ethyl-1H-pyrazole (85 mg, 0.60 mmol) was dissolved in ethyl acetate (3 mL) and methanol (3 mL) was added. Palladium, 10 wt. % on activated carbon, wet (~50 mg) was added to the mixture. The vial was charged with hydrogen gas (via balloon) and the mixture was stirred for 16 h at 25° C. The mixture was passed through a plug of celite and concentrated in vacuo to afford 1-ethyl-1H-pyrazol-3-ylamine (59 mg, 88%) as a golden oil: ESI-LRMS m/e calcd for $C_5H_9N_3$ [M$^+$] 111.08, found 112.4 [M+H$^+$].

2(R)-(3-Chloro-4-methanesulfonyl-phenyl)-3-cyclopentyl-propionic acid (prepared as in PCT WO 2004/052869 A1, Example 1, 175 mg, 0.53 mmol) was dissolved in methylene chloride and a 2.0 M solution of oxalyl chloride in methylene chloride (193 mg, 0.58 mmol) was added. The reaction stirred at 25° C. for 1 h. The reaction was chilled to 0° C. under nitrogen and 2,6-lutidine (142 μL, 1.22 mmol) was added dropwise. The reaction became golden brown, the ice bath was removed and the reaction continued to stir at 25° C. for 30 min. 1-Ethyl-1H-pyrazol-3-ylamine (59 mg, 0.51 mmol) was dissolved in methylene chloride and added dropwise to the reaction. The solution continued to stir at 25° C. for 16 h. The reaction was diluted with methylene chloride, washed with water and saturated aqueous brine solution. The organic layer was dried over magnesium sulfate, filtered and concentrated in vacuo. Purification by ISCO flash column chromatography (Teledyne Isco RediSep Flash Column 40 g; 10% ethyl acetate/hexanes to 70% ethyl acetate/hexanes) afforded 2-(R)-(3-chloro-4-methanesulfonyl-phenyl)-3-cyclopentyl-N-(1-ethyl-1H-pyrazol-3-yl)-propionamide as a white powder (139 mg, 62%) ESI-LRMS m/e calcd for $C_{20}H_{26}ClN_3O_3S$ [M$^+$] 423.1, found 424.1 [M+H$^+$]; $^1$H NMR (400 MHz, CDCl$_3$) δ ppm 1.07-1.21 (m, 2H, CH$_2$), 1.44 (t, J=7.3 Hz, 3H, CH$_3$), 1.47-1.96 (m, 8H, 4×CH$_2$), 2.16-2.29 (m, 1H, CH), 3.26 (s, 3H, SO$_2$CH$_3$), 3.53 (t, J=7.5 Hz, 1H, CH), 4.03 (q, J=7.3 Hz, 2H, NCH2), 6.64 (d, J=2.3 Hz, 1H, Ar), 7.27 (d, J=2.3 Hz, 1H, Ar), 7.46 (dd, J$_o$=8.1, J$_m$=1.7 Hz. 1H, Ar), 7.59 (d, J$_m$=1.7 Hz, 1H, Ar), 7.94 (s, 1H, NH), 8.08 (d, J$_o$=8.1 Hz, 1H, Ar).

Example 39

2-(R)-(3-Chloro-4-methanesulfonyl-phenyl)-3-cyclopentyl-N-(1-butyl-1H-pyrazol-3-yl)-propionamide

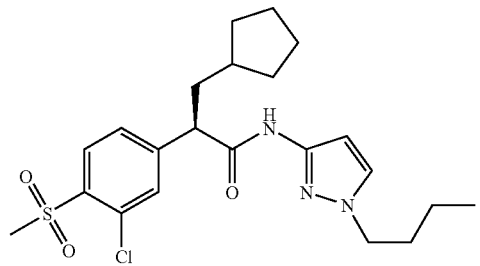

3-Nitro-1H-pyrazole (prepared in example 3, 100 mg, 0.89 mmol) was dissolved in anhydrous N,N-dimethylformamide (4 mL) and a 60% dispersion of sodium hydride in mineral oil (42 mg, 1.06 mmol) was added while stirring under nitrogen. After the effervescence ceased and the reaction stirred for an additional 10 min before 1-iodo-butane (121 μL, 1.06 mmol) was added. The reaction continued to stir under nitrogen for 4 h. The reaction was stored at −25° C. for 16 h. The solution was diluted with ethyl acetate (30 mL), washed with water (2×10 mL), saturated aqueous brine solution (10 mL), dried over magnesium sulfate, filtered and concentrated in vacuo.

Purification by ISCO flash column chromatography (Teledyne Isco RediSep Flash Column 40 g; 25% ethyl acetate/hexanes to 75% ethyl acetate/hexanes) afforded 3-nitro-1-butyl-1H-pyrazole (111 mg, 62%) as a clear oil.

3-Nitro-1-butyl-1H-pyrazole (111 mg, 0.66 mmol) was dissolved in ethyl acetate (3 mL) and methanol (3 mL) was added. Palladium, 10 wt. % on activated carbon, wet (~50 mg) was added to the reaction. The vial was charged with hydrogen gas (via balloon) and the reaction stirred for 16 h at 25° C. The reaction was passed through a plug of celite and concentrated in vacuo to afford 1-butyl-1H-pyrazol-3-ylamine (82 mg, 90%) as a golden oil: ESI-LRMS m/e calcd for $C_7H_{13}N_3$ [M$^+$] 139.12, found 140.3 [M+H$^+$].

2(R)-(3-Chloro-4-methanesulfonyl-phenyl)-3-cyclopentyl-propionic acid (prepared as in PCT WO 2004/052869 A1, Example 1, 194 mg, 0.59 mmol) was dissolved in methylene chloride and a 2.0 M solution of oxalyl chloride in methylene chloride (214 mg, 0.65 mmol) was added. The reaction stirred at 25° C. for 1 h. The reaction was chilled to 0° C. under nitrogen and 2,6-lutidine (157 µL, 1.36 mmol) was added dropwise. The reaction became golden brown, the ice bath was removed and the reaction continued to stir at 25° C. for 30 min. 1-Butyl-1H-pyrazol-3-ylamine (82 mg, 0.59 mmol) was dissolved in methylene chloride and added dropwise to the reaction. The solution continued to stir at 25° C. for 16 h. The reaction was diluted with methylene chloride, washed with water and saturated aqueous brine solution. The organic layer was dried over magnesium sulfate, filtered and concentrated in vacuo. Purification by ISCO flash column chromatography (Teledyne Isco RediSep Flash Column 40 g; 10% ethyl acetate/hexanes to 70% ethyl acetate/hexanes) afforded 2-(R)-(3-chloro-4-methanesulfonyl-phenyl)-3-cyclopentyl-N-(1-butyl-1H-pyrazol-3-yl)-propionamide (150 g, 56%) as a white powder: ESI-LRMS m/e calcd for $C_{22}H_{30}ClN_3O_3S$ [M$^+$] 451.17, found 452.3 [M+H$^+$]; $^1$H NMR (400 MHz, CDCl$_3$) δ ppm 0.93 (t, J=7.3 Hz, 3H, CH$_3$), 1.07-1.21 (m, 2H, CH$_2$), 1.25-1.37 (m, 2H, CH$_2$), 1.45-1.96 (m, 10H, 5×CH$_2$), 2.12-2.31 (m, 1H, CH), 3.26 (s, 3H, SO$_2$CH$_3$), 3.53 (t, J=7.6 Hz, 1H, CH), 3.96 (t, J=7.1 Hz, 2H, NCH2), 6.62 (d, J=2.3 Hz, 1H, Ar), 7.24 (d, J=2.3 Hz, 1H, Ar), 7.45 (dd, J$_o$=8.1, J$_m$=1.8 Hz. H, Ar), 7.58 (d, J$_m$=1.8 Hz, 1H, Ar), 7.85 (s, 1H, NH), 8.08 (d, J$_o$=8.1 Hz, 1 H, Ar).

Example 40

2-(R)-(3-Chloro-4-methanesulfonyl-phenyl)-3-cyclopentyl-N-(1-hexyl-1H-pyrazol-3-yl)-propionamide

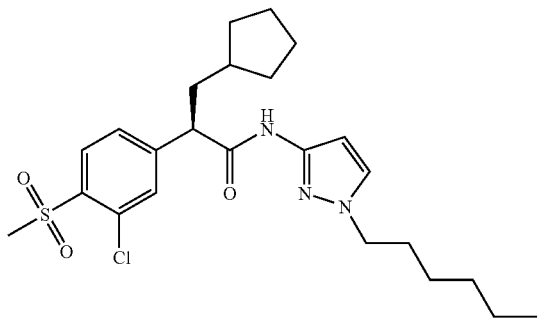

3-Nitro-1H-pyrazole (prepared in example 3, 100 mg, 0.89 mmol) was dissolved in anhydrous N,N-dimethylformamide (4 mL) and a 60% dispersion of sodium hydride in mineral oil (42 mg, 1.06 mmol) was added while stirring under nitrogen. After the effervescence ceased and the reaction stirred for an additional 10 min before 1-bromo-hexane (150 µL, 1.06 mmol) was added. The reaction continued to stir under nitrogen for 4 h. The reaction was stored at −25° C. for 16 h. The solution was diluted with ethyl acetate (30 mL), washed with water (2×10 mL), saturated aqueous brine solution (10 mL), dried over magnesium sulfate, filtered and concentrated in vacuo. Purification by ISCO flash column chromatography (Teledyne Isco RediSep Flash Column 10 g; 25% ethyl acetate/hexanes to 75% ethyl acetate/hexanes) afforded 3-nitro-1-hexyl-1H-pyrazole (118 mg, 56%) as a clear oil.

3-Nitro-1-hexyl-1H-pyrazole (118 mg, 0.60 mmol) was dissolved in ethyl acetate (3 mL) and methanol (3 mL) was added. Palladium, 10 wt. % on activated carbon, wet (~50 mg) was added to the reaction. The vial was charged with hydrogen gas (via balloon) and the reaction stirred for 16 h at 25° C. The mixture was passed through a plug of celite and concentrated in vacuo afforded 1-hexyl-1H-pyrazol-3-ylamine (88 mg, 88%) as a golden oil: ESI-LRMS m/e calcd for $C_9H_{17}N_3$ [M$^+$] 167.15, found 168.4 [M+H$^+$].

2(R)-(3-Chloro-4-methanesulfonyl-phenyl)-3-cyclopentyl-propionic acid (prepared as in PCT WO 2004/052869 A1, Example 1, 174 mg, 0.53 mmol) was dissolved in methylene chloride and a 2.0 M solution of oxalyl chloride in methylene chloride (191 mg, 0.58 mmol) was added. The reaction stirred at 25° C. for 1 h. The reaction was chilled to 0° C. under nitrogen and 2,6-lutidine (140 µL, 1.21 mmol) was added dropwise. The reaction became golden brown, the ice bath was removed and the reaction continued to stir at 25° C. for 30 min. 1-Hexyl-1H-pyrazol-3-ylamine (88 mg, 0.53 mmol) was dissolved in methylene chloride and added dropwise to the reaction. The solution continued to stir at 25° C. for 16 h. The reaction was diluted with methylene chloride, washed with water and saturated aqueous brine solution. The organic layer was dried over magnesium sulfate, filtered and concentrated in vacuo. Purification by ISCO flash column chromatography (Teledyne Isco RediSep Flash Column 40 g; 10% ethyl acetate/hexanes to 70% ethyl acetate/hexanes) to afford 2-(R)-(3-chloro-4-methanesulfonyl-phenyl)-3-cyclopentyl-N-(1-hexyl-1H-pyrazol-3-yl)-propionamide as a white powder (171 mg, 68%) ESI-LRMS m/e calcd for $C_{24}H_{34}ClN_3O_3S$ [M$^+$] 479.2, found 480.5 [M+H$^+$]; $^1$H NMR (400 MHz, CDCl$_3$) δ ppm 0.88 (t, J=6.7 Hz, 3H, CH$_3$), 1.08-1.21 (m, 2H, CH$_2$), 1.24-1.37 (m, 6H, 3×CH$_2$), 1.45-1.94 (m, 10H, 5×CH$_2$), 2.09-2.31 (m, 1H, CH), 3.26 (s, 3H, SO$_2$CH$_3$), 3.53 (t, J=7.6 Hz, 1H, CH), 3.96 (t, J=7.1 Hz, 2H, NCH2), 6.63 (d, J=2.3 Hz, 1H, Ar), 7.24 (d, J=2.3 Hz, 1H, Ar), 7.45 (dd, $J_o$=8.1, $J_m$=1.8 Hz. 1H, Ar), 7.59 (d, $J_m$=1.8 Hz, 1H, Ar), 7.82 (s, 1H, NH), 8.09 (d, $J_o$=8.1 Hz, 1H, Ar).

Example 41

2-(R)-(3-Chloro-4-methanesulfonyl-phenyl)-3-cyclopentyl-N-(1-octyl-1H-pyrazol-3-yl)-propionamide

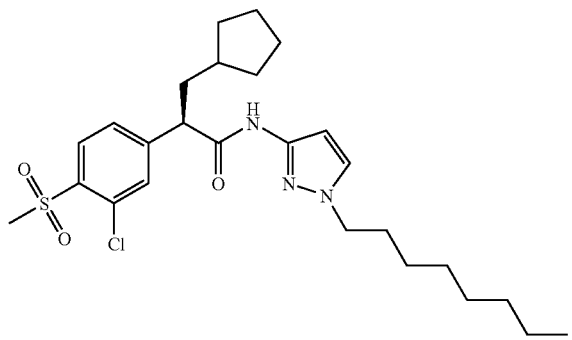

3-Nitro-1H-pyrazole (prepared in example 3, 100 mg, 0.89 mmol) was dissolved in anhydrous N,N-dimethylformamide (4 mL) and a 60% dispersion of sodium hydride in mineral oil (42 mg, 1.06 mmol) was added while stirring under nitrogen. After the effervescence ceased and the reaction stirred for an additional 10 min before 1-bromo-octane (183 μL, 1.06 mmol) was added. The reaction continued to stir under nitrogen for 4 h. The reaction was stored at –25° C. for 16 h. The solution was diluted with ethyl acetate (30 mL), washed with water (2×10 mL), saturated aqueous brine solution (10 mL), dried over magnesium sulfate, filtered and concentrated in vacuo. Purification by ISCO flash column chromatography (Teledyne Isco RediSep Flash Column 40 g; 25% ethyl acetate/hexanes to 75% ethyl acetate/hexanes) afforded 3-nitro-1-octyl-1H-pyrazole (134 mg, 56%) as a clear oil.

3-Nitro-1-octyl-1H-pyrazole (134 mg, 0.60 mmol) was dissolved in ethyl acetate (3 mL) and methanol (3 mL) was added. Palladium, 10 wt. % on activated carbon, wet (~50 mg) was added to the reaction. The vial was charged with hydrogen gas (via balloon) and the reaction stirred for 16 h at 25° C. The reaction was passed through a plug of celite and concentrated in vacuo to afford 1-octyl-1H-pyrazol-3-ylamine (48 mg, 41%) as a golden oil: ESI-LRMS m/e calcd for $C_{11}H_{21}N_3$ [M+] 195.18, found 196.2 [M+H+].

2(R)-(3-Chloro-4-methanesulfonyl-phenyl)-3-cyclopentyl-propionic acid (prepared as in PCT WO 2004/052869 A1, Example 1, 81 mg, 0.25 mmol) was dissolved in methylene chloride and a 2.0 M solution of oxalyl chloride in methylene chloride (90 mg, 0.27 mmol) was added. The reaction stirred at 25° C. for 1 h. The reaction was chilled to 0° C. under nitrogen and 2,6-lutidine (66 μL, 0.57 mmol) was added dropwise.

The reaction became golden brown, the ice bath was removed and the reaction continued to stir at 25° C. for 30 min. 1-Octyl-1H-pyrazol-3-ylamine (48 mg, 0.25 mmol) was dissolved in methylene chloride and added dropwise to the reaction. The solution continued to stir at 25° C. for 16 h. The reaction was diluted with methylene chloride, washed with water and saturated aqueous brine solution. The organic layer was dried over magnesium sulfate, filtered and concentrated in vacuo. Purification by ISCO flash column chromatography (Teledyne Isco RediSep Flash Column 10 g; 10% ethyl acetate/hexanes to 70% ethyl acetate/hexanes) afforded 2-(R)-(3-chloro-4-methanesulfonyl-phenyl)-3-cyclopentyl-N-(1-octyl-1H-pyrazol-3-yl)-propionamide (76 mg, 61%) as a white foam: ESI-LRMS m/e calcd for $C_{26}H_{38}ClN_3O_3S$ [M+] 507.23, found 508.2 [M+H+]; $^1$H NMR (400 MHz, CDCl$_3$) δ ppm 0.88 (t, J=6.8 Hz, 3H, CH$_3$), 1.07-1.21 (m, 2H, CH$_2$), 1.19-1.39 (m, 10H, 5×CH$_2$), 1.42-1.96 (m, 10H, 5×CH$_2$), 2.14-2.30 (m, 1H, CH), 3.26 (s, 3H, SO$_2$CH$_3$), 3.53 (t, J=7.6 Hz, 1H, CH), 3.96 (t, J=7.1 Hz, 2H, NCH2), 6.63 (d, J=2.3 Hz, 1H, Ar), 7.24 (d, J=2.3 Hz, 1H, Ar), 7.45 (dd, $J_o$=8.1, $J_m$=1.7 Hz. 1H, Ar), 7.59 (d, $J_m$=1.7 Hz, 1H, Ar), 7.83 (s, 1H, NH), 8.09 (d, $J_o$=8.1 Hz, 1H, Ar).

Example 42

2-(R)-(3-Chloro-4-methanesulfonyl-phenyl)-3-cyclopentyl-N-(1-iso-butyl-1H-pyrazol-3-yl)-propionamide

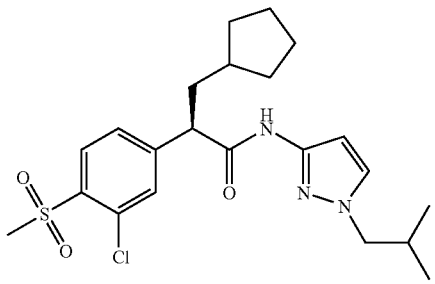

3-Nitro-1H-pyrazole (prepared in example 3, 100 mg, 0.89 mmol) was dissolved in anhydrous N,N-dimethylformamide (4 mL) and a 60% dispersion of sodium hydride in mineral oil (42 mg, 1.06 mmol) was added while stirring under nitrogen. After the effervescence ceased and the reaction stirred for an additional 10 min before 1-bromo-2-methyl-propane (115 μL, 1.06 mmol) was added. The reaction continued to stir under nitrogen for 4 h. The reaction was stored at –25° C. for 16 h. The solution was diluted with ethyl acetate (30 mL), washed with water (2×10 mL), saturated aqueous brine solution (10 mL), dried over magnesium sulfate, filtered and concentrated in vacuo. Purification by ISCO flash column chromatography (Teledyne Isco RediSep Flash Column 10 g; 25% ethyl acetate/hexanes to 75% ethyl acetate/hexanes) afforded 3-nitro-1-iso-butyl-1H-pyrazole (83 mg, 46%) as a white powder.

3-Nitro-1-iso-butyl-1H-pyrazole (83 mg, 0.49 mmol) was dissolved in ethyl acetate (3 mL) and methanol (3 mL) was added. Palladium, 10 wt. % on activated carbon, wet (~50 mg) was added to the reaction. The vial was charged with hydrogen gas (via balloon) and the reaction stirred for 16 h at 25° C. The reaction was passed through a plug of celite and concentrated in vacuo to afford 1-iso-butyl-1H-pyrazol-3-ylamine (59 mg, 86%) as a golden oil: ESI-LRMS m/e calcd for $C_7H_{13}N_3$ [M+] 139.1, found 140.3 [M+H+].

2(R)-(3-Chloro-4-methanesulfonyl-phenyl)-3-cyclopentyl-propionic acid (prepared as in PCT WO 2004/052869 A1, Example 1, 140 mg, 0.42 mmol) was dissolved in methylene chloride and a 2.0 M solution of oxalyl chloride in methylene chloride (154 mg, 0.47 mmol) was added. The reaction stirred at 25° C. for 1 h. The reaction was chilled to 0° C. under nitrogen and 2,6-lutidine (113 μL, 0.98 mmol) was added dropwise. The reaction became golden brown, the ice bath was removed and the reaction continued to stir at 25° C. for 30 min. 1-Iso-butyl-1H-pyrazol-3-ylamine (59 mg, 0.42 mmol)

was dissolved in methylene chloride and added dropwise to the reaction. The solution continued to stir at 25° C. for 16 h. The reaction was diluted with methylene chloride, washed with water and saturated aqueous brine solution. The organic layer was dried over magnesium sulfate, filtered and concentrated in vacuo. Purification by ISCO flash column chromatography (Teledyne Isco RediSep Flash Column 40 g; 10% ethyl acetate/hexanes to 70% ethyl acetate/hexanes) afforded 2-(R)-(3-chloro-4-methanesulfonyl-phenyl)-3-cyclopentyl-N-(1-iso-butyl-1H-pyrazol-3-yl)-propionamide (117 mg, 61%) as a white foam: ESI-LRMS m/e calcd for $C_{22}H_{30}ClN_3O_3S$ [M$^+$] 451.2, found 452.2 [M+H$^+$]; $^1$H NMR (400 MHz, CDCl$_3$) δ ppm 0.89 (dd, J=6.7, 2.2 Hz, 6H, 2×CH$_3$), 1.06-1.20 (m, 2H, CH$_2$), 1.44-1.94 (m, 8H, 4×CH$_2$), 2.07-2.31 (m, 1H, CH), 3.26 (s, 3H, SO$_2$CH$_3$), 3.53 (t, J=7.6 Hz, 1H, CH), 3.76 (d, J=7.2 Hz, 2H, NCH2), 6.64 (d, J=2.3 Hz, 1H, Ar), 7.23 (d, J=2.3 Hz, 1H, Ar), 7.45 (dd, J$_o$=8.2, J$_m$=1.8 Hz, 1H, Ar), 7.59 (d, J$_m$=1.8 Hz, 1H, Ar), 7.80 (s, 1H, NH), 8.09 (d, J$_o$=8.2 Hz, 1H, Ar).

Example 43

2-(R)-(3-Chloro-4-methanesulfonyl-phenyl)-3-cyclopentyl-N-(1-iso-pentyl-1H-pyrazol-3-yl)-propionamide

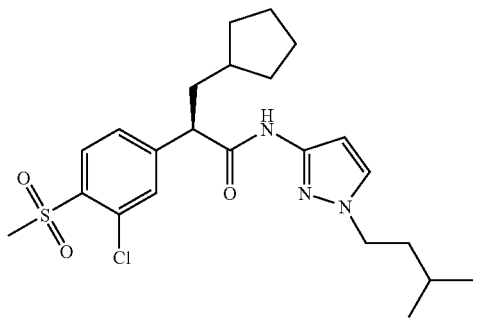

3-Nitro-1H-pyrazole (prepared in example 3, 100 mg, 0.89 mmol) was dissolved in anhydrous N,N-dimethylformamide (4 mL) and a 60% dispersion of sodium hydride in mineral oil (42 mg, 1.06 mmol) was added while stirring under nitrogen. After the effervescence ceased and the reaction stirred for an additional 10 min before 1-bromo-3-methyl-butane (0.133 mL, 1.06 mmol) was added. The reaction continued to stir under nitrogen for 4 h. The reaction was stored at −25° C. for 16 h. The solution was diluted with ethyl acetate (30 mL), washed with water (2×10 mL), saturated aqueous brine solution (10 mL), dried over magnesium sulfate, filtered and concentrated in vacuo. Purification by ISCO flash column chromatography (Teledyne Isco RediSep Flash Column 40 g; 25% ethyl acetate/hexanes to 75% ethyl acetate/hexanes) afforded 3-nitro-1-iso-pentyl-1H-pyrazole (115 mg, 59%) as a clear oil.

3-Nitro-1-iso-pentyl-1H-pyrazole (115 mg, 0.63 mmol) was dissolved in ethyl acetate (3 mL) and methanol (3 mL) was added. Palladium, 10 wt. % on activated carbon, wet (~50 mg) was added to the reaction. The vial was charged with hydrogen gas (via balloon) and the reaction stirred for 16 h at 25° C. The reaction was passed through a plug of celite and concentrated in vacuo to afford 1-iso-pentyl-1H-pyrazol-3-ylamine (89 mg, 93%) as golden oil: ESI-LRMS m/e calcd for $C_8H_{15}N_3$ [M$^+$] 153.1, found 154.3 [M+H$^+$].

2(R)-(3-Chloro-4-methanesulfonyl-phenyl)-3-cyclopentyl-propionic acid (prepared as in PCT WO 2004/052869 A1, Example 1, 192 mg, 0.58 mmol) was dissolved in methylene chloride and a 2.0 M solution of oxalyl chloride in methylene chloride (211 mg, 0.64 mmol) was added. The reaction stirred at 25° C. for 1 h. The reaction was chilled to 0° C. under nitrogen and 2,6-lutidine (155 μL, 1.34 mmol) was added dropwise. The reaction became golden brown, the ice bath was removed and the reaction continued to stir at 25° C. for 30 min. 1-Iso-pentyl-1H-pyrazol-3-ylamine (89 mg, 0.58 mmol) was dissolved in methylene chloride and added dropwise to the reaction. The solution continued to stir at 25° C. for 16 h. The reaction was diluted with methylene chloride, washed with water and saturated aqueous brine solution. The organic layer was dried over magnesium sulfate, filtered and concentrated in vacuo. Purification by ISCO flash column chromatography (Teledyne Isco RediSep Flash Column 40 g; 10% ethyl acetate/hexanes to 70% ethyl acetate/hexanes) afforded 2-(R)-(3-chloro-4-methanesulfonyl-phenyl)-3-cyclopentyl-N-(1-iso-pentyl-1H-pyrazol-3-yl)-propionamide (153 mg, 57%) as a white foam: ESI-LRMS m/e calcd for $C_{23}H_{32}ClN_3O_3S$ [M$^+$] 465.2, found 466.2 [M+H$^+$]; $^1$H NMR (400 MHz, CDCl$_3$) δppm 0.93 (t, J=6.6 Hz, 6H, 2×CH$_3$), 1.05-1.20 (m, 2H, CH$_2$), 1.42-1.96 (m, 11H, CH and 5×CH$_2$), 2.14-2.34 (m, 1H, CH), 3.26 (s, 3H, SO$_2$CH$_3$), 3.52 (t, J=7.6 Hz, 1H, CH), 3.96-4.02 (m, 2H, NCH2), 6.63 (d, J=2.3 Hz, 1H, Ar), 7.25 (d, J=2.3 Hz, 1H, Ar), 7.45 (dd, J$_o$=8.2, J$_m$=1.7 Hz. 1H, Ar), 7.59 (d, J$_m$=1.7 Hz, 1H, Ar), 7.82 (s, 1H, NH), 8.08 (d, J$_o$=8.2 Hz, 1H, Ar).

Example 44

4-{3-[2-(R)-(3-Chloro-4-methanesulfonyl-phenyl)-3-cyclopentyl-propionylamino]-pyrazol-1-ylmethyl}-benzoic acid methyl ester

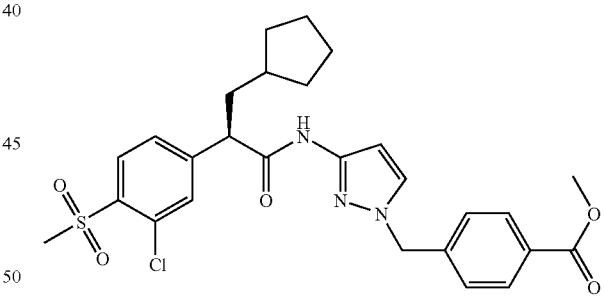

The 3-Nitro-1H-pyrazole (prepared in example 3, 1.18 g, 10.44 mmol) was dissolved in anhydrous N,N-dimethylformamide (15 mL) and a 60% dispersion of sodium hydride in mineral oil (500 mg, 12.53 mmol) was added while stirring under nitrogen. After the effervescence ceased and the reaction stirred for an additional 25 min, the reaction was chilled to 0° C. and the 4-bromomethyl-benzoic acid methyl ester (2.63 g, 11.48 mmol) was added. The reaction continued to stir under nitrogen at 0° C. for 20 min. The solution was poured into ice water; a white precipitate formed and was collected by in vacuo filtration and dried in vacuo for 16 h. Recrystallization from 20% ethyl acetate/hexanes afforded 4-(3-nitro-pyrazol-1-ylmethyl)-benzoic acid methyl ester (1.20 g, 44%), as a white powder upon collection and drying in vacuo: H$^1$-NMR (400 MHz, CDCl$_3$) δ 3.93 (3H, s), 5.43

(2H, s), 6.93 (1H, d, J=2.4 Hz), 7.33 (2H, d, J=8.4 Hz), 7.42 (1H, d, J=2.8 Hz), 8.05 (2H, d, J=8.4 Hz).

The 4-(3-nitro-pyrazol-1-ylmethyl)-benzoic acid methyl ester (1.20 g, 4.59 mmol) was dissolved in ethyl acetate (10 mL) and methanol (10 mL) was added. While stirring, a 50% slurry of raney nickel in water (1 mL) was added followed by hydrazine (1 mL). Immediate effervescence was observed. The reaction continued to stir and bubble for 30 min. The reaction was passed through a plug of celite and concentrated in vacuo to give a yellow oil. The oil was taken up in ethyl acetate (100 mL), washed with water (2×20 mL), saturated aqueous brine solution (20 mL), dried over magnesium sulfate and concentrated in vacuo to give the desired product, 4-(3-amino-pyrazol-1-ylmethyl)-benzoic acid methyl ester (580 mg, 55%) as a beige powder: ESI-LRMS m/e calcd for $C_{12}H_{13}N_3O_2$ [M+] 231.1, found 232.0 [M+H+].

Triphenylphosphine (310 mg, 1.18 mmol) was dissolved in methylene chloride (4 mL) and cooled to 0° C. To this solution was added N-bromosuccinimide (238 mg, 1.34 mmol) and was stirred at 0° C. until it was completely dissolved and became light purple in color. The 2(R)-(3-chloro-4-methanesulfonyl-phenyl)-3-cyclopentyl-propionic acid (prepared as in PCT WO 2004/052869 A1, Example 1; 259 mg, 0.79 mmol) was then added and it was stirred at 0° C. for 20 min and then warmed to 25° C. and stirred for another 30 min. After such time 4-(3-amino-pyrazol-1-ylmethyl)-benzoic acid methyl ester (182 mg, 0.79 mmol) and 2,6-lutidine (274 µL, 2.36 mmol) were added dropwise as a solution in methylene chloride (4 mL) and the reaction was stirred at 25° C. for 16 h. The reaction was then diluted with ethyl acetate (80 mL), washed with water (2×20 mL), saturated aqueous brine solution (1×20 mL), dried over magnesium sulfate and concentrated in vacuo to give an orange oil. Purification by ISCO flash column chromatography (Teledyne Isco RediSep Flash Column 120 g; 20% ethyl acetate/hexanes to 100% ethyl acetate/hexanes) followed by recrystallization from 25% ethyl acetate/hexanes afforded the desired product. The reaction procedure was scaled up by a factor of two according to the same procedure. The combined batches afforded 4-{3-[2-(R)-(3-chloro-4-methanesulfonyl-phenyl)-3-cyclopentyl-propionylamino]-pyrazol-1-ylmethyl}-benzoic acid methyl ester (840 mg, 65%) as a beige powder: ESI-LRMS m/e calcd for $C_{27}H_{30}ClN_3O_5S$ [M+] 543.2, found 544.5 [M+H+]; $^1$H NMR (400 MHz, DMSO-$d_6$) δ ppm 1.01-1.16 (m, 2H, $CH_2$), 1.33-1.80 (m, 8H, 4×$CH_2$), 1.99-2.19 (m, 1H, CH), 3.32 (s, 3H, $SO_2CH_3$), 3.82 (s, 3H, $CO_2CH_3$), 3.84-3.92 (m, 1H, CH), 5.28 (s, 2H, $NCH2$), 6.48 (d, J=2.2 Hz, 1H, Ar), 7.29 (d, $J_o$=8.5 Hz, 2H, Ar), 7.55 (dd, $J_o$=8.2, $J_m$=1.7 Hz. 1H, Ar), 7.65 (d, $J_m$=1.7 Hz, 1H, Ar), 7.75 (d, J=2.2 Hz, 1H, Ar), 7.90 (d, $J_o$=8.5 Hz, 2H, Ar), 7.97 (d, $J_o$=8.2 Hz, 1H, Ar), 10.78 (s, 1H, NH).

Example 45

4-{3-[2-(R)-(3-Chloro-4-methanesulfonyl-phenyl)-3-cyclopentyl-propionylamino]-pyrazol-1-ylmethyl}-benzoic acid

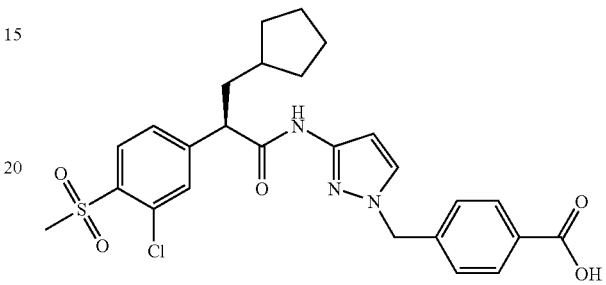

The 4-{3-[2-(R)-(3-Chloro-4-methanesulfonyl-phenyl)-3-cyclopentyl-propionylamino]-pyrazol-1-ylmethyl}-benzoic acid methyl ester (prepared in example 44, 840 mg, 1.54 mmol) was dissolved in dioxane (20 mL) and 6.0 M aqueous hydrochloric acid (20 mL) was added. The reaction was heated to 80° C. in a sealed vial while stirring for 8 h. Upon cooling, the reaction was diluted with water (25 mL) and the product extracted into ethyl acetate (3×50 mL). The combined organic layers were dried over magnesium sulfate and concentrated in vacuo to give the desired product, 4-{3-[2-(R)-(3-Chloro-4-methanesulfonyl-phenyl)-3-cyclopentyl-propionylamino]-pyrazol-1-ylmethyl}-benzoic acid (328 mg, 40%) as a white powder: ESI-LRMS m/e calcd for $C_{26}H_{28}ClN_3O_5S$ [M+] 529.1, found 530.2 [M+H+]; $^1$H NMR (400 MHz, DMSO-$d_6$) δ ppm 1.01-1.13 (m, 2H, $CH_2$), 1.33-1.80 (m, 8H, 4×$CH_2$), 1.94-2.19 (m, 1H, CH), 3.32 (s, 3H, $SO_2CH_3$), 3.83-3.93 (m, 1H, CH), 5.26 (s, 2H, NCH2), 6.47 (d, J=2.2 Hz, 1H, Ar), 7.26 (d, $J_o$=8.4 Hz, 2H, Ar), 7.55 (dd, $J_o$=8.2, $J_m$=1.7 Hz. 1H, Ar), 7.65 (d, $J_m$=1.7 Hz, 1H, Ar), 7.74

(d, J=2.2 Hz, 1H, Ar), 7.87 (d, $J_o$=8.4 Hz, 2H, Ar), 7.97 (d, $J_o$=8.2 Hz, 1H, Ar), 10.78 (s, 1H, NH), 12.88 (br.s., 1H, $CO_2H$).

Example 46

4-{3-[2-(R)-(3-Chloro-4-methanesulfonyl-phenyl)-3-cyclopentyl-propionylamino]-pyrazol-1-ylmethyl}-benzamide

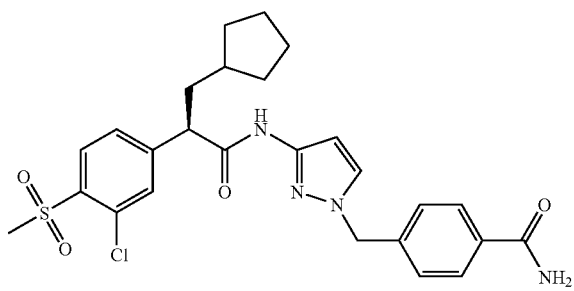

4-{3-[2-(R)-(3-Chloro-4-methanesulfonyl-phenyl)-3-cyclopentyl-propionylamino]-pyrazol-1-ylmethyl}-benzoic acid (prepared in example 45, 100 mg, 0.19 mmol) was suspended in methylene chloride (1 mL) and a 2.0 M solution of oxalyl chloride in methylene chloride (100 μL, 0.20 mmol) was added and the reaction stirred at 25° C. for 10 min. The solution was chilled to 0° C. and 2,6-lutidine (44 μL, 0.38 mmol) was added. The reaction continued to stir at 0° C. for 20 min. Concentrated aqueous ammonium hydroxide (4 drops) was added. The ice bath was removed and the reaction continued to stir at 25° C. for 20 min. The reaction was diluted with ethyl acetate (20 mL), washed with water (2×5 mL), saturated aqueous brine solution (1×5 mL), dried over magnesium sulfate and concentrated in vacuo to a beige foam. Purification by flash column chromatography (Merck silica gel 60, 40-63 μm; 40% ethyl acetate/hexanes to 100% ethyl acetate/hexanes) afforded 4-{3-[2-(3-chloro-4-methanesulfonyl-phenyl)-3-cyclopentyl-propionylamino]-pyrazol-1-ylmethyl}-benzamide (49 mg, 49%) as an off white powder: ESI-LRMS m/e calcd for $C_{26}H_{29}ClN_4O_4S$ [M+] 528.16, found 529.19 [M+H+]; $^1H$ NMR (400 MHz, $CDCl_3$) δ ppm 1.05-1.20 (m, 2H, $CH_2$), 1.35-1.92 (m, 8H, 4×$CH_2$), 2.11-2.26 (m, 1H, CH), 3.23 (s, 3H, $SO_2CH_3$), 3.65 (t, J=7.6 Hz, 1H, CH), 5.18 (s, 2H, $NCH_2$), 6.08 (br.s., 2H, $NH_2$), 6.74 (d, J=2.0 Hz, 1H, Ar), 7.15 (d, $J_o$=8.1 Hz, 2H, Ar), 7.37 (d, J=2.0 Hz, 1H, Ar), 7.43 (dd, $J_o$=8.1, $J_m$=1.6 Hz. 1H, Ar), 7.59 (d, $J_m$=1.6 Hz, 1H, Ar), 7.72 (d, $J_o$=8.1 Hz, 2H, Ar), 7.98 (d, $J_o$=8.1 Hz, 1H, Ar), 8.79 (s, 1H, NH).

Example 47

4-{3-[2-(R)-(3-Chloro-4-methanesulfonyl-phenyl)-3-cyclopentyl-propionylamino]-pyrazol-1-ylmethyl}-N-(3-methoxy-propyl)-benzamide

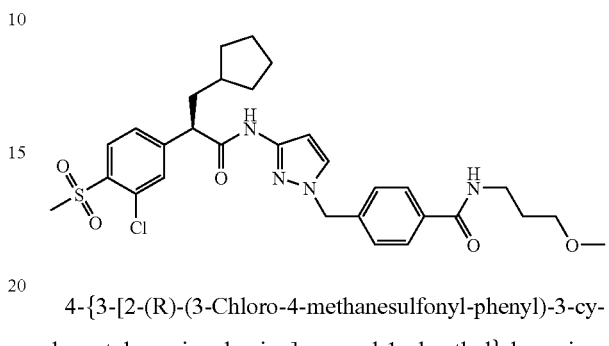

4-{3-[2-(R)-(3-Chloro-4-methanesulfonyl-phenyl)-3-cyclopentyl-propionylamino]-pyrazol-1-ylmethyl}-benzoic acid (prepared in example 45, 40 mg, 0.08 mmol) was suspended in methylene chloride (1 mL) and a 2.0 M solution of oxalyl chloride in methylene chloride (38 μL, 0.08 mmol) was added and the reaction stirred at 25° C. for 20 min. The solution was chilled to 0° C. and 2,6-lutidine (18 μL, 0.15 mmol) was added. The reaction continued to stir at 0° C. for 20 min. The 3-methoxy-propylamine (10 μL, 0.09 mmol) was added, the ice bath was removed and the reaction continued to stir at 25° C. for 16 h. The reaction was diluted with methylene chloride (10 mL), washed with water (2×4 mL), saturated aqueous brine solution (1×4 mL), dried over magnesium sulfate and concentrated in vacuo to a beige foam. Purification by reverse phase preparative HPLC (Column: Thomson C18 ODSA, 5 micron, 50×21.2 mm ID; 30% acetonitrile/water to 100% acetonitrile/water; 30 mL/min flow rate for 15 min run) followed by preparative thin layer chromatography (Merck Silica gel 60 $F_{254}$, 500 μm, 20×20 cm; 100% ethyl acetate) afforded 4-{3-[2-(R)-(3-chloro-4-methanesulfonyl-phenyl)-3-cyclopentyl-propionylamino]-pyrazol-1-ylmethyl}-N-(3-methoxy-propyl)-benzamide (21 mg, 46%) as a white powder: ESI-LRMS m/e calcd for $C_{30}H_{37}ClN_4O_5S$ [M+] 600.22, found 601.47 [M+H+]; $^1H$ NMR (400 MHz, $CDCl_3$) δ ppm 1.07-1.23 (m, 2H, $CH_2$), 1.45-1.98 (m, 10H, 5×$CH_2$), 2.12-2.31 (m, 1H, CH), 3.26 (s, 3H, $SO_2CH_3$), 3.39 (s, 3H, $OCH_3$), 3.51-3.70 (m, 5H, 2×$CH_2$ and CH), 5.20 (s, 2H, $NCH_2$), 6.74 (d, J=2.3 Hz, 1H, Ar), 6.97 (brm, 1H, NH), 7.18 (d, $J_o$=8.1 Hz, 2H, Ar), 7.35 (d, J=2.3 Hz, 1H, Ar), 7.44 (dd, $J_o$=8.1, $J_m$=1.6

Hz. 1H, Ar), 7.59 (d, $J_m$=1.6 Hz, 1H, Ar), 7.71 (d, $J_o$=8.1 Hz, 2H, Ar), 8.07 (d, $J_o$=8.1 Hz, 1H, Ar), 8.16 (s, 1H, NH).

Example 48

4-{3-[2-(R)-(3-Chloro-4-methanesulfonyl-phenyl)-3-cyclopentyl-propionylamino]-pyrazol-1-ylmethyl}-N-(3-hydroxy-propyl)-benzamide

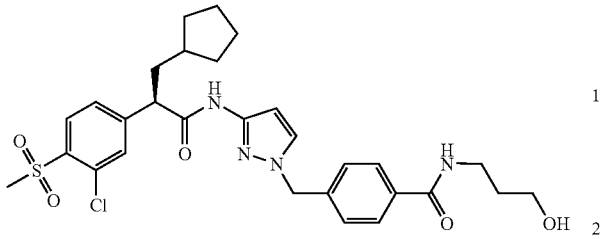

4-{3-[2-(R)-(3-Chloro-4-methanesulfonyl-phenyl)-3-cyclopentyl-propionylamino]-pyrazol-1-ylmethyl}-benzoic acid (prepared in example 45, 40 mg, 0.08 mmol) was suspended in methylene chloride (1 mL) and a 2.0 M solution of oxalyl chloride in methylene chloride (38 μL, 0.08 mmol) was added and the reaction stirred at 25° C. for 20 min. The solution was chilled to 0° C. and 2,6-lutidine (18 μL, 0.15 mmol) was added. The reaction continued to stir at 0° C. for 20 min. 3-Amino-propan-1-ol (7 μL, 0.09 mmol) was added, the ice bath was removed and the reaction continued to stir at 25° C. for 16 h. The reaction was diluted with methylene chloride (10 mL), washed with water (2×4 mL), saturated aqueous brine solution (1×4 mL), dried over magnesium sulfate and concentrated in vacuo to a beige foam. Purification by reverse phase preparative HPLC (Column: Thomson C18 ODSA, 5 micron, 50×21.2 mm ID; 30% acetonitrile/water to 100% acetonitrile/water; 30 mL/min flow rate for 15 min run) followed by preparative thin layer chromatography (Merck Silica gel 60 $F_{254}$, 500 μm, 20×20 cm; 100% ethyl acetate) afforded 4-{3-[2-(R)-(3-chloro-4-methanesulfonyl-phenyl)-3-cyclopentyl-propionylamino]-pyrazol-1-ylmethyl}-N-(3-hydroxy-propyl)-benzamide (14 mg, 32%) as a white waxy solid: ESI-LRMS m/e calcd for $C_{29}H_{35}ClN_4O_5S$ [M$^+$] 586.2, found 587.29 [M+H$^+$]; $^1$H NMR (400 MHz, CDCl$_3$) δ ppm 1.08-1.22 (m, 2H, CH$_2$), 1.43-1.93 (m, 10H, 5×CH$_2$), 2.15-2.31 (m, 1H, CH), 3.26 (s, 3H, SO$_2$CH$_3$), 3.57-3.67 (m, 3H, CH$_2$ and CH), 3.73 (t, J=5.5 Hz, 2H, CH$_2$), 5.18 (s, 2H, NCH$_2$), 6.74 (d, J=2.3 Hz, 1H, Ar), 6.82 (brm, 1H, NH), 7.12 (d, $J_o$=8.1 Hz, 2H, Ar), 7.36 (d, J=2.3 Hz, 1H, Ar), 7.43 (dd, $J_o$=8.1, $J_m$=1.6 Hz. 1H, Ar), 7.59 (d, $J_m$=1.6 Hz, 1H, Ar), 7.67 (d, $J_o$=8.1 Hz, 2H, Ar), 8.04 (d, $J_o$=8.1 Hz, 1H, Ar), 8.32 (s, 1H, NH).

Example 49

4-{3-[2-(R)-(3-Chloro-4-methanesulfonyl-phenyl)-3-cyclopentyl-propionylamino]-pyrazol-1-ylmethyl}-N-(3-dimethylamino-propyl)-benzamide

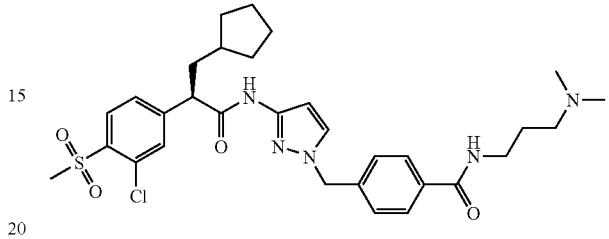

4-{3-[2-(R)-(3-Chloro-4-methanesulfonyl-phenyl)-3-cyclopentyl-propionylamino]-pyrazol-1-ylmethyl}-benzoic acid (prepared in example 45, 40 mg, 0.08 mmol) was suspended in methylene chloride (1 mL) and a 2.0 M solution of oxalyl chloride in methylene chloride (38 μL, 0.08 mmol) was added and the reaction stirred at 25° C. for 20 min. The solution was chilled to 0° C. and 2,6-lutidine (18 μL, 0.15 mmol) was added. The reaction continued to stir at 0° C. for 20 min. N,N-Di-methyl-3-amino-propyl-amine (12 μL, 0.09 mmol) was added, the ice bath was removed and the reaction continued to stir at 25° C. for 16 h. The reaction was diluted with methylene chloride (10 mL), washed with water (2×4 mL), saturated aqueous brine solution (1×4 mL), dried over magnesium sulfate and concentrated in vacuo to a beige foam. Purification by reverse phase preparative HPLC (Column: Thomson C18 ODSA, 5 micron, 50×21.2 mm ID; 30% acetonitrile/water to 100% acetonitrile/water; 30 mL/min flow rate for 15 min run) followed by flash column chromatography (Merck silica gel 60, 40-63 μm; 0.5% ammonium hydroxide/methanol) afforded 4-{3-[2-(R)-(3-chloro-4-methanesulfonyl-phenyl)-3-cyclopentyl-propionylamino]-pyrazol-1-ylmethyl}-N-(3-dimethylamino-propyl)-benzamide (3 mg, 6.5%) as a clear oil: ESI-LRMS m/e calcd for $C_{31}H_{40}ClN_5O_4S$ [M$^+$] 613.25, found 614.21 [M+H$^+$]; $^1$H NMR (400 MHz, CDCl$_3$) δ ppm 1.08-1.24 (m, 2H, CH$_2$), 1.44-1.94 (m, 8H, 4×CH$_2$), 2.10-2.32 (m, 3H, CH), 2.78 (s, 6H, 2×NCH$_3$), 3.06 (t, J=6.4 Hz, 2H, NCH$_2$), 3.25 (s, 3H, SO$_2$CH$_3$), 3.56-3.66 (m, 2H, CH$_2$), 3.69 (t, J=7.6 Hz, 1H, CH), 5.15 (s, 2H, NCH$_2$), 6.72 (d, J=2.3 Hz, 1H, Ar), 7.13 (d, $J_o$=8.1 Hz, 2H, Ar), 7.33 (d, J=2.3 Hz, 1H, Ar), 7.49 (dd, $J_o$=8.1, $J_m$=1.6 Hz. 1H, Ar), 7.65 (d, $J_m$=1.6 Hz, 1H, Ar), 7.91 (d, $J_o$=8.1 Hz, 2H, Ar), 8.05 (d, $J_o$=8.1 Hz, 1H, Ar), 8.37 (brm, 1H, NH), 8.59 (s, 1H, NH).

Example 50

2-(R)-(3-Chloro-4-methanesulfonyl-phenyl)-3-cyclopentyl-N-[1-(3-hydroxy-3-methyl-butyl)-1H-pyrazol-3-yl]-propionamide

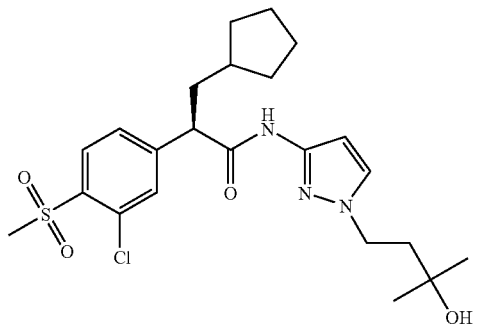

3-Nitro-1H-pyrazole (prepared in example 3, 1.00 g, 8.85 mmol) was dissolved in anhydrous N,N-dimethylformamide (10 mL) and a 60% dispersion of sodium hydride in mineral oil (390 mg, 9.74 mmol) was added while stirring under nitrogen. After the effervescence ceased and the reaction stirred for an additional 10 min, the 1-bromo-3-methyl-but-2-ene (1.33 g, 9.00 mmol) was added. The reaction continued to stir under nitrogen for 20 min. The solution was diluted with ethyl acetate (200 mL), washed with water (2×75 mL), saturated aqueous brine solution (75 mL), dried over magnesium sulfate, filtered and concentrated in vacuo. Purification by flash column chromatography (Merck silica gel 60, 40-63 μm; 5% ethyl acetate/hexanes to 20% ethyl acetate/hexanes) afforded 1-(3-methyl-but-2-enyl)-3-nitro-1H-pyrazole (1.29 g, 81%) as a yellow oil: $H^1$-NMR (400 MHz, CDCl$_3$) δ 1.79 (3H, s), 1.83 (3H, s), 4.80 (2H, d, J=7.2 Hz), 5.45 (1H, t, J=7.2 Hz), 6.88 (1H, s), 7.43 (1H, s).

1-(3-Methyl-but-2-enyl)-3-nitro-1H-pyrazole (1.29 g, 7.13 mmol) was dissolved in dioxane (30 mL). While stirring, a solution containing 50% concentrated sulfuric acid/water (3 mL) was added dropwise. The reaction was heated to 85° C. while stirring for 12 h. The reaction was diluted with water (50 mL) and the product extracted into ethyl acetate (3×60 mL). The combined organic layers were dried over magnesium sulfate and concentrated in vacuo to an oil. Purification by flash column chromatography (Merck silica gel 60, 40-63 μm; 15% ethyl acetate/hexanes to 100% ethyl acetate/hexanes) afforded 2-methyl-4-(3-nitro-pyrazol-1-yl)-butan-2-ol (608 mg, 43%) as a thick golden oil: $H^1$-NMR (400 MHz, CDCl$_3$) δ 1.30 (6H, s), 1.54 (1H, bs), 2.11-2.15 (2H, m), 4.36-4.39 (2H, m), 6.87 (1H, d, J=2.8 Hz), 7.48 (1H, d, J=2.8 Hz).

The 2-methyl-4-(3-nitro-pyrazol-1-yl)-butan-2-ol (601 mg, 3.02 mmol) was dissolved in ethyl acetate (5 mL) and methanol (5 mL) was added. While stirring, a 50% slurry of raney nickel in water (1 mL) was added followed by hydrazine (500 μL). Immediate effervescence was observed. The reaction stirred for 20 min. The reaction was passed through a plug of celite and the filtrate was concentrated in vacuo to give a yellow oil. The oil was dissolved in ethyl acetate (25 mL) and washed with water (10 mL) and brine (10 mL). The combined aqueous phases were back extracted with ethyl acetate (3×25 mL). The combined organic phases were passed through a plug of silica gel, eluting with excess ethyl acetate followed by concentrating the filtrate in vacuo to afford the desired product, 4-(3-amino-pyrazol-1-yl)-2-methyl-butan-2-ol (442 mg, 86%) as a yellow oil: ESI-LRMS m/e calcd for $C_8H_{15}N_3O$ [M$^+$] 169.12. found 170.3 [M+H$^+$], 152.3 [M−H$_2$O+H$^+$], 339.4 [2M+H$^+$].

2-(R)-(3-Chloro-4-methanesulfonyl-phenyl)-3-cyclopentyl-propionic acid (prepared as in PCT WO 2004/052869 A1, Example 1, 825 mg, 2.50 mmol) was suspended in methylene chloride (12.5 mL) and a 2.0 M solution of oxalyl chloride in methylene chloride (1.25 mL, 2.5 mmol) was added and the reaction stirred at 25° C. for 10 min. The solution was chilled to 0° C. and 2,6-lutidine (582 μL, 5.00 mmol) was added. The reaction continued to stir at 0° C. for 10 min. 4-(3-Amino-pyrazol-1-yl)-2-methyl-butan-2-ol (424 mg, 2.50 mmol) was dissolved in methylene chloride (5 mL) and added dropwise to the reaction. The reaction continued to stir at 0° C. for 10 min. The reaction was diluted with methylene chloride (50 mL), washed with water (15 mL), saturated aqueous brine solution (10 mL), 1.0 M aqueous hydrochloric acid solution (10 mL), dried over magnesium sulfate and concentrated in vacuo to give a yellow oil. Purification by flash column chromatography (Merck silica gel 60, 40-63 μm; 35% ethyl acetate/methylene chloride) afforded 2-(R)-(3-chloro-4-methanesulfonyl-phenyl)-3-cyclopentyl-N-[1-(3-hydroxy-3-methyl-butyl)-1H-pyrazol-3-yl]-propionamide (653 mg, 54%) as a white foamy solid: ESI-LRMS m/e calcd for $C_{23}H_{32}ClN_3O_4S$ [M$^+$] 481.18, found 482.35 [M+H$^+$], 464.22 [M−H$_2$O+H$^+$]; $^1$H NMR (400 MHz, CDCl$_3$) δ ppm 1.09-1.23 (m, 2H, CH$_2$), 1.29 (s, 6H, 2×CH$_3$), 1.46-1.94 (m, 8H, 4×CH$_2$), 1.94-2.04 (m, 2 H, CH$_2$), 2.18-2.29 (m, 1H, CH), 3.28 (s, 3H, SO$_2$CH$_3$), 3.55 (t, J=7.5 Hz, 1H, CH), 3.00-4.25 (m, 2H, NCH$_2$), 6.65 (d, J=2.3 Hz, 1H, Ar), 7.29 (d, J=2.3 Hz, 1H, Ar), 7.47 (dd, $J_o$=8.2, $J_m$=1.7 Hz. 1H, Ar), 7.61 (d, $J_m$=1.7 Hz, 1H, Ar), 8.10 (d, $J_o$=8.2 Hz, 1H, Ar), 8.12 (s, 1H, NH).

Example 51

2-(R)-(3-Chloro-4-methanesulfonyl-phenyl)-3-cyclopentyl-N-[1-(3-methyl-but-2-enyl)-1H-pyrazol-3-yl]-propionamide

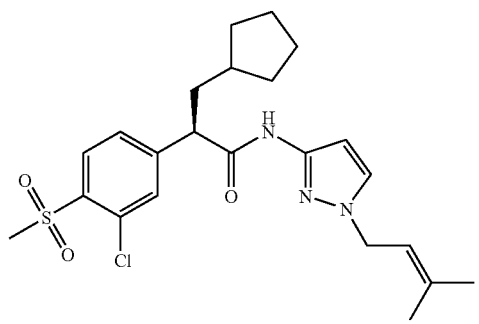

3-Nitro-1H-pyrazole (prepared in example 3, 270 mg, 2.39 mmol) was dissolved in anhydrous N,N-dimethylformamide (3 mL) and a 60% dispersion of sodium hydride in mineral oil (116 mg, 2.90 mmol) was added while stirring under nitrogen. After the effervescence ceased and the reaction stirred for an additional 10 min, the 1-bromo-3-methyl-but-2-ene (390 mg, 2.60 mmol) was added. The reaction continued to stir under nitrogen for 2 h. The solution was diluted with ethyl acetate (75 mL), washed with water (2×25 mL), saturated aqueous brine solution (25 mL), dried over magnesium sulfate, filtered and concentrated in vacuo. Purification by flash column chromatography (Merck silica gel 60, 40-63 μm; 20% ethyl acetate/hexanes) afforded 1-(3-methyl-but-2-enyl)-3-nitro-1H-pyrazole (340 mg, 79%) as a yellow oil: H$^1$-NMR (400 MHz, CDCl$_3$) δ 1.79 (3H, s), 1.83 (3H, s), 4.80 (2H, d, J=7.2 Hz), 5.45 (1H, t, J=7.2 Hz), 6.88 (1H, s), 7.43 (1H, s).

The 1-(3-methyl-but-2-enyl)-3-nitro-1H-pyrazole (175 mg, 0.97 mmol) was dissolved in methanol (2 mL) and ethyl acetate (2 mL) was added. While stirring, a 50% slurry of raney nickel in water (500 μL) was added followed by hydrazine (500 μL). Immediate effervescence was observed. The reaction continued to stir and bubble for 30 min. The reaction was passed through a plug of celite and concentrated in vacuo to give an oil. The oil was taken up in ethyl acetate (40 mL), washed with water (2×10 mL), saturated aqueous brine solution (10 mL), dried over magnesium sulfate and concentrated in vacuo to give the desired product, 1-(3-methyl-but-2-enyl)-1H-pyrazol-3-ylamine (86 mg, 59%) a yellow oil: ESI-LRMS m/e calcd for C$_8$H$_{13}$N$_3$ [M$^+$] 151.11, found 152.2 [M+H$^+$].

Triphenylphosphine (224 mg, 0.85 mmol) was dissolved in methylene chloride (3 mL) and cooled to 0° C. To this solution was added N-bromosuccinimide (172 mg, 0.97 mmol) and was stirred at 0° C. until it was completely dissolved and became light purple in color. The 2-(R)-(3-chloro-4-methanesulfonyl-phenyl)-3-cyclopentyl-propionic acid (prepared as in PCT WO 2004/052869 A1, Example 1; 188 mg, 0.57 mmol) was then added and it was stirred at 0° C. for 20 min and then warmed to 25° C. and stirred for another 30 min. After such time 1-(3-methyl-but-2-enyl)-1H-pyrazol-3-ylamine (86 mg, 0.57 mmol) and 2,6-lutidine (198 μL, 1.71 mmol) were added and the reaction was stirred at 25° C. for 16 h. The reaction was then diluted with ethyl acetate (50 mL), washed with water (2×15 mL), saturated aqueous brine solution (1×15 mL), dried over magnesium sulfate and concentrated in vacuo to give an orange oil. Purification by ISCO flash column chromatography (Teledyne Isco RediSep Flash Column 10 g; 20% ethyl acetate/hexanes to 100% ethyl acetate/hexanes) followed by ISCO flash column chromatography (Teledyne Isco RediSep Flash Column 10 g; 0% ethyl acetate/methylene chloride to 20% ethyl acetate/methylene chloride) afforded 2-(R)-(3-chloro-4-methanesulfonyl-phenyl)-3-cyclopentyl-N-[1-(3-methyl-but-2-enyl)-1H-pyrazol-3-yl]-propionamide (103 mg 39%) as an off white powder: ESI-LRMS m/e calcd for C$_{23}$H$_{30}$ClN$_3$O$_3$S [M$^+$] 463.17, found 464.23 [M+H$^+$]; $^1$H NMR (400 MHz, CDCl$_3$) δ ppm 1.06-1.23 (m, 2H, CH$_2$), 1.46-1.93 (m, 8H, 4×CH$_2$), 1.76 (s, 3H, CH$_3$), 1.80 (s, 3H, CH$_3$), 2.05-2.35 (m, 1H, CH), 3.28 (s, 3H, SO$_2$CH$_3$), 3.53 (t, J=7.6 Hz, 1H, CH), 4.59 (d, J=7.1 Hz, 2H, NCH$_2$), 531-5.43 (m, 1H, vinylic), 6.66 (d, J=2.3 Hz, 1H, Ar), 7.27 (d, J=2.3 Hz, 1H, Ar), 7.46 (dd, J$_o$=8.1, J$_m$=1.7 Hz. 1H, Ar), 7.59 (d, J$_m$=1.7 Hz, 1H, Ar), 7.83 (s, 1H, NH), 8.10 (d, J$_o$=8.1 Hz, 1H, Ar).

Example 52

2-(R)-(3-Chloro-4-methanesulfonyl-phenyl)-3-cyclopentyl-N-[1-(4-hydroxy-but-2-ynyl)-1H-pyrazol-3-yl]-propionamide

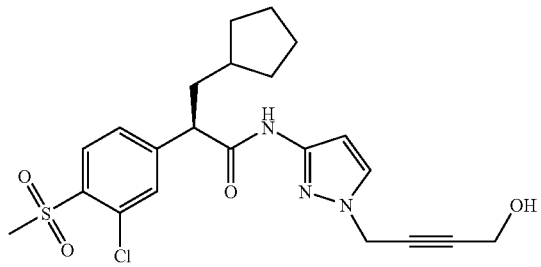

3-Nitro-1H-pyrazole (prepared in example 3, 1.30 g, 11.50 mmol) was dissolved in N,N-dimethylformamide (20 mL) and chilled to 0° C. A 60% dispersion of sodium hydride in mineral oil (552 mg, 13.80 mmol) was added portion wise, the ice bath was removed and the reaction continued to stir for 20 min. The 1,4-dichloro-but-2-yne (2.83 g, 23.00 mmol) was dissolved in N,N-dimethylformamide (5 mL) and chilled to 0° C. The 3-nitro-1H-pyrazole solution was added dropwise to the 1,4-dichloro-but-2-yne solution while stirring at 0° C. The ice bath was removed and the reaction continued to stir for 20 min. The solution was diluted with ethyl acetate (400 mL), washed with water (2×200 mL), saturated aqueous brine solution (2×100 mL), dried over magnesium sulfate and concentrated in vacuo to give a yellow oil. Purification by flash column chromatography (Merck silica gel 60, 40-63 μm; 40% ethyl acetate/hexanes) afforded 1-(4-chloro-but-2-ynyl)-3-nitro-1H-pyrazole (682 mg, 30%) as a yellow oil which eventually solidified: H$^1$-NMR (400 MHz, CDCl$_3$) δ 4.18 (2H, t, J=2.0 Hz), 5.08 (2H, t, J=2.0 Hz), 6.92 (1H, d, J=2.4 Hz), 7.70 (2H, d, J=2.4 Hz).

The 1-(4-chloro-but-2-ynyl)-3-nitro-1H-pyrazole (300 mg, 1.50 mmol) was dissolved in tetrahydrofuran (2 mL) and N,N-dimethylformamide (6 mL). 1.0 M aqueous hydrochloric acid solution (8 mL) was added and the solution was heated to 100° C. while stirring for 36 h in a sealed vial. The solution was diluted with ethyl acetate (100 mL), washed with water (2×50 mL), saturated aqueous brine solution (2×25 mL), dried over magnesium sulfate and concentrated in vacuo to give a waxy yellow solid. Purification by ISCO flash column chromatography (Teledyne Isco RediSep Flash Column 40 g; 15% ethyl acetate/hexanes to 100% ethyl acetate/hexanes) afforded 4-(3-nitro-pyrazol-1-yl)-but-2-yn-1-ol (166 mg, 61%) as an off white solid: H$^1$-NMR (400 MHz, DMSO-d$_6$) δ 4.12 (2H, d, J=6.0 Hz), 5.23 (2H, s), 7.06 (1H, d, J=2.8 Hz), 8.08 (2H, d, J=3.6 Hz).

The 4-(3-nitro-pyrazol-1-yl)-but-2-yn-1-ol (166 mg, 0.91 mmol) and iron powder (250 mg, 4.47 mmoles) were combined and suspended in ethanol (5.5 mL) and a saturated aqueous ammonium chloride solution (3.3 mL) was added. The reaction was heated to 105° C. while stirring for 2 h in a sealed vial. The reaction was diluted with ethyl acetate (100 mL), washed with water (2×50 mL), saturated aqueous brine solution (2×25 mL), dried over magnesium sulfate and concentrated in vacuo to give an off white solid. The solid was dissolved in methylene chloride and passed through a plug of Merck silica gel 60, 40-63 mm, eluting with ethyl acetate to afford the desired product, 4-(3-amino-pyrazol-1-yl)-but-2-yn-1-ol (110 mg, 91%) as an off white solid: ESI-LRMS m/e calcd for $C_7H_9N_3O$ [$M^+$] 151.07, found 152.3 [$M+H^+$], 303.1 [$2M+H^+$].

2-(R)-(3-Chloro-4-methanesulfonyl-phenyl)-3-cyclopentyl-propionic acid (prepared as in PCT WO 2004/052869 A1, Example 1, 241 mg, 0.73 mmol) was suspended in methylene chloride (3.6 mL) and a 2.0 M solution of oxalyl chloride in methylene chloride (364 μL, 0.73 mmol) was added and the reaction stirred at 25° C. for 10 min. The solution was chilled to 0° C. and 2,6-lutidine (170 μL, 1.46 mmol) was added. The reaction continued to stir at 0° C. for 15 min. 4-(3-Amino-pyrazol-1-yl)-but-2-yn-1-ol (110 mg, 0.73 mmol) was dissolved in methylene chloride (3.6 mL) and added dropwise to the reaction. The ice bath was removed and the reaction continued to stir at 25° C. for 30 min. The reaction was diluted with ethyl acetate (50 mL), washed with water (2×15 mL), 1.0 M aqueous hydrochloric acid solution (10 mL), saturated aqueous brine solution (10 mL), dried over magnesium sulfate and concentrated in vacuo to an orange foam. Purification by ISCO flash column chromatography (Teledyne Isco RediSep Flash Column 40 g; 5% ethyl acetate/methylene chloride to 100% ethyl acetate/methylene chloride) afforded 2-(R)-(3-chloro-4-methanesulfonyl-phenyl)-3-cyclopentyl-N-[1-(4-hydroxy-but-2-ynyl)-1H-pyrazol-3-yl]-propionamide (92 mg, 27%) as a white foam: ESI-LRMS m/e calcd for $C_{22}H_{26}ClN_3O_4S$ [$M^+$] 463.1, found 464.1 [$M+H^+$]; $^1$H NMR (400 MHz, CDCl$_3$) δ ppm 1.06-1.24 (m, 2H, CH$_2$), 1.44-1.95 (m, 8H, 4×CH$_2$), 2.10-2.37 (m, 1H, CH), 3.27 (s, 3H, SO$_2$CH$_3$), 3.56 (t, J=7.4 Hz, 1H, CH), 4.31 (t, J=1.7 Hz, 2H, OCH$_2$), 4.82 (t, J=1.7 Hz, 2H, NCH$_2$), 6.72 (d, $J_o$=2.3, 1H, Ar), 7.43 (d, $J_o$=2.3, 1H, Ar), 7.46 (dd, $J_o$=8.2, $J_m$=1.4 Hz. 1H, Ar), 7.59 (d, $J_m$=1.4 Hz, 1H, Ar), 8.08 (brs, 1H, NH), 8.09 (d, $J_o$=8.2 Hz, 1H, Ar).

Example 53

N-[1-(4-Amino-but-2-ynyl)-1H-pyrazol-3-yl]-2-(R)-(3-chloro-4-methanesulfonyl-phenyl)-3-cyclopentyl-propionamide

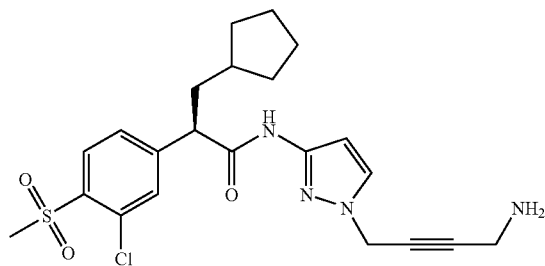

But-2-yne-1,4-diol (8.78 g, 102 mmol), phthalimide (5.00 g, 33.98 mmol) and triphenylphosphine (8.91 g, 33.98 mmol) were combined and dissolved in tetrahydrofuran (165 mL) and then chilled to 0° C. While stirring, diisopropyl azodicarboxylate (10 mL, 50.97 mmol) was added dropwise. The ice bath was removed and the reaction continued to stir at 25° C. for 16 h. The reaction was concentrated in vacuo to give a thick golden oil. Purification by flash column chromatography (Merck silica gel 60, 40-63 μm; 10% ethyl acetate/hexanes to 50% ethyl acetate/hexanes) afforded 2-(4-hydroxy-but-2-ynyl)-isoindole-1,3-dione (2.83 g, 39%) as a white powder: ESI-LRMS m/e calcd for $C_{12}H_9NO_3$ [$M^+$] 215.1, found 216.3 [$M+H^+$], 431.6 [$2M+H^+$].

The 2-(4-hydroxy-but-2-ynyl)-isoindole-1,3-dione (1.29 g, 6.00 mmol), 3-Nitro-1H-pyrazole (prepared in example 3, 655 mg, 5.80 mmol) and triphenylphosphine (1.57 g, 6.00 mmol) were combined and dissolved in tetrahydrofuran (30 mL) and then chilled to 0° C. While stirring, diisopropyl azodicarboxylate (1.77 mL, 9 mmol) was added dropwise. The ice bath was removed and the reaction continued to stir at 25° C. for 1 h. At this point the desired product had precipitated. Collection of the precipitate using in vacuo filtration followed by rinsing with tetrahydrofuran (2×10 mL) then drying in vacuo for 2 h afforded 2-[4-(3-nitro-pyrazol-1-yl)-but-2-ynyl]-isoindole-1,3-dione (1.54 g, 86%) as a white powder: ESI-LRMS m/e calcd for $C_{15}H_{10}N_4O_4$ [$M^+$] 310.07. found 311.17 [$M+H^+$], 621.20 [$2M+H^+$].

The 2-[4-(3-nitro-pyrazol-1-yl)-but-2-ynyl]-isoindole-1,3-dione (1.00 g, 3.23 mmol) was dissolved in ethanol (5 mL) and hydrazine monohydrate (158 μL, 3.23 mmol) was added. The solution was refluxed under nitrogen for 30 min. Upon cooling, the 2,3-dihydro-phthalazine-1,4-dione side product precipitated. The reaction was filtered and rinsed with ethanol (2×3 mL). The filtrate was concentrated in vacuo to give a thick yellow oil. The oil was dissolved in tetrahydrofuran (15 mL), solid sodium bicarbonate (756 mg, 9.00 mmol) and di-tert-butyl dicarbonate (775 mg, 3.55 mmol) was added and the reaction stirred at 25° C. for 4 h. The sodium bicarbonate was filtered off and the filtrate concentrated in vacuo to a thick oil. Purification by flash column chromatography (Merck silica gel 60, 40-63 μm; 15% ethyl acetate/hexanes to 50% ethyl acetate/hexanes) afforded [4-(3-nitro-pyrazol-1-yl)-but-2-ynyl]-carbamic acid tert-butyl ester (423 mg, 47%) as a white waxy solid: H$^1$-NMR (400 MHz, CDCl$_3$) δ 1.45 (9H, s), 3.98 (2H, d, J=5.2 Hz), 4.76-4.86 (1H, bs), 5.01 (2H, t, J=2.0 Hz), 6.90 (1H, d, J=2.8 Hz), 7.74 (1H, d, J=2.4 Hz).

The [4-(3-nitro-pyrazol-1-yl)-but-2-ynyl]-carbamic acid tert-butyl ester (423 mg, 1.51 mmol) was dissolved in ethanol (8 mL). Iron powder (420 mg, 7.51 mmol) was added followed by the addition of a saturated aqueous ammonium chloride solution (5.5 mL). The reaction was heated to 105° C. while stirring in a sealed vial for 45 min. Upon cooling, the reaction was diluted with ethyl acetate (400 mL), washed with water (2×200 mL), saturated aqueous brine solution (100 mL), dried over magnesium sulfate and concentrated in vacuo to afford, [4-(3-amino-pyrazol-1-yl)-but-2-ynyl]-carbamic acid tert-butyl ester (258 mg, 68%) as a yellow oil: ESI-LRMS m/e calcd for $C_{12}H_{18}N_4O_2$ [$M^+$] 250.14, found 251.34 [$M+H^+$], 501.26 [$2M+H^+$].

2-(R)-(3-Chloro-4-methanesulfonyl-phenyl)-3-cyclopentyl-propionic acid (prepared as in PCT WO 2004/052869 A1, Example 1, 330 mg, 1.00 mmol) was dissolved in methylene chloride (5 mL), a 2.0 M solution of oxalyl chloride in methylene chloride (500 μL, 1 mmol) was added and the solution was stirred at 25° C. for 15 min. The solution was chilled to 0° C. and 2,6-lutidine (0.232 mL, 2 mmol) was added dropwise. The reaction continued to stir at 0° C. for 15 min. The [4-(3-amino-pyrazol-1-yl)-but-2-ynyl]-carb acid tert-butyl ester (250 mg, 1.00 mmol) was added as a solution in methylene chloride (5 mL), the ice bath was removed and the solution continued to stir at 25° C. for 25 min. The solution was diluted with methylene chloride (50 mL), washed with water (2×25 mL), saturated aqueous brine solution (1×20 mL), dried over magnesium sulfate and concentrated in vacuo to a yellow foam. Purification by flash column chromatography (Merck silica gel 60, 40-63 μm; 20% ethyl acetate/hexanes to 50% ethyl acetate/hexanes) afforded (4-{3-[2-(R)-(3-chloro-4-methanesulfonyl-phenyl)-3-cyclopentyl-propionylamino]-pyrazol-1-yl}-but-2-ynyl)-carbamic acid tert-butyl ester (246 mg, 44%) as a white foam: ESI-LRMS m/e calcd for $C_{27}H_{35}ClN_4O_5S$ [M$^+$] 562.2, found 463.31 [M−Boc+H$^+$].

(4-{3-[2-(R)-(3-Chloro-4-methanesulfonyl-phenyl)-3-cyclopentyl-propionylamino]-pyrazol-1-yl}-but-2-ynyl)-carbamic acid tert-butyl ester (240 mg, 0.43 mmol) was dissolved in methylene chloride (10 mL) and trifluoroacetic acid (2 mL) was added while stirring. The reaction continued to stir for 45 min. The reaction was concentrated in vacuo at 0° C. to give a yellow oil. The reaction was diluted with ethyl acetate (200 mL), washed with saturated aqueous sodium bicarbonate (2×50 mL), saturated aqueous brine solution (50 mL), dried over magnesium sulfate and concentrated in vacuo to give a yellow oil. Purification by flash column chromatography (Merck silica gel 60, 40-63 μm; 0% methanol/ethyl acetate to 10% methanol/ethyl acetate) afforded N-[1-(4-amino-but-2-ynyl)-1H-pyrazol-3-yl]-2-(R)-(3-chloro-4-methanesulfonyl-phenyl)-3-cyclopentyl-propionamide (128 mg, 69%) as a thick, faintly yellow oil: ESI-LRMS m/e calcd for $C_{22}H_{27}ClN_4O_3S$ [M$^+$] 462.2, found 463.2 [M+H$^+$]; $^1$H NMR (400 MHz, DMSO-d$_6$) δ ppm 1.03-1.21 (m, 2H, CH$_2$), 1.38-1.82 (m, 8H, 4×CH$_2$), 1.98 (brs, 2H, NH$_2$), 2.05-2.24 (m, 1H, CH), 3.29 (t, J=2.0 Hz, 2H, NCH$_2$), 3.33 (s, 3H, SO$_2$CH$_3$), 3.86-3.95 (m, 1H, CH), 4.87 (t, J=2.0 Hz, 2H, NCH$_2$), 6.44 (d, J$_o$=2.3 Hz, 1H, Ar), 7.58 (dd, J$_o$=8.2, J$_m$=1.6 Hz. 1H, Ar), 7.62 (d, J$_o$=2.3 Hz, 1H, Ar), 7.68 (d, J$_m$=1.6 Hz, 1H, Ar), 7.99 (d, J$_o$=8.2 Hz, 1H, Ar), 10.81 (s, 1H, NH).

Example 54

2-(R)-(3-Chloro-4-methanesulfonyl-phenyl)-3-cyclopentyl-N-[1-(4-hydroxy-butyl)-1H-pyrazol-3-yl]-propionamide

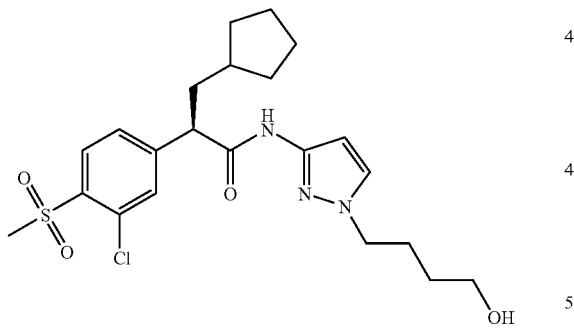

The 4-(3-nitro-pyrazol-1-yl)-but-2-yn-1-ol (prepared in example 52, 113 mg, 0.62 mmol) was dissolved in ethyl acetate (3 mL) and methanol (3 mL) was added. While stirring, a 50% slurry of raney nickel in water (1.3 mL) was added followed by hydrazine (400 μL). Immediate effervescence was observed. The reaction continued to stir and bubble for 25 min. The reaction was passed through a plug of celite and concentrated in vacuo to afford 4-(3-amino-pyrazol-1-yl)-butan-1-ol (93 mg, 98%) as a clear oil: ESI-LRMS m/e calcd for $C_7H_{13}N_3O$ [M$^+$] 155.11, found 156.32 [M+H$^+$].

2-(R)-(3-Chloro-4-methanesulfonyl-phenyl)-3-cyclopentyl-propionic acid (prepared as in PCT WO 2004/052869 A1, Example 1, 200 mg, 0.61 mmol) was dissolved in methylene chloride (3 mL) and a 2.0 M solution of oxalyl chloride in methylene chloride (305 μL, 0.61 mmol) was added and the reaction stirred at 25° C. for 20 min. The solution was chilled to 0° C. and 2,6-lutidine (145 μL, 1.22 mmol) was added. The reaction continued to stir at 0° C. for 20 min. The 4-(3-amino-pyrazol-1-yl)-butan-1-ol (93 mg, 0.61 mmol) was added, the ice bath was removed and the reaction continued to stir at 25° C. for 45 min. The reaction was diluted with methylene chloride (10 mL), washed with water (2×4 mL), saturated aqueous brine solution (1×4 mL), dried over magnesium sulfate and concentrated in vacuo to a beige foam. Purification by reverse phase preparative HPLC (Column: Thomson C18 ODSA, 5 micron, 50×21.2 mm ID; 30% acetonitrile/water to 100% acetonitrile/water; 30 mL/min flow rate for 15 min run) afforded 2-(R)-(3-chloro-4-methanesulfonyl-phenyl)-3-cyclopentyl-N-[1-(4-hydroxy-butyl)-1H-pyrazol-3-yl]-propionamide (35 mg, 12%) as a white foam: ESI-LRMS m/e calcd for $C_{22}H_{30}ClN_3O_4S$ [M$^+$] 467.2, found 468.0 [M+H$^+$], 450.1 [M−H$_2$O+H$^+$]; $^1$H NMR (400 MHz, CDCl$_3$) δ ppm 1.06-1.23 (m, 2H, CH$_2$), 1.45-1.99 (m, 12H, 6×CH$_2$), 2.17-2.30 (m, 1H, CH), 2.71 (brs, 1H, OH), 3.26 (s, 3H, SO$_2$CH$_3$), 3.60 (t, J=7.8 Hz, 1H, CH), 3.69 (t, J=6.2 Hz, 2H, OCH2), 4.09 (t, J=6.6 Hz, 2H, NCH2), 6.70 (s, 1H, Ar), 7.30 (s, 1H, Ar), 7.49 (d, J$_o$=8.3 Hz, 1H, Ar), 7.62 (s, 1H, Ar), 8.10 (d, J$_o$=8.6 Hz, 1H, Ar), 8.47 (brs, 1H, NH).

Example 55

3-{3-[2-(R)-(3-Chloro-4-methanesulfonyl-phenyl)-3-cyclopentyl-propionylamino]-pyrazol-1-ylmethyl}-benzoic acid methyl ester

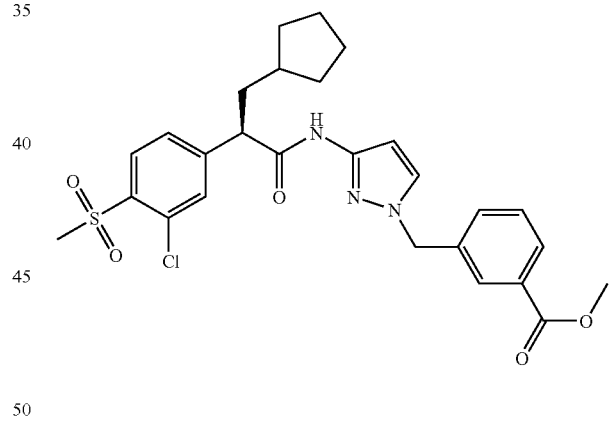

3-Nitro-1H-pyrazole (prepared in example 3, 1.00 g, 8.84 mmol) was dissolved in anhydrous N,N-dimethylformamide (15 mL) and a 60% dispersion of sodium hydride in mineral oil (423 mg, 10.61 mmol) was added while stirring under nitrogen. After the effervescence ceased and the reaction stirred for an additional 25 min, the reaction was chilled to 0° C. and the 3-bromomethyl-benzoic acid methyl ester (2.11 g, 9.20 mmol) was added. The reaction continued to stir under nitrogen at 0° C. for 20 min. The reaction was diluted with ethyl acetate (200 mL), washed with water (2×50 mL), saturated aqueous brine solution (2×20 mL), dried over magnesium sulfate and concentrated in vacuo to give an orange oil. Purification by ISCO flash column chromatography (Teledyne Isco RediSep Flash Column 120 g; 10% ethyl acetate/ hexanes to 60% ethyl acetate/hexanes) afforded 3-(3-nitro-pyrazol-1-ylmethyl)-benzoic acid methyl ester (1.90 g, 82%) as a white waxy solid: H$^1$-NMR (400 MHz, CDCl$_3$) δ 3.93 (3H, s), 5.42 (2H, s), 6.91 (1H, d, J=2.0 Hz), 7.42-7.48 (3H, m), 7.97 (1H, s), 8.03-8.04 (1H, m).

The 3-(3-nitro-pyrazol-1-ylmethyl)-benzoic acid methyl ester (1.78 g, 6.82 mmol) was dissolved in ethyl acetate (5 mL) and methanol (5 mL) was added. While stirring, a 50% slurry of raney nickel in water (1 mL) was added followed by hydrazine (1.5 mL). Immediate effervescence was observed. The reaction continued to stir and bubble for 30 min. The reaction was passed through a plug of celite and concentrated in vacuo to give a yellow oil. The oil was taken up in ethyl acetate (100 mL), washed with water (2×20 mL), saturated aqueous brine solution (20 mL), dried over magnesium sulfate and concentrated in vacuo. Purification by ISCO flash column chromatography (Teledyne Isco RediSep Flash Column 120 g; 15% ethyl acetate/hexanes to 100% ethyl acetate/hexanes) afforded 3-(3-amino-pyrazol-1-ylmethyl)-benzoic acid methyl ester (1.09 g, 69%) as a beige solid: H$^1$-NMR (400 MHz, DMSO-d$_6$) δ 3.83 (3H, s), 4.57 (2H, bs), 5.09 (2H, s), 5.41 (1H, d, J=2.0 Hz), 7.44-7.46 (3H, m), 7.76 (1H, bs), 7.82-7.84 (1H, m).

2-(R)-(3-Chloro-4-methanesulfonyl-phenyl)-3-cyclopentyl-propionic acid (250 mg, 0.76 mmol, prepared as in PCT WO 2004/052869 A1, Example 1) was dissolved in methylene chloride (3.8 mL) and a 2.0 M solution of oxalyl chloride in methylene chloride (380 μL, 0.76 mmol) was added and the reaction stirred at 25° C. for 20 min. The solution was chilled to 0° C. and 2,6-lutidine (180 μL, 1.52 mmol) was added. The reaction continued to stir at 0° C. for 20 min. The 3-(3-amino-pyrazol-1-ylmethyl)-benzoic acid methyl ester (176 mg, 0.76 mmol) was added, the ice bath was removed and the reaction continued to stir at 25° C. for 25 min. The reaction was diluted with methylene chloride (40 mL), washed with water (2×10 mL), saturated aqueous brine solution (1×10 mL), dried over magnesium sulfate and concentrated in vacuo to a beige foam. Purification by flash column chromatography (Merck silica gel 60, 40-63 μm; 0% ethyl acetate/methylene chloride to 15% ethyl acetate/methylene chloride) afforded 3-{3-[2-(R)-(3-chloro-4-methanesulfonyl-phenyl)-3-cyclopentyl-propionylamino]-pyrazol-1-ylmethyl}-benzoic acid methyl ester (196 mg, 47%) as a white foam: ESI-LRMS m/e calcd for C$_{27}$H$_{30}$ClN$_3$O$_5$S [M$^+$] 543.16, found 544.22 [M+H$^+$]; $^1$H NMR (400 MHz, CDCl$_3$) δ ppm 1.05-1.21 (m, 2H, CH$_2$), 1.45-1.94 (m, 8H, 4×CH$_2$), 2.15-2.34 (m, 1H, CH), 3.25 (s, 3H, SO$_2$CH$_3$), 3.52 (t, J=7.5 Hz, 1H, CH), 3.91 (s, 3H, CO$_2$CH$_3$), 5.19 (s, 2H, NCH$_2$), 6.72 (d, J=2.2 Hz, 1H, Ar), 7.34 (m, 2H, Ar), 7.40 (d, J$_o$=7.7 Hz, 1H, Ar), 7.44 (dd, J$_o$=8.3, J$_m$=1.5 Hz. 1H, Ar), 7.58 (d, J$_m$=1.5 Hz, 1H, Ar), 7.84-7.91 (m, 2H, Ar and NH), 7.97 (d, J$_o$=7.7 Hz, 1H, Ar), 8.08 (d, J$_o$=8.3 Hz, 1H, Ar).

Example 56

2-(R)(3-Chloro-4-methanesulfonyl-phenyl)-3-cyclopentyl-N-(1-isopropyl-1H-pyrazol-3-yl)-propionamide

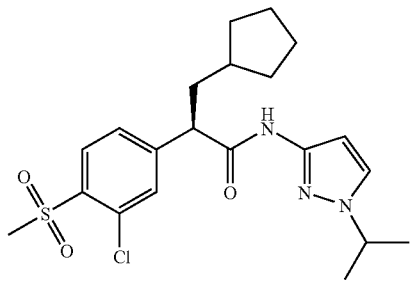

3-Nitro-1H-pyrazole (prepared in example 3, 250 mg, 2.21 mmol) was dissolved in anhydrous N,N-dimethylformamide (5.5 mL) and a 60% dispersion of sodium hydride in mineral oil (97 mg, 2.43 mmol) was added while stirring under nitrogen. After the effervescence ceased and the reaction stirred for an additional 25 min, the reaction was chilled to 0° C. and 2-bromo-propane (324 mg, 2.64 mmol) was added. The reaction continued to stir under nitrogen at 0° C. for 20 min. The ice bath was removed and the reaction continued to stir at 25° C. for 16 h. The reaction was diluted with ethyl acetate (100 mL), washed with water (2×50 mL), saturated aqueous brine solution (2×20 mL), dried over magnesium sulfate and concentrated in vacuo to give an oil. Purification by ISCO flash column chromatography (Teledyne Isco RediSep Flash Column 40 g; 0% ethyl acetate/hexanes to 20% ethyl acetate/hexanes) afforded 1-isopropyl-3-nitro-1H-pyrazole (146 mg, 43%) as a white waxy solid: H$^1$-NMR (400 MHz, CDCl$_3$) δ 1.58 (6H, d, J=6.8 Hz), 4.59 (1H, septet, J=6.4 Hz), 6.88 (1H, d, J=2.8 Hz), 7.47 (1H, d, J=2.0 Hz).

The 1-isopropyl-3-nitro-1H-pyrazole (145 mg, 0.94 mmol) was dissolved in ethyl acetate (4 mL) and methanol (4 mL) was added. While stirring, a 50% slurry of raney nickel in water (1 mL) was added followed by hydrazine (300 μL). Immediate effervescence was observed. The reaction continued to stir and bubble for 30 min. The reaction was passed through a plug of celite and concentrated in vacuo to give the desired product 1-isopropyl-1H-pyrazol-3-ylamine (114 mg, 97%) as a clear oil: ESI-LRMS m/e calcd for C$_6$H$_{11}$N$_3$ [M$^+$] 125.10, found 126.20 [M+H$^+$].

2-(R)-(3-Chloro-4-methanesulfonyl-phenyl)-3-cyclopentyl-propionic acid (prepared as in PCT WO 2004/052869 A1, Example 1, 302 mg, 0.91 mmol) was suspended in methylene chloride (4.5 mL) and a 2.0 M solution of oxalyl chloride in methylene chloride (456 μL, 0.91 mmol) was added and the reaction stirred at 25° C. for 10 min. The solution was chilled to 0° C. and 2,6-lutidine (212 μL, 1.82 mmol) was added. The reaction continued to stir at 0° C. for 15 min. 1-Isopropyl-1H-pyrazol-3-ylamine (114 mg, 0.91 mmol) was dissolved in methylene chloride (4.5 mL) and added dropwise to the reaction. The ice bath was removed and the reaction continued to stir at 25° C. for 30 min. The reaction was diluted with ethyl acetate (50 mL), washed with water (2×15 mL), 1.0 M aqueous hydrochloric acid solution (10 mL), saturated aqueous brine solution (10 mL), dried over magnesium sulfate and concentrated in vacuo to an orange foam. Purification by ISCO flash column chromatography (Teledyne Isco RediSep Flash Column 40 g; 0% ethyl acetate/methylene chloride to 20% ethyl acetate/methylene chloride) afforded 2-(R)-(3-chloro-4-methanesulfonyl-phenyl)-3-cyclopentyl-N-(1-isopropyl-1H-pyrazol-3-yl)-propionamide (183 mg, 46%) as a white foam: ESI-LRMS m/e calcd for $C_{21}H_{28}ClN_3O_3S$ [M+] 437.15, found 438.3 [M+H+]; $^1$H NMR (400 MHz, CDCl$_3$) δ ppm 1.08-1.22 (m, 2H, CH$_2$), 1.46 (d, J=6.6 Hz, 6H, 2×CH$_3$), 1.44-1.94 (m, 8H, CH), 4×CH$_2$), 2.11-2.32 (m, 1H, CH), 3.26 (s, 3H, SO$_2$CH$_3$), 3.53 (t, J=7.5 Hz, 1H, CH), 4.33 (sept, J=6.6 Hz, 1H, NCH), 6.64 (d, $J_o$=2.3, 1H, Ar), 7.30 (d, $J_o$=2.3, 1H, Ar), 7.46 (dd, $J_o$=8.2, $J_m$=1.6 Hz. 1H, Ar), 7.60 (d, $J_m$=1.6 Hz, 1H, Ar), 7.86 (s, 1H, NH), 8.09 (d, $J_o$=8.2 Hz, 1H, Ar).

Example 57

(3-{3-[2-(R)-(3-Chloro-4-methanesulfonyl-phenyl)-3-cyclopentyl-propionylamino]-pyrazol-1-ylmethyl}-phenyl)-carbamic acid tert-butyl ester

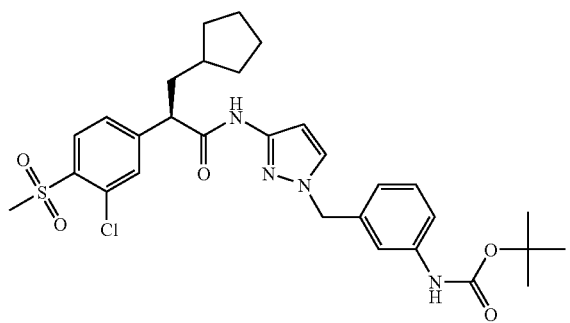

(3-Amino-phenyl)-methanol (850 mg, 6.90 mmol) was suspended in tetrahydrofuran (8 mL) and di-tert-butyl dicarbonate (1.58 g, 7.25 mmol) was added. The solids quickly dissolved with stirring and the resulting solution was heated to 80° C. for 5 h and then at 25° C. for 16 h. The solution was concentrated in vacuo to give a thick yellow oil. Purification by ISCO flash column chromatography (Teledyne Isco RediSep Flash Column 120 g; 5% ethyl acetate/hexanes to 75% ethyl acetate/hexanes) afforded (3-hydroxymethyl-phenyl)-carbamic acid tert-butyl ester (1.67 g, >100%) as a clear oil: H$^1$-NMR (400 MHz, CDCl$_3$) δ 1.52 (9H, s), 2.05 (1H, bs), 4.64 (2H, s), 6.58 (1H, bs), 7.01 (1H, d, J=7.2 Hz), 7.20-7.25 (2H, m), 7.40 (1H, s).

The (3-hydroxymethyl-phenyl)-carbamic acid tert-butyl ester (1.67 g, 7.49 mmol) and triphenylphosphine (2.61 g, 9.96 mmol) were combined and dissolved in tetrahydrofuran (40 mL). Carbon tetrabromide (3.23 g, 9.74 mmol) was dissolved in acetonitrile (20 mL) and added dropwise to the reaction while stirring. After stirring for 5 h, the reaction was concentrated in vacuo to give a thick golden oil. Purification by flash column chromatography (Merck silica gel 60, 40-63 μm; 20% ethyl acetate/hexanes) afforded (3-bromomethyl-phenyl)-carbamic acid tert-butyl ester (1.52 g, 78%) as a white powder: H$^1$-NMR (400 MHz, CDCl$_3$) δ 1.53 (9H, s), 4.46 (2H, s), 6.47 (1H, bs), 7.06 (1H, d, J=7.2 Hz), 7.19-7.27 (2H, m), 7.51 (1H, s).

3-Nitro-1H-pyrazole (prepared in example 3, 595 mg, 5.26 mmol) was dissolved in anhydrous N,N-dimethylformamide (10 mL) and a 60% dispersion of sodium hydride in mineral oil (211 mg, 5.28 mmol) was added while stirring under nitrogen. After the effervescence ceased and the reaction stirred for an additional 25 min, the reaction was chilled to 0° C. and (3-bromomethyl-phenyl)-carbamic acid tert-butyl ester (1.50 g, 5.26 mmol) was added. The reaction continued to stir under nitrogen at 0° C. for 20 min. The reaction was diluted with ethyl acetate (200 mL), washed with water (2×50 mL), saturated aqueous brine solution (2×20 mL), dried over magnesium sulfate and concentrated in vacuo to give a yellow oil. Purification by flash column (Merck silica gel 60, 40-63 μm; 15% ethyl acetate/hexanes) followed by recrystallization from methylene chloride afforded [3-(3-nitro-pyrazol-1-ylmethyl)-phenyl]-carbamic acid tert-butyl ester (782 mg, 47%) as a beige solid: H$^1$-NMR (400 MHz, DMSO-d$_6$) δ 1.45 (9H, s), 5.39 (2H, s), 6.88 (1H, d, J=7.6 Hz), 7.06 (1H, d, J=2.4 Hz), 7.22 (1H, t, J=8.0 Hz), 7.35 (1H, d, J=8.0 Hz), 7.40 (1H, s), 8.11 (1H, d, J=2.8 Hz), 9.36 (1H, s).

The [3-(3-nitro-pyrazol-1-ylmethyl)-phenyl]-carbamic acid tert-butyl ester (782 mg, 2.45 mmol) was dissolved in ethyl acetate (12 mL) and methanol (12 mL) was added. While stirring, a 50% slurry of raney nickel in water (3.1 mL) was added followed by hydrazine (800 μL). Immediate effervescence was observed. The reaction continued to stir and bubble for 30 min. The reaction was passed through a plug of celite and concentrated in vacuo to give the desired product, [3-(3-amino-pyrazol-1-ylmethyl)-phenyl]-carbamic acid tert-butyl ester (698 mg, 98%) as a white solid: ESI-LRMS m/e calcd for $C_{15}H_{20}N_4O_2$ [M+] 288.16, found 289.20 [M+H+].

2-(R)-(3-Chloro-4-methanesulfonyl-phenyl)-3-cyclopentyl-propionic acid (prepared as in PCT WO 2004/052869 A1, Example 1, 500 mg, 1.52 mmol) was suspended in methylene chloride (7.6 mL) and a 2.0 M solution of oxalyl chloride in methylene chloride (760 μL, 1.52 mmol) was added and the reaction stirred at 25° C. for 10 min. The solution was chilled to 0° C. and 2,6-lutidine (354 μL, 3.04 mmol) was added. The reaction continued to stir at 0° C. for 15 min. [3-(3-Amino-pyrazol-1-ylmethyl)-phenyl]-carbamic acid tert-butyl ester (437 mg, 1.52 mmol) was dissolved in methylene chloride (7 mL) and added dropwise to the reaction. The ice bath was removed and the reaction continued to stir at 25° C. for 30 min. The reaction was diluted with ethyl acetate (300 mL), washed with water (2×50 mL), saturated aqueous brine solution (20 mL), dried over magnesium sulfate and concentrated in vacuo to a yellow foam. Purification by ISCO flash column chromatography (Teledyne Isco RediSep Flash Column 120 g; 5% ethyl acetate/methylene chloride to 15% ethyl acetate/methylene chloride) afforded (3-{3-[2-(R)-(3-chloro-4-methanesulfonyl-phenyl)-3-cyclopentyl-propionylamino]-pyrazol-1-ylmethyl}-phenyl)-carbamic acid tert-butyl ester (539 mg 59%) as a pale pink powder: ESI-LRMS m/e calcd for $C_{30}H_{37}ClN_4O_5S$ [M+] 600.22, found 601.50 [M+H+]; $^1$H NMR (400 MHz, CDCl$_3$) δ ppm 1.03-1.23 (m, 2H, CH$_2$), 1.45-1.93 (m, 8H, 4×CH$_2$), 1.51 (s, 9H, 3×CH$_3$), 2.15-2.30 (m, 1H, CH), 3.26 (s, 3H, SO$_2$CH$_3$), 3.54 (t, J=7.8 Hz, 1H, CH), 5.11 (s, 2H, NCH$_2$), 6.49 (brs, 1H, NH), 6.71 (d, J=2.5 Hz, 1H, Ar), 6.82 (m, 1H, Ar), 7.19-7.25 (m, 2H, Ar), 7.26-7.29 (brs, 1H, Ar), 7.31 (d, J=2.5 Hz, 1H, Ar), 7.45 (dd, $J_o$=8.2, $J_m$=1.6 Hz, 1H, Ar), 7.59 (d, $J_m$=1.6 Hz, 1H, Ar), 8.08 (d, $J_o$=8.2 Hz. 1H, Ar), 8.17 (brs, 1H, NH).

Example 58

N-[1-(3-Amino-benzyl)-1H-pyrazol-3-yl]-2-(R)-(3-chloro-4-methanesulfonyl-phenyl)-3-cyclopentyl-propionamide

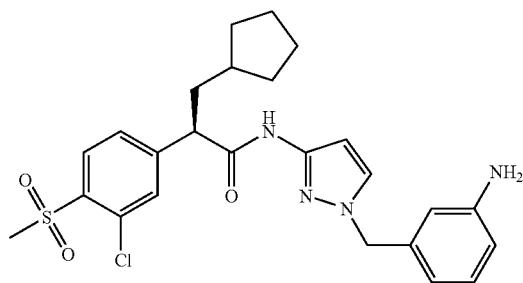

(3-{3-[2-(R)-(3-Chloro-4-methanesulfonyl-phenyl)-3-cyclopentyl-propionylamino]-pyrazol-1-ylmethyl}-phenyl)-carbamic acid tert-butyl ester (prepared in Example 57, 501 mg, 0.83 mmol) was dissolved in methylene chloride (5 mL) and trifluoroacetic acid (500 μL) was added. The reaction stirred at 25° C. for 3 h. The reaction was concentrated in vacuo to half the reaction volume, diluted with toluene and concentrated in vacuo to dryness. The reaction was dissolved in ethyl acetate (25 mL), washed with a saturated aqueous sodium bicarbonate solution (2×10 mL), saturated aqueous brine solution (10 mL), dried over magnesium sulfate and concentrated in vacuo to give the desired product, N-[1-(3-amino-benzyl)-1H-pyrazol-3-yl]-2-(R)-(3-chloro-4-methanesulfonyl-phenyl)-3-cyclopentyl-propionamide (348 mg, 83%) as an off white powder: ESI-LRMS m/e calcd for $C_{25}H_{29}ClN_4O_3S$ [M+] 500.16, found 501.20 [M+H+]; $^1$H NMR (400 MHz, CDCl$_3$) δ ppm 1.06-1.21 (m, 2H, CH$_2$), 1.41-1.92 (m, 8H, 4×CH$_2$), 2.14-2.32 (m, 1H, CH), 3.25 (s, 3H, SO$_2$CH$_3$), 3.53-3.68 (m, 1H, CH), 5.02 (s, 2H, NCH$_2$), 6.45-6.55 (m, 1H, Ar), 6.56-0.665 (m, 2H, Ar), 6.68 (s, 1H, Ar), 7.00-7.14 (m, 1 H, Ar), 7.32 (s, 1H, Ar), 7.45 (d, $J_o$=7.8 Hz. 1H, Ar), 7.60 (s, 1H, Ar), 7.75-8.23 (m, 2H, Ar and NH).

Example 59

N-[1-(3-Acetylamino-benzyl)-1H-pyrazol-3-yl]-2-(R)-(3-chloro-4-methanesulfonyl-phenyl)-3-cyclopentyl-propionamide

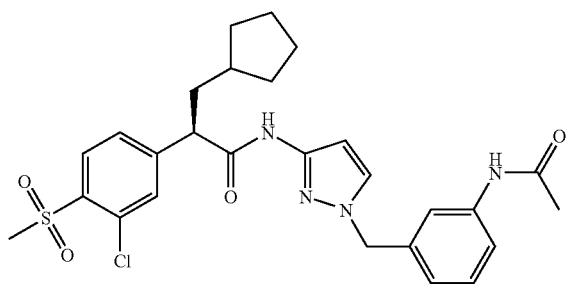

N-[1-(3-Amino-benzyl)-1H-pyrazol-3-yl]-2-(R)-(3-chloro-4-methanesulfonyl-phenyl)-3-cyclopentyl-propionamide (prepared in Example 58, 110 mg, 0.22 mmol) was dissolved in methylene chloride (2 mL) and N-methyl-morpholine (26 μL, 0.24 mmol) was added. Acetyl chloride (16 μL, 0.22 mmol) was added and the reaction stirred at 25° C. for 30 min. The reaction was concentrated in vacuo to give a beige foam. Purification by flash column chromatography (Merck silica gel 60, 40-63 μm; 0% ethyl acetate/methylene chloride to 20% ethyl acetate/methylene chloride) afforded N-[1-(3-acetylamino-benzyl)-1H-pyrazol-3-yl]-2-(R)-(3-chloro-4-methanesulfonyl-phenyl)-3-cyclopentyl-propionamide (68 mg, 57%) as a white powder: ESI-LRMS m/e calcd for $C_{27}H_{31}ClN_4O_4S$ [M+] 542.18, found 543.17 [M+H+]; $^1$H NMR (400 MHz, CDCl$_3$) δ ppm 1.03-1.23 (m, 2H, CH$_2$), 1.41-2.00 (m, 8H, 4×CH$_2$), 2.15 (s, 3H, NCH$_3$), 2.16-2.27 (m, 1H, CH), 3.25 (s, 3H, SO$_2$CH$_3$), 3.55 (t, J=7.5 Hz, 1H, CH), 5.09 (s, 2H, NCH$_2$), 6.69 (d, J=2.3 Hz, 1H, Ar), 6.87 (d, $J_o$=7.5 Hz, 1H, Ar), 7.21-7.28 (m, 2H, NH and Ar), 7.28-7.33 (m, 2H, Ar), 7.35-7.41 (m, 1H, Ar), 7.44 (dd, $J_o$=8.1, $J_m$=1.3 Hz. 1H, Ar), 7.58 (d, $J_m$=1.3 Hz, 1H, Ar), 7.90-8.20 (m, 2H, Ar and NH).

Example 60

2-(R)-(3-Chloro-4-methanesulfonyl-phenyl)-3-cyclopentyl-N-[1-(3-propionylamino-benzyl)-1H-pyrazol-3-yl]-propionamide

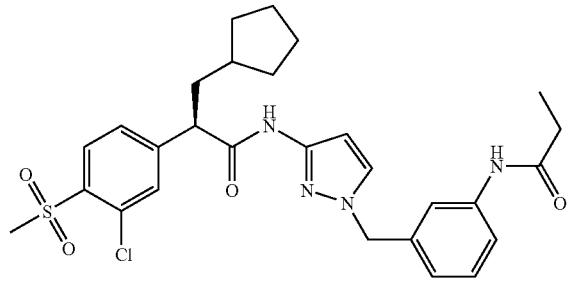

N-[1-(3-Amino-benzyl)-1H-pyrazol-3-yl]-2-(R)-(3-chloro-4-methanesulfonyl-phenyl)-3-cyclopentyl-propionamide prepared in example 58 (110 mg, 0.22 mmol) was dissolved in methylene chloride (2 mL) and N-methyl-morpholine (26 μL, 0.24 mmol) was added. Propionyl chloride (19 μL, 0.22 mmol) was added and the reaction stirred at 25° C. for 30 min. The reaction was concentrated in vacuo to give a beige foam. Purification by flash column chromatography (Merck silica gel 60, 40-63 μm; 0% ethyl acetate/methylene chloride to 20% ethyl acetate/methylene chloride) afforded 2-(R)-(3-chloro-4-methanesulfonyl-phenyl)-3-cyclopentyl-N-[1-(3-propionylamino-benzyl)-1H-pyrazol-3-yl]-propionamide (75 mg, 61%) as a white powder: ESI-LRMS m/e calcd for $C_{28}H_{33}ClN_4O_4S$ [M+] 556.19, found 557.27 [M+H+]; $^1$H NMR (400 MHz, CDCl$_3$) δ ppm 1.07-1.19 (m, 2H, CH$_2$), 1.23 (t, J=7.5 Hz, 3H, CH$_3$), 1.41-1.92 (m, 8H, 4×CH$_2$), 2.15-2.27 (m, 1H, CH), 2.36 (m, 2H, NCOCH$_2$), 3.25 (s, 3H, SO$_2$CH$_3$), 3.56 (t, J=7.75 Hz, 1 H, CH), 5.09 (s, 2H, NCH$_2$), 6.68 (d, J=2.0 Hz, 1H, Ar), 6.86 (d, J$_o$=7.8 Hz, 1H, Ar), 7.18-7.23 (m, 1H, Ar), 7.24 (s, 1H, NH), 7.30 (d, J=2.0 Hz, 1H, Ar), 7.33-7.42 (m, 2H, Ar), 7.44 (d, J$_o$=8.2 Hz. 1H, Ar), 7.58 (s, 1H, Ar), 8.04 (d, J$_o$=8.2 Hz. 1H, Ar), 8.05 (brs, 1H, NH).

Example 61

2-(R)-(3-Chloro-4-methanesulfonyl-phenyl)-3-cyclopentyl-N-[1-(3-ethanesulfonylamino-benzyl)-1H-pyrazol-3-yl]-propionamide

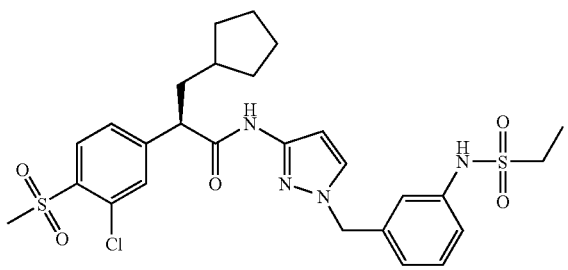

N-[1-(3-Amino-benzyl)-1H-pyrazol-3-yl]-2-(R)-(3-chloro-4-methanesulfonyl-phenyl)-3-cyclopentyl-propionamide (prepared in example 58, 110 mg, 0.22 mmol) was dissolved in methylene chloride (2 mL) and N-methyl-morpholine (26 µL, 0.24 mmol) was added. Ethanesulfonyl chloride (21 µL, 0.22 mmol) was added and the reaction stirred at 25° C. for 30 min. The reaction was warmed to 80° C. for 4 h. The reaction was concentrated in vacuo to give a beige foam. Purification by flash column chromatography (Merck silica gel 60, 40-63 µm; 0% ethyl acetate/methylene chloride to 60% ethyl acetate/methylene chloride) followed by preparative thin layer chromatography (Merck Silica gel 60 F$_{254}$, 500 µm, 20×20 cm; 50% ethyl acetate/methylene chloride) afforded 2-(R)-(3-chloro-4-methanesulfonyl-phenyl)-3-cyclopentyl-N-[1-(3-ethanesulfonylamino-benzyl)-1H-pyrazol-3-yl]-propionamide (14 mg, 11%) as a white powder: ESI-LRMS m/e calcd for C$_{27}$H$_{33}$ClN$_4$O$_5$S$_2$ [M$^+$] 592.2, found 593.7 [M+H$^+$]; $^1$H NMR (400 MHz, DMSO-d$_6$) δ ppm 1.04-1.16 (m, 2H, CH$_2$), 1.14 (t, J=7.3 Hz, 3H, CH$_3$), 1.37-1.83 (m, 8H, 4×CH$_2$), 2.01-2.16 (m, 1H, CH), 3.03 (q, J=7.3 Hz, 2H, SO$_2$CH$_2$), 3.32 (s, 3H, SO$_2$CH$_3$), 3.84-3.92 (m, 1H, CH), 5.15 (s, 2H, NCH$_2$), 6.46 (d, J=2.2 Hz, 1H, Ar), 6.88 (d, J$_o$=7.7 Hz, 1H, Ar), 7.01 (t, J$_m$=1.6 Hz, 1H, Ar), 7.06-7.14 (m, 1H, Ar), 7.24 (t, J$_o$=7.7 Hz, 1H, Ar), 7.56 (dd, J$_o$=8.2, J$_m$=1.6 Hz, 1H, Ar), 7.66 (d, J$_m$=1.6 Hz, 1H, Ar), 7.69 (d, J=2.2 Hz, 1H, Ar), 7.98 (d, J$_o$=8.2 Hz, 1H, Ar), 9.75 (s, 1H, NH), 10.78 (s, 1H, NH).

Example 62

4-(1-{3-[2-(R)-(3-Chlor-4-methanesulfonyl-phenyl)-3-cyclopentyl-propionylamino]-pyrazol-1-yl}-butyl)-benzoic acid methyl ester Formyl-benzoic acid methyl ester (1.00 g, 6.10 mmol) was dissolved in tetrahydrofuran (15 mL), under argon, and chilled to 0° C. A 2.0 M solution of propyl magnesium chloride in diethyl ether (3.05 mL, 6.1 mmol) was added dropwise and the reaction continued to stir at 0° C. for 45 min. 1.0 M aqueous hydrochloric acid solution (10 mL) was added to the reaction and the solution stirred vigorously for 10 min. The solution was diluted with ethyl acetate (100 mL), washed with 1.0 M aqueous hydrochloric acid solution (20 mL), saturated aqueous brine solution (10 mL), dried over magnesium sulfate and concentrated in vacuo to a clear oil. Purification by ISCO flash column chromatography (Teledyne Isco RediSep Flash Column 40 g; 0% ethyl acetate/hexanes to 25% ethyl acetate/hexanes) afforded 4-(1-hydroxy-butyl)-benzoic acid methyl ester (610 mg, 48%) as a clear oil: H$^1$-NMR (400 MHz, CDCl$_3$) δ 0.94 (3H, t, J=7.2 Hz), 1.22-1.52 (2H, m), 1.62-1.84 (2H, m), 2.00 (1H, s), 3.91 (3H, s), 4.74 (1H, t, J=6.8 Hz), 7.40 (2H, d, J=8.4 Hz), 7.99 (2H, d, J=8.0 Hz).

4-(1-Hydroxy-butyl)-benzoic acid methyl ester (605 mg, 2.91 mmol) was dissolved in methylene chloride (14 mL) and a 1.0 M solution of phosphorus tribromide in methylene chloride (6 mL, 6 mmol) was added. The solution stirred at 25° C. for 15 min. Water (5 mL) was added to the reaction and stirred vigorously for 10 min. The organic layer was passed through a plug of Merck silica gel 60, 40-63 mm, eluting with methylene chloride to give the desired product, 4-(1-bromo-butyl)-benzoic acid methyl ester (261 mg, 33%) as a clear oil: H$^1$-NMR (400 MHz, CDCl$_3$) δ 0.95 (3H, t, J=7.2 Hz), 1.22-1.6 (2H, m), 2.02-2.38 (2H, m), 3.92 (3H, s), 4.95 (1H, t, J=7.6 Hz), 7.45 (2H, d, J=8.0 Hz), 8.00 (2H, d, J=8.4 Hz).

3-Nitro-1H-pyrazole (prepared in example 3, 113 mg, 1.00 mmol) was dissolved in anhydrous N,N-dimethylformamide (2.5 mL) and a 60% dispersion of sodium hydride in mineral oil (40 mg, 1.00 mmol) was added while stirring under nitrogen. After the effervescence ceased and the reaction stirred for an additional 25 min, the reaction was chilled to 0° C. and 4-(1-bromo-butyl)-benzoic acid methyl ester (261 mg, 0.97 mmol) was added. The reaction continued to stir under nitrogen at 0° C. for 20 min. The ice bath was removed and the reaction continued to stir at 25° C. for 16 h. The reaction was diluted with ethyl acetate (100 mL), washed with water (2×25 mL), saturated aqueous brine solution (2×10 mL), dried over magnesium sulfate and concentrated in vacuo to give an oil. Purification by ISCO flash column chromatography (Teledyne Isco RediSep Flash Column 40 g; 0% ethyl acetate/hexanes to 20% ethyl acetate/hexanes) afforded 4-[1-(3-nitro-pyrazol-1-yl)-butyl]-benzoic acid methyl ester (127 mg, 42%) as a white waxy solid: ESI-LRMS m/e calcd for $C_{15}H_{17}N_3O_4$ [M$^+$] 303.1, found 304.5 [M+H$^+$].

The 4-[1-(3-nitro-pyrazol-1-yl)-butyl]-benzoic acid methyl ester (127 mg, 0.42 mmol) was dissolved in ethyl acetate (3 mL) and methanol (3 mL) was added. While stirring, a 50% slurry of raney nickel in water (500 μL) was added followed by hydrazine (150 μL). Immediate effervescence was observed. The reaction continued to stir and bubble for 30 min. The reaction was passed through a plug of celite and concentrated in vacuo to afford 4-[1-(3-amino-pyrazol-1-yl)-butyl]-benzoic acid methyl ester (108 mg, 94%) as a clear oil: ESI-LRMS m/e calcd for $C_{15}H_{19}N_3O_2$ [M$^+$] 273.15, found 274.29 [M+H$^+$], 547.43 [2M+H$^+$].

2-(R)-(3-Chloro-4-methanesulfonyl-phenyl)-3-cyclopentyl-propionic acid (prepared as in PCT WO 2004/052869 A1, Example 1, 131 mg, 0.40 mmol) was dissolved in methylene chloride (2 mL) and a 2.0 M solution of oxalyl chloride in methylene chloride (200 μL, 0.40 mmol) was added and the reaction stirred at 25° C. for 10 min. The solution was chilled to 0° C. and 2,6-lutidine (92 μL, 0.79 mmol) was added. The reaction continued to stir at 0° C. for 15 min. 4-[1-(3-Amino-pyrazol-1-yl)-butyl]-benzoic acid methyl ester (108 mg, 0.40 mmol) was dissolved in methylene chloride (2 mL) and added dropwise to the reaction. The ice bath was removed and the reaction continued to stir at 25° C. for 30 min. The reaction was diluted with ethyl acetate (50 mL), washed with water (2×15 mL), 1.0 M aqueous hydrochloric acid solution (10 mL), saturated aqueous brine solution (10 mL), dried over magnesium sulfate and concentrated in vacuo to an orange foam. Purification by ISCO flash column chromatography (Teledyne Isco RediSep Flash Column 10 g; 0% ethyl acetate/methylene chloride to 20% ethyl acetate/methylene chloride) afforded 4-(1-{3-[2-(R)-(3-chloro-4-methanesulfonyl-phenyl)-3-cyclopentyl-propionylamino]-pyrazol-1-yl}-butyl)-benzoic acid methyl ester (110 mg, 47%) as a white foam: ESI-LRMS m/e calcd for $C_{30}H_{36}ClN_3O_5S$ [M$^+$] 585.2, found 586.5 [M+H$^+$]; $^1$H NMR (400 MHz, CDCl$_3$) δ ppm 0.93-1.02 (m, 3H, CH$_3$), 1.05-1.22 (m, 2H, CH$_2$), 1.22-1.40 (m, 2H, CH$_2$), 1.42-2.00 (m, 8H, 4×CH$_2$), 2.02-2.45 (m, 3H, CH$_2$ and CH), 3.26 (s, 3H, SO$_2$CH$_3$), 3.52 (t, J=7.5 Hz, 1H, CH), 3.91 (s, 3H, OCH$_3$), 5.11 (m, 1H, NCH), 6.74 (d, J=2.2 Hz, 1H, Ar), 7.27 (d, J$_o$=8.2 Hz, 2H, Ar), 7.40 (d, J=2.2 Hz, 1H, Ar), 7.45 (dd, J$_o$=8.2, J$_m$=1.6 Hz, 1H, Ar), 7.58 (d, J$_m$=1.6 Hz, 1H, Ar), 7.98 (d, J$_o$=8.2 Hz, 2H, Ar), 8.04 (brs, 1H, NH), 8.09 (d, J$_o$=8.2 Hz, 1H, Ar).

Example 63

3-{3-[2-(R)-(3-Chloro-4-methanesulfonyl-phenyl)-3-cyclopentyl-propionylamino]-pyrazol-1-ylmethyl}-benzamide

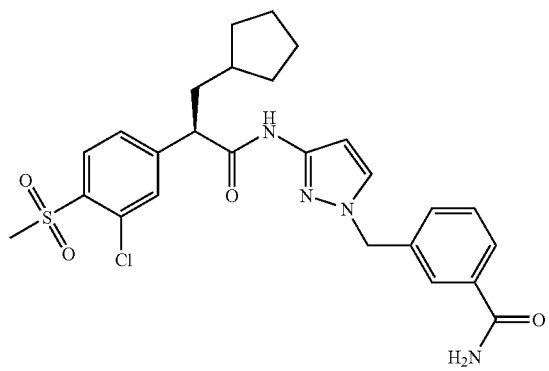

The 3-(3-amino-pyrazol-1-ylmethyl)-benzoic acid methyl ester (prepared in example 55, 900 mg, 3.89 mmol) was dissolved in tetrahydrofuran (6 mL) and methanol (6 mL) was added. A 3.0 N aqueous sodium hydroxide solution (6 mL) was added and the reaction stirred at 25° C. for 1.5 h. 1.0 M aqueous hydrochloric acid solution was added to adjust the pH to ~7.5 followed by the addition of 10% aqueous citric acid to adjust the pH to ~7. The product was extracted into ethyl acetate and the combined organic layers were dried over magnesium sulfate and concentrated in vacuo to give the desired product, 3-(3-amino-pyrazol-1-ylmethyl)-benzoic acid (536 mg, 63%) as a white solid: H$^1$-NMR (400 MHz, DMSO-d$_6$) δ 5.08 (2H, s), 5.41 (1H, d, J=2.0 Hz), 7.41-7.43 (2H, m), 7.45 (1H, d, J=2.4 Hz), 7.73 (1H, s), 7.79-7.82 (1H, m).

2-(R)-(3-Chloro-4-methanesulfonyl-phenyl)-3-cyclopentyl-propionic acid (prepared as in PCT WO 2004/052869 A1, Example 1, 760 mg, 2.30 mmol) was dissolved in methylene chloride (10 mL) and a 2.0 M solution of oxalyl chloride in methylene chloride (1.15 mL, 2.30 mmol) was added and the reaction stirred at 25° C. for 15 min. The solution was chilled to 0° C. and 2,6-lutidine (0.536 mL, 4.6 mmol) was added dropwise. The reaction continued to stir at 0° C. for 15 min. The 3-(3-amino-pyrazol-1-ylmethyl)-benzoic acid (500 mg, 2.30 mmol) was added as a pre-dissolved reaction in methylene chloride (10 mL), the ice bath was removed and the reaction continued to stir at 25° C. for 25 min. The reaction was diluted with methylene chloride (100 mL), washed with water (2×30 mL), saturated aqueous brine solution (1×20 mL), dried over magnesium sulfate and concentrated in vacuo to a beige foam. Recrystallization from 17% ethyl acetate/methylene chloride afforded 3-{3-[2-(R)-(3-chloro-4-methanesulfonyl-phenyl)-3-cyclopentyl-propionylamino]-pyrazol-1-ylmethyl}-benzoic acid (684 mg, 56%) as a white powder: ESI-LRMS m/e calcd for $C_{26}H_{28}ClN_3O_5S$ [M$^+$] 529.14, found 530.26 [M+H$^+$].

3-{3-[2-(R)-(3-Chloro-4-methanesulfonyl-phenyl)-3-cyclopentyl-propionylamino]-pyrazol-1-ylmethyl}-benzoic acid (600 mg, 1.13 mmol) was suspended in methylene chloride (6 mL) and a 2.0 M solution of oxalyl chloride in methylene chloride (567 µL, 1.13 mmol) was added and the reaction stirred at 25° C. for 10 min. The solution was chilled to 0° C. and 2,6-lutidine (264 µL, 2.27 mmol) was added dropwise. The reaction continued to stir at 0° C. for 10 min to afford the crude 3-{3-[2-(R)-(3-chloro-4-methanesulfonyl-phenyl)-3-cyclopentyl-propionylamino]-pyrazol-1-ylmethyl}-benzoyl chloride as a 0.166 M solution in methylene chloride which was used in the following step with no further purification.

To a 0.166 M solution of crude 3-{3-[2-(R)-(3-chloro-4-methanesulfonyl-phenyl)-3-cyclopentyl-propionylamino]-pyrazol-1-ylmethyl}-benzoyl chloride in methylene chloride (1.71 mL, 0.28 mmol) was added ammonium hydroxide (10 drops) and the reaction stirred at 25° C. for 30 min. The solution was diluted with methylene chloride (40 mL), washed with water (2×20 mL), saturated aqueous brine solution (2×20 mL), dried over magnesium sulfate and concentrated in vacuo to an off white foam. Purification by flash column chromatography (Merck silica gel 60, 40-63 µm; 0% ethyl acetate/methylene chloride to 100% ethyl acetate/methylene chloride) afforded 3-{3-[2-(R)-(3-chloro-4-methanesulfonyl-phenyl)-3-cyclopentyl-propionylamino]-pyrazol-1-ylmethyl}-benzamide (91 mg, 61%) as a white powder: ESI-LRMS m/e calcd for $C_{26}H_{29}ClN_4O_4S$ [M$^+$] 528.16, found 529.17 [M+H$^+$]; $^1$H NMR (400 MHz, DMSO-d$_6$) δ ppm 1.02-1.16 (m, 2H, CH$_2$), 1.37-1.76 (m, 8H, 4×CH$_2$), 2.01-2.20 (m, 1H, CH), 3.31 (s, 3H, SO$_2$CH$_3$), 3.83-3.89 (m, 1H, CH), 5.21 (s, 2H, NCH$_2$), 6.45 (d, J=2.2 Hz, 1H, Ar), 7.29-7.35 (m, 2H, Ar), 7.38 (t, J=7.8 Hz, 1H, Ar), 7.55 (dd, J$_o$=8.2, J$_m$=1.5 Hz, 1 H, Ar), 7.65 (d, J$_m$=1.5 Hz, 1H, Ar), 7.72 (d, J=2.2 Hz, 1 H, Ar), 7.73-7.80 (m, 2H, Ar and NH of NH$_2$), 7.92 (brs, 1H, NH of NH$_2$), 7.97 (d, J$_o$=8.2 Hz, 1H, Ar), 10.76 (s, 1H, NH).

Example 64

3-{3-[2-(R)-(3-Chloro-4-methanesulfonyl-phenyl)-3-cyclopentyl-propionylamino]-pyrazol-1-ylmethyl}-N-methyl-benzamide

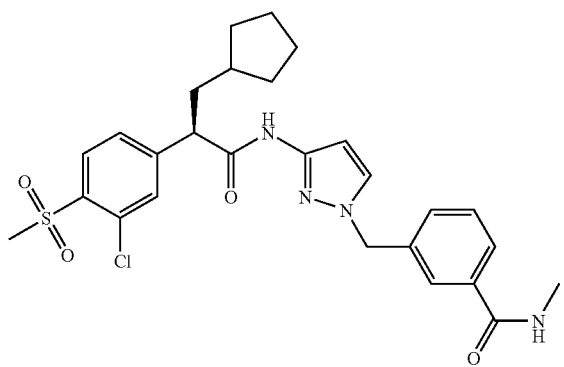

To a 0.166 M solution of crude 3-{3-[2-(R)-(3-chloro-4-methanesulfonyl-phenyl)-3-cyclopentyl-propionylamino]-pyrazol-1-ylmethyl}-benzoyl chloride in methylene chloride (prepared in Example 63, 1.71 mL, 0.28 mmol) was added a 40% solution of methylamine in water (250 µL, 0.32 mmol) and the reaction stirred at 25° C. for 30 min. The solution was diluted with methylene chloride (40 mL), washed with water (2×20 mL), saturated aqueous brine solution (2×20 mL), dried over magnesium sulfate and concentrated in vacuo to an off white foam. Purification by flash column chromatography (Merck silica gel 60, 40-63 µm; 0% ethyl acetate/methylene chloride to 100% ethyl acetate/methylene chloride) afforded 3-{3-[2-(R)-(3-chloro-4-methanesulfonyl-phenyl)-3-cyclopentyl-propionylamino]-pyrazol-1-ylmethyl}-N-methyl-benzamide (61 mg, 39%) as a white powder: ESI-LRMS m/e calcd for $C_{27}H_{31}ClN_4O_4S$ [M$^+$] 542.18, found 543.16 [M+H$^+$]; $^1$H NMR (400 MHz, DMSO-d$_6$) δ ppm 1.04-1.15 (m, 2H, CH$_2$), 1.34-1.79 (m, 8H, 4×CH$_2$), 2.00-2.17 (m, 1H, CH), 2.75 (d, J, 4.5 Hz, 3H, NCH$_3$), 3.32 (s, 3H, SO$_2$CH$_3$), 3.82-3.90 (m, 1H, CH), 5.21 (s, 2H, NCH$_2$), 6.45 (d, J=2.3 Hz, 1H, Ar), 7.28-7.34 (m, 1H, Ar), 7.38 (t, J=7.8 Hz, 1H, Ar), 7.55 (dd, J$_o$=8.3, J$_m$=1.6 Hz, 1H, Ar), 7.65 (d, J$_m$=1.6 Hz, 1H, Ar), 7.67-7.71 (m, 2H, Ar), 7.72 (d, J=2.3 Hz, 1H, Ar), 7.97 (d, J$_o$=8.3 Hz, 1H, Ar), 8.33-8.45 (brm, 1H, NH), 10.76 (s, 1H, NH).

Example 65

3-{3-[2-(R)-(3-Chloro-4-methanesulfonyl-phenyl)-3-cyclopentyl-propionylamino]-pyrazol-1-ylmethyl}-N,N-dimethyl-benzamide

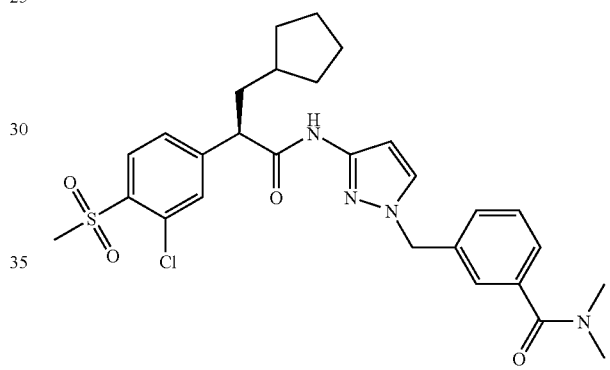

To a 0.166 M solution of crude 3-{3-[2-(R)-(3-chloro-4-methanesulfonyl-phenyl)-3-cyclopentyl-propionylamino]-pyrazol-1-ylmethyl}-benzoyl chloride in methylene chloride (prepared in Example 63, 1.71 mL, 0.28 mmol) was added a 40% solution of dimethylamine in water (250 µL, 0.22 mmol) and the reaction stirred at 25° C. for 30 min. The solution was diluted with methylene chloride (40 mL), washed with water (2×20 mL), saturated aqueous brine solution (2×20 mL), dried over magnesium sulfate and concentrated in vacuo to an off white foam. Purification by flash column chromatography (Merck silica gel 60, 40-63 µm; 0% ethyl acetate/methylene chloride to 100% ethyl acetate/methylene chloride) afforded 3-{3-[2-(R)-(3-chloro-4-methanesulfonyl-phenyl)-3-cyclopentyl-propionylamino]-pyrazol-1-ylmethyl}-N,N-dimethyl-benzamide (72 mg, 46%) as a white powder: ESI-LRMS m/e calcd for $C_{28}H_{33}ClN_4O_4S$ [M$^+$] 556.19, found 557.27 [M+H$^+$]; $^1$H NMR (400 MHz, DMSO-d$_6$) δ ppm 1.02-1.19 (m, 2H, CH$_2$), 1.36-1.78 (m, 8H, 4×CH$_2$), 2.02-2.17 (m, 1H, CH), 2.84 (s, 3H, NCH$_3$), 2.94 (s, 3H, NCH$_3$), 3.32 (s, 3H, SO$_2$CH$_3$), 3.82-3.91 (m, 1H, CH), 5.21 (s, 2H, NCH$_2$), 6.45 (d, J=2.3 Hz, 1H, Ar), 7.17-7.32 (m, 3H, Ar), 7.33-7.40 (m, 1H, Ar), 7.55 (dd, J$_o$=8.3, J$_m$=1.7 Hz, 1H, Ar), 7.65 (d, $J_m$=1.7 Hz, 1H, Ar), 7.73 (d, J=2.3 Hz, 1H, Ar), 7.97 (d, $J_o$=8.3 Hz, 1H, Ar), 10.77 (s, 1H, NH).

Example 66

3-{3-[2-(R)-(3-Chloro-4-methanesulfonyl-phenyl)-3-cyclopentyl-propionylamino]-pyrazol-1-ylmethyl}-N-cyclopropylmethyl-benzamide

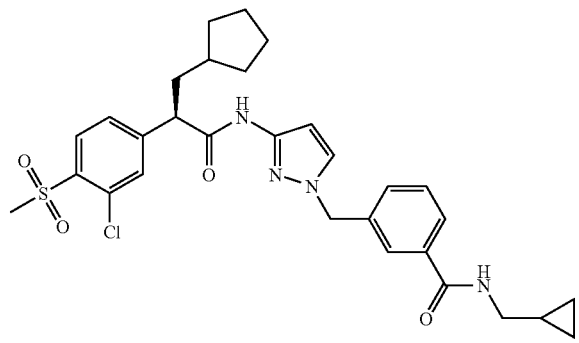

To a 0.166 M solution of crude 3-{3-[2-(R)-(3-chloro-4-methanesulfonyl-phenyl)-3-cyclopentyl-propionylamino]-pyrazol-1-ylmethyl}-benzoyl chloride in methylene chloride (prepared in example 63, 1.71 mL, 0.28 mmol) was added aminomethyl cyclopropane (20 mg, 0.28 mmol) and the reaction stirred at 25° C. for 30 min. The solution was diluted with methylene chloride (40 mL), washed with water (2×20 mL), saturated aqueous brine solution (2×20 mL), dried over magnesium sulfate and concentrated in vacuo to an off white foam. Purification by flash column chromatography (Merck silica gel 60, 40-63 µm; 0% ethyl acetate/methylene chloride to 100% ethyl acetate/methylene chloride) afforded 3-{3-[2-(R)-(3-chloro-4-methanesulfonyl-phenyl)-3-cyclopentyl-propionylamino]-pyrazol-1-ylmethyl}-N-cyclopropylmethyl-benzamide (60 mg, 36%) as a white powder: ESI-LRMS m/e calcd for $C_{30}H_{35}ClN_4O_4S$ [M+] 582.21, found 583.33 [M+H+]; $^1$H NMR (400 MHz, DMSO-$d_6$) δ ppm 0.17-0.27 (m, 2H, CH$_2$), 0.39-0.046 (m, 2H, CH$_2$), 0.98-1.17 (m, 3H, CH and CH$_2$), 1.37-1.78 (m, 8H, 4×CH$_2$), 2.02-2.17 (m, 1H, CH), 3.12 (t, J=6.0 Hz, 2H, NCH$_2$), 3.32 (s, 3H, SO$_2$CH$_3$), 3.83-3.91 (m, 1H, CH), 5.22 (s, 2H, NCH$_2$), 6.46 (d, J=2.0 Hz, 1H, Ar), 7.28-7.36 (m, 1H, Ar), 7.39 (t, J=8.0 Hz, 1H, Ar), 7.56 (d, $J_o$=7.8 Hz, 1H, Ar), 7.65 (d, $J_m$=1.2 Hz, 1H, Ar), 7.69-7.80 (m, 3H, Ar), 7.97 (d, $J_o$=8.2 Hz, 1H, Ar), 8.51 (m, 1H, NH), 10.77 (s, 1H, NH).

Example 67

2-(R)-(3-Chloro-4-methanesulfonyl-phenyl)-3-cyclopentyl-N-[1-(2-hydroxy-ethyl)-1H-pyrazol-3-yl]-propionamide

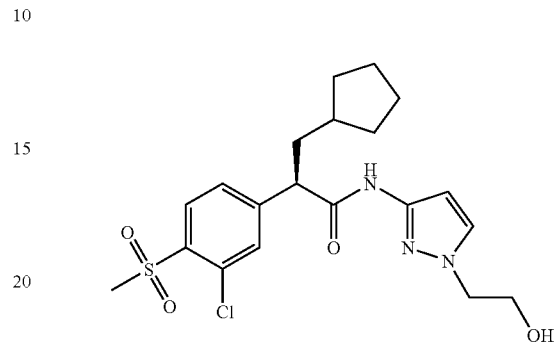

3-Nitro-1H-pyrazole (prepared in example 3, 250 mg, 2.21 mmol) was dissolved in anhydrous N,N-dimethylformamide (5 mL) and a 60% dispersion of sodium hydride in mineral oil (93 mg, 2.32 mmol) was added while stirring under nitrogen. After the effervescence ceased and the reaction stirred for an additional 10 min, (2-bromo-ethoxy)-tert-butyl-dimethyl-silane (598 mg, 2.50 mmol) was added. The reaction continued to stir under nitrogen for 2 h. The solution was diluted with ethyl acetate (200 mL), washed with water (2×75 mL), saturated aqueous brine solution (75 mL), dried over magnesium sulfate, filtered and concentrated in vacuo. Purification by flash column chromatography (Merck silica gel 60, 40-63 µm; 5% ethyl acetate/hexanes to 25% ethyl acetate/hexanes) afforded 1-[2-(tert-butyl-dimethyl-silanyloxy)-ethyl]-3-nitro-1H-pyrazole (508 mg, 84%) as a yellow oil: $H^1$-NMR (400 MHz, DMSO-$d_6$) δ 0.00 (6H, s), 0.86 (9H, s), 4.03 (2H, t, J=5.6 Hz), 4.40 (2H, t, J=5.2 Hz), 7.11 (1H, d, J=2.4 Hz), 8.06 (1H, d, J=2.4 Hz).

The 1-[2-(tert-butyl-dimethyl-silanyloxy)-ethyl]-3-nitro-1H-pyrazole (500 mg, 1.80 mmol) was dissolved in ethyl acetate (15 mL) and methanol (15 mL) was added. Palladium, 10 wt. % on activated carbon, wet (50 mg) was added to the solution and the flask was charged with hydrogen gas via balloon. The reaction stirred at 25° C. for 16 h. The reaction was passed through a plug of Merck silica gel 60, 40-63 µm layered with celite and concentrated in vacuo to give the desired product, 1-[2-(tert-butyl-dimethyl-silanyloxy)-ethyl]-1H-pyrazol-3-ylamine (391 mg, 90%) as a yellow oil: $H^1$-NMR (400 MHz, DMSO-$d_6$) δ 0.00 (6H, s), 0.83 (9H, s), 3.78 (2H, t, J=4.8 Hz), 3.87 (2H, t, J=6.0 Hz), 4.48 (2H, s), 5.33 (1H, d, J=2.0 Hz), 7.22 (1H, d, J=2.0 Hz).

2-(R)-(3-Chloro-4-methanesulfonyl-phenyl)-3-cyclopentyl-propionic acid (prepared as in PCT WO 2004/052869 A1, Example 1, 273 mg, 0.83 mmol) was suspended in methylene chloride (4 mL) and a 2.0 M solution of oxalyl chloride in methylene chloride (413 µL, 0.83 mmol) was added and the reaction stirred at 25° C. for 15 min. The solution was chilled to 0° C. and 2,6-lutidine (192 µL, 1.65 mmol) was added dropwise. The reaction continued to stir at 0° C. for 15 min. The 1-[2-(tert-butyl-dimethyl-silanyloxy)-ethyl]-1H-pyrazol-3-ylamine (200 mg, 0.83 mmol) was added as a pre-dissolved reaction in methylene chloride (4 mL), the ice bath was removed and the reaction continued to stir at 25° C. for 25 min. The reaction was diluted with methylene chloride (100 mL), washed with water (2×30 mL), saturated aqueous brine solution (1×20 mL), dried over magnesium sulfate and concentrated in vacuo to a beige foam. Purification by flash column chromatography (Merck silica gel 60, 40-63 μm; 0% ethyl acetate/methylene chloride to 10% ethyl acetate/methylene chloride) afforded N-{1-[2-(R)-(tert-butyl-dimethyl-silanyloxy)-ethyl]-1H-pyrazol-3-yl}-2-(3-chloro-4-methanesulfonyl-phenyl)-3-cyclopentyl-propionamide (392 mg, 86%) as a white foam: ESI-LRMS m/e calcd for $C_{26}H_{40}ClN_3O_4SSi$ [M⁺] 553.22, found 554.33 [M+H⁺].

N-{1-[2-(R)-(tert-Butyl-dimethyl-silanyloxy)-ethyl]-1H-pyrazol-3-yl}-2-(3-chloro-4-methanesulfonyl-phenyl)-3-cyclopentyl-propionamide (300 mg, 0.54 mmol) was dissolved in ethanol (2.5 mL) and concentrated hydrochloric acid (25 μL) was added. The reaction stirred at 25° C. for 30 min. The reaction was diluted with ethyl acetate (50 mL), washed with water (20 mL), saturated aqueous brine solution (20 mL), dried over magnesium sulfate and concentrated in vacuo to give a beige foam. Purification by flash column chromatography (Merck silica gel 60, 40-63 μm; 0% ethyl acetate/methylene chloride to 50% ethyl acetate/methylene chloride) afforded 2-(R)-(3-chloro-4-methanesulfonyl-phenyl)-3-cyclopentyl-N-[1-(2-hydroxy-ethyl)-1H-pyrazol-3-yl]-propionamide (154 mg, 65%) as a white crystalline powder: ESI-LRMS m/e calcd for $C_{20}H_{26}ClN_3O_4S$ [M⁺] 439.13, found 440.21 [M+H⁺]; ¹H NMR (400 MHz, DMSO-d₆) δ ppm 1.04-1.18 (m, 2H, CH₂), 1.36-1.81 (m, 8H, 4×CH₂), 2.01-2.23 (m, 1H, CH), 3.33 (s, 3H, SO₂CH₃), 3.66 (q, J=5.6 Hz, 2H, OCH₂), 3.86-3.94 (m, 1H, CH), 3.98 (t, J=5.6 Hz, 2H, NCH₂), 4.79 (t, J=5.6 Hz, 1H, OH), 6.39 (d, $J_o$=2.2, 1H, Ar), 7.51 (d, $J_o$=2.2, 1H, Ar), 7.57 (dd, $J_o$=8.2, $J_m$=1.6 Hz, 1H, Ar), 7.67 (d, $J_m$=1.6 Hz, 1H, Ar) 7.98 (d, $J_o$=8.2 Hz, 1H, Ar), 10.74 (s, 1H, NH).

Example 68

4-{3-[2-(R)-(3-Chloro-4-methanesulfonyl-phenyl)-3-cyclopentyl-propionylamino]-pyrazol-1-ylmethyl}-cyclohexanecarboxylic acid methyl ester

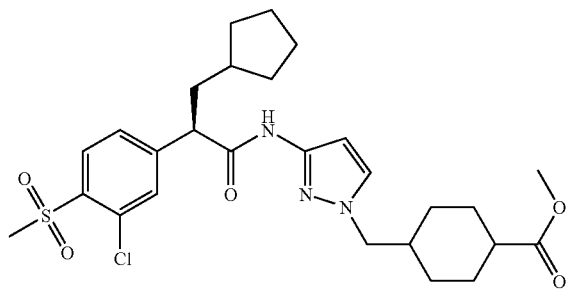

4-Hydroxymethyl-cyclohexanecarboxylic acid methyl ester (250 mg, 1.45 mmol) was dissolved in pyridine (7 mL) and 4-methyl-benzenesulfonyl chloride (692 mg, 3.63 mmol) was dissolved in methylene chloride (4 mL). The 4-methyl-benzenesulfonyl chloride solution was added dropwise to the alcohol solution while stirring. The reaction continued to stir at 25° C. for 16 h. The reaction was concentrated in vacuo to give a thick oil. The oil was dissolved in ethyl acetate (35 mL), washed with water (15 mL), 1.0 M aqueous hydrochloric acid solution (2×15 mL), saturated aqueous sodium bicarbonate solution (2×15 mL), saturated aqueous brine solution (15 mL), dried over magnesium sulfate and concentrated in vacuo to give the desired product, 4-(toluene-4-sulfonyloxymethyl)-cyclohexanecarboxylic acid methyl ester (380 mg, 80%) as a yellow oil: H¹-NMR (400 MHz, CDCl₃) δ 0.92-1.04 (2H, m), 1.33-1.46 (2H, m), 1.60-1.70 (1H, m), 1.80 (2H, dd, J=13.6 Hz, 3.2 Hz), 2.00 (2H, dd, J=14.0 Hz, 3.6 Hz), 2.15-2.26 (1H, m), 2.46 (3H, s), 3.65 (3H, s), 3.83 (2H, d, J=6.4 Hz), 7.34 (2H, d, J=8.4 Hz), 7.77 (2H, d, J=8.4 Hz).

The 3-Nitro-1H-pyrazole (prepared in example 3, 130 mg, 1.16 mmol) was dissolved in N,N-dimethylformamide (4 mL) and a 60% suspension of sodium hydride in mineral oil (50 mg, 1.25 mmol) was added. After the effervescence ceased and the reaction stirred for an additional 10 min, the 4-(toluene-4-sulfonyloxymethyl)-cyclohexanecarboxylic acid methyl ester (380 mg, 1.16 mmol) was added and the reaction was heated to 80° C. while stirring for 4 h. The reaction continued to stir under nitrogen for 2 h. The solution was diluted with ethyl acetate (100 mL), washed with saturated aqueous sodium bicarbonate solution (35 mL), 1.0 M aqueous hydrochloric acid solution (35 mL), dried over magnesium sulfate, filtered and concentrated in vacuo. Purification by flash column chromatography (Merck silica gel 60, 40-63 μm; 5% ethyl acetate/hexanes to 50% ethyl acetate/hexanes) afforded 4-(3-nitro-pyrazol-1-ylmethyl)-cyclohexanecarboxylic acid methyl ester (114 mg, 37%) as a yellow oil: H¹-NMR (400 MHz, CDCl₃) δ 1.00-1.12 (2H, m), 1.36-1.50 (2H, m), 1.68-1.78 (2H, m), 1.90-2.08 (3H, m), 2.20-2.30 (1H, m), 3.66 (3H, s), 4.03 (2H, d, J=7.2 Hz), 6.88 (2H, d, J=2.4 Hz), 7.40 (2H, d, J=8.4 Hz).

The 4-(3-nitro-pyrazol-1-ylmethyl)-cyclohexanecarboxylic acid methyl ester (108 mg, 0.40 mmol) was dissolved in methanol (8 mL) and ethyl acetate (8 mL) was added. While stirring, a 50% slurry of raney nickel in water (1 mL) was added followed by hydrazine (200 μL). Immediate effervescence was observed. The reaction continued to stir and bubble for 30 min. The reaction was passed through a plug of celite and concentrated in vacuo to give an oil. The oil was taken up in ethyl acetate (40 mL), washed with water (2×10 mL), saturated aqueous brine solution (10 mL), dried over magnesium sulfate and concentrated in vacuo to give the desired product, 4-(3-amino-pyrazol-1-ylmethyl)-cyclohexanecarboxylic acid methyl ester (90 mg, 94%) as a waxy solid: ESI-LRMS m/e calcd for $C_{12}H_{19}N_3O_2$ [M⁺] 237.15, found 238.38 [M+H⁺], 475.37 [2M+H⁺].

2-(R)-(3-Chloro-4-methanesulfonyl-phenyl)-3-cyclopentyl-propionic acid (prepared as in PCT WO 2004/052869 A1, Example 1, 125 mg, 0.38 mmol) was dissolved in methylene chloride (2 mL) and a 2.0 M solution of oxalyl chloride in methylene chloride (190 μL, 0.38 mmol) was added and the reaction stirred at 25° C. for 15 min. The solution was chilled to 0° C. and 2,6-lutidine (89 μL, 0.76 mmol) was added dropwise. The reaction continued to stir at 0° C. for 15 min. The 4-(3-amino-pyrazol-1-ylmethyl)-cyclohexanecarboxylic acid methyl ester (90 mg, 0.38 mmol) was added as a pre-dissolved reaction in methylene chloride (2 mL), the ice bath was removed and the reaction continued to stir at 25° C. for 25 min. The reaction was diluted with methylene chloride (100 mL), washed with water (2×30 mL), saturated aqueous brine solution (1×20 mL), dried over magnesium sulfate and concentrated in vacuo to a beige foam. Purification by flash column chromatography (Merck silica gel 60, 40-63 μm; 0% ethyl acetate/methylene chloride to 15% ethyl acetate/methylene chloride) afforded 4-{3-[2-(R)-(3-chloro-4-methanesulfonyl-phenyl)-3-cyclopentyl-propionylamino]-pyrazol-1-ylmethyl}-cyclohexanecarboxylic acid methyl ester (80 mg, 38%) as a white foam: ESI-LRMS m/e calcd for $C_{27}H_{36}ClN_3O_5S$ [M⁺] 549.21, found 550.36 [M+H⁺]; ¹H NMR (400 MHz, CDCl$_3$) δ ppm 0.91-1.07 (m, 2H, CH$_2$), 1.06-1.21 (m, 2H, CH$_2$), 1.32-1.47 (m, 2H, CH$_2$), 1.46-1.56 (m, 2H, CH$_2$), 1.56-1.93 (m, 9H, CH and 4×CH$_2$), 1.93-2.04 (m, 2H, CH$_2$), 2.11-2.32 (m, 2H, 2×CH), 3.26 (s, 3H, SO$_2$CH$_3$), 3.54 (t, J=7.5 Hz, 1H, CH), 3.66 (s, 3H, CO$_2$CH$_3$), 3.80 (d, J=7.0 Hz, 2H, NCH$_2$), 6.64 (d, J$_o$=2.2 Hz, 1H, Ar), 7.21 (d, J$_o$=2.2 Hz, 1H, Ar), 7.46 (dd, J$_o$=8.1, J$_m$=1.7 Hz. 1H, Ar), 7.59 (d, J$_m$=1.7 Hz, 1H, Ar), 7.58 (s, 1H, NH), 8.09 (d, J$_o$=8.1 Hz, 1H, Ar).

Example 69

2-(R)-(3-Chloro-4-methanesulfonyl-phenyl)-3-cyclopentyl-N-(1-cyclopropylmethyl-1H-pyrazol-3-yl)-propionamide

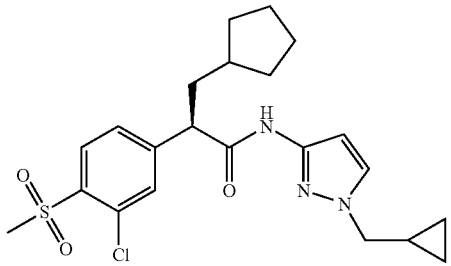

The 3-Nitro-1H-pyrazole (prepared in example 3, 255 mg, 2.26 mmol) was dissolved in tetrahydrofuran (11 mL) and cyclopropyl-methanol (163 mg, 2.26 mmol) was added followed by triphenylphosphine (592 mg, 2.26 mmol). While stirring, diisopropyl azodicarboxylate (667 μL, 3.39 mmol) was added dropwise. A mild exotherm was observed. The reaction continued to stir for 30 min. The solution was diluted with ethyl acetate (100 mL), washed with water (2×35 mL), 1.0 M aqueous hydrochloric acid solution (35 mL), saturated aqueous brine solution (35 mL), dried over magnesium sulfate, filtered and concentrated in vacuo. Purification by flash column chromatography (Merck silica gel 60, 40-63 μm; 5% ethyl acetate/hexanes to 50% ethyl acetate/hexanes) afforded 1-cyclopropylmethyl-3-nitro-1H-pyrazole (217 mg, 58%) as a yellow oil: H$^1$-NMR (400 MHz, CDCl$_3$) δ 0.44 (2H, qt, J=5.6 Hz), 0.73 (2H, qt, J=6.8 Hz), 1.30-1.40 (1H, m), 4.07 (2H, d, J=7.6 Hz), 6.89 (1H, d, J=2.8 Hz), 7.57 (1H, d, J=2.4 Hz).

The 1-cyclopropylmethyl-3-nitro-1H-pyrazole (217 mg, 1.30 mmol) was dissolved in methanol (6 mL) and ethyl acetate (6 mL) was added. While stirring, a 50% slurry of raney nickel in water (1.5 mL) was added followed by hydrazine (250 μL). Immediate effervescence was observed. The reaction continued to stir and bubble for 30 min. The reaction was passed through a plug of celite and concentrated in vacuo to give an oil. The oil was taken up in ethyl acetate (40 mL), washed with water (2×10 mL), saturated aqueous brine solution (10 mL), dried over magnesium sulfate and concentrated in vacuo to give the desired product, 1-cyclopropylmethyl-1H-pyrazol-3-ylamine (169 mg, 95%) as a waxy beige solid: H$^1$-NMR (400 MHz, CDCl$_3$) δ 0.02 (2H, qt, J=5.6 Hz), 0.31 (2H, qt, J=6.8 Hz), 0.88-0.98 (1H, m), 3.20-3.32 (2H, bs), 3.47 (2H, d, J=7.2 Hz), 5.27 (1H, d, J=2.4 Hz), 6.91 (1H, d, J=2.4 Hz).

2-(R)-(3-Chloro-4-methanesulfonyl-phenyl)-3-cyclopentyl-propionic acid (prepared as in PCT WO 2004/052869 A1, Example 1, 410 mg, 1.23 mmol) was suspended in methylene chloride (7 mL) and a 2.0 M solution of oxalyl chloride in methylene chloride (615 μL, 1.23 mmol) was added and the reaction stirred at 25° C. for 15 min. The solution was chilled to 0° C. and 2,6-lutidine (293 μL, 2.46 mmol) was added dropwise. The reaction continued to stir at 0° C. for 15 min. 1-Cyclopropylmethyl-1H-pyrazol-3-ylamine (169 mg, 1.23 mmol) was added as a pre-dissolved reaction in methylene chloride (7 mL), the ice bath was removed and the reaction continued to stir at 25° C. for 25 min. The reaction was diluted with methylene chloride (100 mL), washed with water (2×30 mL), saturated aqueous brine solution (1×20 mL), dried over magnesium sulfate and concentrated in vacuo to a beige foam. Purification by flash column chromatography (Merck silica gel 60, 40-63 μm; 0% ethyl acetate/methylene chloride to 15% ethyl acetate/methylene chloride) followed by recrystallization from 10% methylene chloride/diethyl ether afforded 2-(R)-(3-chloro-4-methanesulfonyl-phenyl)-3-cyclopentyl-N-(1-cyclopropylmethyl-1H-pyrazol-3-yl)-propionamide (162 mg, 29%) as a white crystalline solid: ESI-LRMS m/e calcd for C$_{22}$H$_{28}$ClN$_3$O$_3$S [M$^+$] 449.15, found 450.19 [M+H$^+$]; $^1$H NMR (400 MHz, CDCl$_3$) δ ppm 0.32-0.041 (m, 2H, CH$_2$), 0.63-0.70 (m, 2H, CH$_2$), 1.08-1.31 (m, 3H, CH$_2$), 1.44-1.95 (m, 8H, 4×CH$_2$), 2.13-2.37 (m, 1H, CH), 3.28 (s, 3H, SO$_2$CH$_3$), 3.55 (t, J=7.6 Hz, 1H, CH), 3.85 (d, J=7.0 Hz, 2H, NCH$_2$), 6.67 (d, J$_o$=2.2 Hz, 1H, Ar), 7.38 (d, J$_o$=2.2 Hz, 1H, Ar), 7.46 (dd, J$_o$=8.1, Hz, J$_m$=1.7 Hz. 1H, Ar), 7.60 (d, J$_m$=1.7 Hz, 1H, Ar), 7.90 (s, 1H, NH), 8.09 (d, J$_o$=8.1 Hz, 1H, Ar).

Example 70

Acetic acid 2-{3-[2-(R)-(3-chloro-4-methanesulfonyl-phenyl)-3-cyclopentyl-propionylamino]-pyrazol-1-yl}-ethyl ester

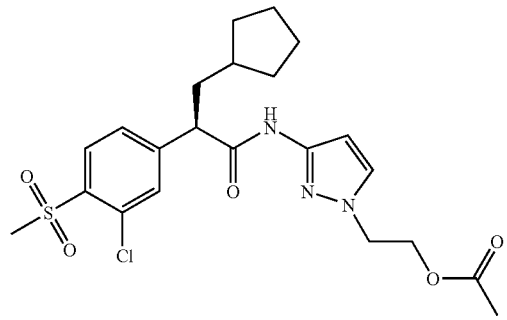

2-(R)-(3-Chloro-4-methanesulfonyl-phenyl)-3-cyclopentyl-N-[1-(2-hydroxy-ethyl)-1H-pyrazol-3-yl]-propionamide (prepared in Example 67, 102 mg, 0.27 mmol) was dissolved in pyridine (2 mL) and acetic anhydride (27 umL, 0.29 mmol) was added. The reaction stirred at 25° C. for 16 h. The solution was diluted with ethyl acetate (40 mL), washed with aqueous 1.0 M hydrochloric acid solution (3×15 mL), saturated aqueous brine solution (1×10 mL), dried over magnesium sulfate and concentrated in vacuo. Purification by flash column chromatography (Merck silica gel 60, 40-63 μm; 50% ethyl acetate/hexanes to 75% ethyl acetate/hexanes) afforded acetic acid 2-{3-[2-(R)-(3-chloro-4-methanesulfonyl-phenyl)-3-cyclopentyl-propionylamino]-pyrazol-1-yl}-ethyl ester (78 mg, 60%) as a white foam: ESI-LRMS m/e calcd for C$_{22}$H$_{28}$ClN$_3$O$_5$S [M$^+$] 481.1, found 482.3 [M+H$^+$]; $^1$H NMR (400 MHz, DMSO-d$_6$) δ ppm 1.02-1.20 (m, 2 H, CH$_2$), 1.39-

1.79 (m, 8H, 4×CH$_2$), 1.95 (s, 3H, COCH3), 2.01-2.19 (m, 1H, CH), 3.33 (s, 3H, SO$_2$CH$_3$), 3.86-3.95 (m, 1H, CH), 4.18-4.24 (m, 2H, OCH$_2$), 4.29 (t, J=5.0 Hz, Hz, 2H, NCH$_2$), 6.43 (d, J$_o$=2.3 Hz, 1H, Ar), 7.55-7.61 (m, 2H, Ar), 7.68 (d, J$_m$=1.7 Hz, 1H, Ar), 7.99 (d, J$_o$=8.2 Hz, 1H, Ar), 10.77 (s, 1H, NH).

Example 71

3-Cyclopentyl-N-[1-(2-hydroxy-ethyl)-1H-pyrazol-3-yl]-2-(R)-(4-methanesulfonyl-phenyl)-propionamide

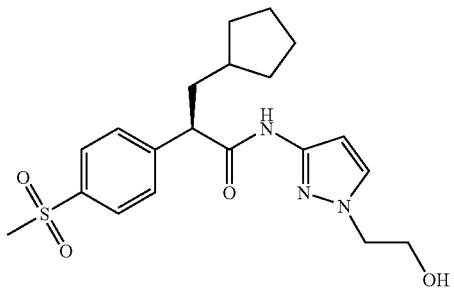

The 3-cyclopentyl-2-(R)-(4-methanesulfonyl-phenyl)-propionic acid (prepared as in PCT WO 2004/052869 A1, Example 3, 184 mg, 0.62 mmol) was dissolved in methylene chloride (3 mL) and a 2.0 M solution of oxalyl chloride in methylene chloride (31 μL, 0.62 mmol) was added and the reaction stirred at 25° C. for 10 min. The solution was chilled to 0° C. and 2,6-lutidine (144 μL, 1.24 mmol) was added dropwise. A strong exotherm and bubbling were observed. The solution continued to stir at 0° C. for 10 min. The 1-[2-(tert-butyl-dimethyl-silanyloxy)-ethyl]-1H-pyrazol-3-ylamine (prepared in Example 67, 150 mg, 0.62 mmol) was added as a solution in methylene chloride (3 mL), the ice bath was removed and the solution continued to stir at 25° C. for 25 min. The solution was diluted with methylene chloride (100 mL), washed with water (2×30 mL), saturated aqueous brine solution (1×20 mL), dried over magnesium sulfate and concentrated in vacuo to a beige foam. Purification by flash column chromatography (Merck silica gel 60, 40-63 μm; 40% ethyl acetate/hexanes) afforded N-{1-[2-(tert-butyl-dimethyl-silanyloxy)-ethyl]-1H-pyrazol-3-yl}-3-cyclopentyl-2-(R)-(4-methanesulfonyl-phenyl)-propionamide (150 mg, 44%) as a white foam: ESI-LRMS m/e calcd for C$_{26}$H$_{41}$N$_3$O$_4$SSi [M$^+$] 519.26, found 520.36 [M+H$^+$].

N-{1-[2-(tert-Butyl-dimethyl-silanyloxy)-ethyl]-1H-pyrazol-3-yl}-3-cyclopentyl-2-(R)-(4-methanesulfonyl-phenyl)-propionamide (135 mg, 0.26 mmol) was dissolved in ethanol (5 mL) and concentrated aqueous hydrochloric acid (100 μL) was added. The reaction stirred at 25° C. for 90 min. The reaction was diluted with ethyl acetate (50 mL), washed with water (20 mL), saturated aqueous brine solution (20 mL), dried over magnesium sulfate and concentrated in vacuo to give a beige foam. The foam was dissolved in methylene chloride (4 mL) and hexanes (4 mL) were added to crystallize the desired product. Collection by filtration followed by rinsing with excess hexanes afforded 3-cyclopentyl-N-[1-(2-hydroxy-ethyl)-1H-pyrazol-3-yl]-2-(R)-(4-methanesulfonyl-phenyl)-propionamide (830 mg, 78%) as colorless crystals: ESI-LRMS m/e calcd for C$_{20}$H$_{27}$N$_3$O$_4$S [M$^+$] 405.17, found 406.35 [M+H$^+$]; $^1$H NMR (400 MHz, DMSO-d$_6$) δ ppm 1.05-1.21 (m, 2H, CH$_2$), 1.38-1.82 (m, 8H, 4×CH$_2$), 2.01-2.23 (m, 1H, CH), 3.17 (s, 3H, SO$_2$CH$_3$), 3.66 (q, J=5.5 Hz, 2H, OCH$_2$), 3.89-3.95 (m, 1H, CH), 3.98 (t, J=5.5 Hz, 2H, NCH$_2$), 4.80 (t, J=5.5 Hz, 1H, OH), 6.40 (d, J$_o$=2.2 Hz, 1H, Ar), 7.51 (d, J$_o$=2.2 Hz, 1H, Ar), 7.62 (d, J$_o$=8.5 Hz, 2H, Ar), 7.85 (d, J$_o$=8.5 Hz, 2H, Ar), 10.70 (s, 1H, NH).

Example 72

2-(R)-(3-Chloro-4-methanesulfonyl-phenyl)-3-cyclopentyl-N-[1-(2-methoxy-ethyl)-1H-pyrazol-3-yl]-propionamide

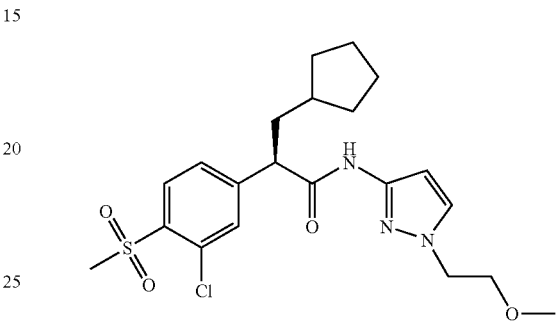

3-Nitro-1H-pyrazole (prepared in example 3, 300 mg, 2.65 mmol) was dissolved in anhydrous N,N-dimethylformamide (6.6 mL) and a 60% dispersion of sodium hydride in mineral oil (106 mg, 2.66 mmol) was added while stirring under nitrogen. After the effervescence ceased and the reaction stirred for an additional 10 min, 1-bromo-2-methoxy-ethane (250 μL, 2.66 mmol) was added. The reaction continued to stir under nitrogen for 16 h. The solution was diluted with ethyl acetate (100 mL), washed with 1.0 M aqueous hydrochloric acid solution (25 mL), water (25 mL), saturated aqueous brine solution (25 mL), dried over magnesium sulfate, filtered and concentrated in vacuo. Purification by flash column chromatography (Merck silica gel 60, 40-63 μm; 40% ethyl acetate/hexanes) afforded 1-(2-methoxy-ethyl)-3-nitro-1H-pyrazole (384 mg, 85%) as a white solid: H$^1$-NMR (400 MHz, CDCl$_3$) δ 3.34 (3H, s), 3.77 (2H, t, J=4.4 Hz), 4.36 (2H, t, J=4.8 Hz), 6.87 (1H, d, J=2.8 Hz), 7.54 (1H, d, J=2.4 Hz).

The 1-(2-methoxy-ethyl)-3-nitro-1H-pyrazole (350 mg, 2.05 mmol) was dissolved in ethyl acetate (5 mL) and methanol (5 mL) was added. Palladium, 10 wt. % on activated carbon, wet (50 mg) was added to the solution and the flask was charged with hydrogen gas via balloon. The reaction stirred at 25° C. for 3 h. The reaction was passed through a plug of Merck silica gel 60, 40-63 μm layered with celite and concentrated in vacuo to give the desired product, 1-(2-methoxy-ethyl)-1H-pyrazol-3-ylamine (266 mg, 92%) as a yellow oil: H$^1$-NMR (400 MHz, CDCl$_3$) δ 3.32 (3H, s), 3.34-3.50 (2H, bs), 3.67 (2H, t, J=5.6 Hz), 4.06 (2H, t, J=5.2 Hz), 5.56 (1H, d, J=2.4 Hz), 7.17 (1H, d, J=2.4 Hz).

2-(R)-(3-Chloro-4-methanesulfonyl-phenyl)-3-cyclopentyl-propionic acid (prepared as in PCT WO 2004/052869 A1, Example 1, 469 mg, 1.42 mmol,) was suspended in methylene chloride (7 mL) and a 2.0 M solution of oxalyl chloride in methylene chloride (710 mL, 1.42 mmol) was added and the reaction stirred at 25° C. for 10 min. The solution was chilled to 0° C. and 2,6-lutidine (331 μL, 2.84 mmol) was added dropwise. The reaction continued to stir at 0° C. for 10 min. The 1-(2-methoxy-ethyl)-1H-pyrazol-3-ylamine (200 mg, 1.42 mmol) was added as a pre-dissolved reaction in methylene chloride (7 mL), the ice bath was removed and the reaction continued to stir at 25° C. for 25 min. The reaction was diluted with methylene chloride (100 mL), washed with water (2×30 mL), saturated aqueous brine solution (1×20 mL), dried over magnesium sulfate and concentrated in vacuo to a beige foam. Purification by flash column chromatography (Merck silica gel 60, 40-63 μm; 0% ethyl acetate/methylene chloride to 20% ethyl acetate/methylene chloride) afforded 2-(R)-(3-chloro-4-methanesulfonyl-phenyl)-3-cyclopentyl-N-[1-(2-methoxy-ethyl)-1H-pyrazol-3-yl]-propionamide (262 mg, 41%) as a white powder: ESI-LRMS m/e calcd for $C_{21}H_{28}ClN_3O_4S$ [M$^+$] 453.15, found 454.26 [M+H$^+$]; $^1$H NMR (400 MHz, CDCl$_3$) δ ppm 1.05-1.23 (m, 2H, CH$_2$), 1.45-1.92 (m, 8H, 4×CH$_2$), 2.14-2.33 (m, 1H, CH), 3.26 (s, 3H, SO$_2$CH$_3$), 3.31 (s, 3H, OCH3), 3.53 (t, J=7.6 Hz, 1H, CH), 3.67 (t, J=5.2 Hz, 2H, OCH$_2$), 4.13 (t, J=5.2 Hz, 2H, NCH$_2$), 6.65 (d, J$_o$=2.3 Hz, 1H, Ar), 7.33 (d, J$_o$=2.3 Hz, 1H, Ar), 7.45 (dd, J$_o$=8.2, J$_m$=1.7 Hz. 1H, Ar), 7.58 (d, J$_m$=1.7 Hz, 1H, Ar), 7.81 (s, 1 H, NH), 8.08 (d, J$_o$=8.2 Hz, 1H, Ar).

Example 73

2-(R)-(3-Chloro-4-methanesulfonyl-phenyl)-3-cyclopentyl-N-[1-(1-hydroxy-cyclopropylmethyl)-1H-pyrazol-3-yl]-propionamide

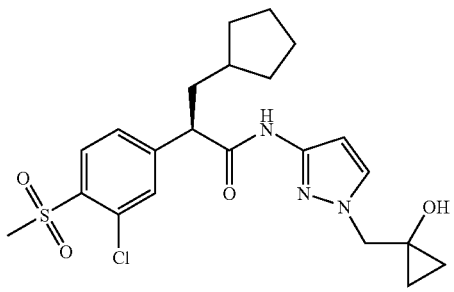

Hydroxy-cyclopropanecarboxylic acid methyl ester (5.07 g, 43.71 mmol) was dissolved in methylene chloride (75 mL) and 3,4-dihydro-2H-pyran (3.86 g, 45.90 mmol) was added followed by pyridinium-p-toluene-sulfonic acid (1.10 g, 4.37 mmol). The reaction stirred at 25° C. for 3 h. The reaction was concentrated in vacuo to give a clear oil. The oil was dissolved in diethyl ether (75 mL), washed with saturated aqueous brine solution (25 mL), dried over sodium sulfate and concentrated in vacuo to an oil. The oil was passed through a plug of silica gel (Merck silica gel 60, 40-63 μm; 100% ethyl acetate) to afford 1-(tetrahydro-pyran-2-yloxy)-cyclopropanecarboxylic acid methyl ester (7.49 g, 86%) as a clear oil: H$^1$-NMR (400 MHz, CDCl$_3$) δ 1.14-1.42 (4H, m), 1.88-3.46 (6H, m), 3.46-3.54 (1H, m), 3.70-3.72 (3H, m), 3.82-3.90 (1H, m), 4.81-4.96 (1H, m).

1-(Tetrahydro-pyran-2-yloxy)-cyclopropanecarboxylic acid methyl ester (3.50 g, 17.50 mmol) was dissolved in diethyl ether (85 mL) and a 2.0 M solution of lithium aluminum hydride in diethyl ether (8.75 mL, 17.50 mmol) was added. Upon complete addition, the reaction was refluxed under nitrogen for 1 h. Upon cooling to 25° C., the excess lithium aluminum hydride was hydrolyzed by the addition of ice chips. The organic layer was seated, washed with water (2×20 mL), dried over magnesium sulfate and concentrated in vacuo to afford [1-(tetrahydro-pyran-2-yloxy)-cyclopropyl]-methanol (2.81 g, 93%) as a clear, thick oil: H$^1$-NMR (400 MHz, CDCl$_3$) δ 0.5-1.0 (4H, m), 1.40-2.0 (6H, m), 3.0-3.2 (2H, m), 3.3-4.3 (2H, m), 4.5-4.7 (1H, m), 4.75-5.0 (1H, m).

[1-(Tetrahydro-pyran-2-yloxy)-cyclopropyl]-methanol (1.00 g, 5.81 mmol), 3-nitro-1H-pyrazole (prepared in example 3, 656 mg, 5.81 mmol), and triphenylphosphine (1.52 g, 5.81 mmol) were combined and dissolved in anhydrous tetrahydrofuran (30 mL). The reaction was chilled to 0° C. under nitrogen. While stirring, diisopropyl azodicarboxylate (1.72 mL, 8.72 mmol) was added dropwise over a period of 2 min. The ice bath was removed and the reaction continued to stir at 25° C. for 30 min. The reaction was concentrated in vacuo to give a thick golden oil. Purification by flash column chromatography (Merck silica gel 60, 40-63 μm; 5% ethyl acetate/hexanes to 35% ethyl acetate/hexanes) afforded 3-nitro-1-[1-(tetrahydro-pyran-2-yloxy)-cyclopropylmethyl]-1H-pyrazole (326 mg, 21%) as a white powder: H$^1$-NMR (400 MHz, CDCl$_3$) δ 0.74-0.82 (1H, m), 0.86-0.94 (1H, m), 0.95-1.02 (1H, m), 1.05-1.03 (1H, m), 1.40-1.70 (5H, m), 1.74-1.84 (1H, m), 3.46-3.54 (1H, m), 3.83-3.90 (1H, m), 3.94 (1H, d, J=14.4 Hz), 4.66-4.72 (1H, m), 4.87-4.94 (1H, m), 6.88 (1H, d, J=2.8 Hz), 7.84 (1H, d, J=2.4 Hz).

The 3-nitro-1-[1-(tetrahydro-pyran-2-yloxy)-cyclopropylmethyl]-1H-pyrazole (326 mg, 1.22 mmol) was dissolved in ethanol (7 mL) and p-toluene sulfonic acid (50 mg, 0.29 mmol) was added. After stirring at 25° C. for 1.5 h, the solution was concentrated in vacuo to give an oil. Purification by flash column chromatography (Merck silica gel 60, 40-63 μm; 50% ethyl acetate/hexanes) afforded 1-(3-nitro-pyrazol-1-ylmethyl)-cyclopropanol (158 mg, 71%) as an oil: H$^1$-NMR (400 MHz, CDCl$_3$) δ 0.81-0.86 (2H, m), 0.97-1.02 (2H, m), 2.78 (1H, bs), 4.31 (2H, s), 6.92 (1H, d, J=2.4 Hz), 7.61 (1H, d, J=2.4 Hz).

The 1-(3-nitro-pyrazol-1-ylmethyl)-cyclopropanol (155 mg, 0.85 mmol) was dissolved in methanol (8 mL) and ethyl acetate (4 mL) was added. While stirring, a 50% slurry of raney nickel in water (800 μL) was added followed by anhydrous hydrazine (300 μL). Immediate effervescence was observed. The reaction continued to stir and bubble for 20 min. Excess of a 50% slurry of raney nickel in water (800 μL) was added to ensure complete consumption of the hydrazine and the reaction continued to stir for an additional 10 min. The reaction was passed through a plug of celite and concentrated in vacuo to give the desired product, 1-(3-amino-pyrazol-1-ylmethyl)-cyclopropanol (122 mg, 94%), as a waxy solid: H$^1$-NMR (400 MHz, CDCl$_3$) δ 0.62-0.67 (2H, m), 0.84-0.91 (2H, m), 1.97 (1H, s), 3.67 (2H, bs), 3.98 (2H, s), 5.61 (1H, d, J=2.4 Hz), 7.14 (1H, d, J=2.4 Hz).

2-(R)-(3-Chloro-4-methanesulfonyl-phenyl)-3-cyclopentyl-propionic acid (prepared as in PCT WO 2004/052869 A1, Example 1, 248 mg, 0.75 mmol) was dissolved in methylene chloride (4 mL) and a 2.0 M solution of oxalyl chloride in methylene chloride (0.376 mL, 0.75 mmol) was added and the reaction stirred at 25° C. for 15 min. The solution was chilled to 0° C. and 2,6-lutidine (175 μL, 1.50 mmol) was added dropwise. The reaction continued to stir at 0° C. for 15 min. The 1-(3-amino-pyrazol-1-ylmethyl)-cyclopropanol (115 mg, 0.75 mmol) was added as a pre-dissolved reaction in methylene chloride (4 mL), the ice bath was removed and the reaction continued to stir at 25° C. for 25 min. The reaction was diluted with methylene chloride (50 mL), washed with water (2×25 mL), saturated aqueous brine solution (1×20 mL), dried over magnesium sulfate and concentrated in vacuo to a beige foam. Purification by flash column chromatography (Merck silica gel 60, 40-63 μm; 0% ethyl acetate/methylene chloride to 80% ethyl acetate/methylene chloride) afforded 2-(R)-(3-chloro-4-methanesulfonyl-phenyl)-3-cyclopentyl-N-[1-(1-hydroxy-cyclopropylmethyl)-1H-pyrazol-3-yl]- propionamide (158 mg, 45%) as a white brittle foam: ESI-LRMS m/e calcd for $C_{22}H_{28}ClN_3O_4S$ [M$^+$] 465.15, found 466.20 [M+H$^+$], 488.11 [M+Na$^+$]; $^1$H NMR (400 MHz, CDCl$_3$) δ ppm 0.65-0.72 (m, 2H, CH$_2$), 0.87-0.92 (m, 2H, CH$_2$), 1.08-1.25 (m, 2H, CH$_2$), 1.44-1.98 (m, 8H, 4×CH$_2$), 2.15-2.38 (m, 1H, CH), 3.24 (brs, 1H, OH), 3.28 (s, 3H, SO$_2$CH$_3$), 3.60 (t, J=7.5 Hz, 1H, CH), 4.06 (s, 2H, NCH$_2$), 6.71 (d, J$_o$=2.3 Hz, 1H, Ar), 7.32 (d, J$_o$=2.3 Hz, 1H, Ar), 7.49 (dd, J$_o$=8.2, J$_m$=1.7 Hz, 1H, Ar), 7.62 (d, J$_m$=1.7 Hz, 1H, Ar), 8.09 (d, J$_o$=8.2 Hz, 1H, Ar), 8.12 (s, 1H, NH).

Example 74

2(R)-(3-Chloro-4-methanesulfonyl-phenyl)-3-cyclopentyl-N-[1-(2-hydroxy-2-methyl-propyl)-1H-pyrazol-3-yl]-propionamide

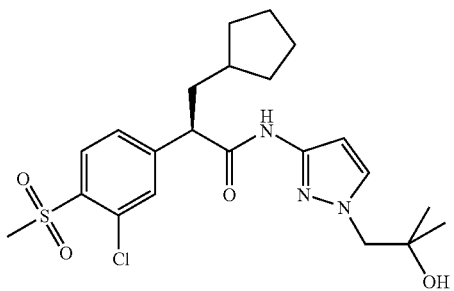

A solution of 3-nitro-1H-pyrazole (prepared in Example 3, 200 mg, 1.77 mmol) in N,N-dimethylformamide (5 mL) was treated with solid potassium carbonate (352 mg, 2.55 mmol) and 2,2-dimethyl-oxirane (314 mL, 3.54 mmol) and placed in a sealed tube and heated to 100° C. for 1 h in an oil bath. After this time the reaction was cooled to 25° C. and diluted with water (10 mL) and extracted with ethyl acetate (3×10 mL). The organic layers were then combined and dried over sodium sulfate, filtered and concentrated in vacuo. Purification by AnaLogix Intelliflash system (12 g column, 50% ethyl acetate/hexanes to 60% ethyl acetate/hexanes) afforded 2-methyl-1-(3-nitro-pyrazol-1-yl)-propan-2-ol (175 mg, 54%) as a clear colorless oil: ES-HRMS m/e calcd for $C_7H_{11}N_3O_3$ (M+H)$^+$ 186.0873, observed 186.0873; $^1$H NMR (300 MHz, CDCl$_3$) δ ppm 1.25 (s, 6H, 2×CH$_3$), 2.11 (br. s., 1H, OH), 4.18 (s, 2H, NCH$_2$), 6.92 (d, J=2.4 Hz, 1H, Ar), 7.60 (d, J=2.4 Hz, 1H, Ar).

In a round bottomed flask was placed 2-methyl-1-(3-nitro-pyrazol-1-yl)-propan-2-ol (170 mg, 0.92 mmol) and N,N-dimethylformamide (5 mL) and it was placed in an ice bath and cooled to 0° C. To this stirred solution was added triethylsilyl chloride (169 mL, 1.01 mmol) and imidazole (156 mg, 2.30 mmol) and it was stirred at 0° C. and slowly warmed to 25° C. and stirred for two days. The reaction was then diluted with ethyl acetate (15 mL) and washed with a saturated aqueous brine solution (10 mL). The aqueous layer was then extracted with ethyl acetate (2×15 mL). The organic layers were then combined and dried over sodium sulfate, filtered and concentrated in vacuo. Purification by AnaLogix Intelliflash system (4 g column, 5% ethyl acetate/hexanes to 20% ethyl acetate/hexanes) afforded 1-(2-methyl-2-triethylsilanyloxy-propyl)-3-nitro-1H-pyrazole (197 mg, 72%) as a clear colorless oil: ES-HRMS m/e calcd for $C_{13}H_{25}N_3O_3Si$ (M+H)$^+$ 300.1738, observed 300.1737; $^1$H NMR (300 MHz, CDCl$_3$) δ ppm 0.58 (q, J=8.0 Hz, 6H, 3×SiCH$_2$), 0.92 (t, J=8.0 Hz, 9H, 3×CH$_3$), 1.26 (s, 6H, 2×CH$_3$), 4.12 (s, 2H, NCH$_2$), 6.89 (d, J=2.5 Hz, 1H, Ar), 7.56 (d, J=2.5 Hz, 1H, Ar).

In a Parr shaker bottle was placed 1-(2-methyl-2-triethylsilanyloxy-propyl)-3-nitro-1H-pyrazole (197 mg, 0.65 mmol), 10% palladium on activated carbon (25 mg) and ethanol (10 mL). The bottle was then placed on the Parr shaker at 50 psi of hydrogen pressure for 1 h. The reaction was then filtered through a pad of celite and washed with ethanol, concentration in vacuo afforded 1-(2-methyl-2-triethylsilanyloxy-propyl)-1H-pyrazol-3-ylamine (191 mg, 100% (wet with some ethanol)) as a clear colorless oil: ES-HRMS m/e calcd for $C_{13}H_{27}N_3OSi$ (M+H)$^+$ 270.1996, observed 270.1995; $^1$H NMR (300 MHz, CDCl$_3$) δ ppm 0.56 (q, J=7.9 Hz, 6H, 3×SiCH$_2$), 0.92 (t, J=7.9 Hz, 9H, 3×CH$_3$), 1.21 (s, 6H, 2×CH$_3$), 2.63 (br.s., 2H, NH$_2$), 3.83 (s, 2H, NCH$_2$), 5.59 (d, J=2.4 Hz, 1H, Ar), 7.22 (d, J=2.4 Hz, 1H, Ar).

A solution of 2(R)-(3-chloro-4-methanesulfonyl-phenyl)-3-cyclopentyl-propionic acid (prepared as in PCT WO 2004/052869 A1, Example 1, 214 mg, 0.65 mmol) was dissolved in methylene chloride (10 mL) and N,N-dimethylfomamide (one drop) and cooled to 0° C. To this solution was added dropwise a solution of oxalyl chloride in methylene chloride (2 M solution, 360 μL, 0.71 mmol) which produced gas evolution and it was then stirred at 0° C. for 15 minutes and 1 h at 25° C. After this time, the reaction was concentrated in vacuo to ⅓ of the original volume. In a separate flask, a solution of 1-(2-methyl-2-triethylsilanyloxy-propyl)-1H-pyrazol-3-ylamine (191 mg, 0.71 mmol), 2,6-lutidine (112 μL, 0.97 mmol) and methylene chloride (10 mL) was cooled to 0° C. in an ice bath. To this solution was added the solution of the prepared acid chloride, diluted with another portion of methylene chloride (2 mL), dropwise. After addition was complete the reaction was then allowed to warm to 25° C. and stirred for 16 hours. After this time the reaction was diluted with water (10 mL) and extracted with methylene chloride (3×10 mL) and then dried over sodium sulfate, filtered and concentrated in vacuo. Purification by AnaLogix Intelliflash system (12 g column, 15% ethyl acetate/hexanes to 45% ethyl acetate/hexanes) produced desired product with some 2,6-lutidine present. This material was then dissolved in methylene chloride (20 mL) and washed with an aqueous 1 N hydrochloric acid solution (10 mL). The aqueous layer was then washed with methylene chloride (2×10 mL), the organic layers combined and dried over sodium sulfate, filtered and concentrated in vacuo to afford 2(R)-(3-chloro-4-methanesulfonyl-phenyl)-3-cyclopentyl-N-[1-(2-methyl-2-triethylsilanyloxy-propyl)-1H-pyrazol-3-yl]-propionamide (288 mg, 77%) as an off-white foam: [α]$^{31}_{589}$=−11.7° (c=0.24, methylene chloride); ES-HRMS m/e calcd for $C_{28}H_{44}N_3O_4SSiCl$ (M+H)$^+$ 582.2583, observed 582.2587; $^1$H NMR (300 MHz, DMSO-d$_6$) δ ppm 0.51 (q, J=7.8 Hz, 6H, 3×SiCH$_2$), 0.85 (t, J=7.8 Hz, 9H, 3×CH$_3$), 1.02-1.20 (m, 2H, CH$_2$), 1.14 (s, 3 H, CH$_3$), 1.17 (s, 3H, CH$_3$), 1.33-1.81 (m, 8H, 4×CH$_2$), 1.94-2.23 (m, 1H, CH), 3.34 (s, 3H, SO$_2$CH$_3$), 3.89 (s, 2H, NCH$_2$), 3.89-3.97 (m, 1H, ArCH), 6.45 (d, J=2.3 Hz, 1 H, Ar), 7.45 (d, J=2.3 Hz, 1H, Ar), 7.59 (dd, J$_o$=8.4 Hz, J$_m$=1.6 Hz, 1H, Ar), 7.70 (d, J$_m$=1.6 Hz, 1H, Ar), 8.01 (d, J$_o$=8.4 Hz, 1H, Ar), 10.79 (s, 1H, NH).

In a flask containing 2(R)-(3-chloro-4-methanesulfonyl-phenyl)-3-cyclopentyl-N-[1-(2-methyl-2-triethylsilanyloxy-propyl)-1H-pyrazol-3-yl]-propionamide (80 mg, 0.14 mmol) was added tetrahydrofuran (2 mL), water (500 μL) and acetic acid (2 mL) and was stirred at 25° C. until complete by thin layer chromatography. It was then diluted with water (10 mL) and extracted with ethyl acetate (3×10 mL). The organics were than combined and washed with a saturated aqueous solution of sodium bicarbonate (10 mL) and dried over magnesium sulfate, filtered and concentrated. Purification by AnaLogix Intelliflash system (4 g silica gel column, 15% ethyl acetate/hexanes to 50% ethyl acetate/hexanes) afforded 2(R)-(3-chloro-4-methanesulfonyl-phenyl)-3-cyclopentyl-N-[1-(2-hydroxy-2-methyl-propyl)-1H-pyrazol-3-yl]-propionamide (40 mg, 63%) as a white foam: $[\alpha]^{31}_{589}=-8.2°$ (c=0.11, methylene chloride); ES-HRMS m/e calcd for $C_{22}H_{30}N_3O_4SCl$ (M+H)$^+$ 468.1719, observed 468.1717; $^1$H NMR (300 MHz, DMSO-d$_6$) δ ppm 1.03 (s, 3H, CH$_3$), 1.04 (s, 3H, CH$_3$), 1.06-1.20 (m, 2H, CH$_2$), 1.35-1.84 (m, 8 H, 4×CH$_2$), 2.00-2.17 (m, 1H, CH), 3.34 (s, 3H, SO$_2$CH$_3$), 3.86 (s, 2H, NCH$_2$), 3.92 (dd, J=8.3, 6.8 Hz, 1H, ArCH), 4.65 (s, 1H, OH), 6.45 (d, J=2.3 Hz, 1H, Ar), 7.51 (d, J=2.3 Hz, 1H, Ar), 7.59 (dd, J$_o$=8.3 Hz, J$_m$=1.6 Hz, 1H, Ar), 7.70 (d, J$_m$=1.6 Hz, 1H, Ar), 8.01 (d, J$_o$=8.3 Hz, 1H, Ar), 10.81 (s, 1H, NH).

Example 75

Cyclopentyl-2(R)-(3,4-dichloro-phenyl)-N-(1-methyl-1H-pyrazol-3-yl)-propionamide

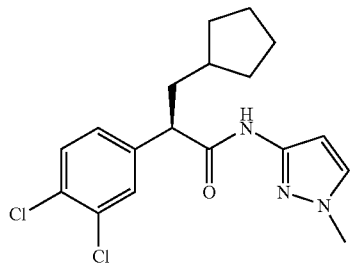

In a round bottom flask under argon was placed triphenylphosphine (120 mg, 0.46 mmol) and methylene chloride (10 mL) and it was cooled to 0° C. in an ice bath. To this was added N-bromosuccinimide (81 mg, 0.46 mmol) and it was stirred for 15 minutes at 0° C. To this was then added 3-cyclopentyl-2(R)-(3,4-dichloro-phenyl)-propionic acid (prepared as in PCT WO 2002/046173 A1, Example 3, 100 mg, 0.35 mmol) and it was stirred for an additional 5 minutes at 0° C. and then warmed to 25° C. and stirred for 10 minutes. The solution was recooled to 0° C. and then 1-methyl-1H-pyrazol-3-ylamine (68 mg, 0.70 mmol) in methylene chloride (500 µL) and 2,6-lutidine (160 µL, 1.4 mmol) were added to the flask and it was stirred at 0° C. and then warmed to 25° C. and stirred for 2.5 h. After this time the reaction was diluted with methylene chloride and then washed with an aqueous 1 N hydrochloric acid solution and saturated aqueous brine solution. Flash chromatography using Biotage system (40S column, Silica gel, 50% ethyl acetate/hexanes) provided a white foam, this material was then lyophilized to afford 3-cyclopentyl-2(R)-(3,4-dichloro-phenyl)-N-(1-methyl-1H-pyrazol-3-yl)-propionamide (62 mg, 48%) as a white powder: $[\alpha]^{27}_{589}=-15.6°$ (c=0.27, methanol); ES-HRMS m/e calcd for $C_{18}H_{21}N_3OCl_2$ (M+H)$^+$ 366.1135, observed 366.1135; $^1$H NMR (300 MHz, DMSO-d$_6$) δ ppm 1.01-1.19 (m, 2H, CH$_2$), 1.34-1.80 (m, 8H, 4×CH$_2$), 1.95-2.14 (m, 1H, CH), 3.70 (s, 3H, NCH$_3$), 3.79 (dd, J=8.6, 6.0 Hz, 1H, ArCH), 6.30-6.44 (m, 1H, Ar), 7.34 (dd, J$_o$=8.4 Hz, J$_m$=1.3 Hz, 1H, Ar), 7.51 (d, J$_m$=1.3 Hz, 1H, Ar), 7.54-7.65 (m, 2H, Ar), 10.66 (s, 1H, NH).

Example 76

2(R)-(3-Chloro-4-methanesulfonyl-phenyl)-N-[1-(2-hydroxy-ethyl)-1H-pyrazol-3-yl]-3-(tetrahydro-pyran-4-yl)-propionamide

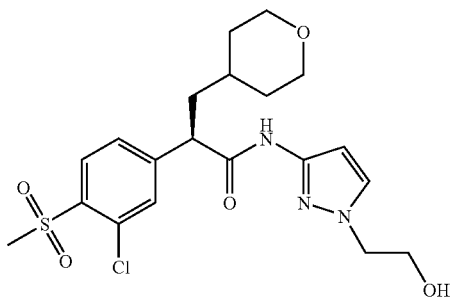

A solution of 2-(3-chloro-4-methanesulfonyl-phenyl)-3-(tetrahydro-pyran-4-yl)-propionic acid (prepared as in PCT WO 2003/095438 A1, Example 20, 144 mg, 0.41 mmol) was dissolved in methylene chloride (4 mL) and N,N-dimethylformamide (three drops) at 25° C. To this solution was added dropwise a solution of oxalyl chloride in methylene chloride (2 M solution, 0.21 mL, 0.43 mmol) which produced gas evolution and it was then stirred at 25° C. for 30 minutes. After this time, the reaction was cooled to 0° C. and 2,6-lutidine (100 µL, 0.83 mmol) was added to the flask and it was stirred for 15 min. To this was then added a solution of 1-[2-(tert-butyl-dimethyl-silanyloxy)-ethyl]-1H-pyrazol-3-ylamine (prepared in Example 67, 100 mg, 0.41 mmol) in methylene chloride (2 mL) and the reaction was allowed to warm up to 25° C. and stirred for 1 h. After this time the reaction was diluted with a small amount of methanol in methylene chloride and washed with aqueous 1 N hydrochloric acid solution and then a saturated aqueous brine solution/water reaction (1/1). Flash chromatography using Biotage system (40S column, Silica gel, 50% ethyl acetate/hexanes) afforded N-{1-[2-(tert-butyl-dimethyl-silanyloxy)-ethyl]-1H-pyrazol-3-yl}-2-(3-chloro-4-methanesulfonyl-phenyl)-3-(tetrahydro-pyran-4-yl)-propionamide (158 mg, 67%) as an off-white foam: ES-HRMS m/e calcd for $C_{26}H_{40}N_3O_5SSiCl$ (M+H)$^+$ 570.2219, observed 570.2210; $^1$H NMR (400 MHz, DMSO-d$_6$) δ ppm −0.08 (s, 6H, 2×SiCH$_3$), 0.78 (s, 9H, 3×CH$_3$), 1.13-1.27 (m, 2H, CH$_2$), 1.29-1.43 (m, 1H, CH of CH$_2$), 1.50-1.71 (m, 3H, CH of CH$_2$ and CH$_2$), 2.01-2.12 (m, 1H, CH), 3.20 (m, 2H, OCH$_2$), 3.34 (s, 3H, SO$_2$CH$_3$), 3.76-3.88 (m, 4 H, OCH$_2$ and SiOCH$_2$), 3.97-4.10 (m, 3H, CH and NCH$_2$), 6.42 (d, J=2.3 Hz, 1H, Ar), 7.53 (d, J=2.3 Hz, 1H, Ar), 7.60 (dd, J$_o$=8.2 Hz, J$_m$=1.6 Hz, 1H, Ar), 7.71 (d, J$_m$=1.6 Hz, 1H, Ar), 8.01 (d, J$_o$=8.2 Hz, 1H, Ar), 10.81 (s, 1H, NH).

In a flask containing N-{1-[2-(tert-butyl-dimethyl-silanyloxy)-ethyl]-1H-pyrazol-3-yl}-2-(3-chloro-4-methanesulfonyl-phenyl)-3-(tetrahydro-pyran-4-yl)-propionamide (150 mg, 0.26 mmol) was added ethanol (5 mL) and concentrated hydrochloric acid (three drops) and was stirred at 25° C. for 30 minutes. It was then diluted with ethyl acetate (50 mL) and washed with water (1×20 mL) and saturated aqueous brine solution (1×20 mL). The organic layer was then dried over sodium sulfate and absorbed onto silica gel (2 g) and purified on Biotage Flash purification system (40S column, silica gel, 5% methanol/ethyl acetate) which afforded 2-(3-chloro-4-methanesulfonyl-phenyl)-N-[1-(2-hydroxy-ethyl)-1H-pyrazol-3-yl]-3-(tetrahydro-pyran-4-yl)-propionamide (107 mg, 89%) as a white foam: ES-HRMS m/e calcd for $C_{20}H_{26}N_3O_5SCl$ $(M+H)^+$ 456.1355, observed 456.1354; $^1H$ NMR (400 MHz, DMSO-$d_6$) δ ppm 1.12-1.27 (m, 2H, $CH_2$), 1.29-1.42 (m, 1H, CH of $CH_2$), 1.49-1.70 (m, 3H, CH of $CH_2$ and $CH_2$), 2.00-2.14 (m, 1H, CH), 3.20 (m, 2H, $OCH_2$), 3.34 (s, 3H, $SO_2CH_3$), 3.67 (q, J=5.5 Hz, 2H, $OCH_2$), 3.75-3.86 (m, 2H, $OCH_2$), 3.95-4.08 (m, 3H, CH and $NCH_2$), 4.83 (t, J=5.3 Hz, 1H, OH), 6.41 (d, J=2.3 Hz, 1H, Ar), 7.54 (d, J=2.3 Hz, 1H, Ar), 7.60 (dd, $J_o$=8.2 Hz, $J_m$=1.6 Hz, 1H, Ar), 7.71 (d, $J_m$=1.6 Hz, 1H, Ar), 8.01 (d, $J_o$=8.2 Hz, 1H, Ar), 10.81 (s, 1H, NH).

The racemic material was then seated using supercritical fluid chromatography (SFC) on a Berger MiniGram Supercritical Fluid Chromatography (SFC) system (Mettler-Toledo AutoChem Berger Instruments, Newark, Del.) (Chiral column: Chiralcel OD, 250 mm×10.0 mm i.d., 5 µm-particle size, temperature: 30° C., flow rate of 9.5 mL/min, and $CO_2$ pressure of 100 bar, 20% methanol as mobile phase modifier (e.g. 80% $CO_2$/20% MeOH). UV Detection: 220 nm) to afford the two pure enantiomers; the first peak (active enantiomer) was 2(R)-(3-chloro-4-methanesulfonyl-phenyl)-N-[1-(2-hydroxy-ethyl)-1H-pyrazol-3-yl]-3-(tetrahydro-pyran-4-yl)-propionamide isolated as white solid: $[α]_{589}$=–11.7° (c=0.24, methanol); ES-HRMS m/e calcd for $C_{20}H_{26}N_3O_5SCl$ $(M+H)^+$ 456.1355, observed 456.1352; $^1H$ NMR (400 MHz, DMSO-$d_6$) δ ppm 1.12-1.27 (m, 2H, $CH_2$), 1.29-1.42 (m, 1H, CH of $CH_2$), 1.49-1.70 (m, 3H, CH of $CH_2$ and $CH_2$), 2.00-2.14 (m, 1H, CH), 3.20 (m, 2H, $OCH_2$), 3.34 (s, 3H, $SO_2CH_3$), 3.67 (q, J=5.5 Hz, 2H, $OCH_2$), 3.75-3.86 (m, 2H, $OCH_2$), 3.95-4.08 (m, 3H, CH and $NCH_2$). 4.83 (t, J=5.3 Hz, 1H, OH), 6.41 (d, J=2.3 Hz, 1H, Ar), 7.54 (d, J=2.3 Hz, 1H, Ar), 7.60 (dd, $J_o$=8.2 Hz, $J_m$=1.6 Hz, 1H, Ar), 7.71 (d, $J_m$=1.6 Hz, 1H, Ar), 8.01 (d, $J_o$=1H, Ar), 10.81 (s, 1H, NH).

Example 77

2(R)-(3-Chloro-4-methanesulfonyl-phenyl)-3-cyclopentyl-N-[1-(2-hydroxy-propyl)-1H-pyrazol-3-yl]-propionamide

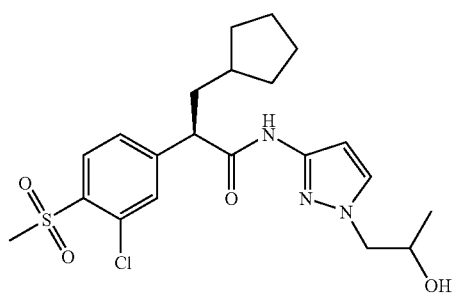

A solution of 3-nitro-1H-pyrazole (prepared in Example 3, 400 mg, 3.54 mmol) in N,N-dimethylformamide (5 mL) was treated with solid potassium carbonate (734 mg, 5.31 mmol) and 2-methyl-oxirane (500 µL, 3.54 mmol) and placed in a sealed tube and heated at 100° C. for 1 h in an oil bath. After this time the reaction was cooled to 25° C. and diluted with water (30 mL) and extracted with ethyl acetate (3×20 mL). The organic layers were then combined and washed with saturated aqueous brine solution (2×20 mL) and then dried over sodium sulfate, filtered and concentrated in vacuo with silica gel (2 g) and purified by Biotage Flash Chromatography (40S column, Silica gel, 60% ethyl acetate/hexanes) to afford 1-(3-nitro-pyrazol-1-yl)-propan-2-ol (332 mg, 55%) as a clear colorless oil: ES-HRMS m/e calcd for $C_6H_9N_3O_3$ $(M+H)^+$ 172.0717, observed 172.0716; 36730-255 $^1H$ NMR (300 MHz, $CDCl_3$) δ ppm 1.28 (d, J=6.3 Hz, 3H, $CH_3$), 2.15 (br. s., 1H, OH), 4.03-4.13 (m, 1H, CH of $CH_2$), 4.23-4.38 (m, 2H, OCH and CH of $CH_2$), 6.91 (d, J=2.4 Hz, 1H, Ar), 7.56 (d, J=2.4 Hz, 1H, Ar).

In a Parr shaker bottle was placed 1-(3-nitro-pyrazol-1-yl)-propan-2-ol (58 mg, 0.34 mmol), 10% palladium on activated carbon (12 mg) and ethanol (5 mL). The bottle was then placed on the Parr shaker at 50 psi of hydrogen pressure for 1 h. The reaction was then filtered through a pad of celite and washed with ethanol and concentration in vacuo afforded 1-(3-amino-pyrazol-1-yl)-propan-2-ol (46 mg, 96%) as a clear colorless oil and taken on to the next step without characterization.

A solution of 2(R)-(3-chloro-4-methanesulfonyl-phenyl)-3-cyclopentyl-propionic acid (prepared as in PCT WO 2004/052869 A1, Example 1, 106 mg, 0.32 mmol) was dissolved in methylene chloride (2 mL) and N,N-dimethylfomamide (two drops) at 25° C. under argon. To this solution was added dropwise a solution of oxalyl chloride in methylene chloride (2 M solution, 170 µL, 0.33 mmol) which produced gas evolution and it was then stirred at 25° C. for 30 minutes. After this time, the reaction was cooled to 0° C. and 2,6-lutidine (80 µL, 0.64 mmol) was added to the flask and it was stirred for 15 min. To this was then added a solution of 1-(3-amino-pyrazol-1-yl)-propan-2-ol (45 mg, 0.32 mmol) in methylene chloride (1 mL) and the reaction was allowed to warm up to 25° C. and stirred for 45 minutes. After this time the reaction was diluted with a small amount of methanol in methylene chloride and washed with aqueous 1 N hydrochloric acid solution (1×15 mL) and then a saturated aqueous brine solution (1×15 mL). The organics were then dried over sodium sulfate, filtered and concentrated in vacuo with silica gel (2 g) and purified by Biotage Flash Chromatography (40S column, Silica gel, 50% ethyl acetate/hexanes to 100% ethyl acetate) afforded 2(R)-(3-chloro-4-methanesulfonyl-phenyl)-3-cyclopentyl-N-[1-(2-hydroxy-propyl)-1H-pyrazol-3-yl]-propionamide (88 mg, 61%, diastereomeric mixture 1:1) as a white foam: ES-HRMS m/e calcd for $C_{21}H_{28}N_3O_4SCl$ $(M+H)^+$ 454.1562, observed 454.1559.

The 1:1 diastereomeric mixture was seated into the single diastereomeric compounds; 2(R)-(3-chloro-4-methanesulfonyl-phenyl)-3-cyclopentyl-N-[1-(2(R)-hydroxy-propyl)-1H-pyrazol-3-yl]-propionamide and 2(R)-(3-chloro-4-methanesulfonyl-phenyl)-3-cyclopentyl-N-[1-(2(S)-hydroxy-propyl)-1H-pyrazol-3-yl]-propionamide, by supercritical fluid chromatography (SFC) on a Berger MiniGram Supercritical Fluid Chromatography (SFC) system (Mettler-Toledo AutoChem Berger Instruments, Newark, Del.) (Chiral column: Chiralcel OJ, 250 mm×25 mm i.d., 5 µm-particle size, temperature: 30° C., flow rate of 2 mL/min, and $CO_2$ pressure of 5 bar, 15% methanol as mobile phase modifier (e.g. 85% $CO_2$/15% MeOH). UV Detection: 220 nm) to afford the two pure diastereomers (both of which are active); the first peak to elute was isolated as an amorphous freeze dried white solid: $[α]^{30}_{589}$=–22.9° (c=0.21, methanol); ES-HRMS m/e calcd for $C_{21}H_{28}N_3O_4SCl$ $(M+H)^+$ 454.1562, observed 454.1561; $^1H$ NMR (400 MHz, DMSO-$d_6$) δ ppm 1.00 (d, J=6.0 Hz, 3H, $CH_3$), 1.05-1.18 (m, 2H, $CH_2$), 1.37-1.79 (m, 8H, 4×$CH_2$), 2.05-2.14 (m, 1H, CH), 3.34 (s, 3H, $SO_2CH_3$), 3.82-3.96 (m, 4H, NCH$_2$, OCH and ArCH), 4.84 (d, J=4.7 Hz, 1H, OH), 6.42 (d, J=2.3 Hz, 1H, Ar), 7.52 (d, J=2.3 Hz, 1H, Ar), 7.59 (dd, J$_o$=8.2 Hz, J$_m$=1.7 Hz, 1H, Ar), 7.70 (d, J$_m$=1.7 Hz, 1H, Ar), 8.01 (d, J$_o$=8.2 Hz, 1H, Ar), 10.79 (s, 1H, NH).

The second peak to elute was isolated as an amorphous freeze dried white solid: [α]$^{30}_{589}$=+7.5° (c=0.20, methanol); ES-HRMS m/e calcd for C$_{21}$H$_{28}$N$_3$O$_4$SCl (M+H)$^+$ 454.1562, observed 454.1561; 36730-271B $^1$H NMR (400 MHz, DMSO-d$_6$) δ ppm 1.00 (d, J=6.0 Hz, 3H, CH$_3$), 1.05-1.18 (m, 2H, CH$_2$), 1.37-1.79 (m, 8H, 4×CH$_2$), 2.05-2.14 (m, 1H, CH), 3.34 (s, 3H, SO$_2$CH$_3$), 3.82-3.96 (m, 4H, NCH$_2$, OCH and ArCH), 4.86 (d, J=4.7 Hz, 1H, OH), 6.42 (d, J=2.2 Hz, 1H, Ar), 7.52 (d, J=2.2 Hz, 1H, Ar), 7.59 (dd, J$_o$=8.2 Hz, J$_m$=1.6 Hz, 1H, Ar), 7.70 (d, J$_m$=1.6 Hz, 1H, Ar), 8.01 (d, J$_o$=8.2 Hz, 1H, Ar), 10.79 (s, 1H, NH).

Example 78

3-Cyclopentyl-N-[1-(2-hydroxy-ethyl)-1H-pyrazol-3-yl]-2(R)-(4-methanesulfonyl-3-methyl-phenyl)-propionamide

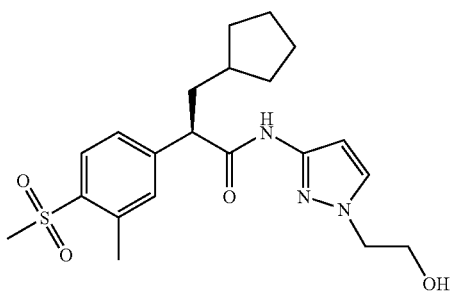

Cyclopentyl-2(R)-(4-methanesulfonyl-3-methyl-phenyl)-propionic acid (prepared as in PCT WO 2004/052869 A1, Example 57, 193 mg, 0.62 mmol) was dissolved in methylene chloride (4 mL) and N,N-dimethylfomamide (three drops) at 25° C. under argon. To this solution was added dropwise a solution of oxalyl chloride in methylene chloride (2 M solution, 320 μL, 0.65 mmol) which produced gas evolution and it was then stirred at 25° C. for 30 minutes. After this time, the reaction was cooled to 0° C. and 2,6-lutidine (150 μL, 1.24 mmol) was added to the flask and it was stirred for 15 min. To this was then added a solution of 1-[2-(tert-butyl-dimethyl-silanyloxy)-ethyl]-1H-pyrazol-3-ylamine (prepared in Example 67, 150 mg, 0.62 mmol) in methylene chloride (2 mL) and the reaction was allowed to warm up to 25° C. and stirred for 2 h. After this time the reaction was diluted with a small amount of methanol in methylene chloride and concentrated in vacuo with silica gel (2 g) and purified by Biotage Flash Chromatography (40S column, Silica gel, 50% ethyl acetate/hexanes). The combined fractions were then washed with a 1 N aqueous hydrochloric acid solution and then a saturated brine solution, dried over sodium sulfate and concentrated in vacuo to afford N-{1-[2-(tert-butyl-dimethyl-silanyloxy)-ethyl]-1H-pyrazol-3-yl}-3-cyclopentyl-2(R)-(4-methanesulfonyl-3-methyl-phenyl)-propionamide (309 mg, 94%) as a colorless gum: [α]$^{30}_{589}$=−9.70° (c=0.33, methanol); ES-HRMS m/e calcd for C$_{27}$H$_{43}$N$_3$O$_4$SSi (M+H)$^+$ 534.2817, observed 534.2814; $^1$H NMR (300 MHz, DMSO-d$_6$) δ ppm −0.09 (s, 6H, 2×SiCH$_3$), 0.78 (s, 9H, 3×CH$_3$), 1.02-1.20 (m, 2H, CH$_2$), 1.36-1.84 (m, 8H, 4×CH$_2$), 2.04-2.17 (m, 1H, CH), 2.62 (s, 3H, ArCH$_3$), 3.17 (s, 3H, SO$_2$CH$_3$), 3.80-3.90 (m, 3H, ArCH and SiOCH$_2$), 4.04 (t, J=5.4 Hz, 2H, NCH$_2$), 6.41 (d, J=2.3 Hz, 1H, Ar), 7.41-7.47 (m, 2 H, Ar), 7.51 (d, J=2.3 Hz, 1H, Ar), 7.84 (d, J$_o$=8.8 Hz, 1H, Ar), 10.73 (s, 1H, NH)

In a flask containing N-{1-[2-(tert-butyl-dimethyl-silanyloxy)-ethyl]-1H-pyrazol-3-yl}-3-cyclopentyl-2(R)-(4-methanesulfonyl-3-methyl-phenyl)-propionamide (300 mg, 0.56 mmol) was added ethanol (10 mL) and concentrated hydrochloric acid (seven drops) and was stirred at 25° C. for 2 h. It was then diluted with ethyl acetate (100 mL) and washed with water (1×30 mL) and saturated aqueous brine solution (1×30 mL). The organic layer was then dried over sodium sulfate and absorbed onto silica gel (2.5 g) and purified on Biotage Flash chromatography system (40S column, silica gel, 5% methanol/ethyl acetate) afforded 3-cyclopentyl-N-[1-(2-hydroxy-ethyl)-1H-pyrazol-3-yl]-2(R)-(4-methanesulfonyl-3-methyl-phenyl)-propionamide (194 mg, 83%) as a white foam: [α]$^{28}_{589}$=−19.0° (c=0.20, methanol); ES-HRMS m/e calcd for C$_{21}$H$_{29}$N$_3$O$_4$S (M+H)$^+$ 420.1952, observed 420.1949; $^1$H NMR (400 MHz, DMSO-d$_6$) δ ppm 1.03-1.18 (m, 2H, CH$_2$), 1.37-1.80 (m, 8H, 4×CH$_2$), 2.06-2.17 (m, 1H, CH) ArCH$_3$), 3.16 (s, 3H, SO$_2$CH$_3$), 3.66 (q, J=5.6 Hz, 2H, OCH$_2$), 3.85 (dd, J=8.8 Hz, J=5.7 Hz, 1H, ArCH), 3.98 (t, J=5.6 Hz, 2H, NCH$_2$), 4.82 (t, J=5.6 Hz, 1H, OH), 6.40 (d, J=2.2 Hz, 1H, Ar), 7.41-7.46 (m, 2H, Ar), 7.52 (d, J=2.2 Hz, 1H, Ar), 7.83 (d, J$_o$=8.5 Hz, 1H, Ar), 10.72 (s, 1H, NH).

Example 79

3-Cyclopentyl-N-[1-(2-hydroxy-ethyl)-1H-pyrazol-3-yl]-2(R)-(3-trifluoromethyl-phenyl)-propionamide

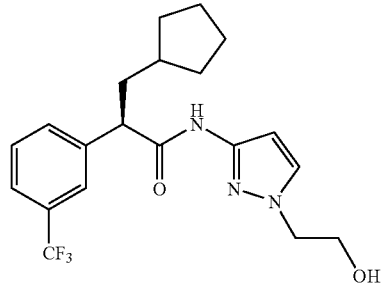

A reaction of (3-trifluoromethyl-phenyl)-acetic acid (5.10 g, 25 mmol) and potassium carbonate (10.36 g, 75 mmol) in acetone (40 mL) was stirred and cooled to −10° C. This suspension was then treated dropwise with trimethylacetyl chloride (3.23 mL, 26.30 mmol) keeping the temperature of the reaction around −10° C. during the addition. The stirring was continued for 15 minutes at −10° C., then warmed to 0° C. and stirred for 10 minutes. The reaction was then recooled to −10° C. and treated with (1R,2R)-(−)-pseudoephedrine (6.20 g, 37.50 mmol) using a powder addition funnel to slowly add the solid. The reaction was then stirred another 10 minutes at −10° C. and then warmed to 25° C. and stirred for 1 h. The reaction was then treated with water (50 mL) and extracted with ethyl acetate (2×100 mL). The organics were then washed with water (2×50 mL) and the organic layer was dried over sodium sulfate and concentrated in vacuo. Flash chromatography (Merck Silica gel 60, 230-400 mesh, 60% ethyl acetate/hexanes) afforded N-(2(R)-hydroxy-1(R)-methyl-2(R)-phenyl-ethyl)-N-methyl-2-(3-trifluoromethyl-phenyl)-acetamide (6.58 g, 75%) as a viscous colorless oil:

$[\alpha]^{26}_{589}$=−75.1° (c=0.51, chloroform); ES-HRMS m/e calcd for $C_{19}H_{20}N_1O_2F_3$ (M+H)$^+$ 352.1519, observed 352.1517; $^1$H NMR (300 MHz, CDCl$_3$) δ ppm 0.92, 1.13 (2×d, J=6.9 Hz, 3H, CH$_3$), 2.18, 3.88 (2×m, 1H, OH), 2.87, 2.98 (2×s, 3H, NCH$_3$), 3.75, 3.86 (2×s, 2H, CH$_2$), 4.02, 4.48-4.67 (2×m, 2H, NCH and OCH), 7.25-7.56 (m, 9H, Ar).

A solution of N-(2(R)-hydroxy-1(R)-methyl-2(R)-phenyl-ethyl)-N-methyl-2-(3-trifluoromethyl-phenyl)-acetamide (6.49 g, 18.47 mmol) in dry tetrahydrofuran (100 mL) was cooled to −25° C. and then treated dropwise with a 1.0 M solution of lithium bis(trimethylsilyl)amide in tetrahydrofuran (39.0 mL, 36.94 mmol) while keeping the temperature below 15° C. The solution was then warmed to 0° C. and stirred for 30 min. At this time, the reaction was treated dropwise with iodomethylcyclopentane (prepared in PCT WO2004/052869 A1 Example 1, 4.85 g, 23.09 mmol) in 2,3-dimethyl-3,4,5,6-tetrahydro-2(1H)-pyrimidinone (4.76 mL, 39.34 mmol). The reaction was then stirred at 0° C. for 2 h. The reaction was then diluted with toluene (300 mL) and transferred to a separatory funnel and washed with a 1 N aqueous hydrochloric acid solution (1×200 mL), a saturated aqueous sodium bicarbonate solution (1×200 mL) and then a brine solution (1×200 mL) The aqueous layers were then back-extracted with toluene (1×300 mL). The organic layers were combined and then dried over sodium sulfate and concentrated. Flash chromatography (Merck Silica gel 60, 230-400 mesh, 40% ethyl acetate/hexanes to 60% ethyl acetate/hexanes) afforded 3-cyclopentyl-N-(2(R)-hydroxy-1(R)-methyl-2(R)-phenyl-ethyl)-N-methyl-2(R)-(3-trifluoromethyl-phenyl)-propionamide (3.31 g, 41%) as a pale amber gum: $[\alpha]^{30}_{589}$=−52.0° (c=0.46, methanol); ES-HRMS m/e calcd for $C_{25}H_{30}N_1O_2F_3$ (M+H)$^+$ 456.2121, observed 456.2119; $^1$H NMR (300 MHz, DMSO-d$_6$) δ ppm 0.48, 0.98 (2×d, J=6.6 Hz, 3H, CH$_3$), 0.92-1.14 (m, 2H, CH$_2$), 1.31-1.76 (m, 8H, 4×CH$_2$), 1.80-2.00 (m, 1H, CH), 2.73, 2.76 (2×s, 3H, NCH$_3$), 3.95-4.15, 4.67 (2×m, 2H, NCH and OCH), 4.49 (m, 1H, ArCHCO), 5.23, 5.56 (2×m, 1H, OH), 7.10 (m, 2H, Ar), 7.22-7.65 (m, 7H, Ar).

A solution of 3-cyclopentyl-N-(2(R)-hydroxy-1(R)-methyl-2(R)-phenyl-ethyl)-N-methyl-2(R)-(3-trifluoromethyl-phenyl)-propionamide (3.31 g, 7.64 mmol) in dioxane (15 mL) was treated with a 9 N aqueous sulfuric acid solution (11 mL). The resulting solution was then heated at 110° C. for 16 h. The reaction was then cooled and concentrated in vacuo to remove most of the dioxane and then diluted with water (300 mL) and extracted with chloroform/methanol solution (3:2, 2×150 mL) and then concentrated. The resulting material was then azeotroped with acetonitrile and then dissolved in methylene chloride and concentrated with silica gel (4 g) and purified on Biotage Flash chromatography system (40M column, silica gel, 40% ethyl acetate/hexanes) afforded 3-cyclopentyl-2(R)-(3-trifluoromethyl-phenyl)-propionic acid (1.58 g, 72%) as a pale amber oil which solidified on standing: $[\alpha]^{23}_{589}$=−37.9° (c=0.38, methanol); ES-HRMS m/e calcd for $C_{15}H_{17}O_2F_3$ (M+H)$^+$ 287.1254, observed 287.1254; $^1$H NMR (300 MHz, DMSO-d$_6$) δ ppm 0.99-1.16 (m, 2H, CH$_2$), 1.32-1.76 (m, 8H, 4×CH$_2$), 1.92-2.05 (m, 1H, CH), 3.67 (t, J=7.5 Hz, 1H, ArCH), 7.51-7.67 (m, 4H, Ar), 12.52 (br. s., 1H, CO$_2$H).

3-cyclopentyl-2(R)-(3-trifluoromethyl-phenyl)-propionic acid (92 mg, 0.32 mmol) was dissolved in methylene chloride (2 mL) and N,N-dimethylformamide (three drops) at 25° C. under argon. To this solution was added dropwise a solution of oxalyl chloride in methylene chloride (2 M solution, 190 μL, 0.35 mmol) which produced gas evolution and it was then stirred at 25° C. for 30 minutes. After this time, the reaction was cooled to 0° C. and 2,6-lutidine (80 μL, 0.64 mmol) was added to the flask and it was stirred for 15 min. To this was then added a solution of 1-[2-(tert-butyl-dimethyl-silanyloxy)-ethyl]-1H-pyrazol-3-ylamine (prepared in Example 67, 78 mg, 0.32 mmol) in methylene chloride (1 mL) and the reaction was allowed to warm up to 25° C. and stirred for 2 h. After this time the reaction quenched with a small amount of methanol and then diluted with methylene chloride. The reaction was then transferred to a separatory funnel and washed with 1 N aqueous hydrochloric acid solution (1×10 mL) and then a saturated brine solution (1×10 mL). The organic layer was then dried over sodium sulfate and concentrated with silica gel (2 g) in vacuo and purified on Biotage Flash chromatography system (40M column, silica gel, 40% ethyl acetate/hexanes) (40S column, Silica gel, 20% ethyl acetate/hexanes) to afford N-{1-[2-(tert-butyl-dimethyl-silanyloxy)-ethyl]-1H-pyrazol-3-yl}-3-cyclopentyl-2(R)-(3-trifluoromethyl-phenyl)-propionamide as a colorless gum: $[\alpha]^{25}_{589}$=−14.5° (c=0.22, methanol); ES-HRMS m/e calcd for $C_{26}H_{38}N_3O_2SiF_3$ (M+H)$^+$ 510.2758, observed 510.2749; $^1$H NMR (400 MHz, DMSO-d$_6$) δ ppm −0.09 (s, 6H, 2×SiCH$_3$), 0.77 (s, 9H, 3×CH$_3$), 1.06-1.18 (m, 2H, CH$_2$), 1.37-1.79 (m, 8H, 4×CH$_2$), 2.08-2.18 (m, 1H, CH), 3.84 (t, J=5.1 Hz, 2H, OCH$_2$), 3.90 (dd, J=9.4, 5.3 Hz, 1H, ArCH), 4.04 (t, J=5.1 Hz, 2H, NCH$_2$), 6.41 (d, J=2.3 Hz, 1H, Ar), 7.51 (d, J=2.3 Hz, 1H, Ar), 7.54-7.72 (m, 4H, Ar), 10.72 (s, 1H, NH).

In a flask containing N-{1-[2-(tert-butyl-dimethyl-silanyloxy)-ethyl]-1H-pyrazol-3-yl}-3-cyclopentyl-2(R)-(3-trifluoromethyl-phenyl)-propionamide (66 mg, 0.13 mmol) was added ethanol (3 mL) and concentrated hydrochloric acid (three drops) and was stirred at 25° C. for 2 h. It was then diluted with ethyl acetate (30 mL) and washed with water (1×10 mL) and saturated aqueous brine solution (1×10 mL). The organic layer was then dried over sodium sulfate and absorbed onto silica gel (2 g) and purified on Biotage Flash chromatography system (40S column, silica gel, 80% ethyl acetate/hexanes) afforded 3-cyclopentyl-N-[1-(2-hydroxy-ethyl)-1H-pyrazol-3-yl]-2(R)-(3-trifluoromethyl-phenyl)-propionamide (26 mg, 51%) as a colorless gum: $[\alpha]^{26}_{589}$=−22.5° (c=0.16, methanol); ES-HRMS m/e calcd for $C_{20}H_{24}N_3O_2F_3$ (M+H)$^+$ 396.1894, observed 396.1892; $^1$H NMR (400 MHz, DMSO-d$_6$) δ ppm 1.04-1.20 (m, 2H, CH$_2$), 1.35-1.80 (m, 8H, 4×CH$_2$), 2.07-2.19 (m, 1H, CH), 3.67 (q, J=5.6 Hz, 2H, OCH$_2$), 3.89 (dd, J=9.0, 5.5 Hz, 1H, ArCH), 3.99 (t, J=5.6 Hz, 2H, NCH$_2$), 4.83 (t, J=5.6 Hz, 1H, OH), 6.42 (d, J=2.2 Hz, 1H, Ar), 7.53 (d, J=2.2 Hz, 1H, Ar), 7.54-7.73 (m, 4H, Ar), 10.74 (s, 1H, NH).

Example 80

3-Cyclopentyl-N-[1-(2-hydroxy-2-methyl-propyl)-1H-pyrazol-3-yl]-2(R)-(4-methanesulfonyl-3-methyl-phenyl)-propionamide

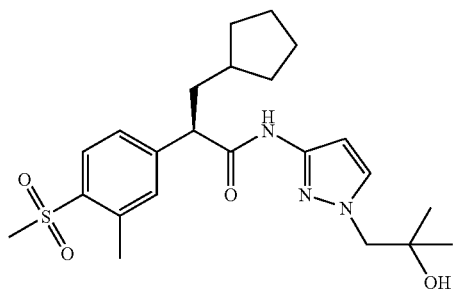

In a Parr shaker bottle was placed 2-methyl-1-(3-nitro-pyrazol-1-yl)-propan-2-ol (prepared in example 74, 100 mg, 0.54 mmol), 10% palladium on activated carbon (10 mg) and ethanol (5 mL). The bottle was then placed on the Parr shaker at 50 psi of hydrogen pressure for 1 h. The reaction was then filtered through a pad of celite and washed with ethanol and concentration in vacuo afforded 1-(3-amino-pyrazol-1-yl)-2-methyl-propan-2-ol (78 mg, 94%) and taken on to the next step without characterization.

A solution of 3-cyclopentyl-2(R)-(4-methanesulfonyl-3-methyl-phenyl)-propionic acid (prepared as in PCT WO 2004/052869 A1, Example 57, 145 mg, 0.47 mmol) was dissolved in methylene chloride (10 mL) and N,N-dimethyl-fomamide (one drop) and cooled to 0° C. To this solution was added dropwise a solution of oxalyl chloride in methylene chloride (2 M solution, 270 µL, 0.54 mmol) which produced gas evolution and it was then stirred at 0° C. for 15 minutes and 1 h at 25° C. After this time, the reaction was concentrated in vacuo to ⅓ of the original volume. In a separate flask a solution of 1-(3-amino-pyrazol-1-yl)-2-methyl-propan-2-ol (80 mg, 0.52 mmol), 2,6-lutidine (82 µL, 0.71 mmol) and methylene chloride (10 mL) was cooled to 0° C. in an ice bath. To this solution was added the solution of the prepared acid chloride diluted with another portion of methylene chloride (2 mL) dropwise. After addition was complete the reaction was then allowed to warm to 25° C. and stirred for 16 hours. After this time the reaction was diluted with methylene chloride (10 mL) and washed with a saturated aqueous sodium bicarbonate solution (1×15 mL) and a 1 N aqueous hydrochloric acid solution (1×15 mL) and then dried over magnesium sulfate, filtered and concentrated in vacuo. Purification an AnaLogix Intelliflash system (12 g column, 50% ethyl acetate/hexanes to 80% ethyl acetate/hexanes) afforded 3-cyclopentyl-N-[1-(2-hydroxy-2-methyl-propyl)-1H-pyrazol-3-yl]-2(R)-(4-methanesulfonyl-3-methyl-phenyl)-propionamide (152 mg, 73%) as a white foam: [α]$^{30}_{589}$=−20.0° (c=0.13, methylene chloride); ES-HRMS m/e calcd for $C_{23}H_{33}N_3O_4S$ (M+H)$^+$ 448.2265, observed 448.2260; $^1$H NMR (300 MHz, DMSO-d$_6$) δ ppm 1.02 (s, 3H, CH$_3$), 1.04 (s, 3H, CH$_3$), 1.03-1.17 (m, 2H, CH$_2$), 1.36-1.83 (m, 8H, 4×CH$_2$), 2.00-2.17 (m, 1H, CH), 2.62 (s, 3H, ArCH$_3$), 3.17 (s, 3H, SO$_2$CH$_3$), 3.86 (s, 2H, NCH$_2$), 3.82-3.94 (m, 1H, ArCH), 4.65 (s, 1H, OH), 6.45 (d, J=2.1 Hz, 1H, Ar), 7.41-7.47 (m, 2H, Ar), 7.50 (d, J=2.1 Hz, 1H, Ar), 7.84 (d, J$_o$=8.8 Hz, 1H, Ar), 10.75 (s, 1H, NH). 37022-193 $^1$H NMR (300 MHz, DMSO-d$_6$) δ ppm 1.42-1.59 (m, 1H, CH of CH$_2$), 1.76-2.28 (m, 8H, CH, CH of CH$_2$, and 3×CH$_2$), 3.32 (m, 3 H, SO$_2$CH$_3$), 3.65 (q, J=5.4 Hz, 2H, OCH$_2$), 3.88-4.05 (m, 3H, ArCH and NCH$_2$), 4.82 (t, J=5.3 Hz, 1H, OH), 6.40 (d, J=2.0 Hz, 1H, Ar), 7.53 (d, J=2.0 Hz, 1H, Ar), 7.60 (d, J$_o$=8.2 Hz, 1H, Ar), 7.71 (s, 1H, Ar), 8.00 (d, J$_o$=8.2 Hz, 1H, Ar), 10.83 (s, 1H, NH).

Example 81

3-Cyclopentyl-2(R)-(4-methanesulfonyl-3-methyl-phenyl)-N-[1-(2-methoxy-ethyl)-1H-pyrazol-3-yl]-propionamide

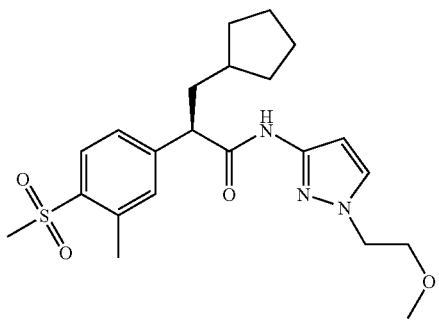

A solution of 3-cyclopentyl-2(R)-(4-methanesulfonyl-3-methyl-phenyl)-propionic acid (prepared as in PCT WO 2004/052869 A1, Example 57, 120 mg, 0.39 mmol) was dissolved in methylene chloride (5 mL) and N,N-dimethyl-fomamide (one drop) and cooled to 0° C. To this solution was added dropwise a solution of oxalyl chloride in methylene chloride (2 M solution, 222 µL, 0.44 mmol) which produced gas evolution and it was then warmed to 25° C. and stirred for 1 h. After this time, the reaction was concentrated in vacuo to about 1 mL and then enough methylene chloride was added to bring the total volume to 4 mL. This resulted in a roughly 0.096 M solution of 3-cyclopentyl-2(R)-(4-methanesulfonyl-3-methyl-phenyl)-propionyl chloride which was used crude without purification.

In a round bottom flask was placed 1-(2-methoxy-ethyl)-1H-pyrazol-3-ylamine (prepared in Example 72, 30 mg, 0.21 mmol), 2,6-lutidine (34 µL, 0.29 mmol) and methylene chloride (5 mL). This solution was then cooled to 0° C. and to it was added dropwise a solution of 3-cyclopentyl-2(R)-(4-methanesulfonyl-3-methyl-phenyl)-propionyl chloride in methylene chloride (0.096 M solution, 2 mL, 0.19 mmol). The reaction was then allowed to warm up to 25° C. and stirred for 16 h. After this time the reaction was quenched with a saturated aqueous sodium bicarbonate solution (10 mL) and then extracted with methylene chloride (3×10 mL). The organic extracts were then combined and washed with a 1 N aqueous hydrochloric acid solution (1×10 mL) and then dried over magnesium sulfate, filtered and concentrated in vacuo. Purification on an AnaLogix Intelliflash system (4 g column, 30% ethyl acetate/hexanes to 75% ethyl acetate/hexanes) afforded 3-cyclopentyl-2(R)-(4-methanesulfonyl-3-methyl-phenyl)-N-[1-(2-methoxy-ethyl)-1H-pyrazol-3-yl]-propionamide (57 mg, 65%) as a white foam: [α]$^{31}_{589}$=−29.5° (c=0.21, methylene chloride); ES-HRMS m/e calcd for $C_{22}H_{31}N_3O_4S$ (M+H)$^+$ 434.2108, observed 434.2108; $^1$H NMR (300 MHz, DMSO-d$_6$) δ ppm 1.02-1.20 (m, 2H, CH$_2$), 1.36-1.82 (m, 8H, 4×CH$_2$), 2.03-2.20 (m, 1H, CH), 2.62 (s, 3H, ArCH$_3$), 3.17 (s, 3H, SO$_2$CH$_3$), 3.19 (s, 3H, OCH$_3$), 3.61 (t, J=5.2 Hz, 2H, OCH$_2$), 3.82-3.94 (m, 1H, ArCH), 4.11 (t, J=5.2 Hz, 2H, NCH$_2$), 6.41 (d, J=2.4 Hz, 1H, Ar), 7.41-7.47 (m, 2H, Ar), 7.54 (d, J=2.4 Hz, 1H, Ar), 7.84 (d, J$_o$=8.8 Hz, 1H, Ar), 10.75 (s, 1H, NH).

Example 82

3-Cyclopentyl-N-[1-(3-hydroxy-propyl)-1H-pyrazol-3-yl]-2(R)-(4-methanesulfonyl-3-methyl-phenyl)-propionamide

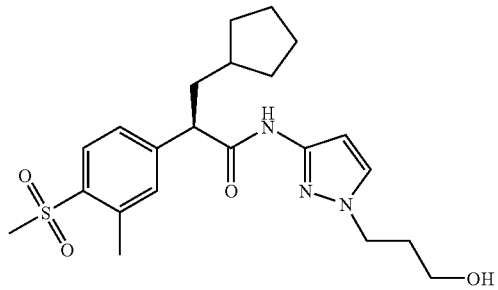

In a round bottom flask was placed 3-(3-amino-pyrazol-1-yl)-propan-1-ol (prepared in Example 23, 30 mg, 0.21 mmol), 2,6-lutidine (34 µL, 0.29 mmol) and methylene chloride (5 mL). This solution was then cooled to 0° C. and to it was added dropwise a solution of 3-cyclopentyl-2(R)-(4-methanesulfonyl-3-methyl-phenyl)-propionyl chloride in methylene chloride (prepared in example 81, 0.096 M solution, 2 mL, 0.19 mmol). The reaction was then allowed to warm up to 25° C. and stirred for 16 h. After this time the reaction was quenched with a saturated aqueous sodium bicarbonate solution (10 mL) and then extracted with methylene chloride (3×10 mL). The organic extracts were then combined and washed with a 1 N aqueous hydrochloric acid solution (1×10 mL) and then dried over magnesium sulfate, filtered and concentrated in vacuo. Purification on an AnaLogix Intelliflash system (4 g column, 50% ethyl acetate/hexanes to 100% ethyl acetate/hexanes) afforded 3-cyclopentyl-N-[1-(3-hydroxy-propyl)-1H-pyrazol-3-yl]-2(R)-(4-methanesulfonyl-3-methyl-phenyl)-propionamide (59 mg, 67%) as a white foam: [α]$^{31}_{589}$=−21.2° (c=0.17, methylene chloride); ES-HRMS m/e calcd for C$_{22}$H$_{31}$N$_3$O$_4$S (M+H)$^+$ 434.2108, observed 434.2109; $^1$H NMR (300 MHz, DMSO-d$_6$) δ ppm 1.01-1.19 (m, 2H, CH$_2$), 1.35-1.81 (m, 8H, 4×CH$_2$), 1.78-1.90 (m, 2H, CH$_2$), 2.03-2.16 (m, 1H, CH), 2.62 (s, 3H, ArCH$_3$), 3.17 (s, 3H, SO$_2$CH$_3$), 3.27-3.39 (m, 2H, OCH$_2$), 3.82-3.94 (m, 1H, ArCH), 4.01 (t, J=6.9 Hz, 2H, NCH$_2$), 4.56 (t, J=5.0 Hz, 1 H, OH), 6.40 (d, J=2.1 Hz, 1H, Ar), 7.41-7.49 (m, 2H, Ar), 7.54 (d, J=2.1 Hz, 1H, Ar), 7.84 (d, J$_o$=8.8 Hz, 1H, Ar), 10.74 (s, 1H, NH).

Example 83

3-Cyclopentyl-N-[1-(2-hydroxy-2-methyl-propyl)-1H-pyrazol-3-yl]-2(R)-(3-trifluoromethyl-phenyl)-propionamide

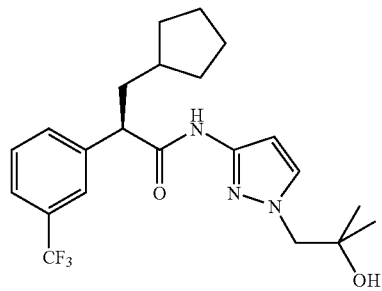

A solution of 3-cyclopentyl-2(R)-(3-trifluoromethyl-phenyl)-propionic acid (prepared as in Example 79, 210 mg, 0.73 mmol) was dissolved in methylene chloride (10 mL) and N,N-dimethylfomamide (one drop) and cooled to 0° C. To this solution was added dropwise a solution of oxalyl chloride in methylene chloride (2 M solution, 421 µL, 0.84 mmol) which produced gas evolution and it was then warmed to 25° C. and stirred for 1 h. After this time, the reaction was concentrated in vacuo to about 1.5 mL and then enough methylene chloride was added to bring the total volume to 6 mL. This resulted in a roughly 0.12 M solution of 3-cyclopentyl-2(R)-(3-trifluoromethyl-phenyl)-propionyl chloride which was used crude without purification.

In a round bottom flask was placed 1-(3-amino-pyrazol-1-yl)-2-methyl-propan-2-ol (prepared in Example 80 42 mg, 0.27 mmol), 2,6-lutidine (42 µL, 0.37 mmol) and methylene chloride (5 mL). This solution was then cooled to 0° C. and to it was added dropwise a solution of 3-cyclopentyl-2(R)-(3-trifluoromethyl-phenyl)-propionyl chloride in methylene chloride (0.12 M solution, 2 mL, 0.24 mmol). The reaction was then allowed to warm up to 25° C. and stirred for 16 h. After this time the reaction was diluted with methylene chloride (5 mL). The reaction was then washed with a saturated aqueous sodium bicarbonate solution (10 mL) and a 1 N aqueous hydrochloric acid solution (1×10 mL) and then dried over magnesium sulfate, filtered and concentrated in vacuo. Purification on an AnaLogix Intelliflash system (4 g column, 20% ethyl acetate/hexanes to 60% ethyl acetate/hexanes) afforded 3-cyclopentyl-N-[1-(2-hydroxy-2-methyl-propyl)-1H-pyrazol-3-yl]-2(R)-(3-trifluoromethyl-phenyl)-propionamide (83 mg, 81%) as a white foam: [α]$^{31}_{589}$=−25.0° (c=0.14, methylene chloride); ES-HRMS m/e calcd for C$_{22}$H$_{28}$N$_3$O$_2$F$_3$ (M+H)$^+$ 424.2207, observed 424.2207; $^1$H NMR (300 MHz, DMSO-d$_6$) δ ppm 1.03 (s, 3H, CH$_3$), 1.04 (s, 3H, CH$_3$), 1.05-1.19 (m, 2H, CH$_2$), 1.32-1.80 (m, 8 H, 4×CH$_2$), 2.01-2.21 (m, 1H, CH), 3.86 (s, 2H, NCH$_2$), 3.82-

3.94 (m, 1H, ArCH), 4.64 (s, 1H, OH), 6.46 (d, J=2.3 Hz, 1H, Ar), 7.50 (d, J=2.3 Hz, 1H, Ar), 7.52-7.74 (m, 4H, Ar), 10.75 (s, 1H, NH).

Example 84

3-Cyclopentyl-N-[1-(2-methoxy-ethyl)-1H-pyrazol-3-yl]-2(R)-(3-trifluoromethyl-phenyl)-propionamide

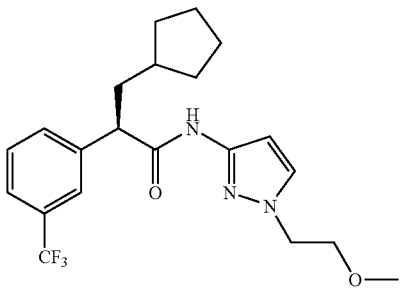

In a round bottom flask was placed 1-(2-methoxy-ethyl)-1H-pyrazol-3-yl-amine (prepared in Example 72, 38 mg, 0.27 mmol), 2,6-lutidine (42 μL, 0.37 mmol) and methylene chloride (5 mL). This solution was then cooled to 0° C. and to it was added dropwise a solution of 3-cyclopentyl-2(R)-(3-trifluoromethyl-phenyl)-propionyl chloride in methylene chloride (prepared in Example 83, 0.12 M solution, 2 mL, 0.24 mmol). The reaction was then allowed to warm up to 25° C. and stirred for 16 h. After this time the reaction was diluted with methylene chloride (5 mL). The reaction was then washed with a saturated aqueous sodium bicarbonate solution (10 mL) and a 1 N aqueous hydrochloric acid solution (1×10 mL) and then dried over magnesium sulfate, filtered and concentrated in vacuo. Purification on an AnaLogix Intelliflash system (4 g column, 20% ethyl acetate/hexanes to 60% ethyl acetate/hexanes) afforded 3-cyclopentyl-N-[1-(2-methoxy-ethyl)-1H-pyrazol-3-yl]-2(R)-(3-trifluoromethyl-phenyl)-propionamide (85 mg, 86%) as a colorless oil: $[\alpha]^{30}_{589}$=−18.8° (c=0.16, methylene chloride); ES-HRMS m/e calcd for $C_{21}H_{26}N_3O_2F_3$ (M+H)$^+$ 410.2050, observed 410.2050; $^1$H NMR (300 MHz, DMSO-$d_6$) δ ppm 1.05-1.19 (m, 2H, $CH_2$), 1.35-1.81 (m, 8H, 4×$CH_2$), 2.05-2.19 (m, 1H, CH), 3.19 (s, 3H, $OCH_3$), 3.61 (t, J=5.3 Hz, 2H, $OCH_2$), 3.86-3.94 (m, 1H, ArCH), 4.11 (t, J=5.3 Hz, 2H, $NCH_2$), 6.42 (d, J=2.3 Hz, 1H, Ar), 7.54 (d, J=2.3 Hz, 1H, Ar), 7.55-7.75 (m, 4H, Ar), 10.75 (s, 1H, NH).

Example 85

3-Cyclopentyl-N-[1-(3-hydroxy-propyl)-1H-pyrazol-3-yl]-2(R)-(3-trifluoromethyl-phenyl)-propionamide

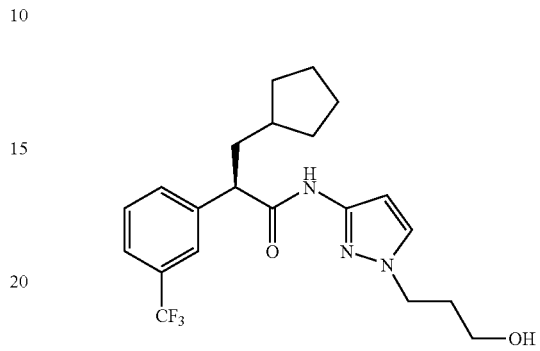

In a round bottom flask was placed 3-(3-amino-pyrazol-1-yl)-propan-1-ol (prepared in Example 23, 38 mg, 0.27 mmol), 2,6-lutidine (42 μL, 0.37 mmol) and methylene chloride (5 mL). This solution was then cooled to 0° C. and to it was added dropwise a solution of 3-cyclopentyl-2(R)-(3-trifluoromethyl-phenyl)-propionyl chloride in methylene chloride (prepared in Example 83, 0.12 M solution, 2 mL, 0.24 mmol). The reaction was then allowed to warm up to 25° C. and stirred for 16 h. After this time the reaction was diluted with methylene chloride (5 mL). The reaction was then washed with a saturated aqueous sodium bicarbonate solution (10 mL) and a 1 N aqueous hydrochloric acid solution (1×10 mL) and then dried over magnesium sulfate, filtered and concentrated in vacuo. Purification on an AnaLogix Intelliflash system (4 g column, 50% ethyl acetate/hexanes to 80% ethyl acetate/hexanes) afforded 3-cyclopentyl-N-[1-(3-hydroxy-propyl)-1H-pyrazol-3-yl]-2(R)-(3-trifluoromethyl-phenyl)-propionamide (56 mg, 57%) as a colorless oil: $[\alpha]^{30}_{589}$=−20.0° (c=0.11, methylene chloride); ES-HRMS m/e calcd for $C_{21}H_{26}N_3O_2F_3$ (M+H)$^+$ 410.2050, observed 410.2050; $^1$H NMR (300 MHz, DMSO-$d_6$) δ ppm 1.01-1.19 (m, 2H, $CH_2$), 1.34-1.80 (m, 8H, 4×$CH_2$), 1.79-1.91 (m, 2H, $CH_2$), 2.03-2.21 (m, 1H, CH), 3.29-3.38 (m, 2H, $OCH_2$), 3.84-3.93 (m, 1H, ArCH), 4.01 (t, J=6.9 Hz, 2H, $NCH_2$), 4.55 (t, J=5.0 Hz, 1H, OH), 6.41 (d, J=2.3 Hz, 1H, Ar), 7.54 (d, J=2.3 Hz, 1H, Ar), 7.55-7.74 (m, 4H, Ar), 10.74 (s, 1H, NH).

Example 86

2-(3,4-Dichloro-phenyl)-N-[1-(2-hydroxy-2-methyl-propyl)-1H-pyrazol-3-yl]-3-(tetrahydro-pyran-2-yl)-propionamide

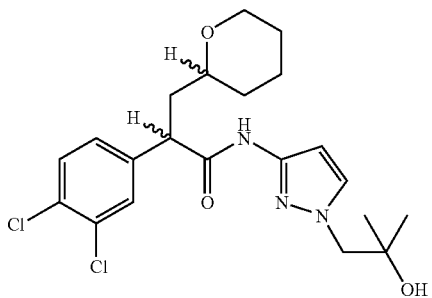

A solution of 2-(3,4-dichloro-phenyl)-3-(tetrahydro-pyran-2-yl)-propionic acid (prepared as in PCT WO 2003/095438 A1, Example 9, 290 mg, 0.96 mmol) was dissolved in methylene chloride (10 mL) and N,N-dimethylfomamide (one drop) and cooled to 0° C. To this solution was added dropwise a solution of oxalyl chloride in methylene chloride (2 M solution, 550 µL, 1.09 mmol) which produced gas evolution and it was then stirred at 0° C. for 15 minutes and 30 min at 25° C. After this time, the reaction was concentrated in vacuo to ⅓ of the original volume. In a separate flask a solution of 1-(3-amino-pyrazol-1-yl)-2-methyl-propan-2-ol (prepared in Example 80, 163 mg, 1.05 mmol), 2,6-lutidine (158 µL, 1.43 mmol) and methylene chloride (10 mL) was cooled to 0° C. in an ice bath. To this solution was then added the solution of the prepared acid chloride diluted with another portion of methylene chloride (2 mL) dropwise. After addition was complete the reaction was then allowed to warm to 25° C. and stirred for 16 hours. After this time the reaction was diluted with methylene chloride (10 mL) and washed with a saturated aqueous sodium bicarbonate solution (1×20 mL) and the aqueous layers were than extracted with methylene chloride (2×10 mL). The combined organic layers were then washed with a 1 N aqueous hydrochloric acid solution (1×20 mL) and then dried over sodium sulfate, filtered and concentrated in vacuo. Purification on an AnaLogix Intelliflash system (12 g column, 50% ethyl acetate/hexanes to 65% ethyl acetate/hexanes) afforded 2-(3,4-dichloro-phenyl)-N-[1-(2-hydroxy-2-methyl-propyl)-1H-pyrazol-3-yl]-3-(tetrahydro-pyran-2-yl)-propionamide (339 mg, 81%) as a white foam (reaction of a set of racemic diastereomers, 4 compounds) ES-HRMS m/e calcd for $C_{21}H_{27}N_3O_3Cl_2$ (M+H)⁺ 440.1502, observed 440.1500; ¹H NMR (300 MHz, DMSO-$d_6$) δ ppm 1.00-1.03 (3×bs, 6H, 2×CH₃), 1.14-2.28 (7×m, 8H, 4×CH₂), 3.04-3.30 (m, 2H, OCH₂), 3.77-4.05 (m, 4H, ArCH and NCH₂ and OCH), 4.62, 4.63 (2×s, 1H, OH), 6.42, 6.43 (2×d, J=2.3 Hz, 1H, Ar), 7.30, 7.33 (2×m, 1H, Ar), 7.47-7.50 (m, 1H, Ar), 7.54-7.60 (m, 2H, Ar), 10.62, 10.68 (2×s, 1H, NH).

Example 87

2(R)-(3-Chloro-4-methanesulfonyl-phenyl)-N-[1-(2-hydroxy-2-methyl-propyl)-1H-pyrazol-3-yl]-3-(tetrahydro-furan-2(R)-yl)-propionamide

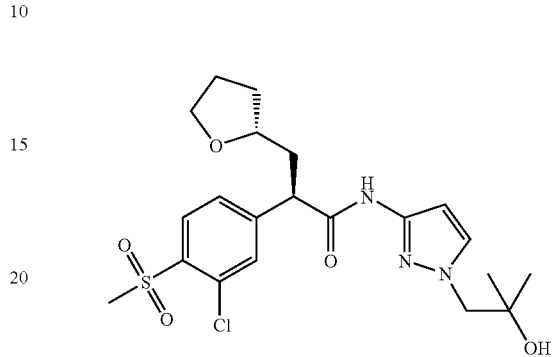

In a round bottom flask was placed (R)-(tetrahydro-furan-2-yl)-methanol (prepared as in PCT WO 2003/095438 A1, Example 3, 4.65 g, 45.5 mmol), methylene chloride (100 mL) and triethylamine (8.4 mL, 60.6 mmol) and it was cooled to 0° C. To this cooled solution was then added a solution of p-toluenesulfonyl chloride (10.4 g, 54.6 mmol) in methylene chloride (30 mL) dropwise. Once the addition was complete the reaction was then warmed to 25° C. and stirred for 16 h. The reaction was then diluted with water (50 mL) and extracted with methylene chloride (3×30 mL). The combined organic extracts were then dried over sodium sulfate, filtered and concentrated in vacuo. Purification on an AnaLogix Intelliflash system (80 g column, 3% ethyl acetate/hexanes to 40% ethyl acetate/hexanes) afforded toluene-4-sulfonic acid tetrahydro-furan-2(R)-ylmethyl ester (8.37 g, 72%) as a clear colorless oil: $[\alpha]^{32}_{589}$=−14.4° (c=0.72, methylene chloride); ES-HRMS m/e calcd for $C_{12}H_{16}O_4S$ (M+H)⁺ 257.0842, observed 257.0841; ¹H NMR (300 MHz, CDCl₃) δ ppm 1.95-2.08 (m, 1H, CH of CH₂), 2.14-2.40 (m, 3H, CH₂ and CH of CH₂), 4.02-4.19 (m, 2H, OCH₂), 4.29-4.49 (m, 3H, OCH and OCH₂), 7.69 (d, J=8.0 Hz, 2H, Ar), 8.15 (d, J=8.0 Hz, 2H, Ar).

In a flask was placed toluene-4-sulfonic acid tetrahydro-furan-2(R)-ylmethyl ester (8.37 g, 32.6 mmol), sodium iodide (6.36 g, 42.4 mmol) and acetone (100 mL) and it was heated at 60° C. for 24 h. After this time there was still starting material present by TLC so another portion of sodium iodide (500 mg) was added and it was stirred at 60° C. for another 8 h. The reaction still showed starting material was not consumed but the reaction was worked up anyway. The reaction was cooled to 25° C. and the solids were filtered off. The filtrate was concentrated in vacuo and then the residue dissolved in methylene chloride and the solids filtered off. The filtrate was concentrated in vacuo to yield the crude product. Purification on an AnaLogix Intelliflash system (80 g column, 5% ethyl acetate/hexanes to 35% ethyl acetate/hexanes) afforded 2(R)-iodomethyl-tetrahydro-furan (4.89 g, 71%) as a yellow oil: $[\alpha]^{23}_{589}$=−16.9° (c=0.16, methylene chloride); EI-HRMS m/e calcd for $C_5H_9OI$ (M⁺) 211.9693, observed 211.9692; ¹H NMR (300 MHz, CDCl₃) δ ppm 1.80-2.02 (m, 1H, CH of CH₂), 2.11-2.47 (m, 3H, CH₂ and CH of CH₂), 3.42-3.58 (brs, 2H, ICH₂), 4.04-4.34 (2×m, 3H, OCH and OCH₂).

In a round bottom flask under argon was placed tetrahydrofuran (15 mL) and diisopropyl amine (357 μL, 2.55 mmol) and it was cooled to −78° C. in a dry ice/acetone bath. To this cooled solution was then added n-butyl lithium (2.5 M solution in hexanes, 970 μL, 2.43 mmol) and it was stirred for 15 min at −78° C. To this cooled solution was then added a solution of (3-chloro-4-methylsulfanyl-phenyl)-acetic acid methyl ester (prepared as in PCT WO 2003/095438 A1, Example 4, 511 mg, 2.21 mmol) in tetrahydrofuran (5 mL) and 1,3-dimethyl-3,4,5,6-tetrahydro-2(1H)-pyrimidinone (2 mL) dropwise. This was then stirred for one hour at −78° C. After such time, 2(R)-iodomethyl-tetrahydro-furan (657 mg, 3.1 mmol) in 1,3-dimethyl-3,4,5,6-tetrahydro-2(1H)-pyrimidinone (1 mL) was added dropwise at −78° C. The reaction was then allowed to slowly warm to 25° C. and it was stirred for 16 h. After such time, the reaction was quenched with a saturated aqueous ammonium chloride solution (20 mL) and then extracted with ethyl acetate (3×20 mL). The organics were dried over magnesium sulfate, filtered and then concentrated in vacuo. Purification on an AnaLogix Intelliflash system (40 g column, 5% ethyl acetate/hexanes to 20% ethyl acetate/hexanes) afforded 2-(3-chloro-4-methylsulfanyl-phenyl)-3-(tetrahydro-furan-2(R)-yl)-propionic acid methyl ester (237 mg, 34%) as a reaction of two diastereomers which was a light yellow oil: ES-HRMS m/e calcd for $C_{15}H_{19}O_3SCl$ (M+Na)$^+$ 337.0635, observed 337.0635.

The mixture of diastereomers of 2-(3-chloro-4-methylsulfanyl-phenyl)-3-(tetrahydro-furan-2(R)-yl)-propionic acid methyl ester (237 mg, 0.75 mmol) were dissolved in methanol (5 mL) and then sodium tungstate dihydrate (12 mg, 0.04 mmol) was added and the solution cooled to 0° C. To this cooled solution was then added a 30% aqueous solution of hydrogen peroxide (5 mL) and the ice bath was removed and the reaction allowed to warm to 25° C. and stirred for 16 h. After this time, the reaction was cooled to 0° C. in an ice bath and it was treated very slowly with a saturated aqueous solution of sodium nitrite (10 mL). The reaction was then transferred to a separatory funnel and extracted with a solution of chloroform/methanol (3/2) (3×20 mL). The extracts were than concentrated in vacuo and then redissolved in methylene chloride and dried over magnesium sulfate, filtered and concentrated in vacuo. Purification on an AnaLogix Intelliflash system (4 g column, 30% ethyl acetate/hexanes to 45% ethyl acetate/hexanes) afforded 2-(3-chloro-4-methanesulfonyl-phenyl)-3-(tetrahydro-furan-2(R)-yl)-propionic acid methyl ester (180 mg, 69%) as a reaction of two diastereomers which was a clear colorless oil.

2-(3-chloro-4-methanesulfonyl-phenyl)-3-(tetrahydro-furan-2(R)-yl)-propionic acid methyl ester (180 mg, 0.52 mmol) was dissolved in ethanol (5 mL) and treated with a solution of lithium hydroxide monohydrate (54 mg, 1.3 mmol) in water (1 mL) at 25° C. It was stirred at 25° C. until the starting material was all consumed by TLC. The reaction was then concentrated in vacuo to remove the ethanol. The remaining aqueous layer was then acidified to pH=2 with an aqueous 1N hydrochloric acid solution. This was then extracted with ethyl acetate (3×20 mL), the organic layers combined and dried over magnesium sulfate, filtered and concentrated in vacuo to afford 2-(3-chloro-4-methanesulfonyl-phenyl)-3-(tetrahydro-furan-2(R)-yl)-propionic acid (168 mg, 98%) as a reaction of two diastereomers as a white foam: ES-HRMS m/e calcd for $C_{14}H_{17}O_5SCl$ (M+H)$^+$ 333.0558, observed 333.0553; $^1$H NMR (300 MHz, DMSO-d$_6$) δ ppm 1.35-1.49 (m, 1H, CH of CH$_2$), 1.66-1.99 (m, 4H, 4×CH of CH$_2$), 2.06-2.23 (m, 1H, CH of CH$_2$), 3.34, 3.35 (2×s, 3H, SO$_2$CH$_3$), 3.42-3.85 (m, 4H, OCH$_2$ and OCH and ArCH), 7.54 (2×dd, J$_o$=8.1 Hz, J$_m$=1.7 Hz, 1H, Ar), 7.66 (2×d, J$_m$=1.7 Hz, 1H, Ar), 7.99 (2×d, J$_o$=8.1 Hz, 1H, Ar), 12.69 (brs, 1H, CO$_2$H).

A solution of 2-(3-chloro-4-methanesulfonyl-phenyl)-3-(tetrahydro-furan-2(R)-yl)-propionic acid (168 mg, 0.51 mmol) was dissolved in methylene chloride (10 mL) and N,N-dimethylfomamide (one drop) and cooled to 0° C. To this solution was added dropwise a solution of oxalyl chloride in methylene chloride (2 M solution, 291 μL, 0.58 mmol) which produced gas evolution and it was then stirred at 0° C. for 15 minutes and 30 min at 25° C. After this time, the reaction was concentrated in vacuo to ⅓ of the original volume. In a separate flask a solution of 1-(3-amino-pyrazol-1-yl)-2-methyl-propan-2-ol (prepared in Example 80, 86 mg, 0.56 mmol), 2,6-lutidine (84 μL, 0.76 mmol) and methylene chloride (10 mL) was cooled to 0° C. in an ice bath. To this solution was then added the solution of the prepared acid chloride diluted with another portion of methylene chloride (2 mL) dropwise. After addition was complete the reaction was then allowed to warm to 25° C. and stirred for 16 hours. After this time the reaction was diluted with methylene chloride (10 mL) and washed with a saturated aqueous sodium bicarbonate solution (1×20 mL) and the aqueous layers were than extracted with methylene chloride (2×10 mL). The combined organic layers were then washed with a 1 N aqueous hydrochloric acid solution (1×20 mL) and then dried over sodium sulfate, filtered and concentrated in vacuo. Purification on an AnaLogix Intelliflash system (12 g column, 70% ethyl acetate/hexanes to 90% ethyl acetate/hexanes) afforded 2-(3-chloro-4-methanesulfonyl-phenyl)-N-[1-(2-hydroxy-2-methyl-propyl)-1H-pyrazol-3-yl]-3-(tetrahydro-furan-2(R)-yl)-propionamide (155 mg, 65%) as a mixture of roughly 1:1 mixture of diastereomers as a white foam: ES-HRMS m/e calcd for $C_{21}H_{28}N_3O_5SCl$ (M+H)$^+$ 470.1511, observed 470.1504; $^1$H NMR (300 MHz, DMSO-d$_6$) δ ppm 1.02, 1.03 (2×s, 6H, 2×CH$_3$), 1.37-1.52 (m, 1H, CH of CH$_2$), 1.64-1.99 (m, 4H, 4×CH of CH$_2$), 2.08-2.40 (m, 1H, CH of CH$_2$), 3.34, 3.35 (2×s, 3H, SO$_2$CH$_3$), 3.43-3.77 (m, 3H, OCH$_2$ and OCH), 3.86 (brs, 2H, NCH$_2$), 3.97-4.12 (m, 1H, ArCH), 4.62, 4.63 (2×s, 1H, OH), 6.43 (m, 1H, Ar), 7.49 (m, 1H, Ar), 7.59 (2×dd, J$_o$=8.2 Hz, J$_m$=1.7 Hz, 1H, Ar), 7.69 (2×d, J$_m$=1.7 Hz, 1H, Ar), 7.99 (2×d, J$_o$=8.2 Hz, 1H, Ar), 10.75, 10.81 (2×s, 1 H, NH).

The 1:1 diastereomeric mixture was separated into the single diastereomers by supercritical fluid chromatography (SFC) on a Berger MultiGram II Supercritical Fluid Chromatography (SFC) system (Mettler-Toledo AutoChem Berger Instruments, Newark, Del.) (Chiral column: Daicel OD-H, 250 mm×30 mm i.d., 5 μm-particle size, temperature: 35° C., flow rate of 70 mL/min, and 100 bar back pressure, 1:1 ethanol/acetonitrile as mobile phase modifier (e.g. 50% ethanol/50% acetonitrile). UV Detection: 220 nm) to afford the two pure diastereomers: the first peak to elute was the 2(R)-(3-chloro-4-methanesulfonyl-phenyl)-N-[1-(2-hydroxy-2-methyl-propyl)-1H-pyrazol-3-yl]-3-(tetrahydro-furan-2(R)-yl)-propionamide diastereomer which was isolated as a white foam (44 mg) [α]$^{26}_{589}$=−32.7° (c=0.15, methylene chloride); ES-HRMS m/e calcd for $C_{21}H_{28}N_3O_5SCl$ (M+H)$^+$ 470.1511, observed 470.1507; $^1$H NMR (300 MHz, DMSO-d$_6$) δ ppm 1.02 (s, 6H, 2×CH$_3$), 1.37-1.50 (m, 1H, CH of CH$_2$), 1.71-2.01 (m, 4H, 4×CH of CH$_2$), 2.08-2.21 (m, 1H, CH of CH$_2$), 3.35 (s, 3H, SO$_2$CH$_3$), 3.43-3.59 (m, 2H, OCH$_2$), 3.67-3.77 (m, 1H, OCH), 3.86 (brs, 2H, NCH$_2$), 3.97-4.05 (m, 1H, ArCH), 4.66 (s, 1H, OH), 6.44 (d, J=2.3 Hz, 1H, Ar), 7.51 (d, J=2.3 Hz, 1H, Ar), 7.60 (d, $J_o$=8.2 Hz, 1H, Ar), 7.71 (s, 1H, Ar), 8.01 (d, $J_o$=8.2 Hz, 1H, Ar), 10.77 (s, 1H, NH).

Example 88

2(R)-(3,4-Dichloro-phenyl)-N-[1-(2-hydroxy-2-methyl-propyl)-1H-pyrazol-3-yl]-3-(tetrahydro-pyran-4-yl)-propionamide

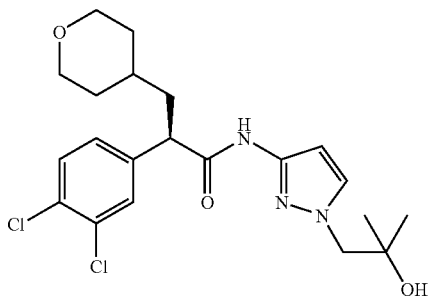

In a round bottom flask under argon was placed tetrahydrofuran (50 mL) and 1,1,1,3,3,3-hexamethyldisilazane (3.21 mL, 15.33 mmol) and it was cooled to −78° C. in a dry ice/acetone bath. To this cooled solution was then added n-butyl lithium (2.5 M solution in hexanes, 5.8 mL, 14.38 mmol) and it was stirred for 15 min at −78° C. To this cooled solution was then added a solution of (3,4-dichloro-phenyl)-acetic acid methyl ester (prepared as in PCT WO 2003/095438 A1, Example 1, 3.00 g, 13.69 mmol) in tetrahydrofuran (40 mL) dropwise. This was then stirred for 10 min at −78° C. then at 0° C. for 45 min which resulted in an amber solution. After such time, the reaction was cooled back to −78° C. and a solution of 4-iodomethyl-tetrahydro-pyran (prepared as in PCT WO 2003/095438 A1, Example 20, 3.71 g, 16.43 mmol) in 1,3-dimethyl-3,4,5,6-tetrahydro-2(1H)-pyrimidinone (2.5 mL, 20.54 mmol) was added dropwise at −78° C. The reaction was then allowed to slowly warm to 0° C. and it was stirred for 16 h. After such time, the reaction was diluted with ethyl acetate (500 mL) and washed with a saturated aqueous ammonium chloride solution (1×100 mL) followed by a saturated sodium chloride solution wash (1×100 mL). The organics were dried over sodium sulfate, filtered and then concentrated in vacuo. Flash column chromatography (Merck Silica gel 60, 230-400 mesh, 10% ethyl acetate/hexanes to 20% ethyl acetate/hexanes) afforded 2-(3,4-dichloro-phenyl)-3-(tetrahydro-pyran-4-yl)-propionic acid methyl ester (2.26 g, 52%) as a gold viscous oil: $^1$H NMR (300 MHz, CDCl$_3$) δ ppm 1.22-1.47 (m, 3H, CH$_2$ and CH of CH$_2$), 1.54-1.75 (m, 3H, CH$_2$ and CH of CH$_2$), 1.96-2.07 (m, 1H, CH), 3.25-3.36 (m, 2H, OCH$_2$), 3.64 (t, J=7.4 Hz, 1H, ArCH), 3.89-3.97 (m, 2H, OCH$_2$), 7.15 (dd, $J_o$=8.3 Hz, $J_m$=2.0 Hz, 1H, Ar), 7.37-7.42 (m, 2H, Ar).

2-(3,4-Dichloro-phenyl)-3-(tetrahydro-pyran-4-yl)-propionic acid methyl ester (2.26 g, 7.12 mmol) was dissolved in tetrahydrofuran:ethanol:water (6:3:2) reaction (100 mL) and treated with lithium hydroxide monohydrate (1.50 g, 35.6 mmol) at 25° C. It was stirred at 25° C. for 2 h. The reaction was then diluted with a 1 M aqueous solution of potassium hydrogen sulfate (200 mL) and then extracted with ethyl acetate (1×300 mL), the organic layers combined and dried over sodium sulfate, filtered and concentrated in vacuo with silica gel (4 g) and purified by Biotage Flash Chromatography (40M column, Silica gel, 10% methanol/ethyl acetate) to afford 2-(3,4-dichloro-phenyl)-3-(tetrahydro-pyran-4-yl)-propionic acid (2.00 g, 93%) as an off white solid.

2-(3,4-Dichloro-phenyl)-3-(tetrahydro-pyran-4-yl)-propionic acid (152 mg, 0.50 mmol) was dissolved in methylene chloride (5 mL) and N,N-dimethylfomamide (three drops) at 25° C. under argon. To this solution was added dropwise a solution of oxalyl chloride in methylene chloride (2 M solution, 270 μL, 0.53 mmol) which produced gas evolution and it was then stirred at 25° C. for 30 minutes. After this time, the reaction was concentrated in vacuo and the residue was then taken up in methylene chloride (5 mL). This solution was then added dropwise to a flask containing a solution of 1-(3-amino-pyrazol-1-yl)-2-methyl-propan-2-ol (prepared in Example 80, 78 mg, 0.50 mmol), 2,6-lutidine (130 μL, 1.00 mmol), and methylene chloride (5 mL) which was 0° C. The reaction was allowed to warm to 25° C. and stirred for a period of 2 h. After this time, the reaction was quenched with a small amount of methanol and then concentrated in vacuo. It was then dissolved in ethyl acetate (25 mL) and washed with a 1N hydrochloric acid solution (1×10 mL) and a saturated aqueous sodium chloride solution (1×10 mL). The organic layer was then dried over sodium sulfate and concentrated with silica gel (2 g) in vacuo and purified on Biotage Flash chromatography system (40S column, silica gel, 100% ethyl acetate) to afford 2-(3,4-dichloro-phenyl)-N-[1-(2-hydroxy-2-methyl-propyl)-1H-pyrazol-3-yl]-3-(tetrahydro-pyran-4-yl)-propionamide (149 mg, 81%) a 1:1 enantiomeric reaction as a white foam.

The 1:1 reaction of enantiomers of 2-(3,4-dichloro-phenyl)-N-[1-(2-hydroxy-2-methyl-propyl)-1H-pyrazol-3-yl]-3-(tetrahydro-pyran-4-yl)-propionamide was separated into the single compounds by supercritical fluid chromatography (SFC) on a Berger MultiGram II Supercritical Fluid Chromatography (SFC) system (Mettler-Toledo AutoChem Berger Instruments, Newark, Del.) (Chiral column: Daicel OD-H, 250 mm×30 mm i.d., 5 μm-particle size, temperature: 35° C., flow rate of 70 mL/min, and 100 bar back pressure, 20% methanol as mobile phase modifier and UV Detection: 220 nm) to afford the two pure enantiomers. The first peak to elute was the active 2(R)-(3,4-dichloro-phenyl)-N-[1-(2-hydroxy-2-methyl-propyl)-1H-pyrazol-3-yl]-3-(tetrahydro-pyran-4-yl)-propionamide enantiomer which was isolated as a white foam (73 mg) [α]$^{25}_{589}$=−13.91° (c=0.23, methylene chloride); ES-HRMS m/e calcd for $C_{21}H_{27}N_3O_3Cl_2$ (M+H)$^+$ 440.1502, observed 440.1500; $^1$H NMR (300 MHz, DMSO-d$_6$) δ ppm 1.02 (s, 6H, 2×CH$_3$), 1.07-1.67 (m, 6H, 3×CH$_2$), 1.90-2.04 (m, 1H, CH), 3.10-3.24 (m, 2H, OCH$_2$), 3.71-3.94 (m, 5H, ArCH and NCH$_2$ and OCH$_2$), 4.62 (s, 1H, OH), 6.42 (d, J=2.3 Hz, 1H, Ar), 7.33 (dd, $J_o$=8.3 Hz, $J_m$=1.9 Hz, 1H, Ar), 7.48 (d, J=2.3 Hz, 1H, Ar), 7.57 (d, J$_m$=1.9 Hz, 1H, Ar), 7.57 (d, J$_o$=8.3 Hz, 1H, Ar), 10.70 (s, 1H, NH).

Example 89

N-[1-(2-Hydroxy-2-methyl-propyl)-1H-pyrazol-3-yl]-2(R)-(4-methanesulfonyl-3-methyl-phenyl)-3-(tetrahydro-pyran-4-yl)-propionamide

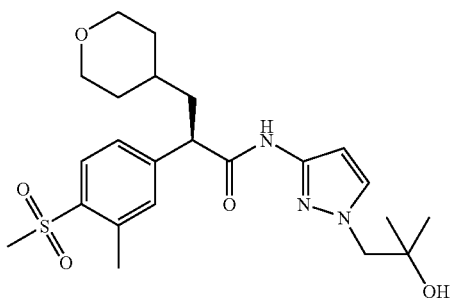

(3-Methyl-4-methylsulfanyl-phenyl)-acetic acid (prepared as in PCT WO 2004/052869 A1, Example 57, 1.50 g, 7.64 mmol) was placed in a pressure bottle with methanol (15 mL) and concentrated sulfuric acid (9 drops) and heated at 70° C. for 16 h and then stirred at 25° C. for 2 days. The reaction was then diluted with chloroform and concentrated with silica gel (4 g) in vacuo and purified on Biotage Flash chromatography system (40M column, silica gel, 20% ethyl acetate/hexanes) to afford (3-methyl-4-methylsulfanyl-phenyl)-acetic acid methyl ester (1.34 g, 83%) as an amber oil.

In a round bottom flask under argon was placed tetrahydrofuran (30 mL) and 1,1,1,3,3,3-hexamethyldisilazane (1.50 mL, 7.13 mmol) and it was cooled to −78° C. in a dry ice/acetone bath. To this cooled solution was then added n-butyl lithium (2.5 M solution in hexanes, 2.70 mL, 6.69 mmol) and it was stirred for 15 min at −78° C. To this cooled solution was then added a solution of (3-methyl-4-methylsulfanyl-phenyl)-acetic acid methyl ester (1.34 g, 6.37 mmol) in tetrahydrofuran (20 mL) dropwise. This was then stirred for 10 min at −78° C. then at 0° C. for 1 h which resulted in an gold colored solution. After such time, the reaction was cooled back to −78° C. and a solution of 4-iodomethyl-tetrahydropyran (prepared as in PCT WO 2003/095438 A1, Example 20, 1.73 g, 7.64 mmol) in 1,3-dimethyl-3,4,5,6-tetrahydro-2 (1H)-pyrimidinone (1.17 mL, 9.56 mmol) was added dropwise at −78° C. The reaction was then allowed to slowly warm to 0° C. and it was stirred for 16 h. After such time, the reaction was diluted with ethyl acetate (250 mL) and washed with a saturated aqueous ammonium chloride solution (1×50 mL) followed by a saturated sodium chloride solution wash (1×50 mL). The organics were dried over sodium sulfate, filtered and then concentrated with silica gel (4 g) in vacuo and purified on Biotage Flash chromatography system (40M column, silica gel, 10% ethyl acetate/hexanes) to afford 2-(3-methyl-4-methylsulfanyl-phenyl)-3-(tetrahydro-pyran-4-yl)-propionic acid methyl ester (1.49 g, 76%) as a gold oil.

In a flask was placed 2-(3-methyl-4-methylsulfanyl-phenyl)-3-(tetrahydro-pyran-4-yl)-propionic acid methyl ester (1.49 g, 4.83 mmol) and formic acid (10 mL) and it was cooled to 0° C. in an ice bath. To this cooled solution was then added slowly a 30% aqueous solution of hydrogen peroxide (40 mL). The reaction was allowed to slowly warm to 25° C. and stirred for 16 h. The reaction was then cooled to 0° C. in an ice bath and to this was slowly added a saturated aqueous solution of sodium nitrite (20 mL). The solution was transferred to a separatory funnel and extracted with chloroform/methanol (3/2) (2×40 mL) and concentrated in vacuo. The residue was taken up in acetonitrile and then concentrated with silica gel (4 g) in vacuo and purified on Biotage Flash chromatography system (40S column, silica gel, 50% ethyl acetate/hexanes) to afford 2-(4-methanesulfonyl-3-methyl-phenyl)-3-(tetrahydro-pyran-4-yl)-propionic acid methyl ester (1.30 g, 79%) as a colorless oil.

2-(4-Methanesulfonyl-3-methyl-phenyl)-3-(tetrahydro-pyran-4-yl)-propionic acid methyl ester (1.30 g, 3.82 mmol) was dissolved in tetrahydrofuran:ethanol:water (6:3:2) reaction (50 mL) and treated with lithium hydroxide monohydrate (800 mg, 19.1 mmol) at 25° C. It was stirred at 25° C. for 2 h. The reaction was then diluted with a 1 M aqueous solution of potassium hydrogen sulfate (100 mL) and then extracted with ethyl acetate (1×200 mL), the organic layer was then dried over sodium sulfate, filtered and concentrated in vacuo with silica gel (2 g) and purified by Biotage Flash Chromatography (40S column, Silica gel, 10% methanol/ethyl acetate) to afford 2-(4-methanesulfonyl-3-methyl-phenyl)-3-(tetrahydro-pyran-4-yl)-propionic acid (1.15 g, 92%) as a colorless oil.

The 1:1 reaction of enantiomers of 2-(4-methanesulfonyl-3-methyl-phenyl)-3-(tetrahydro-pyran-4-yl)-propionic acid was separated into the single compounds by supercritical fluid chromatography (SFC) on a Berger MultiGram II Supercritical Fluid Chromatography (SFC) system (Mettler-Toledo AutoChem Berger Instruments, Newark, Del.) (Chiral column: Daicel OJ-H, 250 mm×30 mm i.d., 5 μm-particle size, temperature: 35° C., flow rate of 70 mL/min, and 100 bar back pressure, 10% methanol as mobile phase modifier and UV Detection: 220 nm) to afford the two pure enantiomers. The second peak to elute was the 2(R)-(4-methanesulfonyl-3-methyl-phenyl)-3-(tetrahydro-pyran-4-yl)-propionic acid enantiomer which was isolated as a white foam (496 mg) $[\alpha]^{26}_{589}$=−42.3° (c=0.26, methanol); ES-HRMS m/e calcd for $C_{16}H_{22}O_5S$ (M+H)$^+$ 327.1261, observed 327.1259; $^1$H NMR (300 MHz, DMSO-d$_6$) δ ppm 1.07-1.14 (m, 3H, CH$_2$ and CH of CH$_2$), 1.50-1.70 (m, 3H, CH$_2$ and CH of CH$_2$), 1.87-2.00 (m, 1 H, CH), 2.62 (s, 3H, ArCH$_3$), 3.11-3.23 (m, 2H, OCH$_2$), 3.20 (s, 3H, SO$_2$CH$_3$), 3.72 (t, J=7.8 Hz, 1H, ArCH), 3.72-3.82 (m, 2H, OCH$_2$), 7.36-7.41 (m, 2H, Ar), 7.83 (d, J$_o$=8.7 Hz, 1H, Ar), 12.56 (s, 1H, CO$_2$H).

2(R)-(4-methanesulfonyl-3-methyl-phenyl)-3-(tetrahydro-pyran-4-yl)-propionic acid (75 mg, 0.23 mmol) was dissolved in methylene chloride (2 mL) and N,N-dimethylfomamide (two drops) at 25° C. under argon. To this solution was added dropwise a solution of oxalyl chloride in methylene chloride (2 M solution, 120 μL, 0.24 mmol) which produced gas evolution and it was then stirred at 25° C. for 30 minutes. After this time, the reaction was concentrated in vacuo and the residue was then taken up in methylene chloride (2 mL). This solution was then added dropwise to a flask containing a solution of 1-(3-amino-pyrazol-1-yl)-2-methyl-propan-2-ol (prepared in Example 80, 36 mg, 0.23 mmol), 2,6-lutidine (54 μL, 0.46 mmol), and methylene chloride (2 mL) which was cooled to 0° C. The reaction was allowed to warm to 25° C. and stirred for a period of 2 h. After this time, the reaction quenched with a small amount of methanol and then concentrated in vacuo. It was then dissolved in ethyl acetate (25 mL) and washed with a 1N hydrochloric acid solution (1×10 mL) and a saturated aqueous sodium chloride solution (1×10 mL). The organic layer was then dried over sodium sulfate and concentrated with silica gel (2 g) in vacuo and purified on Biotage Flash chromatography system (40S column, silica gel, 10% methanol/ethyl acetate) to afford N-[1-(2-hydroxy-2-methyl-propyl)-1H-pyrazol-3-yl]-2(R)-(4-methanesulfonyl-3-methyl-phenyl)-3-(tetrahydro-pyran-4-yl)-propionamide (70 mg, 66%) as a white foam: $[\alpha]^{30}_{589}$=−6.9° (c=0.16, methanol); ES-HRMS m/e calcd for $C_{23}H_{33}N_3O_5S$ (M+H)$^+$ 464.2214, observed 464.2208; $^1$H NMR (300 MHz, DMSO-$d_6$) δ ppm 1.03, 1.04 (2×s, 6 H, 2×$CH_3$), 1.07-1.43 (m, 3H, 3×CH of 2×$CH_2$), 1.49-1.70 (m, 3H, 3×CH of 2×$CH_2$), 1.98-2.12 (m, 1H, CH), 2.62 (s, 3H, Ar$CH_3$), 3.14-3.25 (m, 2H, O$CH_2$), 3.17 (s, 3H, $SO_2CH_3$), 3.73-3.83 (m, 2H, O$CH_2$), 3.84 (s, 2H, N$CH_2$), 3.90-3.99 (m, 1H, ArCH), 4.64 (s, 1H, OH), 6.43 (d, J=2.3 Hz, 1H, Ar), 7.41-7.46 (m, 2H, Ar), 7.48 (d, J=2.3 Hz, 1H, Ar),), 7.83 (d, J=8.5 Hz, 1H, Ar), 10.72 (s, 1H, NH)

Example 90

2(R)-(3-Chloro-4-methanesulfonyl-phenyl)-N-[1-(2-hydroxy-2-methyl-propyl)-1H-pyrazol-3-yl]-3-(tetrahydro-pyran-4-yl)-propionamide

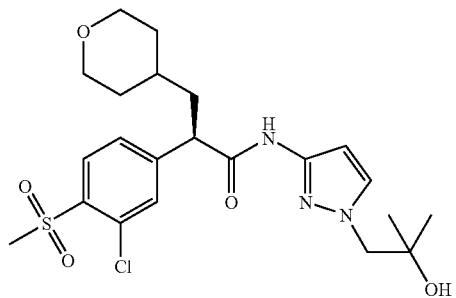

A solution of 2-(3-chloro-4-methanesulfonyl-phenyl)-3-(tetrahydro-pyran-4-yl)-propionic acid (prepared as in PCT WO 2003/095438 A1, Example 20, 86 mg, 0.25 mmol) was dissolved in methylene chloride (3 mL) and N,N-dimethylfomamide (three drops) at 25° C. To this solution was added dropwise a solution of oxalyl chloride in methylene chloride (2 M solution, 0.14 mL, 0.26 mmol) which produced gas evolution and it was then stirred at 25° C. for 30 minutes. After this time, the reaction was concentrated in vacuo and the residue was then taken up in methylene chloride (3 mL). This solution was then added dropwise to a flask containing a solution of 1-(3-amino-pyrazol-1-yl)-2-methyl-propan-2-ol (prepared in Example 80, 39 mg, 0.25 mmol), 2,6-lutidine (58 μL, 0.49 mmol), and methylene chloride (2 mL) which was cooled to 0° C. The reaction was allowed to warm to 25° C. and stirred for a period of 2 h. After this time, the reaction quenched with a small amount of methanol and then concentrated with silica gel (2 g) in vacuo and purified on Biotage Flash chromatography system (40S column, silica gel, 50% ethyl acetate/hexanes) to afford 2-(3-chloro-4-methanesulfonyl-phenyl)-N-[1-(2-hydroxy-2-methyl-propyl)-1H-pyrazol-3-yl]-3-(tetrahydro-pyran-4-yl)-propionamide (69 mg, 57%) as a white foam.

The racemic material 2-(3-chloro-4-methanesulfonyl-phenyl)-N-[1-(2-hydroxy-2-methyl-propyl)-1H-pyrazol-3-yl]-3-(tetrahydro-pyran-4-yl)-propionamide was then separated using supercritical fluid chromatography (SFC) on a Berger MultiGramII Supercritical Fluid Chromatography (SFC) system (Mettler-Toledo AutoChem Berger Instruments, Newark, Del.) (Chiral column: Chiralcel AD-H, 250 mm×30.0 mm i.d., 5 μm-particle size, temperature: 35° C., flow rate of 70 mL/min, and 100 bar back pressure, 30% methanol as mobile phase modifier (e.g. 70% $CO_2$/30% MeOH). UV Detection: 220 nm) to afford the two pure enantiomers; the active enantiomer 2(R)-(3-chloro-4-methanesulfonyl-phenyl)-N-[1-(2-hydroxy-2-methyl-propyl)-1H-pyrazol-3-yl]-3-(tetrahydro-pyran-4-yl)-propionamide (26 mg) isolated as colorless gum: ES-HRMS m/e calcd for $C_{22}H_{30}N_3O_5SCl$ (M+H)$^+$ 484.1668, observed 484.1665.

Example 91

2-(3-Chloro-4-methanesulfonyl-phenyl)-N-[1-(2-hydroxy-ethyl)-1H-pyrazol-3-yl]-3-(tetrahydro-furan-3-yl)-propionamide

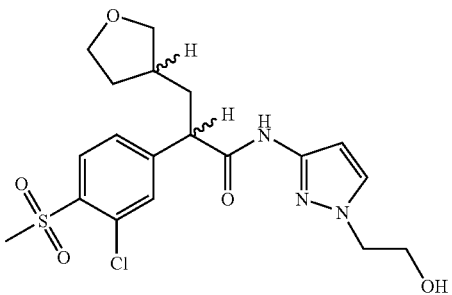

In a round bottom flask was placed triphenylphosphine (3.3 g, 12.73 mmol), imidazole (1.73 g, 25.48 mmol) and methylene chloride (20 ml) and it was cooled to 0° C. in an ice bath. To this cooled solution was added iodine (3.2 g, 12.73 mmol). Once the iodine was dissolved (30 min) a solution of tetrahydro-3-furan methanol (1.0 g, 9.79 mmol) in methylene chloride (10 ml) was added dropwise. The reaction was stirred at 0° C. for 2 h and then at 25° C. for 1 h. After this time the reaction was poured into ice cold water and extracted with methylene chloride (2×50 ml). The combined organic layers were dried over sodium sulfate, filtered and concentrated in vacuo. Purification on an AnaLogix Intelliflash system (80 g column, 30% ethyl acetate/hexanes) afforded 3-iodomethyl-tetrahydro-furan (1.35 g, 67%) as a clear oil: $^1$H NMR (300 MHz, $CDCl_3$) δ ppm 1.56-1.71 (m, 1H, CH of $CH_2$), 2.06-2.23 (m, 1H, CH of $CH_2$), 2.56-2.74 (m, 1 H, CH), 3.20 (d, J=7.3 Hz, 2H, I$CH_2$), 3.50 (dd, J=8.9, 6.1 Hz, 1H, OCH of O$CH_2$), 3.74-3.85 (m, 1H, OCH of O$CH_2$), 3.85-4.00 (m, 2H, 2×OCH of O$CH_2$).

In a round bottom flask was placed tetrahydrofuran (20 mL) and 1,1,1,3,3,3-hexamethyldisilazane (0.97 mL, 4.66 mmol) and it was cooled to −78° C. in a dry ice/acetone bath. To this cooled solution was then added n-butyl lithium (2.5 M solution in hexanes, 1.75 mL, 4.37 mmol) and it was stirred for 15 min at −78° C. To this was then added a solution of (3-chloro-4-methylsulfanyl-phenyl)-acetic acid methyl ester (prepared as in PCT WO 2003/095438 A1, Example 4, 0.96 g, 4.16 mmol) in tetrahydrofuran (6 mL) dropwise. The reaction was then stirred for 15 min at −78° C. then at 0° C. for 1 h which resulted in a yellow solution. After such time, the reaction was cooled back to −78° C. and a solution of 3-iodomethyl-tetrahydro-furan (1.32 g, 6.23 mmol) in tetrahydrofuran (6 ml) and 1,3-dimethyl-3,4,5,6-tetrahydro-2(1H)-pyrimidinone (0.75 mL, 6.24 mmol) was added dropwise at −78° C. The reaction was stirred at −78° C. for 15 min, at 0° C. for 2.5 h and then was stored in a freezer overnight. After such time, the reaction was diluted with ethyl acetate and washed with a saturated aqueous ammonium chloride solution followed by a saturated sodium chloride solution wash. The organics were dried over sodium sulfate, filtered and then concentrated in vacuo. Purification on an AnaLogix Intelliflash system (120 g column, 20% ethyl acetate/hexanes to 30% ethyl acetate/hexanes) afforded 2-(3-chloro-4-methylsulfanyl-phenyl)-3-(tetrahydro-furan-3-yl)-propionic acid methyl ester (1.0 g, 77%) as a yellow oil: $^1$H NMR (300 MHz, CDCl$_3$) δ ppm 1.42-1.62 (m, 1H, CH of CH$_2$), 1.79-1.94 (m, 1H, CH of CH$_2$), 1.94-2.21 (m, 3H, CH and CH$_2$), 2.47 (s, 3H, SCH$_3$), 3.26-3.38 (m, 1H, OCH of OCH$_2$), 3.45-3.52 (m, 1H, ArCH), 3.65-3.75 (m, 1H, OCH of OCH$_2$), 3.67 (s, 3H, OCH$_3$), 3.76-3.94 (m, 2H, 2×OCH of OCH$_2$), 7.11 (d, J$_o$=8.2 Hz, 1H, Ar), 7.19 (dd, J$_o$=8.2 Hz, J$_m$=1.7 Hz, 1H, Ar), 7.30 (d, J$_m$=1.7 Hz, 1H, Ar).

To the 2-(3-chloro-4-methylsulfanyl-phenyl)-3-(tetrahydro-furan-3-yl)-propionic acid methyl ester (0.96 g, 3.06 mmol) dissolved in methanol (10 ml) and then sodium tungstate dihydrate (50 mg, 0.15 mmol) was added and the solution cooled to 0° C. To this cooled solution a 30% aqueous solution of hydrogen peroxide (5 mL) was added and the ice bath was removed. The reaction was allowed to warm to 25° C. and stirred for 18 h. After this time, the reaction was cooled to 0° C. in an ice bath and it was treated very slowly with a saturated aqueous solution of sodium nitrite (10 mL). The reaction was then transferred to a separatory funnel and extracted with a solution of chloroform/methanol (3/2) (2×20 mL). The extracts were than concentrated in vacuo and then dissolved in methylene chloride and dried over magnesium sulfate, filtered and concentrated in vacuo to afford 2-(3-chloro-4-methanesulfonyl-phenyl)-3-(tetrahydro-furan-3-yl)-propionic acid methyl ester (0.85 g, 80%) as a clear colorless oil: $^1$H NMR (300 MHz, DMSO-d6) δ ppm 1.40-1.54 (m, 1H, CH of CH$_2$), 1.78-1.99 (m, 3H, 3×CH of 2×CH$_2$), 2.01-2.14 (m, 1H, CH), 3.17-3.29 (m, 1H, OCH of OCH$_2$), 3.37 (s, 3H, SO$_2$CH$_3$), 3.51-3.78 (m, 3H, ArCH and 2×OCH of 2×OCH$_2$), 3.61 (s, 3H, OCH$_3$), 3.84-3.94 (m, 1H, OCH of OCH$_2$), 7.59 (brd, J$_o$=8.2 Hz, 1H, Ar), 7.74 (brs, 1H, Ar), 8.02 (d, J$_o$=8.2 Hz, 1H, Ar).

2-(3-Chloro-4-methanesulfonyl-phenyl)-3-(tetrahydro-furan-3-yl)-propionic acid methyl ester (0.85 g, 2.45 mmol) was dissolved in methanol (10 ml) and treated with a solution of lithium hydroxide monohydrate (0.51 g, 12.15 mmol) in water (1 ml) at 25° C. It was stirred at 25° C. for 2 h or until the starting material was all consumed by TLC. The reaction was then concentrated in vacuo to remove the methanol. The remaining aqueous layer was then diluted with water and acidified to pH=2 with an aqueous 1N hydrochloric acid solution. This was then extracted with methylene chloride (2×50 mL). The organic layers were combined and dried over magnesium sulfate, filtered and concentrated in vacuo to afford 2-(3-chloro-4-methanesulfonyl-phenyl)-3-(tetrahydro-furan-3-yl)-propionic acid (0.68 g, 84%) as a white solid: $^1$H NMR (300 MHz, DMSO-d6) δ ppm 1.41-1.56 (m, 1H, CH of CH$_2$), 1.74-2.12 (m, 4H, CH and 3×CH of 2×CH$_2$), 3.16-3.30 (m, 1H, OCH of OCH$_2$), 3.37 (s, 3H, SO$_2$CH$_3$), 3.51-3.79 (m, 4H, ArCH and 3×OCH of 2×OCH$_2$), 7.57 (2×dd, J$_o$=8.3 Hz, J$_m$=1.7 Hz, 1H, Ar), 7.71 (2×d, J$_m$=1.7 Hz, 1H, Ar), 8.00 (2×d, J$_o$=8.3 Hz, 1H, Ar), 12.76 (brs, 1H, CO$_2$H).

A solution of 2-(3-chloro-4-methanesulfonyl-phenyl)-3-(tetrahydro-furan-3-yl)-propionic acid (100 mg, 0.30 mmol) in methylene chloride (8 mL) was cooled to 0° C. To this solution was then added dropwise a solution of oxalyl chloride in methylene chloride (2 M solution, 180 μL, 0.36 mmol) and N,N-dimethylfomamide (two drops) which produced gas evolution and it was then stirred at 0° C. for 20 minutes and 40 min at 25° C. After this time, the reaction was concentrated in vacuo and azeotroped with methylene chloride (10 ml). In a separate flask a solution of 1-[2-(tert-butyl-dimethyl-silanyloxy)-ethyl]-1H-pyrazol-3-ylamine (prepared in Example 67, 80 mg, 0.33 mmol), 2,6-lutidine (52 μL, 0.45 mmol) in methylene chloride (6 mL) was cooled to 0° C. in an ice bath. To this solution was then dropwise the solution of the prepared acid chloride diluted with another portion of methylene chloride (6 mL). After addition was complete, the reaction was stirred at 0° C. for 15 min and at 25° C. for 3 hours. After this time it was concentrated in vacuo and purified on an AnaLogix Intelliflash system (40 g column, 30% ethyl acetate/hexanes to 60% ethyl acetate/hexanes) to afford N-{1-[2-(tert-butyl-dimethyl-silanyloxy)-ethyl]-1H-pyrazol-3-yl}-2-(3-chloro-4-methanesulfonyl-phenyl)-3-(tetrahydro-furan-3-yl)-propionamide (138 mg, 86%) as a clear colorless oil: $^1$H NMR (300 MHz, DMSO-d6) δ ppm −0.09-0.06 (2×s, 6H, 2×SiCH$_3$), 0.77, 0.82 (2×s, 9H, 3×CH$_3$), 1.44-1.57 (m, 1H, CH of CH$_2$), 1.70-2.22 (m, 4H, CH and 3×CH of 2×CH$_2$), 3.22-3.29 (m, 1H, OCH of OCH$_2$), 3.33, 3.34 (2×s, 3H, SO$_2$CH$_3$), 3.51-3.63 (m, 1H, OCH of OCH$_2$), 3.66-3.94 (m, 5H, ArCH, SiOCH$_2$, and 2×OCH of 2×OCH$_2$), 4.01-4.08 (m, 2H, NCH$_2$), 6.41 (d, J=2.2 Hz, 1H, Ar), 7.53 (d, J=2.2 Hz, 1H, Ar), 7.60 (2×dd, J$_o$=8.2 Hz, J$_m$=1.6 Hz, 1H, Ar), 7.71 (2×d, J$_m$=1.6 Hz, 1H, Ar), 8.01 (d, J$_o$=8.2 Hz, 1H, Ar), 10.82, 10.83 (2×s, 1H, NH).

In a flask containing N-{1-[2-(tert-butyl-dimethyl-silanyloxy)-ethyl]-1H-pyrazol-3-yl}-2-(3-chloro-4-methanesulfonyl-phenyl)-3-(tetrahydro-furan-3-yl)-propionamide (138 mg, 0.25 mmol) was added ethanol (6 ml) and concentrated hydrochloric acid (5 drops) and was stirred at 25° C. for 2 h. The reaction was then concentrated in vacuo to remove the ethanol, diluted with ethyl acetate (50 ml) and washed with a saturated aqueous sodium bicarbonate solution. The organic layer was then dried over magnesium sulfate, filtered and concentrated in vacuo. Purification on an AnaLogix Intelliflash system (12 g column, 5% methanol/ethyl acetate) afforded 2-(3-chloro-4-methanesulfonyl-phenyl)-N-[1-(2-hydroxy-ethyl)-1H-pyrazol-3-yl]-3-(tetrahydro-furan-3-yl)-propionamide (76 mg, 69%) as an off-white solid: $^1$H NMR (300 MHz, DMSO-d6) δ ppm 1.45-1.57 (m, 1H, CH of CH$_2$), 1.68-1.84 (m, 1H, CH of CH$_2$), 1.88-2.02 (m, 2 H, 2×CH of 2×CH$_2$), 2.06-2.22 (m, 1H, CH), 3.22-3.30 (m, 1H, OCH of OCH$_2$), 3.31 (s, 3H, SO$_2$CH$_3$), 3.53-3.77 (m, 5H, ArCH, SiOCH$_2$, and 2×OCH of 2×OCH$_2$), 3.83-3.93 (m, 1H, OCH of OCH$_2$), 3.97-4.02 (m, 2H, NCH$_2$), 4.82 (t, J=5.4 Hz, 1H, OH), 6.42 (d, J=2.2 Hz, 1H, Ar), 7.54 (d, J=2.2 Hz, 1H, Ar), 7.60 (2×dd, J$_o$=8.3 Hz, J$_m$=1.7 Hz, 1H, Ar), 7.71, 7.72 (2×d, J$_m$=1.7 Hz, 1H, Ar), 8.01 (d, J$_o$=8.3 Hz, 1H, Ar), 10.81, 10.82 (2×s, 1H, NH).

Example 92

2(R)-(3-Chloro-4-methanesulfonyl-phenyl)-N-[1-(2-hydroxy-2-methyl-propyl)-1H-pyrazol-3-yl]-3-oxetan-3-yl-propionamide

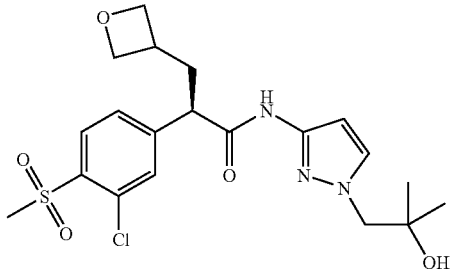

Diethyl 2,2-bis(hydroxymethyl)malonate (20 g, 90.82 mmol), acetone (20 ml), 2,2-dimethoxypropane (20 ml), and concentrated sulfuric acid (0.2 ml) were stirred at 25° C. for 2 days. The reaction was slowly poured into saturated aqueous sodium carbonate. The organic supernatant was separated and concentrated in vacuo. The residue was then dissolved in ether, rinsed with saturated aqueous sodium carbonate and brine, and then dried over magnesium sulfate, filtered and concentrated in vacuo to afford crude 2,2-dimethyl-[1,3]dioxane-5,5-dicarboxylic acid diethyl ester (21.4 g, 91%) as a light yellow oil: $^1$H NMR (300 MHz, CDCl$_3$) δ ppm 1.27 (t, J=7.1 Hz, 6H, 2×CH$_3$), 1.42 (s, 6H, 2×CH$_3$), 4.24 (q, J=7.1 Hz, 4H, 2×OCH$_2$), 4.29 (s, 4H, 2×OCH$_2$).

To the solution of 2,2-dimethyl-[1,3]dioxane-5,5-dicarboxylic acid diethyl ester (19.75 g, 75.96 mmol) in dimethyl sulfoxide (80 ml) was added sodium chloride (4.4 g, 75.76 mmol) and water (2 ml). The reaction was refluxed for 7 h. After such time, it was poured into saturated sodium chloride solution (500 ml) and extracted with ether (4×200 ml). The combined organics were washed with water, dried over sodium sulfate, filtered and concentrated in vacuo. The residual oil was distilled under reduced pressure. Three fractions collected between 100° C. and 120° C. were combined to afford 2,2-dimethyl-[1,3]dioxane-5-carboxylic acid ethyl ester (7.58 g, 53%) as a clear oil (*J. Org. Chem.* 1986, 51, 2637) $^1$H NMR (300 MHz, CDCl$_3$) δ ppm 1.26 (t, J=7.1 Hz, 3H, CH$_3$), 1.41 (s, 3H, CH$_3$), 1.44 (s, 3H, CH$_3$), 2.74-2.85 (m, 1H, CH), 3.96-4.30 (m, 6H, 3×OCH$_2$).

A solution of 2,2-dimethyl-[1,3]dioxane-5-carboxylic acid ethyl ester (7.03 g, 37.35 mmol) in tetrahydrofuran (20 ml) was added dropwise to a cooled to 0° C. suspension of lithium aluminum hydride (1.8 g, 48.55 mmol) in tetrahydrofuran (20 ml). The reaction was stirred at 0° C. for 20 min and at 25° C. for 2 h. After such time, ethyl acetate (1 ml) and a few crystals of sodium sulphate decahydrate were added with caution. After stirring at 25° C. for 1 h saturated sodium chloride solution was added and the product extracted with ethyl acetate (3×100 ml). The organics were washed with water, dried over magnesium sulfate, filtered and concentrated in vacuo to afford (2,2-dimethyl-[1,3]dioxan-5-yl)-methanol (4.09 g, 76%) as a clear oil: $^1$H NMR (300 MHz, CDCl$_3$) δ ppm 1.39 (s, 3H, CH$_3$), 1.44 (s, 3H, CH$_3$), 1.79-1.90 (m, 1H, CH), 2.15-2.26 (brs, 1H, OH), 3.69-3.81 (m, 2H, 2×OCH of 2×OCH$_2$), 3.74 (d, J=6.8 Hz, 2H, OCH$_2$), 3.96-4.05 (m, 2H, 2×OCH of 2×OCH$_2$).

To a stirred suspension of sodium hydride (2.0 g, 42.02 mmol, 50% dispersion in oil) in tetrahydrofuran (20.0 ml) was added dropwise a solution of (2,2-dimethyl-[1,3]dioxan-5-yl)-methanol (4.09 g, 28.01 mmol) in tetrahydrofuran (10 ml) at 0° C. it was then stirred at 0° C. for 10 min and at 25° C. for 20 min. After that time, the reaction was cooled back to 0° C. and benzyl bromide (4.7 ml, 39.22 mmol) and tetrabutylammonium iodide (0.1 g, 0.27 mmol) were added. The reaction was stirred overnight at 25° C. After such time, the reaction was diluted with ethyl acetate and washed with water. The organic layer was dried over magnesium sulfate, filtered and then concentrated in vacuo. Purification on an AnaLogix Intelliflash system (120 g column, 15% ethyl acetate/hexanes to 25% ethyl acetate/hexanes) afforded 5-benzyloxymethyl-2,2-dimethyl-[1,3]dioxane (5.28 g, 80%) as a clear oil: $^1$H NMR (300 MHz, CDCl$_3$) δ ppm 1.40 (s, 3H, CH$_3$), 1.43 (s, 3H, CH$_3$), 1.97-2.09 (m, 1H, CH), 3.53 (d, J=6.8 Hz, 2H, OCH$_2$), 3.79 (dd, J$_{gem}$=11.9 Hz, J=6.4 Hz, 2H, 2×OCH of 2×OCH$_2$), 3.98 (dd, J$_{gem}$=11.9 Hz, J=4.3 Hz, 2H, 2×OCH of 2×OCH$_2$), 4.52 (s, 2H, OCH$_2$Ar), 7.27-7.39 (m, 5H, Ar).

Benzyloxymethyl-2,2-dimethyl-[1,3]dioxane (5.54 g, 23.44 mmol) was dissolved in methanol (20 ml) and then 3N hydrochloric acid (3 ml) was added. The reaction was stirred at 25° C. for 30 min. After this point the pH was adjusted to 8 with solid sodium bicarbonate and evaporated. The residue was dissolved in ethyl acetate, filtered through a short silica gel pad, washed with ethyl acetate and concentrated in vacuo to afford 2-benzyloxymethyl-propane-1,3-diol (4.39 g, 95%) as an off-white solid: $^1$H NMR (300 MHz, CDCl$_3$) δ ppm 1.99-2.07 (m, 1H, CH), 2.74 (s, 2H, 2×OH), 3.60 (d, J=5.7 Hz, 2 H, OCH$_2$), 3.78 (d, J=5.4 Hz, 4H, 2×OCH$_2$), 4.50 (s, 2H, OCH$_2$Ar), 7.25-7.38 (m, 5H, Ar).

To a solution of 2-benzyloxymethyl-propane-1,3-diol (4.39 g, 22.36 mmol) in tetrahydrofuran (60 ml) stirred at −5° C., was added n-butyllithium in hexane (2.5 M, 11.18 ml, 27.96 mmol) and after 20 min, a solution of p-toluenesulfonyl chloride (5.12 g, 26.85 mmol) in tetrahydrofuran (20 ml) was added. The reaction was allowed to warm to 25° C. and then stirred for 2 h. To this solution was added water slowly and then extracted with ethyl acetate. The organics were dried over magnesium sulfate, filtered and concentrated in vacuo. The residue was then dissolved in tert-butyl alcohol (90 ml) and potassium tert-butoxide (7.5 g, 66.83 mmol) was added, and the reaction was refluxed for 30 min and then stirred at 25° C. for 30 min. After such a time it was diluted with water (500 ml) and extracted with ether (2×250 ml). The extracts were combined and dried over magnesium sulfate, filtered and concentrated in vacuo. Purification on an AnaLogix Intelliflash system (120 g column, 20% ethyl acetate/hexanes to 30% ethyl acetate/hexanes) afforded 3-benzyloxymethyl-oxetane (2.02 g, 51%) as a light yellow oil: $^1$H NMR (300 MHz, CDCl$_3$) δ ppm 3.19-3.32 (m, 1H, CH), 3.71 (d, J=6.9 Hz, 2H, OCH$_2$), 4.42-4.48 (m, 2 H, 2×OCH of 2×OCH$_2$), 4.55 (s, 2H, OCH$_2$Ar), 4.77-4.83 (m, 2H, 2×OCH of 2×OCH$_2$), 7.27-7.40 (m 5H, Ar).

In a Parr shaker bottle was placed 3-benzyloxymethyl-oxetane (2.7 g, 15.17 mmol), 10% palladium on activated carbon (0.8 g) and methanol (50 ml). The bottle was then placed on the Parr shaker at 45 psi of hydrogen pressure for total of 3 days. The reaction was then filtered through a pad of celite and washed with a solution of methanol/methylene chloride (⅓) and concentration in vacuo afforded oxetan-3-yl-methanol (1.27 g, 95%) as a light yellow oil: $^1$H NMR (300

MHz, CDCl$_3$) δ ppm 1.55 (brs, 1H, OH), 3.09-3.23 (m, 1H, CH), 3.90 (d, J=6.7 Hz, 2H, OCH$_2$), 4.44-4.50 (m, 2 H, 2×OCH of 2×OCH$_2$), 4.78-4.84 (m, 2H, 2×OCH of 2×OCH$_2$).

In a round bottom flask was placed triphenylphosphine (4.3 g, 16.41 mmol) and imidazole (2.2 g, 32.31 mmol) in methylene chloride (30 ml) and it was cooled to 0° C. in an ice bath. To this cooled solution was added iodine (4.1 g, 16.15 mmol). Once the iodine was dissolved (30 min) a solution of oxetan-3-yl-methanol (1.1 g, 12.50 mmol) in methylene chloride (10 ml) was added dropwise. The reaction was stirred at 0° C. for 30 min and then at 25° C. for 1 h. After this time, the reaction was poured into ice cold water and extracted with methylene chloride (2×50 ml). The combined organic layers were dried over sodium sulfate, filtered and concentrated in vacuo. Purification on an AnaLogix Intelliflash system (80 g column, 30% ethyl acetate/hexanes) afforded 3-iodomethyl-oxetane (0.88 g, 37%) as a clear oil: $^1$H NMR (300 MHz, CDCl$_3$) δ ppm 3.32-3.45 (m, 3H, CH and I CH$_2$), 4.26-4.33 (m, 2H, 2×OCH of 2×OCH$_2$), 4.67-4.74 (m, 2H, 2×OCH of 2×OCH$_2$).

In a round bottom flask under argon was placed tetrahydrofuran (15 mL) and 1,1,1,3,3,3-hexamethyldisilazane (0.57 mL, 2.72 mmol) and it was cooled to −78° C. in a dry ice/acetone bath. To this cooled solution was then added n-butyl lithium (2.5 M solution in hexanes, 1.0 mL, 2.55 mmol) and it was stirred for 15 min at −78° C. To this was then dropwise added a solution of (3-chloro-4-methylsulfanyl-phenyl)-acetic acid methyl ester (prepared as in PCT WO 2003/095438 A1, Example 4, 0.56 g, 2.44 mmol) in tetrahydrofuran (5 mL). The reaction was then stirred for 15 min at −78° C. then at 0° C. for 1 h. After such time, it was cooled back to −78° C. and a solution of 3-iodomethyl-oxetane (0.58 g, 2.93 mmol) in tetrahydrofuran (5 ml) and 1,3-dimethyl-3,4,5,6-tetrahydro-2(1H)-pyrimidinone (0.44 mL, 3.64 mmol) was added dropwise at −78° C. The reaction was stirred at 0° C. for 3 h and then it was diluted with ethyl acetate and washed with a saturated aqueous ammonium chloride solution followed by a saturated aqueous sodium chloride solution. The organics were dried over sodium sulfate, filtered and then concentrated in vacuo. Purification on an AnaLogix Intelliflash system (40 g column, 30% ethyl acetate/hexanes to 40% ethyl acetate/hexanes) afforded 2-(3-chloro-4-methylsulfanyl-phenyl)-3-oxetan-3-yl-propionic acid methyl ester (0.51 g, 70%) as a clear oil: $^1$H NMR (300 MHz, DMSO-d$_6$) δ ppm 1.97-2.13 (m, 1H, CH of CH$_2$), 2.22-2.34 (m, 1H, CH of CH$_2$), 2.46 (s, 3H, SCH$_3$), 2.71-2.87 (m, 1H, CH), 3.54-3.66 (m, 1H, ArCHCO), 3.57 (s, 3H, OCH$_3$), 4.09 (t, J=6.2 Hz, 1H, OCH of OCH$_2$), 4.23 (t, J=6.2 Hz, 1H, OCH of OCH$_2$), 4.40 (dd, J=7.8, 5.9 Hz, 1H, OCH of OCH$_2$), 4.53 (dd, J=7.8, 5.9 Hz, 1H, OCH of OCH$_2$), 7.23-7.26 (m, 2H, Ar), 7.36 (brs, 1H, Ar).

2-(3-Chloro-4-methylsulfanyl-phenyl)-3-oxetan-3-yl-propionic acid methyl ester (1.28, 4.27 mmol) was dissolved in methanol (10 ml) and then sodium tungstate dihydrate (70 mg, 0.21 mmol) was added and the solution cooled to 0° C. To this cooled solution was then added a 30% aqueous solution of hydrogen peroxide (5 mL) and the ice bath was removed and the reaction allowed to warm to 25° C. and stirred for 24 h. After this time, there was still starting material present by TLC so another portion of sodium tungstate dihydrate (70 mg, 0.21 mmol) was added and the reaction stirred for additional 24 h. The reaction was diluted with water and extracted with methylene chloride (3×50 ml). The combined organic extracts were then dried over sodium sulfate, filtered and concentrated in vacuo. Purification on an AnaLogix Intelliflash system (80 g column, 50% ethyl acetate/hexanes to 100% ethyl acetate) afforded 2-(3-chloro-4-methanesulfonyl-phenyl)-3-oxetan-3-yl-propionic acid methyl ester (1.0 g, 71%) as a clear oil: $^1$H NMR (300 MHz, DMSO-d$_6$) δ ppm 2.04-2.19 (m, 1H, CH of CH$_2$), 2.30-2.45 (m, 1H, CH of CH$_2$), 2.73-2.87 (m, 1H, CH), 3.36 (s, 3H, SO$_2$CH$_3$), 3.60 (s, 3H, OCH$_3$), 3.82 (t, J=7.8 Hz, 1H, ArCHCO), 4.12 (t, J=6.0 Hz, 1H, OCH of OCH$_2$), 4.25 (t, J=6.0 Hz, 1H, OCH of OCH$_2$), 4.43 (dd, J=7.8, 5.9 Hz, 1H, OCH of OCH$_2$), 4.55 (dd, J=7.8, 5.9 Hz, 1H, OCH of OCH$_2$), 7.54 (dd, J$_o$=8.6 Hz, J$_m$=1.6 Hz, 1H, Ar), 7.70 (d, J$_m$=1.6 Hz, 1H, Ar), 8.00 (d, J$_o$=8.6 Hz, 1H, Ar).

2-(3-Chloro-4-methanesulfonyl-phenyl)-3-oxetan-3-yl-propionic acid methyl ester (1.0 g, 3.00 mmol) was dissolved in methanol (50 ml) and treated with a solution of lithium hydroxide monohydrate (0.50 g, 11.92 mmol) in water (1 ml) at 25° C. It was stirred at 25° C. for 1.5 h. The reaction was then concentrated in vacuo to remove the methanol. The remaining aqueous layer was then diluted with water and acidified to pH=3 with an aqueous 1N hydrochloric acid solution. This was then extracted with methylene chloride (3×50 mL), the organic layers combined and dried over magnesium sulfate, filtered and concentrated in vacuo to afford 2-(3-chloro-4-methanesulfonyl-phenyl)-3-oxetan-3-yl-propionic acid (0.87 g, 91%) as a white solid: $^1$H NMR (300 MHz, DMSO-d$_6$) δ ppm 2.01-2.14 (m, 1H, CH of CH$_2$), 2.25-2.41 (m, 1H, CH of CH$_2$), 2.75-2.89 (m, 1H, CH), 3.36 (s, 3H, SO$_2$CH$_3$), 3.68 (t, J=7.8 Hz, 1H, ArCHCO), 4.13 (t, J=6.3 Hz, 1H, OCH of OCH$_2$), 4.27 (t, J=6.3 Hz, 1H, OCH of OCH$_2$), 4.44 (dd, J=7.9, 5.9 Hz, 1H, OCH of OCH$_2$), 4.57 (dd, J=7.9, 5.9 Hz, 1H, OCH of OCH$_2$), 7.54 (dd, J$_o$=8.1 Hz, J$_m$=1.7 Hz, 1H, Ar), 7.68 (d, J$_m$=1.7 Hz, 1H, Ar), 8.00 (d, J$_o$=8.1 Hz, 1H, Ar), 12.77 (brs, 1H, CO$_2$H).

A reaction of 2-(3-chloro-4-methanesulfonyl-phenyl)-3-oxetan-3-yl-propionic acid (0.18 g, 0.56 mmol), 1-(3-amino-pyrazol-1-yl)-2-methyl-propan-2-ol (prepared in Example 80, 0.1 g, 0.64 mmol), and triethyl amine (0.17 ml, 1.24 mmol) in methylene chloride (15 mL) was cooled to 0° C. To this solution was added benzotriazol-1-yloxytris(dimethylamino)phosphonium hexafluorophosphate (0.25 g, 0.56 mmol). The reaction was allowed to warm to 25° C. and stirred for 24 h. After this time, the reaction was concentrated in vacuo. Purification on an AnaLogix Intelliflash system (40 g column, 3% methanol/methylene chloride to 5% methanol/methylene chloride) afforded 2-(3-chloro-4-methanesulfonyl-phenyl)-N-[1-(2-hydroxy-2-methyl-propyl)-1H-pyrazol-3-yl]-3-oxetan-3-yl-propionamide (0.1 g, 40%) as a 1:1 enantiomeric reaction as a white gummy solid: $^1$H NMR (300 MHz, DMSO-d$_6$) δ ppm 1.02 (s, 3H, CH$_3$), 1.04 (s, 3H, CH$_3$), 2.01-2.15 (m, 1H, CH of CH$_2$), 2.32-2.47 (m, 1H, CH of CH$_2$), 2.75-2.91 (m, 1H, CH), 3.31 (s, 3H, SO$_2$CH$_3$), 3.69-3.79 (m, 1H, ArCHCO), 3.85 (s, 2H, NCH$_2$), 4.16-4.30 (m, 2H, 2×OCH of 2×OCH$_2$), 4.47-4.57 (m, 2H, 2×OCH of 2×OCH$_2$), 4.65 (s, 1H, OH), 6.44 (d, J=2.4 Hz, 1H, Ar), 7.52 (d, J=2.4 Hz, 1H, Ar), 7.57 (dd, J$_o$=8.3 Hz, J$_m$=1.4 Hz, 1H, Ar), 7.70 (d, J$_m$=1.4 Hz, 1H, Ar), 8.00 (d, J$_o$=8.3 Hz, 1H, Ar), 10.77 (s, 1H, NH).

The 1:1 reaction of enantiomers of 2-(3-chloro-4-methanesulfonyl-phenyl)-N-[1-(2-hydroxy-2-methyl-propyl)-1H-pyrazol-3-yl]-3-oxetan-3-yl-propionamide was separated into the single compounds by supercritical fluid chromatography (SFC) on a Berger MultiGram II Supercritical Fluid Chromatography (SFC) system (Mettler-Toledo AutoChem Berger Instruments, Newark, Del.) (Chiral column: Daicel AD-H, 250 mm×30 mm i.d., 5 μm-particle size, temperature: 35° C., flow rate of 70 mL/min, and 100 bar back pressure, methanol as mobile phase modifier and UV Detection: 220 nm) to afford the two pure enantiomers. The first peak to elute was the active 2(R)-(3-chloro-4-methanesulfonyl-phenyl)-N-[1-(2-hydroxy-2-methyl-propyl)-1H-pyrazol-3-yl]-3-oxetan-3-yl-propionamide enantiomer which was isolated as an off-white solid (29 mg) [α]$^{30}_{589}$=+4.70° (c=0.47, chloroform); $^1$H NMR (300 MHz, DMSO-d$_6$) δ ppm 1.02 (s, 3H, CH$_3$), 1.04 (s, 3H, CH$_3$), 2.01-2.15 (m, 1H, CH of CH$_2$), 2.32-2.47 (m, 1H, CH of CH$_2$), 2.75-2.91 (m, 1H, CH), 3.33 (s, 3H, SO$_2$CH$_3$), 3.69-3.79 (m, 1H, ArCHCO), 3.85 (s, 2H, NCH$_2$), 4.16-4.30 (m, 2H, 2×OCH of 2×OCH$_2$), 4.47-4.57 (m, 2H, 2×OCH of 2×OCH$_2$), 4.65 (s, 1H, OH), 6.44 (d, J=2.4 Hz, 1H, Ar), 7.52 (d, J=2.4 Hz, 1 H, Ar), 7.57 (dd, J$_o$=8.4 Hz, J$_m$=1.6 Hz, 1H, Ar), 7.70 (d, J$_m$=1.6 Hz, 1H, Ar), 8.00 (d, J$_o$=8.4 Hz, 1H, Ar), 10.77 (s, 1H, NH).

Example 93

2(R)-(3-Chloro-4-methanesulfonyl-phenyl)-N-[1-(2-hydroxy-2-methyl-propyl)-1H-pyrazol-3-yl]-3-(3-oxo-cyclobutyl)-propionamide

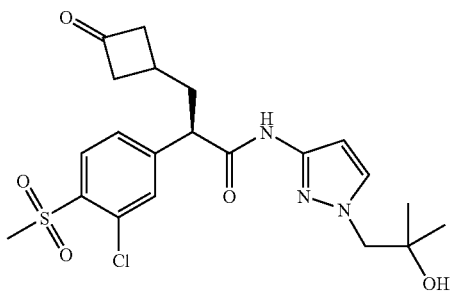

To a solution of acetone (12.6 ml) in methanol (150 ml), bromine (20 ml) was added dropwise over the time of 1 h. Initially the reaction was slightly exothermic so an ice bath was applied. Upon completion of addition, the ice bath was removed and the resulting deep red reaction was stirred at 25° C. for 24 h. After such time, the reaction was cooled in an ice/acetone bath and stirred for 1 h. Filtration of the precipitate and wash with cold methanol afforded 1,3-dibromo-2,2-dimethoxy-propane (14.72 g, 32%) as a white solid: $^1$H NMR (300 MHz, CDCl$_3$) δ ppm 3.30 (s, 6H, 2×OCH$_3$), 3.59 (s, 4H, 2×BrCH$_2$).

Diethyl malonate (14.3 ml, 94.20 mmol) was added to a stirred suspension of sodium hydride (4.75 g, 98.90 mmol, 50% dispersion in oil) in N,N-dimethylformamide (40 ml) at a rate such that the temperature was maintained below 40° C. On cessation of hydrogen evolution, the 1,3-dibromo-2,2-dimethoxy-propane (12.34 g, 47.09 mmol) was added in one portion and the reaction was heated at 135° C. for 48 h. To the cooled reaction was added an aqueous solution of ammonium chloride (100 g in 1.6 L) and extracted with hexane (4×50 ml). The combined extracts were then washed with water and aqueous saturated sodium bicarbonate solution, dried over magnesium sulfate and concentrated in vacuo. Unreacted 1,3-dibromo-2,2-dimethoxy-propane (6.9 g) was recovered by recrystallization from methanol. The filtrate was evaporated and more volatile fractions were removed by distillation under reduced pressure affording 3,3-dimethoxy-cyclobutane-1,1-dicarboxylic acid diethyl ester (3.05 g, 25%) as a light yellow oil: $^1$H NMR (300 MHz, CDCl$_3$) δ ppm 1.26 (t, J=6.9 Hz, 6H, 2×CH$_3$), 2.73 (s, 4H, 2×CH$_2$), 3.15 (s, 6H, 2×OCH$_3$), 4.22 (q, J=6.9 Hz, 4H, 2×OCH$_2$).

3,3-Dimethoxy-cyclobutane-1,1-dicarboxylic acid diethyl ester (4.72 g, 18.15 mmol) was stirred with 20% hydrochloric acid (50 ml) at reflux for 50 h. After cooling, the solution was continuously extracted with ether for 20 h. The ether was removed at reduced pressure and the residue was treated with hexanes and cooled. Filtration and wash with hexanes afforded 3-oxo-cyclobutanecarboxylic acid (1.4 g, 70%) as a brown solid.

To the solution of 3-oxo-cyclobutanecarboxylic acid (1.0 g, 8.77 mmol) in methanol (12 ml) was added trimethyl orthoformate (6 ml, 58.29 mmol) and a catalytic amount of p-toluenesulfonic acid monohydrate. The reaction was stirred at reflux for 2 h. After such time it was cooled and concentrated in vacuo to remove the methanol. The remaining residue was dissolved in ether and then washed with a saturated aqueous sodium bicarbonate solution, dried over sodium sulfate, filtered and concentrated in vacuo to afford 3,3-dimethoxy-cyclobutanecarboxylic acid methyl ester (1.48 g, 97%) as a yellow oil: $^1$H NMR (300 MHz, CDCl$_3$) δ ppm 2.33-2.51 (m, 4H, 2×CH$_2$), 2.82-2.97 (m, 1H, CH), 3.16 (s, 3H, OCH$_3$), 3.18 (s, 3H, OCH$_3$), 3.71 (s, 3H, CO$_2$CH$_3$).

A solution of 3,3-dimethoxy-cyclobutanecarboxylic acid methyl ester (1.48 g, 8.49 mmol) in tetrahydrofuran (5 ml) was added dropwise to a cooled 0° C. suspension of lithium aluminum hydride (0.39 g, 10.19 mmol) in tetrahydrofuran (15 ml). The reaction was allowed to warm to 25° C. and stirred for 17 h. After such time, ethyl acetate (1 ml) and a few crystals of sodium sulphate decahydrate were added with caution and stirred until gas evolution stopped. The resulting residue was filtered through a short celite pad and washed with ethyl acetate and then concentrated in vacuo to afford (3,3-dimethoxy-cyclobutyl)-methanol (1.04 g, 84%) as a light yellow oil: $^1$H NMR (300 MHz, CDCl$_3$) δ ppm 1.57 (brs, 1H, OH), 1.82-1.97 (m, 2H, CH$_2$), 2.23-2.36 (m, 3H, CH$_2$ and CH), 3.14 (s, 3H, OCH$_3$), 3.16 (s, 3H, OCH$_3$), 3.64-3.68 (m, 2H, OCH$_2$).

In a round bottom flask was placed triphenylphosphine (2.42 g, 9.25 mmol) and imidazole (1.26 g, 18.49 mmol) in methylene chloride (20 ml) and it was cooled to 0° C. in an ice bath. To this cooled solution was added iodine (2.35 g, 9.25 mmol). Once the iodine dissolved a solution of (3,3-dimethoxy-cyclobutyl)-methanol (1.04 g, 7.11 mmol) in methylene chloride (10 ml) was added. The reaction was stirred at 0° C. for 30 min and then at 25° C. for 2 h. After this time the reaction was poured into ice cold water (50 ml) and extracted with methylene chloride (2×30 ml). The combined organic layers were washed with 1.0 N sodium thiosulfate (50 ml), dried over sodium sulfate, filtered and concentrated in vacuo. Flash column chromatography (Merck Silica gel 60, 230-400 mesh, 30% ethyl acetate/hexanes to 40% ethyl acetate/hexanes) afforded 3-iodomethyl-1,1-dimethoxy-cyclobutane (1.34 g, 74%) as a light yellow oil: $^1$H NMR (300 MHz, CDCl$_3$) δ ppm 1.72-1.81 (m, 2H, CH$_2$), 2.28-2.53 (m, 3H, CH$_2$ and CH), 3.14 (s, 3H, OCH$_3$), 3.16 (s, 3H, OCH$_3$), 3.29 (d, J=7.7 Hz, 2H, ICH$_2$).

In a round bottom flask was placed tetrahydrofuran (20 mL) and 1,1,1,3,3,3-hexamethyldisilazane (1.4 mL, 6.95 mmol) and it was cooled to −78° C. in a dry ice/acetone bath. To this cooled solution was then added n-butyl lithium (2.5 M solution in hexanes, 2.7 mL, 6.65 mmol) and it was stirred for 15 min at −78° C. To this cooled solution was then added a solution of 2-(3-chloro-4-methylsulfanyl-phenyl)-N-(2(R)-hydroxy-1(R)-methyl-2(R)-phenyl-ethyl)-N-methyl-acetamide (prepared as in PCT WO 2004/052869, Example 1, 1.1 g, 3.00 mmol) in tetrahydrofuran (5 mL) dropwise. This was then stirred for 15 min at −78° C. then at 0° C. for 20 min.

After such time, the reaction was cooled back to −78° C. and a solution of 3-iodomethyl-1,1-dimethoxy-cyclobutane (1.0 g, 3.90 mmol) in tetrahydrofuran (3 ml) and 1,3-dimethyl-3,4,5,6-tetrahydro-2(1H)-pyrimidinone (0.80 mL, 6.65 mmol) was added dropwise at −78° C. at the same time. The reaction was stirred at −78° C. for 1 h, at 0° C. for 2 h and then at 25° C. for 18 h. After such time, the reaction was diluted with ethyl acetate and washed with a saturated aqueous ammonium chloride solution followed by a 10% sulfuric acid wash, water and then saturated aqueous sodium bicarbonate solution wash. The organics were dried over sodium sulfate, filtered and then concentrated in vacuo. Flash column chromatography (Merck Silica gel 60, 230-400 mesh, acetone/acetate/hexanes 2:3:7 to acetone/ethyl acetate/hexanes 2:3:5) afforded 2(R)-(3-chloro-4-methylsulfanyl-phenyl)-3-(3,3-dimethoxy-cyclobutyl)-N-(2(R)-hydroxy-1(R)-methyl-2(R)-phenyl-ethyl)-N-methyl-propionamide (1.04 g, 70%) as a white solid: $^1$H NMR (400 MHz, DMSO-d$_6$) δ ppm 0.56, 0.90 (2×d, J=6.8 Hz, 3H, CH$_3$), 1.49-2.24 (m, 7H, 3×CH$_2$ and CH), 2.44, 2.49 (2×s, 3H, SCH$_3$), 2.75, 2.75 (2×s, 3H, NCH$_3$), 2.98, 2.99 (4×s, 6H, 2×OCH$_3$), 3.77, 3.89 (2×t, J=7.0 Hz, 1H, ArCHCO), 4.01, 4.68 (2×brm, 1H, NCH), 4.47-4.53 (m, 1H, OCH), 5.23, 5.27 (2×d, J=4.0 Hz, 1H, OH), 7.11-7.45 (m, 8H, Ar).

To the solution of 2(R)-(3-chloro-4-methylsulfanyl-phenyl)-3-(3,3-dimethoxy-cyclobutyl)-N-(2(R)-hydroxy-1(R)-methyl-2(R)-phenyl-ethyl)-N-methyl-propionamide (0.67 g, 1.36 mmol) in 1,4 dioxane (5 ml) was slowly added 9 N sulfuric acid (4 ml) and the reaction was refluxed for 30 min and stirred at 25° C. for 17 h. After this time there was still starting material present by HPLC so the reaction was refluxed for an additional 2 h. The reaction was cooled to 0° C. and water (20 ml) was added with caution, then it was stirred for 1 h. The resulting solids were filtered off and washed with water. Resulted solids were dissolved in glacial acetic acid (5 ml) with heating. A small amount of water was added to the hot solution which was then cooled to 25° C. followed by addition of more water (10 ml). After stirring for 1 h the solids were filtered off, washed with water and dried to afford 2(R)-(3-chloro-4-methylsulfanyl-phenyl)-3-(3-oxo-cyclobutyl)-propionic acid (0.318 g, 79%) as a brown solid: $[\alpha]^{27}_{589}$=−67.2° (c=1.1, chloroform); $^1$H NMR (300 MHz, CDCl$_3$) δ ppm 2.04-2.18 (m, 1H, CH of CH$_2$), 2.22-2.24 (m, 2H, CH and CH of CH$_2$), 2.47 (s, 3H, SCH$_3$), 2.60-2.84 (m, 2H, 2×CH or 2×CH$_2$), 3.03-3.23 (m, 2H, 2×CH or 2×CH$_2$), 3.51 (m, 1H, ArCHCO$_2$), 7.13 (d, J$_o$=8.4 Hz, 1H, Ar), 7.21 (d, J$_o$=8.4 Hz, 1H, Ar), 7.33 (s, 1H, Ar).

To the solution of 2(R)-(3-chloro-4-methylsulfanyl-phenyl)-3-(3-oxo-cyclobutyl)-propionic acid (0.56 g, 1.88 mmol) dissolved in acetone (15 ml) and cooled to 0° C. in an ice bath was added potassium peroxymonosulfate (Oxone R, 2.3 g, 3.76 mmol) in water (6 ml). The ice bath was removed and the reaction stirred at 25° C. for 20 min. After such a time, it was filtered and washed with acetone and then concentrated in vacuo to remove acetone. The residue was dissolved in ethyl acetate, washed with water and then saturated aqueous sodium chloride solution, dried over sodium sulfate, filtered and concentrated in vacuo. The resulting reaction was dissolved in methanol and cooled to 0° C. in an ice bath. To this was slowly added potassium permanganate (0.32 g, 2.02 mmol) dissolved in water (8 ml). The reaction was then allowed to warm to 25° C. and stirred for 3 h. After this time it was filtered through short celite pad, washed with methanol and evaporated in vacuo. Purification on an AnaLogix Intelliflash system (40 g column, 3% methanol/methylene chloride+1% acetic acid) afforded 2(R)-(3-chloro-4-methanesulfonyl-phenyl)-3-(3-oxo-cyclobutyl)-propionic acid (0.13 g, 21%) as a white foam: $^1$H NMR (300 MHz, CDCl$_3$) δ ppm 2.07-2.18 (m, 1H, CH of CH$_2$), 2.26-2.50 (m, 2H, CH and CH of CH$_2$), 2.64-2.85 (m, 2H, 2×CH or 2×CH$_2$), 3.09-3.24 (m, 2H, 2×CH or 2×CH$_2$), 3.28 (s, 3H, SO$_2$CH$_3$), 3.65 (t, J=7.4 Hz, 1H, ArCHCO$_2$), 7.44 (dd, J$_m$=1.6 Hz, J$_o$=8.2 Hz, 1H, Ar), 7.55 (d, J$_m$=1.6 Hz, 1H, Ar), 8.15 (d, J$_o$=8.2 Hz, 1 H, Ar).

A solution of 2(R)-(3-chloro-4-methanesulfonyl-phenyl)-3-(3-oxo-cyclobutyl)-propionic acid (0.12 g, 0.36 mmol) in methylene chloride (10 ml) was cooled to 0° C. To this solution was added dropwise a solution of oxalyl chloride in methylene chloride (2 M solution, 0.22 ml, 0.43 mmol) and N,N-dimethylfomamide (two drops) which produced gas evolution and then it was stirred at 0° C. for 20 minutes and 40 min at 25° C. After this time, the reaction was concentrated in vacuo and azeotroped with methylene chloride (10 ml). The reaction was redissolved in methylene chloride (10 ml) to afford the crude 2-(3-chloro-4-methanesulfonyl-phenyl)-3-(3-oxo-cyclobutyl)-propionyl chloride as a 0.012M solution which was used in the following step with no further purification.

A solution of 2(R)-(3-chloro-4-methanesulfonyl-phenyl)-3-(3-oxo-cyclobutyl)-propionyl chloride in methylene chloride (0.036 M solution, 5 mL, 0.18 mmol) was slowly added to a cooled to 0° C. solution of 1-(3-amino-pyrazol-1-yl)-2-methyl-propan-2-ol (prepared in Example 80, 31 mg, 0.20 mmol) and 2,6-lutidine (31 μl, 0.27 mmol) in methylene chloride (6 ml). The reaction continued to stir at 0° C. for 15 min and then at 25° C. for 4 h. After concentration in vacuo it was purified on an AnaLogix Intelliflash system (40 g column, 100% ethyl acetate) to afford 2(R)-(3-chloro-4-methanesulfonyl-phenyl)-N-[1-(2-hydroxy-2-methyl-propyl)-1H-pyrazol-3-yl]-3-(3-oxo-cyclobutyl)-propionamide (54 mg, 63%) as an off-white solid: $[\alpha]^{30}_{589}$=−6.60° (c=5.9, CHCl$_3$); $^1$H NMR (300 MHz, DMSO-d$_6$) δ ppm 1.03, 1.04 (2×s, 6H, 2×CH$_3$), 1.93-2.40 (m, 3H, CH and CH$_2$), 2.66-2.85 (m, 2H, 2×CH or 2×CH$_2$), 2.98-3.12 (m, 2H, 2×CH or 2×CH$_2$), 3.34 (s, 3H, SO$_2$CH$_3$), 3.87 (s, 2H, NCH$_2$), 3.85-3.91 (m, 1H, ArCHCO$_2$), 6.46 (d, J=2.3 Hz, 1H, Ar), 7.52 (d, J=2.3 Hz, 1H, Ar), 7.61 (dd, J$_m$=1.6 Hz, J$_o$=8.3 Hz, 1H, Ar), 7.73 (d, J$_m$=1.6 Hz, 1H, Ar), 8.02 (d, J$_o$=8.3 Hz, 1H, Ar), 10.84 (s, 1H, NH).

Example 94

2(R)-(3-chloro-4-methanesulfonyl-phenyl)-N-[1-(2-methoxy-2-methyl-propyl)-1H-pyrazol-3-yl]-3-(3-oxo-cyclobutyl)-propionamide

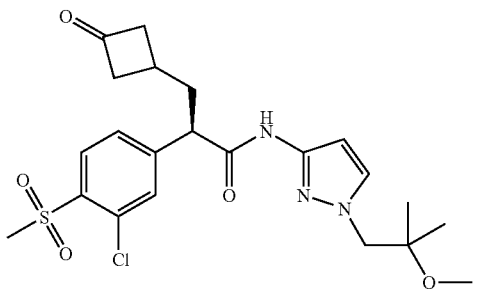

In a round neck flask was placed 2-methyl-1-(3-nitro-pyrazol-1-yl)-propan-2-ol (Example 74, 1.39 g, 7.51 mmol) dissolved in N,N-dimethylformamide (25 mL). To this solution was added sodium hydride (667 mg, 9.01 mmol, 60% dispersion in oil) and it was stirred for 15 min until gas evolution ceased. To this was then added methyl iodide (700 µL, 11.26 mmol) and it was stirred for 2 h at 25° C. The reaction was then quenched with water (250 mL). The reaction was transferred to a separatory funnel and extracted with ethyl acetate (250 mL). The organics were dried over sodium sulfate and then concentrated with silica gel (3 g) in vacuo and purified on Biotage Flash chromatography system (40M column, silica gel, 20% ethyl acetate/hexanes) to afford 1-(2-methoxy-2-methyl-propyl)-3-nitro-1H-pyrazole (1.33 g, 88%) as a colorless oil.

In a Parr shaker bottle was placed 1-(2-methoxy-2-methyl-propyl)-3-nitro-1H-pyrazole (1.33 g, 6.68 mmol), 10% palladium on activated carbon (135 mg) and ethanol (50 mL). The bottle was then placed on the Parr shaker at 50 psi of hydrogen pressure for 2 h. The reaction was then filtered through a pad of celite and washed with ethanol and concentration in vacuo with silica gel (3 g) and purified on Biotage Flash chromatography system (40S column, silica gel, 5% methanol/ethyl acetate) to afford 1-(2-methoxy-2-methyl-propyl)-1H-pyrazol-3-ylamine (802 mg, 71%) as a colorless oil: ES-HRMS m/e calcd for $C_{23}H_{33}N_3O_5S$ $(M+H)^+$ 464.2214, observed 464.2208; $^1$H NMR (300 MHz, DMSO-$d_6$) δ ppm 1.04 (s, 6H, 2×CH$_3$), 3.13 (s, 3H, OCH$_3$), 3.80 (s, 2H, NCH$_2$), 4.48 (brs, 2H, NH$_2$), 5.38 (d, J=2.3 Hz, 1H, Ar), 7.21 (d, J=2.3 Hz, 1H, Ar).

In a round bottom flask was placed sodium periodate (0.29 g, 1.36 mmol) in water (1.0 ml). To this was added a solution of 2(R)-(3-chloro-4-methylsulfanyl-phenyl)-3-(3-oxo-cyclobutyl)-propionic acid (prepared as in Example 93, 0.22 g, 0.74 mmol) in methanol (3 ml) and the reaction was stirred at 25° C. for 6 h. After this time, the solids were filtered off and the filtrate was concentrated in vacuo and azeotroped with acetonitrile (2×10 ml). The resulted in an off-white solid that was then dissolved in methanol (4 ml) and to this was added potassium permanganate (0.17 g, 1.07 mmol) in water (2 ml) and stirred at 25° C. for 5 h. After this time, there was still starting material present by HPLC so another portion of potassium permanganate (80 mg, 0.51 mmol) in water (1 ml) and it was stirred overnight. The reaction still showed starting material was not consumed but it was worked up anyway. The reaction was filtered through celite and washed with a solution of methanol/methylene chloride (1:1). The organics were concentrated in vacuo and azeotroped with acetonitrile (3×10 ml). Purification on an AnaLogix Intelliflash system (40 g column, 3% methanol/methylene chloride+1% acetic acid) afforded 2(R)-(3-chloro-4-methanesulfonyl-phenyl)-3-(3-oxo-cyclobutyl)-propionic acid (65 mg, 27%) as a white gummy solid: $^1$H NMR (300 MHz, DMSO-$d_6$) δ ppm 1.93-2.32 (m, 3H, CH and CH$_2$), 2.63-2.80 (m, 2H, 2×CH or 2×CH$_2$), 2.90-3.13 (m, 2H, 2×CH or 2×CH$_2$), 3.35 (s, 3H, SO$_2$CH$_3$), 3.72 (t, J=7.6 Hz, 1H, ArCHCO$_2$), 7.58 (dd, $J_m$=1.6 Hz, $J_o$=8.2 Hz, 1H, Ar), 7.72 (d, $J_m$=1.6 Hz, 1H, Ar), 8.02 (d, $J_o$=8.2 Hz, 1 H, Ar), 12.81 (brs, 1H, CO$_2$H).

A solution of 2(R)-(3-chloro-4-methanesulfonyl-phenyl)-3-(3-oxo-cyclobutyl)-propionic acid (65 mg, 0.20 mmol) in methylene chloride (8 mL) was cooled to 0° C. To this solution was added dropwise a solution of oxalyl chloride in methylene chloride (2 M solution, 120 µL, 0.24 mmol) and N,N-dimethylfomamide (one drop) which was then stirred at 0° C. for 20 minutes and 40 min at 25° C. After this time, the reaction was concentrated in vacuo and azeotroped with methylene chloride (10 ml). In a separate flask a solution of 1-(2-methoxy-2-methyl-propyl)-1H-pyrazol-3-ylamine (36 mg, 0.22 mmol), 2,6-lutidine (34 µL, 0.29 mmol) in methylene chloride (8 mL) was cooled to 0° C. in an ice bath. To this solution was then added the solution of the prepared acid chloride in methylene chloride (5 mL) dropwise. After addition was complete the reaction was then stirred at 0° C. for 15 min and at 25° C. for 18 h. After this time the reaction was concentrated in vacuo. Purification on an AnaLogix Intelliflash system (40 g column, 50% ethyl acetate/hexanes to 100% ethyl acetate) afforded 2(R)-(3-chloro-4-methanesulfonyl-phenyl)-N-[1-(2-methoxy-2-methyl-propyl)-1H-pyrazol-3-yl]-3-(3-oxo-cyclobutyl)-propionamide (49 mg, 52%) as an off-white solid: $[α]^{29}_{589}$=-14.0° (c=0.55, CHCl$_3$); $^1$H NMR (300 MHz, DMSO-$d_6$) δ ppm 1.04, 1.05 (2×s, 6H, 2×CH$_3$), 1.93-2.40 (m, 3H, CH and CH$_2$), 2.69-2.84 (m, 2H, 2×CH or 2×CH$_2$), 2.99-3.12 (m, 2H, 2×CH or 2×CH$_2$), 3.14 (s, 3H, OCH$_3$), 3.34 (s, 3H, SO$_2$CH$_3$), 3.88 (t, J=7.8 Hz, 1H, ArCHCO$_2$), 3.98 (s, 2H, NCH$_2$), 6.47 (d, J=2.3 Hz, 1H, Ar), 7.49 (d, J=2.3 Hz, 1H, Ar), 7.61 (dd, $J_m$=1.2 Hz, $J_o$=8.3 Hz, 1H, Ar), 7.73 (d, $J_m$=1.2 Hz, 1H, Ar), 8.02 (d, $J_o$=8.3 Hz, 1H, Ar), 10.84 (s, 1H, NH).

Example 95

3-Cyclopentyl-N-[1-(2-hydroxy-2-methyl-propyl)-1H-pyrazol-3-yl]-2-(R)-(4-methanesulfonyl-phenyl)-propionamide

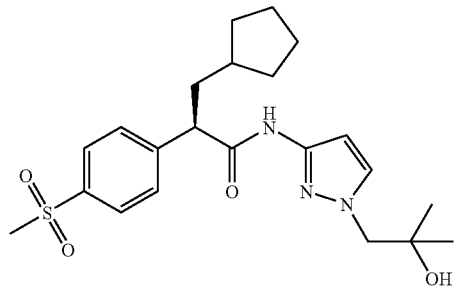

A solution of 3-cyclopentyl-2-(R)-(4-methanesulfonyl-phenyl)-propionic acid (prepared as in PCT WO 2004/052869 A1, Example 3, 60 mg, 0.20 mmol) was dissolved in methylene chloride (10 mL) and N,N-dimethylformamide (one drop) and cooled to 0° C. To this solution was added dropwise a solution of oxalyl chloride in methylene chloride (2 M solution, 117 µL, 0.23 mmol) which produced gas evolution and it was then stirred at 0° C. for 15 minutes and 1 h at 25° C. After this time, the reaction was concentrated in vacuo to ⅙ of the original volume. In a separate flask a solution of 1-(3-amino-pyrazol-1-yl)-2-methyl-propan-2-ol (prepared as in Example 80, 34 mg, 0.22 mmol), 2,6-lutidine (35 µL, 0.30 mmol) and methylene chloride (5 mL) was cooled to 0° C. in an ice bath. To this solution was added the solution of the prepared acid chloride diluted with another portion of methylene chloride (2 mL) dropwise. After addition was complete, the reaction was then allowed to warm to 25° C. and stirred for 16 hours. After this time the reaction was diluted with methylene chloride (10 mL) and washed with a saturated aqueous sodium bicarbonate solution (1×10 mL) and a 1 N aqueous hydrochloric acid solution (1×10 mL) and then dried over magnesium sulfate, filtered and concentrated in vacuo. Purification an AnaLogix Intelliflash system (4 g column, 20% ethyl acetate/hexanes to 80% ethyl acetate/hexanes) afforded 3-cyclopentyl-N-[1-(2-hydroxy-2-methyl-propyl)-1H-pyrazol-3-yl]-2-(R)-(4-methanesulfonyl-phenyl)-propionamide (65 mg, 75%) as a white foam: $[\alpha]^{30}_{589}$=−20.0° (c=0.13, methylene chloride); ES-HRMS m/e calcd for $C_{22}H_{31}N_3O_4S$ (M+H)$^+$ 434.2108, observed 434.2108; H$^1$-NMR (300 MHz, DMSO-d$_6$) δ ppm 1.03 (s, 3H, CH$_3$), 1.04 (s, 3H, CH$_3$), 1.10 (m, 2 H, CH$_2$), 1.35-1.80 (m, 8H, 4×CH$_2$), 2.08 (m, 1H, CH), 3.18 (s, 3H, SO$_2$CH$_3$), 3.86 (s, 2H, NCH$_2$), 3.93 (m, 1H, ArCHCO), 4.65 (s, 1H, OH), 6.45 (d, J=2.1 Hz, 1H, Ar), 7.50 (d, J=2.1 Hz, 1H, Ar), 7.64 (d, J=8.2 Hz, 2H, Ar), 7.88 (d, J=8.2 Hz, 2H, Ar), 10.78 (s, 1H, NH).

(2-hydroxy-2-methyl-propyl)-1H-pyrazol-3-yl]-3-((R)-3-oxo-cyclopentyl)-propionamide (88 mg, 91%) as a white foam: $[\alpha]^{30}_{589}$=−79.0° (c=0.10, methylene chloride); ES-HRMS m/e calcd for $C_{22}H_{28}N_3O_5SCl$ (M+H)$^+$ 482.1511, observed 482.1511; $^1$H NMR (300 MHz, DMSO-d$_6$) δ ppm 1.03 (s, 3H, CH$_3$), 1.04 (s, 3H, CH$_3$), 1.50 (m, 1H, CH), 1.79-2.29 (m, 8H, 4×CH$_2$), 3.34 (s, 3H, SO$_2$CH$_3$), 3.87 (s, 2H, NCH$_{22}$), 3.96 (m, 1H, ArCHCO), 4.65 (s, 1H, OH), 6.45 (d, J=1.7 Hz, 1H, Ar), 7.51 (d, J=1.7 Hz, 1H, Ar), 7.62 (d, J$_o$=8.0 Hz, 1H, Ar), 7.73 (s, 1H, Ar), 8.02 (d, J$_o$=8.0 Hz, 1H, Ar), 10.85 (s, 1 H, NH).

Example 96

(R)-2-(3-Chloro-4-methanesulfonyl-phenyl)-N-[1-(2-hydroxy-2-methyl-propyl)-1H-pyrazol-3-yl]-3-((R)-3-oxo-cyclopentyl)-propionamide Example 97

(R)-2-(3-Chloro-4-methanesulfonyl-phenyl)-N-[1-(2-methoxy-ethyl)-1H-pyrazol-3-yl]-3-((R)-3-oxo-cyclopentyl)-propionamide

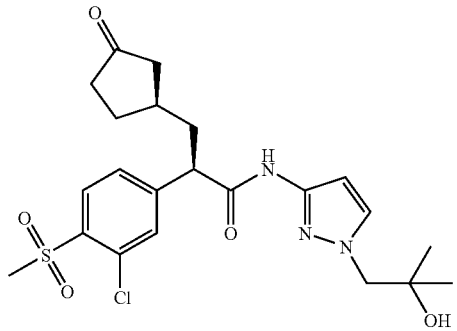

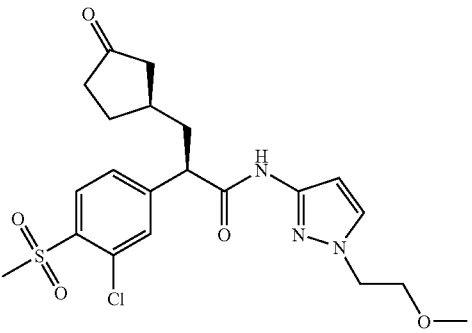

A solution of (R)-2-(3-chloro-4-methanesulfonyl-phenyl)-3-((R)-3-oxo-cyclopentyl)-propionic acid (prepared as in PCT WO 2003/095438, Example 48, 280 mg, 0.81 mmol) was dissolved in methylene chloride (15 mL) and N,N-dimethylformamide (one drop) and cooled to 0° C. To this solution was added dropwise a solution of oxalyl chloride in methylene chloride (2 M solution, 467 µL, 0.93 mmol) which produced gas evolution and it was then warmed to 25° C. and stirred for 1 h. After this time, the reaction was concentrated in vacuo to about 3 mL and then another portion of methylene chloride (~5 mL) was added to produce a roughly 0.10 M solution of (R)-2-(3-chloro-4-methanesulfonyl-phenyl)-3-((R)-3-oxo-cyclopentyl)-propionyl chloride which was used.

In a round bottom flask was placed 1-(3-amino-pyrazol-1-yl)-2-methyl-propan-2-ol (prepared as in Example 80, 35 mg, 0.22 mmol), 2,6-lutidine (35 µL, 0.30 mmol) and methylene chloride (5 mL) which was then cooled to 0° C. in an ice bath. To this solution was then added dropwise a solution of (R)-2-(3-chloro-4-methanesulfonyl-phenyl)-3-((R)-3-oxo-cyclopentyl)-propionyl chloride in methylene chloride (~0.10 M solution, 2 mL, 0.20 mmol). The reaction was then allowed to warm up to 25° C. and stirred for 16 h. After this time the reaction mixture was diluted with methylene chloride (5 mL) transferred to a separatory funnel and washed with a saturated aqueous sodium bicarbonate solution (10 mL) and then a 1 N aqueous hydrochloric acid solution (10 mL) and then dried over magnesium sulfate, filtered and concentrated in vacuo. Purification on an AnaLogix Intelliflash system (4 g column, 50% ethyl acetate/hexanes to 100% ethyl acetate/hexanes) afforded (R)-2-(3-chloro-4-methanesulfonyl-phenyl)-N-[1-

In a round bottom flask was placed 1-(2-methoxy-ethyl)-1H-pyrazol-3-ylamine (prepared in Example 72, 32 mg, 0.22 mmol), 2,6-lutidine (35 µL, 0.30 mmol) and methylene chloride (5 mL) which was then cooled to 0° C. in an ice bath. To this solution was then added dropwise a solution of (R)-2-(3-chloro-4-methanesulfonyl-phenyl)-3-((R)-3-oxo-cyclopentyl)-propionyl chloride in methylene chloride (prepared as in Example 96, ~0.10 M solution, 2 mL, 0.20 mmol). The reaction was then allowed to warm up to 25° C. and stirred for 16 h. After this time the reaction mixture was diluted with methylene chloride (5 mL) transferred to a separatory funnel and washed with a saturated aqueous sodium bicarbonate solution (10 mL) and then a 1 N aqueous hydrochloric acid solution (10 mL) and then dried over magnesium sulfate, filtered and concentrated in vacuo. Purification on an AnaLogix Intelliflash system (4 g column, 60% ethyl acetate/hexanes to 100% ethyl acetate/hexanes) afforded (R)-2-(3-chloro-4-methanesulfonyl-phenyl)-N-[1-(2-methoxy-ethyl)-1H-pyrazol-3-yl]-3-((R)-3-oxo-cyclopentyl)-propionamide (71 mg, 76%) as a white foam: $[\alpha]^{30}_{589}$=−90.0° (c=0.14, methylene chloride); ES-HRMS m/e calcd for $C_{21}H_{26}N_3O_5SCl$ (M+H)$^+$ 468.1355, observed 468.1354; $^1$H NMR (300 MHz, DMSO-d$_6$) δ 1.51 (m, 1H, CH), 1.79-2.29 (m, 8 H, 4×CH$_2$), 3.19 (s, 3H, OCH$_3$), 3.34 (s, 3H, SO$_2$CH$_3$), 3.61 (t, J=5.1 Hz, 2H, OCH$_2$), 3.95 (m, 1H, ArCHCO), 4.12 (t, J=5.1 Hz, 2H, NCH$_2$), 6.42 (d, J=2.0 Hz, 1H, Ar), 7.55 (d, J=2.0 Hz, 1H, Ar), 7.62 (d, $J_o$=8.1 Hz, 1H, Ar), 7.73 (s, 1H, Ar), 8.02 (d, $J_o$=8.1 Hz, 1H, Ar), 10.85 (s, 1H, NH).

Example 98

(R)-2-(3-Chloro-4-methanesulfonyl-phenyl)-N-[1-(3-hydroxy-propyl)-1H-pyrazol-3-yl]-3-((R)-3-oxo-cyclopentyl)-propionamide

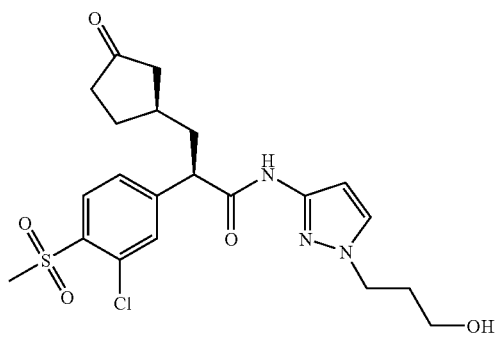

In a round bottom flask was placed 3-(3-amino-pyrazol-1-yl)-propan-1-ol (prepared in Example 23, 32 mg, 0.22 mmol), 2,6-lutidine (35 μL, 0.30 mmol) and methylene chloride (5 mL) which was then cooled to 0° C. in an ice bath. To this solution was then added dropwise a solution of (R)-2-(3-chloro-4-methanesulfonyl-phenyl)-3-((R)-3-oxo-cyclopentyl)-propionyl chloride in methylene chloride (prepared as in Example 96, ~0.10 M solution, 2 mL, 0.20 mmol). The reaction was then allowed to warm up to 25° C. and stirred for 16 h. After this time the reaction mixture was diluted with methylene chloride (5 mL) transferred to a separatory funnel and washed with a saturated aqueous sodium bicarbonate solution (10 mL) and then a 1 N aqueous hydrochloric acid solution (10 mL) and then dried over magnesium sulfate, filtered and concentrated in vacuo. Purification on an AnaLogix Intelliflash system (4 g column, 70% ethyl acetate/hexanes to 100% ethyl acetate/hexanes) afforded (R)-2-(3-chloro-4-methanesulfonyl-phenyl)-N-[1-(3-hydroxy-propyl)-1H-pyrazol-3-yl]-3-((R)-3-oxo-cyclopentyl)-propionamide (83 mg, 88%) as a white foam: $[\alpha]^{30}_{589}$=−88.0° (c=0.10, methylene chloride); ES-HRMS m/e calcd for $C_{21}H_{26}N_3O_5SCl$ (M+H)$^+$ 468.1355, observed 468.1354; $^1$H NMR (300 MHz, DMSO-$d_6$) δ 1.51 (m, 1H, CH), 1.78-2.32 (m, 10H, 5×CH$_2$), 3.34 (brs, 5H, OCH$_2$ and SO$_2$CH$_3$), 3.95 (m, 1H, ArCHCO), 4.02 (t, J=6.5 Hz, 2H, NCH$_2$), 4.56 (t, J=4.7 Hz, 1H, OH), 6.41 (s, 1H, Ar), 7.56 (s, 1H, Ar), 7.61 (d, $J_o$=8.3 Hz, 1H, Ar), 7.73 (s, 1H, Ar), 8.02 (d, $J_o$=8.3 Hz, 1H, Ar), 10.84 (s, 1 H, NH).

Example 99

(R)-2-(3-Chloro-4-methanesulfonyl-phenyl)-N-[1-(2-hydroxy-ethyl)-1H-pyrazol-3-yl]-3-((R)-3-oxo-cyclopentyl)-propionamide

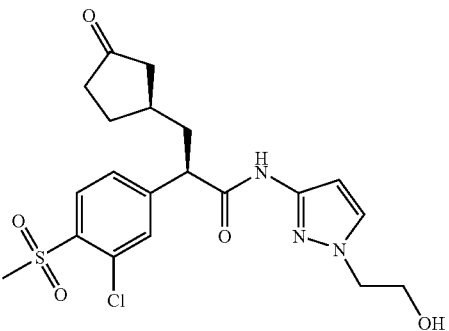

In a round bottom flask was placed 1-[2-(tert-butyl-dimethyl-silanyloxy)-ethyl]-1H-pyrazol-3-ylamine (prepared in Example 67, 54 mg, 0.22 mmol), 2,6-lutidine (35 μL, 0.30 mmol) and methylene chloride (5 mL) which was then cooled to 0° C. in an ice bath. To this solution was then added dropwise a solution of (R)-2-(3-chloro-4-methanesulfonyl-phenyl)-3-((R)-3-oxo-cyclopentyl)-propionyl chloride in methylene chloride (prepared as in Example 96, ~0.10 M solution, 2 mL, 0.20 mmol). The reaction was then allowed to warm up to 25° C. and stirred for 16 h. After this time the reaction mixture was diluted with methylene chloride (5 mL) transferred to a separatory funnel and washed with a saturated aqueous sodium bicarbonate solution (10 mL) and then a 1 N aqueous hydrochloric acid solution (10 mL) and then dried over magnesium sulfate, filtered and concentrated in vacuo. Purification on an AnaLogix Intelliflash system (4 g column, 50% ethyl acetate/hexanes to 70% ethyl acetate/hexanes) afforded (R)—N-{1-[2-(tert-butyl-dimethyl-silanyloxy)-ethyl]-1H-pyrazol-3-yl}-2-(3-chloro-4-methanesulfonyl-phenyl)-3-((R)-3-oxo-cyclopentyl)-propionamide (88 mg, 77%) as a yellow foam: $[\alpha]^{30}_{589}$=−74.3° (c=0.14, methylene chloride); ES-HRMS m/e calcd for $C_{26}H_{38}N_3O_5SSiCl$ (M+H)$^+$ 568.2063, observed 568.2063; $^1$H NMR (300 MHz, DMSO-$d_6$) δ −0.09 (s, 6H, 2×SiCH$_3$), 0.77 (s, 9H, 3×CH$_3$), 1.51 (m, 1H, CH), 1.79-2.29 (m, 8 H, 4×CH$_2$), 3.34 (s, 3H, SO$_2$CH$_3$), 3.84 (m, 2H, OCH$_2$), 3.96 (m, 1H, ArCHCO), 3.96 (m, 2H, NCH$_2$), 6.41 (d, J=2.2 Hz, 1H, Ar), 7.53 (d, J=2.2 Hz, 1H, Ar), 7.61 (dd, $J_o$=8.2 Hz, $J_m$=1.4 Hz, 1H, Ar), 7.73 (d, $J_m$=1.4 Hz, 1H, Ar), 8.01 (d, $J_o$=8.2 Hz, 1H, Ar), 10.83 (s, 1H, NH).

In a round bottom flask was placed (R)—N-{1-[2-(tert-butyl-dimethyl-silanyloxy)-ethyl]-1H-pyrazol-3-yl}-2-(3-chloro-4-methanesulfonyl-phenyl)-3-((R)-3-oxo-cyclopentyl)-propionamide (85 mg, 0.15 mmol), tetrahydrofuran (2 mL), water (0.5 mL) and acetic acid (2 mL). This solution was then stirred at 25° C. until all starting material is consumed (~4 hr). The reaction was then diluted with water (10 mL) and transferred to a separatory funnel where it was extracted with ethyl acetate (3×10 mL). The organic layers were combined and then washed with saturated aqueous sodium bicarbonate solution (10 mL), dried over magnesium sulfate, filtered and concentrated in vacuo. Purification on an AnaLogix Intelliflash system (4 g column, 100% ethyl acetate to 5% methanol/ethyl acetate) afforded (R)-2-(3-chloro-4-methanesulfonyl-phenyl)-N-[1-(2-hydroxy-ethyl)-1H-pyrazol-3-yl]-3-((R)-3-oxo-cyclopentyl)-propionamide (67 mg, 99%) as a white foam: $[\alpha]^{29}_{589}$=–11.5° (c=0.13, methylene chloride); ES-HRMS m/e calcd for $C_{20}H_{24}N_3O_5SCl$ (M+H)$^+$ 454.1198, observed 454.1193; $^1$H NMR (300 MHz, DMSO-$d_6$) δ 1.51 (m, 1H, CH), 1.78-2.30 (m, 8H, 4×CH$_2$), 3.34 (s, 3H, SO$_2$CH$_3$), 3.67 (q, J=5.4 Hz, 2H, OCH$_2$), 3.96 (m, 1H, ArCHCO), 4.00 (m, 2H, NCH$_2$), 4.84 (t, J=5.4 Hz, 1H, OH), 6.41 (d, J=2.1 Hz, 1H, Ar), 7.55 (d, J=2.1 Hz, 1H, Ar), 7.62 (d, $J_o$=8.3 Hz, 1H, Ar), 7.73 (s, 1H, Ar), 8.02 (d, $J_o$=8.3 Hz, 1H, Ar), 10.85 (s, 1H, NH).

Example 100

(R)-3-Cyclopentyl-N-[1-(2-hydroxy-2-methyl-propyl)-1H-pyrazol-3-yl]-2-(4-methanesulfonyl-3-methoxy-phenyl)-propionamide

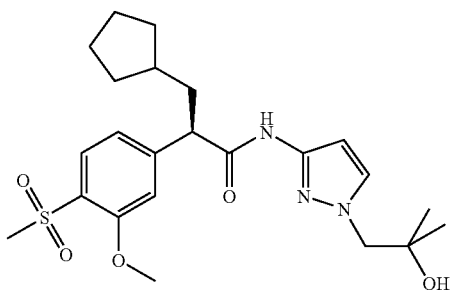

In a round bottom flask under argon was placed methanol (50 mL) and to it was added in small portions sodium metal (1.15 g, 45.35 mmol). This was stirred at 25° C. for 1 h. It was then concentrated in vacuo and azeotroped with acetonitrile. To this solid residue under argon was then added 2-(3-chloro-4-methanesulfonyl-phenyl)-3-cyclopentyl-propionic acid (prepared as in PCT WO200058293, Example 12, 3.00 g, 9.07 mmol) in dimethylsulfoxide (25 mL). This was then stirred and heated at 75° C. for 1 h. Let the solution cool back to 25° C. and then diluted it with water (120 mL). The solution was then filtered through celite and washed with water. The pH of the filterate was then adjusted pH=2 using a 1 N aqueous hydrochloric acid solution. It was then extracted with ethyl acetate (200 mL) and dried using sodium sulfate. The solution was filtered and concentrated in vacuo. The crude racemic material was then separated into the chiral components by supercritical fluid chromatography (SFC) on a Berger MultiGram II Supercritical Fluid Chromatography (SFC) system (Mettler-Toledo AutoChem Berger Instruments, Newark, Del.) (Chiral column: Daicel OJ-H, 250 mm×30 mm i.d., 5 μm-particle size, temperature: 35° C., flow rate of 70 mL/min, and 100 bar back pressure, 12% of a 1:1 ethanol/acetonitrile as mobile phase modifier and UV Detection: 220 nm) to afford (R)-3-cyclopentyl-2-(4-methanesulfonyl-3-methoxy-phenyl)-propionic acid (second compound to elute, 1.31 g, 44%) as a white foam: $[\alpha]^{31}_{589}$=–47.4° (c=0.23, methanol); ES-HRMS m/e calcd for $C_{16}H_{22}O_5S$ (M+H)$^+$ 327.1261, observed 327.1262; $^1$H NMR (300 MHz, DMSO-$d_6$) δ 1.10 (m, 2H, CH$_2$), 1.36-1.81 (m, 8H, 4×CH$_2$), 2.00 (m, 1H, CH), 3.22 (s, 3H, SO$_2$CH$_3$), 3.66 (t, J=7.7 Hz, 1H, ArCHCO), 3.95 (s, 3H, OCH$_3$), 7.10 (dd, $J_m$=1.4 Hz, $J_o$=8.1 Hz, 1H, Ar), 7.22 (d, $J_m$=1.4 Hz, 1H, Ar), 7.74 (d, $J_o$=8.1 Hz, 1H, Ar), 12.56 (s, 1H, CO$_2$H).

A solution of (R)-3-cyclopentyl-2-(4-methanesulfonyl-3-methoxy-phenyl)-propionic acid (60 mg, 0.18 mmol) was dissolved in methylene chloride (5 mL) and N,N-dimethylformamide (one drop) and cooled to 0° C. To this solution was added dropwise a solution of oxalyl chloride in methylene chloride (2 M solution, 110 μL, 0.21 mmol) which produced gas evolution and it was then warmed to 25° C. and stirred for 1 h. After this time, the reaction was concentrated in vacuo to about 2 mL. In a separate round bottom flask was placed 1-(3-amino-pyrazol-1-yl)-2-methyl-propan-2-ol (prepared as in Example 80, 31 mg, 0.20 mmol), 2,6-lutidine (32 μL, 0.28 mmol) and methylene chloride (5 mL) which was then cooled to 0° C. in an ice bath. To this solution was then added dropwise the above solution acid chloride. The reaction was then allowed to warm up to 25° C. and stirred for 16 h. After this time the reaction mixture was diluted with methylene chloride (5 mL) transferred to a separatory funnel and washed with a saturated aqueous sodium bicarbonate solution (10 mL) and then a 1 N aqueous hydrochloric acid solution (10 mL) and then dried over magnesium sulfate, filtered and concentrated in vacuo. Purification on an AnaLogix Intelliflash system (4 g column, 70% ethyl acetate/hexanes to 85% ethyl acetate/hexanes) afforded (R)-3-cyclopentyl-N-[1-(2-hydroxy-2-methyl-propyl)-1H-pyrazol-3-yl]-2-(4-methanesulfonyl-3-methoxy-phenyl)-propionamide (61 mg, 73%) as a white foam: $[\alpha]^{28}_{589}$=–26.0° (c=0.10, methanol); ES-HRMS m/e calcd for $C_{23}H_{33}N_3O_5S$ (M+H)$^+$ 464.2214, observed 464.2211; $^1$H NMR (300 MHz, DMSO-$d_6$) δ ppm 1.03 (s, 3H, CH$_3$), 1.04 (s, 3H, CH$_3$), 1.10 (m, 2H, CH$_2$), 1.35-1.80 (m, 8H, 4×CH$_2$), 2.11 (m, 1H, CH), 3.20 (s, 3H, SO$_2$CH$_3$), 3.86 (s, 2H, NCH$_2$), 3.90 (br, 1H, ArCHCO), 3.95 (s, 3H, OCH$_3$), 4.65 (s, 1H, OH), 6.46 (s, 1H, Ar), 7.15 (d, $J_o$=8.2 Hz, 1H, Ar), 7.27 (s, 1H, Ar), 7.50 (s, 1H, Ar), 7.74 (d, $J_o$=8.2 Hz, 1H, Ar), 10.73 (s, 1H, NH).

Example 101

(R)-2-(3-Chloro-4-methanesulfonyl-phenyl)-3-cyclopentyl-N-[1-(2-isopropoxy-ethyl)-1H-pyrazol-3-yl]-propionamide

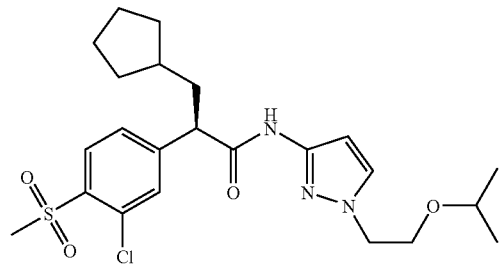

In a round bottom flask was placed 2-isopropoxy-ethanol (700 mg, 6.72 mmol) dissolved in methylene chloride (15 mL) and cooled to 0° C. in an ice bath. To this solution was added triethylamine (1.2 mL, 8.7 mmol) and para-toluenesulfonyl chloride (1.54 g, 8.06 mmol). The resulting solution was then slowly allowed to warm to 25° C. and was stirred for 16 h. After this time, the reaction was transferred to a separatory funnel and washed with water (15 mL). The aqueous layer was then extracted with methylene chloride (2×20 mL).

The organic layers were combined and then dried over sodium sulfate, filtered and concentrated in vacuo. Purification on an AnaLogix Intelliflash system (40 g column, 25% ethyl acetate/hexanes) afforded toluene-4-sulfonic acid 2-isopropoxy-ethyl ester (1.41 g, 81%).

In a round bottom flask were combined toluene-4-sulfonic acid 2-isopropoxy-ethyl ester (1.41 g, 5.45 mmol) and sodium iodide (1.06 g, 7.09 mmol) in acetone (15 mL). The reaction mixture was then heated at 60° C. for 16 h. After this time the reaction was then cooled to 25° C. and the solids were filtered off and washed with acetone. The filtrate was then concentrated in vacuo. This residue was then treated with methylene chloride and the solids filtered off. The filtrate was then concentrated in vacuo to afford 2-(2-iodo-ethoxy)-propane (896 mg, 77%) as a light yellow oil: EI-HRMS m/e calcd for $C_5H_{11}IO$ (M$^+$) 213.9855, observed 213.9860; $^1$H NMR (300 MHz, CDCl$_3$) δ 1.81 (d, J=6.2 Hz, 6H, 2×CH$_3$), 3.23 (t, J=7.0 Hz, 2H, ICH$_2$), 3.66 (m, 1H, OCH), 3.69 (t, J=7.0 Hz, 2H, OCH$_2$).

In a round bottom flask was placed 3-nitro-1H-pyrazole (prepared in example 3, 315 mg, 2.79 mmol) and dry N,N-dimethylformamide (5 mL). This solution was then treated with sodium hydride (95%, 80 mg, 3.35 mmol) and gas evolution occurred. It was then stirred another 15 min at 25° C. 2-(2-Iodo-ethoxy)-propane (896 mg, 4.18 mmol) was then added to the reaction mixture and the reaction was stirred at 25° C. for 6 h. The reaction was then diluted with ethyl acetate (10 mL) and washed with water (2×10 mL). The aqueous layers were then combined and extracted with ethyl acetate (2×10 mL). The organic layers were combined and washed with a saturated aqueous brine solution (10 mL) and then dried over sodium sulfate, filtered and concentrated in vacuo. Purification on an AnaLogix Intelliflash system (12 g column, 25% ethyl acetate/hexanes to 35% ethyl acetate/hexanes) afforded 1-(2-isopropoxy-ethyl)-3-nitro-1H-pyrazole (428 mg, 77%) as a light yellow oil.

In a Parr shaker bottle was placed 1-(2-isopropoxy-ethyl)-3-nitro-1H-pyrazole (428 mg, 2.14 mmol), 10% palladium on activated carbon (50 mg) and ethanol (20 mL). The bottle was then placed on the Parr shaker at 50 psi of hydrogen pressure for 2 h. The reaction was then filtered through a pad of celite and washed with ethanol, concentration in vacuo afforded 1-(2-isopropoxy-ethyl)-1H-pyrazol-3-ylamine (360 mg, 99%) as a clear light yellow oil: ES-HRMS m/e calcd for $C_8H_{15}N_3$ (M+H)$^+$ 170.1288, observed 170.1287; $^1$H NMR (300 MHz, CDCl$_3$) δ 1.10 (d, J=6.0 Hz, 6H, 2×CH$_3$), 3.43 (br, 2 H, NH$_2$), 3.49 (m, 1H, OCH), 3.70 (t, J=5.6 Hz, 2H, OCH$_2$), 4.05 (t, J=5.6 Hz, 2H, NCH$_2$), 5.57 (d, J=2.3 Hz, 1H, Ar), 7.22 (d, J=2.3 Hz, 1H, Ar).

A solution of 2(R)-(3-chloro-4-methanesulfonyl-phenyl)-3-cyclopentyl-propionic acid (prepared as in PCT WO 2004/052869 A1, Example 1, 120 mg, 0.36 mmol) was dissolved in methylene chloride (5 mL) and N,N-dimethylformamide (one drop) and cooled to 0° C. To this solution was added dropwise a solution of oxalyl chloride in methylene chloride (2 M solution, 210 μL, 0.42 mmol) which produced gas evolution and it was then allowed to warm to 25° C. and stirred 1 h at 25° C. After this time, the reaction was concentrated in vacuo to ⅓ of the original volume. In a separate flask, a solution of 1-(2-isopropoxy-ethyl)-1H-pyrazol-3-ylamine (67 mg, 0.40 mmol), 2,6-lutidine (63 μL, 0.54 mmol) and methylene chloride (5 mL) was cooled to 0° C. in an ice bath. To this solution was added the solution of the prepared acid chloride, diluted with another portion of methylene chloride (2 mL), dropwise. After addition was complete the reaction was then allowed to warm to 25° C. and stirred for 16 hours.

After this time the reaction mixture was diluted with methylene chloride (10 mL) transferred to a separatory funnel and washed with a saturated aqueous sodium bicarbonate solution (10 mL) and then a 1 N aqueous hydrochloric acid solution (10 mL) and then dried over magnesium sulfate, filtered and concentrated in vacuo. Purification on an AnaLogix Intelliflash system (4 g column, 40% ethyl acetate/hexanes to 60% ethyl acetate/hexanes) afforded (R)-2-(3-chloro-4-methanesulfonyl-phenyl)-3-cyclopentyl-N-[1-(2-isopropoxy-ethyl)-1H-pyrazol-3-yl]-propionamide (168 mg, 96%) as a white foam: [α]$^{28}_{589}$=+10.0° (c=0.43, methylene chloride); ES-HRMS m/e calcd for $C_{23}H_{32}N_3O_4SCl$ (M+H)$^+$ 482.1875, observed 482.1874; $^1$H NMR (300 MHz, DMSO-d$_6$) δ 1.01 (d, J=6.1 Hz, 6H, 2×CH$_3$), 1.11 (m, 2H, CH$_2$), 1.38-1.80 (m, 8H, 4×CH$_2$), 2.09 (m, 1H, CH), 3.34 (s, 3 H, SO$_2$CH$_3$), 3.47 (m, 1H, OCH), 3.64 (t, J=5.5 Hz, 2H, OCH$_2$), 3.91 (m, 1H, ArCHCO), 4.08 (t, J=5.5 Hz, 2H, NCH$_2$), 6.41 (d, J=2.2 Hz, 1H, Ar), 7.54 (d, J=2.2 Hz, 1H, Ar), 7.59 (dd, J$_m$=1.6 Hz, J$_o$=8.2 Hz, 1H, Ar), 7.70 (d, J$_m$=1.6 Hz, 1H, Ar), 8.01 (d, J$_o$=8.2 Hz, 1H, Ar), 10.78 (s, 1H, NH).

Example 102

(R)-3-Cyclopentyl-2-(3,4-dichloro-phenyl)-N-[1-(2-hydroxy-2-methyl-propyl)-1H-pyrazol-3-yl]-propionamide

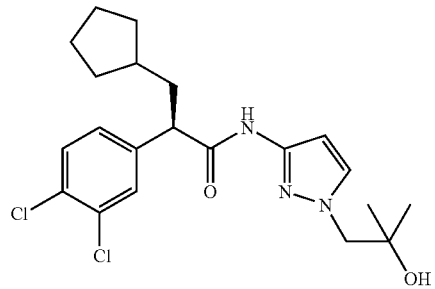

A solution of 3-cyclopentyl-2(R)-(3,4-dichloro-phenyl)-propionic acid (prepared as in PCT WO 2002/046173 A1, Example 3, 375 mg, 1.31 mmol) was dissolved in methylene chloride (20 mL) and N,N-dimethylformamide (one drop) and cooled to 0° C. To this solution was added dropwise a solution of oxalyl chloride in methylene chloride (2 M solution, 753 μL, 1.76 mmol) which produced gas evolution and it was then warmed to 25° C. and stirred for 1 h. After this time, the reaction was concentrated in vacuo to about 5 mL and then another portion of methylene chloride (~3 mL) was added to produce a roughly 0.16 M solution of 3-cyclopentyl-2(R)-(3,4-dichloro-phenyl)-propionyl chloride which was used.

In a round bottom flask was placed 1-(3-amino-pyrazol-1-yl)-2-methyl-propan-2-ol (prepared as in Example 80, 56 mg, 0.36 mmol), 2,6-lutidine (57 μL, 0.49 mmol) and methylene chloride (5 mL) which was then cooled to 0° C. in an ice bath. To this solution was then added dropwise a solution of 3-cyclopentyl-2(R)-(3,4-dichloro-phenyl)-propionyl chloride in methylene chloride (~0.16 M solution, 2 mL, 0.33 mmol).

The reaction was then allowed to warm up to 25° C. and stirred for 16 h. After this time the reaction mixture was diluted with methylene chloride (5 mL) transferred to a separatory funnel and washed with a saturated aqueous sodium bicarbonate solution (10 mL) and then a 1 N aqueous hydrochloric acid solution (10 mL) and then dried over magnesium sulfate, filtered and concentrated in vacuo. Purification on an AnaLogix Intelliflash system (4 g column, 20% ethyl acetate/hexanes to 45% ethyl acetate/hexanes) afforded (R)-3-cyclopentyl-2-(3,4-dichloro-phenyl)-N-[1-(2-hydroxy-2-methyl-propyl)-1H-pyrazol-3-yl]-propionamide (102 mg, 74%) as a white foam: $[\alpha]^{30}_{589}=-13.3°$ (c=0.12, methylene chloride); ES-HRMS m/e calcd for $C_{21}H_{27}N_3O_2Cl_2$ (M+H)+ 424.1553, observed 454.1553; 1H NMR (300 MHz, DMSO-$d_6$) δ ppm 1.04 (s, 6H, 2×$CH_3$), 1.09 (m, 2H, $CH_2$), 1.34-1.79 (m, 8H, 4×$CH_2$), 2.03 (m, 1H, CH), 3.80 (m, 1H, ArCHCO), 3.86 (s, 2H, $NCH_2$), 4.65 (s, 1H, OH), 6.45 (s, 1H, Ar), 7.35 (brd, 1H, Ar), 7.51 (s, 1H, Ar), 7.58 (m, 2H, Ar), 10.73 (s, 1H, NH).

Example 103

(R)-3-Cyclopentyl-2-(3,4-dichloro-phenyl)-N-[1-(2-methoxy-ethyl)-1H-pyrazol-3-yl]-propionamide

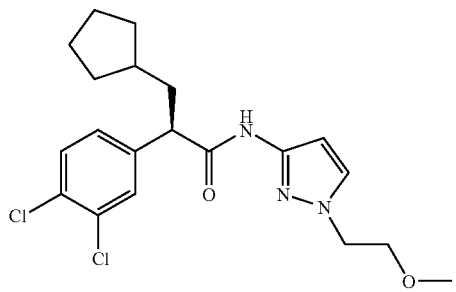

In a round bottom flask was placed 1-(2-methoxy-ethyl)-1H-pyrazol-3-ylamine (prepared in Example 72, 51 mg, 0.36 mmol), 2,6-lutidine (57 μL, 0.49 mmol) and methylene chloride (5 mL) which was then cooled to 0° C. in an ice bath. To this solution was then added dropwise a solution of 3-cyclopentyl-2(R)-(3,4-dichloro-phenyl)-propionyl chloride in methylene chloride (prepared as in Example 102, ~0.16 M solution, 2 mL, 0.33 mmol). The reaction was then allowed to warm up to 25° C. and stirred for 16 h. After this time the reaction mixture was diluted with methylene chloride (5 mL) transferred to a separatory funnel and washed with a saturated aqueous sodium bicarbonate solution (10 mL) and then a 1 N aqueous hydrochloric acid solution (10 mL) and then dried over magnesium sulfate, filtered and concentrated in vacuo. Purification on an AnaLogix Intelliflash system (4 g column, 25% ethyl acetate/hexanes to 45% ethyl acetate/hexanes) afforded (R)-3-cyclopentyl-2-(3,4-dichloro-phenyl)-N-[1-(2-methoxy-ethyl)-1H-pyrazol-3-yl]-propionamide (85 mg, 63%) as a white foam: $[\alpha]^{30}_{589}=-24.0°$ (c=0.10, methylene chloride); ES-HRMS m/e calcd for $C_{20}H_{25}N_3O_2Cl_2$ (M+H)+ 410.1397, observed 410.1396; 1H NMR (300 MHz, DMSO-$d_6$) δ 1.09 (m, 2H, $CH_2$), 1.38-1.79 (m, 8H, 4×$CH_2$), 2.05 (m, 1H, CH), 3.19 (s, 3H, $OCH_3$), 3.61 (t, J=5.4 Hz, 2H, $OCH_2$), 3.79 (m, 1H, ArCHCO), 4.12 (t, J=5.4 Hz, 2H, $NCH_2$), 6.41 (d, J=2.2 Hz, 1H, Ar), 7.34 (dd, $J_m$=2.1 Hz, $J_o$=8.4 Hz, 1H, Ar), 7.54 (d, J=2.2 Hz, 1H, Ar), 7.59 (d, $J_o$=8.4 Hz, 1H, Ar), 7.59 (d, $J_m$=2.1 Hz, 1H, Ar), 10.72 (s, 1H, NH).

Example 104

(R)-3-cyclopentyl-2-(3,4-dichloro-phenyl)-N-[1-(3-hydroxy-propyl)-1H-pyrazol-3-yl]-propionamide

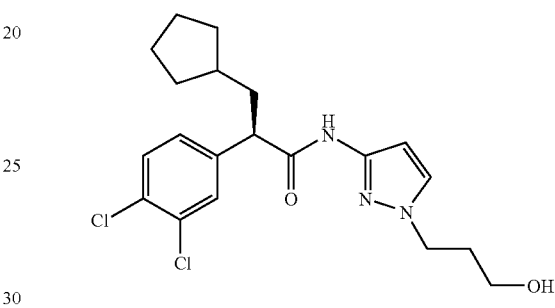

In a round bottom flask was placed 3-(3-amino-pyrazol-1-yl)-propan-1-ol (prepared in Example 23, 51 mg, 0.36 mmol), 2,6-lutidine (57 μL, 0.49 mmol) and methylene chloride (5 mL) which was then cooled to 0° C. in an ice bath. To this solution was then added dropwise a solution of 3-cyclopentyl-2(R)-(3,4-dichloro-phenyl)-propionyl chloride in methylene chloride (prepared as in Example 102, ~0.16 M solution, 2 mL, 0.33 mmol). The reaction was then allowed to warm up to 25° C. and stirred for 16 h. After this time the reaction mixture was diluted with methylene chloride (5 mL) transferred to a separatory funnel and washed with a saturated aqueous sodium bicarbonate solution (10 mL) and then a 1 N aqueous hydrochloric acid solution (10 mL) and then dried over magnesium sulfate, filtered and concentrated in vacuo. Purification on an AnaLogix Intelliflash system (4 g column, 40% ethyl acetate/hexanes to 65% ethyl acetate/hexanes) afforded (R)-3-cyclopentyl-2-(3,4-dichloro-phenyl)-N-[1-(3-hydroxy-propyl)-1H-pyrazol-3-yl]-propionamide (99 mg, 74%) as a white foam: $[\alpha]^{30}_{589}=-27.3°$ (c=0.11, methylene chloride); ES-HRMS m/e calcd for $C_{20}H_{25}N_3O_2Cl_2$ (M+H)+ 410.1397, observed 410.1398; 1H NMR (400 MHz, DMSO-$d_6$) δ 1.10 (m, 2H, $CH_2$), 1.35-1.78 (m, 8H, 4×$CH_2$), 1.85 (m, 2H, $CH_2$), 2.04 (m, 1H, CH), 3.34 (t, J=6.4 Hz, 2H, $OCH_2$), 3.79 (m, 1H, ArCHCO), 4.02 (t, J=6.8 Hz, 2H, $NCH_2$), 4.56 (br, 1H, OH), 6.41 (d, J=2.2 Hz, 1H, Ar), 7.35 (dd, $J_m$=2.0 Hz, $J_o$=8.4 Hz, 1H, Ar), 7.55 (d, J=2.2 Hz, 1H, Ar), 7.59 (d, $J_o$=8.4 Hz, 1H, Ar), 7.59 (s, 1H, Ar), 10.71 (s, 1H, NH).

Example 105

(R)-3-Cyclopentyl-2-(3,4-dichloro-phenyl)-N-[1-(2-hydroxy-ethyl)-1H-pyrazol-3-yl]-propionamide

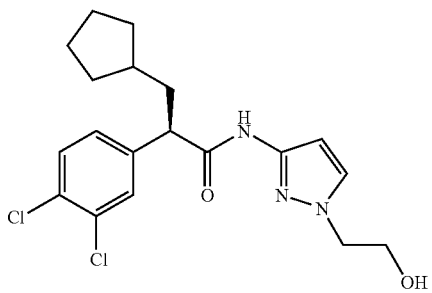

In a round bottom flask was placed 1-[2-(tert-butyl-dimethyl-silanyloxy)-ethyl]-1H-pyrazol-3-ylamine (prepared in Example 67, 86 mg, 0.36 mmol), 2,6-lutidine (57 µL, 0.49 mmol) and methylene chloride (5 mL) which was then cooled to 0° C. in an ice bath. To this solution was then added dropwise a solution of 3-cyclopentyl-2(R)-(3,4-dichloro-phenyl)-propionyl chloride in methylene chloride (prepared as in Example 102, ~0.16 M solution, 2 mL, 0.33 mmol). The reaction was then allowed to warm up to 25° C. and stirred for 16 h. After this time the reaction mixture was diluted with methylene chloride (5 mL) transferred to a separatory funnel and washed with a saturated aqueous sodium bicarbonate solution (10 mL) and then a 1 N aqueous hydrochloric acid solution (10 mL) and then dried over magnesium sulfate, filtered and concentrated in vacuo. Purification on an AnaLogix Intelliflash system (4 g column, 20% ethyl acetate/hexanes) afforded (R)—N-{1-[2-(tert-butyl-dimethyl-silanyloxy)-ethyl]-1H-pyrazol-3-yl}-3-cyclopentyl-2-(3,4-dichloro-phenyl)-propionamide (128 mg, 77%) as a white foam: $[\alpha]^{30}_{589}$=−74.3° (c=0.14, methylene chloride); ES-HRMS m/e calcd for $C_{25}H_{37}N_3O_2SiCl_2$ $(M+H)^+$ 510.2105, observed 510.2105; $^1$H NMR (300 MHz, DMSO-$d_6$) δ −0.09 (s, 6H, 2×SiCH$_3$), 0.77 (s, 9H, 3×CH$_3$), 1.10 (m, 2H, CH$_2$), 1.35-1.80 (m, 8H, 4×CH$_2$), 2.05 (m, 1H, CH), 3.81 (m, 1H, ArCHCO), 3.84 (t, J=5.4 Hz, 2H, OCH$_2$), 4.04 (t, J=5.4 Hz, 2 H, NCH$_2$), 6.40 (d, J=2.3 Hz, 1H, Ar), 7.34 (dd, $J_m$=2.1 Hz, $J_o$=8.3 Hz, 1H, Ar), 7.51 (d, J=2.3 Hz, 1H, Ar), 7.58 (d, $J_o$=8.3 Hz, 1H, Ar), 7.59 (d, $J_m$=2.1 Hz, 1H, Ar), 10.68 (s, 1H, NH).

In a round bottom flask was placed (R)—N-{1-[2-(tert-butyl-dimethyl-silanyloxy)-ethyl]-1H-pyrazol-3-yl}-3-cyclopentyl-2-(3,4-dichloro-phenyl)-propionamide (128 mg, 0.25 mmol), ethanol (10 mL) and concentrated hydrochloric acid (2 drops). This solution was then stirred at 25° C. until all starting material is consumed (~1 hr). The reaction was then diluted with ethyl acetate (30 mL) and transferred to a separatory funnel where it was washed with a saturated aqueous solution of sodium bicarbonate (10 mL). The aqueous layer was then extracted with ethyl acetate (3×10 mL). The organic layers were then combined dried over magnesium sulfate, filtered and concentrated in vacuo. Purification on an AnaLogix Intelliflash system (4 g column, 20% ethyl acetate/hexanes to 60% ethyl acetate/hexanes) afforded (R)-3-cyclopentyl-2-(3,4-dichloro-phenyl)-N-[1-(2-hydroxy-ethyl)-1H-pyrazol-3-yl]-propionamide (89 mg, 90%) as a white foam: $[\alpha]^{30}_{589}$=−22.2° (c=0.18, methylene chloride); ES-HRMS m/e calcd for $C_{19}H_{23}N_3O_2Cl_2$ $(M+H)^+$ 418.1059, observed 418.1061; $^1$H NMR (300 MHz, DMSO-$d_6$) δ 1.10 (m, 2H, CH$_2$), 1.35-1.79 (m, 8H, 4×CH$_2$), 2.05 (m, 1H, CH), 3.67 (q, J=5.6 Hz, 2H, OCH$_2$), 3.79 (m, 1H, ArCHCO), 4.00 (t, J=5.6 Hz, 2H, NCH$_2$), 4.83 (t, J=5.4 Hz, 1H, OH), 6.40 (d, J=2.2 Hz, 1H, Ar), 7.34 (dd, $J_m$=2.0 Hz, $J_o$=8.2 Hz, 1H, Ar), 7.53 (d, J=2.2 Hz, 1H, Ar), 7.58 (d, $J_o$=8.2 Hz, 1H, Ar), 7.59 (s, 1H, Ar), 10.71 (s, 1H, NH).

Example 106

2-(3-Chloro-4-methanesulfonyl-phenyl)-3-((R)-3,3-difluoro-cyclopentyl)-N-[1-(2-hydroxy-2-methyl-propyl)-1H-pyrazol-3-yl]-propionamide

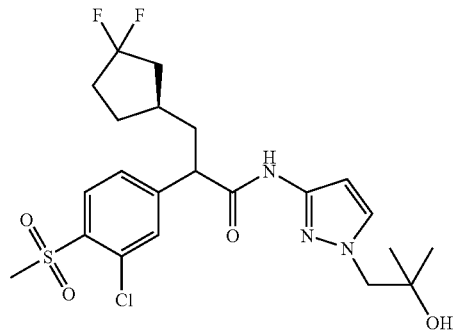

In a round bottom flask was placed (R)-2-(3-chloro-4-methanesulfonyl-phenyl)-3-((R)-3-oxo-cyclopentyl)-propionic acid (prepared as in PCT WO 2003/095438, Example 48, 500 mg, 1.45 mmol) and methylene chloride (5 mL). To this solution was then added (diethylamino)sulfur trifluoride (957 µL, 7.25 mmol) and the reaction was then heated in an oil bath at 60° C. for 8 h it was then cooled to 25° C. and stirred for 40 h. After this time, the reaction was quenched with methanol (2 mL) and water (10 mL). It was transferred to a separatory funnel and the layers separated. The aqueous layer was then extracted with methylene chloride (3×20 mL). The organics combined and dried over sodium sulfate, filtered and concentrated in vacuo. Purification on an AnaLogix Intelliflash system (12 g column, 15% ethyl acetate/hexanes to 40% ethyl acetate/hexanes) afforded (R)-2-(3-chloro-4-methanesulfonyl-phenyl)-3-((R)-3,3-difluoro-cyclopentyl)-propionic acid methyl ester (294 mg, 53%) as a yellow oil: $[\alpha]^{28}_{589}$=−67.2° (c=0.18, methylene chloride); ES-HRMS m/e calcd for $C_{16}H_{19}O_4SClF_2$ $(M+Na)^+$ 403.0553, observed 403.0552; $^1$H NMR (300 MHz, DMSO-$d_6$) δ 0.78-1.21 (m, 6H, 3×CH$_2$), 1.52-1.99 (m, 7 H, CH and 3×CH$_2$), 3.65 (s, 3H, OCH$_3$), 4.56, 4.61 (2×d, $J_{vis}$=17.9 Hz, 2H, NCH$_2$), 4.79 (dd, J=4.6 Hz, J=11.3 Hz, 1H, NCH), 7.50 (m, 1H, Ar), 7.59 (m, 2H, Ar).

(R)-2-(3-Chloro-4-methanesulfonyl-phenyl)-3-((R)-3,3-difluoro-cyclopentyl)-propionic acid methyl ester (294 mg, 0.77 mmol) was dissolved in ethanol (8 mL) and treated with a solution of lithium hydroxide monohydrate (81 mg, 1.9 mmol) in water (2 mL) at 25° C. It was stirred at 25° C. until the starting material was all consumed by TLC (~1 hr). The reaction was then concentrated in vacuo to remove the ethanol. The remaining aqueous layer was then acidified to pH=2 with an aqueous 1N hydrochloric acid solution. This was then extracted with ethyl acetate (3×20 mL), the organic layers combined and dried over magnesium sulfate, filtered and concentrated in vacuo to afford 2-(3-chloro-4-methanesulfonyl-phenyl)-3-((R)-3,3-difluoro-cyclopentyl)-propionic acid (242 mg, 86%) as a mixture of two diastereomers as a light yellow foam: ES-HRMS m/e calcd for $C_{15}H_{17}O_4SClF_2$ (M+Na)$^+$ 389.0396, observed 389.0394; $^1$H NMR (300 MHz, CDCl$_3$) δ 1.06-2.38 (m, 9H, CH and 4×CH$_2$), 3.28 (s, 3H, SO$_2$CH$_3$), 3.65 (m, 1H, ArCH), 7.42 (m, 1H, Ar), 7.54 (m, 1H, Ar), 8.14 (m, 1H, Ar).

A solution of 2-(3-chloro-4-methanesulfonyl-phenyl)-3-((R)-3,3-difluoro-cyclopentyl)-propionic acid (240 mg, 0.65 mmol) was dissolved in methylene chloride (10 mL) and N,N-dimethylformamide (one drop) and cooled to 0° C. To this solution was added dropwise a solution of oxalyl chloride in methylene chloride (2 M solution, 376 μL, 0.75 mmol) which produced gas evolution and was stirred at 0° C. for 15 min and then warmed to 25° C. and stirred for 1 h. After this time, the reaction was concentrated in vacuo to about 2 mL and then another portion of methylene chloride (~2 mL) was added to produce a roughly 0.16 M solution of 2-(3-chloro-4-methanesulfonyl-phenyl)-3-((R)-3,3-difluoro-cyclopentyl)-propionyl chloride which was used.

In a round bottom flask was placed 1-(3-amino-pyrazol-1-yl)-2-methyl-propan-2-ol (prepared as in Example 80, 56 mg, 0.36 mmol), 2,6-lutidine (54 μL, 0.49 mmol) and methylene chloride (10 mL) which was then cooled to 0° C. in an ice bath. To this solution was then added dropwise a solution of 2-(3-chloro-4-methanesulfonyl-phenyl)-3-((R)-3,3-difluoro-cyclopentyl)-propionyl chloride (~0.16 M solution, 2 mL, 0.33 mmol). The reaction was then allowed to warm up to 25° C. and stirred for 16 h. After this time the reaction mixture was quenched with a saturated aqueous sodium bicarbonate solution (10 mL) and then diluted with methylene chloride (10 mL) transferred to a separatory funnel and the layers separated. The aqueous layer was then extracted methylene chloride (3×10 mL). The organics were combined and then washed with a 1 N aqueous hydrochloric acid solution (10 mL) and then dried over magnesium sulfate, filtered and concentrated in vacuo. Purification on an AnaLogix Intelliflash system (12 g column, 55% ethyl acetate/hexanes) afforded 2-(3-chloro-4-methanesulfonyl-phenyl)-3-((R)-3,3-difluoro-cyclopentyl)-N-[1-(2-hydroxy-2-methyl-propyl)-1H-pyrazol-3-yl]-propionamide (as a mixture of two diastereomers, 90 mg, 55%) as a white foam: ES-HRMS m/e calcd for $C_{22}H_{28}N_3O_4SClF_2$ (M+H)$^+$ 504.1530, observed 504.1526; $^1$H NMR (300 MHz, DMSO-d$_6$) δ 1.03 (s, 3H, CH$_3$), 1.04 (s, 3H, CH$_3$), 1.42 (m, 1H, CH), 1.68-2.33 (m, 8H, 4×CH$_2$), 3.34 (s, 3H, SO$_2$CH$_3$), 3.87 (s, 2H, NCH$_2$), 3.90 (m, 1H, ArCHCO), 4.66 (s, 1H, OH), 6.45 (d, J=2.2 Hz, 1H, Ar), 7.52 (d, J=2.2 Hz, 1H, Ar), 7.60 (d, J$_o$=8.3 Hz, 1 H, Ar), 7.71 (s, 1H, Ar), 8.02 (d, J$_o$=8.3 Hz, 1H, Ar), 10.85 (s, 1H, NH).

Example 107

2-(3-Chloro-4-methanesulfonyl-phenyl)-3-((R)-3,3-difluoro-cyclopentyl)-N-[1-(2-methoxy-2-methyl-propyl)-1H-pyrazol-3-yl]-propionamide

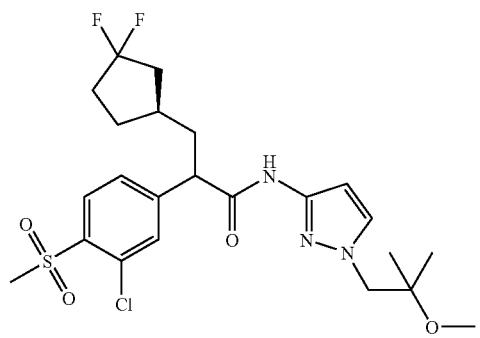

In a round bottom flask was placed 1-(2-methoxy-2-methyl-propyl)-1H-pyrazol-3-ylamine (prepared as in Example 94, 61 mg, 0.36 mmol), 2,6-lutidine (54 μL, 0.49 mmol) and methylene chloride (10 mL) which was then cooled to 0° C. in an ice bath. To this solution was then added dropwise a solution of 2-(3-chloro-4-methanesulfonyl-phenyl)-3-((R)-3,3-difluoro-cyclopentyl)-propionyl chloride (prepared as in Example 106, ~0.16 M solution, 2 mL, 0.33 mmol). The reaction was then allowed to warm up to 25° C. and stirred for 16 h. After this time the reaction mixture was quenched with a saturated aqueous sodium bicarbonate solution (10 mL) and then diluted with methylene chloride (10 mL) transferred to a separatory funnel and the layers separated. The aqueous layer was then extracted methylene chloride (3×10 mL). The organics were combined and then washed with a 1 N aqueous hydrochloric acid solution (10 mL) and then dried over magnesium sulfate, filtered and concentrated in vacuo. Purification on an AnaLogix Intelliflash system (12 g column, 35% ethyl acetate/hexanes to 70% ethyl acetate/hexanes) afforded 2-(3-chloro-4-methanesulfonyl-phenyl)-3-((R)-3,3-difluoro-cyclopentyl)-N-[1-(2-methoxy-2-methyl-propyl)-1H-pyrazol-3-yl]-propionamide (as a mixture of two diastereomers, 130 mg, 77%) as an off-white foam: ES-HRMS m/e calcd for $C_{23}H_{30}N_3O_4SClF_2$ (M+H)$^+$ 518.1687, observed 518.1684; $^1$H NMR (300 MHz, DMSO-d$_6$) δ 1.04 (s, 3H, CH$_3$), 1.05 (s, 3H, CH$_3$), 1.42 (m, 1H, CH), 1.64-2.31 (m, 8H, 4×CH$_2$), 3.14 (s, 3H, OCH$_3$), 3.34 (s, 3H, SO$_2$CH$_3$), 3.91 (m, 1 H, ArCHCO), 3.97 (s, 2 H, NCH$_2$), 6.45 (d, J=2.2 Hz, 1H, Ar), 7.48 (d, J=2.2 Hz, 1H, Ar), 7.60 (d, J$_o$=8.2 Hz, 1H, Ar), 7.71 (s, 1H, Ar), 8.02 (d, J$_o$=8.2 Hz, 1H, Ar), 10.84 (s, 1H, NH).

Example 108

N-[1-(2-Hydroxy-2-methyl-propyl)-1H-pyrazol-3-yl]-2-(4-methanesulfonyl-3-methyl-phenyl)-3-(R)-tetrahydro-furan-2-yl-propionamide

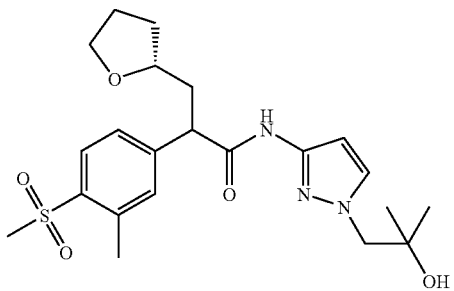

In a round bottom flask under argon was placed tetrahydrofuran (30 mL) and diisopropyl amine (787 µL, 5.62 mmol) and it was cooled to −78° C. in a dry ice/acetone bath. To this cooled solution was then added n-butyl lithium (2.5 M solution in hexanes, 2.2 mL, 5.38 mmol) and it was stirred for 15 min at −78° C. To this cooled solution was then added a solution of (3-methyl-4-methylsulfanyl-phenyl)-acetic acid methyl ester (prepared as in Example 89, 1.03 g, 4.89 mmol) in tetrahydrofuran (10 mL) and 1,3-dimethyl-3,4,5,6-tetrahydro-2(1H)-pyrimidinone (3 mL) dropwise. This was then stirred for one hour at −78° C. After such time, 2(R)-iodomethyl-tetrahydro-furan (Example 87, 1.55 g, 7.33 mmol) in 1,3-dimethyl-3,4,5,6-tetrahydro-2(1H)-pyrimidinone (2 mL) was added dropwise at −78° C. The reaction was then allowed to slowly warm to 25° C. and it was stirred for 16 h. After such time, the reaction was quenched with a saturated aqueous ammonium chloride solution (30 mL) and then extracted with ethyl acetate (3×20 mL). The organics were dried over magnesium sulfate, filtered and then concentrated in vacuo. Purification on an AnaLogix Intelliflash system (40 g column, 2% ethyl acetate/hexanes) afforded 2-(3-methyl-4-methylsulfanyl-phenyl)-3-(R)-tetrahydro-furan-2-yl-propionic acid methyl ester (952 mg, 79%) as a mixture of two diastereomers which was a yellow oil.

The mixture of diastereomers of 2-(3-methyl-4-methylsulfanyl-phenyl)-3-(R)-tetrahydro-furan-2-yl-propionic acid methyl ester (200 mg, 0.68 mmol) were dissolved in methanol (5 mL) and then sodium tungstate dihydrate (11 mg, 0.03 mmol) was added and the solution cooled to 0° C. To this cooled solution was then added a 30% aqueous solution of hydrogen peroxide (5 mL) and the ice bath was removed and the reaction allowed to warm to 25° C. and stirred for 16 h. After this time, the reaction was cooled to 0° C. in an ice bath and it was treated very slowly with a saturated aqueous solution of sodium nitrite (5 mL). The reaction was then transferred to a separatory funnel and extracted with a solution of chloroform/methanol (3/2) (3×20 mL). The extracts were than concentrated in vacuo and then redissolved in methylene chloride and dried over magnesium sulfate, filtered and concentrated in vacuo. Purification on an AnaLogix Intelliflash system (12 g column, 35% ethyl acetate/hexanes to 50% ethyl acetate/hexanes) afforded 2-(4-methanesulfonyl-3-methyl-phenyl)-3-(R)-tetrahydro-furan-2-yl-propionic acid methyl ester (123 mg, 56%) as a mixture of two diastereomers which was a sticky white solid.

The diastereomeric mixture of 2-(4-methanesulfonyl-3-methyl-phenyl)-3-(R)-tetrahydro-furan-2-yl-propionic acid methyl ester (123 mg, 0.38 mmol) was dissolved in ethanol (4 mL) and treated with a solution of lithium hydroxide monohydrate (23 mg, 0.94 mmol) in water (1 mL) at 25° C. It was stirred at 25° C. until the starting material was all consumed by TLC. The reaction was then concentrated in vacuo to remove the ethanol. The remaining aqueous layer was then acidified to pH=2 with an aqueous 1N hydrochloric acid solution. This was then extracted with ethyl acetate (3×20 mL), the organic layers combined and dried over magnesium sulfate, filtered and concentrated in vacuo to afford 2-(4-methanesulfonyl-3-methyl-phenyl)-3-(R)-tetrahydro-furan-2-yl-propionic acid (108 mg, 92%) as a mixture of two diastereomers as a foam.

A solution of the diastereomeric mixture of 2-(4-methanesulfonyl-3-methyl-phenyl)-3-(R)-tetrahydro-furan-2-yl-propionic acid (108 mg, 0.35 mmol) was dissolved in methylene chloride (5 mL) and N,N-dimethylfomamide (one drop) and cooled to 0° C. To this solution was added dropwise a solution of oxalyl chloride in methylene chloride (2 M solution, 199 µL, 0.40 mmol) which produced gas evolution and it was then stirred at 0° C. for 15 minutes and 30 min at 25° C. After this time, the reaction was concentrated in vacuo to ~1 mL. In a separate flask a solution of 1-(3-amino-pyrazol-1-yl)-2-methyl-propan-2-ol (prepared in Example 80, 60 mg, 0.38 mmol), 2,6-lutidine (57 µL, 0.52 mmol) and methylene chloride (5 mL) was cooled to 0° C. in an ice bath. To this solution was then added the solution of the prepared acid chloride diluted with another portion of methylene chloride (2 mL) dropwise. After addition was complete the reaction was then allowed to warm to 25° C. and stirred for 16 hours. After this time the reaction was diluted with methylene chloride (10 mL) and washed with a saturated aqueous sodium bicarbonate solution (1×20 mL) and the aqueous layers were than extracted with methylene chloride (2×10 mL). The combined organic layers were then washed with a 1 N aqueous hydrochloric acid solution (1×10 mL) and then dried over magnesium sulfate, filtered and concentrated in vacuo. Purification on an AnaLogix Intelliflash system (12 g column, 55% ethyl acetate/hexanes to 95% ethyl acetate/hexanes) afforded N-[1-(2-hydroxy-2-methyl-propyl)-1H-pyrazol-3-yl]-2-(4-methanesulfonyl-3-methyl-phenyl)-3-(R)-tetrahydro-furan-2-yl-propionamide (99 mg, 64%) as a roughly 1:1 mixture of diastereomers as a white foam: ES-HRMS m/e calcd for $C_{22}H_{31}N_3O_5S$ (M+Na)$^+$ 472.1876, observed 472.1879; $^1$H NMR (300 MHz, DMSO-d$_6$) δ 1.03 (s, 6H, 2×CH$_3$), 1.43 (m, 1H, CH of CH$_2$), 1.61-1.98 (m, 4H, 2×CH$_2$), 2.09-2.40 (m, 1H, CH of CH$_2$), 2.61 (s, 3H, ArCH$_3$), 3.17 (s, 3H, SO$_2$CH$_3$), 3.43-3.78 (m, 3H, OCH and OCH$_2$), 3.85 (s, 2H, NCH$_2$), 3.91-4.06 (m, 1H, ArCHCO), 4.64 (s, 1H, OH), 6.44 (m, 1 H, Ar), 7.47 (brs, 1H, Ar), 7.45 (brd, 1H, Ar), 7.50 (m, 1H, Ar), 7.85 (brd, 1H, Ar), 10.70, 10.76 (2×s, 1H, NH).

Example 109

(R)-2-(3-Chloro-4-methanesulfonyl-phenyl)-3-((R)-3,3-difluoro-cyclopentyl)-N-[1-(2-hydroxy-2-methyl-propyl)-1H-pyrazol-3-yl]-propionamide

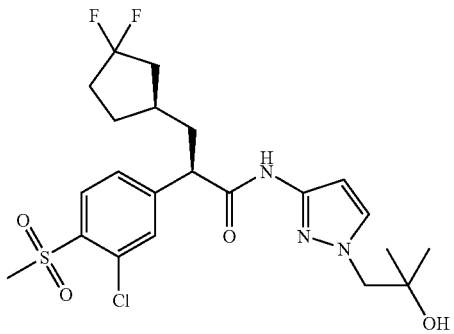

The ~1:1 diastereomeric mixture of 2-(3-chloro-4-methanesulfonyl-phenyl)-3-((R)-3,3-difluoro-cyclopentyl)-N-[1-(2-hydroxy-2-methyl-propyl)-1H-pyrazol-3-yl]-propionamide (prepared in Example 106, 90 mg) was separated into the single diastereomers by supercritical fluid chromatography (SFC) on a Berger MultiGram II Supercritical Fluid Chromatography (SFC) system (Mettler-Toledo AutoChem Berger Instruments, Newark, Del.) (Chiral column: Daicel OD-H, 250 mm×30 mm i.d., 5 μm-particle size, temperature: 35° C., flow rate of 70 mL/min, and 100 bar back pressure, 20% methanol as mobile phase modifier, UV Detection: 220 nm) to afford the two pure diastereomers: the first peak to elute was the (R)-2-(3-chloro-4-methanesulfonyl-phenyl)-3-((R)-3,3-difluoro-cyclopentyl)-N-[1-(2-hydroxy-2-methyl-propyl)-1H-pyrazol-3-yl]-propionamide diastereomer which was isolated as a white foam (29 mg) $[\alpha]^{25}_{589}$=−14.0° (c=0.10, methylene chloride); ES-HRMS m/e calcd for $C_{22}H_{28}N_3O_4SClF_2$ (M+Na)$^+$ 526.1349, observed 526.1346; $^1$H NMR (400 MHz, CDCl$_3$) δ 1.15 (s, 3H, CH$_3$), 1.17 (s, 3H, CH$_3$), 1.45 (m, 1H, CH), 1.55 (brs, 1H, OH), 1.66-2.39 (m, 8H, 4×CH$_2$), 3.28 (s, 3H, SO$_2$CH$_3$), 3.53 (m, 1H, ArCHCO), 3.94 (s, 2H, NCH$_2$), 6.72 (brs, 1 H, Ar), 7.33 (brs, 1H, Ar), 7.48 (d, J$_o$=8.2 Hz, 1H, Ar), 7.61 (s, 1H, Ar), 7.94 (brs, 1 H, NH), 8.14 (d, J$_o$=8.2 Hz, 1H, Ar).

Example 110

(R)-2-(3-Chloro-4-methanesulfonyl-phenyl)-3-((R)-3,3-difluoro-cyclopentyl)-N-[1-(2-methoxy-2-methyl-propyl)-1H-pyrazol-3-yl]-propionamide

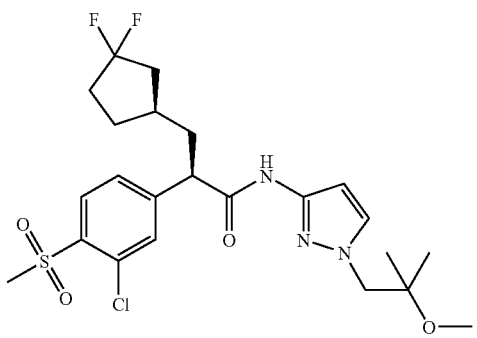

The ~1:1 diastereomeric mixture of 2-(3-chloro-4-methanesulfonyl-phenyl)-3-((R)-3,3-difluoro-cyclopentyl)-N-[1-(2-methoxy-2-methyl-propyl)-1H-pyrazol-3-yl]-propionamide (prepared in Example 107, 130 mg) was separated into the single diastereomers by supercritical fluid chromatography (SFC) on a Berger MultiGram II Supercritical Fluid Chromatography (SFC) system (Mettler-Toledo AutoChem Berger Instruments, Newark, Del.) (Chiral column: Daicel OD-H, 250 mm×30 mm i.d., 5 μm-particle size, temperature: 35° C., flow rate of 70 mL/min, and 100 bar back pressure, 20% methanol as mobile phase modifier, UV Detection: 220 nm) to afford the two pure diastereomers: the first peak to elute was the (R)-2-(3-chloro-4-methanesulfonyl-phenyl)-3-((R)-3,3-difluoro-cyclopentyl)-N-[1-(2-methoxy-2-methyl-propyl)-1H-pyrazol-3-yl]-propionamide diastereomer which was isolated as a white foam (49 mg) $[\alpha]^{31}_{589}$=−21.7° (c=0.12, methylene chloride); ES-HRMS m/e calcd for $C_{23}H_{30}N_3O_4SClF_2$ (M+Na)$^+$ 540.1506, observed 540.1505; $^1$H NMR (400 MHz, DMSO-d$_6$) δ 1.04 (s, 3H, CH$_3$), 1.05 (s, 3H, CH$_3$), 1.41 (m, 1H, CH), 1.68-2.25 (m, 8H, 4×CH$_2$), 3.14 (s, 3H, OCH$_3$), 3.34 (s, 3H, SO$_2$CH$_3$), 3.91 (m, 1H, ArCHCO), 3.97 (s, 2H, NCH$_2$), 6.45 (d, J=2.2 Hz, 1H, Ar), 7.48 (d, J=2.2 Hz, 1H, Ar), 7.60 (dd, $J_m$=1.4 Hz, $J_o$=8.2 Hz, 1H, Ar), 7.71 (d, $J_m$=1.4 Hz, 1H, Ar), 8.01 (d, $J_o$=8.2 Hz, 1H, Ar), 10.83 (s, 1H, NH).

Example 111

(R)—N-[1-(2-Hydroxy-2-methyl-propyl)-1H-pyrazol-3-yl]-2-(4-methanesulfonyl-3-methyl-phenyl)-3-(R)-tetrahydro-furan-2-yl-propionamide

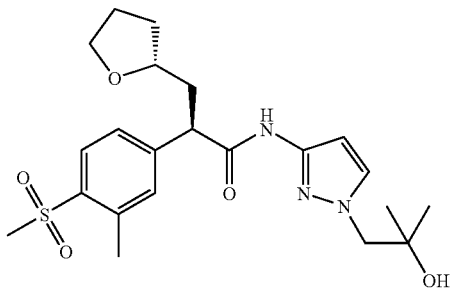

The ~1:1 diastereomeric mixture of N-[1-(2-hydroxy-2-methyl-propyl)-1H-pyrazol-3-yl]-2-(4-methanesulfonyl-3-methyl-phenyl)-3-(R)-tetrahydro-furan-2-yl-propionamide (prepared in Example 108, 90 mg) was separated into the single diastereomers by supercritical fluid chromatography (SFC) on a Berger MultiGram II Supercritical Fluid Chromatography (SFC) system (Mettler-Toledo AutoChem Berger Instruments, Newark, Del.) (Chiral column: (R,R)-Whelk O 1, 250 mm×20 mm i.d., 10 μm-particle size, temperature: 35° C., flow rate of 70 mL/min, and 100 bar back pressure, 25% methanol as mobile phase modifier, UV Detection: 220 nm) to afford the two pure diastereomers: the first peak to elute was the (R)—N-[1-(2-hydroxy-2-methyl-propyl)-1H-pyrazol-3-yl]-2-(4-methanesulfonyl-3-methyl-phenyl)-3-(R)-tetrahydro-furan-2-yl-propionamide diastereomer which was isolated as a white foam (39 mg): $[\alpha]^{31}_{589}$=–41.3° (c=0.15, methylene chloride); ES-HRMS m/e calcd for $C_{22}H_{31}N_3O_5S$ (M+H)+ 450.2057, observed 450.2056; $^1$H NMR (400 MHz, DMSO-$d_6$) δ 1.02 (s, 3H, $CH_3$), 1.03 (s, 3H, $CH_3$), 1.41 (m, 1H, CH of $CH_2$), 1.68-1.93 (m, 4H, 2×$CH_2$), 2.17 (m, 1H, CH of $CH_2$), 2.62 (s, 3H, Ar$CH_3$), 3.18 (s, 3H, $SO_2CH_3$), 3.45-3.57 (m, 2H, OCH and OCH of $OCH_2$), 3.72 (m, 1H, OCH of $OCH_2$), 3.86 (s, 2H, $NCH_2$), 3.95 (t, J=7.5 Hz, 1H, ArCHCO), 4.64 (s, 1H, OH), 6.44 (d, J=2.3 Hz, 1H, Ar), 7.44 (brs, 1H, Ar), 7.45 (brd, 1H, Ar,) 7.49 (d, J=2.3 Hz, 1H, Ar), 7.85 (d, $J_o$=8.0 Hz, 1H, Ar), 10.70 (s, 1H, NH).

Example 112

2-(3-Chloro-4-methanesulfonyl-phenyl)-3-((S)-3,3-difluoro-cyclopentyl)-N-[1-(2-hydroxy-2-methyl-propyl)-1H-pyrazol-3-yl]-propionamide

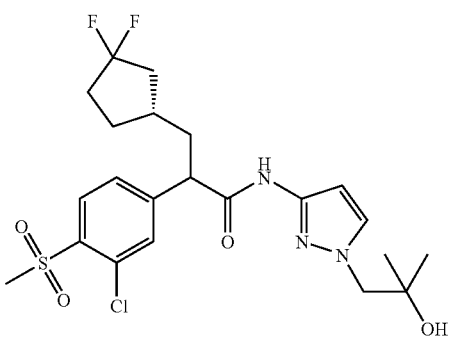

In a round bottom flask was placed (R)-2-(3-chloro-4-methanesulfonyl-phenyl)-3-((S)-3-oxo-cyclopentyl)-propionic acid (prepared as in PCT WO 2003/095438, Example 47, 520 mg, 1.51 mmol) and methylene chloride (15 mL). To this solution was then added (diethylamino) sulfur trifluoride (952 μL, 7.5 mmol) and the reaction was then heated in an oil bath at 60° C. for 16 h. After this time, the reaction was quenched with methanol (2 mL) and water (10 mL). It was transferred to a separatory funnel and the layers separated. The aqueous layer was then extracted with methylene chloride (3×15 mL). The organics combined and dried over magnesium sulfate, filtered and concentrated in vacuo. Purification on an AnaLogix Intelliflash system (12 g column, 25% ethyl acetate/hexanes to 50% ethyl acetate/hexanes) afforded (R)-2-(3-chloro-4-methanesulfonyl-phenyl)-3-((S)-3,3-difluoro-cyclopentyl)-propionic acid methyl ester (224 mg, 39%) as a yellow oil: $[\alpha]^{30}_{589}$=–44.1° (c=0.22, methylene chloride); EI-HRMS m/e calcd for $C_{16}H_{19}O_4SClF_2$ (M+) 380.0661, observed 380.0660; $^1$H NMR (300 MHz, $CDCl_3$) δ 1.38-2.35 (m, 9H, CH and 4×$CH_2$), 3.28 (s, 3H, $SO_2CH_3$), 3.63 (m, 1 H, ArCH), 3.71 (s, 3H, $OCH_3$), 7.41 (m, 1H, Ar), 7.53 (brs, 1H, Ar), 8.12 (m, 1 H, Ar).

(R)-2-(3-Chloro-4-methanesulfonyl-phenyl)-3-((S)-3,3-difluoro-cyclopentyl)-propionic acid methyl ester (224 mg, 0.59 mmol) was dissolved in ethanol (8 mL) and treated with a solution of lithium hydroxide monohydrate (62 mg, 1.47 mmol) in water (2 mL) at 25° C. It was stirred at 25° C. until the starting material was all consumed by TLC (~1 hr). The reaction was then concentrated in vacuo to remove the ethanol. The remaining aqueous layer was then acidified to pH=2 with an aqueous 1N hydrochloric acid solution. This was then extracted with ethyl acetate (3×20 mL), the organic layers combined and dried over magnesium sulfate, filtered and concentrated in vacuo to afford 2-(3-chloro-4-methanesulfonyl-phenyl)-3-((S)-3,3-difluoro-cyclopentyl)-propionic acid (210 mg, 97%) as a mixture of two diastereomers as a clear colorless oil.

A solution of 2-(3-chloro-4-methanesulfonyl-phenyl)-3-((S)-3,3-difluoro-cyclopentyl)-propionic acid (210 mg, 0.57 mmol) was dissolved in methylene chloride (10 mL) and N,N-dimethylformamide (one drop) and cooled to 0° C. To this solution was added dropwise a solution of oxalyl chloride in methylene chloride (2 M solution, 329 μL, 0.66 mmol) which produced gas evolution and was stirred at 0° C. for 15 min and then warmed to 25° C. and stirred for 1 h. After this time, the reaction was concentrated in vacuo to about 2 mL. In another round bottom flask was placed 1-(3-amino-pyrazol-1-yl)-2-methyl-propan-2-ol (prepared as in Example 80, 97 mg, 0.63 mmol), 2,6-lutidine (95 μL, 0.86 mmol) and methylene chloride (10 mL) which was then cooled to 0° C. in an ice bath. To this solution was then added the solution of the prepared acid chloride diluted with another portion of methylene chloride (2 mL) dropwise. The reaction was then allowed to warm up to 25° C. and stirred for 16 h. After this time the reaction mixture diluted with methylene chloride (10 mL). The organic layers were then washed with a saturated aqueous sodium bicarbonate solution (10 mL). The aqueous layer was then extracted with methylene chloride (2×10 mL). The organics were combined and then washed with a 1 N aqueous hydrochloric acid solution (10 mL) and then dried over magnesium sulfate, filtered and concentrated in vacuo. Purification on an Isco flash system (12 g column, 40% ethyl acetate/hexanes to 65% ethyl acetate/hexanes) afforded 2-(3-chloro-4-methanesulfonyl-phenyl)-3-((S)-3,3-difluoro-cyclopentyl)-N-[1-(2-hydroxy-2-methyl-propyl)-1H-pyrazol-3-yl]-propionamide (as a mixture of two diastereomers, 207 mg, 72%) as a light yellow foam: ES-HRMS m/e calcd for $C_{22}H_{28}N_3O_4SClF_2$ (M+H)$^+$ 504.1530, observed 504.1526; $^1$H NMR (300 MHz, DMSO-d$_6$) δ 1.03 (s, 3H, CH$_3$), 1.04 (s, 3H, CH$_3$), 1.42 (m, 1H, CH), 1.65-2.29 (m, 8H, 4×CH$_2$), 3.34 (s, 3H, SO$_2$CH$_3$), 3.87 (s, 2H, NCH$_2$), 3.90 (m, 1H, ArCHCO), 4.65 (s, 1H, OH), 6.45 (d, J=2.0 Hz, 1H, Ar), 7.52 (d, J=2.0 Hz, 1H, Ar), 7.60 (d, J$_o$=8.3 Hz, 1H, Ar), 7.71 (s, 1H, Ar), 8.01 (d, J$_o$=8.3 Hz, 1H, Ar), 10.85 (s, 1H, NH).

Example 113

(R)-3-Cyclopentyl-N-[1-(2-hydroxy-ethyl)-1H-pyrazol-3-yl]-2-(4-methanesulfonyl-3-methoxy-phenyl)-propionamide

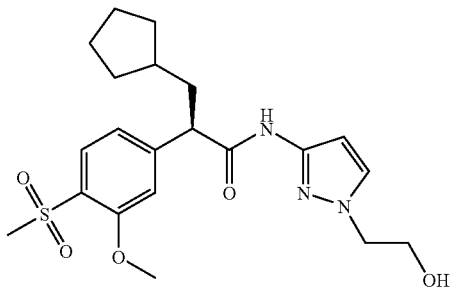

In a round bottom flask under argon was placed (R)-3-cyclopentyl-2-(4-methanesulfonyl-3-methoxy-phenyl)-propionic acid (prepared in Example 100, 61 mg, 0.19 mmol) which was dissolved in methylene chloride (2 mL) and N,N-dimethylformamide (2 drops). To this solution was then added a solution of oxalyl chloride in methylene chloride (2.0 M solution, 100 μL, 0.20 mmol). Upon addition there was gas evolution. The reaction was stirred for 30 min at 25° C. After such time the reaction was cooled to 0° C. in an ice bath and 2,6-lutidine (47 μL, 0.38 mmol) and the reaction was stirred for 30 min at 0° C. To the solution was then added 1-[2-(tert-butyl-dimethyl-silanyloxy)-ethyl]-1H-pyrazol-3-ylamine (prepared in Example 67, 45 mg, 0.19 mmol). The reaction was then warmed to 25° C. and stirred for 2 h. After this time, the reaction was quenched with a small amount of methanol and then concentrated with silica gel (2 g) in vacuo and purified on Biotage Flash chromatography system (40S column, silica gel, 50% ethyl acetate/hexanes) to afford (R)—N-{1-[2-(tert-Butyl-dimethyl-silanyloxy)-ethyl]-1H-pyrazol-3-yl}-3-cyclopentyl-2-(4-methanesulfonyl-3-methoxy-phenyl)-propionamide (15 mg, 15%).

In a round bottom flask was placed (R)—N-{1-[2-(tert-Butyl-dimethyl-silanyloxy)-ethyl]-1H-pyrazol-3-yl}-3-cyclopentyl-2-(4-methanesulfonyl-3-methoxy-phenyl)-propionamide (14 mg, 0.03 mmol), tetrahydrofuran (2 mL), water (0.5 mL) and acetic acid (2 mL). It was stirred at 25° C. for 2 h and after this time concentrated hydrochloric acid (2 drops) was added and the reaction was complete in 20 min. The reaction was worked up and then purified on a Biotage Flash chromatography system (12M column, silica gel, 10% methanol/ethyl acetate) to afford (R)-3-cyclopentyl-N-[1-(2-hydroxy-ethyl)-1H-pyrazol-3-yl]-2-(4-methanesulfonyl-3-methoxy-phenyl)-propionamide (4 mg, 31%): $[\alpha]^{30}_{589}$=−40.0° (c=0.10, methanol); ES-HRMS m/e calcd for $C_{21}H_{29}N_3O_5S$ (M+H)$^+$ 436.1901, observed 436.1902; $^1$H NMR (300 MHz, DMSO-d$_6$) δ 1.13 (m, 2H, CH$_2$), 1.36-1.83 (m, 8H, 4×CH$_2$), 2.13 (m, 1H, CH), 3.20 (s, 3H, SO$_2$CH$_3$), 3.66 (m, 2 H, OCH$_2$), 3.86 (m, 1H, ArCHCO), 3.95 (s, 3H, OCH$_3$), 3.99 (t, J=5.7 Hz, 2 H, NCH$_2$), 4.83 (t, J=5.3 Hz, 1H, OH), 6.41 (d, J=2.2 Hz, 1H, Ar), 7.14 (dd, J$_m$=1.2 Hz, J$_o$=8.2 Hz, 1H, Ar), 7.27 (d, J$_m$=1.2 Hz, 1H, Ar), 7.53 (d, J=2.2 Hz, 1H, Ar), 7.73 (d, J$_o$=8.2 Hz, 1H, Ar), 10.72 (s, 1H, NH).

Example 114

(R)-2-(3-Cyano-4-methanesulfonyl-phenyl)-3-cyclopentyl-N-[1-(2-hydroxy-ethyl)-1H-pyrazol-3-yl]-propionamide

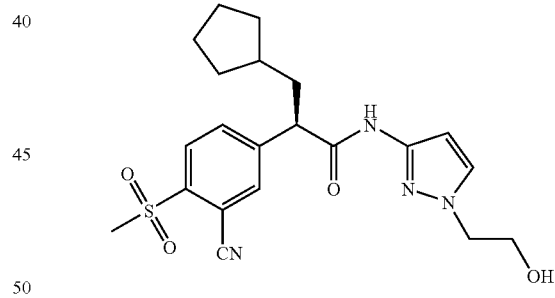

A racemic mixture of 2-(3-cyano-4-methanesulfonyl-phenyl)-3-cyclopentyl-propionic acid (prepared in PCT WO2002046173 Example 26, 1.45 g) was separated into the single chiral compounds by supercritical fluid chromatography (SFC) on a Berger MultiGram II Supercritical Fluid Chromatography (SFC) system (Mettler-Toledo AutoChem Berger Instruments, Newark, Del.) (Chiral column: Daicel OJ-H, 250 mm×30 mm i.d., 5 μm-particle size, temperature: 35° C., flow rate of 70 mL/min, and 100 bar back pressure, 15% methanol as mobile phase modifier and WV Detection: 220 nm)) to afford the two pure enantiomers: the second peak to elute was the (R)-2-(3-cyano-4-methanesulfonyl-phenyl)-3-cyclopentyl-propionic acid which was isolated as a white solid (615 mg): $[\alpha]^{29}_{589}$=−39.5° (c=0.21, methanol); ES-HRMS m/e calcd for $C_{16}H_{19}NO_4S$ (M+Na)$^+$ 344.0927, observed 344.0927; $^1$H NMR (400 MHz, CDCl$_3$) δ 1.12 (m, 2H, CH$_2$), 1.44-1.92 (m, 8H, 4×CH$_2$), 2.16 (m, 1H, CH), 3.28 (s, 3H, SO$_2$CH$_3$), 3.77 (t, J=7.7 Hz, 1H, ArCH), 7.77 (dd, J$_m$=1.8 Hz, J$_o$=8.2 Hz, 1H, Ar), 7.89 (d, J$_m$=1.8 Hz, 1H, Ar), 8.16 (d, J$_o$=8.2 Hz, 1H, Ar).

In a round bottom flask was placed (R)-2-(3-cyano-4-methanesulfonyl-phenyl)-3-cyclopentyl-propionic acid (75 mg, 0.23 mmol), methylene chloride (2 mL) and N,N-dimethylformamide (3 drops). To this solution was then added a solution of oxalyl chloride in methylene chloride (2.0 M solution, 130 μL, 0.26 mmol). Upon addition there was gas evolution. This was stirred for 30 min at 25° C. after which time it was concentrated in vacuo. The residue was then dissolved in methylene chloride (2 mL) and added dropwise into a solution of 1-[2-(tert-butyl-dimethyl-silanyloxy)-ethyl]-1H-pyrazol-3-ylamine (prepared in Example 67, 56 mg, 0.23 mmol), 2,6-lutidine (55 μL, 0.46 mmol) and methylene chloride (2 mL) at 0° C. It was then allowed to warm to 25° C. and stirred for 2 h. After this time, the reaction was quenched with a small amount of methanol and then concentrated with silica gel (2 g) in vacuo and purified on Biotage Flash chromatography system (40S column, silica gel, 40% ethyl acetate/hexanes) to afford (R)—N-{1-[2-(tert-butyl-dimethyl-silanyloxy)-ethyl]-1H-pyrazol-3-yl}-2-(3-cyano-4-methanesulfonyl-phenyl)-3-cyclopentyl-propionamide (105 mg, 84%) as a white foam: $[\alpha]^{24}_{589}$=−11.0° (c=0.20, methanol); ES-HRMS m/e calcd for C$_{27}$H$_{40}$N$_4$O$_4$SSi (M+H)$^+$ 545.2613, observed 545.2603; $^1$H NMR (400 MHz, CDCl$_3$) δ −0.05 (s, 6H, 2×SiCH$_3$), 0.84 (s, 9H, 3×CH$_3$), 1.14 (m, 2H, CH$_2$), 1.46-1.94 (m, 8H, 4×CH$_2$), 2.24 (m, 1H, CH), 3.27 (s, 3H, SO$_2$CH$_3$), 3.59 (t, J=7.6 Hz, 1H, ArCH), 3.87 (t, J=5.3 Hz, 2H, OCH$_2$), 4.08 (t, J=5.3 Hz, 2H, NCH$_2$), 6.62 (d, J=2.2 Hz, 1H, Ar), 7.35 (d, J=2.2 Hz, 1H, Ar), 7.84 (dd, J$_m$=1.8 Hz, J$_o$=8.3 Hz, 1H, Ar), 7.91 (brs, 1H, NH), 7.97 (d, J$_m$=1.8 Hz, 1H, Ar), 8.15 (d, J$_o$=8.3 Hz, 1H, Ar).

In a round bottom flask was placed (R)—N-{1-[2-(tert-butyl-dimethyl-silanyloxy)-ethyl]-1H-pyrazol-3-yl}-2-(3-cyano-4-methanesulfonyl-phenyl)-3-cyclopentyl-propionamide (102 mg, 0.19 mmol), ethanol (2 mL), and concentrated hydrochloric acid (3 drops). It was stirred at 25° C. for 1 h. The reaction was then diluted with some acetonitrile and concentrated with silica gel (2 g) in vacuo and purified on a Biotage Flash chromatography system (40S column, silica gel, 100% ethyl acetate to 10% methanol/ethyl acetate) to afford (R)-2-(3-cyano-4-methanesulfonyl-phenyl)-3-cyclopentyl-N-[1-(2-hydroxy-ethyl)-1H-pyrazol-3-yl]-propionamide (63 mg, 77%) as a light yellow solid: $[\alpha]^{30}_{589}$=−40.0° (c=0.10, methanol); ES-HRMS m/e calcd for C$_{21}$H$_{26}$N$_4$O$_4$S (M+H)$^+$ 431.1748, observed 431.1749; $^1$H NMR (400 MHz, DMSO-d$_6$) δ 1.12 (m, 2H, CH$_2$), 1.38-1.78 (m, 8H, 4×CH$_2$), 2.12 (m, 1H, CH), 3.36 (s, 3H, SO$_2$CH$_3$), 3.67 (m, 2H, OCH$_2$), 3.86 (m, 3H, ArCHCO and NCH$_2$), 4.83 (t, J=5.3 Hz, 1 H, OH), 6.41 (d, J=2.2 Hz, 1H, Ar), 7.54 (d, J=2.2 Hz, 1H, Ar), 7.95 (dd, J$_m$=1.6 Hz, J$_o$=8.2 Hz, 1H, Ar), 8.11 (d, J$_m$=1.6 Hz, 1H, Ar), 8.11 (d, J$_o$=8.2 Hz, 1H, Ar), 10.83 (s, 1H, NH).

Example 115

(R)-2-(3-Cyano-4-methanesulfonyl-phenyl)-3-cyclopentyl-N-[1-(2-hydroxy-2-methyl-propyl)-1H-pyrazol-3-yl]-propionamide

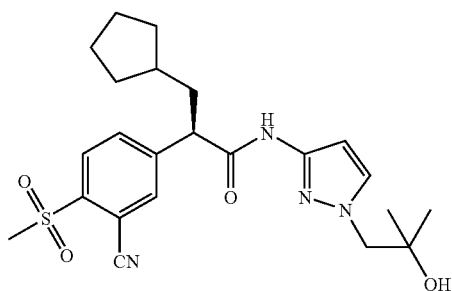

In a round bottom flask was placed (R)-2-(3-cyano-4-methanesulfonyl-phenyl)-3-cyclopentyl-propionic acid (prepared in Example 114, 65 mg, 0.20 mmol), methylene chloride (2 mL) and N,N-dimethylformamide (2 drops). To this solution was then added a solution of oxalyl chloride in methylene chloride (2.0 M solution, 110 μL, 0.22 mmol). Upon addition there was gas evolution. This was stirred for 30 min at 25° C. after which time it was concentrated in vacuo. The residue was then dissolved in methylene chloride (2 mL) and added dropwise into a solution of 1-(3-amino-pyrazol-1-yl)-2-methyl-propan-2-ol (prepared as in Example 80, 29 mg, 0.19 mmol), 2,6-lutidine (46 μL, 0.40 mmol) and methylene chloride (2 mL) at 0° C. It was then allowed to warm to 25° C. and stirred for 1 h. After this time, the reaction was quenched with a small amount of methanol, diluted with methylene chloride and then concentrated with silica gel (2 g) in vacuo and purified on Biotage Flash chromatography system (40S column, silica gel, 50% ethyl acetate/hexanes to 80% ethyl acetate/hexanes) to afford (R)-2-(3-cyano-4-methanesulfonyl-phenyl)-3-cyclopentyl-N-[1-(2-hydroxy-2-methyl-propyl)-1H-pyrazol-3-yl]-propionamide (57 mg, 62%) as a white foam: $[\alpha]^{25}_{589}$=−5.3° (c=0.17, methanol); ES-HRMS m/e calcd for C$_{23}$H$_{30}$N$_4$O$_4$S (M+H)$^+$ 459.2061, observed 459.2060; $^1$H NMR (300 MHz, DMSO-d$_6$) δ 1.03 (s, 3H, CH$_3$), 1.04 (s, 3H, CH$_3$), 1.11 (m, 2H, CH$_2$), 1.38-1.80 (m, 8H, 4×CH$_2$), 2.11 (m, 1H, CH), 3.36 (s, 3H, SO$_2$CH$_3$), 3.87 (s, 2H, NCH$_2$), 3.99 (m, 1H, ArCHCO), 4.65 (s, 1H, OH), 6.44 (d, J=2.2 Hz, 1H, Ar), 7.51 (d, J=2.2 Hz, 1H, Ar), 7.95

(dd, $J_m$=1.6 Hz, $J_o$=8.2 Hz, 1H, Ar), 8.10 (d, $J_m$=1.6 Hz, 1H, Ar), 8.10 (d, $J_o$=8.2 Hz, 1H, Ar), 10.84 (s, 1H, NH).

Example 116

(R)-2-(3-Cyano-4-methanesulfonyl-phenyl)-3-cyclopentyl-N-[1-(3-hydroxy-propyl)-1H-pyrazol-3-yl]-propionamide

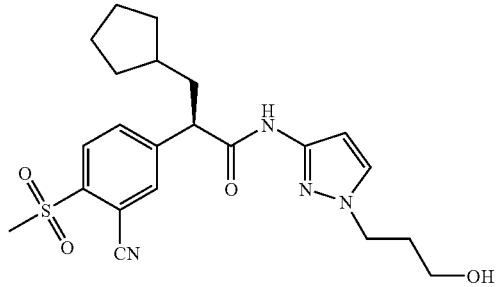

In a round bottom flask was placed (R)-2-(3-cyano-4-methanesulfonyl-phenyl)-3-cyclopentyl-propionic acid (prepared in Example 114, 65 mg, 0.20 mmol), methylene chloride (2 mL) and N,N-dimethylformamide (2 drops). To this solution was then added a solution of oxalyl chloride in methylene chloride (2.0 M solution, 110 μL, 0.22 mmol). Upon addition there was gas evolution. This was stirred for 30 min at 25° C. after which time it was concentrated in vacuo. The residue was then dissolved in methylene chloride (2 mL) and added dropwise into a solution of 3-(3-amino-pyrazol-1-yl)-propan-1-ol (prepared in Example 23, 29 mg, 0.20 mmol), 2,6-lutidine (46 μL, 0.40 mmol) and methylene chloride (2 mL) at 0° C. It was then allowed to warm to 25° C. and stirred for 1 h. After this time, the reaction was quenched with a small amount of methanol, diluted with methylene chloride and then concentrated with silica gel (2 g) in vacuo and purified on Biotage Flash chromatography system (40S column, silica gel, 50% ethyl acetate/hexanes to 10% methanol/ethyl acetate) to afford (R)-2-(3-cyano-4-methanesulfonyl-phenyl)-3-cyclopentyl-N-[1-(3-hydroxy-propyl)-1H-pyrazol-3-yl]-propionamide (60 mg, 68%) as a white foam: $[\alpha]^{25}_{589}$=−6.2° (c=0.21, methanol); ES-HRMS m/e calcd for $C_{22}H_{28}N_4O_4S$ (M+H)$^+$ 445.1904, observed 445.1903; $^1$H NMR (300 MHz, DMSO-$d_6$) δ 1.11 (m, 2H, $CH_2$), 1.38-1.90 (m, 10H, 5×$CH_2$), 2.12 (m, 1H, CH), 3.33 (brm, 2H, $OCH_2$), 3.36 (s, 3H, $SO_2CH_3$), 3.98 (m, 1H, ArCHCO), 4.02 (t, J=7.1 Hz, 2H, $NCH_2$), 4.56 (t, J=5.0 Hz, 1H, OH), 6.40 (d, J=2.2 Hz, 1H, Ar), 7.55 (d, J=2.2 Hz, 1H, Ar), 7.94 (dd, $J_m$=1.6 Hz, $J_o$=8.2 Hz, 1H, Ar), 8.10 (d, $J_m$=1.6 Hz, 1H, Ar), 8.10 (d, $J_o$=8.2 Hz, 1H, Ar), 10.83 (s, 1H, NH).

Example 117

(R)-2-(3-Cyano-4-methanesulfonyl-phenyl)-3-cyclopentyl-N-[1-(2-methoxy-ethyl)-1H-pyrazol-3-yl]-propionamide

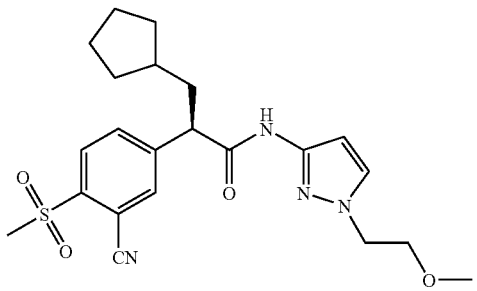

In a round bottom flask was placed (R)-2-(3-cyano-4-methanesulfonyl-phenyl)-3-cyclopentyl-propionic acid (prepared in Example 114, 65 mg, 0.20 mmol), methylene chloride (2 mL) and N,N-dimethylformamide (2 drops). To this solution was then added a solution of oxalyl chloride in methylene chloride (2.0 M solution, 110 μL, 0.22 mmol). Upon addition there was gas evolution. This was stirred for 30 min at 25° C. after which time it was concentrated in vacuo. The residue was then dissolved in methylene chloride (2 mL) and added dropwise into a solution of 1-(2-methoxy-ethyl)-1H-pyrazol-3-ylamine (prepared in Example 72, 29 mg, 0.20 mmol), 2,6-lutidine (46 μL, 0.40 mmol) and methylene chloride (2 mL) at 0° C. It was then allowed to warm to 25° C. and stirred for 1 h. After this time, the reaction was quenched with a small amount of methanol, diluted with methylene chloride and then concentrated with silica gel (2 g) in vacuo and purified on Biotage Flash chromatography system (40S column, silica gel, 50% ethyl acetate/hexanes to 80% ethyl acetate/hexanes) to afford (R)-2-(3-cyano-4-methanesulfonyl-phenyl)-3-cyclopentyl-N-[1-(2-methoxy-ethyl)-1H-pyrazol-3-yl]-propionamide (67 mg, 75%) as a colorless gum: $[\alpha]^{25}_{589}$=−9.4° (c=0.16, methanol); ES-HRMS m/e calcd for $C_{22}H_{28}N_4O_4S$ (M+H)$^+$ 445.1904, observed 445.1904; $^1$H NMR (300 MHz, DMSO-$d_6$) δ 1.12 (m, 2H, $CH_2$), 1.38-1.80 (m, 8H, 4×$CH_2$), 2.12 (m, 1H, CH), 3.19 (s, 3H, $OCH_3$), 3.36 (s, 3H, $SO_2CH_3$), 3.61 (t, J=5.3 Hz, 2H, $OCH_2$), 3.89 (m, 1H, ArCHCO), 4.12 (t, J=5.3 Hz, 2H, $NCH_2$), 6.41 (d, J=2.2 Hz, 1H, Ar), 7.55 (d, J=2.2 Hz, 1H, Ar), 7.95 (dd, $J_m$=1.6 Hz, $J_o$=8.2 Hz, 1H, Ar), 8.11 (d, $J_m$=1.6 Hz, 1H, Ar), 8.11 (d, $J_o$=8.2 Hz, 1H, Ar), 10.84 (s, 1H, NH).

Example 118

(R)—N-[1-(2-Hydroxy-ethyl)-1H-pyrazol-3-yl]-3-((R)-3-oxo-cyclopentyl)-2-(3-trifluoromethyl-phenyl)-propionamide

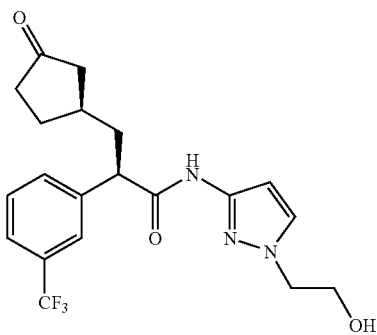

In a round bottom flask under argon was placed dry tetrahydrofuran (40 mL) and 1,1,1,3,3,3-hexamethyldisilazane (4.15 mL, 19.64 mmol). This solution was then cooled to −78° C. and treated dropwise with a solution of n-butyl lithium (2.5M solution in hexanes, 7.53 mL, 18.79 mmol). It was then stirred at −78° C. for 15 min. To this was then slowly added a solution of N-(2(R)-hydroxy-1(R)-methyl-2(R)-phenyl-ethyl)-N-methyl-2-(3-trifluoromethyl-phenyl)-acetamide (prepared as in Example 79, 3.00 g, 8.54 mmol) in dry tetrahydrofuran (30 mL) which resulted in a dark amber solution. The solution was then warmed to 0° C. and stirred for 30 min. After this time the reaction was then cooled back to −78° C. and treated dropwise with a solution (S)-2-iodomethyl-8,8-dimethyl-6,10-dioxa-spiro[4.5]decane (*J. Org. Chem.* 1983, 22, 4152-4., 3.70 g, 11.96 mmol) in 2,3-dimethyl-3,4,5,6-tetrahydro-2(1H)-pyrimidinone (2.26 mL, 18.79 mmol). The reaction was then stirred at 0° C. for 16 h. The reaction was then diluted with ethyl acetate (200 mL) and transferred to a separatory funnel and washed with a saturated aqueous ammonium chloride solution (100 mL) and then a saturated aqueous brine solution (100 mL). The organic layers were combined and then dried over sodium sulfate and concentrated in vacuo. Flash chromatography (Merck Silica gel 60, 230-400 mesh, 50% ethyl acetate/hexanes) afforded (R)-3-((R)-8,8-dimethyl-6,10-dioxa-spiro[4.5]dec-2-yl)-N-((1R,2R)-2-hydroxy-1-methyl-2-phenyl-ethyl)-N-methyl-2-(3-trifluoromethyl-phenyl)-propionamide (2.77 g, 60%) as a light gold foam: $[\alpha]^{26}_{589}$=−64.0° (c=0.20, methanol); ES-HRMS m/e calcd for $C_{30}H_{38}NO_4F_3$ (M+H)$^+$ 534.2826, observed 534.2824; $^1$H NMR (300 MHz, CDCl$_3$) δ 0.54, 1.14 (2×d, J=6.7 Hz, 3H, CH$_3$), 0.96 (m, 6H, 2×CH$_3$), 1.18-2.32 (m, 10H, OH and CH and 4×CH$_2$), 2.73, 2.91 (2×s, 3H, NCH$_3$), 3.46 (s, 4H, 2×OCH$_2$), 3.69, 4.09 (2×brm, 1H, ArCHCO), 4.39 (br, 1H, NCH), 4.52 (brm, 1H, OCH), 7.23-7.55 (m, 9H, Ar).

A solution of (R)-3-((R)-8,8-dimethyl-6,10-dioxa-spiro[4.5]dec-2-yl)-N-((1R,2R)-2-hydroxy-1-methyl-2-phenyl-ethyl)-N-methyl-2-(3-trifluoromethyl-phenyl)-propionamide (250 mg, 0.47 mmol) in dioxane (2.5 mL) was treated with a 9 N aqueous sulfuric acid solution (1.5 mL). The resulting solution was then heated at 110° C. for 16 h. The reaction was then cooled and diluted with water (50 mL) and extracted with a chloroform/methanol solution (3:2, 2×25 mL) and then concentrated. The resulting residue was then dissolved in acetonitrile and concentrated with silica gel (2 g) and purified on Biotage Flash chromatography system (40S column, silica gel, 60% ethyl acetate/hexanes) to afford (R)-3-((R)-3-oxo-cyclopentyl)-2-(3-trifluoromethyl-phenyl)-propionic acid (102 mg, 73%) as a pale yellow oil: $[\alpha]^{22}_{589}$=−86.1° (c=0.18, methanol); ES-HRMS m/e calcd for $C_{15}H_{15}O_3F_3$ (M+Na)$^+$ 323.0865, observed 323.0865; $^1$H NMR (400 MHz, CDCl$_3$) δ 1.55 (m, 1H, CH), 1.82-2.47 (m, 8H, 4×CH$_2$), 3.73 (t, J=7.8 Hz, 1H, ArCHCO), 7.47-7.61 (m, 4H, Ar).

(R)-3-((R)-3-Oxo-cyclopentyl)-2-(3-trifluoromethyl-phenyl)-propionic acid (85 mg, 0.28 mmol) was dissolved in methylene chloride (2 mL) and N,N-dimethylfomamide (three drops) at 25° C. under argon. To this solution was added dropwise a solution of oxalyl chloride in methylene chloride (2 M solution, 150 μL, 0.29 mmol) which produced gas evolution and it was then stirred at 25° C. for 30 minutes after which time it was concentrated in vacuo. The residue was then dissolved in methylene chloride (2 mL) and added dropwise into a solution of 1-[2-(tert-butyl-dimethyl-silanyloxy)-ethyl]-1H-pyrazol-3-ylamine (prepared in Example 67, 68 mg, 0.28 mmol), 2,6-lutidine (66 μL, 0.56 mmol) and methylene chloride (2 mL) at 0° C. It was then allowed to warm to 25° C. and stirred for 1.5 h. After this time, the reaction was quenched with a small amount of methanol and then concentrated with silica gel (2 g) in vacuo and purified on Biotage Flash chromatography system (40S column, silica gel, 50% ethyl acetate/hexanes) to afford (R)—N-{1-[2-(tert-butyl-dimethyl-silanyloxy)-ethyl]-1H-pyrazol-3-yl}-3-((R)-3-oxo-cyclopentyl)-2-(3-trifluoromethyl-phenyl)-propionamide (85 mg, 57%) as a yellow oil: $[\alpha]^{25}_{589}$=−9.4° (c=0.16, methanol); ES-HRMS m/e calcd for $C_{26}H_{36}N_3O_3SiF_3$ (M+Na)$^+$ 546.2370, observed 546.2367; $^1$H NMR (300 MHz, CDCl$_3$) δ -0.06 (s, 6H, 2×SiCH$_3$), 0.83 (s, 9H, 3×CH$_3$), 1.57 (m, 1H, CH), 1.82-2.47 (m, 8H, 4×CH$_2$), 3.57 (m, 1H, ArCHCO), 3.85 (t, J=5.3 Hz, 2H, OCH$_2$), 4.05 (t, J=5.3 Hz, 2H, NCH$_2$), 6.64 (d, J=2.2 Hz, 1H, Ar), 7.32 (d, J=2.2 Hz, 1H, Ar), 7.46-7.62 (m, 4H, Ar), 7.67 (brs, 1H, NH).

In a flask containing (R)—N-{1-[2-(tert-butyl-dimethyl-silanyloxy)-ethyl]-1H-pyrazol-3-yl}-3-((R)-3-oxo-cyclopentyl)-2-(3-trifluoromethyl-phenyl)-propionamide (70 mg, 0.13 mmol) was added ethanol (2 mL) and concentrated hydrochloric acid (three drops) and it was stirred at 25° C. for 1 h. It was then diluted with acetonitrile and absorbed onto silica gel (2 g) in vacuo and purified on Biotage Flash chromatography system (40S column, silica gel, 80% ethyl acetate/hexanes to 10% methanol/ethyl acetate) to afford (R)—N-[1-(2-hydroxy-ethyl)-1H-pyrazol-3-yl]-3-((R)-3-oxo-cyclopentyl)-2-(3-trifluoromethyl-phenyl)-propionamide (49 mg, 89%) as a yellow foam: $[\alpha]^{25}_{589}$=−79.3° (c=0.14, methanol); ES-HRMS m/e calcd for $C_{20}H_{22}N_3O_3F_3$ (M+H)$^+$ 410.1686, observed 410.1687; $^1$H NMR (300 MHz, DMSO-d$_6$) δ 1.51 (m, 1H, CH), 1.73-2.30 (m, 8H, 4×CH$_2$), 3.66 (m, 2H, OCH$_2$), 3.95 (m, 1H, ArCHCO), 3.99 (m, 2H, NCH$_2$), 4.83 (t, J=5.4 Hz, 1H, OH), 6.41 (d, J=2.0 Hz, 1H, Ar), 7.54 (d, J=2.0 Hz, 1 H, Ar), 7.60 (m, 2H, Ar), 7.69 (brd, 1H, Ar), 7.73 (brs, 1H, Ar), 10.79 (s, 1H, NH).

Example 119

(R)—N-[1-(2-Hydroxy-2-methyl-propyl)-1H-pyrazol-3-yl]-3-((R)-3-oxo-cyclopentyl)-2-(3-trifluoromethyl-phenyl)-propionamide

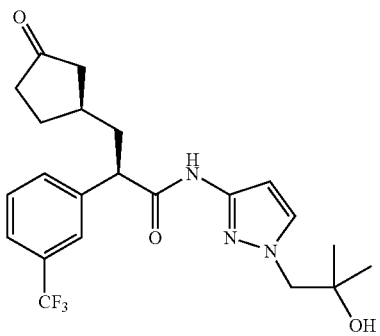

(R)-3-((R)-3-Oxo-cyclopentyl)-2-(3-trifluoromethyl-phenyl)-propionic acid (prepared in Example 118, 90 mg, 0.30 mmol) was dissolved in methylene chloride (3 mL) and N,N-dimethylformamide (three drops) at 25° C. under argon. To this solution was added dropwise a solution of oxalyl chloride in methylene chloride (2 M solution, 160 µL, 0.32 mmol) which produced gas evolution and it was then stirred at 25° C. for 30 minutes after which time it was concentrated in vacuo. The residue was then dissolved in methylene chloride (3 mL) and added dropwise into a solution of 1-(3-amino-pyrazol-1-yl)-2-methyl-propan-2-ol (prepared as in Example 80, 47 mg, 0.30 mmol), 2,6-lutidine (70 µL, 0.60 mmol) and methylene chloride (3 mL) at 0° C. It was then allowed to warm to 25° C. and stirred for 1 h. After this time, the reaction was quenched with a small amount of methanol and diluted with methylene chloride and then concentrated with silica gel (2 g) in vacuo and purified on Biotage Flash chromatography system (40S column, silica gel, 50% ethyl acetate/hexanes to 100% ethyl acetate) to afford (R)—N-[1-(2-hydroxy-2-methyl-propyl)-1H-pyrazol-3-yl]-3-((R)-3-oxo-cyclopentyl)-2-(3-trifluoromethyl-phenyl)-propionamide (84 mg) which still contained impurities. This material was then cleaned up by using reverse phase HPLC. The purified material was then concentrated in vacuo then dissolved in ethyl acetate and washed with a saturated aqueous sodium bicarbonate solution and then brine, dried over sodium sulfate and concentrated in vacuo to afford pure (R)—N-[1-(2-hydroxy-2-methyl-propyl)-1H-pyrazol-3-yl]-3-((R)-3-oxo-cyclopentyl)-2-(3-trifluoromethyl-phenyl)-propionamide (53 mg, 40%) as a white foam: $[\alpha]^{29}_{589}$=−67.5° (c=0.12, methanol); ES-HRMS m/e calcd for $C_{22}H_{26}N_3O_3F_3$ (M+H)$^+$ 438.1999, observed 438.1999; $^1$H NMR (300 MHz, DMSO-d$_6$) δ 1.03 (s, 3H, CH$_3$), 1.04 (s, 3H, CH$_3$), 1.50 (m, 1H, CH), 1.73-2.30 (m, 8H, 4×CH$_2$), 3.87 (s, 2H, NCH$_2$), 3.95 (m, 1H, ArCHCO), 4.64 (s, 1H, OH), 6.46 (d, J=2.2 Hz, 1H, Ar), 7.50 (d, J=2.2 Hz, 1H, Ar), 7.60 (m, 2H, Ar), 7.69 (brd, 1H, Ar), 7.73 (brs, 1H, Ar), 10.79 (s, 1H, NH).

Example 120

(R)—N-[1-(2-Methoxy-ethyl)-1H-pyrazol-3-yl]-3-((R)-3-oxo-cyclopentyl)-2-(3-trifluoromethyl-phenyl)-propionamide

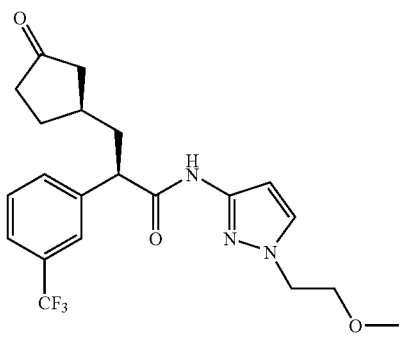

(R)-3-((R)-3-Oxo-cyclopentyl)-2-(3-trifluoromethyl-phenyl)-propionic acid (prepared in Example 118, 90 mg, 0.30 mmol) was dissolved in methylene chloride (3 mL) and N,N-dimethylformamide (three drops) at 25° C. under argon. To this solution was added dropwise a solution of oxalyl chloride in methylene chloride (2 M solution, 160 µL, 0.32 mmol) which produced gas evolution and it was then stirred at 25° C. for 30 minutes after which time it was concentrated in vacuo. The residue was then dissolved in methylene chloride (3 mL) and added dropwise into a solution of 1-(2-methoxy-ethyl)-1H-pyrazol-3-ylamine (prepared in Example 72, 42 mg, 0.20 mmol), 2,6-lutidine (70 µL, 0.60 mmol) and methylene chloride (3 mL) at 0° C. It was then allowed to warm to 25° C. and stirred for 1 h. After this time, the reaction was quenched with a small amount of methanol and diluted with methylene chloride and then concentrated with silica gel (2 g) in vacuo and purified on Biotage Flash chromatography system (40S column, silica gel, 50% ethyl acetate/hexanes to 100% ethyl acetate) to afford (R)—N-[1-(2-methoxy-ethyl)-1H-pyrazol-3-yl]-3-((R)-3-oxo-cyclopentyl)-2-(3-trifluoromethyl-phenyl)-propionamide (79 mg, 62%) as a pale yellow gum: $[\alpha]^{29}_{589}$=−79.3° (c=0.14, methanol); ES-HRMS m/e calcd for $C_{21}H_{24}N_3O_3F_3$ (M+H)$^+$ 424.1843, observed 424.1841; $^1$H NMR (300 MHz, DMSO-d$_6$) δ 1.51 (m, 1H, CH), 1.74-2.29 (m, 8H, 4×CH$_2$), 3.19 (s, 3H, OCH$_3$), 3.61 (t, J=5.3 Hz, 2H, OCH$_2$), 3.94 (m, 1H, ArCHCO), 4.12 (t, J=5.3 Hz, 2H, NCH$_2$), 6.42 (d, J=2.2 Hz, 1H, Ar), 7.54 (d, J=2.2 Hz, 1H, Ar), 7.60 (m, 2H, Ar), 7.69 (brd, 1H, Ar), 7.73 (brs, 1H, Ar), 10.80 (s, 1H, NH).

Example 121

(R)—N-[1-(3-Hydroxy-propyl)-1H-pyrazol-3-yl]-3-((R)-3-oxo-cyclopentyl)-2-(3-trifluoromethyl-phenyl)-propionamide

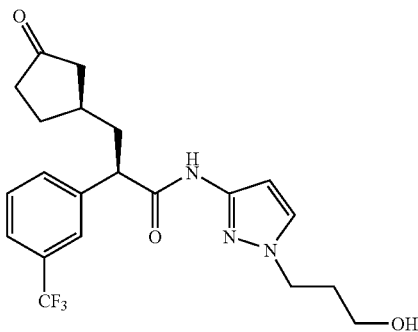

(R)-3-((R)-3-Oxo-cyclopentyl)-2-(3-trifluoromethyl-phenyl)-propionic acid (prepared in Example 118, 90 mg, 0.30 mmol) was dissolved in methylene chloride (3 mL) and N,N-dimethylformamide (three drops) at 25° C. under argon. To this solution was added dropwise a solution of oxalyl chloride in methylene chloride (2 M solution, 160 μL, 0.32 mmol) which produced gas evolution and it was then stirred at 25° C. for 30 minutes after which time it was concentrated in vacuo. The residue was then dissolved in methylene chloride (3 mL) and added dropwise into a solution of 3-(3-amino-pyrazol-1-yl)-propan-1-ol (prepared in Example 23, 43 mg, 0.30 mmol), 2,6-lutidine (70 μL, 0.60 mmol) and methylene chloride (3 mL) at 0° C. It was then allowed to warm to 25° C. and stirred for 1 h. After this time, the reaction was quenched with a small amount of methanol and diluted with methylene chloride and then concentrated with silica gel (2 g) in vacuo and purified on Biotage Flash chromatography system (40S column, silica gel, 50% ethyl acetate/hexanes to 5% methanol/ethyl acetate) to afford (R)—N-[1-(3-hydroxy-propyl)-1H-pyrazol-3-yl]-3-((R)-3-oxo-cyclopentyl)-2-(3-trifluoromethyl-phenyl)-propionamide (63 mg, 50%) as an off white foam: $[\alpha]^{29}_{589}$=–60.6° (c=0.16, methanol); ES-HRMS m/e calcd for $C_{21}H_{24}N_3O_3F_3$ (M+H)$^+$ 424.1843, observed 424.1842; $^1$H NMR (300 MHz, DMSO-d$_6$) δ 1.51 (m, 1H, CH), 1.74-2.29 (m, 10H, 5×CH$_2$), 3.33 (m, 2H, OCH$_2$), 3.94 (m, 1H, ArCHCO), 4.02 (t, J=6.8 Hz, 2H, NCH$_2$), 4.55 (t, J=5.4 Hz, 1H, OH), 6.41 (d, J=2.2 Hz, 1H, Ar), 7.55 (d, J=2.2 Hz, 1H, Ar), 7.60 (m, 2H, Ar), 7.69 (brd, 1H, Ar), 7.73 (brs, 1H, Ar), 10.78 (s, 1H, NH).

Example 122

(R)—N-[1-(2-Hydroxy-ethyl)-1H-pyrazol-3-yl]-2-(4-methanesulfonyl-3-methyl-phenyl)-3-((R)-3-oxo-cyclopentyl)-propionamide

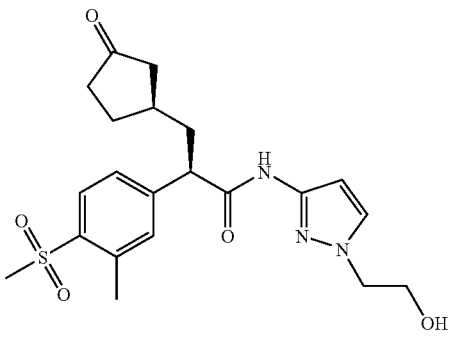

In a round bottom flask under argon was placed dry tetrahydrofuran (30 mL) and 1,1,1,3,3,3-hexamethyldisilazane (4.25 mL, 20.08 mmol). This solution was then cooled to –78° C. and treated dropwise with a solution of n-butyl lithium (2.5M solution in hexanes, 7.70 mL, 19.21 mmol). It was then stirred at –78° C. for 15 min. To this was then slowly added a solution of N-((1R,2R)-2-hydroxy-1-methyl-2-phenyl-ethyl)-N-methyl-2-(3-methyl-4-methylsulfanyl-phenyl)-acetamide (prepared as in PCT WO 2004/052869 A1, Example 57, 3.00 g, 8.73 mmol) in dry tetrahydrofuran (30 mL). The solution was then warmed to 0° C. and stirred for 60 min which resulted in an orange solution. After this time the reaction was then cooled back to –78° C. and treated dropwise with a solution (S)-2-iodomethyl-8,8-dimethyl-6,10-dioxa-spiro[4.5]decane (J. Org. Chem. 1983, 22, 4152-4., 3.78 g, 12.22 mmol) in 2,3-dimethyl-3,4,5,6-tetrahydro-2(1H)-pyrimidinone (2.31 mL, 19.21 mmol). The reaction was then stirred at 0° C. for 16 h. The reaction was then diluted with ethyl acetate (200 mL) and transferred to a separatory funnel and washed with a saturated aqueous ammonium chloride solution (100 mL) and then a saturated aqueous brine solution (100 mL). The organic layers were combined and then dried over sodium sulfate and concentrated in vacuo. Flash chromatography (Merck Silica gel 60, 230-400 mesh, 50% ethyl acetate/hexanes) afforded (R)-3-((R)-8,8-dimethyl-6,10-dioxa-spiro[4.5]dec-2-yl)-N-((1R,2R)-2-hydroxy-1-methyl-2-phenyl-ethyl)-N-methyl-2-(3-methyl-4-methylsulfanyl-phenyl)-propionamide (4.18 g, 91%) as a white foam: $[\alpha]^{28}_{589}$=–59.2° (c=0.26, methanol); ES-HRMS m/e calcd for $C_{31}H_{43}NO_4S$ (M+H)$^+$ 526.2986, observed 526.2976.

A solution of (R)-3-((R)-8,8-dimethyl-6,10-dioxa-spiro[4.5]dec-2-yl)-N-((1R,2R)-2-hydroxy-1-methyl-2-phenyl-ethyl)-N-methyl-2-(3-methyl-4-methylsulfanyl-phenyl)-propionamide (1.35 g, 2.57 mmol) in dioxane (14 mL) was treated with a 9 N aqueous sulfuric acid solution (8 mL). The resulting solution was then heated at 110° C. for 16 h. The reaction was then cooled and diluted with water (150 mL) and extracted with a chloroform/methanol solution (3:2, 2×50 mL) and then combined the organic extracts and concentrated. The resulting residue was then dissolved in acetonitrile and concentrated with silica gel (3 g) and purified on Biotage Flash chromatography system (40 L column, silica gel, 60% ethyl acetate/hexanes) to afford (R)-2-(3-methyl-4-methylsulfanyl-phenyl)-3-((R)-3-oxo-cyclopentyl)-propionic acid (674 mg, 90%) as a pale yellow gum: $[\alpha]^{28}_{958}$=–115.4° (c=0.35, methanol); ES-HRMS m/e calcd for $C_{16}H_{20}O_3S$ (M+Na)$^+$ 315.1025, observed 315.1025; $^1$H NMR (300 MHz, DMSO-$d_6$) δ 1.46 (m, 1H, CH), 1.76-2.32 (m, 8H, 4×CH$_2$), 2.22 (s, 3H, ArCH$_3$), 2.44 (s, 3H, SCH$_3$), 3.48 (m, 1H, ArCHCO), 7.14 (m, 3H, Ar), 12.31 (s, 1H, CO$_2$H).

In a flask was placed sodium periodate (725 mg, 3.38 mmol) and water (6 mL). To this solution was then added (R)-2-(3-methyl-4-methylsulfanyl-phenyl)-3-((R)-3-oxo-cyclopentyl)-propionic acid (525 mg, 1.80 mmol) in methanol (11 mL). The reaction was then stirred at 25° C. for 1 h after which time there was a white precipitate. The reaction was then filtered through a plug of celite and the celite pad washed with chloroform. The filterate was concentrated in vacuo and then azeotroped with acetonitrile. The residue was then dissolved in methanol (20 mL) and added slowly to a solution of potassium permanganate (425 mg, 2.70 mmol) in water (5 mL) and stirred at 25° C. for 1 h. After this time the reaction turned dark brown and the solids were filtered off and washed with methanol. The filterate was concentrated in vacuo and the residue was dissolved in acetonitrile with a small amount of methanol and then concentrated with silica gel (2 g) in vacuo and purified on Biotage Flash chromatography system (40M column, silica gel, 20% methanol/ethyl acetate) to afford (R)-2-(4-methanesulfonyl-3-methyl-phenyl)-3-((R)-3-oxo-cyclopentyl)-propionic acid (523 mg, 90%) as a white solid: $[\alpha]^{31}_{589}$=–90.0° (c=0.15, methanol); ES-HRMS m/e calcd for $C_{16}H_{20}O_5S$ (M+H)$^+$ 325.1104, observed 325.1104; $^1$H NMR (300 MHz, DMSO-$d_6$) δ 1.48 (m, 1H, CH), 1.78-2.35 (m, 8H, 4×CH$_2$), 2.63 (s, 3H, ArCH$_3$), 3.20 (s, 3H, SO$_2$CH$_3$), 3.67 (t, J=7.6 Hz, 1H, ArCHCO), 7.42 (m, 2H, Ar), 7.85 (d, J$_o$=8.6 Hz, 1H, Ar), 12.64 (s, 1H, CO$_2$H).

(R)-2-(4-methanesulfonyl-3-methyl-phenyl)-3-((R)-3-oxo-cyclopentyl)-propionic acid (85 mg, 0.26 mmol) was dissolved in methylene chloride (2 mL) and N,N-dimethylformamide (three drops) at 25° C. under argon. To this solution was added dropwise a solution of oxalyl chloride in methylene chloride (2 M solution, 140 µL, 0.27 mmol) which produced gas evolution and it was then stirred at 25° C. for 30 minutes after which time it was concentrated in vacuo. The residue was then dissolved in methylene chloride (2 mL) and added dropwise into a solution of 1-[2-(tert-butyl-dimethyl-silanyloxy)-ethyl]-1H-pyrazol-3-ylamine (prepared in Example 67, 63 mg, 0.26 mmol), 2,6-lutidine (62 µL, 0.52 mmol) and methylene chloride (2 mL) at 0° C. It was then allowed to warm to 25° C. and stirred for 1 h. After this time, the reaction was quenched with a small amount of methanol and then concentrated with silica gel (2 g) in vacuo and purified on Biotage Flash chromatography system (40S column, silica gel, 50% ethyl acetate/hexanes to 80% ethyl acetate/hexanes) to afford (R)—N-{1-[2-(tert-butyl-dimethyl-silanyloxy)-ethyl]-1H-pyrazol-3-yl}-2-(4-methanesulfonyl-3-methyl-phenyl)-3-((R)-3-oxo-cyclopentyl)-propionamide (109 mg, 77%) as a yellow oil: $[\alpha]^{25}_{589}$=–50.0° (c=0.21, methanol); ES-HRMS m/e calcd for $C_{27}H_{41}N_3O_5SSi$ (M+H)$^+$ 548.2609, observed 548.2609; $^1$H NMR (300 MHz, CDCl$_3$) δ –0.06 (s, 6H, 2×SiCH$_3$), 0.84 (s, 9H, 3×CH$_3$), 1.57 (m, 1H, CH), 1.82-2.47 (m, 8H, 4×CH$_2$), 2.72 (s, 3H, ArCH$_3$), 3.09 (s, 3H, SO$_2$CH$_3$), 3.55 (t, J=7.3 Hz, 1H, ArCHCO), 3.85 (t, J=5.3 Hz, 2H, OCH$_2$), 4.06 (t, J=5.3 Hz, 2H, NCH$_2$), 6.64 (d, J=2.2 Hz, 1H, Ar), 7.35 (m, 3H, Ar), 7.75 (brs, 1H, NH), 8.03 (d, J$_o$=8.2 Hz, 1H, Ar).

In a flask containing (R)—N-{1-[2-(tert-butyl-dimethyl-silanyloxy)-ethyl]-1H-pyrazol-3-yl}-2-(4-methanesulfonyl-3-methyl-phenyl)-3-((R)-3-oxo-cyclopentyl)-propionamide (100 mg, 0.18 mmol) was added ethanol (3 mL) and concentrated hydrochloric acid (three drops) and it was stirred at 25° C. for 45 min. It was then diluted with acetonitrile and absorbed onto silica gel (2 g) in vacuo and purified on Biotage Flash chromatography system (40S column, silica gel, 80% ethyl acetate/hexanes to 10% methanol/ethyl acetate) to afford (R)—N-[1-(2-hydroxy-ethyl)-1H-pyrazol-3-yl]-2-(4-methanesulfonyl-3-methyl-phenyl)-3-((R)-3-oxo-cyclopentyl)-propionamide (55 mg, 69%) as a yellow foam: $[\alpha]^{32}_{589}$=–73.6° (c=0.14, methanol); ES-HRMS m/e calcd for $C_{21}H_{27}N_3O_5S$ (M+H)$^+$ 434.1745, observed 434.1745; $^1$H NMR (400 MHz, DMSO-$d_6$) δ 1.51 (m, 1H, CH), 1.77-2.28 (m, 8H, 4×CH$_2$), 2.63 (s, 3H, ArCH$_3$), 3.18 (s, 3H, SO$_2$CH$_3$), 3.67 (q, J=5.5 Hz, 2H, OCH$_2$), 3.91 (m, 1H, ArCHCO), 3.99 (t, J=5.5 Hz, 2H, NCH$_2$), 4.82 (t, J=5.5 Hz, 1H, OH), 6.41 (d, J=2.2 Hz, 1H, Ar), 7.46 (brs, 1H, Ar), 7.47 (brd, 1H, Ar), 7.53 (d, J=2.2 Hz, 1H, Ar), 7.86 (d, J$_o$=8.5 Hz, 1H, Ar), 10.77 (s, 1H, NH).

Example 123

(R)—N-[1-(2-Hydroxy-2-methyl-propyl)-1H-pyrazol-3-yl]-2-(4-methanesulfonyl-3-methyl-phenyl)-3-((R)-3-oxo-cyclopentyl)-propionamide

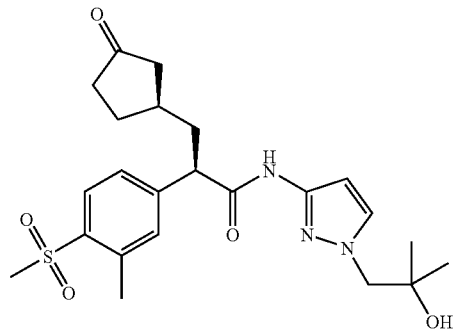

(R)-2-(4-Methanesulfonyl-3-methyl-phenyl)-3-((R)-3-oxo-cyclopentyl)-propionic acid (prepared in Example 122, 65 mg, 0.20 mmol) was dissolved in methylene chloride (2 mL) and N,N-dimethylformamide (two drops) at 25° C. under argon. To this solution was added dropwise a solution of oxalyl chloride in methylene chloride (2 M solution, 110 µL, 0.21 mmol) which produced gas evolution and it was then stirred at 25° C. for 30 minutes after which time it was concentrated in vacuo. The residue was then dissolved in methylene chloride (2 mL) and added dropwise into a solution of 1-(3-amino-pyrazol-1-yl)-2-methyl-propan-2-ol (prepared as in Example 80, 31 mg, 0.20 mmol), 2,6-lutidine (46 µL, 0.40 mmol) and methylene chloride (2 mL) at 0° C. It was then allowed to warm to 25° C. and stirred for 1 h. After this time, the reaction was quenched with a small amount of methanol and diluted with methylene chloride and then concentrated with silica gel (2 g) in vacuo and purified on Biotage Flash chromatography system (40S column, silica gel, 50% ethyl acetate/hexanes to 100% ethyl acetate) to afford (R)—N-[1-(2-hydroxy-2-methyl-propyl)-1H-pyrazol-3-yl]-2-(4-methanesulfonyl-3-methyl-phenyl)-3-((R)-3-oxo-cyclopentyl)-propionamide (71 mg, 77%) as a white foam: $[\alpha]^{32}_{589}$=–63.3° (c=0.15, methanol); ES-HRMS m/e calcd for $C_{23}H_{31}N_3O_5S$ (M+H)$^+$ 462.2057, observed 462.2058; $^1$H NMR (300 MHz, DMSO-$d_6$) δ 1.03 (s, 3H, CH$_3$), 1.04 (s, 3H, CH$_3$), 1.50 (m, 1H, CH), 1.76-2.30 (m, 8H, 4×CH$_2$), 2.62 (s, 3H, ArCH$_3$), 3.18 (s, 3H, SO$_2$CH$_3$), 3.86 (s, 2H, NCH$_2$), 3.91 (m, 1H, ArCHCO), 4.65 (s, 1H, OH), 6.45 (d, J=2.2 Hz, 1H, Ar), 7.46 (brs, 1H, Ar), 7.47 (brd, 1H, Ar), 7.50 (d, J=2.2 Hz, 1 H, Ar), 7.85 (d, J$_o$=8.5 Hz, 1H, Ar), 10.79 (s, 1H, NH).

Example 124

(R)—N-[1-(3-Hydroxy-propyl)-1H-pyrazol-3-yl]-2-(4-methanesulfonyl-3-methyl-phenyl)-3-((R)-3-oxo-cyclopentyl)-propionamide

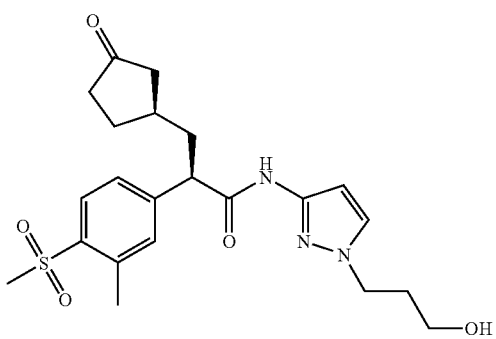

(R)-2-(4-Methanesulfonyl-3-methyl-phenyl)-3-((R)-3-oxo-cyclopentyl)-propionic acid (prepared in Example 122, 65 mg, 0.20 mmol) was dissolved in methylene chloride (2 mL) and N,N-dimethylformamide (two drops) at 25° C. under argon. To this solution was added dropwise a solution of oxalyl chloride in methylene chloride (2 M solution, 110 μL, 0.21 mmol) which produced gas evolution and it was then stirred at 25° C. for 30 minutes after which time it was concentrated in vacuo. The residue was then dissolved in methylene chloride (2 mL) and added dropwise into a solution of 3-(3-amino-pyrazol-1-yl)-propan-1-ol (prepared in Example 23, 29 mg, 0.20 mmol), 2,6-lutidine (46 μL, 0.40 mmol) and methylene chloride (2 mL) at 0° C. It was then allowed to warm to 25° C. and stirred for 1 h. After this time, the reaction was quenched with a small amount of methanol and diluted with methylene chloride and then concentrated with silica gel (2 g) in vacuo and purified on Biotage Flash chromatography system (40S column, silica gel, 80% ethyl acetate/hexanes to 10% methanol/ethyl acetate) to afford (R)—N-[1-(3-hydroxy-propyl)-1H-pyrazol-3-yl]-2-(4-methanesulfonyl-3-methyl-phenyl)-3-((R)-3-oxo-cyclopentyl)-propionamide (74 mg, 83%) as a colorless gum: [α]$^{32}_{589}$=−23.3° (c=0.15, methanol); ES-HRMS m/e calcd for C$_{22}$H$_{29}$N$_3$O$_5$S (M+H)$^+$ 448.1901, observed 448.1901; $^1$H NMR (300 MHz, DMSO-d$_6$) δ 1.50 (m, 1H, CH), 1.76-2.29 (m, 10H, 5×CH$_2$), 2.62 (s, 3H, ArCH$_3$), 3.18 (s, 3H, SO$_2$CH$_3$), 3.33 (m, 2H, OCH$_2$), 3.90 (m, 1H, ArCHCO), 4.01 (t, J=6.9 Hz, 2H, NCH$_2$), 4.56 (t, J=5.1 Hz, 1H, OH), 6.41 (d, J=2.2 Hz, 1H, Ar), 7.45 (brs, 1H, Ar), 7.46 (brd, 1H, Ar), 7.54 (d, J=2.2 Hz, 1H, Ar), 7.85 (d, J$_o$=8.6 Hz, 1H, Ar), 10.78 (s, 1H, NH).

Example 125

(R)-2-(4-Methanesulfonyl-3-methyl-phenyl)-N-[1-(2-methoxy-ethyl)-1H-pyrazol-3-yl]-3-((R)-3-oxo-cyclopentyl)-propionamide

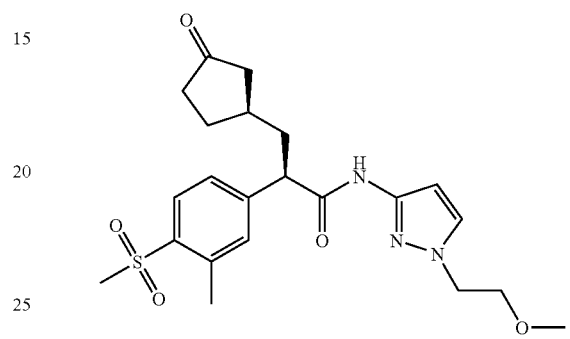

(R)-2-(4-Methanesulfonyl-3-methyl-phenyl)-3-((R)-3-oxo-cyclopentyl)-propionic acid (prepared in Example 122, 97 mg, 0.30 mmol) was dissolved in methylene chloride (3 mL) and N,N-dimethylfomamide (three drops) at 25° C. under argon. To this solution was added dropwise a solution of oxalyl chloride in methylene chloride (2 M solution, 160 μL, 0.32 mmol) which produced gas evolution and it was then stirred at 25° C. for 30 minutes after which time it was concentrated in vacuo. The residue was then dissolved in methylene chloride (3 mL) and added dropwise into a solution of 1-(2-methoxy-ethyl)-1H-pyrazol-3-ylamine (prepared in Example 72, 42 mg, 0.20 mmol), 2,6-lutidine (70 μL, 0.60 mmol) and methylene chloride (3 mL) at 0° C. It was then allowed to warm to 25° C. and stirred for 1 h. After this time, the reaction was quenched with a small amount of methanol and diluted with methylene chloride and then concentrated with silica gel (2 g) in vacuo and purified on Biotage Flash chromatography system (40S column, silica gel, 50% ethyl acetate/hexanes to 5% methanol/ethyl acetate) to afford (R)-2-(4-methanesulfonyl-3-methyl-phenyl)-N-[1-(2-methoxy-ethyl)-1H-pyrazol-3-yl]-3-((R)-3-oxo-cyclopentyl)-propionamide (121 mg, 90%) as a colorless gum: [α]$^{30}_{589}$=−53.5° (c=0.17, methanol); ES-HRMS m/e calcd for C$_{22}$H$_{29}$N$_3$O$_5$S (M+H)$^+$ 448.1901, observed 448.1900; $^1$H NMR (300 MHz, DMSO-d$_6$) δ 1.50 (m, 1H, CH), 1.75-2.30 (m, 8H, 4×CH$_2$), 2.62 (s, 3H, ArCH$_3$), 3.17 (s, 3H, OCH$_3$), 3.19 (s, 3H, SO$_2$CH$_3$), 3.61 (t, J=5.3 Hz, 2H, OCH$_2$), 3.90 (m, 1H, ArCHCO), 4.11 (t, J=5.3 Hz, 2H, NCH$_2$), 6.41 (d, J=2.2

Hz, 1H, Ar), 7.45 (brs, 1H, Ar), 7.47 (brd, 1H, Ar), 7.54 (d, J=2.2 Hz, 1H, Ar), 7.85 (d, $J_o$=8.6 Hz, 1H, Ar), 10.79 (s, 1H, NH).

Example 126

(R)-2-(3-Chloro-4-methanesulfonyl-phenyl)-3-cyclopentyl-N-[1-(2-methoxy-2-methyl-propyl)-1H-pyrazol-3-yl]-propionamide

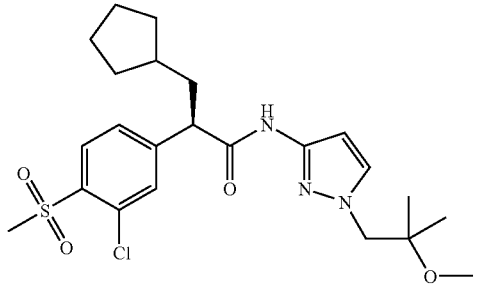

In a round bottom flask, 2(R)-(3-chloro-4-methanesulfonyl-phenyl)-3-cyclopentyl-propionic acid (prepared as in PCT WO 2004/052869 A1, Example 1, 165 mg, 0.50 mmol) was dissolved in methylene chloride (5 mL) and N,N-dimethylformamide (three drops) at 25° C. under argon. To this solution was added dropwise a solution of oxalyl chloride in methylene chloride (2 M solution, 270 µL, 0.53 mmol) which produced gas evolution and it was then stirred at 25° C. for 30 minutes after which time it was concentrated in vacuo. The residue was then dissolved in methylene chloride (5 mL) and added dropwise into a solution of 1-(2-methoxy-2-methyl-propyl)-1H-pyrazol-3-ylamine (prepared in Example 94, 85 mg, 0.50 mmol), 2,6-lutidine (130 µL, 1.00 mmol) and methylene chloride (5 mL) at 0° C. It was then allowed to warm to 25° C. and stirred for 1.5 h. After this time, the reaction was quenched with a small amount of methanol. This was then diluted with ethyl acetate with a very small amount of methanol (<10%) and the organics washed with a saturated 1N aqueous hydrochloric acid solution and a saturated aqueous brine solution it was dried over sodium sulfate, filtered and concentrated with silica gel (2 g) in vacuo and purified on Biotage Flash chromatography system (40S column, silica gel, 50% ethyl acetate/hexanes) to afford (R)-2-(3-chloro-4-methanesulfonyl-phenyl)-3-cyclopentyl-N-[1-(2-methoxy-2-methyl-propyl)-1H-pyrazol-3-yl]-propionamide (211 mg, 90%) as a white foam: $[\alpha]^{31}_{589}$=−3.04° (c=0.23, methanol); ES-HRMS m/e calcd for $C_{23}H_{32}N_3O_4SCl$ (M+H)$^+$ 482.1875, observed 482.1873; $^1$H NMR (300 MHz, DMSO-d$_6$) δ 1.04 (s, 3H, CH$_3$), 1.05 (s, 3H, CH$_3$), 1.11 (m, 2H, CH$_2$), 1.36-1.80 (m, 8H, 4×CH$_2$), 2.09 (m, 1H, CH), 3.13 (s, 3H, OCH$_3$), 3.33 (s, 3H, SO$_2$CH$_3$), 3.92 (m, 1H, ArCHCO), 3.97 (s, 2H, NCH$_2$), 6.45 (d, J=2.2 Hz, 1H, Ar), 7.74 (d, J=2.2 Hz, 1H, Ar), 7.59 (dd, $J_m$=1.5 Hz, $J_o$=8.2 Hz, 1H, Ar), 7.70 (d, $J_m$=1.5 Hz, 1H, Ar), 8.00 (d, $J_o$=8.2 Hz, 1H, Ar), 10.80 (s, 1H, NH).

Example 127

(R)-2-(3-Chloro-4-methanesulfonyl-phenyl)-3-cyclobutyl-N-[1-(2-hydroxy-2-methyl-propyl)-1H-pyrazol-3-yl]-propionamide

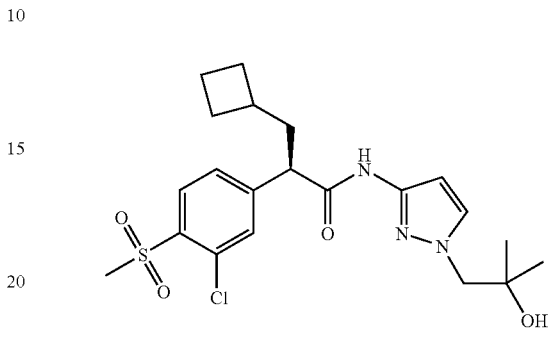

In a two-necked round bottom flask under argon was placed dry tetrahydrofuran (20 mL) and 1,1,1,3,3,3-hexamethyldisilazane (1.42 mL, 6.72 mmol). This solution was then cooled to −78° C. and treated dropwise with a solution of n-butyl lithium (2.5 M solution in hexanes, 2.60 mL, 6.42 mmol). It was then stirred at −78° C. for 15 min. To this was then slowly added a solution of 2-(3-chloro-4-methylsulfanyl-phenyl)-N-((1R,2R)-2-hydroxy-1-methyl-2-phenyl-ethyl)-N-methyl-acetamide (prepared as in PCT WO 2004/052869 A1, Example 1, 1.06 g, 2.92 mmol) in dry tetrahydrofuran (20 mL). The solution was then warmed to 0° C. and stirred for 1 h. After this time the yellow solution was then cooled back to −78° C. and treated dropwise with a solution of bromomethyl-cyclobutane (610 mg, 4.09 mmol) in 2,3-dimethyl-3,4,5,6-tetrahydro-2(1H)-pyrimidinone (0.80 mL, 6.42 mmol). The reaction was then warmed and stirred at 0° C. for 16 h. The reaction was then diluted with ethyl acetate (120 mL) and transferred to a separatory funnel and washed with a saturated aqueous ammonium chloride solution (40 mL) and then a saturated aqueous brine solution (40 mL). The organic layers were combined and then dried over sodium sulfate and concentrated in vacuo with silica gel (4 g) and purified on Biotage Flash chromatography system (40M column, silica gel, 50% ethyl acetate/hexanes to 80% ethyl acetate/hexanes) to afford (R)-2-(3-chloro-4-methylsulfanyl-phenyl)-3-cyclobutyl-N-((1R,2R)-2-hydroxy-1-methyl-2-phenyl-ethyl)-N-methyl-propionamide (361 mg, 29%).

A solution of (R)-2-(3-chloro-4-methylsulfanyl-phenyl)-3-cyclobutyl-N-((1R,2R)-2-hydroxy-1-methyl-2-phenyl-ethyl)-N-methyl-propionamide (330 mg, 0.76 mmol) in dioxane (4 mL) was treated with a 9 N aqueous sulfuric acid solution (2 mL). The resulting solution was then heated at 110° C. for 16 h. The reaction was then cooled and diluted with water (75 mL) and extracted with a chloroform/methanol solution (3:2, 2×50 mL) and then concentrated. The resulting residue was then dissolved in acetonitrile and concentrated with silica gel (3 g) and purified on Biotage Flash chromatography system (40S column, silica gel, 80% ethyl acetate/hexanes) to afford (R)-2-(3-chloro-4-methylsulfanyl-phenyl)-3-cyclobutyl-propionic acid (154 mg, 71%) as a yellow viscous oil: $[\alpha]^{30}_{589}$=−48.3° (c=0.18, methylene chloride); ES-HRMS m/e calcd for $C_{14}H_{17}O_2SCl$ (M+Na)$^+$ 307.0530, observed 307.0530; $^1$H NMR (300 MHz, DMSO-d$_6$) δ 1.47-2.16 (m, 9H, CH and 4×CH$_2$), 2.47 (s, 3H, SCH$_3$), 3.40 (t, J=7.3 Hz, 1H, ArCHCO), 7.25 (s, 2H, Ar), 7.34 (s, 1H, Ar), 12.41 (s, 1H, CO$_2$H).

In a flask was placed sodium periodate (187 mg, 0.86 mmol) and water (1.5 mL). To this solution was then added dropwise (R)-2-(3-chloro-4-methylsulfanyl-phenyl)-3-cyclobutyl-propionic acid (132 mg, 0.46 mmol) in methanol (3.5 mL). The reaction was then stirred at 25° C. for 1 h after which time there was a white precipitate forming. Thin layer chromatography indicated the reaction was not complete so another portion of sodium periodate (120 mg, 0.5 mmol) in water (1 mL) was added and stirred another 1 h, the reaction was then stored at 4° C. for 16 h. The reaction was then filtered through a plug of celite and was concentrated in vacuo and then azeotroped with acetonitrile. The residue was then dissolved in methanol (6 mL) and added slowly to a solution of potassium permanganate (85 mg, 0.51 mmol) in water (1.5 mL) and stirred at 25° C. for 1 h. After this time the reaction was concentrated in vacuo and the residue was dissolved in acetonitrile and then concentrated with silica gel (2 g) in vacuo and purified on Biotage Flash chromatography system (40S column, silica gel, 80% ethyl acetate/hexanes to 10% methanol/ethyl acetate) to afford (R)-2-(3-chloro-4-methanesulfonyl-phenyl)-3-cyclobutyl-propionic acid (95 mg, 65%) as a colorless gum: [α]$^{30}_{589}$=−42.0° (c=0.20, methylene chloride); ES-HRMS m/e calcd for C$_{14}$H$_{17}$O$_4$SCl (M+Na)$^+$ 339.0428, observed 339.0427; $^1$H NMR (300 MHz, DMSO-d$_6$) δ 1.49-2.16 (m, 9H, CH and 4×CH$_2$), 3.36 (s, 3H, SO$_2$CH$_3$), 3.60 (t, J=7.3 Hz, 1H, ArCHCO), 7.54 (dd, J$_m$=1.5 Hz, J$_o$=8.2 Hz, 1H, Ar), 7.67 (d, J$_m$=1.5 Hz, 1H, Ar), 7.99 (d, J$_o$=8.2 Hz, 1H, Ar), 12.71 (s, 1H, CO$_2$H).

In a flask (R)-2-(3-chloro-4-methanesulfonyl-phenyl)-3-cyclobutyl-propionic acid (85 mg, 0.27 mmol) was dissolved in methylene chloride (2 mL) and N,N-dimethylformamide (two drops) at 25° C. under argon. To this solution was added dropwise a solution of oxalyl chloride in methylene chloride (2 M solution, 140 μL, 0.28 mmol) which produced gas evolution and it was then stirred at 25° C. for 30 minutes after which time it was concentrated in vacuo. The residue was then dissolved in methylene chloride (2 mL) and added dropwise into a solution of 1-(3-amino-pyrazol-1-yl)-2-methyl-propan-2-ol (prepared as in Example 80, 42 mg, 0.27 mmol), 2,6-lutidine (63 μL, 0.54 mmol) and methylene chloride (2 mL) at 0° C. It was then allowed to warm to 25° C. and stirred for 1.5 h. After this time, the reaction was quenched with a small amount of methanol and diluted with ethyl acetate (20 mL). This was then washed with a 1 N aqueous hydrochloric acid solution (10 mL) and a saturated aqueous brine solution (10 mL). It was then dried over sodium sulfate, filtered and concentrated with silica gel (2 g) in vacuo and then purified on Biotage Flash chromatography system (40S column, silica gel, 100% ethyl acetate/hexanes to 10% methanol/ethyl acetate) to afford (R)-2-(3-chloro-4-methanesulfonyl-phenyl)-3-cyclobutyl-N-[1-(2-hydroxy-2-methyl-propyl)-1H-pyrazol-3-yl]-propionamide (80 mg, 66%) as a white foam: ES-HRMS m/e calcd for C$_{21}$H$_{28}$N$_3$O$_4$SCl (M+H)$^+$ 454.1562, observed 454.1557; $^1$H NMR (300 MHz, DMSO-d$_6$) δ 1.03 (s, 3H, CH$_3$), 1.04 (s, 3H, CH$_3$), 1.49-2.21 (m, 9H, CH and 4×CH$_2$), 3.33 (s, 3H, SO$_2$CH$_3$), 3.79 (m, 1H, ArCHCO), 3.87 (s, 2H, NCH$_2$), 4.65 (s, 1H, OH), 6.44 (d, J=2.2 Hz, 1H, Ar), 7.51 (d, J=2.2 Hz, 1H, Ar), 7.57 (dd, J$_m$=1.5 Hz, J$_o$=8.2 Hz, 1H, Ar), 7.67 (d, J$_m$=1.5 Hz, 1H, Ar), 8.00 (d, J$_o$=8.2 Hz, 1H, Ar), 10.76 (s, 1H, NH).

Example 128

(R)-3-Cyclobutyl-N-[1-(2-hydroxy-2-methyl-propyl)-1H-pyrazol-3-yl]-2-(4-methanesulfonyl-3-methyl-phenyl)-propionamide

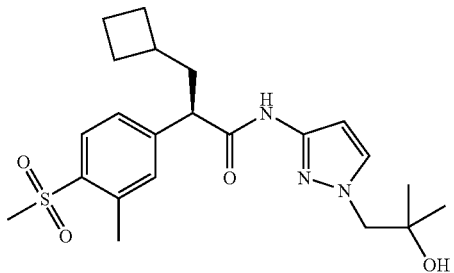

In a two-necked round bottom flask under argon was placed dry tetrahydrofuran (20 mL) and 1,1,1,3,3,3-hexamethyldisilazane (1.42 mL, 6.72 mmol). This solution was then cooled to −78° C. and treated dropwise with a solution of n-butyl lithium (2.5 M solution in hexanes, 2.60 mL, 6.42 mmol). It was then stirred at −78° C. for 15 min. To this was then slowly added a solution of N-((1R,2R)-2-hydroxy-1-methyl-2-phenyl-ethyl)-N-methyl-2-(3-methyl-4-methylsulfanyl-phenyl)-acetamide (prepared as in PCT WO2004/052869 A1, Example 57, 1.00 g, 2.92 mmol) in dry tetrahydrofuran (20 mL). The solution was then warmed to 0° C. and stirred for 1 h. After this time the yellow solution was then cooled back to −78° C. and treated dropwise with a solution of bromomethyl-cyclobutane (610 mg, 4.09 mmol) in 2,3-dimethyl-3,4,5,6-tetrahydro-2(1H)-pyrimidinone (0.80 mL, 6.42 mmol). The reaction was then warmed and stirred at 0° C. for 20 h. The reaction was then diluted with ethyl acetate (200 mL) and transferred to a separatory funnel and washed with a saturated aqueous ammonium chloride solution (50 mL) and then a saturated aqueous brine solution (50 mL). The organic layers were combined and then dried over sodium sulfate and concentrated in vacuo with silica gel (4 g) and purified on Biotage Flash chromatography system (40M column, silica gel, 40% ethyl acetate/hexanes) to afford (R)-3-cyclobutyl-N-((1R,2R)-2-hydroxy-1-methyl-2-phenyl-ethyl)-N-methyl-2-(3-methyl-4-methylsulfanyl-phenyl)-propionamide (302 mg, 25%) as a white solid: ES-HRMS m/e calcd for C$_{25}$H$_{33}$NO$_2$S (M+H)$^+$ 412.2305, observed 412.2303; $^1$H NMR (300 MHz, DMSO-d$_6$, rotamers) δ 0.49, 0.88 (2×d, J=6.9 Hz, 3H, CH$_3$), 1.37-2.09 (m, 9H, CH and 4×CH$_2$), 2.16, 2.20 (2×s, 3H, ArCH$_3$), 2.39, 2.44 (2×s, 3H, NCH$_3$), 2.68, 2.72 (2×s, 3H, SCH$_3$), 3.60, 3.74 (2×t, J=7.1 Hz, 1H, ArCHCO), 4.00, 4.65 (2×m, 1H, NCH), 4.48 (m, 1H, OCH), 5.22, 5.52 (2×d, J=3.9 Hz, 1H, OH), 6.95-7.18 (m, 5H, Ar), 7.24-7.40 (m, 3H, Ar).

A solution of (R)-3-cyclobutyl-N-((1R,2R)-2-hydroxy-1-methyl-2-phenyl-ethyl)-N-methyl-2-(3-methyl-4-methylsulfanyl-phenyl)-propionamide (300 mg, 0.73 mmol) in dioxane (4 mL) was treated with a 9 N aqueous sulfuric acid solution (2 mL). The resulting solution was then heated at 110° C. for 16 h. The reaction was then cooled and diluted with water (75 mL) and extracted with a chloroform/methanol solution (3:2, 2×50 mL) and then concentrated. The resulting residue was then dissolved in methylene chloride and concentrated with silica gel (2 g) and purified on Biotage Flash chromatography system (40S column, silica gel, 80% ethyl acetate/hexanes) to afford (R)-3-cyclobutyl-2-(3-methyl-4-methylsulfanyl-phenyl)-propionic acid (148 mg, 77%): [α]$^{30}_{589}$=−48.3° (c=0.18, methylene chloride); EI-HRMS m/e calcd for $C_{15}H_{20}O_2S$ (M$^+$) 264.1184, observed 264.1183; $^1$H NMR (300 MHz, DMSO-d$_6$) δ 1.47-2.14 (m, 9H, CH and 4×CH$_2$), 2.21 (s, 3H, ArCH$_3$), 2.43 (s, 3H, SCH$_3$), 3.30 (t, J=7.4 Hz, 1H, ArCHCO), 7.05-7.15 (m, 3H, Ar), 12.28 (s, 1H, CO$_2$H).

In a flask was placed sodium periodate (203 mg, 0.94 mmol) and water (1.5 mL). To this solution was then added dropwise (R)-3-cyclobutyl-2-(3-methyl-4-methylsulfanyl-phenyl)-propionic acid (132 mg, 0.50 mmol) in methanol (3.5 mL). The reaction was then stirred at 25° C. for 1 h after which time there was a white precipitate. The reaction was then filtered through a plug of celite and washed with methanol and stored in the freezer as a solution for 16 h and then concentrated in vacuo. The residue was then dissolved in methanol (6 mL) and added slowly to a solution of potassium permanganate (92 mg, 0.55 mmol) in water (1.5 mL) and stirred at 25° C. for 45 min. After this time the reaction was filtered through celite and washed with methanol. It was then concentrated in vacuo and the residue was dissolved in acetonitrile and then concentrated with silica gel (2 g) in vacuo and purified on Biotage Flash chromatography system (40S column, silica gel, 80% ethyl acetate/hexanes to 10% methanol/ethyl acetate) to afford (R)-3-cyclobutyl-2-(4-methanesulfonyl-3-methyl-phenyl)-propionic acid (103 mg, 70%) as a colorless oil: [α]$^{30}_{589}$=−42.0° (c=0.20, methylene chloride); ES-HRMS m/e calcd for $C_{15}H_{20}O_4S$ (M+H)$^+$ 297.1155, observed 297.1155; $^1$H NMR (300 MHz, DMSO-d$_6$) δ 1.47-2.14 (m, 9H, CH and 4×CH$_2$), 2.62 (s, 3H, ArCH$_3$), 3.20 (s, 3H, SO$_2$CH$_3$), 3.48 (t, J=7.4 Hz, 1H, ArCHCO), 7.36 (m, 2H, Ar), 7.84 (d, J$_o$=8.3 Hz, 1H, Ar), 12.55 (s, 1H, CO$_2$H).

In a flask (R)-3-cyclobutyl-2-(4-methanesulfonyl-3-methyl-phenyl)-propionic acid (88 mg, 0.30 mmol) was dissolved in methylene chloride (2 mL) and N,N-dimethylformamide (two drops) at 25° C. under argon. To this solution was added dropwise a solution of oxalyl chloride in methylene chloride (2 M solution, 160 μL, 0.32 mmol) which produced gas evolution and it was then stirred at 25° C. for 30 minutes after which time it was concentrated in vacuo. The residue was then dissolved in methylene chloride (2 mL) and added dropwise into a solution of 1-(3-amino-pyrazol-1-yl)-2-methyl-propan-2-ol (prepared as in Example 80, 47 mg, 0.30 mmol), 2,6-lutidine (70 μL, 0.60 mmol) and methylene chloride (2 mL) at 0° C. It was then allowed to warm to 25° C. and stirred for 1 h. After this time, the reaction was quenched with a small amount of methanol and diluted with ethyl acetate (20 mL). This was then washed with a 1 N aqueous hydrochloric acid solution (10 mL) and a saturated aqueous brine solution (10 mL). It was then dried over sodium sulfate, filtered and concentrated with silica gel (2 g) in vacuo and then purified on Biotage Flash chromatography system (40S column, silica gel, 50% ethyl acetate/hexanes to 80% ethyl acetate) to afford (R)-3-cyclobutyl-N-[1-(2-hydroxy-2-methyl-propyl)-1H-pyrazol-3-yl]-2-(4-methanesulfonyl-3-methyl-phenyl)-propionamide (93 mg, 72%) as a white foam: [α]$^{29}_{589}$32 −14.7° (c=0.19, methylene chloride); ES-HRMS m/e calcd for $C_{22}H_{31}N_3O_4S$ (M+H)$^+$ 434.2108, observed 434.2108; $^1$H NMR (300 MHz, DMSO-d$_6$) δ 1.03 (s, 3H, CH$_3$), 1.04 (s, 3H, CH$_3$), 1.49-2.21 (m, 9 H, CH and 4×CH$_2$), 2.62 (s, 3H, ArCH$_3$), 3.17 (s, 3H, SO$_2$CH$_3$), 3.73 (m, 1H, ArCHCO), 3.86 (s, 2H, NCH$_2$), 4.64 (s, 1H, OH), 6.44 (d, J=2.2 Hz, 1H, Ar), 7.42 (m, 2H, Ar), 7.50 (d, J=2.2 Hz, 1H, Ar), 7.84 (d, J$_o$=8.6 Hz, 1H, Ar), 10.70 (s, 1H, NH).

Example 129

(R)-3-Cyclopentyl-2-(4-cyclopropanesulfonyl-phenyl)-N-[1-(2-hydroxy-2-methyl-propyl)-1H-pyrazol-3-yl]-propionamide

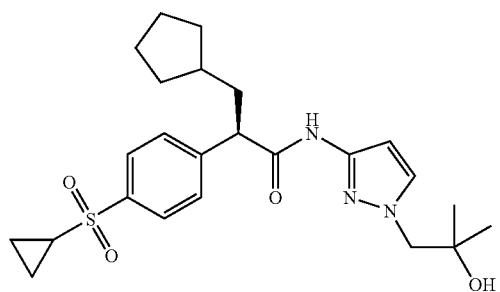

In a round bottom flask was placed methylene chloride (100 mL) and aluminum trichloride (9.87 g, 74.01 mmol) and it was cooled to 0° C. in an ice bath. To this was then added dropwise chloro-oxo-acetic acid ethyl ester (6.46 mL, 58.03 mmol) keeping the temperature of the solution below 5° C. and it was then stirred for 30 min at 0° C. After this time a solution of cyclopropylsulfanyl-benzene (8.00 g, 53.24 mmol) in methylene chloride (5 mL) was added dropwise while keeping the temperature of the solution below 5° C. The ice bath was then removed and the reaction allowed to warm up to 25° C. and stirred for 3 h. The reaction was then cooled back down to 0° C. in an ice bath and added dropwise ice water (20 mL) keeping the temperature of the solution below 20° C. It was then stirred for 15 min and then transferred to a separatory funnel and separated. The organic phase was then washed with water (2×25 mL), saturated aqueous sodium bicarbonate solution (2×25 mL) and water (25 mL) and then dried over magnesium sulfate, filtered and concentrated in vacuo to afford (4-cyclopropylsulfanyl-phenyl)-oxo-acetic acid ethyl ester (12.19 g, 91%) as a yellow oil and used without further purification.

In a flask (4-cyclopropylsulfanyl-phenyl)-oxo-acetic acid ethyl ester (9.19 g, 36.71 mmol) was dissolved in toluene (20 mL) and heated to 50° C. in an oil bath. To this heated solution was then added an aqueous sodium hydroxide solution (3 M solution, 15.17 mL, 45.52 mmol) dropwise keeping the temperature of the reaction below 60° C. The reaction was then stirred at 50° C. for 1.5 h. After this time the reaction was removed from the oil bath and concentrated hydrochloric acid (3.5 mL, 42.2 mmol) was added dropwise while the reaction was still at 50° C. It was then allowed to cool to 25° C. and stirred for 16 h. The solids were filtered off and washed with water (10 mL) and toluene (10 mL) to afford (4-cyclopropylsulfanyl-phenyl)-oxo-acetic acid (3.41 g, 42%) as a white solid and used without purification.

Hydrazine hydrate (4.77 mL, 153.4 mmol) was placed in a three neck flask fitted with an overhead stirring rod and a reflux condenser and cooled in a dry ice acetone bath at −78° C. After the solution reached −50° C. the bath was removed and (4-cyclopropylsulfanyl-phenyl)-oxo-acetic acid (3.41 g, 15.34 mmol) was added in one portion. The temperature increased due to an exotherm and it was then heated in an oil bath to 80° C. After the reaction was at 80° C. it was treated with potassium hydroxide (593 mg, 9.20 mmol) and stirred vigorously. When the reaction returned to 80° C. a second portion of potassium hydroxide (593 mg, 9.20 mmol) was added and allowed to cool back to 80° C. This cycle was repeated two more times adding potassium hydroxide (593 mg, 9.20 mmol) each time. The reaction was then heated at 100° C. for 16 h over which time the reaction became a homogenous clear yellow solution. It was then cooled to 25° C. and water (3 mL) added to the reaction. It was then transferred to a separatory funnel and another portion of water (3 mL) was added and diethyl ether (10 mL). The layers were separated and the aqueous layer separated into a flask. The organic layer was then extracted with water (5 mL) and this aqueous layer combined with the first. To the aqueous layers was then added heptane (5 mL) and stirred vigorously. This solution was cooled to 0° C. in an ice bath and was treated dropwise with concentrated hydrochloric acid (~7 mL) over 30 min until the aqueous layer was at pH=2 keeping the temperature of the solution below 50° C. during the addition process and it turned cloudy. It was then allowed to cool to 25° C. and stirred for 3 h. It was then filtered to remove the solids and the solids were washed with 1N aqueous hydrochloric acid (1.5 mL), water (2×1.5 mL), heptane (5 mL) and 1:1 heptane:diethyl ether (5 mL) and the solid was then dried in a vacuum oven to afford (4-cyclopropylsulfanyl-phenyl)-acetic acid (2.70 g, 85%) as a yellow solid.

To a three neck round bottom flask was added a stir bar, dropping funnel, argon inlet and thermometer. It was then charged with (4-cyclopropylsulfanyl-phenyl)-acetic acid (1.20 g, 5.76 mmol), acetone (15 mL) and potassium carbonate (2.39 g, 17.28 mmol) and cooled to −10° C. To this cooled heterogenous solution was then added trimethylacetyl chloride (745 µL, 6.05 mmol) dropwise slowly to keep the temperature below −10° C. throughout the addition. It was then stirred at −10° C. for 15 min, then warmed to 0° C. and stirred for an additional 10 min and then recooled to −10° C. To the reaction was then added (1R,2R)-(−)-pseudoephedrine (1.43 g, 8.64 mmol) in one portion which resulted in an exotherm and then allowed to cool back down. It was then stirred at −10° C. for 10 min and then warmed to 25° C. and stirred for 1 h. After such time, the reaction was then quenched with water (10 mL) and poured into a separatory funnel and added ethyl acetate (25 mL). The layers were separated and the organic layer was washed with water (2×10 mL) and the organic layers were then back extracted with ethyl acetate (3×25 mL) dried over magnesium sulfate, filtered and concentrated in vacuo. Purification on an AnaLogix Intelliflash system (120 g column, 40% ethyl acetate/hexanes to 65% ethyl acetate/hexanes) afforded 2-(4-cyclopropylsulfanyl-phenyl)-N-((1R,2R)-2-hydroxy-1-methyl-2-phenyl-ethyl)-N-methyl-acetamide (1.75 g, 85%) as a white solid: $[\alpha]^{25}_{589}$=−52.6° (c=0.19, methanol); ES-HRMS m/e calcd for $C_{21}H_{25}NO_2S$ (M+Na)$^+$ 378.1498, observed 378.1498; $^1$H NMR (300 MHz, DMSO-d$_6$, rotamers) δ 0.56 (m, 2H, 2×CH of 2CH$_2$), 0.80, 0.85 (2×d, J=6.9 Hz, 3H, CH$_3$), 1.06 (m, 2H, 2×CH of 2CH$_2$), 2.26 (m, 1H, SCH), 2.78, 2.85 (2×s, 3H, NCH$_3$), 3.51, 3.77 (AB, J$_{gem}$=15.6 Hz, 1H, ArCH$_2$), 3.59 (s, 1H, ArCH$_2$), 3.98, 4.66 (2×m, 1H, NCH), 4.53 (m, 1H, OCH), 5.32, 5.54 (2×d, J=4.2 Hz, 1H, OH), 7.07, 7.08 (2×d, J=8.4 Hz, 2H, Ar), 7.22-7.41 (m, 7H, Ar).

A round bottom flask with a stir bar and argon inlet was charged with tetrahydrofuran (10 mL) and cooled to −78° C. 1,1,1,3,3,3-hexamethyldisilazane (1.2 mL, 5.69 mmol) was then added followed by the dropwise addition of a solution of n-butyl lithium (2.5M solution in hexanes, 2.12 mL, 5.32 mmol) and it was stirred at −78° C. for 15 min. After this time, a solution of 2-(4-cyclopropylsulfanyl-phenyl)-N-((1R,2R)-2-hydroxy-1-methyl-2-phenyl-ethyl)-N-methyl-acetamide (900 mg, 2.53 mmol) in tetrahydrofuran (6 mL) was added dropwise over 10 min keeping the reaction below −60° C. It was then stirred for 15 min, warmed to 0° C. and stirred for 20 min and then recooled to −78° C. It was then treated with a solution of iodomethylcyclopentane (prepared in PCT WO 2004/052869 A1 Example 1, 798 mg, 3.79 mmol) in 2,3-dimethyl-3,4,5,6-tetrahydro-2(1H)-pyrimidinone (643 µL, 5.32 mmol) dropwise. The reaction was then stirred at −78° C. for 30 min and then warmed to 0° C. and stirred for 3 h. The reaction was then diluted with ethyl acetate (30 mL) and washed with a saturated aqueous ammonium chloride solution (3×10 mL). The aqueous layers were then combined and extracted with ethyl acetate (2×10 mL). The organics were then washed with a saturated aqueous brine solution (15 mL) and dried over sodium sulfate, filtered and concentrated in vacuo. Purification on an AnaLogix Intelliflash system (12 g column, 25% ethyl acetate/hexanes to 40% ethyl acetate/hexanes) afforded (R)-3-cyclopentyl-2-(4-cyclopropylsulfanyl-phenyl)-N-((1R,2R)-2-hydroxy-1-methyl-2-phenyl-ethyl)-N-methyl-propionamide (719 mg, 65%) as a clear colorless oil: $[\alpha]^{25}_{589}$=−52.6° (c=0.19, methanol); ES-HRMS m/e calcd for $C_{27}H_{35}NO_2S$ (M+H)$^+$ 438.2462, observed 438.2461.

A solution of (R)-3-cyclopentyl-2-(4-cyclopropylsulfanyl-phenyl)-N-((1R,2R)-2-hydroxy-1-methyl-2-phenyl-ethyl)-N-methyl-propionamide (715 mg, 1.63 mmol) in dioxane (5 mL) was treated with a 9 N aqueous sulfuric acid solution (1.3 mL). The resulting solution was then heated at 105° C. for 16 h. The reaction was then cooled and diluted with water (13 mL) and extracted with a chloroform/methanol solution (3:2, 3×20 mL) and then combined the organic extracts dried over magnesium sulfate, filtered and concentrated. Purification on an AnaLogix Intelliflash system (12 g column, 10% ethyl acetate/hexanes to 80% ethyl acetate/hexanes) afforded (R)-3-cyclopentyl-2-(4-cyclopropylsulfanyl-phenyl)-propionic acid (278 mg, 59%) as a white solid: $[\alpha]^{25}_{589}$=−52.6° (c=0.19, methanol); ES-HRMS m/e calcd for $C_{17}H_{22}O_2S$ (M−H)$^-$ 289.1268, observed 289.1268; $^1$H NMR (300 MHz, CDCl$_3$) δ 1.61-2.05 (m, 4H, 2×CH$_2$), 2.45 (s, 3 H, ArCH$_3$), 3.76 (m, 2H, OCH$_2$), 4.00 (m, 2H, SO$_3$CH$_2$), 4.08 (m, 1H, OCH), 7.35 (brd, 2H, Ar), 7.81 (brd, 2H, Ar).

In a flask was placed (R)-3-cyclopentyl-2-(4-cyclopropyl-sulfanyl-phenyl)-propionic acid (120 mg, 0.41 mmol) with tetrahydrofuran (500 µL) and formic acid (780 µL, 2.06 mmol). It was cooled to 0° C. in an ice bath and then treated with a 30% solution of hydrogen peroxide (234 µL, 2.06 mmol). It was then allowed to warm slowly to 25° C. and stirred for 16 h. It was then cooled to 0° C. and quenched by the slow addition of a saturated aqueous sodium sulfite solution (3 mL) and extracted with ethyl acetate (3×20 mL) dried over magnesium sulfate, filtered and concentrated in vacuo. Purification on an AnaLogix Intelliflash system (12 g column, 20% ethyl acetate/hexanes to 100% ethyl acetate) afforded (R)-3-cyclopentyl-2-(4-cyclopropanesulfonyl-phenyl)-propionic acid (123 mg, 92%) as a white solid.

A solution of (R)-3-cyclopentyl-2-(4-cyclopropanesulfonyl-phenyl)-propionic acid (50 mg, 0.16 mmol) was dissolved in methylene chloride (5 mL) and N,N-dimethylformamide (one drop) and cooled to 0° C. To this solution was added dropwise a solution of oxalyl chloride in methylene chloride (2 M solution, 93 µL, 0.19 mmol) which produced gas evolution and it was stirred at 0° C. for 10 min and it was then allowed to warm to 25° C. and stirred 25 min at 25° C. After this time, the reaction was concentrated in vacuo to ~1 mL. In a separate flask, a solution of 1-(3-amino-pyrazol-1-yl)-2-methyl-propan-2-ol (prepared as in Example 80, 36 mg, 0.23 mmol), 2,6-lutidine (34 µL, 0.31 mmol) and methylene chloride (5 mL) was cooled to 0° C. in an ice bath. To this solution was added the solution of the prepared acid chloride, diluted with another portion of methylene chloride (1 mL), dropwise. After addition was complete the reaction was then allowed to warm to 25° C. and stirred for 16 hours. After this time the reaction mixture quenched with a saturated aqueous sodium bicarbonate solution (10 mL) and transferred to a separatory funnel where it was extracted with methylene chloride (3×10 mL). The organic layers were then washed with a 1 N aqueous hydrochloric acid solution (10 mL) and then dried over magnesium sulfate, filtered and concentrated in vacuo. Purification on an AnaLogix Intelliflash system (12 g column, 55% ethyl acetate/hexanes to 70% ethyl acetate/hexanes) afforded (R)-3-cyclopentyl-2-(4-cyclopropane-sulfonyl-phenyl)-N-[1-(2-hydroxy-2-methyl-propyl)-1H-pyrazol-3-yl]-propionamide (42 mg, 59%) as a white foam: $[\alpha]^{30}_{589}=-12.0°$ (c=0.10, methylene chloride); ES-HRMS m/e calcd for $C_{24}H_{33}N_3O_4S$ $(M+H)^+$ 460.2265, observed 460.2264; $^1H$ NMR (300 MHz, DMSO-$d_6$) δ ppm 0.96-1.21 (m, 6H, 3×$CH_2$), 1.03 (s, 3H, $CH_3$), 1.04 (s, 3H, $CH_3$), 1.35-1.81 (m, 8H, 4×$CH_2$), 2.10 (m, 1H, CH), 2.81 (m, 1H, SCH), 3.86 (s, 2H, $NCH_2$), 3.93 (m, 1H, ArCHCO), 4.65 (s, 1H, OH), 6.45 (d, J=2.1 Hz, 1H, Ar), 7.50 (d, J=2.1 Hz, 1H, Ar), 7.63 (d, J=8.2 Hz, 2H, Ar), 7.84 (d, J=8.2 Hz, 2H, Ar), 10.78 (s, 1H, NH).

Example 130

(R)-3-Cyclopentyl-N-[1-(2-hydroxy-2-methyl-propyl)-1H-pyrazol-3-yl]-2-[4-(propane-2-sulfonyl)-phenyl]-propionamide

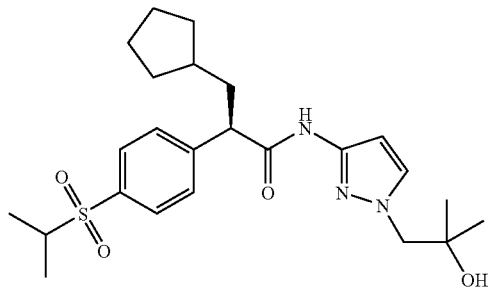

In a round bottom flask was placed methylene chloride (70 mL) and aluminum trichloride (6.09 g, 45.65 mmol) and it was cooled to 0° C. in an ice bath. To this was then added dropwise chloro-oxo-acetic acid ethyl ester (3.98 mL, 35.79 mmol) keeping the temperature of the solution below 5° C. and it was then stirred for 30 min at 0° C. After this time a solution of isopropylsulfanyl-benzene (5.00 g, 32.84 mmol) in methylene chloride (5 mL) was added dropwise while keeping the temperature of the solution below 5° C. The ice bath was then removed and the reaction allowed to warm up to 25° C. and stirred for 3 h. The reaction was then cooled back down to 0° C. in an ice bath and added dropwise ice water (20 mL) keeping the temperature of the solution below 20° C. It was then stirred for 15 min and then transferred to a separatory funnel and separated. The organic phase was then washed with water (2×25 mL), saturated aqueous sodium bicarbonate solution (2×25 mL) and water (25 mL) and then dried over magnesium sulfate, filtered and concentrated in vacuo to afford (4-isopropylsulfanyl-phenyl)-oxo-acetic acid ethyl ester (5.85 g, 71%) as a yellow oil and used without further purification.

In a flask (4-isopropylsulfanyl-phenyl)-oxo-acetic acid ethyl ester (4.00 g, 15.85 mmol) was dissolved in toluene (10 mL) and heated to 50° C. in an oil bath. To this heated solution was then added an aqueous sodium hydroxide solution (3 M solution, 6.55 mL, 19.66 mmol) dropwise keeping the temperature of the reaction below 60° C. The reaction was then stirred at 50° C. for 1.5 h. After this time the reaction was removed from the oil bath and concentrated hydrochloric acid (1.52 mL, 18.23 mmol) was added dropwise while the reaction was still at 50° C. It was then allowed to cool to 25° C. and stirred for 16 h. Filter off the solid which turned out to be hygroscopic so the filter paper was washed with methylene chloride and transferred the filterate to a separatory funnel. The aqueous layer was extracted with methylene chloride (3×20 mL) and then the organics were dried over magnesium sulfate, filtered and concentrated in vacuo to afford (4-isopropylsulfanyl-phenyl)-oxo-acetic acid (3.35 g, 94%) as a yellow oily solid (there was a small impurity but the material was carried on without purification).

Hydrazine hydrate (8.0 mL) was placed in a three neck flask fitted with a mechanical stirrer and a reflux condenser and cooled in a dry ice acetone bath at −78° C. After the solution reached −50° C. (4-isopropylsulfanyl-phenyl)-oxo-acetic acid (4.50 g, 20.00 mmol) was added in one portion, an additional amount of hydrazine hydrate (2 mL) was used to help transfer this material to the reaction flask. The temperature increased due to an exotherm and it was then heated in an oil bath to 80° C. After the reaction was at 80° C. it was treated with potassium hydroxide (700 mg, 12.48 mmol) and stirred vigorously. The addition of potassium hydroxide (700 mg, 12.48 mmol) was repeated three more times at an interval of 5 minutes. The reaction was then heated at 95° C. for 16 h. It was then cooled to 25° C. and water (7 mL) added to the reaction. It was then transferred to a separatory funnel and another portion of water (7 mL) was added and diethyl ether (15 mL). The layers were separated and the aqueous layer separated into a flask. The organic layer was then extracted with water (7 mL) and this aqueous layer combined with the first. To the aqueous layers was then added heptane (10 mL) and stirred vigorously. This solution was cooled to 0° C. in an ice bath and was treated dropwise with concentrated hydrochloric acid (~20 mL) over 30 min until the aqueous layer was at pH=2 keeping the temperature of the solution below 30° C. during the addition process. It was then allowed to cool to 25° C. and stirred for 1 h which resulted in a yellow gum separating out. The solution was extracted with chloroform/methanol (3:2, 2×50 mL) and concentrated the residue was then treated with acetonitrile and concentrated and then chloroform and then concentrated which afforded (4-isopropylsulfanyl-phenyl)-acetic acid (2.16 g, 51%) as a yellow semisolid: ES-HRMS m/e calcd for $C_{11}H_{14}O_2S$ $(M+H)^+$ 211.0788, observed 211.0786; $^1H$ NMR (300 MHz, DMSO-$d_6$) δ 1.22 (d, J=6.6 Hz, 6H, 2×$CH_3$), 3.44 (m, 1H, SCH), 3.55 (s, 2H, $ArCH_2$), 7.21 (d, J=8.4 Hz, 2H, Ar), 7.31 (d, J=8.4 Hz, 2H, Ar).

A two neck round bottom flask was charged with (4-isopropylsulfanyl-phenyl)-acetic acid (1.05 g, 5.00 mmol), acetone (15 mL) and potassium carbonate (2.07 g, 15.00 mmol) and cooled to −10° C. To this cooled heterogenous solution was then added trimethylacetyl chloride (650 μL, 5.25 mmol) dropwise slowly to keep the temperature below −10° C. throughout the addition. It was then stirred at −10° C. for 15 min, then warmed to 0° C. and stirred for an additional 10 min and then recooled to −10° C. To the reaction was then added (1R,2R)-(−)-pseudoephedrine (1.24 g, 7.50 mmol) in one portion. It was then stirred at −10° C. for 10 min and then warmed to 25° C. and stirred for 1 h. After such time, the reaction was then quenched with water (25 mL) and poured into a separatory funnel and extracted with ethyl acetate (2×30 mL). The organic layers were then washed with a saturated aqueous brine solution (25 mL) dried over sodium sulfate, filtered and concentrated with silica gel (4 g) in vacuo and then purified on Biotage Flash chromatography system (40M column, silica gel, 60% ethyl acetate/hexanes) to afford N-((1R,2R)-2-hydroxy-1-methyl-2-phenyl-ethyl)-2-(4-isopropylsulfanyl-phenyl)-N-methyl-acetamide (1.08 g, 60%) as a yellow oil: ES-HRMS m/e calcd for $C_{21}H_{27}NO_2S$ (M+Na)$^+$ 380.1654, observed 380.1653; $^1$H NMR (300 MHz, CDCl$_3$, rotamers) δ 0.25, 1.24 (2×d, J=6.7 Hz, 3H, CH$_3$), 1.08 (m, 2H, CH$_2$), 1.15, 1.30 (2×d, J=7.0 Hz, 6H, 2×CH$_3$), 1.42-1.90 (m, 8H, 4×CH$_2$), 2.10 (m, 1H, CH), 2.72, 2.91 (2×s, 3H, NCH$_3$), 3.35 (m, 1H, SCH), 3.60, 3.98 (m, 1H, ArCHCO), 4.13, 4.34 (2×brm, 1H, NCH), 4.54 (d, J=8.9 Hz, 0.3H, OCH), 4.60 (d, J=7.2 Hz, 0.7H, OCH), 7.18 (m, 2H, Ar), 7.24-7.47 (m, 7H, Ar).

In a round bottom flask under argon was placed dry tetrahydrofuran (10 mL) and 1,1,1,3,3,3-hexamethyldisilazane (1.47 mL, 6.95 mmol). This solution was then cooled to −78° C. and treated dropwise with a solution of n-butyl lithium (2.5 M solution in hexanes, 2.66 mL, 6.64 mmol). It was then stirred at −78° C. for 15 min. To this was then slowly added a solution of N-(1R,2R)-2-hydroxy-1-methyl-2-phenyl-ethyl)-2-(4-isopropylsulfanyl-phenyl)-N-methyl-acetamide (1.08 g, 3.02 mmol) in dry tetrahydrofuran (10 mL). The solution was then warmed to 0° C. and stirred for 1 h. After this time the reaction was then cooled back to −78° C. and treated dropwise with a solution of iodomethylcyclopentane (prepared in PCT WO2004/052869 A1 Example 1, 888 mg, 4.23 mmol) in 2,3-dimethyl-3,4,5,6-tetrahydro-2(1H)-pyrimidinone (800 μL, 6.64 mmol). The reaction was then warmed to 0° C. and stirred for 16 h. The reaction was then diluted with ethyl acetate (100 mL) and transferred to a separatory funnel and washed with a saturated aqueous ammonium chloride solution (50 mL) and then a saturated aqueous brine solution (50 mL). The organic layers were combined and then dried over sodium sulfate and concentrated in vacuo with silica gel (4 g) and then purified on Biotage Flash chromatography system (40S column, silica gel, 20% ethyl acetate/hexanes to 40% ethyl acetate/hexanes) to afford (R)-3-cyclopentyl-N-((1R,2R)-2-hydroxy-1-methyl-2-phenyl-ethyl)-2-(4-isopropylsulfanyl-phenyl)-N-methyl-propionamide (839 mg, 63%) as a yellow viscous oil: ES-HRMS m/e calcd for $C_{27}H_{37}NO_2S$ (M+H)$^+$ 440.2618, observed 440.2167.

A solution of (R)-3-cyclopentyl-N-((1R,2R)-2-hydroxy-1-methyl-2-phenyl-ethyl)-2-(4-isopropylsulfanyl-phenyl)-N-methyl-propionamide (830 mg, 1.89 mmol) in dioxane (10 mL) was treated with a 9 N aqueous sulfuric acid solution (6.0 mL). The resulting solution was then heated at 110° C. for 16 h. The reaction was then cooled and diluted with water (100 mL) and extracted with a chloroform/methanol solution (3:2, 2×50 mL). The organics were concentrated and then the residue dissolved in acetonitrile and silica gel (4 g) was added and it was concentrated in vacuo and then purified on Biotage Flash chromatography system (40S column, silica gel, 60% ethyl acetate/hexanes) to afford (R)-3-cyclopentyl-2-(4-isopropylsulfanyl-phenyl)-propionic acid (479 mg, 87%) as a yellow viscous oil: $[\alpha]^{28}_{589}$=−52.3° (c=0.22, methanol); ES-HRMS m/e calcd for $C_{17}H_{24}O_2S$ (M+Na)$^+$ 315.1389, observed 315.1388; $^1$H NMR JT (300 MHz, DMSO-d$_6$) δ 1.07 (m, 2H, CH$_2$), 1.22 (d, J=6.6 Hz, 6H, 2×CH$_3$), 1.37-1.78 (m, 8H, 4×CH$_2$), 1.94 (m, 1H, CH), 3.45 (m, 1H, SCH), 3.49 (d, J=7.5 Hz, 1H, ArCHCO), 7.25 (d, J=8.4 Hz, 2H, Ar), 7.32 (d, J=8.4 Hz, 2H, Ar), 12.35 (br, 1H, CO$_2$H).

In a flask was placed (R)-3-cyclopentyl-2-(4-isopropylsulfanyl-phenyl)-propionic acid (250 mg, 0.86 mmol) with tetrahydrofuran (1 mL) and formic acid (1.6 mL, 4.30 mmol). It was cooled to 0° C. in an ice bath and then treated with a 30% solution of hydrogen peroxide (500 μL, 4.30 mmol). It was then allowed to warm slowly to 25° C. and stirred for 16 h. It was then cooled to 0° C. and quenched by the slow addition of a saturated aqueous sodium sulfite solution (~6 mL) and then diluted with water (20 mL) and extracted with chloroform/methanol (3:2, 2×20 mL) and concentrated in vacuo. The residue was then dissolved in acetonitrile and silica gel (3 g) added and it was concentrated and then purified on Biotage Flash chromatography system (40S column, silica gel, 60% ethyl acetate) which afforded (R)-3-cyclopentyl-2-[4-(propane-2-sulfonyl)-phenyl]-propionic acid (235 mg, 85%) as a white solid: $[\alpha]^{30}_{589}$=−43.0° (c=0.20, methanol); ES-HRMS m/e calcd for $C_{17}H_{24}O_4S$ (M+H)$^+$ 325.1468, observed 325.1467; $^1$H NMR (300 MHz, DMSO-d$_6$) δ 1.08 (m, 2H, CH$_2$), 1.14 (d, J=6.6 Hz, 6H, 2×CH$_3$), 1.33-1.81 (m, 8H, 4×CH$_2$), 2.01 (m, 1H, CH), 3.40 (m, 1H, SCH), 3.69 (d, J=7.6 Hz, 1H, ArCHCO), 7.60 (d, J=8.4 Hz, 2H, Ar), 7.81 (d, J=8.4 Hz, 2H, Ar), 12.59 (br, 1H, CO$_2$H).

(R)-3-cyclopentyl-2-[4-(propane-2-sulfonyl)-phenyl]-propionic acid (100 mg, 0.31 mmol) was dissolved in methylene chloride (3 mL) and N,N-dimethylformamide (three drops) at 25° C. under argon. To this solution was added dropwise a solution of oxalyl chloride in methylene chloride (2 M solution, 180 μL, 0.33 mmol) which produced gas evolution and it was then stirred at 25° C. for 15 minutes after which time it was concentrated in vacuo. The residue was then dissolved in methylene chloride (3 mL) and added dropwise into a solution of 1-(3-amino-pyrazol-1-yl)-2-methyl-propan-2-ol (prepared as in Example 80, 50 mg, 0.31 mmol), 2,6-lutidine (100 μL, 0.62 mmol) and methylene chloride (3 mL) at 0° C. It was then allowed to warm to 25° C. and stirred for 3 h. After this time, the reaction was quenched with a small amount of methanol and diluted with methylene chloride. It was then washed with 1 N aqueous hydrochloric acid solution and saturated aqueous brine solution dried over sodium sulfate and then concentrated with silica gel (2 g) in vacuo and purified on Biotage Flash chromatography system (40S column, silica gel, 60% ethyl acetate/hexanes to 100% ethyl acetate) to afford (R)-3-cyclopentyl-N-[1-(2-hydroxy-2-methyl-propyl)-1H-pyrazol-3-yl]-2-[4-(propane-2-sulfonyl)-phenyl]-propionamide (83 mg, 58%) as a white foam: $[\alpha]^{30}_{589}$=−8.3° (c=0.18, methanol); ES-HRMS m/e calcd for $C_{24}H_{35}N_3O_4S$ (M+H)$^+$ 462.2421, observed 462.2421; $^1$H NMR (300 MHz, DMSO-d$_6$) δ ppm 1.03 (s, 3H, CH$_3$), 1.04 (s, 3H, CH$_3$), 1.11 (m, 2H, CH$_2$), 1.13 (d, J=6.9 Hz, 6H, 2×CH$_3$), 1.35-1.80 (m, 8H, 4×CH$_2$), 2.10 (m, 1H, CH), 3.36 (m, 1H, SO$_2$CH), 3.86 (s, 2H, NCH$_2$), 3.93 (m, 1H, ArCHCO), 4.65 (s, 1H, OH), 6.46 (d, J=2.4 Hz, 1H, Ar), 7.50

(d, J=2.4 Hz, 1H, Ar), 7.64 (d, J=8.4 Hz, 2H, Ar), 7.80 (d, J=8.4 Hz, 2H, Ar), 10.79 (s, 1H, NH).

Example 131

(R)-3-Cyclopentyl-N-[1-((R)-2,3-dihydroxy-propyl)-1H-pyrazol-3-yl]-2-(4-methanesulfonyl-3-methyl-phenyl)-propionamide

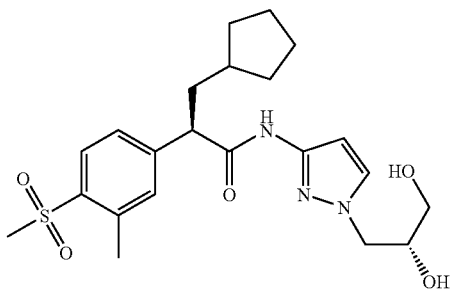

A solution of 3-cyclopentyl-2(R)-(4-methanesulfonyl-3-methyl-phenyl)-propionic acid (prepared as in PCT WO 2004/052869 A1, Example 57, 360 mg, 1.16 mmol) was dissolved in methylene chloride (8 mL) and cooled to 0° C. To this solution was added dropwise a solution of oxalyl chloride in methylene chloride (2 M solution, 640 µL, 1.27 mmol) and N,N-dimethylformamide (one drop) and it was then stirred at 0° C. for 20 minutes and 30 minutes at 25° C. After this time, the reaction was concentrated in vacuo. In a separate flask a solution of 3-(3-amino-pyrazol-1-yl)-propane-(R)-1,2-diol (prepared as in Example 35, 200 mg, 1.27 mmol), 2,6-lutidine (200 µL, 1.74 mmol) and methylene chloride (6 mL) was cooled to 0° C. in an ice bath. To this solution was added the solution of the prepared acid chloride diluted with another portion of methylene chloride (8 mL) dropwise. After addition was complete the reaction was stirred at 0° C. for 30 minutes then allowed to warm to 25° C. and stirred for 18 h. After this time the reaction was diluted with methylene chloride (20 mL) and washed with a saturated aqueous sodium bicarbonate solution (20 mL) and a 1 N aqueous hydrochloric acid solution (20 mL). Each aqueous phase was backextracted with ethyl acetate (30 mL). The combined organic layers were dried over magnesium sulfate, filtered and concentrated in vacuo. Purification an AnaLogix Intelliflash system (80 g column, 100% ethyl acetate) afforded (R)-3-cyclopentyl-N-[1-((R)-2,3-dihydroxy-propyl)-1H-pyrazol-3-yl]-2-(4-methanesulfonyl-3-methyl-phenyl)-propionamide (220 mg, 42%) as an off-white solid: $[\alpha]^{30}_{589}$=+5.80° (c=0.65, methanol); ES-HRMS m/e calcd for $C_{22}H_{31}N_3O_5S$ (M+H)$^+$ 450.2057, observed 450.2057; 1H NMR (300 MHz, DMSO-d6) δ ppm 1.09 (m, 2H, CH2), 1.33-1.81 (m, 8H, 4×CH2), 2.10 (m, 1H, CH), 2.61 (s, 3H, ArCH3), 3.17 (s, 3 H, SO2CH3), 3.26 (s, 2H, OCH2), 3.72 (brm, 1H, OCH), 3.82 (dd, J=7.6 Hz, 13.5 Hz, 1H, NCH of NCH2), 3.83 (m, 1H, ArCHCO), 4.05 (dd, J=4.0 Hz, 13.5 Hz, 1H, NCH of NCH2), 4.70 (t, J=5.6 Hz, 1H, OH), 4.92 (d, J=5.3 Hz, 1H, OH), 6.41 (d, J=2.3 Hz, 1H, Ar), 7.44 (m, 2H, Ar), 7.50 (d, J=2.3 Hz, 1H, Ar), 7.84 (d, J$_o$=8.7 Hz, 1H, Ar), 10.74 (s, 1H, NH).

Example 132

(R)-2-(3-Chloro-4-methanesulfonyl-phenyl)-3-cyclopentyl-N-[1-(2,3-dihydroxy-3-methyl-butyl)-1H-pyrazol-3-yl]-propionamide

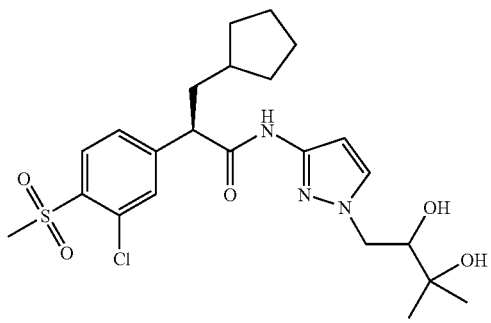

A mixture of potassium ferricyanide (21 mg, 0.06 mmol), potassium carbonate (8.9 mg, 0.06 mmol), and (DHQ)$_2$PHAL (0.3 mg, 3%) was treated with a solution of water/tert-butyl alcohol (5 mL, 1:1) and stirred at 25° C. for 5 min (until clear solution obtained). The reaction mixture was treated with a 0.2 M solution of osmium tetroxide in toluene (1µ, 1%) and cooled to 0° C. To this was added 2-(R)-(3-chloro-4-methanesulfonyl-phenyl)-3-cyclopentyl-N-[1-(3-methyl-but-2-enyl)-1H-pyrazol-3-yl]-propionamide (prepared as in Example 51, 10 mg, 0.022 mmol) and methane sulfonamide (2 mg, 0.02 mmol). The heterogeneous mixture was stirred at 0° C. for 20 h. After such time the cooling bath was removed and the mixture was treated while stirring with ethyl acetate (15 mL) and sodium sulfite (50 mg, 0.39 mmol). To this solution was added water (20 mL) and the phases were separated. The aqueous phase was backextracted with ethyl acetate. The combined organic layers were dried over sodium sulfate, filtered, and concentrated in vacuo. Purification an AnaLogix Intelliflash system (4 g column, 70% ethyl acetate/hexanes to 100% ethyl acetate) afforded (R)-2-(3-chloro-4-methanesulfonyl-phenyl)-3-cyclopentyl-N-[1-(2,3-dihydroxy-3-methyl-butyl)-1H-pyrazol-3yl]propionamide (6.7 mg, 63%) as a single diastereomer of unknown stereochemistry at the hydroxyl carbon center: $[\alpha]^{29}_{589}$=–10.2° (c=0.48, methanol); ES-HRMS m/e calcd for $C_{23}H_{32}ClN_3O_5S$ (M+H)$^+$ 498.1824, observed 498.1824; 1H NMR (400 MHz, DMSO-d6) δ ppm 1.05 (s, 3H, CH3), 1.09 (s, 3H, CH3), 1.11 (m, 2H, CH2) 1.39-1.79 (m, 8H, 4×CH2), 2.10 (m, 1H, CH), 3.34 (s, 3H, SO2CH3), 3.46 (m, 1H, OCH), 3.75 (dd, J=9.6 Hz, 13.5 Hz, 1H, NCH of NCH2), 3.90 (m, 1H, ArCHCO), 4.21 (d, J=13.5 Hz, 1H, NCH of NCH2), 4.42 (s, 1H, OH), 4.82 (d, J=6.3 Hz, 1H, OH), 6.39 (d, J=2.3 Hz, 1H, Ar), 7.51

(d, J=2.3 Hz, 1H, Ar), 7.59 (dd, $J_o$=8.3, $J_m$=1.6 Hz, 1H, Ar), 7.70 (d, $J_m$=1.6 Hz, 1H, Ar), 8.01 (d, $J_o$=8.3 Hz, 1H, Ar), 10.78 (s, 1H, NH).

Example 133

(R)—N-[1-(2-Amino-ethyl)-1H-pyrazol-3-yl]-2-(3-chloro-4-methanesulfonyl-phenyl)-3-cyclopentyl-propionamide

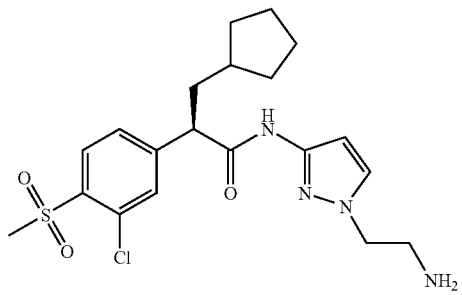

To a solution of 3-nitro-1H-pyrazole (prepared in example 3, 1.56 g, 13.79 mmol) in anhydrous N,N-dimethylformamide (20 mL), a 60% dispersion of sodium hydride in mineral oil (592 mg, 25.72 mmol) was added while stirring under nitrogen. After the effervescence ceased and the mixture was stirred for additional 15 min, (2-bromoethyl)-carbamic acid tert-butyl ester (3.94 g, 17.58 mmol) was added. The mixture was continued to stir under nitrogen for an additional 12 h. The solvent was removed in vacuo and diluted with methylene chloride and washed with 1 N hydrochloric acid and brine. The crude product thus obtained was purified by ISCO flash column chromatography (Teledyne Isco RediSep Flash Column 40 g; 0% ethyl acetate/hexanes to 50% ethyl acetate/hexanes) to afford 1-(2-ethyl-carbamic acid tert-butylester)-3-nitro-1H-pyrazole (1.07 g, 30%) as a white solid.

To a solution containing 1-(2-ethyl-carbamic acid tert-butylester)-3-nitro-1H-pyrazole (205 mg, 0.80 mmol) in ethanol (10 mL), palladium, 10 wt. % on activated carbon, wet (~50 mg) was added to the solution. The vial was charged with hydrogen gas (via balloon) and the mixture was stirred for 3 h at 25° C. The mixture was passed through a plug of celite and concentrated in vacuo to afford the desired 1-(2-ethyl-carbamic acid tert-butylester)-3-amino-1H-pyrazole (177 mg, 86%) as a solid.

To a solution containing 2(R)-(3-chloro-4-methanesulfonyl-phenyl)-3-cyclopentyl-propionic acid (prepared as in PCT WO 2004/052869 A1, Example 1, 216 mg, 0.30 mmol) in methylene chloride (10 mL), was then added a 2.0 M solution of oxalylchloride in methylene chloride (343 µL, 0.68 mmol) at 25° C. and N,N'-dimethylformamide (3 drops). Effervescence was observed. The mixture was stirred for 30 min under nitrogen. The mixture was concentrated to dryness. The residue was re-dissolved in methylene chloride (5 mL). This solution was added to a solution of 1-(2-ethyl-carbamic acid tert-butylester)-3-amino-1H-pyrazole (169 mg, 0.65 mmol) and 2,6-lutidine (152 µL, 1.31 mmol). The reaction was allowed to proceed for 2 h. The reaction solution was washed with 2 M aqueous hydrochloric acid solution, brine and dried over magnesium sulfate, concentrated in vacuo and purified by ISCO flash column chromatography (Teledyne Isco RediSep Flash Column 40 g; 0% methanol/methylene chloride to 10% methanol/methylene chloride) to afford (2R-{3-[2-(3-chloro-4-methanesulfonyl-phenyl)-3-cyclopentyl-propionylamino]-pyrazol-1-yl}-ethyl)-carbamic acid tert-butyl ester (312 mg, 89%) as a white solid.

A solution of (2R-{3-[2-(3-chloro-4-methanesulfonyl-phenyl)-3-cyclopentyl-propionylamino]-pyrazol-1-yl}-ethyl)-carbamic acid tert-butyl ester (107 mg, 0.20 mmol) in dichloromethane (3 mL) and trifluoroacetic acid (2 mL) was stirred at 25° C. for 2 h. The reaction mixture was concentrated and diluted with dichloromethane and washed with aqueous sodium bicarbonate and brine. The organic layer, on concentration afforded (2R-{3-[2-(3-chloro-4-methanesulfonyl-phenyl)-3-cyclopentyl-propionylamino]-pyrazol-1-yl}-ethyl)-amine (63 mg, 72%) as an amorphous off white solid: ES-HRMS m/e calcd for $C_{20}H_{27}N_4O_3SCl$ (M+H)$^+$ 439.1565, observed 439.1565; $^1$H NMR (400 MHz, DMSO-$d_6$) δ ppm 1.11 (m, 2H, $CH_2$), 1.37-1.80 (m, 8H, 4×$CH_2$), 2.07 (m, 1H, CH), 2.89 (t, J=6.1 Hz, 2H, $CH_2N$), 3.12 (br, 2H, $NH_2$), 3.34 (s, 3H, $SO_2CH_3$), 3.92 (dd, J=6.4 Hz, 8.5 Hz, 1H, ArCHCO), 3.95 (t, J=6.1 Hz, 2H, ArNCH$_2$), 6.42 (d, J=2.2 Hz, 1H, Ar), 7.56 (d, J=2.2 Hz, 1H, Ar), 7.60 (dd, $J_m$=1.5 Hz, $J_o$=8.3 Hz, 1H, Ar), 7.70 (d, $J_m$=1.5 Hz, 1H, Ar), 8.01 (d, $J_o$=8.7 Hz, 1H, Ar), 10.80 (s, 1H, NH).

Example 134

(R)-3-Cyclopentyl-N-[1-(2-hydroxy-2-methyl-propyl)-1H-pyrazol-3-yl]-2-(3-methanesulfonyl-phenyl)-propionamide

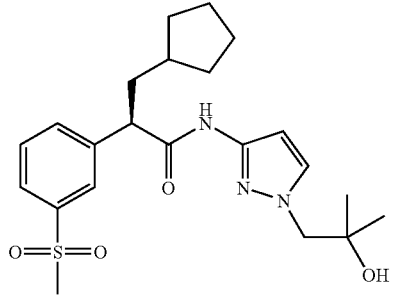

To a stirred solution of 3-(methylthio)phenyl acetic acid (3.0 g, 16.46 mmol) in anhydrous tetrahydrofuran (20 mL) potassium carbonate (5.68 g, 41.15 mmol) was added and stirring continued at 25° C. for 30 min. The reaction was cooled in an ice water bath and trimethylacetyl chloride (2.08 g, 17.28 mmol) was added slowly via syringe and stirring continued at 0° C. for 30 min. 1R,2R-(−)-Pseudoephedrine (3.54 g, 21.40 mmol) was added slowly at 0° C. and stirring continued for 30 min. Water (20 mL) was added and the reaction was allowed to warm to 25° C. The reaction was poured into water (20 mL) and extracted with ethyl acetate. The ethyl acetate fractions were washed with water, 2 N aqueous hydrochloric acid, saturated sodium bicarbonate and saturated sodium chloride solution and then dried over magnesium sulfate. Filtration and concentration afforded N-((1R,2R)-2-hydroxy-1-methyl-2-phenyl-ethyl)-N-methyl-2-(3-methylsulfanyl-phenyl)-acetamide (1.60 g, 30%) as yellow oil. The product was used without further purification.

To a solution of 1,1,1,3,3,3-Hexamethyldisilazane (1.81 g, 11.19 mmol) in tetrahydrofuran (15 mL) cooled to −20° C. under nitrogen was added n-butyllithium (6.4 mL of a 1.6 M solution, 10.21 mmol) slowly keeping the temperature at −20° C. for 30 min. N-((1R,2R)-2-hydroxy-1-methyl-2-phenyl-ethyl)-N-methyl-2-(3-methylsulfanyl-phenyl)-acetamide (1.60 g, 4.86 mmol) in tetrahydrofuran (15 mL) was added slowly to the reaction maintaining the temperature at −20° C. After the addition was complete the reaction was warmed to 0° C. and stirred for 30 min. A solution of 2,3-dimethyl-3,4,5,6-tetrahydro-2(1H)-pyrimidinone (1.31 g, 10.21 mmol) and iodomethylcyclopentane (prepared in PCT WO2004/052869 A1 Example 1, 1.23 g, 5.84 mmol) were added to the reaction at 0° C. and stirring continued for 3 h. The reaction was poured into water (60 mL) and extracted with ethyl acetate. The ethyl acetate fractions were washed with water, 2 N aqueous hydrochloric acid solution, saturated sodium bicarbonate and saturated sodium chloride solution and then dried over magnesium sulfate. Filtration and concentration afforded the crude product which was purified by ISCO flash column chromatography (Teledyne Isco RediSep Flash Column 40 g; 0% ethyl acetate/hexanes to 50% ethyl acetate/hexanes) to yield (R)-3-cyclopentyl-N-((1R,2R)-2-hydroxy-1-methyl-2-phenyl-ethyl)-N-methyl-2-(3-methylsulfanyl-phenyl)-propionamide (1.16 g, 58%) as a clear sticky solid.

To a stirred solution of (R)-3-cyclopentyl-N-((1R,2R)-2-hydroxy-1-methyl-2-phenyl-ethyl)-N-methyl-2-(3-methylsulfanyl-phenyl)-propionamide (1.16 g, 2.82 mmol) in 1,4-dioxane (10 mL) was added 9 N aqueous sulfuric acid (10 mL) and the reaction was stirred at 110° C. for 18 h. The reaction was cooled to 25° C. and diluted with water (25 mL) and poured into methylene chloride (30 mL). The layers were separated and the aqueous layer was extracted with methylene chloride (2×30 mL). The combined methylene chloride layers were washed with water and saturated sodium chloride solution and then dried over magnesium sulfate. Filtration and concentration afforded the crude product which was purified by ISCO flash column chromatography (Teledyne Isco RediSep Flash Column 40 g; 0% ethyl acetate/hexanes to 50% ethyl acetate/hexanes) to yield (R)-3-cyclopentyl-2-(3-methylsulfanyl-phenyl)-propionic acid (712 mg, 96%) as a white solid.

To a stirred solution of sodium periodate (1.07 g, 4.98 mmol) in water (10 mL) was added a solution of (R)-3-cyclopentyl-2-(3-methylsulfanyl-phenyl)-propionic acid (700 mg, 2.65 mmol) in methanol (15 mL) and the reaction was stirred at 25° C. for 1 h. The reaction mixture was filtered through a pad of celite and the solids were washed with methanol and chloroform. The filtrate was concentrated and azeotroped with benzene to remove any traces of water to yield (R)-3-cyclopentyl-2-(3-methylsulfinyl-phenyl)-propionic acid as a white solid which was then dissolved into methanol (20 mL). To this stirred solution was slowly added potassium permanganate (630 mg, 3.98 mmol) in water (6 mL) and the reaction stirred at 25° C. for 1 h. The reaction mixture was filtered through a pad of celite and the solids washed with methanol. Concentrate the filtrate to yield (R)-3-cyclopentyl-2-(3-methylsulfonyl-phenyl)-propionic acid (705 mg, 90%) as a white solid.

To a stirred solution of (R)-3-cyclopentyl-2-(3-methylsulfonyl-phenyl)-propionic acid (200 mg, 0.65 mmol) in benzene (10 mL) was added oxalyl chloride (123 mg, 0.97 mmol) and DMF (1 drop) and the reaction was stirred at 25° C. for 1 h. The reaction was concentrated under reduced pressure and the residue was dissolved into methylene chloride (10 mL) under a nitrogen atmosphere. To this stirred solution was added N,N'-diisopropylethylamine (125 mg, 0.97 mmol) and 1-(3-amino-pyrazol-1-yl)-2-methyl-propan-2-ol (prepared as in Example 80, 130 mg, 0.84 mmol). The reaction was stirred at 25° C. for 18 h and then diluted with methylene chloride (30 mL). The methylene chloride was washed with water, 2 N aqueous hydrochloric acid solution, saturated sodium bicarbonate and saturated sodium chloride solution and then dried over magnesium sulfate. Filtration and concentration afforded the crude product which was purified by flash column chromatography (Biotage 40S Flash Column; 80% ethyl acetate/hexanes) to yield (R)-3-cyclopentyl-N-[1-(2-hydroxy-2-methyl-propyl)-1H-pyrazol-3-yl]-2-(3-methanesulfonyl-phenyl)-propionamide (92 mg, 32%) as a white solid: $[\alpha]^{28}_{589}=-8.9°$ (c=0.1, methanol); ES-HRMS m/e calcd for $C_{22}H_{31}N_3O_4S$ (M+H)$^+$ 434.2108, observed 434.2108; $^1$H NMR (400 MHz, DMSO-d$_6$) δ ppm 1.03 (s, 3H, CH$_3$), 1.05 (s, 3H, CH$_3$), 1.12 (m, 2H, CH$_2$), 1.37-1.79 (m, 8H, 4×CH$_2$), 2.13 m, 1H, CH), 3.21 (s, 3H, SO$_2$CH$_3$), 3.86 (s, 2H, NCH$_2$), 3.93 (m, 1H, ArCHCO), 4.64 (s, 1H, OH), 6.46 (d, J=2.2 Hz, 1H, Ar), 7.50 (d, J=2.2 Hz, 1H, Ar), 7.61 (t, J=7.7 Hz, 1H, Ar), 7.73 (d, J=7.7 Hz, 1H, Ar), 7.82 (d, J=7.7 Hz, 1H, Ar), 7.93 (s, 1H, Ar), 10.78 (s, 1H, NH).

Example 135

(R)-3-Cyclopentyl-2-(3-methanesulfonyl-phenyl)-N-[1-(2-methoxy-2-methyl-propyl)-1H-pyrazol-3-yl]-propionamide

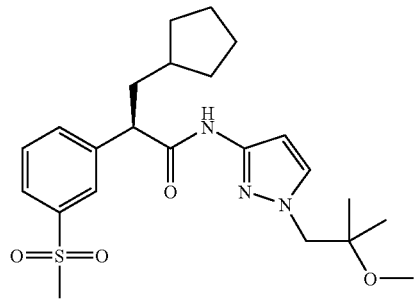

To a stirred solution of (R)-3-cyclopentyl-2-(3-methylsulfonyl-phenyl)-propionic acid (prepared in Example 134, 200 mg, 0.65 mmol) in benzene (10 mL) was added oxalyl chloride (123 mg, 0.97 mmol) and DMF (1 drop) and the reaction was stirred at 25° C. for 3 h. The reaction was concentrated under reduced pressure and the residue was dissolved into methylene chloride (10 mL) under a nitrogen atmosphere. To this stirred solution was added N,N'-diisopropylethylamine (125 mg, 0.97 mmol) and 1-(2-methoxy-2-methyl-propyl)-1H-pyrazol-3-ylamine (prepared in Example 94, 130 mg, 0.84 mmol). The reaction was stirred at 25° C. for 18 h and then diluted with methylene chloride (30 mL). The methylene chloride was washed with water, 2 N aqueous hydrochloric acid solution, saturated sodium bicarbonate and saturated sodium chloride solution and then dried over magnesium sulfate. Filtration and concentration afforded the crude product which was purified by flash column chromatography (Biotage 40S Flash Column; 70% ethyl acetate/hexanes) to yield (R)-3-cyclopentyl-2-(3-methanesulfonyl-phenyl)-N-[1-(2-methoxy-2-methyl-propyl)-1H-pyrazol-3-yl]-propionamide (157 mg, 55%) as a white solid: ES-HRMS m/e calcd for $C_{23}H_{33}N_3O_4S$ (M+H)$^+$ 448.2265, observed 448.2265; $^1$H NMR (300 MHz, DMSO-d$_6$) δ ppm 1.04 (s, 3H, CH$_3$), 1.05 (s, 3H, CH$_3$), 1.10 (m, 2H, CH$_2$), 1.35-1.80 (m, 8H, 4×CH$_2$), 2.13 (m, 1H, CH), 3.13 (s, 3H, OCH$_3$), 3.21 (s, 3H, SO$_2$CH$_3$), 3.94 (m, 1H, ArCHCO), 3.96 (s, 2H, NCH$_2$), 6.46 (d, J=2.1 Hz, 1H, Ar), 7.47 (d, J=2.1 Hz, 1H, Ar), 7.61 (t, J=7.7 Hz, 1H, Ar), 7.73 (d, J=7.7 Hz, 1H, Ar), 7.82 (d, J=7.7 Hz, 1H, Ar), 7.94 (s, 1H, Ar), 10.79 (s, 1H, NH).

Example 136

3-Cyclopentyl-2-(1,1-dioxo-benzo[b]thiophen-5-yl)-N-[1-(2-hydroxy-2-methyl-propyl)-1H-pyrazol-3-yl]-propionamide

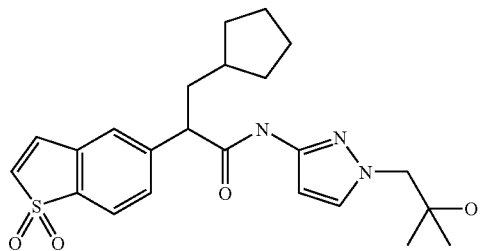

In a flask was placed 5-methyl-benzo[b]thiophene (3.64 g, 24.56 mmol) and carbon tetrachloride (75 mL). To the reaction mixture was then added N-bromosuccinimide (5.68 g, 31.92 mmol) and benzoyl peroxide (892 mg, 3.68 mmol) and it was the final solution was then heated at 76° C. for 6 h. After this time the reaction mixture was cooled to 0° C. in an ice bath and the solids were filtered off and the filterate was concentrated in vacuo and purified on an AnaLogix Intelliflash system (120 g column, 3% ethyl acetate/hexanes) to afford 5-bromomethyl-benzo[b]thiophene (5.27 g, 94%) as a yellow solid.

In a round bottom flask was placed 5-bromomethyl-benzo[b]thiophene (5.27 g, 23.20 mmol), sodium cyanide (1.59 g, 32.49 mmol) and N,N-dimethylformamide (50 mL) and it was stirred for 24 h at 25° C. After this time, the reaction mixture was dissolved in water (30 mL) and extracted with ethyl acetate (3×30 mL), dried over sodium sulfate and purified on an AnaLogix Intelliflash system (120 g column, 3% ethyl acetate/hexanes to 20% ethyl acetate/hexanes) to afford benzo[b]thiophen-5-yl-acetonitrile (2.23 g, 55%) as a yellow solid.

In a round bottom flask was placed benzo[b]thiophen-5-yl-acetonitrile (700 mg, 4.04 mmol), tetrabutyl ammonium hydrogen sulfate (1.37 g, 4.04 mmol) and a 47% by weight solution of aqueous sodium hydroxide (646 μl, 8.08 mmol). To this well stirred mixture was added iodomethylcyclopentane (prepared in PCT WO 2004/052869 A1 Example 1, 1.69 g, 8.08 mmol) and the vigorously stirred mixture was heated to reflux for 6 h. The reaction was then diluted with water (5 mL) and methylene chloride (10 mL) and extracted with methylene chloride (3×20 mL). The organics were combined and dried over sodium sulfate, filtered and concentrated in vacuo. Purification an AnaLogix Intelliflash system (40 g column, 3% ethyl acetate/hexanes to 5% ethyl acetate/hexanes) afforded 2-benzo[b]thiophen-5-yl-3-cyclopentyl-propionitrile (416 mg, 40%) as a yellow oil: ES-HRMS m/e calcd for $C_{16}H_{17}NS$ (M+H)$^+$ 256.115, observed 256.115.

In a round bottom flask was placed 2-benzo[b]thiophen-5-yl-3-cyclopentyl-propionitrile (50 mg, 0.19 mmol) and a 1:1 mixture of 45% aqueous potassium hydroxide solution:ethanol (2 mL) and it was heated at reflux until the reaction was complete (~6 h). After this time the ethanol is removed in vacuo and the resulting solution is treated with 1 N aqueous hydrochloric acid until the pH=2. It was then extracted with ethyl acetate (3×10 mL), dried over magnesium sulfate, filtered and concentrated in vacuo. This afforded 2-benzo[b]thiophen-5-yl-3-cyclopentyl-propionic acid (45 mg, 84%) as a brownish solid which was ~75% pure, this material was used in the next step with no purification.

In a flask was placed 2-benzo[b]thiophen-5-yl-3-cyclopentyl-propionic acid (45 mg, 0.16 mmol) with formic acid (1.5 mL). It was cooled to 0° C. in an ice bath and then treated with a 30% solution of hydrogen peroxide (1.5 mL). It was then allowed to warm slowly to 25° C. and stirred for 6 h. It was then cooled to 0° C. and quenched by the slow addition of a saturated aqueous sodium sulfite solution and extracted with ethyl acetate (3×20 mL) dried over magnesium sulfate, filtered and concentrated in vacuo and azeotroped with toluene to afford 3-cyclopentyl-2-(1,1-dioxo-benzo[b]thiophen-5-yl)-propionic acid (36 mg, 73%) as a light brown solid, which was used in the next reaction without purification.

A solution of 3-cyclopentyl-2-(1,1-dioxo-benzo[b]thiophen-5-yl)-propionic acid (36 mg, 0.12 mmol) was dissolved in methylene chloride (5 mL) and N,N-dimethylformamide (one drop) and cooled to 0° C. To this solution was added dropwise a solution of oxalyl chloride in methylene chloride (2 M solution, 67 μL, 0.14 mmol) which produced gas evolution and it was stirred at 0° C. for 10 min and it was then allowed to warm to 25° C. and stirred for 1 h. After this time, the reaction was concentrated in vacuo to ~1.5 mL. In a separate flask, a solution of 1-(3-amino-pyrazol-1-yl)-2-methyl-propan-2-ol (prepared as in Example 80, 20 mg, 0.13 mmol), 2,6-lutidine (20 μL, 0.18 mmol) and methylene chloride (5 mL) was cooled to 0° C. in an ice bath. To this solution was added the solution of the prepared acid chloride, diluted with another portion of methylene chloride (1 mL), dropwise. After addition was complete the reaction was then allowed to warm to 25° C. and stirred for 16 hours. After this time the reaction mixture quenched with a saturated aqueous sodium bicarbonate solution (10 mL) and transferred to a separatory funnel where it was extracted with methylene chloride (3×10 mL). The organic layers were then washed with a 1 N aqueous hydrochloric acid solution (20 mL) and then dried over sodium sulfate, filtered and concentrated in vacuo. Purification on an AnaLogix Intelliflash system (4 g column, 50% ethyl acetate/hexanes to 75% ethyl acetate/hexanes) afforded 3-cyclopentyl-2-(1,1-dioxo-benzo[b]thiophen-5-yl)-N-[1-(2-hydroxy-2-methyl-propyl)-1H-pyrazol-3-yl]-propionamide (23 mg, 43%) as an off-white foam (as a racemic mixture): ES-HRMS m/e calcd for $C_{23}H_{29}N_3O_4S$ (M+H)$^+$ 444.1952, observed 444.1949; $^1$H NMR (400 MHz, DMSO-d6) δ ppm 1.03 (s, 3 H, $CH_3$), 1.05 (s, 3H, $CH_3$), 1.11 (m, 2H, $CH_2$), 1.37-1.78 (m, 8H, 4×$CH_2$), 2.06 m, 1 H, CH), 3.87 (s, 2H, $NCH_2$), 3.93 (t, J=7.5 Hz, 1H, ArCHCO), 4.64 (s, 1H, OH), 6.45 (d, J=2.2 Hz, 1H, Ar), 7.35 (d, J=6.9 Hz, 1H, Ar), 7.51 (d, J=2.1 Hz, 1H, Ar), 7.58 (dd, $J_o$=7.8 Hz, $J_m$=1.3 Hz, 1H, Ar), 7.61 (d, $J_m$=1.3 Hz, 1H, Ar), 7.67 (d, J=6.9 Hz, 1H, Ar), 7.79 (d, $J_o$=7.8 Hz, 1H, Ar), 10.78 (s, 1H, NH).

Example 137

(R)-3-Cyclopentyl-2-(1,1-dioxo-benzo[b]thiophen-5-yl)-N-[1-(2-hydroxy-2-methyl-propyl)-1H-pyrazol-3-yl]-propionamide

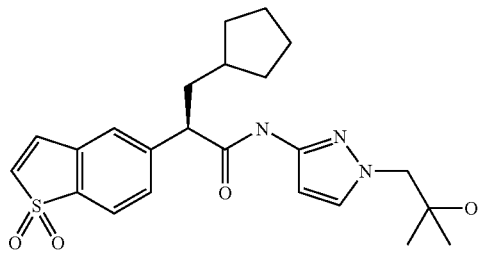

The racemic mixture of 3-cyclopentyl-2-(1,1-dioxo-benzo[b]thiophen-5-yl)-N-[1-(2-hydroxy-2-methyl-propyl)-1H-pyrazol-3-yl]-propionamide (prepared in Example 136, 20 mg) was separated into the single enantiomers by supercritical fluid chromatography (SFC) on a Berger MultiGram II Supercritical Fluid Chromatography (SFC) system (Mettler-Toledo AutoChem Berger Instruments, Newark, Del.) (Chiral column: (R,R)-Whelk O 1, 250 mm×20 mm i.d., 10 μm-particle size, temperature: 35° C., flow rate of 50 mL/min, and 100 bar back pressure, 40% methanol as mobile phase modifier, UV Detection: 220 nm) to afford the pure enantiomer: the first peak to elute was the (R)-3-cyclopentyl-2-(1,1-dioxo-benzo[b]thiophen-5-yl)-N-[1-(2-hydroxy-2-methyl-propyl)-1H-pyrazol-3-yl]-propionamide enantiomer which was isolated as a white solid (7 mg): $[\alpha]^{31}_{589}$=5.0° (c=0.18, methylene chloride); ES-HRMS m/e calcd for $C_{23}H_{29}N_3O_4S$ $(M+H)^+$ 444.1952, observed 444.1950; $^1$H NMR (400 MHz, DMSO-$d_6$) δ ppm 1.03 (s, 3 H, $CH_3$), 1.04 (s, 3H, $CH_3$), 1.11 (m, 2H, $CH_2$), 1.37-1.78 (m, 8H, 4×$CH_2$), 2.06 (m, 1 H, CH), 3.87 (s, 2H, $NCH_2$), 3.93 (dd, J=6.9 Hz, 8.1 Hz, 1H, ArCHCO), 4.64 (s, 1H, OH), 6.45 (d, J=2.2 Hz, 1H, Ar), 7.35 (d, J=6.9 Hz, 1H, Ar), 7.51 (d, J=2.1 Hz, 1H, Ar), 7.58 (dd, $J_o$=7.8 Hz, $J_m$=1.3 Hz, 1H, Ar), 7.61 (d, $J_m$=1.3 Hz, 1H, Ar), 7.67 (d, J=6.9 Hz, 1H, Ar), 7.79 (d, $J_o$=7.8 Hz, 1H, Ar), 10.78 (s, 1H, NH).

Example 138

3-Cyclopentyl-2-(1,1-dioxo-2,3-dihydro-benzo[b]thiophen-5-yl)-N-[1-(2-hydroxy-2-methyl-propyl)-1H-pyrazol-3-yl]-propionamide

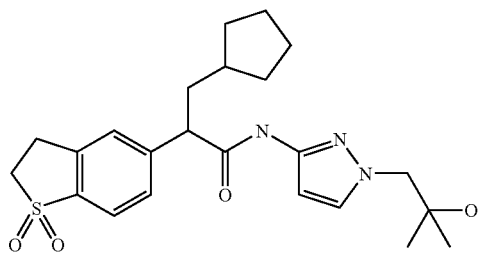

In a Parr shaker bottle was placed benzo[b]thiophene 1,1-dioxide (5.0 g, 30.08 mmol), palladium on activated carbon (500 mg) and ethanol (100 mL). The bottle was placed on a Parr shaker and charged with 50 psi of hydrogen for 1 h. The reaction mixture was removed from the Parr shaker and filtered through a plug of celite and concentrated in vacuo to afford 2,3-dihydro-benzo[b]thiophene 1,1-dioxide (5.06 g, 100%) as a white solid.

A suspension of 2,3-dihydro-benzo[b]thiophene 1,1-dioxide (5.06 g, 30.08 mmol) in diethyl ether (150 mL) was added to a suspension of lithium aluminum hydride (10.27 g, 270.27 mmol) in diethyl ether (150 mL) at 25° C. After this time it was heated to reflux for 4 h (caution: if heating is too rapid it can exotherm rapidly and cause loss of material through the reflux condenser). It was then cooled to 0° C. in an ice bath and water (50 mL) was added very slowly. The resulting material was dissolved in 4 M aqueous hydrochloric acid (1 L). The aqueous layer was then extracted with diethyl ether (3×200 mL). The organic layers were combined and dried over magnesium sulfate, filtered and concentrated in vacuo. The material was purified by passing it through a plug of silica gel using pentane as the solvent to afford 2,3-dihydro-benzo[b]thiophene (1.88 g, 46%) as a clear colorless oil.

To a solution of 2,3-dihydro-benzo[b]thiophene (1.88 g, 13.8 mmol) in methylene chloride (20 mL) at −10° C. was added dropwise a solution of acetyl chloride (1.85 mL, 25.9 mmol) and aluminum chloride (1.84 g, 13.8 mmol) in methylene chloride (20 mL) keeping the temperature below −6° C. during the addition period. After the addition is complete the reaction mixture was stirred for an additional 30 min at −10° C. and then added ice (40 mL) and concentrated hydrochloric acid (6 mL) and extracted with methylene chloride (3×20 mL), dried over magnesium sulfate, filtered and concentrated in vacuo. Purification on an AnaLogix Intelliflash system (80 g column, 10% diethyl ether/hexanes) afforded 1-(2,3-dihydro-benzo[b]thiophen-5-yl)-ethanone (1.93 g, 78%) as a clear colorless oil.

In a flask was placed 1-(2,3-dihydro-benzo[b]thiophen-5-yl)-ethanone, morpholine (1.41 mL, 16.19 mmol), sulfur (345 mg, 10.79 mmol) and p-toluenesulfonic acid monohydrate (41 mg, 0.22 mmol) and it was heated at 129° C. for 5 h. After that time, the reaction was cooled to 25° C. and methanol (6 mL) was added. The reaction mixture was concentrated in vacuo and then purified on an AnaLogix Intelliflash system (80 g column, 15% diethyl ether/hexanes to 30% ethyl acetate/hexanes) to afford 2-(2,3-dihydro-benzo[b]thiophen-5-yl)-1-morpholin-4-yl-ethanethione (1.85 g, 61%) as a brown solid.

In a round bottom flask with a reflux condenser was placed 2-(2,3-dihydro-benzo[b]thiophen-5-yl)-1-morpholin-4-yl-ethanethione (1.85 g, 6.62 mmol) and to it was added acetic acid (7.7 mL), concentrated sulfuric acid (1.1 mL) and water (2 mL). The reaction mixture was then heated at 100° C. for 4 h. After this time the solution was added to water (40 mL) and extracted with ethyl acetate (3×50 mL). The organics were dried over sodium sulfate, filtered and concentrated in vacuo. Purified using reverse phase HPLC to afford (2,3-dihydro-benzo[b]thiophen-5-yl)-acetic acid (525 mg, 41%) as a white solid.

In a round bottom flask was placed (2,3-dihydro-benzo[b]thiophen-5-yl)-acetic acid (525 mg, 2.70 mmol), methanol (15 mL) and hydrochloric acid (2 drops). The reaction mixture was heated to 65° C. for 16 h. It was then concentrated in vacuo to remove the methanol, diluted with water (20 mL) and extracted with ethyl acetate (3×20 mL). The organic layers were combined and washed with a saturated aqueous sodium bicarbonate solution (10 mL), dried over magnesium sulfate, filtered and concentrated in vacuo to afford (2,3-dihydro-benzo[b]thiophen-5-yl)-acetic acid methyl ester (528 mg, 94%) as a yellow oil: ES-HRMS m/e calcd for $C_{11}H_{12}O_2S$ (M+H)$^+$ 209.0631, observed 209.0631.

A round bottom flask with a stir bar and argon inlet was charged with tetrahydrofuran (10 mL) and cooled to −78° C. Diisopropyl amine (155 µL, 1.10 mmol) was then added followed by the dropwise addition of a solution of n-butyl lithium (2.5M solution in hexanes, 422 µL, 1.06 mmol) and it was stirred at −78° C. for 15 min. After this time, a solution of (2,3-dihydro-benzo[b]thiophen-5-yl)-acetic acid methyl ester (200 mg, 0.96 mmol) in tetrahydrofuran (3 mL) and 2,3-dimethyl-3,4,5,6-tetrahydro-2(1H)-pyrimidinone (0.5 mL) was added dropwise. It was then stirred for 1 h at −78° C. It was then treated with a solution of iodomethylcyclopentane (prepared in PCT WO2004/052869 A1 Example 1, 302 mg, 1.44 mmol) in 2,3-dimethyl-3,4,5,6-tetrahydro-2(1H)-pyrimidinone (0.5 mL) dropwise. The reaction was then stirred at −78° C. and gradually allowed to warm to 25° C. and stirred at 25° C. for 16 h. The reaction was then diluted with a saturated aqueous ammonium chloride solution (30 mL). The aqueous layer was and extracted with ethyl acetate (3×20 mL). The organics were then dried over magnesium sulfate, filtered and concentrated in vacuo. Purification on an AnaLogix Intelliflash system (12 g column, 2% ethyl acetate/hexanes) afforded 3-cyclopentyl-2-(2,3-dihydro-benzo[b]thiophen-5-yl)-propionic acid methyl ester (193 mg, 69).

In a flask was placed 3-cyclopentyl-2-(2,3-dihydro-benzo[b]thiophen-5-yl)-propionic acid methyl ester (192 mg, 0.66 mmol) with formic acid (2.0 mL) and tetrahydrofuran (2 mL). It was cooled to 0° C. in an ice bath and then treated with a 30% solution of hydrogen peroxide (1.5 mL). It was then allowed to warm slowly to 25° C. and stirred for 16 h. It was then cooled to 0° C. and quenched by the slow addition of a saturated aqueous sodium sulfite solution and extracted with ethyl acetate (3×20 mL) dried over magnesium sulfate, filtered and concentrated in vacuo to afford 3-cyclopentyl-2-(1,1-dioxo-2,3-dihydro-benzo[b]thiophen-5-yl)-propionic acid methyl ester (184 mg, 87%) as a white solid.

3-Cyclopentyl-2-(1,1-dioxo-2,3-dihydro-benzo[b]thiophen-5-yl)-propionic acid methyl ester (184 mg, 0.57 mmol) was dissolved in ethanol (4 mL) and treated with a solution of lithium hydroxide monohydrate (34 mg, 1.43 mmol) in water (1.5 mL) at 25° C. It was stirred at 25° C. until the starting material was all consumed by TLC (~1 hr). The reaction was then concentrated in vacuo to remove the ethanol. The remaining aqueous layer was then acidified to pH=2 with an aqueous 1N hydrochloric acid solution. This was then extracted with ethyl acetate (3×20 mL), the organic layers combined and dried over magnesium sulfate, filtered and concentrated in vacuo to afford 3-cyclopentyl-2-(1,1-dioxo-2,3-dihydro-benzo[b]thiophen-5-yl)-propionic acid (114 mg, 65%) as a white solid: EI-HRMS m/e calcd for $C_{16}H_{20}O_4S$ (M$^+$) 308.1082, observed 308.1075.

A solution of 3-cyclopentyl-2-(1,1-dioxo-2,3-dihydro-benzo[b]thiophen-5-yl)-propionic acid (114 mg, 0.37 mmol) was dissolved in methylene chloride (5 mL) and N,N-dimethylformamide (one drop) and cooled to 0° C. To this solution was added dropwise a solution of oxalyl chloride in methylene chloride (2 M solution, 212 µL, 0.43 mmol) which produced gas evolution and it was stirred at 0° C. for 15 min and it was then allowed to warm to 25° C. and stirred for 1 h. After this time, the reaction was concentrated in vacuo to ~1.5 mL. In a separate flask, a solution of 1-(3-amino-pyrazol-1-yl)-2-methyl-propan-2-ol (prepared as in Example 80, 63 mg, 0.41 mmol), 2,6-lutidine (61 µL, 0.55 mmol) and methylene chloride (5 mL) was cooled to 0° C. in an ice bath. To this solution was added the solution of the prepared acid chloride, diluted with another portion of methylene chloride (1 mL), dropwise. After addition was complete the reaction was then allowed to warm to 25° C. and stirred for 16 hours. After this time the reaction mixture was diluted with methylene chloride (10 mL) and washed with a saturated aqueous sodium bicarbonate solution (15 mL). The aqueous layer was then extracted with methylene chloride (2×10 mL). The organic layers were then washed with a 1 N aqueous hydrochloric acid solution (10 mL) and then dried over magnesium sulfate, filtered and concentrated in vacuo. Purification using reverse phase HPLC afforded 3-cyclopentyl-2-(1,1-dioxo-2,3-dihydro-benzo[b]thiophen-5-yl)-N-[1-(2-hydroxy-2-methyl-propyl)-1H-pyrazol-3-yl]-propionamide (103 mg, 63%) as a white foam (as a racemic mixture): ES-HRMS m/e calcd for $C_{23}H_{31}N_3O_4S$ (M+H)$^+$ 446.2108, observed 446.2109; $^1$H NMR (300 MHz, DMSO-d6) δ ppm 1.03 (s, 3H, $CH_3$), 1.04 (s, 3 H, $CH_3$), 1.10 (m, 2H, $CH_2$), 1.38-1.79 (m, 8H, 4×$CH_2$), 2.07 (m, 1H, CH), 3.33 (t, J=6.8 Hz, 2H, Ar$CH_2$), 3.56 (t, J=6.8 Hz, 2H, $SO_2CH_2$), 3.86 (s, 2 H, $NCH_2$), 3.91 (m, 1 H, ArCHCO), 4.65 (s, 1H, OH), 6.45 (d, J=2.2 Hz, 1H, Ar), 7.51 (m, 3H, Ar), 7.69 (d, J$_o$=8.5 Hz, 1H, Ar), 10.75 (s, 1H, NH).

Example 139

(R)-2-(3-Chloro-4-methanesulfonyl-phenyl)-3-cyclopentyl-N-[1-(2,3-dihydroxy-3-methyl-butyl)-1H-pyrazol-3-yl]-propionamide

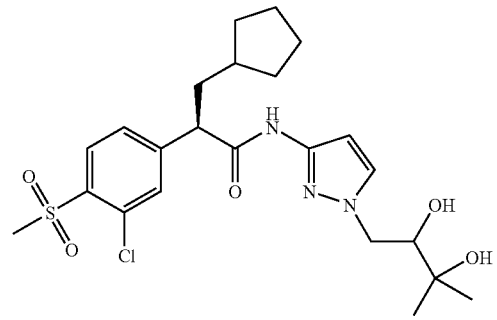

A mixture of potassium ferricyanide (0.06 mmol, 3.0 equiv.), potassium carbonate (0.06 mmol, 3.0 equiv.), and (DHQD)$_2$PHAL (0.0006 mmol, 0.03 equiv.) is treated with a solution of water/tert-butyl alcohol (5 mL, 1:1) and is stirred at 25° C. for 5 min. The reaction mixture is treated with a 0.2 M solution of osmium tetroxide in toluene (0.0002 mmol, 0.01 equiv.) and cooled to 0° C. To this is added 2-(R)-(3-chloro-4-methanesulfonyl-phenyl)-3-cyclopentyl-N-[1-(3-methyl-but-2-enyl)-1H-pyrazol-3-yl]-propionamide (prepared as in Example 51, 0.02 mmol, 1 equiv.) and methane sulfonamide (0.02 equiv.). The heterogeneous mixture is stirred at 0° C. for 20 h. After such time the cooling bath is removed and the mixture is treated while stirring with ethyl acetate (15 mL) and sodium sulfite (0.36 mmol, 18 equiv.). To this solution is added water (20 mL) and the phases are separated. The aqueous phase is backextracted with ethyl acetate. The combined organic layers were dried over sodium sulfate, filtered, and concentrated in vacuo. Purification on an AnaLogix Intelliflash system would produce (R)-2-(3-chloro-4-methanesulfonyl-phenyl)-3-cyclopentyl-N-[1-(2,3-dihydroxy-3-methyl-butyl)-1H-pyrazol-3-yl]propionamide as a single diastereomer of unknown stereochemistry at the hydroxyl carbon center but opposite configuration at the hydroxyl stereocenter of Example 132.

Example 140

(R)-2-(3-Chloro-4-cyclopentanesulfonyl-phenyl)-3-cyclopentyl-N-[1-(2-hydroxy-2-methyl-propyl)-1H-pyrazol-3-yl]-propionamide

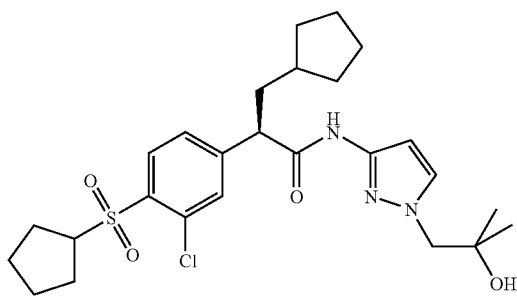

In a sealed tube fitted with a septum to allow for the contents to be placed under an argon atmosphere is placed 2-chloro-benzenethiol (20 mmol) and N,N-dimethylformamide (15 mL). To this solution under argon is then added in small portions sodium hydride (1.1 equiv.). After addition is complete the reaction mixture is stirred for another 20 min at 25° C. To this solution is then added cyclopentyl bromide (1.1 equiv) and the reaction is then sealed and the tube placed in an oil bath and heated to 100° C. for 20 h. After such time the reaction mixture is cooled to 25° C. and then poured onto crushed ice and extracted with diethyl ether. The combined organic layers are then washed with a saturated aqueous solution of sodium bicarbonate, dried over sodium sulfate and concentrated in vacuo. The resulting liquid is then distilled to yield 1-chloro-2-cyclopentylsulfanyl-benzene.

In a round bottom flask is placed methylene chloride (100 mL) and aluminum trichloride (1.39 equiv) and it is cooled to 0° C. in an ice bath. To this solution is then added dropwise chloro-oxo-acetic acid ethyl ester (1.09 equiv.) keeping the temperature of the solution below 5° C. and it is then stirred for 30 min at 0° C. After this time a solution of 1-chloro-2-cyclopentylsulfanyl-benzene (50.0 mmol) in methylene chloride (5 mL) is added dropwise while keeping the temperature of the solution below 5° C. The ice bath is then removed and the reaction is allowed to warm up to 25° C. and is stirred for 3 h. The reaction is then cooled back down to 0° C. in an ice bath and ice water (20 mL) is then added dropwise keeping the temperature of the solution below 20° C. It is then stirred for 15 min and then transferred to a separatory funnel and separated. The organic phase is then washed with water (2×25 mL), saturated aqueous sodium bicarbonate solution (2×25 mL) and water (25 mL) and then dried over magnesium sulfate, filtered and concentrated in vacuo to afford (3-chloro-4-cyclopentylsulfanyl-phenyl)-oxo-acetic acid ethyl ester.

In a flask (3-chloro-4-cyclopentylsulfanyl-phenyl)-oxo-acetic acid ethyl ester (35.00 mmol) is dissolved in toluene (20 mL) and heated to 50° C. in an oil bath. To this heated solution is then added an aqueous sodium hydroxide solution (3 M solution, 1.24 equiv.) dropwise keeping the temperature of the reaction below 60° C. The reaction is then stirred at 50° C. for 1.5 h. After this time the reaction is removed from the oil bath and concentrated hydrochloric acid (1.52 equiv.) is added dropwise while the reaction is still at 50° C. It is then allowed to cool to 25° C. and stirred for 16 h. The solids are filtered off and washed with water (10 mL) and toluene (10 mL) to afford (3-chloro-4-cyclopentyllsulfanyl-phenyl)-oxo-acetic acid.

Hydrazine hydrate (10 equiv.) is placed in a three neck flask fitted with an overhead mechanical stirrer and a reflux condenser and cooled in a dry ice acetone bath at −78° C. After the solution reached −50° C. the bath is removed and (3-chloro-4-cyclopentylsulfanyl-phenyl)-oxo-acetic acid (15.00 mmol) is added in one portion. It is then heated in an oil bath to 80° C. After the reaction is at 80° C. it is treated with potassium hydroxide (0.60 equiv.) and stirred vigorously. When the reaction returns to 80° C. a second portion of potassium hydroxide (0.60 equiv.) is added and allowed to cool back to 80° C. This cycle is repeated two more times adding potassium hydroxide (0.60 equiv.) each time. The reaction is then heated at 100° C. for 16 h. It is then cooled to 25° C. and water (3 mL) added to the reaction. It was then transferred to a separatory funnel and another portion of water (3 mL) is added and diethyl ether (10 mL). The layers are separated and the aqueous layer separated into a flask. The organic layer is then extracted with water (5 mL) and this aqueous layer combined with the first. To the aqueous layer is then added heptane (5 mL) and stirred vigorously. This solution is cooled to 0° C. in an ice bath and is treated dropwise with concentrated hydrochloric acid (~7 mL) over 30 min until the aqueous layer is at pH=2 keeping the temperature of the solution below 50° C. during the addition process. It is then allowed to cool to 25° C. and stirred for 3 h. It is then filtered to remove the solids and the solids are washed with 1N aqueous hydrochloric acid (1.5 mL), water (2×1.5 mL), heptane (5 mL) and 1:1 heptane:diethyl ether (5 mL) and the solid is then dried in a vacuum oven to afford (3-chloro-4-cyclopentylsulfanyl-phenyl)-acetic acid.

To a three neck round bottom flask is added a stir bar, dropping funnel, argon inlet and thermometer. It is then charged (3-chloro-4-cyclopentylsulfanyl-phenyl)-acetic acid (5.00 mmol), acetone (15 mL) and potassium carbonate (3.0 equiv.) and cooled to −10° C. To this cooled solution is then added trimethylacetyl chloride (1.05 equiv.) dropwise slowly to keep the temperature below −10° C. throughout the addition. It is then stirred at −10° C. for 15 min, then warmed to 0° C. and stirred for an additional 10 min and then recooled to −10° C. To the reaction is then added (1R,2R)-(−)-pseudoephedrine (1.5 equiv.) in one portion. It is then stirred at −10° C. for 10 min and then warmed to 25° C. and stirred for 1 h. After such time, the reaction is quenched with water (10 mL) and poured into a separatory funnel and added ethyl acetate (25 mL). The layers are separated and the organic layer is washed with water (2×10 mL) and the organic layers are then back extracted with ethyl acetate (3×25 mL) dried over magnesium sulfate, filtered and concentrated in vacuo. Purification on an AnaLogix Intelliflash system (silica gel cartridge) will afford 2-(3-chloro-4-cyclopentylsulfanyl-phenyl)-N-((1R,2R)-2-hydroxy-1-methyl-2-phenyl-ethyl)-N-methyl-acetamide.

A round bottom flask with a stir bar and argon inlet is charged with tetrahydrofuran (10 mL) and cooled to −78° C. 1,1,1,3,3,3-hexamethyldisilazane (2.25 equiv.) Is then added followed by the dropwise addition of a solution of n-butyl lithium (2.5 M solution in hexanes, 2.10 equiv.) and it is stirred at −78° C. for 15 min. After this time, a solution of 2-(4-cyclopropylsulfanyl-phenyl)-N-((1R,2R)-2-hydroxy-1-methyl-2-phenyl-ethyl)-N-methyl-acetamide (2.5 mmol) in tetrahydrofuran (6 mL) is added dropwise over 10 min keeping the reaction below −60° C. It is then stirred for 15 min, warmed to 0° C. and stirred for 20 min and then recooled to −78° C. It is then treated with a solution of iodomethylcyclopentane (prepared in PCT WO2004/052869 A1 Example 1, 1.50 equiv.) in 2,3-dimethyl-3,4,5,6-tetrahydro-2(1H)-pyrimidinone (2.10 equiv.) dropwise. The reaction is then stirred at −78° C. for 30 min and then warmed to 0° C. and stirred for 3 h. The reaction is then diluted with ethyl acetate (30 mL) and washed with a saturated aqueous ammonium chloride solution (3×10 mL). The aqueous layers are then combined and extracted with ethyl acetate (2×10 mL). The organics are then washed with a saturated aqueous brine solution (15 mL) and dried over sodium sulfate, filtered and concentrated in vacuo. Purification on an AnaLogix Intelliflash system (silica gel column) will afford (R)-3-cyclopentyl-2-(3-chloro-4-cyclopentylsulfanyl-phenyl)-N-((1R,2R)-2-hydroxy-1-methyl-2-phenyl-ethyl)-N-methyl-propionamide.

A solution of (R)-3-cyclopentyl-2-(3-chloro-4-cyclopentylsulfanyl-phenyl)-N-((1R,2R)-2-hydroxy-1-methyl-2-phenyl-ethyl)-N-methyl-propionamide (1.5 mmol) in dioxane (5 mL) is treated with a 9 N aqueous sulfuric acid solution (1.5 mL). The resulting solution is then heated at 105° C. for 16 h. The reaction is then cooled and diluted with water (13 mL) and extracted with a chloroform/methanol solution (3:2, 3×20 mL) and then combined the organic extracts and dried over magnesium sulfate, filtered and concentrated. Purification on an AnaLogix Intelliflash system (silica gel column) will afford (R)-2-(3-chloro-4-cyclopentylsulfanyl-phenyl)-3-cyclopentyl-propionic acid.

In a flask was placed (R)-2-(3-chloro-4-cyclopentylsulfanyl-phenyl)-3-cyclopentyl-propionic acid (0.50 mmol) with tetrahydrofuran (500 μL) and formic acid (5.0 equiv.). It is cooled to 0° C. in an ice bath and then treated with a 30% solution of hydrogen peroxide (5.0 equiv.). It is then allowed to warm slowly to 25° C. and stirred for 16 h. It is then cooled to 0° C. and quenched by the slow addition of a saturated aqueous sodium sulfite solution (3 mL) and extracted with ethyl acetate (3×20 mL) dried over magnesium sulfate, filtered and concentrated in vacuo. Purification on an AnaLogix Intelliflash system (silica gel column) will afford (R)-2-(3-chloro-4-cyclopentanesulfonyl-phenyl)-3-cyclopentyl-propionic acid.

A solution of (R)-2-(3-chloro-4-cyclopentanesulfonyl-phenyl)-3-cyclopentyl-propionic acid (0.15 mmol) is dissolved in methylene chloride (5 mL) and N,N-dimethylformamide (one drop) and cooled to 0° C. To this solution is added dropwise a solution of oxalyl chloride in methylene chloride (2 M solution, 1.2 equiv.) and it is then allowed to warm to 25° C. and stirred 1 h at 25° C. After this time, the reaction is concentrated in vacuo to ⅓ of the original volume. In a separate flask, a solution of 1-(3-amino-pyrazol-1-yl)-2-methyl-propan-2-ol (prepared as in Example 80, 1.5 equiv.), 2,6-lutidine (2.0 equiv.) and methylene chloride (5 mL) is cooled to 0° C. in an ice bath. To this solution is added the solution of the prepared acid chloride, diluted with another portion of methylene chloride (2 mL) dropwise. After the addition is complete the reaction is then allowed to warm to 25° C. and stirred for 16 hours. After this time the reaction mixture is diluted with methylene chloride (10 mL) transferred to a separatory funnel and washed with a saturated aqueous sodium bicarbonate solution (10 mL) and then a 1 N aqueous hydrochloric acid solution (10 mL) and then dried over magnesium sulfate, filtered and concentrated in vacuo. Purification on an AnaLogix Intelliflash system (silica gel column) will afford (R)-2-(3-chloro-4-cyclopentanesulfonyl-phenyl)-3-cyclopentyl-N-[1-(2-hydroxy-2-methyl-propyl)-1H-pyrazol-3-yl]-propionamide.

Example 141

In Vitro Glucokinase Activity

The compounds of formula I which include the compounds set forth in the Examples activated glucokinase in vitro by the procedure of this Example. In this manner, they increase the flux of glucose metabolism which causes increased insulin secretion. Therefore, the compounds of formula I are glucokinase activators useful for increasing insulin secretion.

Glucokinase In Vitro Assay Protocol: Glucokinase (GK) was assayed by coupling the production of glucose-6-phosphate to the generation of NADH with glucose-6-phosphate dehydrogenase (G6PDH, 0.75-1 kunits/mg; Boehringer Mannheim, Indianapolis, Ind.) from *Leuconostoc mesenteroides* as the coupling enzyme (Scheme 2).

Scheme 2

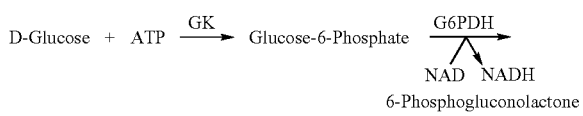

Recombinant human liver GK1 was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C. in a flat bottom 96-well tissue culture plate from Costar (Cambridge, Mass.) with a final incubation volume of 120 μL. The incubation reaction contained the following: 25 mM Hepes buffer (pH 7.1), 25 mM KCl, 5 mM D-glucose, 1 mM ATP, 1.8 mM NAD, 2 mM $MgCl_2$, 1 μM sorbitol-6-phosphate, 1 mM dithiothreitol, test drug or 10% DMSO, 1.8 unit/ml G6PDH, and GK (see below). All organic reagents were >98% pure and were from Boehringer Mannheim with the exceptions of D-glucose and Hepes which were from Sigma Chemical Co, St Louis, Mo. Test compounds were dissolved in DMSO and were added to the incubation reaction minus GST-GK in a volume of 12 μL to yield a final DMSO concentration of 10%. This mix was pre-incubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 μL GST-GK.

After addition of enzyme, the increase in optical density (OD) at 340 nm was monitored over a 10 minute incubation period as a measure of GK activity. Sufficient GST-GK was added to produce an increase in $OD_{340}$ of 0.08 to 0.1 units over the 10 minute incubation period in wells containing 10% DMSO but no test compound. Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of GK, i.e., the $SC_{1.5}$, was calculated.

All of the compounds of formula I described in the Examples had an $SC_{1.5}$ less than or equal to 100 μM and the Table below provides for representative values:

| Example | SC1.5 (μM) |
|---|---|
| 2 | 0.28 |
| 8 | 0.2 |
| 11 | 0.45 |
| 24 | 0.083 |
| 44 | 0.061 |
| 47 | 0.03 |
| 56 | 0.13 |
| 76 | 5.3 |
| 79 | 1.433 |
| 85 | 0.779 |

REFERENCES

Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. *Biochem. J* 309:167-173, 1995.

Neet, K., Keenan, R. P., and Tippett, P. S. Observation of a kinetic slow transition in monomeric glucokinase. *Biochemistry* 29; 770-777, 1990.

Example 142

In Vivo Glucokinase Activity

Glucokinase Activator in vivo Screen Protocol in Lean and Diet Induced Obese Mice: Lean or Diet-Induced Obese (DIO) C57BL/6J mice were orally dosed via gavage with Glucokinase (GK) activator (50 mg/kg body weight for lean mice, 25 mg/kg body weight for DIO mice) following a two hour fasting period. Blood glucose determinations were made four times during the six hour post-dose study period.

C57Bl/6J mice were obtained from Jackson Laboratory (Bar Harbor, Me.) and were maintained in a light-dark cycle with lights on from 0600-1800 hr. For studies in lean mice, the mice were received at age six weeks and given ad libitum access to control diet (LabDiet 5001 chow, PMI Nutrition, Brentwood, Mo.), and were at least age 11 weeks at the time of study. For studies in the DIO model, the mice were received at age five weeks and given ad libitum access to Bio-Serv F3282 High Fat Diet (Frenchtown, N.J.), and were at least age 16 weeks at the time of study. The experiments were conducted during the light phase of the light-dark cycle. Mice (n=6) are weighed and fasted for a two hour period prior to oral treatment. GK activators are formulated in Gelucire vehicle (Ethanol:Gelucire44/14:PEG400q.s. 4:66:30 v/w/v. For studies in lean mice, the mice were dosed orally with 5.0 μL per gram of body weight with 5 ml/kg×10.0 mg/ml formulation to equal a 50 mg/kg dose. For studies in DIO mice, the mice were dosed orally with 5.0 μL per gram of body weight with 5.0 mg/ml×5 mg/ml formulation to equal a 25 mg/kg dose. Immediately prior to dosing, a pre-dose (time zero) blood glucose reading was acquired by snipping off a small portion of the animal's tail (~1 mm) and collecting 15 μL blood into a heparinized capillary tube for analysis. Following GK activator administration, additional blood glucose readings were taken at 2, 4 and 6 hours post dose from the same tail wound. Results were interpreted by comparing the mean blood glucose values of six vehicle treated mice with six GK activator treated mice over the six hour study duration.

Preferred compounds were considered to be those that exhibited a statistically significant (p≦0.05) decrease in blood glucose compared to vehicle for two consecutive assay time points.

The Table below provides data for % glucose lowering of a representative number of compounds of the present invention vs control at 2 hours post 25 mg/kg dose in DIO mice:

| Example | % gluc @ 2 H |
|---|---|
| 7 | −15.3 |
| 33 | −9.8 |
| 35 | −33.2 |
| 73 | −48.5 |
| 78 | −26.7 |
| 81 | −31.4 |
| 82 | −38.3 |
| 84 | −24.5 |
| 85 | −20.5 |

It is to be understood that the invention is not limited to the particular embodiments of the invention described above, as variations of the particular embodiments may be made and still fall within the scope of the appended claims.

What is claimed is:

1. A compound of the formula (I):

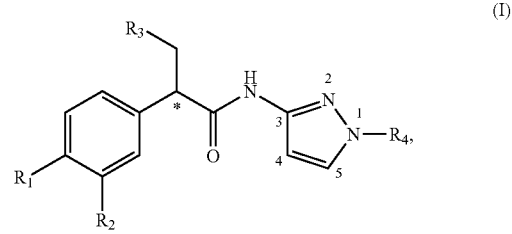

wherein:

$R_1$ and $R_2$ are, independently, hydrogen, halogen, amino, hydroxyamino, cyano, nitro, lower alkyl, —$OR_5$, —$C(O)OR_6$, perfluoro-lower alkyl, lower alkyl thio, perfluoro-lower alkyl thio, lower alkyl sulfinyl, lower alkyl sulfonyl, cycloloweralkyl sulfonyl, lower alkoxy lower alkyl sulfonyl, perfluoro-lower alkyl sulfonyl or sulfonamido;

or $R_1$ and $R_2$, together with the phenyl ring to which they are attached, combine to form a 2,3-dihydro-benzo[b]thiophene, 2,3-dihydro-benzo[b]thiophene 1-oxide, 2,3-dihydro-benzo[b]thiophene 1,1-dioxide, benzo[b]thiophene, benzo[b]thiophene 1-oxide, benzo[b]thiophene 1,1-dioxide, thiochroman, thiochroman 1-oxide or thiochroman 1,1-dioxide group;

$R_3$ is a cycloalkyl, a bicycloalkyl or a mono- or bicyclic heterocycle with 1-3 hetero atoms selected from N, O and S, said cycloalkyl or heterocycle being unsubstituted or mono-, bi- or trisubstituted with halogen, lower alkyl, lower alkyoxy, carbonyl or lower alkyl sulfonyl;

R$_4$ is hydrogen,

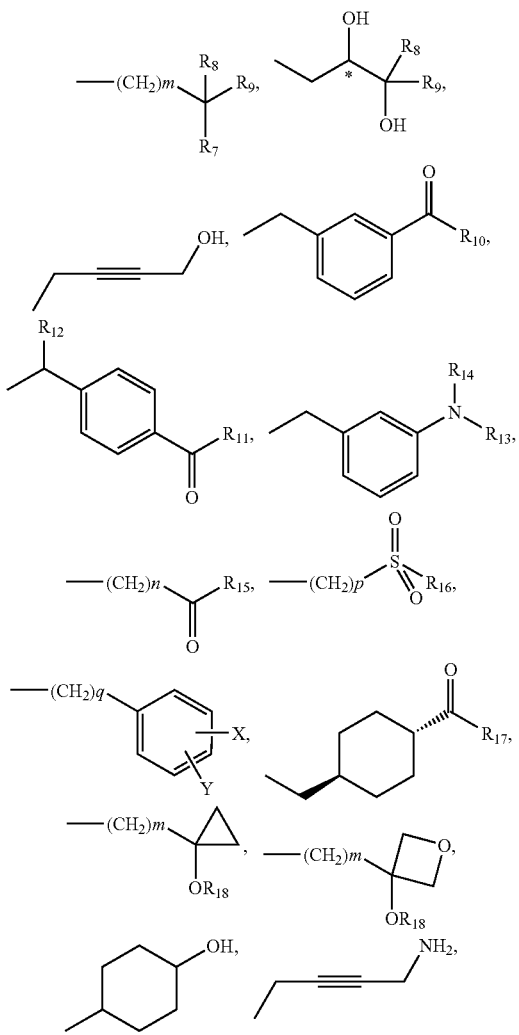

or alkyl having 1 to 10 carbon atoms;

R$_5$ is hydrogen, alkyl having from 1 to 6 carbons, phenyl, benzyl, substituted phenyl or substituted benzyl;

R$_6$ is hydrogen, alkyl having from 1 to 6 carbons, benzyl or substituted benzyl;

R$_7$ is hydrogen, hydroxy, alkoxy, perfluoroalkoxy, amino, alkyl amino, or dialkylamino, methylene hydroxy, C(O)OY', where Y' is H or lower alkyl;

R$_8$ is hydrogen or lower alkyl;

R$_9$ is hydrogen, cycloalkyl or lower alkyl;

R$_{10}$ is hydroxy, lower alkoxy, amino, methylamino, dimethylamino or —NH$_2$CH$_2$-cycloalkyl;

R$_{11}$ is hydroxy, amide, amide-loweralkyl, cyclopropyl methyl amide, methoxy, NHCH$_2$CH$_2$CH$_2$L, wherein L is methoxy, hydroxy or dimethylamino;

R$_{12}$ is hydrogen or lower alkyl;

R$_{13}$ is hydrogen or lower alkyl;

R$_{14}$ is hydrogen, lower alkyl, SO$_2$X', wherein X' is lower alkyl, or C(O)Y''', where Y'' is lower alkyl or O-alkyl;

R$_{15}$ is hydroxy, methoxy, t-butoxy, lower alkyl, 2-hydroxy-2-methyl-propyl, amino, methylamino, propylamino, dimethylamino, diethylamino, morpholino, anilino, benzylamino, allylcarbamoyl-lower alkyl, allylamino, pyrazin-2-ylamino, and NH—(CH$_2$)$_v$Z, wherein Z is methoxy or morpholino;

R$_{16}$ is lower alkyl;

R$_{17}$ is methoxy;

R$_{18}$ is H, lower alkyl, C(O)R where R is lower alkyl;

X, Y are, independently, hydrogen, halogen, cyano, lower alkyl, methoxy, SO$_2$X'' where X'' is alkyl, or cycloalkyl m is 0, 1, 2, 3 or 4; wherein if m=0 R$_7$ can not be hydroxy, alkoxy, perfluoroalkoxy, amino, alkyl amino, or dialkylamino;

n is 0, 1, 2;

p is 0, 1;

q is 0, 1, 2;

v is 2, 3; and wherein if R$_3$ is tetrahydropyran, then R$_2$ is not hydrogen or lower alkyl, or a pharmaceutically acceptable salt thereof.

2. The compound according to claim 1, wherein R$_1$ is methanesulfonyl, chloro or hydrogen.

3. The compound according to claim 1, wherein R$_2$ is hydrogen, chloro, methyl, trifluoromethyl, tetrahydro-furan-2-yl or cyano.

4. The compound according to claim 1, wherein R$_3$ is

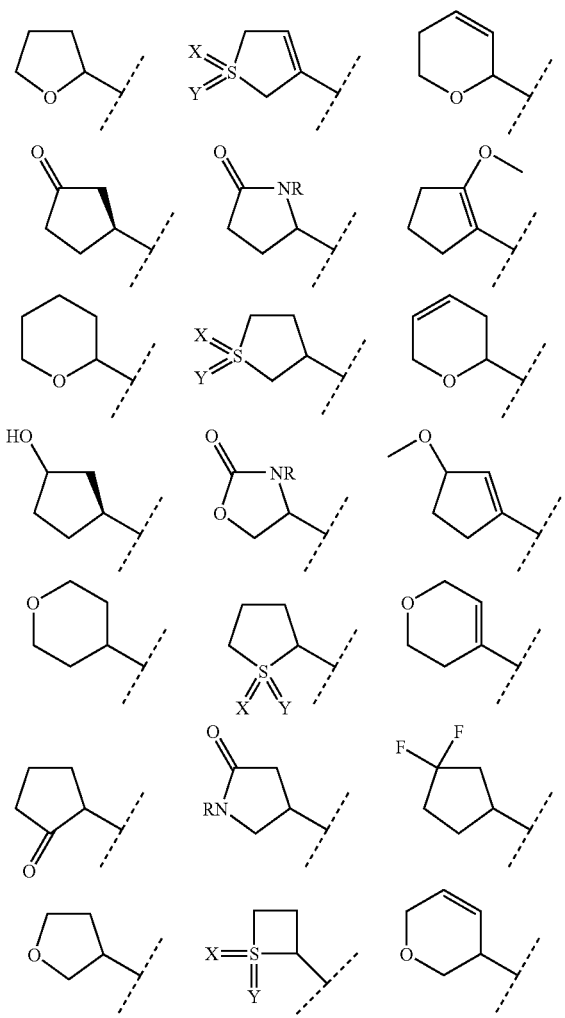

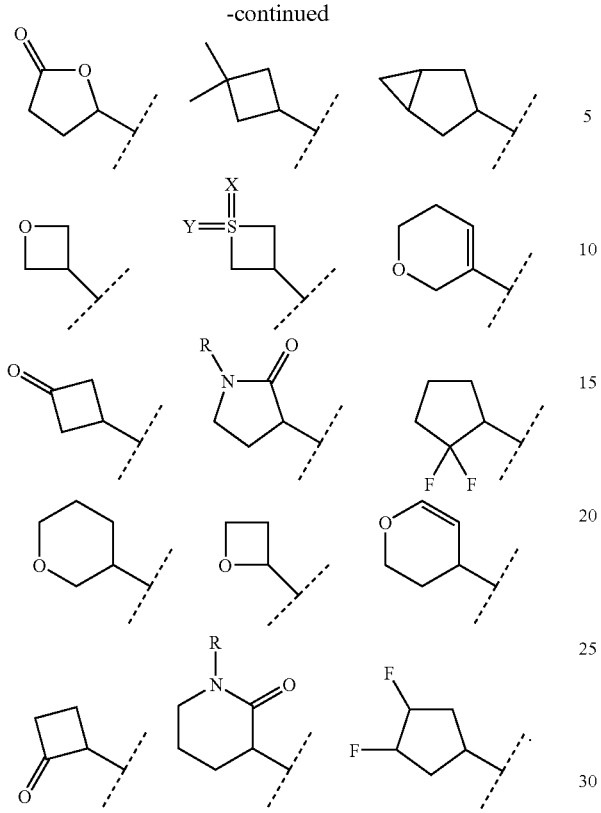

5. The compound according to claim 1, wherein $R_3$ is $(C_3-C_7)$-cycloalkyl.

6. The compound according to claim 5, wherein $R_3$ is cyclopentyl or tetrahydro-pyran-4-yl.

7. The compound according to claim 1, wherein $R_4$ is methyl, hexyl, carboxymethyl, methylcarbamoylmethyl, dimethylcarbamoylmethyl, diethylcarbamoylmethyl, 2-morpholin-4-yl-2-oxo-ethyl, 2-tert-butoxycarbonyl-ethyl, 2-carboxy-ethyl, 2-methylcarbamoyl-ethyl, 2-propylcarbamoyl-ethyl, 2-dimethylcarbamoyl-ethyl, 3-morpholin-4-yl-3-oxo-propyl, 2-(3-methoxy-propylcarbamoyl)-ethyl, 2-allylcarbamoyl-ethyl, 2-methoxycarbonyl-ethyl, carbamoylmethyl, methanesulfonylmethyl, 3-hydroxy-propyl, benzyl, 4-chloro-benzyl, 4-cyano-benzyl, 4-methyl-benzyl, 4-methoxy-benzyl, 3,4-dichloro-benzyl, phenethyl, propionyl, propyl, ethanesulfonyl, methylcarbamoyl, 3-hydroxy-3-methyl-butyryl, ethyl, butyl, octyl, isobutyl, 3-methyl-butyl, 4-carboxy-benzyl, 4-carbamoyl-benzyl, 3-hydroxy-3-methyl-butyl, 3-methyl-but-2-enyl, 4-hydroxy-but-2-ynyl, 4-hydroxy-butyl, isopropyl, 3-amino-benzyl, 3-carbamoyl-benzyl, 2-hydroxy-ethyl, cyclopropylmethyl, 2-acetoxy-ethyl, 2-methoxy-ethyl, 1-hydroxy-cyclopropylmethyl, 2-hydroxy-2-methyl-propyl, 2-hydroxy-propyl, tetrahydro-furan-2-yl, 2-methoxy-ethyl or 3-hydroxy-propyl.

8. The compound according to claim 1, wherein:
$R_1$ is methanesulfonyl, chloro or hydrogen; and
$R_3$ is cyclopentyl or tetrahydro-pyran-4-yl.

9. The compound according to claim 1, wherein:
$R_1$ is methanesulfonyl, chloro or hydrogen; and
$R_4$ is methyl, hexyl, carboxymethyl, methylcarbamoylmethyl, dimethylcarbamoylmethyl, diethylcarbamoylmethyl, 2-morpholin-4-yl-2-oxo-ethyl, 2-tert-butoxycarbonyl-ethyl, 2-carboxy-ethyl, 2-methylcarbamoyl-ethyl, 2-propylcarbamoyl-ethyl, 2-dimethylcarbamoyl-ethyl, 3-morpholin-4-yl-3-oxo-propyl, 2-(3-methoxy-propylcarbamoyl)-ethyl, 2-allylcarbamoyl-ethyl, 2-methoxycarbonyl-ethyl, carbamoylmethyl, methanesulfonylmethyl, 3-hydroxy-propyl, benzyl, 4-chloro-benzyl, 4-cyano-benzyl, 4-methyl-benzyl, 4-methoxy-benzyl, 3,4-dichloro-benzyl, phenethyl, propionyl, propyl, ethanesulfonyl, methylcarbamoyl, 3-hydroxy-3-methyl-butyryl, ethyl, butyl, octyl, isobutyl, 3-methyl-butyl, 4-carboxy-benzyl, 4-carbamoyl-benzyl, 3-hydroxy-3-methyl-butyl, 3-methyl-but-2-enyl, 4-hydroxy-but-2-ynyl, 4-hydroxy-butyl, isopropyl, 3-amino-benzyl, 3-carbamoyl-benzyl, 2-hydroxy-ethyl, cyclopropylmethyl, 2-acetoxy-ethyl, 2-methoxy-ethyl, 1-hydroxy-cyclopropylmethyl, 2-hydroxy-2-methyl-propyl, 2-hydroxy-propyl, tetrahydro-furan-2-yl, 2-methoxy-ethyl or 3-hydroxy-propyl.

10. The compound according to claim 1, wherein:
$R_2$ is chloro, methyl, trifluoromethyl or cyano; and
$R_3$ is cyclopentyl or tetrahydro-pyran-4-yl.

11. The compound according to claim 1, wherein:
$R_2$ is chloro, methyl, trifluoromethyl or cyano; and
$R_4$ is methyl, hexyl, carboxymethyl, methylcarbamoylmethyl, dimethylcarbamoylmethyl, diethylcarbamoylmethyl, 2-morpholin-4-yl-2-oxo-ethyl, 2-tert-butoxycarbonyl-ethyl, 2-carboxy-ethyl, 2-methylcarbamoyl-ethyl, 2-propylcarbamoyl-ethyl, 2-dimethylcarbamoyl-ethyl, 3-morpholin-4-yl-3-oxo-propyl, 2-(3-methoxy-propylcarbamoyl)-ethyl, 2-allylcarbamoyl-ethyl, 2-methoxycarbonyl-ethyl, carbamoylmethyl, methanesulfonylmethyl, 3-hydroxy-propyl, benzyl, 4-chloro-benzyl, 4-cyano-benzyl, 4-methyl-benzyl, 4-methoxy-benzyl, 3,4-dichloro-benzyl, phenethyl, propionyl, propyl, ethanesulfonyl, methylcarbamoyl, 3-hydroxy-3-methyl-butyryl, ethyl, butyl, octyl, isobutyl, 3-methyl-butyl, 4-carboxy-benzyl, 4-carbamoyl-benzyl, 3-hydroxy-3-methyl-butyl, 3-methyl-but-2-enyl, 4-hydroxy-but-2-ynyl, 4-hydroxy-butyl, isopropyl, 3-amino-benzyl, 3-carbamoyl-benzyl, 2-hydroxy-ethyl, cyclopropylmethyl, 2-acetoxy-ethyl, 2-methoxy-ethyl, 1-hydroxy-cyclopropylmethyl, 2-hydroxy-2-methyl-propyl, 2-hydroxy-propyl, tetrahydro-furan-2-yl, 2-methoxy-ethyl or 3-hydroxy-propyl.

12. The compound according to claim 1, wherein:
$R_1$ is methanesulfonyl; and
$R_2$ is chloro or methyl.

13. The compound according to claim 1, wherein:
$R_1$ is methanesulfonyl; and
$R_3$ is cyclopentyl.

14. The compound according to claim 1, wherein said compound is:
2(R)-(3-Chloro-4-methanesulfonyl-phenyl)-3-cyclopentyl-N-[1-((S)-2,3-dihydroxy-propyl)-1H-pyrazol-3-yl]-propionamide,
2(R)-(3-Chloro-4-methanesulfonyl-phenyl)-3-cyclopentyl-N-[1-((R)-2,3-dihydroxy-propyl)-1H-pyrazol-3-yl]-propionamide
Acetic acid-{3-[2(R)-(3-chloro-4-methanesulfonyl-phenyl)-3-cyclopentyl-propionylamino]-pyrazol-1-yl}-ethyl ester,
2(R)-(3-Chloro-4-methanesulfonyl-phenyl)-3-cyclopentyl-N-[1-(2-hydroxy-2-methyl-propyl)-1H-pyrazol-3-yl]-propionamide,
3-Cyclopentyl-N-[1-(2-hydroxy-ethyl)-1H-pyrazol-3-yl]-2(R)-(4-methanesulfonyl-3-methyl-phenyl)-propionamide, 2(R)-(3-Chloro-4-methanesulfonyl-phenyl)-3-cyclopentyl-N-[1-(1-hydroxy-cyclopropylmethyl)-1H-pyrazol-3-yl]-propionamide,
3-Cyclopentyl-N-[1-(2-hydroxy-2-methyl-propyl)-1H-pyrazol-3-yl]-2(R)-(4-methanesulfonyl-3-methyl-phenyl)-propionamide,
3-Cyclopentyl-2(R)-(4-methanesulfonyl-3-methyl-phenyl)-N-[1-(2-methoxy-ethyl)-1H-pyrazol-3-yl]-propionamide, or
3-Cyclopentyl-N-[1-(2-hydroxy-2-methyl-propyl)-1H-pyrazol-3-yl]-2(R)-(3-trifluoromethyl-phenyl)-propionamide.

15. The compound according to claim 1, wherein said compound is:
3-Cyclopentyl-N-[1-(3-hydroxy-propyl)-1H-pyrazol-3-yl]-2(R)-(3-trifluoromethyl-phenyl)-propionamide,
(R)-2-(3-Cyano-4-methanesulfonyl-phenyl)-3-cyclopentyl-N-[1-(2-hydroxy-ethyl)-1H-pyrazol-3-yl]-propionamide,
(R)-2-(3-Chloro-4-methanesulfonyl-phenyl)-3-cyclopentyl-N-[1-(2-methoxy-2-methyl-propyl)-1H-pyrazol-3-yl]-propionamide,
N-[1-(2-Hydroxy-2-methyl-propyl)-1H-pyrazol-3-yl]-2(R)-(4-methanesulfonyl-3-methyl-phenyl)-3-(tetrahydro-pyran-4-yl)-propionamide,
2(R)-(3-Chloro-4-methanesulfonyl-phenyl)-N-[1-(2-hydroxy-2-methyl-propyl)-1H-pyrazol-3-yl]-3-(tetrahydro-furan-2(R)-yl)-propionamide,
2(R)-(3-Chloro-4-methanesulfonyl-phenyl)-N-[1-(2-hydroxy-2-methyl-propyl)-1H-pyrazol-3-yl]-3-(3-oxo-cyclobutyl)-propionamide,
(R)-3-Cyclopentyl-2-(3,4-dichloro-phenyl)-N-[1-(2-hydroxy-ethyl)-1H-pyrazol-3-yl]-propionamide, or
(R)-3-Cyclopentyl-2-(3,4-dichloro-phenyl)-N-[1-(3-hydroxy-propyl)-1H-pyrazol-3-yl]-propionamide.

16. The compound according to claim 1, wherein said compound is:
(R)-3-Cyclopentyl-2-(3,4-dichloro-phenyl)-N-[1-(2-methoxy-ethyl)-1H-pyrazol-3-yl]-propionamide,
(R)-3-Cyclopentyl-2-(3,4-dichloro-phenyl)-N-[1-(2-hydroxy-2-methyl-propyl)-1H-pyrazol-3-yl]-propionamide,
(R)-2-(3-Chloro-4-methanesulfonyl-phenyl)-3-cyclopentyl-N-[1-(2-isopropoxy-ethyl)-1H-pyrazol-3-yl]-propionamide,
(R)-2-(3-Chloro-4-methanesulfonyl-phenyl)-N-[1-(2-hydroxy-ethyl)-1H-pyrazol-3-yl]-3-((R)-3-oxo-cyclopentyl)-propionamide,
3-Cyclopentyl-N-[1-(2-hydroxy-2-methyl-propyl)-1H-pyrazol-3-yl]-2-(R)-(4-methanesulfonyl-phenyl)-propionamide,
3-Cyclopentyl-N-[1-(2-methoxy-ethyl)-1H-pyrazol-3-yl]-2(R)-(3-trifluoromethyl-phenyl)-propionamide,
3-Cyclopentyl-N-[1-(3-hydroxy-propyl)-1H-pyrazol-3-yl]-2(R)-(4-methanesulfonyl-3-methyl-phenyl)-propionamide,
2(R)-(3-Chloro-4-methanesulfonyl-phenyl)-N-[1-(2-hydroxy-ethyl)-1H-pyrazol-3-yl]-3-(tetrahydro-pyran-4-yl)-propionamide, or
2(R)-(3-Chloro-4-methanesulfonyl-phenyl)-3-cyclopentyl-N-[1-(2-methoxy-ethyl)-1H-pyrazol-3-yl]-propionamide.

17. The compound according to claim 1, wherein:
$R_1$ is methanesulfonyl, cyclopropanesulfonyl, or isopropanesulfonyl;
$R_2$ is chloro or hydrogen;
$R_3$ is cyclopentyl or cyclobutyl.

18. The compound according to claim 1, wherein said compound is:
2(R)-(3-Chloro-4-methanesulfonyl-phenyl)-3-cyclopentyl-N-[1-(4-methanesulfonyl-benzyl)-1H-pyrazol-3-yl]-propionamide,
2(R)-(3-Chloro-4-methanesulfonyl-phenyl)-3-cyclopentyl-N-[1-(3-hydroxy-propyl)-1H-pyrazol-3-yl]-propionamide,
N-(1-Benzyl-1H-pyrazol-3-yl)-2(R)-(3-chloro-4-methanesulfonyl-phenyl)-3-cyclopentyl-propionamide,
2-(R)-(3-Chloro-4-methanesulfonyl-phenyl)-3-cyclopentyl-N-(1-ethyl-1H-pyrazol-3-yl)-propionamide,
2-(R)-(3-Chloro-4-methanesulfonyl-phenyl)-3-cyclopentyl-N-(1-cyclopropylmethyl-1H-pyrazol-3-yl)-propionamide,
2(R)-(3-Chloro-4-methanesulfonyl-phenyl)-3-cyclopentyl-N-[1-(4-methoxy-benzyl)-1H-pyrazol-3-yl]-propionamide,
2-(R)-(3-Chloro-4-methanesulfonyl-phenyl)-3-cyclopentyl-N-(1-butyl-1H-pyrazol-3-yl)-propionamide,
2-(R)-(3-Chloro-4-methanesulfonyl-phenyl)-3-cyclopentyl-N-(1-iso-pentyl-1H-pyrazol-3-yl)-propionamide,
4-{3-[2-(R)-(3-Chloro-4-methanesulfonyl-phenyl)-3-cyclopentyl-propionylamino]-pyrazol-1-ylmethyl}-N-(3-methoxy-propyl)-benzamide,
3-{3-[2-(R)-(3-Chloro-4-methanesulfonyl-phenyl)-3-cyclopentyl-propionylamino]-pyrazol-1-ylmethyl}-N-methyl-benzamide,
2-(R)-(3-Chloro-4-methanesulfonyl-phenyl)-3-cyclopentyl-N-[1-(2-hydroxy-ethyl)-1H-pyrazol-3-yl]-propionamide,
4-{3-[2-(R)-(3-Chloro-4-methanesulfonyl-phenyl)-3-cyclopentyl-propionylamino]-pyrazol-1-ylmethyl}-cyclohexanecarboxylic acid methyl ester,
(R)-2-(3-Chloro-4-methanesulfonyl-phenyl)-3-((R)-3,3-difluoro-cyclopentyl)-N-[1-(2-hydroxy-2-methyl-propyl)-1H-pyrazol-3-yl]-propionamide,
(R)-2-(3-Chloro-4-methanesulfonyl-phenyl)-3-((R)-3,3-difluoro-cyclopentyl)-N-[1-(2-methoxy-2-methyl-propyl)-1H-pyrazol-3-yl]-propionamide,
(R)-2-(3-Cyano-4-methanesulfonyl-phenyl)-3-cyclopentyl-N-[1-(2-hydroxy-2-methyl-propyl)-1H-pyrazol-3-yl]-propionamide,
(R)-2-(3-Chloro-4-methanesulfonyl-phenyl)-3-cyclobutyl-N-[1-(2-hydroxy-2-methyl-propyl)-1H-pyrazol-3-yl]-propionamide,
(R)-3-Cyclopentyl-2-(4-cyclopropanesulfonyl-phenyl)-N-[1-(2-hydroxy-2-methyl-propyl)-1H-pyrazol-3-yl]-propionamide, or
(R)-3-Cyclopentyl-N-[1-(2-hydroxy-2-methyl-propyl)-1H-pyrazol-3-yl]-2-[4-(propane-2-sulfonyl)-phenyl]-propionamide.

19. A pharmaceutical composition, comprising a therapeutically effective amount of a compound according to claim 1 and a pharmaceutically acceptable carrier.

20. A method for treating a metabolic disease and/or disorder, comprising the step of administering a therapeutically effective amount of a compound according to claim 1 to a patient in need thereof.

21. The method according to claim 20, wherein said disease is diabetes mellitus.

* * * * *